US012667559B2

(12) United States Patent
Zhou et al.

(10) Patent No.: US 12,667,559 B2
(45) Date of Patent: Jun. 30, 2026

(54) DIHYDRONAPHTHYRIDINONE COMPOUND, AND PREPARATION METHOD THEREFOR AND MEDICAL USE THEREOF

(71) Applicants: GENFLEET THERAPEUTICS (SHANGHAI) INC., Shanghai (CN); ZHEJIANG GENFLEET THERAPEUTICS CO., LTD., Zhejiang (CN)

(72) Inventors: Fusheng Zhou, Shanghai (CN); Xiaoming Xu, Shanghai (CN); Leitao Zhang, Shanghai (CN); Xin Li, Shanghai (CN); Lili Tang, Shanghai (CN); Jiong Lan, Shanghai (CN)

(73) Assignees: Genfleet Therapeutics (Shanghai) Inc., Shanghai (CN); Zhejiang Genfleet Therapeutics Co., Ltd., Zhejiang (CN)

( * ) Notice: Subject to any disclaimer, the term of this patent is extended or adjusted under 35 U.S.C. 154(b) by 816 days.

(21) Appl. No.: 17/799,637

(22) PCT Filed: Feb. 9, 2021

(86) PCT No.: PCT/CN2021/076160
§ 371 (c)(1),
(2) Date: Aug. 12, 2022

(87) PCT Pub. No.: WO2021/160109
PCT Pub. Date: Aug. 19, 2021

(65) Prior Publication Data

US 2023/0139111 A1 May 4, 2023

(30) Foreign Application Priority Data

Feb. 13, 2020 (CN) ......................... 202010090252.3
Jan. 19, 2021 (CN) ......................... 202110070075.7

(51) Int. Cl.
*A61K 31/4375* (2006.01)
*A61K 31/4184* (2006.01)
*A61K 31/4188* (2006.01)
*A61K 31/423* (2006.01)
*A61K 31/5025* (2006.01)

(52) U.S. Cl.
CPC ...... *A61K 31/4375* (2013.01); *A61K 31/4184* (2013.01); *A61K 31/4188* (2013.01); *A61K 31/423* (2013.01); *A61K 31/5025* (2013.01)

(58) Field of Classification Search
CPC .............. A61K 31/5025; A61K 31/423; A61K 31/4188; A61K 31/4184; A61K 31/4375
See application file for complete search history.

(56) References Cited

FOREIGN PATENT DOCUMENTS

| | | | |
|---|---|---|---|
| CN | 102361857 | | 2/2012 |
| CN | 105916503 | | 8/2016 |
| CN | 110325526 | | 10/2019 |
| CN | 110520423 | | 11/2019 |
| JP | 7323637 | | 8/2023 |
| WO | WO-2010/052222 | | 5/2010 |
| WO | WO2011/076732 | | 6/2011 |
| WO | WO-2011/076734 | | 6/2011 |
| WO | WO2013/076732 | | 10/2013 |
| WO | WO-2015/108861 | | 7/2015 |
| WO | WO-2018/148626 | | 8/2018 |
| WO | WO 2018/160406 | * | 9/2018 |
| WO | WO 2020/192562 | | 10/2020 |

OTHER PUBLICATIONS

Berghe et al. "Differential signaling to apoptotic and necrotic cell death by Fas-associated death domain protein FADD." *Journal of Biological Chemistry* 279.9 (2004): 7925-7933.
Bonnet et al. "The adaptor protein FADD protects epidermal keratinocytes from necroptosis in vivo and prevents skin inflammation." *Immunity* 35.4 (2011): 572-582.
Chaudhary et al. "Death receptor 5, a new member of the TNFR family, and DR4 induce FADD-dependent apoptosis and activate the NF-κB pathway." *Immunity* 7.6 (1997): 821-830.
Cusson-Hermance, et al. "Rip1 mediates the Trif-dependent toll-like receptor 3-and 4-induced NF-κB activation but does not contribute to interferon regulatory factor 3 activation." *Journal of Biological Chemistry* 280.44 (2005): 36560-36566.
Degterev et al. "Chemical inhibitor of nonapoptotic cell death with therapeutic potential for ischemic brain injury." *Nature chemical biology* 1.2 (2005): 112-119.
Duprez et al. "RIP kinase-dependent necrosis drives lethal systemic inflammatory response syndrome." *Immunity* 35.6 (2011): 908-918.
Ea et al. "Activation of IKK by TNFα requires site-specific ubiquitination of RIP1 and polyubiquitin binding by NEMO." *Molecular cell* 22.2 (2006): 245-257.
Ermolaeva et al. "Function of TRADD in tumor necrosis factor receptor 1 signaling and in TRIF-dependent inflammatory responses." *Nature immunology* 9.9 (2008): 1037-1046.
(Continued)

*Primary Examiner* — Marcos L Sznaidman
(74) *Attorney, Agent, or Firm* — Fish & Richardson P.C.

(57) ABSTRACT

Provided are a dihydronaphthyridinone compound as shown in formula (I), which compound has a selective inhibitory effect on RIPK1, and a pharmaceutically acceptable salt, a stereoisomer, a solvate or a prodrug thereof. In addition, provided are a pharmaceutical composition containing the compound, and the use thereof in the preparation of a drug for treating RIPK1-related diseases or conditions.

(I)

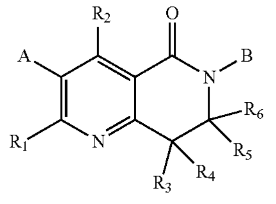

19 Claims, No Drawings

(56) References Cited

OTHER PUBLICATIONS

Geiss et al. "Ring around the Ro-sie: RNA-mediated alterations of PNPase activity." *Cell* 153.1 (2013): 12-14.
He et al. "Receptor interacting protein kinase-3 determines cellular necrotic response to TNF-α." *Cell* 137.6 (2009): 1100-1111.
Hsu et al. "TNF-dependent recruitment of the protein kinase RIP to the TNF receptor-1 signaling complex." *Immunity* 4.4 (1996): 387-396.
Kono et al. "How dying cells alert the immune system to danger." *Nature Reviews Immunology* 8.4 (2008): 279-289.
Linkermann et al. "Rip1 (receptor-interacting protein kinase 1) mediates necroptosis and contributes to renal ischemia/reperfusion injury." *Kidney international* 81.8 (2012): 751-761.
Mahoney, et al. "Both cIAP1 and cIÅP2 regulate TNFα-mediated NF-κB activation." *Proceedings of the National Academy of Sciences* 105.33 (2008): 11778-11783.
Meylan et al. "RIP1 is an essential mediator of Toll-like receptor 3-induced NF-κB activation." *Nature immunology* 5.5 (2004): 503-507.
Meylan et al. "The RIP kinases: crucial Integrators of cellular stress." *Trends in biochemical sciences* 30.3 (2005): 151-159.
Micheau et al. "Induction of TNF receptor I-mediated apoptosis via two sequential signaling complexes." *Cell* 114.2 (2003): 181-190.
Moriwaki et al. "RIP3: a molecular switch for necrosis and inflammation." *Genes & development* 27.15 (2013): 1640-1649.
Murakami et al. "Receptor interacting protein kinase mediates necrotic cone but not rod cell death in a mouse model of inherited degeneration." *Proceedings of the National Academy of Sciences* 109.36 (2012): 14598-14603.
O'Donnell et al. "RIP1 comes back to life as a cell death regulator in TNFR1 signaling." *The FEBS journal* 278.6 (2011): 877-887.
Rebsamen et al. "DAI/ZBP1 recruits RIP1 and RIP3 through RIP homotypic interaction motifs to activate NF-κb." *EMBO reports* 10.8 (2009): 916-922.
Rodrigue-Gervais et al. "Cellular inhibitor of apoptosis protein cIAP2 protects against pulmonary tissue necrosis during influenza virus infection to promote host survival." *Cell host & microbe* 15.1 (2014): 23-35.
Rosenbaum et al. "Necroptosis, a novel form of caspase-independent cell death, contributes to neuronal damage in a retinal ischemia-reperfusion injury model." *Journal of neuroscience research* 88.7 (2010): 1569-1576.
Stanger et al. "RIP: a novel protein containing a death domain that interacts with Fas/APO-1 (CD95) in yeast and causes cell death." *Cell* 81.4 (1995): 513-523.
Sun et al. "RIP3, a novel apoptosis-inducing kinase." *Journal of Biological Chemistry* 274.24 (1999): 16871-16875.
Sun et al. "Mixed lineage kinase domain-like protein mediates necrosis signaling downstream of RIP3 kinase." *Cell* 148.1-2 (2012): 213-227.
Trichonas et al. "Receptor interacting protein kinases mediate retinal detachment-induced photoreceptor necrosis and compensate for inhibition of apoptosis." *Proceedings of the National Academy of Sciences* 107.50 (2010): 21695-21700.
Tristao et al. "NEC-1 protects against nonapoptotic cell death in cisplatin-induced kidney injury." *Renal failure* 34.3 (2012): 373-377.
Wang et al. "The mitochondrial phosphatase PGAM5 functions at the convergence point of multiple necrotic death pathways." *Cell* 148.1-2 (2012): 228-243.
Wang et al. "Necrostatin-1 suppresses autophagy and apoptosis in mice traumatic brain injury model." *Neurochemical research* 37.9 (2012): 1849-1858.
Welz et al. "FADD prevents RIP3-mediated epithelial cell necrosis and chronic intestinal inflammation." *Nature* 477.7364 (2011): 330-334.
Vandenabeele et al. "The role of the kinases RIP1 and RIP3 in TNF-induced necrosis." *Science signaling* 3.115 (2010): re4-re4.
Vanlangenakker et al. "TNF-induced necroptosis in L929 cells is tightly regulated by multiple TNFR1 complex I and II members." *Cell death & disease* 2.11 (2011): e230-e230.
Vitner et al. "RIPK3 as a potential therapeutic target for Gaucher's disease." *Nature medicine* 20.2 (2014): 204-208.
Yu et al. "Identification of RIP3, a RIP-like kinase that activates apoptosis and NFκB." *Current biology* 9.10 (1999): 539-S3.
Zhang et al. "The RING domain of TRAF2 plays an essential role in the inhibition of TNFα-induced cell death but not in the activation of NF-κB." *Journal of molecular biology* 396.3 (2010): 528-539.
Zhang et al. "TRAIL activates JNK and NF-κB through RIP1-dependent and-independent pathways." *Cellular signalling* 27.2 (2015): 306-314.
Zhao et al. "Mixed lineage kinase domain-like is a key receptor interacting protein 3 downstream component of TNF-induced necrosis." *Proceedings of the National Academy of Sciences* 109.14 (2012): 5322-5327.
Zhu et al. "Necrostatin-1 ameliorates symptoms in R6/2 transgenic mouse model of Huntington's disease." *Cell death & disease* 2.1 (2011): e115-e115.
Office Action (including translation) for BR112022016124-7, issued Feb. 25, 2025, pp. 1-6.
Office Action (including translation) for SA522440081, issue date unknown, pp. 1-10.
First Notice of Examination Action for CN 202180014761.0 (including machine translation), issued Mar. 4, 2023, 14 pages.
Notice of Reasons for Refusal for JP 2022-549239 (including machine translation), issued Aug. 22, 2023, 9 pages.
REQUEST Substantive Examination for RU 2022124121/04(052010) (including machine translation), issued Apr. 7, 2023, 24 pages.

* cited by examiner

DIHYDRONAPHTHYRIDINONE COMPOUND, AND PREPARATION METHOD THEREFOR AND MEDICAL USE THEREOF

CROSS REFERENCE TO RELATED APPLICATIONS

This application is a national stage application under 35 U.S.C. § 371 of International Application No. PCT/CN2021/076160, filed internationally on Feb. 9, 2021, which claims priority to Chinese patent application Nos. 202010090252.3 filed Feb. 13, 2020, and 202110070075.7 filed Jan. 19, 2021. The contents of the above patent applications are incorporated by reference herein in their entireties for all purposes.

TECHNICAL FIELD

The present disclosure relates to the technical field of medicament, and in particular relates to a dihydronaphthyridinone compound, use thereof as a RIPK1 inhibitor and a pharmaceutical composition prepared thereby.

BACKGROUND

Receptor-interacting protein 1 (RIP1) kinase is a Tyrosine Kinase-Like (TKL) family serine/threonine protein kinase involved in innate immune signaling. RIP1 kinase is a protein-containing RHIM domain, with an N-terminal kinase domain and a C-terminal death domain ((2005) Trends Biochem. Sci. 30, 151-159). The death domain of RIP1 mediates an interaction with other proteins containing a death domain, and the proteins include Fas and TNFR-1 ((1995) Cell 81 513-523), TRAIL-R1 and TRAIL-R2 ((1997) Immunity 7, 821-830) and TRADD ((1996) Immunity 4, 387-396), while RHIM domain is critical for binding other proteins containing a RHIM domain, such as TRIF ((2004) Nat Immunol. 5, 503-507), DAI ((2009) EMBO Rep. 10, 916-922) and RIP3 ((1999) J. Biol. Chem. 274, 16871-16875), (1999) Curr. Biol. 9, 539-542), and exerts many of its effects through these interactions.

The role for RIP1 in cell signaling has been assessed under various conditions (including TLR3 ((2004) Nat Immunol. 5, 503-507), TLR4 ((2005) J. Biol. Chem. 280, 36560-36566), TRAIL (CellSignal. 2015 February; 27(2): 306-14) and FAS ((2004) J. Biol. Chem. 279, 7925-7933)), but is best understood in the context of mediating signals downstream of the death receptor TNFR1 ((2003) Cell 114, 181-190). Engagement of the TNFR by TNF leads to an oligomerization, and a recruitment of multiple proteins, including linear K63-linked polyubiquitinated RIP1 ((2006) Mol. Cell 22, 245-257), TRAF2/5 ((2010) J. Mol. Biol. 396, 528-539), TRADD ((2008) Nat. Immunol. 9, 1037-1046) and cIAPs ((2008) Proc. Natl. Acad. Sci. USA. 105, 11778-11783), to the cytoplasmic tail of the receptor. The complex that is dependent on RIP1 as a scaffolding protein (i.e. kinase independent), termed complex I, provides a platform for pro-survival signaling through an activation of NFκB and MAP kinases pathways ((2010) Sci. Signal. 115, re4). In addition, binding of TNF to its receptor (by e.g. A20 and CYLD proteins or inhibition of cIAP inhibition) under conditions promoting a deubiquitination of RIP1 results in a receptor internalization and a formation of complex II or DISC (a death-inducing signaling complex) ((2011) Cell Death Dis. 2,e230). Formation of the DISC (contains RIP1, TRADD, FADD and caspase 8) results in an activation of caspase 8 and also an onset of programmed apoptotic cell death in a RIP1 kinase independent manner ((2012) FEBS J 278, 877-887). Apoptosis is largely a quiescent form of cell death, and is involved in routine processes such as development and cellular homeostasis.

Under conditions where DISC is formed and RIP3 is expressed, but apoptosis is inhibited (such as FADD/caspase 8 deletion, caspase inhibition or viral infection), a third RIP1 kinase-dependent may exist. RIP3 can now enter this complex, become phosphorylated by RIP1 and initiate a caspase-independent programmed necrotic cell apoptosis through an activation of MLKL and PGAM5 ((2012) Cell 148, 213-227); ((2012) Cell 148, 228-243); ((2012) Proc. Natl. Acad. Sci. USA. 109, 5322-5327). As opposed to apoptosis, programmed necrosis (not to be confused with passive necrosis which is not programmed) results in a release of danger-associated molecular patterns (DAMP) from cells. These DAMP are capable of providing a "danger signal" to surrounding cells and tissues, eliciting proinflammatory responses including an inflammasome activation, a cytokine production and a cellular recruiting response (2008 Nat. Rev. Immunol 8, 279-289).

Dysregulation of RIP1 kinase-mediated programmed cell death has been linked to various inflammations, as demonstrated by use of RIP3 knockout mice (where RIP1-mediated programmed necrosis is completely blocked) and by Necrostatin-1 (a tool inhibitor of RIP1 kinase activity with a poor oral bioavailability). RIP3 knockout mice have been shown to be protective in inflammatory bowel disease (including ulcerative colitis and Crohn's disease) ((2011) Nature 477, 330-334), psoriasis ((2011) Immunity 35, 572-582), retinal-detachment-induced photoreceptor necrosis ((2010) PNAS 107, 21695-21700), retinitis pigmentosa ((2012) Proc. Natl. Acad. Sci., 109:36, 14598-14603), cerulein-induced acute pancreatitis ((2009) Cell 137, 1100-1111) and sepsis/systemic inflammatory response syndrome (SIRS) ((2011) Immunity 35, 908-918). Necrostatin-1 has been shown to be effective in alleviating ischemic brain injury ((2005) Nat. Chem. Biol. 1, 112-119), retinal ischemia/reperfusion injury ((2010) J. Neurosci. Res. 88, 1569-1576), Huntington's disease ((2011) Cell Death Dis. 2e115), renal ischemia-reperfusion injury ((2012) Kidney Int. 81, 751-761), Cisplatin induced kidney injury ((2012) Ren. Fail. 34, 373-377) and traumatic brain injury ((2012) Neurochem. Res. 37, 1849-1858). Other diseases or conditions regulated at least in part by RIP1-dependent apoptosis, necrosis or cytokine production include hematological and solid organ malignancies ((2013) Genes Dev. 27:1640-1649), bacterial infections and viral infections ((2014) Cell Host & Microbe 15, 23-35) (including, but not limited to, tuberculosis and influenza ((2013) Cell 153, 1-14)) and lysosomal storage disease (particularly, Gaucher disease, Nature Medicine Advance Online Publication, 19 Jan. 2014, doi: 10.1038/nm. 3449).

A potent and selective small molecule inhibitor of RIP1 kinase activity is capable of blocking RIP1-dependent necrosis, thereby providing a therapeutic effect in diseases or events associated with DAMP, cell death, and/or inflammation.

SUMMARY

The present disclosure provides a dihydronaphthyridinone compound, which, as a RIPK1 inhibitor, has the advantages of high activity, good selectivity, and low toxicity and side effects.

In a first aspect, the present disclosure provides a dihydronaphthyridinone compound, or a pharmaceutically acceptable salt, stereoisomer, solvate or prodrug thereof, wherein the compound has a structure represented by formula (I):

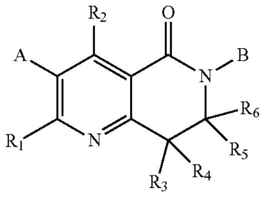

(I)

wherein, $R_1$ and $R_2$ are each independently hydrogen, halogen, substituted or unsubstituted $C_{1-6}$ alkyl, substituted or unsubstituted $C_{1-6}$ alkoxy or substituted or unsubstituted $NR_{a0}R_{b0}$, wherein $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl; the "substituted" in $R_1$ and $R_2$ means that 1, 2, 3 or 4 hydrogen atoms in the group are substituted with substituent(s) each independently selected from group S;

the definition for $R_3$, $R_4$, $R_5$ and $R_6$ are selected from one of the following groups:

(i) $R_3$, $R_4$, $R_5$ and $R_6$ are each independently hydrogen, halogen, substituted or unsubstituted $C_{1-6}$alkyl, or substituted or unsubstituted $C_{3-8}$ cycloalkyl; the "substituted" means that 1, 2, 3 or 4 hydrogen atoms in the group are substituted with substituent(s) each independently selected from group S;

(ii) $R_3$ and $R_4$ form together with the carbon atom adjacent thereto a substituted or unsubstituted $C_{3-8}$ cycloalkyl ring or a substituted or unsubstituted 3- to 6-membered heterocycloalkyl ring; $R_5$ and $R_6$ are each independently hydrogen, halogen, substituted or unsubstituted $C_{1-6}$ alkyl, or substituted or unsubstituted $C_{3-8}$ cycloalkyl; the "substituted" means that 1, 2, 3 or 4 hydrogen atoms in the group are substituted with substituent(s) each independently selected from group S;

(iii) $R_3$ and $R_4$ are each independently hydrogen, halogen, substituted or unsubstituted $C_{1-6}$ alkyl, or substituted or unsubstituted $C_{3-8}$ cycloalkyl; $R_5$ and $R_6$ form together with the carbon atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

(iv) $R_4$ and $R_5$ form together with the carbon atom adjacent thereto a substituted or unsubstituted $C_{3-8}$ cycloalkyl ring or a substituted or unsubstituted 3- to 6-membered heterocycloalkyl ring; $R_3$ and $R_6$ are each independently hydrogen, halogen, substituted or unsubstituted $C_{1-6}$ alkyl, or substituted or unsubstituted $C_{3-8}$ cycloalkyl; the "substituted" means that 1, 2, 3 or 4 hydrogen atoms in the group are substituted with substituent(s) each independently selected from group S;

B is-L-$R_0$, wherein, $R_0$ is substituted or unsubstituted $C_{6-14}$ aryl, substituted or unsubstituted 5- to 14-membered heteroaryl or substituted or unsubstituted 5- to 14-membered heterocycloalkyl; the "substituted" in $R_0$ means that 1, 2, 3 or 4 hydrogen atoms in the group are substituted with substituent(s) each independently selected from group S;

L is a bond, $-(CR_{11}R_{12})_{t1}-(CR_{21}R_{22})_{t2}-(CR_{31}R_{32})_{t3}-(CR_{41}R_{42})_{t4}-(O)_{t5}-$ or $-(CR_{13}R_{14})_{t1}-(CR_{23}R_{24})_{t2}-(NR_{33})_{t3}-(CR_{43}R_{44})_{t4}-(O)_{t5}-$, wherein t1, t2, t3, t4 and t5 are each independently 0 or 1;

the definition for $R_{11}$, $R_{12}$, $R_{21}$, $R_{22}$, $R_{31}$, $R_{32}$, $R_{41}$ and $R_{42}$ are selected from one of the following groups:

(a2)

$R_{11}$, $R_{12}$, $R_{41}$ and $R_{42}$ are each independently hydrogen, deuterium, halogen, hydroxyl, hydroxymethyl, hydroxyethyl or $C_{1-3}$ alkyl;

$R_{21}$, $R_{22}$, $R_{31}$ and $R_{32}$ are each independently hydrogen, deuterium, halogen, hydroxyl, hydroxymethyl, hydroxyethyl or $C_{1-3}$ alkyl;

(b2)

$R_{11}$, $R_{12}$, $R_{41}$ and $R_{42}$ are each independently hydrogen, deuterium, halogen, hydroxyl, hydroxymethyl, hydroxyethyl or $C_{1-3}$ alkyl;

$R_{21}$ and $R_{22}$ form together with the carbon atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

$R_{31}$ and $R_{32}$ are each independently hydrogen, deuterium, halogen, hydroxyl, hydroxymethyl, hydroxyethyl or $C_{1-3}$ alkyl;

(c2)

$R_{11}$, $R_{12}$, $R_{41}$ and $R_{42}$ are each independently hydrogen, deuterium, halogen, hydroxyl, hydroxymethyl, hydroxyethyl or $C_{1-3}$ alkyl;

$R_{21}$ and $R_{22}$ are each independently hydrogen, deuterium, halogen, hydroxyl, hydroxymethyl, hydroxyethyl or $C_{1-3}$ alkyl;

$R_{31}$ and $R_{32}$ form together with the carbon atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

(d2)

$R_{11}$, $R_{12}$, $R_{41}$ and $R_{42}$ are each independently hydrogen, deuterium, halogen, hydroxyl, hydroxymethyl, hydroxyethyl or $C_{1-3}$ alkyl;

$R_{22}$ and $R_{32}$ are each independently hydrogen, deuterium, halogen, hydroxyl, hydroxymethyl, hydroxyethyl or $C_{1-3}$ alkyl;

$R_{21}$ and $R_{31}$ form together with the atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

(e2)

$R_{12}$, $R_{41}$ and $R_{42}$ are each independently hydrogen, deuterium, halogen, hydroxyl, hydroxymethyl, hydroxyethyl or $C_{1-3}$ alkyl;

$R_{21}$, $R_{22}$ and $R_{32}$ are each independently hydrogen, deuterium, halogen, hydroxyl, hydroxymethyl, hydroxyethyl or $C_{1-3}$ alkyl;

$R_{11}$ and $R_{31}$ form together with the atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

the definition for $R_{13}$, $R_{14}$, $R_{23}$, $R_{24}$, $R_{33}$, $R_{43}$ and $R_{44}$ are selected from one of the following groups:

(a3)

$R_{13}$, $R_{14}$, $R_{23}$, $R_{24}$, $R_{43}$ and $R_{44}$ are each independently hydrogen, deuterium, halogen, hydroxyl, hydroxymethyl, hydroxyethyl or $C_{1-3}$ alkyl;

$R_{33}$ is hydrogen, deuterium, hydroxymethyl, hydroxyethyl or $C_{1-3}$ alkyl;

(b3)

$R_{13}$, $R_{14}$, $R_{43}$ and $R_{44}$ are each independently hydrogen, deuterium, halogen, hydroxyl, hydroxymethyl, hydroxyethyl or $C_{1-3}$ alkyl;

$R_{23}$ and $R_{24}$ form together with the carbon atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

$R_{33}$ is hydrogen, deuterium, hydroxymethyl, hydroxyethyl or $C_{1-3}$ alkyl;

(c3)

$R_{13}$, $R_{14}$, $R_{23}$, $R_{43}$ and $R_{44}$ are each independently hydrogen, deuterium, halogen, hydroxyl, hydroxymethyl, hydroxyethyl or $C_{1-3}$ alkyl;

$R_{24}$ and $R_{33}$ form together with the atom adjacent thereto a substituted or unsubstituted 3- to 6-membered nitrogen-containing heterocycloalkyl ring; the "substituted" means that 1, 2, 3 or 4 hydrogen atoms in the group are substituted with substituent(s) each independently selected from group S;

(d3)

$R_{13}$, $R_{23}$, $R_{24}$, $R_{43}$ and $R_{44}$ are each independently hydrogen, deuterium, halogen, hydroxyl, hydroxymethyl, hydroxyethyl or $C_{1-3}$ alkyl;

$R_{14}$ and $R_{33}$ form together with the atom adjacent thereto a substituted or unsubstituted 3- to 6-membered nitrogen-containing heterocycloalkyl ring; the "substituted" means that 1, 2, 3 or 4 hydrogen atoms in the group are substituted with substituent(s) each independently selected from group S;

A is (i) substituted or unsubstituted 5- or 6-membered monocyclic heteroaryl, wherein the "substituted" means that 1, 2, 3 or 4 hydrogen atoms in the group are substituted with substituent(s) each independently selected from group S;

(ii) substituted or unsubstituted 8- to 10-membered bicyclic heteroaryl, wherein the 8- to 10-membered bicyclic heteroaryl is formed by fusing a 5- or 6-membered monocyclic heteroaryl ring with a 5- or 6-membered monocyclic heteroaryl ring, wherein the "substituted" means that 1, 2, 3 or 4 hydrogen atoms in the group are substituted with substituent(s) each independently selected from group S;

(iii) substituted or unsubstituted 9- or 10-membered bicyclic heteroaryl; the 9- or 10-membered bicyclic heteroaryl is formed by fusing a benzene ring with a 5- or 6-membered monocyclic heteroaryl ring; wherein the 5- or 6-membered monocyclic heteroaryl ring is selected from:

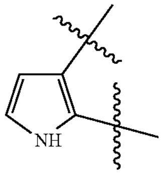 , 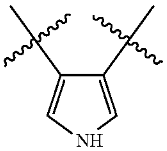 , 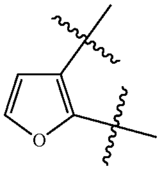 ,

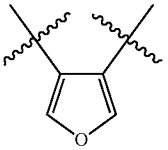 , 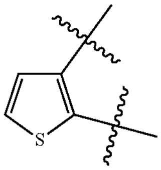 , 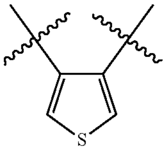 ,

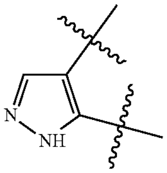 , 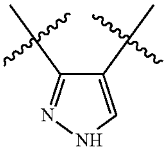 , 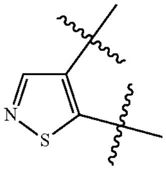 ,

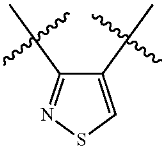 , 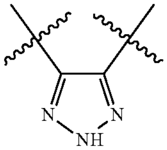 , 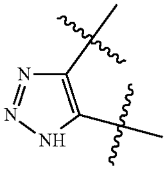 ,

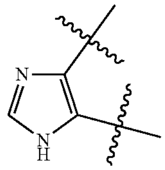 , 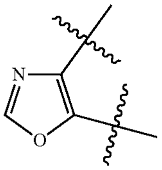 , 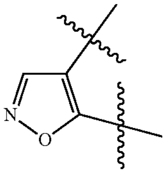 ,

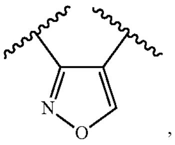 , 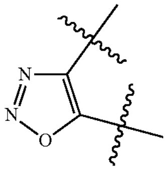 , 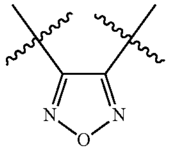 ,

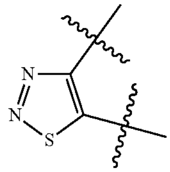 , 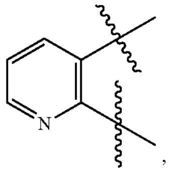 , 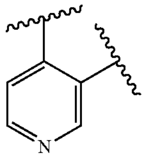 ,

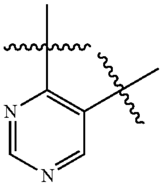 , 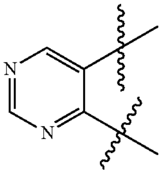 , 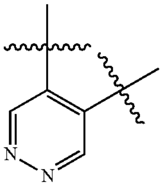 ,

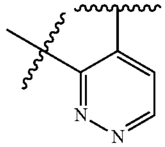 , and 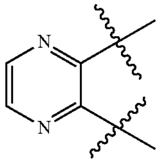 , wherein the attached two carbon atoms represented by "〰" are adjacent pairs of carbon atoms shared when fused with other rings;

the "substituted" means that 1, 2, 3 or 4 hydrogen atoms in the group are substituted with substituent(s) each independently selected from group S;

(iv) substituted or unsubstituted 8- to 10-membered bicyclic heteroaryl; the 8- to 10-membered bicyclic heteroaryl is formed by fusing a 5- or 6-membered monocyclic heteroaryl ring with a 5- or 6-membered monocyclic heterocycloalkyl ring, wherein the "substituted" means that 1, 2, 3 or 4 hydrogen atoms in the group are substituted with substituent(s) each independently selected from group S; or (v) substituted or unsubstituted benzothiazole, wherein the "substituted" means that 1, 2, 3 or 4 hydrogen atoms in the group are substituted with substituent(s) each independently selected from group S';

in the above groups, the substituents from group S are selected from deuterium, halogen, nitro, oxo, —$C_{1-6}$ alkyl, -halo $C_{1-6}$ alkyl, -deuterated $C_{1-6}$ alkyl, —S—$C_{1-6}$ alkyl, —S-halo $C_{1-6}$ alkyl, —$(CR_{a1}R_{b1})_u$-cyano, —$(CR_{a1}R_{b1})_u$-hydroxyl, —$(CR_{a1}R_{b1})_u$—$C_{1-6}$ alkoxy, —$(CR_{a1}R_{b1})_u$-halo $C_{1-6}$ alkoxy, —$(CR_{a1}R_{b1})_u$-halo $C_{1-6}$ alkyl, —$(CR_{a1}R_{b1})_u$-deuterated $C_{1-6}$ alkoxy, —$(CR_{a1}R_{b1})_u$-deuterated $C_{1-6}$ alkyl, —$(CR_{a1}R_{b1})_u$-3- to 6-membered heterocycloalkyl, —$(CR_{a1}R_{b1})_u$—$C_{3-8}$ cycloalkyl, —$(CR_{a1}R_{b1})_u$-phenyl, —$(CR_{a1}R_{b1})_u$-5- or 6-membered monocyclic heteroaryl, —$(CR_{a1}R_{b1})_u$—O—$(CR_{a2}R_{b2})_v$-halo $C_{1-6}$ alkyl, —$(CR_{a1}R_{b1})_u$—O—$(CR_{a2}R_{b2})_v$—$C_{3-8}$ cycloalkyl, —$(CR_{a1}R_{b1})_u$—O—$(CR_{a2}R_{b2})_v$-3- to 6-membered heterocycloalkyl, —$(CR_{a1}R_{b1})_u$—O—$(CR_{a2}R_{b2})_v$-phenyl, —$(CR_{a1}R_{b1})_u$—O—$(CR_{a2}R_{b2})_v$-5- or 6-membered monocyclic heteroaryl, —$(CR_{a1}R_{b1})_u$—S—$(CR_{a2}R_{b2})_v$-phenyl, —$(CR_{a1}R_{b1})_u$—$SO_2$—$(CR_{a2}R_{b2})_v$-phenyl, —$(CR_{a1}R_{b1})_u$—O—C(O)$NR_{a0}R_{b0}$, —$(CR_{a1}R_{b1})_u$—O—$(CR_{a2}R_{b2})_v$—$C_{1-6}$ alkoxy, —$(CR_{a1}R_{b1})_u$—O—$(CR_{a2}R_{b2})_v$-hydroxyl, —$(CR_{a1}R_{b1})_u$—$SO_2C_{1-6}$ alkyl, —$(CR_{a1}R_{b1})_u$—$SO_2NR_{a0}R_{b0}$, —$(CR_{a1}R_{b1})_u$—C(O)$NR_{a0}R_{b0}$, —$(CR_{a1}R_{b1})_u$—C(O)phenyl, —$(CR_{a1}R_{b1})_u$—C(O)$C_{1-6}$ alkyl, —C(O)O$C_{1-6}$ alkyl, —C(O)—$(CR_{a2}R_{b2})_v$-hydroxyl, —$(CR_{a1}R_{b1})_u$—$NR_{a0}R_{b0}$, —$NR_{a0}$C(O)—$C_{1-6}$ alkyl, —$NR_{a0}$C(O)-deuterated $C_{1-6}$ alkyl, —$NR_{a0}$C(O)—$(CR_{a1}R_{b1})_u$-hydroxyl, —$NR_{a0}$C(O)—$(CR_{a1}R_{b1})_u$—O—$(CR_{a2}R_{b2})_v$—C(O)$C_{1-6}$ alkyl, —$NR_{a0}$C(O)—$(CR_{a1}R_{b1})_u$—O—$(CR_{a2}R_{b2})_v$-phenyl, —$NR_{a0}$C(O)—$C_{3-8}$ cycloalkyl, —$NR_{a0}$C(O)—$(CR_{a1}R_{b1})_u$—$NR_{a0}R_{b0}$, and —$NR_{a0}$C(O)-halo $C_{1-6}$ alkyl, wherein the $C_{3-8}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$ alkyl; $R_{a1}$, $R_{b1}$, $R_{a2}$ and $R_{b2}$ are the same or different, and are each independently hydrogen, hydroxyl, $C_{1-3}$ alkyl or halo $C_{1-3}$ alkyl;

in the above groups, the substituents from group S' are selected from deuterium, halogen, nitro, oxo, —$C_{1-6}$ alkyl, -halo $C_{1-6}$ alkyl, -deuterated $C_{1-6}$ alkyl, —S—$C_{1-6}$ alkyl, —S-halo $C_{1-6}$ alkyl, —$(CR_{a1}'R_{b1}')_{u'}$-cyano, —$(CR_{a1}'R_{b1}')_{u'}$-hydroxyl, —$(CR_{a1}'R_{b1}')_{u'}$-$C_{1-6}$ alkoxy, —$(CR_{a1}'R_{b1}')_{u'}$-halo $C_{1-6}$ alkoxy, —$(CR_{a1}'R_{b1}')_{u'}$-halo $C_{1-6}$ alkyl, —$(CR_{a1}'R_{b1}')_{u'}$-3- to 6-membered heterocycloalkyl, —$(CR_{a1}'R_{b1}')_{u'}$-$C_{3-8}$ cycloalkyl, —$(CR_{a1}'R_{b1}')_{u'}$-phenyl, —$(CR_{a1}'R_{b1}')_{u'}$-5- or 6- membered monocyclic heteroaryl, —$(CR_{a1}'R_{b1}')_{u'}$—O—$(CR_{a2}'R_{b2}')_{v'}$-halo $C_{1-6}$alkyl, —$(CR_{a1}'R_{b1}')_{u'}$—O—$(CR_{a2}'R_{b2}')_{v'}$-$C_{3-8}$ cycloalkyl, —$(CR_{a1}'R_{b1}')_{u'}$—O—$(CR_{a2}'R_{b2}')_{v'}$-3- to 6-membered heterocycloalkyl, —$(CR_{a1}'R_{b1}')_{u'}$—O—$(CR_{a2}'R_{b2}')_{v'}$-phenyl, —$(CR_{a1}'R_{b1}')_{u'}$—O—$(CR_{a2}'R_{b2}')_{v'}$-5- or 6-membered monocyclic heteroaryl, —$(CR_{a1}'R_{b1}')_{u}$—S—$(CR_{a2}'R_{b2}')_{v'}$-phenyl, —$(CR_{a1}'R_{b1}')_{u'}$—$SO_2$—$(CR_{a2}'R_{b2}')_{v'}$-phenyl, —$(CR_{a1}'R_{b1}')_{u'}$—O—C(O)$NR_{a0}$'$R_{b0}$', —$(CR_{a1}'R_{b1}')_{u'}$—O—$(CR_{a2}'R_{b2}')_{v'}$-$C_{1-6}$ alkoxy, —$(CR_{a1}'R_{b1}')_{u'}$—O—$(CR_{a2}'R_{b2}')_{v'}$-hydroxyl, —$(CR_{a1}'R_{b1}')_{u'}$—$SO_2C_{1-6}$ alkyl, —$(CR_{a1}'R_{b1}')_{u'}$—$SO_2NR_{a0}'R_{b0}'$, —$(CR_{a1}'R_{b1}')_{u'}$-C(O)$NR_{a0}'R_{b0}'$, —$(CR_{a1}'R_{b1}')_{u'}$—C(O)phenyl, —$(CR_{a1}'R_{b1}')_{u'}$—C(O)$C_{1-6}$ alkyl, —C(O)O$C_{1-6}$ alkyl, and —C(O)—$(CR_{a2}'R_{b2}')_{v'}$-hydroxyl, wherein the $C_{3-8}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u' and v' are each independently 0, 1, 2, 3 or 4; $R_{a0}'$ and $R_{b0}'$ are each independently hydrogen or $C_{1-3}$ alkyl; or $R_{a0}'$ and $R_{b0}'$ form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$ alkyl; $R_{a1}'$, $R_{b1}'$, $R_{a2}'$ and $R_{b2}'$ are the same or different, and are each independently hydrogen, hydroxyl, $C_{1-3}$ alkyl or halo $C_{1-3}$ alkyl.

In an embodiment of the present disclosure, when A is substituted or unsubstituted 5- or 6-membered monocyclic heteroaryl, the 5- or 6-membered monocyclic heteroaryl is selected from thiophene, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine and pyrazine.

In an embodiment of the present disclosure, with regard to A, in the 8- to 10-membered bicyclic heteroaryl formed by fusing a 5- or 6-membered monocyclic heteroaryl ring with a 5- or 6-membered monocyclic heteroaryl ring, the 5- or 6-membered monocyclic heteroaryl ring is selected from:

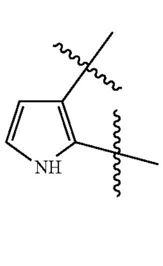, 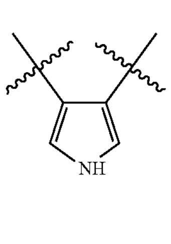, 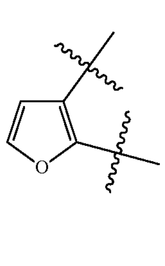,

-continued

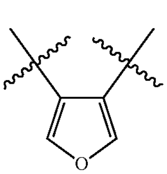 , 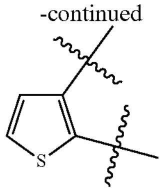 , 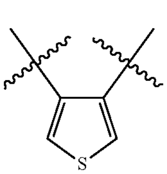 ,

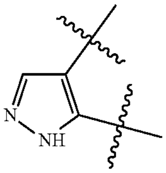 , 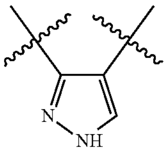 , 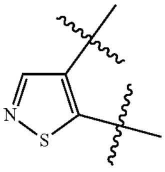 ,

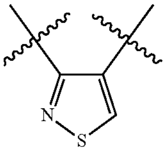 , 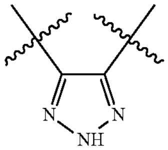 , 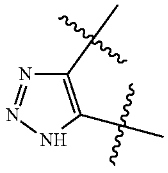 ,

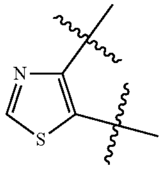 , 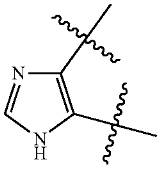 , 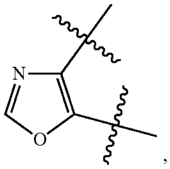 ,

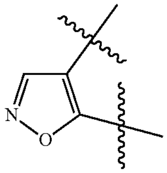 , 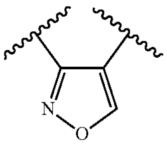 , 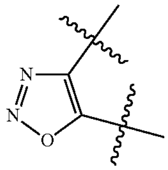 ,

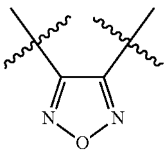 , 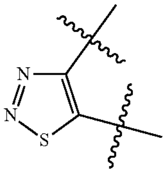 , 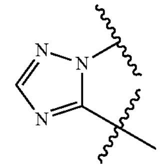 ,

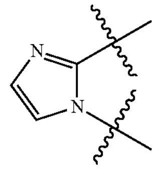 , 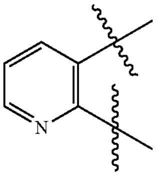 , 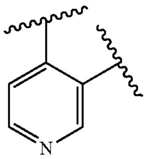 ,

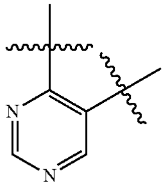 , 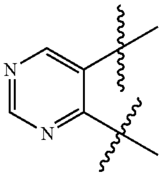 , 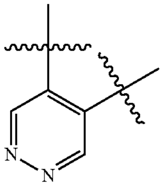 ,

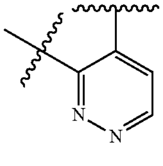 , and 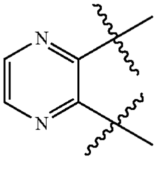 , wherein the attached two carbon atoms represented by “ ~ ” are adjacent pairs of carbon atoms shared when fused with other rings.

In an embodiment of the present disclosure, with regard to A, the 8- to 10-membered bicyclic heteroaryl formed by fusing a 5- or 6-membered monocyclic heteroaryl ring with a 5- or 6-membered monocyclic heteroaryl ring has a structure represented by formula (A1), formula (A2) or formula (A3):

A1

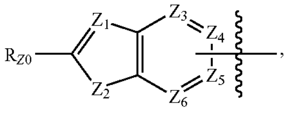

A2

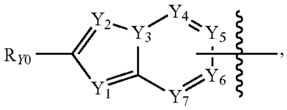

A3

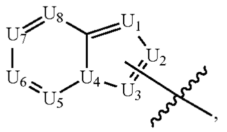

wherein $Z_1$ is N or $CR_{Z1}$; $Z_2$ is $NR_{Z2}$ or O; $Z_3$ is N or $CR_{Z3}$; $Z_4$ is N or $CR_{Z4}$; $Z_5$ is N or $CR_{Z5}$; $Z_6$ is N or $CR_{Z6}$; $Z_3$, $Z_4$, $Z_5$ and $Z_6$ are not N at the same time; and at least one of $Z_3$, $Z_4$, $Z_5$ and $Z_6$ is N;

$Y_1$ is N or $CR_{Y1}$; $Y_2$ is N or $CR_{Y2}$; $Y_3$ is N or $CR_{Y3}$; $Y_4$ is N or $CR_{Y4}$; $Y_5$ is N or $CR_{Y5}$; $Y_6$ is N or $CR_{Y6}$; $Y_7$ is N or $CR_{Y7}$; $Y_3$, $Y_4$, $Y_5$, $Y_6$ and $Y_7$ are not N at the same time; and at least one of $Y_1$, $Y_2$, $Y_3$, $Y_4$, $Y_5$, $Y_6$ and $Y_7$ is N;

$U_1$ is N or $CR_{U1}$; $U_2$ is N or $CR_{U2}$; $U_3$ is N or $CR_{U3}$; $U_4$ is N or $CR_{U4}$; $U_5$ is N or $CR_{U5}$; $U_6$ is N or $CR_{U6}$; $U_7$ is N or $CR_{U7}$; $U_8$ is N or $CR_{U8}$; $U_4$, $U_5$, $U_6$, $U_7$ and $U_8$ are not N at the same time; and at least one of $U_1$, $U_2$, $U_3$, $U_4$, $U_5$, $U_6$, $U_7$ and $U_8$ is N;

$R_{Z0}$, $R_{Y0}$, $R_{Z1}$, $R_{Z2}$, $R_{Z3}$, $R_{Z4}$, $R_{Z5}$, $R_{Z6}$, $R_{Y1}$, $R_{Y2}$, $R_{Y3}$, $R_{Y4}$, $R_{Y5}$, $R_{Y6}$, $R_{Y7}$, $R_{U1}$, $R_{U2}$, $R_{U3}$, $R_{U4}$, $R_{U5}$, $R_{U6}$, $R_{U7}$ and $R_{U8}$ are each independently hydrogen or the substituents from group S.

In an embodiment of the present disclosure the 9- or 10-membered bicyclic heteroaryl said in A formed by fusing a benzene ring with a 5- or 6-membered monocyclic heteroaryl ring has a structure represented by formula (A4):

A4

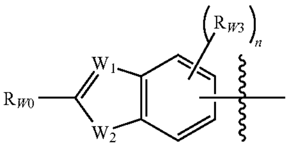

wherein $W_1$ is N or $CR_{W1}$; $W_2$ is $NR_{W2}$ or O; n is 1, 2 or 3; $R_{W0}$, $R_{W1}$, $R_{W2}$ and $R_{W3}$ are each independently hydrogen or the substituents from group S.

In an embodiment of the present disclosure the 8- to 10-membered bicyclic heteroaryl said in A formed by fusing a 5- or 6-membered monocyclic heteroaryl ring with a 5- or 6-membered monocyclic heterocycloalkyl ring has a structure represented by formula (A5):

A5

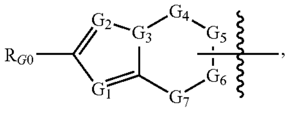

wherein $G_1$ is N or $CR_{G1}$; $G_2$ is N or $CR_{G2}$; $G_3$ is N or $CR_{G3}$; $G_4$ is $NR_{G4a}$, O or $CR_{G4b}R_{G4c}$; $G_5$ is $NR_{G5a}$, O or $CR_{G5b}R_{G5c}$; $G_6$ is $NR_{G6a}$, O or $CR_{G6b}R_{G6c}$; $G_7$ is $NR_{G7a}$, O or $CR_{G7b}R_{G7c}$; at least one of $G_3$, $G_4$, $G_5$, $G_6$ and $G_7$ is N; and the ring part of -$G_3$-$G_4$-$G_5$-$G_6$-$G_7$- does not comprise —O—O—, —O—N— or —N—N—; $R_{G0}$, $R_{G1}$, $R_{G2}$, $R_{G3}$, $R_{G4a}$, $R_{G4b}$, $R_{G4c}$, $R_{G5a}$, $R_{G5b}$, $R_{G5c}$, $R_{G6a}$, $R_{G6b}$, $R_{G6c}$, $R_{G7a}$, $R_{G7b}$ and $R_{G7c}$, are each independently hydrogen or the substituents from group S.

In an embodiment of the present disclosure, with regard to A, the benzothiazole has a structure represented by formula (A6):

A6

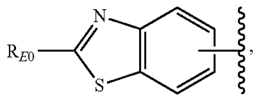

wherein $R_{E0}$ is hydrogen or the substituents from group S'.

In an embodiment of the present disclosure, $Z_1$ is N; $Z_2$ is $NR_{Z2}$ or O.

In an embodiment of the present disclosure, $Y_1$ is N; $Y_2$ is N or $CR_{Y2}$; $Y_3$ is N; $Y_4$ is N or $CR_{Y4}$; $Y_5$ is $CR_{Y5}$; $Y_6$ is $CR_{Y6}$; $Y_7$ is $CR_{Y7}$.

In an embodiment of the present disclosure, $Y_1$ is N; $Y_2$ is N or CH; $Y_3$ is N; $Y_4$ is N or CH; $Y_5$ is CH; $Y_6$ is CH; $Y_7$ is CH.

In an embodiment of the present disclosure, $U_1$ is $CR_{U1}$; $U_2$ is $CR_{U2}$; $U_3$ is $CR_{U3}$; $U_4$ is N; $U_5$ is N; $U_6$ is $CR_{U6}$; $U_7$ is N; $U_8$ is $CR_{U8}$.

In an embodiment of the present disclosure, $U_1$ is $CR_{U1}$; $U_2$ is CH; $U_3$ is CH; $U_4$ is N; $U_5$ is N; $U_6$ is CH; $U_7$ is N; $U_8$ is $CR_{U8}$.

In an embodiment of the present disclosure, $G_1$ is N; $G_2$ is N; $G_3$ is N; $G_4$ is $CR_{G4b}R_{G4c}$; $G_5$ is $CR_{G5b}R_{G5c}$; $G_6$ is $NR_{G6a}$; $G_7$ is $CR_{G7b}R_{G7c}$.

In an embodiment of the present disclosure, $G_1$ is N; $G_2$ is N; $G_3$ is N; $G_4$ is $CH_2$; $G_5$ is $CH_2$; $G_6$ is $NR_{G6a}$; $G_7$ is $CH_2$.

In an embodiment of the present disclosure, $R_{Z1}$, $R_{Z3}$, $R_{Z4}$, $R_{Z5}$ and $R_{Z6}$ are each independently hydrogen, deuterium, halogen, $C_{1-6}$ alkyl, $C_{1-6}$ alkoxy, halo $C_{1-6}$ alkyl or $NR_{a0}R_{b0}$; $R_{Z2}$ is hydrogen, deuterium or $C_{1-6}$ alkyl.

In an embodiment of the present disclosure, $R_{Y1}$, $R_{Y2}$, $R_{Y3}$, $R_{Y4}$, $R_{Y5}$, $R_{Y6}$ and $R_{Y7}$ are each independently hydrogen, deuterium, halogen, $C_{1-6}$ alkyl, $C_{1-6}$ alkoxy, halo $C_{1-6}$ alkyl or $NR_{a0}R_{b0}$.

In an embodiment of the present disclosure, the substituents from group S are each independently selected from halogen, nitro, oxo, —$C_{1-6}$ alkyl, -halo $C_{1-6}$ alkyl, -deuterated $C_{1-6}$ alkyl, —S—$C_{1-6}$ alkyl, —S-halo $C_{1-6}$ alkyl, —$(CH_2)_u$-cyano, —$(CH_2)_u$-hydroxyl, —$(CH_2)_u$—$C_{1-6}$ alkoxy, —$(CH_2)_u$-halo $C_{1-6}$ alkoxy, —$(CH_2)_u$-halo $C_{1-6}$ alkyl, —$(CH_2)_u$-3- to 6-membered heterocycloalkyl, —$(CH_2)_u$—$C_{3-8}$cycloalkyl, —$(CH_2)_u$-phenyl, —$(CH_2)_u$-5- or 6-membered monocyclic heteroaryl, —$(CH_2)_u$—O—$(CH_2)_v$-halo $C_{1-6}$ alkyl, —$(CH_2)_u$—O—$(CH_2)_v$—$C_{3-8}$ cycloalkyl, —$(CH_2)_u$—O—$(CH_2)_v$-3- to 6-membered heterocycloalkyl, —$(CH_2)_u$—O—$(CH_2)_v$-phenyl, —$(CH_2)_u$—O—$(CH_2)_v$-5- or 6-membered monocyclic heteroaryl, —$(CH_2)_u$—S—$(CH_2)_v$-phenyl, —$(CH_2)_u$—$SO_2$—$(CH_2)_v$-phenyl, —$(CH_2)_u$—O—C(O)$NR_{a0}R_{b0}$, —$(CH_2)_u$—O—$(CH_2)_v$—$C_{1-6}$ alkoxy, —$(CH_2)_u$—O—$(CH_2)_v$-hydroxyl, —$(CH_2)_u$—$SO_2C_{1-6}$ alkyl, —$(CH_2)_u$—$SO_2NR_{a0}R_{b0}$, —$(CH_2)_u$—C(O)$NR_{a0}R_{b0}$, —$(CH_2)_u$—C(O)$C_{1-6}$ alkyl, —C(O)O$C_{1-6}$alkyl, —C(O)—$(CH_2)_v$-hydroxyl, —$(CH_2)_u$—$NR_{a0}R_{b0}$, —$NR_{a0}$C(O)—$C_{1-6}$ alkyl, —$NR_{a0}$C(O)-deuterated $C_{1-6}$alkyl, —$NR_{a0}$C(O)—$(CH_2)_u$-hydroxyl, —$NR_{a0}$C(O)—$C_{3-8}$cycloalkyl, —$NR_{a0}$C(O)—$(CH_2)_u$—$NR_{a0}R_{b0}$, —$NR_{a0}$C(O)—$(CH_2)_u$ hydroxyl, and —$NR_{a0}$C(O)-halo $C_{1-6}$ alkyl, wherein the $C_{3-8}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$alkyl; $R_{a1}$, $R_{b1}$, $R_{a2}$ and $R_{b2}$ are the same or different, and are each independently hydrogen, hydroxyl, $C_{1-3}$ alkyl or halo $C_{1-3}$ alkyl.

In an embodiment of the present disclosure, the substituents from group S are each independently selected from deuterium, halogen, nitro, oxo, —$C_{1-3}$ alkyl, -halo $C_{1-3}$ alkyl, -deuterated $C_{1-3}$ alkyl, —S—$C_{1-3}$ alkyl, —S-halo $C_{1-3}$ alkyl, —$(CR_{a1}R_{b1})_u$-cyano, —$(CR_{a1}R_{b1})_u$-hydroxyl, —$(CR_{a1}R_{b1})_u$—$C_{1-3}$ alkoxy, —$(CR_{a1}R_{b1})_u$-halo $C_{1-3}$ alkoxy, —$(CR_{a1}R_{b1})_u$-halo $C_{1-3}$ alkyl, —$(CR_{a1}R_{b1})_u$-deuterated $C_{1-3}$ alkoxy, —$(CR_{a1}R_{b1})_u$-deuterated $C_{1-3}$ alkyl, —$(CR_{a1}R_{b1})_u$-3- to 6-membered heterocycloalkyl, —$(CR_{a1}R_{b1})_u$—$C_{3-6}$ cycloalkyl, —$(CR_{a1}R_{b1})_u$-phenyl, —$(CR_{a1}R_{b1})_u$-5- or 6-membered monocyclic heteroaryl, —$(CR_{a1}R_{b1})_u$—O—$(CR_{a2}R_{b2})_v$-halo $C_{1-3}$ alkyl, —$(CR_{a1}R_{b1})_u$—O—$(CR_{a2}R_{b2})_v$—$C_{3-6}$ cycloalkyl, —$(CR_{a1}R_{b1})_u$—O—$(CR_{a2}R_{b2})_v$-3- to 6-membered heterocycloalkyl, —$(CR_{a1}R_{b1})_u$—O—$(CR_{a2}R_{b2})_v$-phenyl, —$(CR_{a1}R_{b1})_u$—O—$(CR_{a2}R_{b2})_v$-5- or 6-membered monocyclic heteroaryl, —$(CR_{a1}R_{b1})_u$—S—$(CR_{a2}R_{b2})_v$-phenyl, —$(CR_{a1}R_{b1})_u$—$SO_2$—$(CR_{a2}R_{b2})_v$-phenyl, —$(CR_{a1}R_{b1})_u$—O—C(O)$NR_{a0}R_{b0}$, —$(CR_{a1}R_{b1})_u$—S—$(CR_{a2}R_{b2})_v$—$C_{1-3}$ alkoxy, —$(CR_{a1}R_{b1})_u$—O—$(CR_{a2}R_{b2})_v$-hydroxyl, —$(CR_{a1}R_{b1})_u$—$SO_2C_{1-3}$ alkyl, —$(CR_{a1}R_{b1})_u$—$SO_2NR_{a0}R_{b0}$, —$(CR_{a1}R_{b1})_u$—C(O)$NR_{a0}R_{b0}$, —$(CR_{a1}R_{b1})_u$ —C(O)phenyl, —$(CR_{a1}R_{b1})_u$—C(O)$C_{1-3}$ alkyl, —C(O)O$C_{1-3}$ alkyl, —C(O)—$(CR_{a2}R_{b2})_v$-hydroxyl, —$(CR_{a1}R_{b1})_u$—$NR_{a0}R_{b0}$, —$NR_{a0}$C(O)—$C_{1-3}$ alkyl, —$NR_{a0}$C(O)-deuterated $C_{1-3}$ alkyl, —$NR_{a0}$C(O)—$(CR_{a1}R_{b1})_u$-hydroxyl, —$NR_{a0}$C(O)—$(CR_{a1}R_{b1})_u$—O—$(CR_{a2}R_{b2})_v$—C(O)$C_{1-6}$ alkyl, —$NR_{a0}$C(O)—$(CR_{a1}R_{b1})_u$—O—$(CR_{a2}R_{b2})_v$- phenyl, —$NR_{a0}$C(O)—$C_{3-6}$ cycloalkyl, —$NR_{a0}$C(O)—$(CR_{a1}R_{b1})_u$—$NR_{a0}R_{b0}$, and —$NR_{a0}$C(O)-halo $C_{1-3}$ alkyl, wherein the $C_{3-6}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 6-membered nitrogen-containing heterocycloalkyl, wherein the 3- to 6-membered nitrogen-containing heterocycloalkyl is optionally substituted with 1, 2 or 3 halogens or $C_{1-3}$ alkyl; $R_{a1}$, $R_{b1}$, $R_{a2}$ and $R_{b2}$ are the same or different, and are each independently hydrogen, hydroxyl, $C_{1-3}$ alkyl or halo $C_{1-3}$ alkyl.

In an embodiment of the present disclosure, the substituents from group S are each independently selected from deuterium, halogen, nitro, oxo, —$C_{1-3}$ alkyl, -halo $C_{1-3}$ alkyl, -deuterated $C_{1-3}$ alkyl, —S—$C_{1-3}$ alkyl, —S-halo $C_{1-3}$ alkyl, —$(CH_2)_u$-cyano, —$(CH_2)_u$-hydroxyl, —$(CH_2)_u$—$C_{1-3}$ alkoxy, —$(CH_2)_u$-halo $C_{1-3}$ alkoxy, —$(CH_2)_u$-halo $C_{1-3}$ alkyl, —$(CH_2)_u$-deuterated $C_{1-3}$ alkoxy, —$(CH_2)_u$-deuterated $C_{1-3}$ alkyl, —$(CH_2)_u$-3- to 6-membered heterocycloalkyl, —$(CH_2)_u$—$C_{3-6}$ cycloalkyl, —$(CH_2)_u$-phenyl, —$(CH_2)_u$-5- or 6-membered monocyclic heteroaryl, —$(CH_2)_u$—O—$(CH_2)_v$-halo $C_{1-3}$ alkyl, —$(CH_2)_u$—O—$(CH_2)_v$—$C_{3-6}$ cycloalkyl, —$(CH_2)_u$—O—$(CH_2)_v$-3- to 6-membered heterocycloalkyl, —$(CH_2)_u$—O—$(CH_2)_v$-phenyl, —$(CH_2)_u$—O—$(CH_2)_v$-5- or 6-membered monocyclic heteroaryl, —$(CH_2)_u$—S—$(CH_2)_v$-phenyl, —$(CH_2)_u$—$SO_2$—$(CH_2)_v$-phenyl, —$(CH_2)_u$—O—C(O)$NR_{a0}R_{b0}$, —$(CH_2)_u$—$(CH_2)_v$—$C_{1-3}$ alkoxy, —$(CH_2)_u$—O—$(CH_2)_v$-hydroxyl, —$(CH_2)_u$—$SO_2C_{1-3}$ alkyl, —$(CH_2)_u$—$SO_2NR_{a0}R_{b0}$, —$(CH_2)_u$—C(O)$NR_{a0}R_{b0}$, —$(CH_2)_u$—C(O) phenyl, —$(CH_2)_u$—C(O)$C_{1-3}$alkyl, —C(O)O$C_{1-3}$ alkyl, —C(O)—$(CH_2)_v$-hydroxyl, —$(CH_2)_u$—$NR_{a0}R_{b0}$, —$NR_{a0}$C(O)—$C_{1-3}$ alkyl, —$NR_{a0}$C(O)-deuterated $C_{1-3}$ alkyl, —$NR_{a0}$C(O)—$(CH_2)_u$-hydroxyl, —$NR_{a0}$C(O)—$(CH_2)_u$—O—$(CH_2)_v$—C(O)$C_{1-6}$ alkyl, —$NR_{a0}$C(O)—$(CH_2)_u$—O—$(CH_2)_v$-phenyl, —$NR_{a0}$C(O)—$C_{3-6}$ cycloalkyl, —$NR_{a0}$C(O)—$(CH_2)_u$—$NR_{a0}R_{b0}$, and —$NR_{a0}$C(O)-halo $C_{1-3}$ alkyl, wherein the $C_{3-6}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$alkyl; or $R_{a0}$ and $R_{b0}$ form together with the nitrogen atom adjacent thereto a 3- to 6-membered nitrogen-containing heterocycloalkyl, wherein the 3- to 6-membered nitrogen-containing heterocycloalkyl is optionally substituted with 1, 2 or 3 halogens or $C_{1-3}$ alkyl; $R_{a1}$, $R_{b1}$, $R_{a2}$ and $R_{b2}$ are the same or different, and are each independently hydrogen, hydroxyl, $C_{1-3}$ alkyl or halo $C_{1-3}$ alkyl.

In an embodiment of the present disclosure, the substituents from group S' are selected from halogen, nitro, oxo, —$C_{1-6}$ alkyl, -halo $C_{1-6}$ alkyl, -deuterated $C_{1-6}$ alkyl, —S—$C_{1-6}$ alkyl, —S-halo $C_{1-6}$ alkyl, —$(CH_2)_u$'-cyano, —$(CH_2)_u$'-hydroxyl, —$(CH_2)_u$'-$C_{1-6}$ alkoxy, —$(CH_2)_u$'-halo $C_{1-6}$ alkoxy, —$(CH_2)_u$'-halo $C_{1-6}$ alkyl, —$(CH_2)_u$'-3- to 6-membered heterocycloalkyl, —$(CH_2)_u$'-$C_{3-8}$ cycloalkyl, —$(CH_2)_u$'-phenyl, —$(CH_2)_u$'-5- or 6-membered monocyclic heteroaryl, —$(CH_2)_u$'—O—$(CH_2)_v$'-halo $C_{1-6}$ alkyl, —$(CH_2)_u$'—O—$(CH_2)_v$'-$C_{3-8}$ cycloalkyl, —$(CH_2)_u$'—O—$(CH_2)_v$'-3- to 6-membered heterocycloalkyl, —$(CH_2)_u$'—O—$(CH_2)_v$'-phenyl, —$(CH_2)_u$'—O—$(CH_2)_v$'-5- or 6-membered monocyclic heteroaryl, —$(CH_2)_u$'—S—$(CH_2)_v$'-phenyl, —$(CH_2)_u$'—$SO_2$—$(CH_2)_v$'-phenyl, —$(CH_2)_u$'—O—C(O)$NR_{a0}$'$R_{b0}$', —$(CH_2)_u$'—O—$(CH_2)_v$'-$C_{1-6}$ alkoxy, —$(CH_2)_u$'—O—$(CH_2)_v$'-hydroxyl, —$(CH_2)_u$'—$SO_2C_{1-6}$ alkyl, —$(CH_2)_u$'—$SO_2NR_{a0}$'$R_{b0}$', —$(CH_2)_u$'—C(O)$NR_{a0}$'$R_{b0}$', —$(CH_2)_u$'—C(O)$C_{1-6}$ alkyl, —C(O)O$C_{1-6}$ alkyl, and —C(O)—$(CR_{a2}$'$R_{b2}$'$)_v$'-hydroxyl, wherein the $C_{3-8}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u' and v' are each independently 0, 1, 2, 3 or 4; $R_{a0}$' and $R_{b0}$' are each independently hydrogen or $C_{1-3}$ alkyl; or $R_{a0}$' and $R_{b0}$' form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$ alkyl; $R_{a1}$', $R_{b1}$', $R_{a2}$' and $R_{b2}$' are the same or different, and are each independently hydrogen, hydroxyl, $C_{1-3}$ alkyl or halo $C_{1-3}$ alkyl.

In an embodiment of the present disclosure, the substituents from group S' are selected from deuterium, halogen, nitro, oxo, —$C_{1-3}$ alkyl, -halo $C_{1-3}$ alkyl, -deuterated $C_{1-3}$ alkyl, —S—$C_{1-3}$ alkyl, —S-halo $C_{1-3}$ alkyl, —$(CR_{a1}$'$R_{b1}$'$)_u$'-cyano, —$(CR_{a1}$'$R_{b1}$'$)_u$'-hydroxyl, —$(CR_{a1}$'$R_{b1}$'$)_u$'-$C_{1-3}$ alkoxy, —$(CR_{a1}$'$R_{b1}$'$)_u$'-halo $C_{1-3}$ alkoxy, —$(CR_{a1}$'$R_{b1}$'$)_u$'-halo $C_{1-3}$ alkyl, —$(CR_{a1}$'$R_{b1}$'$)_u$'-3- to 6-membered heterocycloalkyl, —$(CR_{a1}$'$R_{b1}$'$)_u$'-$C_{3-6}$ cycloalkyl, —$(CR_{a1}$'$R_{b1}$'$)_u$'-phenyl, —$(CR_{a1}$'$R_{b1}$'$)_u$'-5- or 6-membered monocyclic heteroaryl, —$(CR_{a1}$'$R_{b1}$'$)_u$'—O—$(CR_{a2}$'$R_{b2}$'$)_v$'-halo $C_{1-3}$ alkyl, —$(CR_{a1}$'$R_{b1}$'$)_u$'-O—$(CR_{a2}$'$R_{b2}$'$)_v$'-$C_{3-6}$ cycloalkyl, —$(CR_{a1}$'$R_{b1}$'$)_u$'—O—$(CR_{a2}$'$R_{b2}$'$)_v$'-3- to 6-membered heterocycloalkyl, —$(CR_{a1}$'$R_{b1}$'$)_u$'—O—$(CR_{a2}$'$R_{b2}$'$)_v$-phenyl, —$(CR_{a1}$'$R_{b1}$'$)_u$'—O—$(CR_{a2}$'$R_{b2}$'$)_v$'-5- or 6-membered monocyclic heteroaryl, —$(CR_{a1}$'$R_{b1}$'$)_u$—S—$(CR_{a2}$'$R_{b2}$'$)_v$'-phenyl, —$(CR_{a1}$'$R_{b1}$'$)_u$'—$SO_2$—$(CR_{a2}$'$R_{b2}$'$)_v$'-phenyl, —$(CR_{a1}$'$R_{b1}$'$)_u$'—O—C(O)$NR_{a0}$'$R_{b0}$', —$(CR_{a1}$'$R_{b1}$'$)_u$'—O—$(CR_{a2}$'$R_{b2}$'$)_v$'-$C_{1-3}$ alkoxy, —$(CR_{a1}$'$R_{b1}$'$)_u$'—O—$(CR_{a2}$'$R_{b2}$'$)_v$'-hydroxyl, —$(CR_{a1}$'$R_{b1}$'$)_u$'—$SO_2C_{1-3}$ alkyl, —$(CR_{a1}$'$R_{b1}$'$)_u$'-$SO_2NR_{a0}$'$R_{b0}$', —$(CR_{a1}$'$R_{b1}$'$)_u$'—C(O)$NR_{a0}$'$R_{b0}$', —$(CR_{a1}$'$R_{b1}$'$)_u$'—C(O) phenyl, —$(CR_{a1}$'$R_{b1}$'$)_u$'—C(O)$C_{1-3}$ alkyl, —C(O)O$C_{1-3}$alkyl, and —C(O)—$(CR_{a2}$'$R_{b2}$'$)_v$'-hydroxyl, wherein the $C_{3-6}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$cycloalkyl and halo $C_{3-6}$ cycloalkyl; u' and v' are each independently 0, 1, 2, 3 or 4; $R_{a0}$' and $R_{b0}$' are each independently hydrogen or $C_{1-3}$ alkyl; or $R_{a0}$' and $R_{b0}$' form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$ alkyl; $R_{a1}$', $R_{b1}$', $R_{a2}$' and $R_{b2}$' are the same or different, and are each independently hydrogen, hydroxyl, $C_{1-3}$ alkyl or halo $C_{1-3}$ alkyl.

In an embodiment of the present disclosure, the substituents from group S' are selected from deuterium, halogen, nitro, oxo, —$C_{1-3}$ alkyl, -halo $C_{1-3}$ alkyl, -deuterated $C_{1-3}$ alkyl, —S—$C_{1-3}$alkyl, —S-halo $C_{1-3}$ alkyl, —$(CH_2)_u$'-cyano, —$(CH_2)_u$'-hydroxyl, —$(CH_2)_u$'-$C_{1-3}$ alkoxy, —$(CH_2)_u$'-halo $C_{1-3}$ alkoxy, —$(CH_2)_u$'-halo $C_{1-3}$ alkyl, —$(CH_2)_u$'-3- to 6-membered heterocycloalkyl, —$(CH_2)_u$'-$C_{3-6}$ cycloalkyl, —$(CH_2)_u$'-phenyl, —$(CH_2)_u$'-5- or 6-membered monocyclic heteroaryl, —$(CH_2)_u$'—O—$(CH_2)_v$'-halo $C_{1-3}$ alkyl, —$(CH_2)_u$'—O—$(CH_2)_v$'-$C_{3-6}$ cycloalkyl, —$(CH_2)_u$'—O—$(CH_2)_v$'-3- to 6-membered heterocycloalkyl, —$(CH_2)_u$'—O—$(CH_2)_v$-phenyl, —$(CH_2)_u$'—O—$(CH_2)_v$'-5- or 6-membered monocyclic heteroaryl, —$(CH_2)_u$—S—$(CH_2)_v$'-phenyl, —$(CH_2)_u$'—$SO_2$—$(CH_2)_v$'-phenyl, —$(CH_2)_u$'—O—C(O)$NR_{a0}$'$R_{b0}$', —$(CH_2)_u$'—O—$(CH_2)_v$'-

$C_{1-3}$alkoxy, —$(CH_2)_u$'—O—$(CH_2)_v$'-hydroxyl, —$(CH_2)_u$'—$SO_2C_{1-3}$ alkyl, —$(CH_2)_u$'—$SO_2NR_{a0}$'$R_{b0}$', —$(CH_2)_u$'—C(O)$NR_{a0}$'$R_{b0}$', —$(CH_2)_u$'—C(O)phenyl, —$(CH_2)_u$'—C(O)$C_{1-3}$ alkyl, —C(O)O$C_{1-3}$ alkyl, and —C(O)—$(CH_2)_v$'-hydroxyl, wherein the $C_{3-6}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$cycloalkyl and halo $C_{3-6}$ cycloalkyl; u' and v' are each independently 0, 1, 2, 3 or 4; $R_{a0}$' and $R_{b0}$' are each independently hydrogen or $C_{1-3}$ alkyl; or $R_{a0}$' and $R_{b0}$' form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$ alkyl; $R_{a1}$', $R_{b1}$', $R_{a2}$' and $R_{b2}$' are the same or different, and are each independently hydrogen, hydroxyl, $C_{1-3}$ alkyl or halo $C_{1-3}$ alkyl.

In an embodiment of the present disclosure, in the substituents from group S and group S', the 3- to 6-membered heterocycloalkyl is selected from aziridine, ethylene oxide, azetidine, azetidine-2-one, oxetane, oxetane-2-one, oxazolidine, pyrrolidine-2-one, pyrrolidine-2,5-dione, 1,3-dioxolane, dihydrofuran-2(3H)-one, dihydrofuran-2,5-dione, piperidine-2-one, piperidine-2,6-dione, tetrahydro-2H-pyran-2-one, imidazolidine, tetrahydrofuran, tetrahydrothiophene, tetrahydropyrrole, 1,3-dioxolane-2-one, oxazolidine-2-one, imidazolidine-2-one, piperidine, piperazine, piperazine-2-one, morpholine, morpholine-3-one, morpholine-2-one, thiomorpholine-3-one 1,1-dioxide, thiomorpholine, thiomorpholine-1,1-dioxide, tetrahydropyran, 1,2-dihydroazetidine, 1,2-dihydrooxetadiene, 2,5-dihydro-1H-pyrrole, 2,5-dihydrofuran, 2,3-dihydrofuran, 2,3-dihydro-1H-pyrrole, 3,4-dihydro-2H-pyran, 1,2,3,4-tetrahydropyridine, 3,6-dihydro-2H-pyran, 1,2,3,6-tetrahydropyridine, 1,3-oxazinane, hexahydropyrimidine, 1,4-dioxane, tetrahydropyrimidine-2(1H)-one, 1,4-dioxane-2-one, and 5,6-dihydro-2H-pyran-2-one.

In an embodiment of the present disclosure, in the substituents from group S and group S', the $C_{3-8}$ cycloalkyl is selected from cyclopropyl, cyclobutyl, cyclopentyl, cyclopentenyl, cyclohexyl, cyclohexenyl, cyclohexadienyl, cyclobutanone, cyclobutane-1,2-dione, cyclopentanone, cyclopentane-1,3-dione, cyclohexanone, and cyclohexane-1,3-dione.

In an embodiment of the present disclosure, in the substituents from group S and group S', the 5- or 6-membered monocyclic heteroaryl is selected from thiophene, N-alkylpyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine.

In an embodiment of the present disclosure, the compound has a structure represented by formula (I-1):

(I-1)

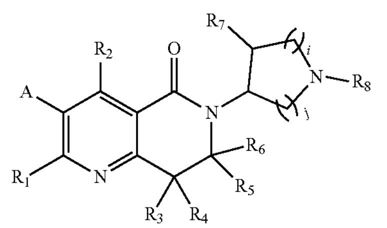

wherein, A, $R_1$, $R_2$, $R_3$, $R_4$, $R_5$ and $R_6$ are as defined above; i and j are each independently 0, 1 or 2; and i and j are not 0 at the same time;

$R_7$ is hydrogen, deuterium, halogen, nitro, oxo, —$C_{1-6}$ alkyl, -halo $C_{1-6}$ alkyl, -deuterated $C_{1-6}$ alkyl, —S—$C_{1-6}$ alkyl, —S-halo $C_{1-6}$ alkyl, —$(CR_{a1}R_{b1})_u$-cyano, —$(CR_{a1}R_{b1})_u$-hydroxyl, —$(CR_{a1}R_{b1})_u$—$C_{1-6}$ alkoxy, —$(CR_{a1}R_{b1})_u$-halo $C_{1-6}$ alkoxy, —$(CR_{a1}R_{b1})_u$ -halo $C_{1-6}$ alkyl, —$(CR_{a1}R_{b1})_u$-deuterated $C_{1-6}$ alkoxy, —$(CR_{a1}R_{b1})_u$-deuterated $C_{1-6}$ alkyl, —$(CR_{a1}R_{b1})_u$-3- to 6-membered heterocycloalkyl, —$(CR_{a1}R_{b1})_u$—$C_{3-8}$ cycloalkyl, —$(CR_{a1}R_{b1})_u$-phenyl, —$(CR_{a1}R_{b1})_u$-5- or 6-membered monocyclic heteroaryl, —$(CR_{a1}R_{b1})_u$—O—$(CR_{a2}R_{b2})_v$-halo $C_{1-6}$ alkyl, —$(CR_{a1}R_{b1})_u$—O—$(CR_{a2}R_{b2})_v$—$C_{3-8}$ cycloalkyl, —$(CR_{a1}R_{b1})_u$—O—$(CR_{a2}R_{b2})_v$-3- to 6-membered heterocycloalkyl, —$(CR_{a1}R_{b1})_u$—O—$(CR_{a2}R_{b2})_v$- phenyl, —$(CR_{a1}R_{b1})_u$ —O—$(CR_{a2}R_{b2})_v$-5- or 6-membered monocyclic heteroaryl, —$(CR_{a1}R_{b1})_u$—S—$(CR_{a2}R_{b2})_v$ -phenyl, —$(CR_{a1}R_{b1})_u$—$SO_2$—$(CR_{a2}R_{b2})_v$ -phenyl, —$(CR_{a1}R_{b1})_u$—O—C(O)$NR_{a0}R_{b0}$, —$(CR_{a1}R_{b1})_u$—O—$(CR_{a2}R_{b2})_v$—$C_{1-6}$ alkoxy, —$(CR_{a1}R_{b1})_u$—O—$(CR_{a2}R_{b2})_v$-hydroxyl, —$(CR_{a1}R_{b1})_u$—$SO_2C_{1-6}$ alkyl, —$(CR_{a1}R_{b1})_u$—$SO_2NR_{a0}R_{b0}$, —$(CR_{a1}R_{b1})_u$—C(O)$NR_{a0}R_{b0}$, —$(CR_{a1}R_{b1})_u$—C(O)phenyl, —$(CR_{a1}R_{b1})_u$—C(O)$C_{1-6}$ alkyl, —C(O)O$C_{1-6}$ alkyl, —C(O)—$(CR_{a2}R_{b2})_v$-hydroxyl, —$(CR_{a1}R_{b1})_u$—$NR_{a0}R_{b0}$, —$NR_{a0}$C(O)—$C_{1-6}$ alkyl, —$NR_{a0}$C(O)-deuterated $C_{1-6}$ alkyl, —$NR_{a0}$C(O)—$(CR_{a1}R_{b1})_u$-hydroxyl, —$NR_{a0}$C(O)—$(CR_{a1}R_{b1})_u$—O—$(CR_{a2}R_{b2})_v$—C(O)$C_{1-6}$ alkyl, —$NR_{a0}$C(O)—$(CR_{a1}R_{b1})_u$—O—$(CR_{a2}R_{b2})_v$-phenyl, —$NR_{a0}$C(O)—$C_{3-8}$ cycloalkyl, —$NR_{a0}$C(O)—$(CR_{a1}R_{b1})_u$—$NR_{a0}R_{b0}$, or —$NR_{a0}$C(O)-halo $C_{1-6}$ alkyl, wherein the $C_{3-8}$cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$ alkyl; $R_{a1}$, $R_{b1}$, $R_{a2}$ and $R_{b2}$ are the same or different, and are each independently hydrogen, hydroxyl, $C_{1-3}$ alkyl or halo $C_{1-3}$ alkyl;

$R_8$ is hydrogen, —$(CR_{a1}R_{b1})_u$—$SO_2$—$(CR_{a2}R_{b2})_v$-phenyl, —$(CR_{a1}R_{b1})_u$—$SO_2C_{1-6}$ alkyl, —$(CR_{a1}R_{b1})_u$—$SO_2NR_{a0}R_{b0}$, —$(CR_{a1}R_{b1})_u$—C(O)$NR_{a0}R_{b0}$, —$(CR_{a1}R_{b1})_u$—C(O)phenyl, —$(CR_{a1}R_{b1})_u$—C(O)$C_{1-}$ $_6$alkyl, or —C(O)—$(CR_{a2}R_{b2})_v$-hydroxyl, wherein the phenyl and $C_{1-6}$ alkyl are optionally substituted with 1, 2, 3 or 4 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl; $R_{a1}$, $R_{b1}$, $R_{a2}$ and $R_{b2}$ are the same or different, and are each independently hydrogen, hydroxyl, $C_{1-3}$ alkyl or halo $C_{1-3}$ alkyl;

the rest of the groups are as defined above.

In an embodiment of the present disclosure, the compound of formula (I-1) has a structure represented by formula (I-1-a), formula (I-1-b), formula (I-1-c) or formula (I-1-d):

I-1-a

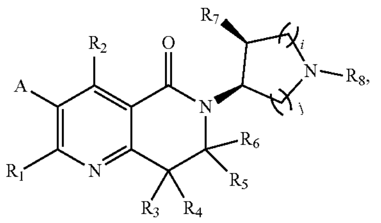

I-1-b

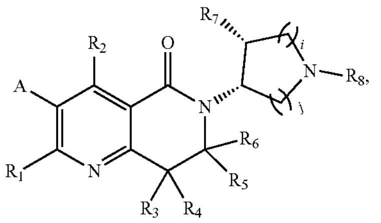

I-1-c

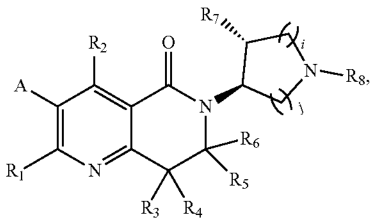

I-1-d

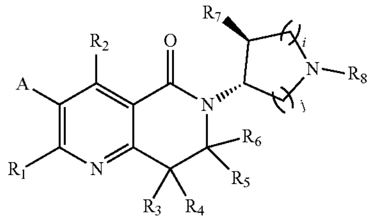

in each formula, each group is as defined above.

In an embodiment of the present disclosure, the compound has a structure represented by formula (I-2):

(I-2)

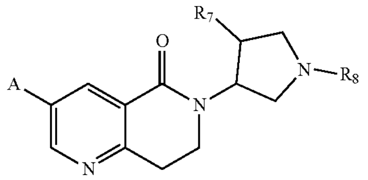

wherein, A, $R_7$ and $R_8$ are as defined above.

In an embodiment of the present disclosure, the compound of formula (I-2) has a structure represented by formula (I-2-a), formula (I-2-b), formula (I-2-c) or formula (I-2-d):

I-2-a

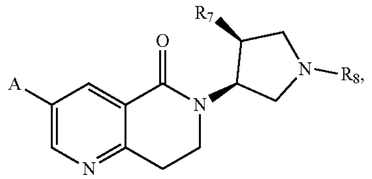

I-2-b

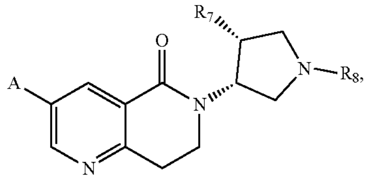

I-2-c

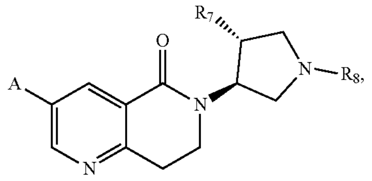

I-2-d

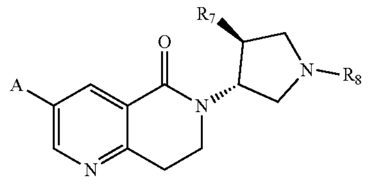

in each formula, each group is as defined above.

In an embodiment of the present disclosure, $R_7$ is hydrogen, deuterium, halogen, nitro, —$C_{1-3}$ alkyl, -halo $C_{1-3}$ alkyl, -deuterated $C_{1-3}$ alkyl, —S—$C_{1-3}$ alkyl, —S-halo $C_{1-3}$ alkyl, —$(CH_2)_u$-cyano, —$(CH_2)_u$-hydroxyl, —$(CH_2)_u$—$C_{1-6}$ alkoxy, —$(CH_2)_u$-halo $C_{1-6}$ alkoxy, —$(CH_2)_u$-halo $C_{1-6}$ alkyl, —$(CH_2)_u$-deuterated $C_{1-6}$ alkoxy, —$(CH_2)_u$-deuterated $C_{1-6}$ alkyl, —$(CH_2)_u$-3- to 6-membered heterocycloalkyl, —$(CH_2)_u$—$C_{3-8}$ cycloalkyl, —$(CH_2)_u$-phenyl, —$(CH_2)_u$ -5- or 6-membered monocyclic heteroaryl, —$(CH_2)_u$—O—$(CH_2)_v$-halo $C_{1-6}$ alkyl, —$(CH_2)_u$—O—$(CH_2)_v$—$C_{3-8}$ cycloalkyl, —$(CH_2)_u$—O—$(CH_2)_v$-3- to 6-membered heterocycloalkyl, —$(CH_2)_u$—O—$(CH_2)_v$-phenyl, —$(CH_2)_u$—O—$(CH_2)_v$-5- or 6-membered monocyclic heteroaryl, —$(CH_2)_u$—S—$(CH_2)_v$-phenyl, —$(CH_2)_u$—$SO_2$—$(CH_2)_v$-phenyl, —$(CH_2)_u$—O—C(O)$NR_{a0}R_{b0}$, —$(CH_2)_u$—O—$(CH_2)_v$—$C_{1-6}$ alkoxy, —$(CH_2)_u$—O—$(CH_2)_v$-hydroxyl, —$(CH_2)_u$—$SO_2C_{1-6}$ alkyl, —$(CH_2)_u$—$SO_2NR_{a0}R_{b0}$, —$(CH_2)_u$—$C(O)NR_{a0}R_{b0}$, —$(CH_2)_u$—C(O)phenyl, —$(CH_2)_u$—$C(O)C_{1-6}$ alkyl, —$C(O)OC_{1-6}$ alkyl, —C(O)—$(CH_2)_v$-hydroxyl, —$(CH_2)_u$—$NR_{a0}R_{b0}$, —$NR_{a0}C(O)$—$C_{1-6}$ alkyl, —$NR_{a0}C(O)$-deuterated $C_{1-6}$ alkyl, —$NR_{a0}C(O)$—$(CH_2)_u$-hydroxyl, —$NR_{a0}C(O)$—$C_{3-8}$ cycloalkyl, —$NR_{a0}C(O)$—$(CH_2)_u NR_{a0}R_{b0}$, —$NR_{a0}C(O)$—$(CH_2)_u$—O—$(CH_2)_v$—$C(O)C_{1-6}$ alkyl, —$NR_{a0}C(O)$—$(CH_2)_u$—O—$(CH_2)_v$-phenyl, or —$NR_{a0}C(O)$-halo $C_{1-6}$ alkyl, wherein the $C_{3-8}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$ alkyl.

In an embodiment of the present disclosure, $R_7$ is hydrogen, deuterium, halogen, nitro, —$C_{1-3}$ alkyl, -halo $C_{1-3}$ alkyl, or -deuterated $C_{1-3}$ alkyl.

In an embodiment of the present disclosure, $R_8$ is hydrogen, —$(CR_{a1}R_{b1})_u$—$SO_2$—$(CR_{a2}R_{b2})_v$-phenyl, —$(CR_{a1}R_{b1})_u$—$SO_2C_{1-3}$ alkyl, —$(CR_{a1}R_{b1})_u$—$SO_2NR_{a0}R_{b0}$, —$(CR_{a1}R_{b1})_u$—$C(O)NR_{a0}R_{b0}$, —$(CR_{a1}R_{b1})_u$ —C(O)phenyl, —$(CR_{a1}R_{b1})_u$—$C(O)C_{1-3}$ alkyl, or —C(O)—$(CR_{a2}R_{b2})_v$-hydroxyl, wherein the phenyl and $C_{1-3}$ alkyl are optionally substituted with 1, 2, 3 or 4 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl; $R_{a1}$, $R_{b1}$, $R_{a2}$ and $R_{b2}$ are the same or different, and are each independently hydrogen, hydroxyl, $C_{1-3}$ alkyl or halo $C_{1-3}$ alkyl.

In an embodiment of the present disclosure, $R_8$ is hydrogen, —$(CH_2)_u$—$SO_2$—$(CH_2)_v$-phenyl, —$(CH_2)_u$—$SO_2C_{1-6}$ alkyl, —$(CH_2)_u$—$SO_2NR_{a0}R_{b0}$, —$(CH_2)_u$—$C(O)NR_{a0}R_{b0}$, —$(CH_2)_u$—C(O)phenyl, —$(CH_2)_u$—$C(O)C_{1-6}$ alkyl, or —C(O)—$(CH_2)_v$-hydroxyl, wherein the phenyl and $C_{1-6}$ alkyl are optionally substituted with 1, 2, 3 or 4 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl.

In an embodiment of the present disclosure, $R_8$ is hydrogen, —$(CH_2)_u$—$C(O)NR_{a0}R_{b0}$, —$(CH_2)_u$—C(O)phenyl, —$(CH_2)_u$—$C(O)C_{1-3}$ alkyl, or —C(O)—$(CH_2)_v$-hydroxyl, wherein the phenyl and $C_1$-3 alkyl are optionally substituted with 1, 2, 3 or 4 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl.

In an embodiment of the present disclosure, $R_8$ is hydrogen, —C(O)phenyl, or —$C(O)C_{1-6}$alkyl, wherein the phenyl, and $C_{1-6}$ alkyl are optionally substituted with 1, 2, 3 or 4 substituents selected from hydroxyl, halogen, and halo $C_{1-3}$ alkyl.

In an embodiment of the present disclosure, $R_8$ is hydrogen, —C(O)phenyl, or —$C(O)C_{1-3}$ alkyl, wherein the $C_{1-3}$ alkyl is methyl, ethyl, n-propyl or isopropyl; the phenyl, and $C_{1-3}$ alkyl are optionally substituted with 1, 2, 3 or 4 substituents selected from hydroxyl, fluorine, chlorine, monochloromethyl, dichloromethyl, trichloromethyl, monochloroethyl, 1,2-dichloroethyl, trichloroethyl, monofluoromethyl, difluoromethyl, trifluoromethyl, monofluoroethyl, difluoroethyl, and trifluoroethyl.

In an embodiment of the present disclosure, $R_8$ has a structure represented by formula (I-1-1):

I-1-1

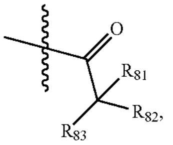

wherein $R_{81}$, $R_{82}$ and $R_{83}$ are each independently hydrogen, hydroxyl, halogen, $C_{1-3}$ alkyl, halo $C_{1-3}$ alkyl or $C_{1-3}$ alkoxy.

In an embodiment of the present disclosure, $R_8$ has a structure as follows:

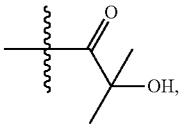

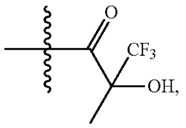

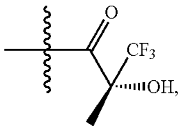

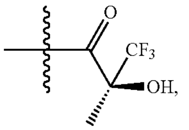

or

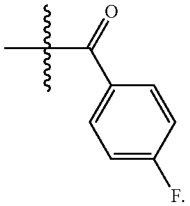

In an embodiment of the present disclosure, A has a structure selected from:

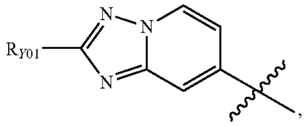

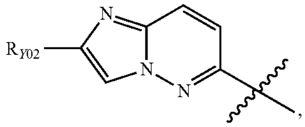

-continued

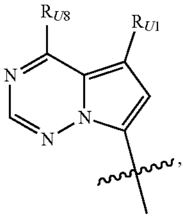, and

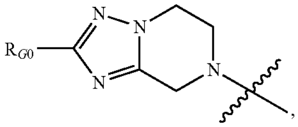, wherein $R_{Y01}$, $R_{Y02}$, $R_{U8}$, $R_{U1}$ and $R_{G0}$ are each independently hydrogen or the substituents from group S.

In an embodiment of the present disclosure, A is substituted or unsubstituted pyridine, substituted or unsubstituted benzimidazole, substituted or unsubstituted benzoxazole, substituted or unsubstituted benzopyridine, substituted or unsubstituted pyrrolotriazine, substituted or unsubstituted tetrahydro-triazolopyrazine, substituted or unsubstituted imidazopyridazine, or substituted or unsubstituted triazolopyridine, wherein the "substituted" means that 1, 2, 3 or 4 hydrogen atoms in the group are substituted with substituent(s) each independently selected from group S.

In an embodiment of the present disclosure, A is or substituted or unsubstituted benzothiazole, wherein the "substituted" means that 1, 2, 3 or 4 hydrogen atoms in the group are substituted with substituent(s) each independently selected from group S'.

In an embodiment of the present disclosure, A is substituted or unsubstituted pyridine, substituted or unsubstituted benzimidazole, substituted or unsubstituted benzoxazole, substituted or unsubstituted pyrrolotriazine, substituted or unsubstituted 5,6,7,8-tetrahydro-triazolopyrazine, substituted or unsubstituted imidazopyridazine, or substituted or unsubstituted [1,2,4]triazolo[1,5-a]pyridine; the "substituted" means that 1, 2, 3 or 4 hydrogen atoms in the group are substituted with substituent(s) each independently selected from group S.

In an embodiment of the present disclosure, A is substituted or unsubstituted pyridine, substituted or unsubstituted 1H-benzimidazole, substituted or unsubstituted benzoxazole, substituted or unsubstituted [2,1-f]pyrrolo[1,2,4]triazine, substituted or unsubstituted 5,6,7,8-tetrahydro-[1,2,4]triazolo[1,5-a]pyrazine, or substituted or unsubstituted imidazo[1,2-b]pyridazine, or substituted or unsubstituted [1,2,4]triazolo[1,5-a]pyridine; the "substituted" means that 1, 2, 3 or 4 hydrogen atoms in the group are substituted with substituent(s) each independently selected from group S.

In an embodiment of the present disclosure, A is selected from:

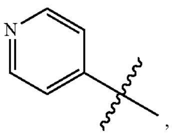, 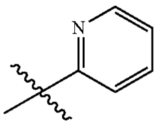, 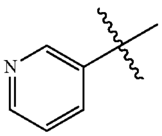,

-continued

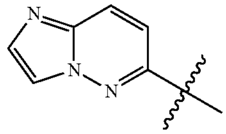, 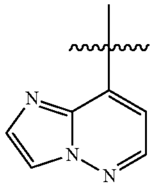,

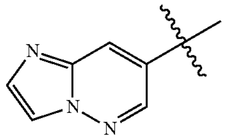, 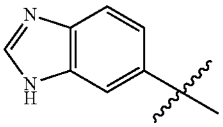,

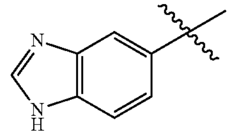, 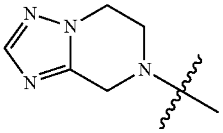,

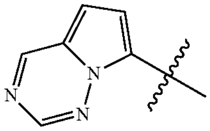, 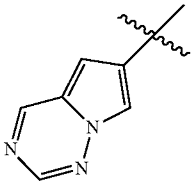,

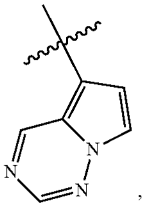, 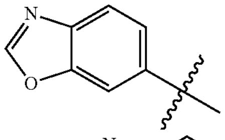,

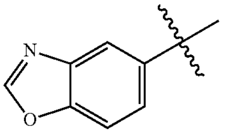, 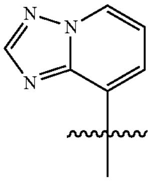,

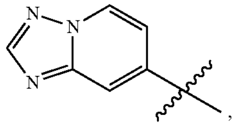, 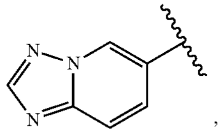, and

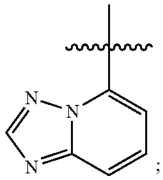;

the above groups are each independently unsubstituted or substituted; the "substituted" means that 1, 2, 3 or 4 hydrogen atoms in the group are substituted with substituent(s) each independently selected from group S.

In an embodiment of the present disclosure, A has a structure selected from:

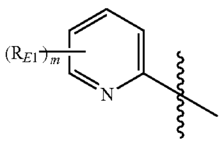, 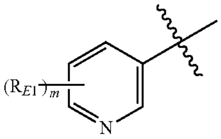,

-continued
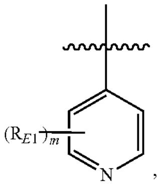,
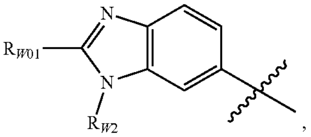,
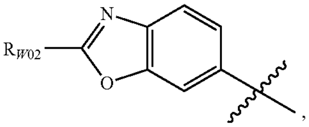,
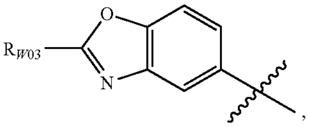,
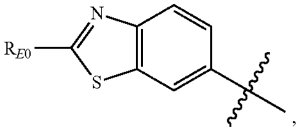,
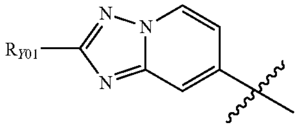,
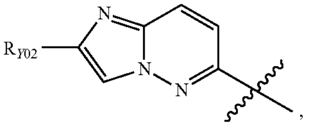,
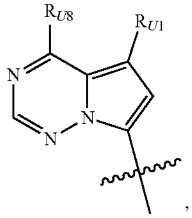, and
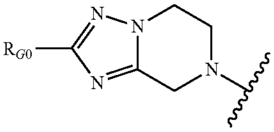,
wherein $R_{E1}$, $R_{W01}$, $R_{W2}$, $R_{W02}$, $R_{W03}$, $R_{Y01}$, $R_{Y02}$, $R_{U8}$, $R_{U1}$ and $R_{G0}$ are each independently hydrogen or the substituent from group S; $R_{E0}$ is hydrogen or the substituent from group S'; m is 1, 2, 3 or 4.
In an embodiment of the present disclosure, A is selected from:
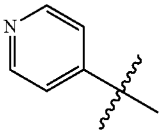,
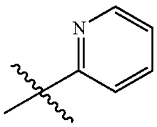,
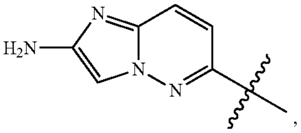,
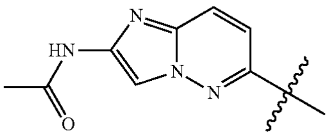,
-continued
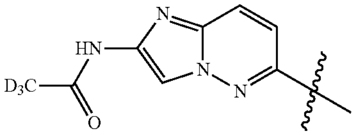,
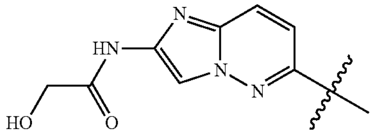,
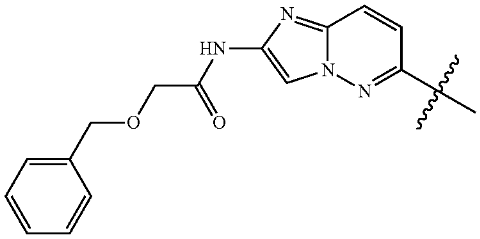,
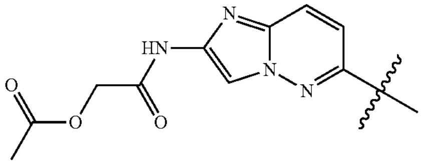,
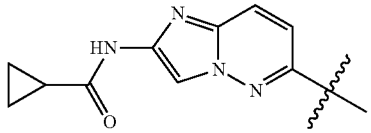,
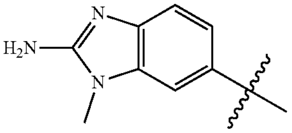,
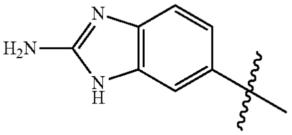,
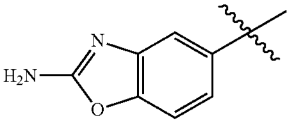,
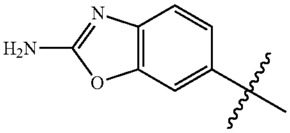,
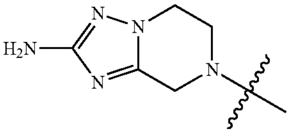,
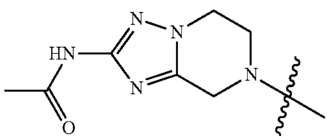,
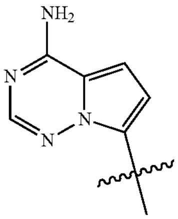, -continued

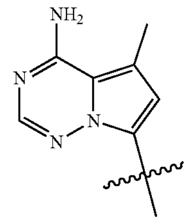
,
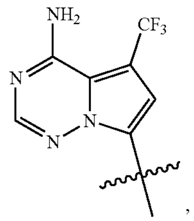
,
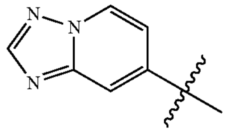
,
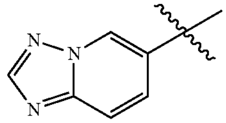
,
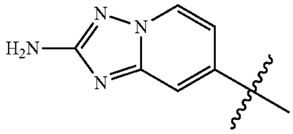
,
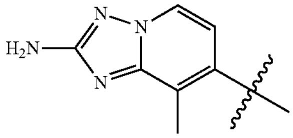
,
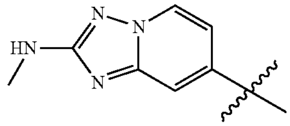
,
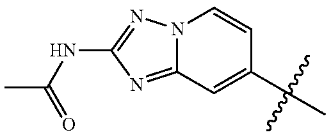
, and
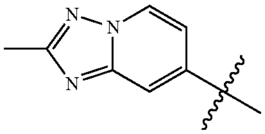
.

In an embodiment of the present disclosure, A is substituted or unsubstituted benzothiazole; the "substituted" means that 1, 2, 3 or 4 hydrogen atoms in the group are substituted with substituent(s) each independently selected from group S'.

In an embodiment of the present disclosure, A is substituted or unsubstituted

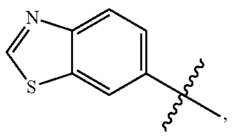
, or
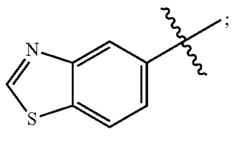
;

the "substituted" means that 1, 2, 3 or 4 hydrogen atoms in the group are substituted with substituent(s) each independently selected from group S'.

In an embodiment of the present disclosure, A is

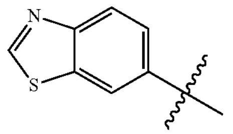
or
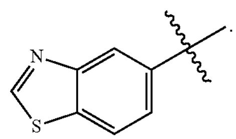
.

In an embodiment of the present disclosure, $R_1$ and $R_2$ are each independently hydrogen, halogen, $C_{1-3}$ alkyl or halo $C_{1-3}$ alkyl.

In an embodiment of the present disclosure, $R_3$, $R_4$, $R_5$ and $R_6$ are each independently hydrogen, $C_{1-3}$ alkyl or halo $C_{1-3}$ alkyl.

In an embodiment of the present disclosure, with regard to $R_0$, the $C_{6-14}$ aryl is phenyl, naphthyl, or is a 9- or 10-membered aromatic fused bicyclic ring formed by fusing phenyl with a non-aromatic ring; the non-aromatic ring is 3- to 6-membered saturated or partially unsaturated monocyclic heterocycloalkyl or 3- to 6-membered saturated or partially unsaturated monocyclic cycloalkyl, wherein the 3- to 6-membered saturated or partially unsaturated monocyclic heterocycloalkyl is selected from aziridine, ethylene oxide, azetidine, azetidine-2-one, oxetane, oxetane-2-one, oxazolidine, pyrrolidine-2-one, pyrrolidine-2,5-dione, 1,3-dioxolane, dihydrofuran-2(3H)-one, dihydrofuran-2,5-dione, piperidine-2-one, piperidine-2,6-dione, tetrahydro-2H-pyran-2-one, imidazolidine, tetrahydrofuran, tetrahydrothiophene, tetrahydropyrrole, 1,3-dioxolane-2-one, oxazolidine-2-one, imidazolidine-2-one, piperidine, piperazine, piperazine-2-one, morpholine, morpholine-3-one, morpholine-2-one, thiomorpholine-3-one 1,1-dioxide, thiomorpholine, thiomorpholine-1,1-dioxide, tetrahydropyran, 1,2-dihydroazetidine, 1,2-dihydrooxetadiene, 2,5-dihydro-1H-pyrrole, 2,5-dihydrofuran, 2,3-dihydrofuran, 2,3-dihydro-1H-pyrrole, 3,4-dihydro-2H-pyran, 1,2,3,4-tetrahydropyridine, 3,6-dihydro-2H-pyran, 1,2,3,6-tetrahydropyridine, 1,3-oxazinane, hexahydropyrimidine, 1,4-dioxane, tetrahydropyrimidine-2(1H)-one, 1,4-dioxane-2-one, and 5,6-dihydro-2H-pyran-2-one; the 3- to 6-membered saturated or partially unsaturated monocyclic cycloalkyl is selected from cyclopropyl, cyclobutyl, cyclopentyl, cyclopentenyl, cyclohexyl, cyclohexenyl, cyclohexadienyl, cyclobutanone, cyclobutane-1,2-dione, cyclopentanone, cyclopentane-1,3-dione, cyclohexanone, and cyclohexane-1,3-dione; the phenyl, naphthyl, or 9- or 10-membered aromatic fused bicyclic ring is unsubstituted or substituted with 1, 2, 3 or 4 substituents each independently selected from group S.

In an embodiment of the present disclosure, with regard to $R_0$, the $C_{6-14}$ aryl is phenyl.

In an embodiment of the present disclosure, with regard to $R_0$, the 5- to 14-membered heteroaryl is 5- or 6-membered monocyclic heteroaryl, wherein the 5- or 6-membered monocyclic heteroaryl is selected from thiophene, N-alkylpyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine; the 5- or 6-membered monocyclic heteroaryl is unsubstituted or substituted with 1, 2, 3 or 4 substituents each independently selected from group S.

In an embodiment of the present disclosure, with regard to $R_0$, when the 5- to 14-membered heteroaryl is 5- or 6-membered monocyclic heteroaryl, the monocyclic heteroaryl is selected from the following structures:

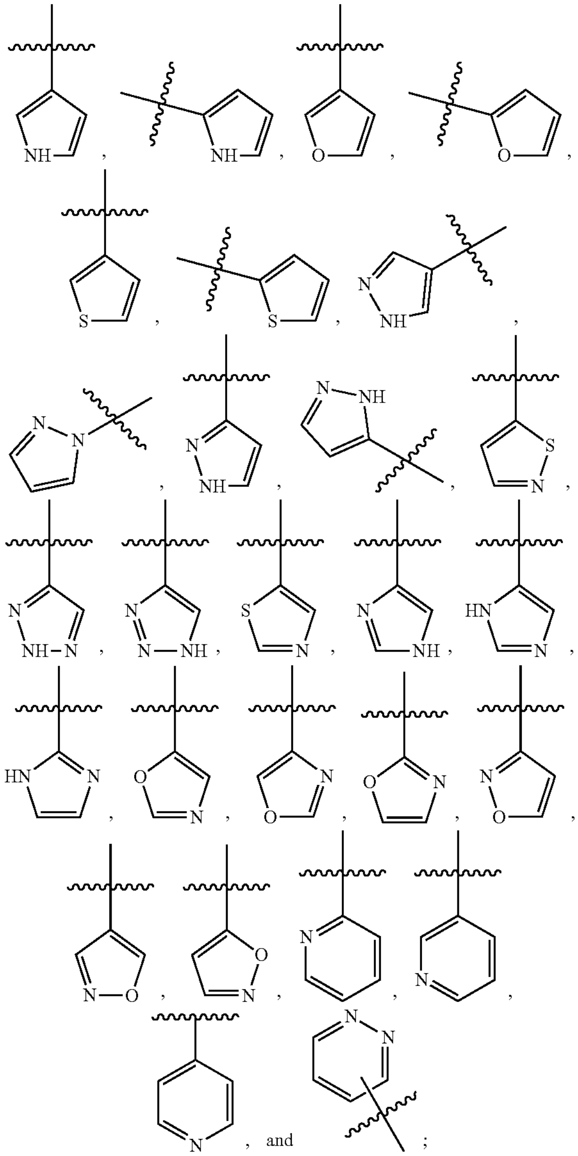

the above 5- or 6-membered monocyclic heteroaryl is unsubstituted or substituted with 1, 2, 3 or 4 substituents each independently selected from group S.

In an embodiment of the present disclosure, with regard to $R_0$, the 5- to 14-membered heteroaryl is 9- or 10-membered bicyclic heteroaryl formed by fusing phenyl with 5- or 6-membered monocyclic heteroaryl, wherein the 5- or 6-membered monocyclic heteroaryl is selected from thiophene, N-alkyl pyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine; the 9- or 10-membered bicyclic heteroaryl is unsubstituted or substituted with 1, 2, 3 or 4 substituents each independently selected from group S.

In an embodiment of the present disclosure, the 9- or 10-membered bicyclic heteroaryl formed by fusing phenyl with 5- or 6-membered monocyclic heteroaryl has a structure represented by formula (A1) or formula (B1):

A1

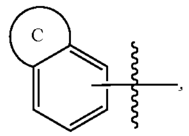

B1

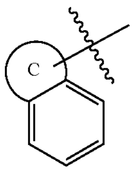

wherein ring C is 5- or 6-membered monocyclic heteroaryl, wherein the 5- or 6-membered monocyclic heteroaryl is selected from thiophene, N-alkyl pyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine; the 9- or 10-membered bicyclic heteroaryl is unsubstituted or substituted with 1, 2, 3 or 4 substituents each independently selected from group S.

In an embodiment of the present disclosure, ring C is selected from the following structure:

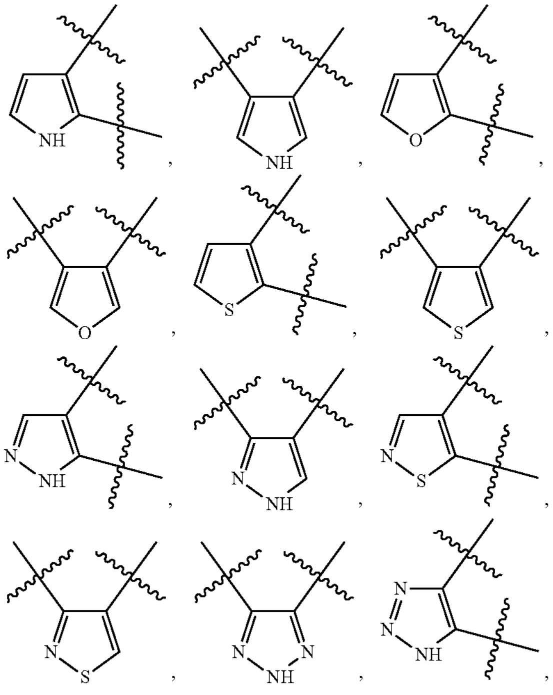

-continued

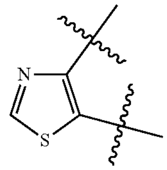, 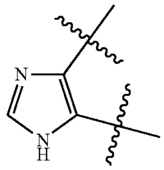, 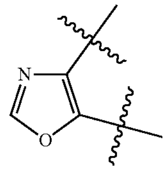,

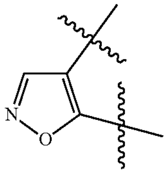, 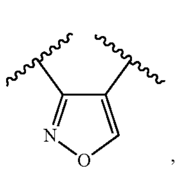, 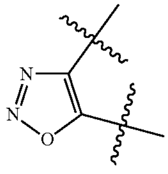,

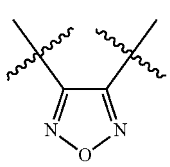, 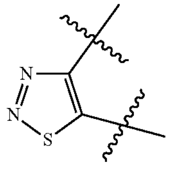, 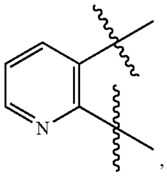,

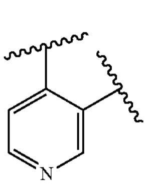, 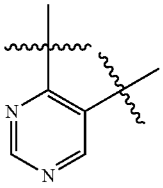, 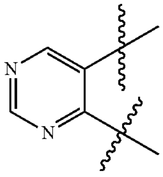,

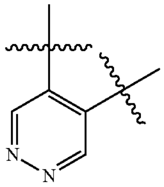, 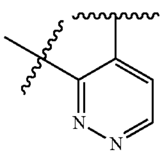, and 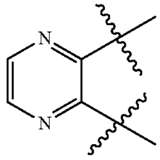, wherein the attached two carbon atoms represented by "~" are adjacent pairs of carbon atoms shared when fused with phenyl.

In an embodiment of the present disclosure, the 9- or 10-membered bicyclic heteroaryl formed by fusing phenyl with 5- or 6-membered monocyclic heteroaryl is selected from benzoxazole, benzisoxazole, benzimidazole, benzothiazole, benzisothiazole, benzotriazole, benzofuran, benzothiophene, indole, indazole, isoindole, quinoline, isoquinoline, quinazoline, quinoxaline, and cinnoline; the 9- or 10-membered bicyclic heteroaryl is unsubstituted or substituted with 1, 2, 3 or 4 substituents each independently selected from group S.

In an embodiment of the present disclosure, the 9- or 10-membered bicyclic heteroaryl formed by fusing phenyl with 5- or 6-membered monocyclic heteroaryl is selected from benzo[d]isoxazole, 1H-indole, isoindole, 1H-benzo[d]imidazole, benzo[d]isothiazole, 1H-benzo[d][1,2,3]triazole, benzo[d]oxazole, benzo[d]thiazole, indazole, benzofuran, benzo[b]thiophene, quinoline, isoquinoline, quinazoline, quinoxaline, and cinnoline; the 9- or 10-membered bicyclic heteroaryl is unsubstituted or substituted with 1, 2, 3 or 4 substituents each independently selected from group S.

In an embodiment of the present disclosure, the 9- or 10-membered bicyclic heteroaryl formed by fusing phenyl with 5- or 6-membered monocyclic heteroaryl is selected from the following structures:

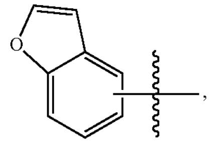, 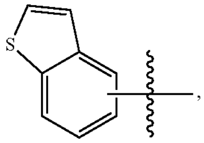,

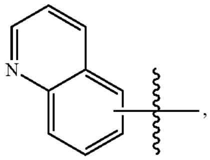, 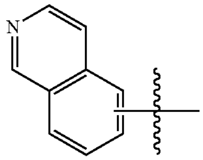,

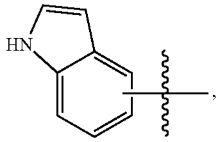, 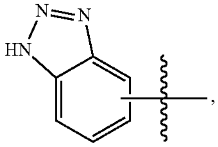,

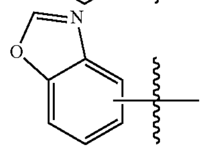, 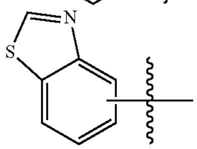,

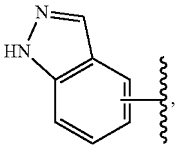, 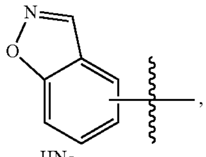,

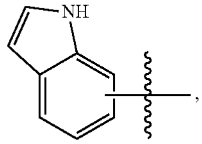, 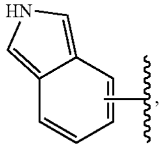,

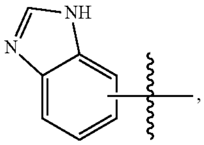, 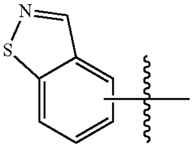,

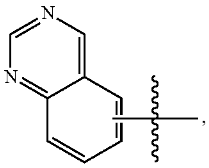, 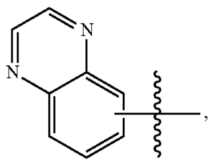, and

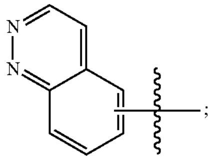;

the above 9- or 10-membered bicyclic heteroaryl is unsubstituted or substituted with 1, 2, 3 or 4 substituents each independently selected from group S.

In an embodiment of the present disclosure, with regard to $R_0$, the 5- to 14-membered heteroaryl is 8- to 10-membered bicyclic heteroaryl formed by fusing 5- or 6-membered monocyclic heteroaryl with 5- or 6-membered monocyclic heteroaryl, wherein the 5- or 6-membered monocyclic heteroaryl is selected from thiophene, N-alkylpyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine; the 8- to 10-membered bicyclic heteroaryl is unsubstituted or substituted with 1, 2, 3 or 4 substituents each independently selected from group S.

In an embodiment of the present disclosure, the 8- to 10-membered bicyclic heteroaryl formed by fusing 5- or 6-membered monocyclic heteroaryl with 5- or 6-membered monocyclic heteroaryl has a structure represented by formula (C) or formula (D):

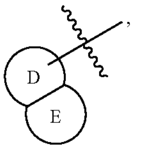

C

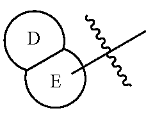

D wherein ring D and ring E are 5- or 6-membered monocyclic heteroaryl, wherein the 5- or 6-membered monocyclic heteroaryl is selected from thiophene, N-alkyl pyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine; the 8- to 10-membered bicyclic heteroaryl is unsubstituted or substituted with 1, 2, 3 or 4 substituents each independently selected from group S.

In an embodiment of the present disclosure, ring D and ring E are selected from the following structures:

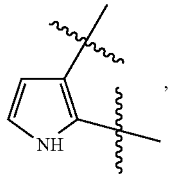, 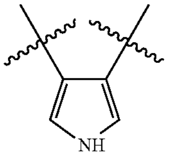, 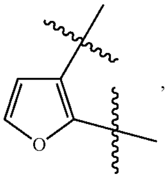, 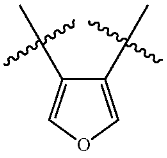, 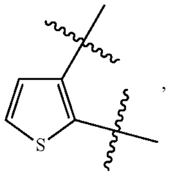, 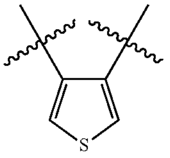, 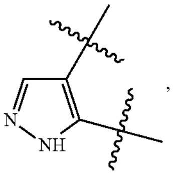, 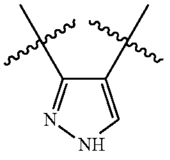, 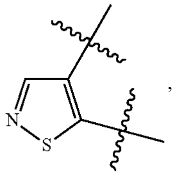, 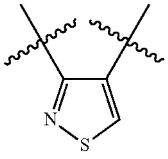, 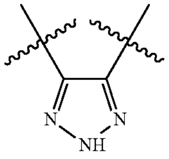, 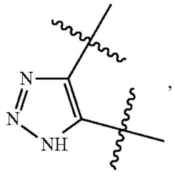, -continued

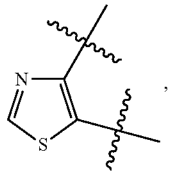, 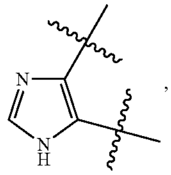, 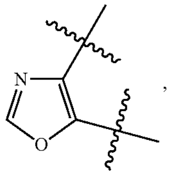, 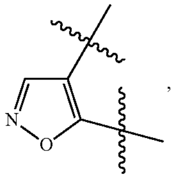, 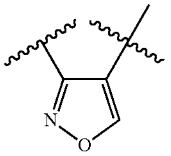, 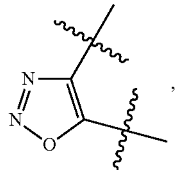, 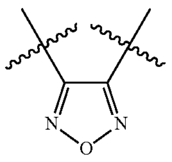, 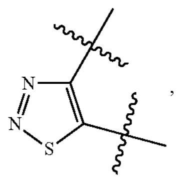, 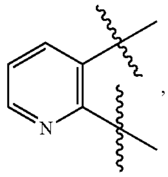, 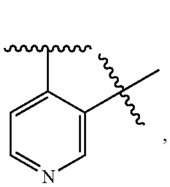, 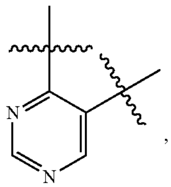, 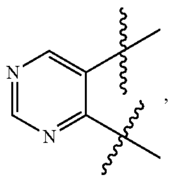, 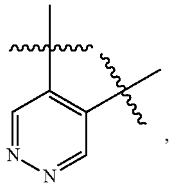, 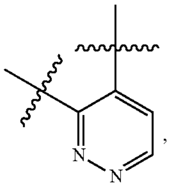, and 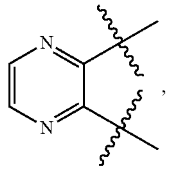, wherein the attached two carbon atoms represented by " ~~~ " are adjacent pairs of carbon atoms shared when fused with other rings.

In an embodiment of the present disclosure, the 8- to 10-membered bicyclic heteroaryl formed by fusing 5- or 6-membered monocyclic heteroaryl with 5- or 6-membered monocyclic heteroaryl is selected from pyridopyrimidine and naphthyridine.

In an embodiment of the present disclosure, the 8- to 10-membered bicyclic heteroaryl formed by fusing 5- or 6-membered monocyclic heteroaryl with 5- or 6-membered monocyclic heteroaryl is selected from pyrido[3,2-d]pyrimidine, pyrido[2,3-d]pyrimidine, pyrido[3,4-d]pyrimidine, pyrido[4,3-d]pyrimidine, 1,8-naphthyridine, 1,7-naphthyridine, 1,6-naphthyridine, and 1,5-naphthyridine.

In an embodiment of the present disclosure, the 8- to 10-bicyclic heteroaryl formed by fusing 5- or 6-membered monocyclic heteroaryl with 5- or 6-membered monocyclic heteroaryl is selected from the following structures:

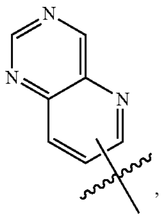
,
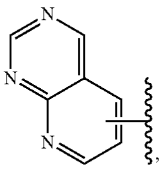
,
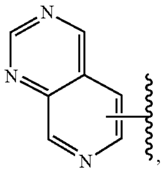
,
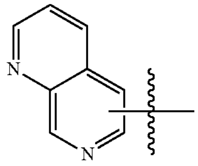
,
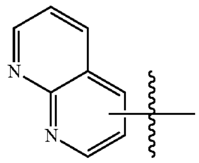
,
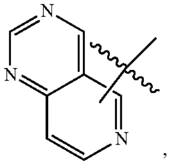
,
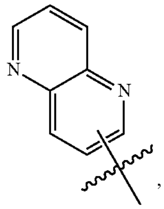
, and
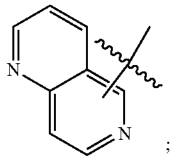
;

the above 8- to 10-membered bicyclic heteroaryl is unsubstituted or substituted with 1, 2, 3 or 4 substituents each independently selected from group S.

In an embodiment of the present disclosure, with regard to $R_0$, the 5- to 14-membered heteroaryl is 8- to 10-membered bicyclic heteroaryl formed by fusing 5- or 6-membered monocyclic heteroaryl with a non-aromatic ring, wherein the non-aromatic ring is 3- to 6-membered saturated or partially unsaturated monocyclic heterocycloalkyl or 3- to 6-membered saturated or partially unsaturated monocyclic cycloalkyl; the 5- or 6-membered monocyclic heteroaryl is selected from thiophene, N-alkylpyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine; the 3- to 6-membered saturated or partially unsaturated monocyclic heterocycloalkyl is selected from aziridine, ethylene oxide, azetidine, azetidine-2-one, oxetane, oxetane-2-one, oxazolidine, pyrrolidine-2-one, pyrrolidine-2,5-dione, 1,3-dioxolane, dihydrofuran-2(3H)-one, dihydrofuran-2,5-dione, piperidine-2-one, piperidine-2,6-dione, tetrahydro-2H-pyran-2-one, imidazolidine, tetrahydrofuran, tetrahydrothiophene, tetrahydropyrrole, 1,3-dioxolane-2-one, oxazolidine-2-one, imidazolidine-2-one, piperidine, piperazine, piperazine-2-one, morpholine, morpholine-3-one, morpholine-2-one, thiomorpholine-3-one 1,1-dioxide, thiomorpholine, thiomorpholine-1,1-dioxide, tetrahydropyran, 1,2-dihydroazetidine, 1,2-dihydrooxetadiene, 2,5-dihydro-1H-pyrrole, 2,5-dihydrofuran, 2,3-dihydrofuran, 2,3-dihydro-1H-pyrrole, 3,4-dihydro-2H-pyran, 1,2,3,4-tetrahydropyridine, 3,6-dihydro-2H-pyran, 1,2,3,6-tetrahydropyridine, 1,3-oxazinane, hexahydropyrimidine, 1,4-dioxane, tetrahydropyrimidine-2 (1H)-one, 1,4-dioxane-2-one, and 5,6-dihydro-2H-pyran-2-one; the 3- to 6-membered saturated or partially unsaturated monocyclic cycloalkyl is selected from cyclopropyl, cyclobutyl, cyclopentyl, cyclopentenyl, cyclohexyl, cyclohexenyl, cyclohexadienyl, cyclobutanone, cyclobutane-1,2-dione, cyclopentanone, cyclopentane-1,3-dione, cyclohexanone, and cyclohexane-1,3-dione; the 8- to 10-membered bicyclic heteroaryl is unsubstituted or substituted with 1, 2, 3 or 4 substituents each independently selected from group S.

In an embodiment of the present disclosure, with regard to $R_0$, the 5- to 14-membered heterocycloalkyl is 5- to 6-membered heterocycloalkyl, wherein the 5- to 6-membered heterocycloalkyl is selected from oxazolidine, pyrrolidine-2-one, pyrrolidine-2,5-dione, 1,3-dioxolane, dihydrofuran-2(3H)-one, dihydrofuran-2,5-dione, piperidine-2-one, piperidine-2,6-dione, tetrahydro-2H-pyran-2-one, imidazolidine, tetrahydrofuran, tetrahydrothiophene, tetrahydropyrrole, 1,3-dioxolane-2-one, oxazolidine-2-one, imidazolidine-2-one, piperidine, piperazine, piperazine-2-one, morpholine, morpholine-3-one, morpholine-2-one, thiomorpholine-3-one 1,1-dioxide, thiomorpholine, thiomorpholine-1,1-dioxide, tetrahydropyran, 1,2-dihydroazetidine, 1,2-dihydrooxetadiene, 2,5-dihydro-1H-pyrrole, 2,5-dihydrofuran, 2,3-dihydrofuran, 2,3-dihydro-1H-pyrrole, 3,4-dihydro-2H-pyran, 1,2,3,4-tetrahydropyridine, 3,6-dihydro-2H-pyran, 1,2,3,6-tetrahydropyridine, 1,3-oxazinane, hexahydropyrimidine, 1,4-dioxane, tetrahydropyrimidine-2 (1H)-one, 1,4-dioxane-2-one, and 5,6-dihydro-2H-pyran-2-one; the 5- to 6-membered heterocycloalkyl is unsubstituted or substituted with 1, 2, 3 or 4 substituents each independently selected from group S.

In an embodiment of the present disclosure, with regard to $R_0$, the 5- to 14-membered heterocycloalkyl is 5- to 6-membered heterocycloalkyl, wherein the 5- to 6-membered heterocycloalkyl is selected from tetrahydrofuran, tetrahydrothiophene, tetrahydropyrrole, piperidine, piperazine, morpholine, thiomorpholine, thiomorpholine-1,1-dioxide and tetrahydropyran; the 5- to 6-membered heterocycloalkyl is unsubstituted or substituted with 1, 2, 3 or 4 substituents each independently selected from group S.

In an embodiment of the present disclosure, $R_0$ is substituted or unsubstituted phenyl, substituted or unsubstituted pyridyl, substituted or unsubstituted pyrazolyl or substituted or unsubstituted tetrahydropyrrolyl; the "substituted" means that 1, 2, 3 or 4 hydrogen atoms in the group are substituted with substituent(s) each independently selected from group S.

In an embodiment of the present disclosure, $R_0$ is selected from the following structures:

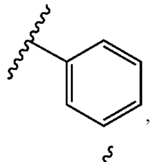
,
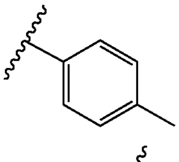
,
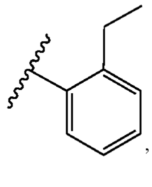
,
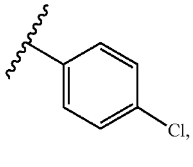
,
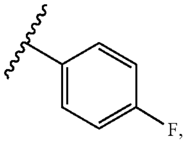
,

-continued
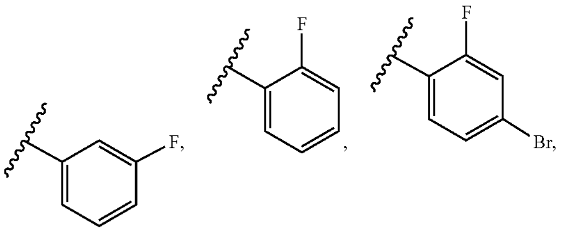
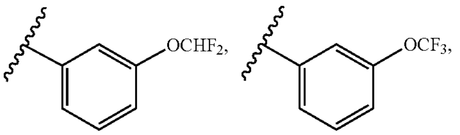
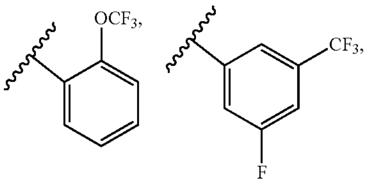
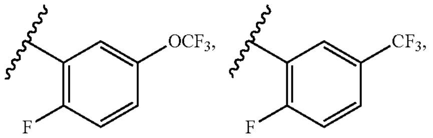
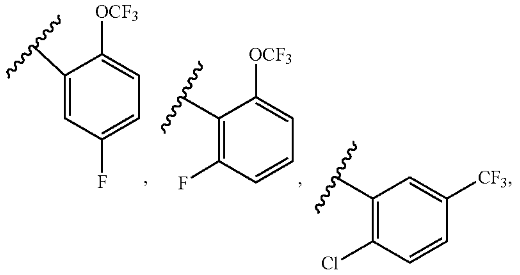
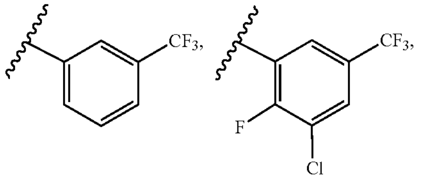
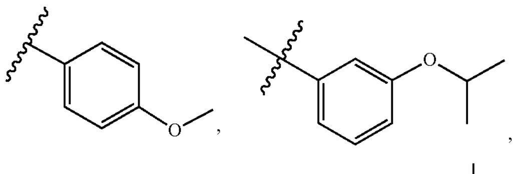
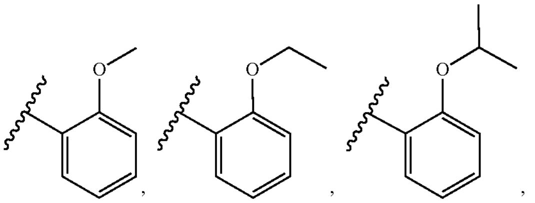
-continued
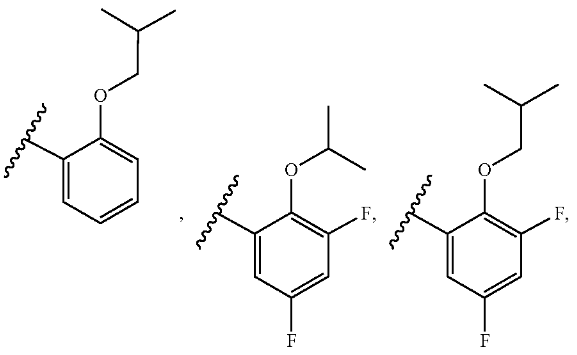
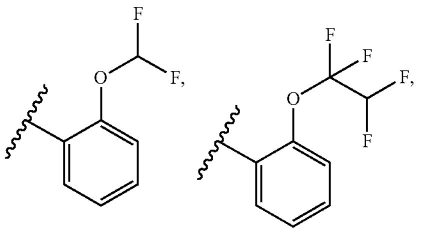
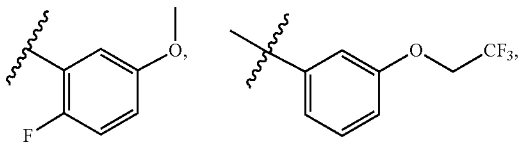
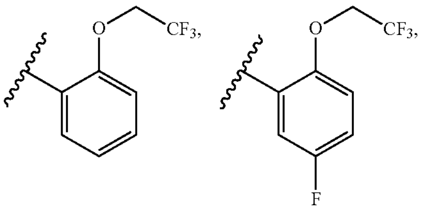
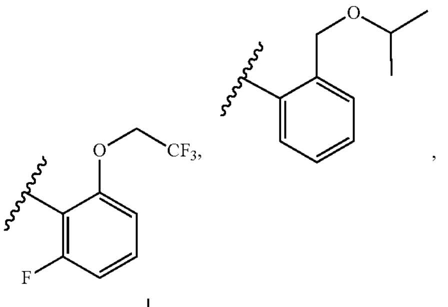
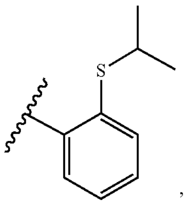
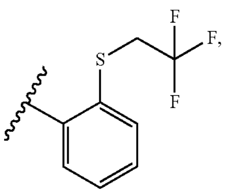

-continued
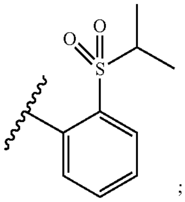
;
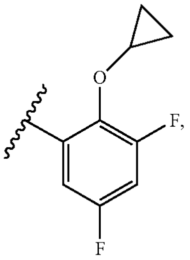
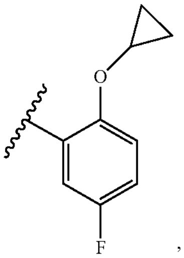
,
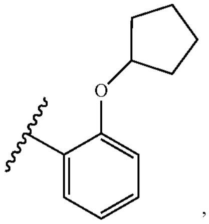
,
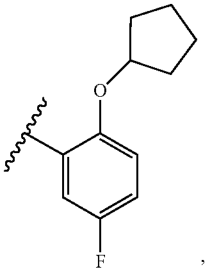
,
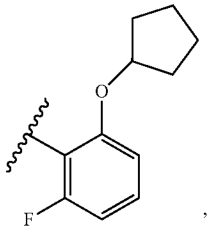
,
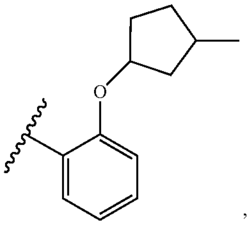
,
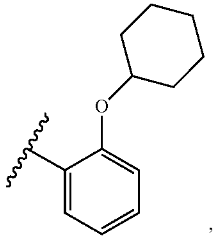
,
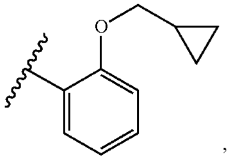
,
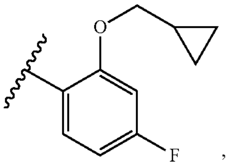
,
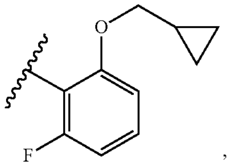
,
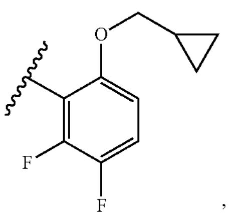
,
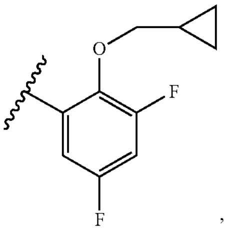
,
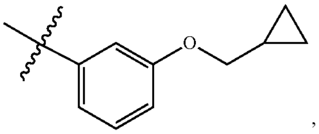
,
-continued
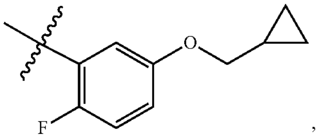
,
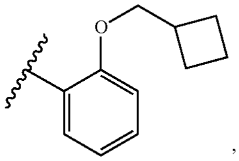
,
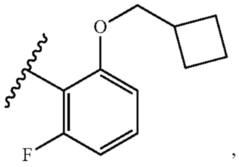
,
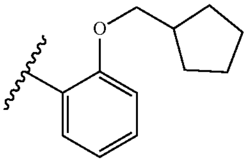
,
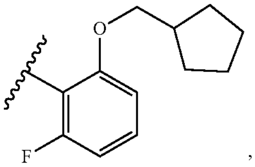
,
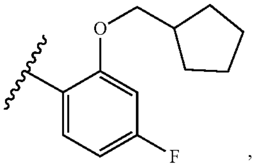
,
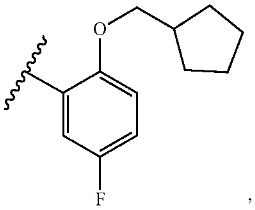
,
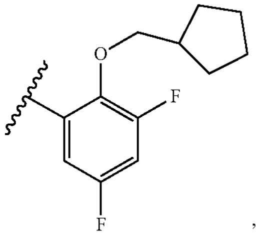
,
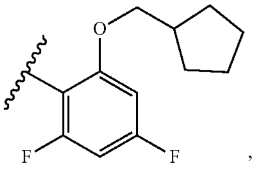
,
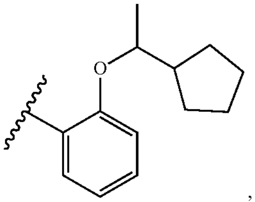
,
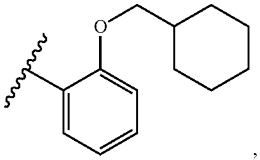
,
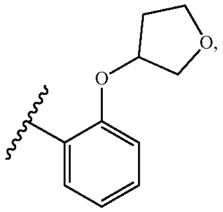
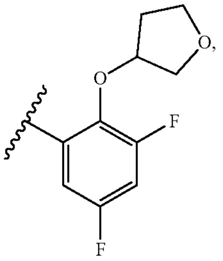
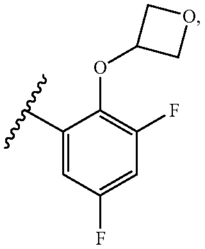

-continued
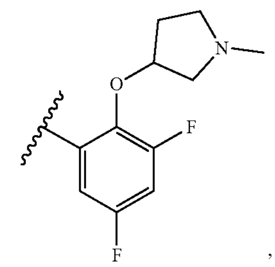
,
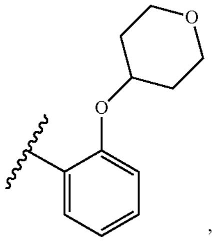
,
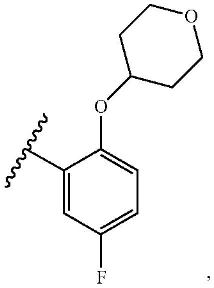
,
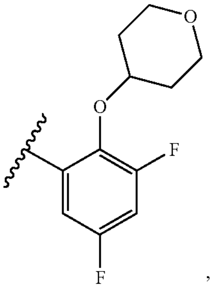
,
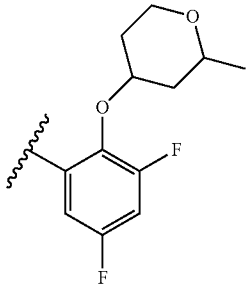
,
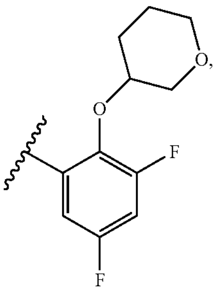
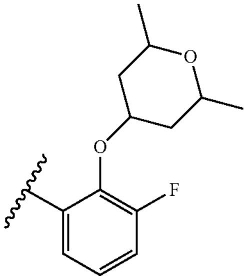
,
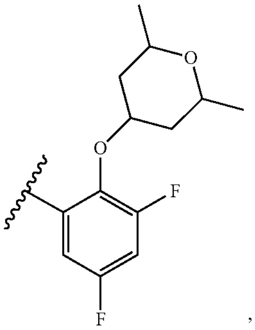
,
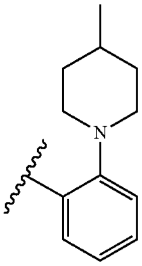
,
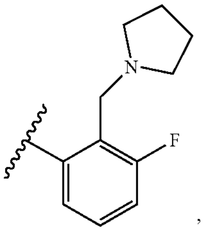
,
-continued
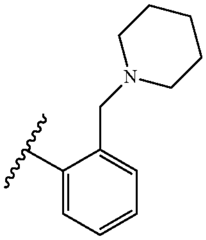
,
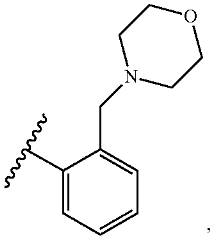
,
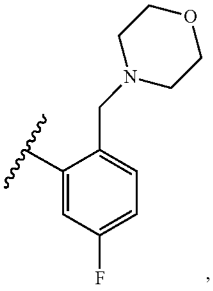
,
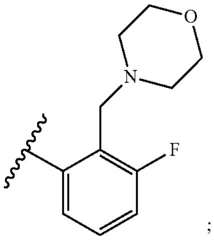
;
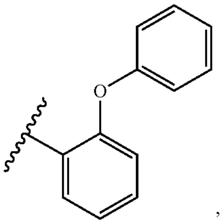
,
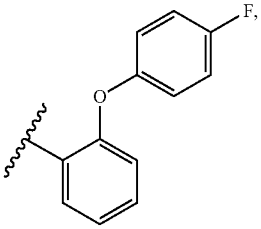
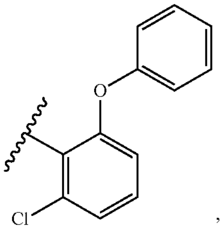
,
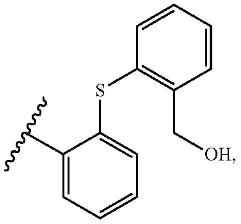
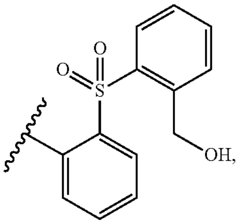
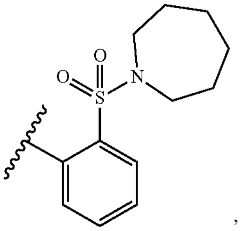
, -continued
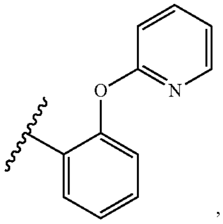
,
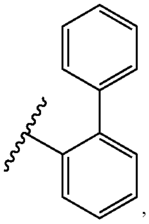
,
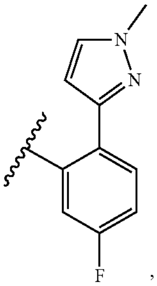
,
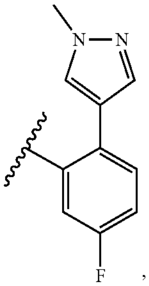
,
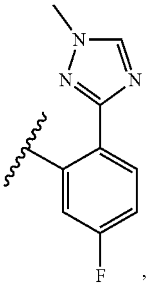
,
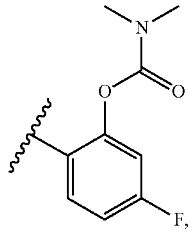
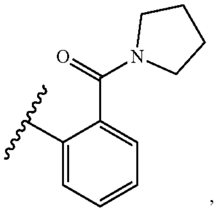
,
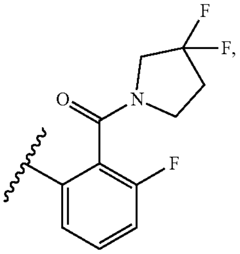
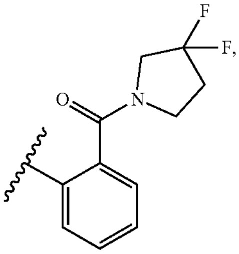
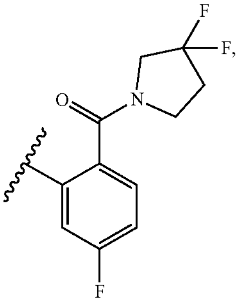
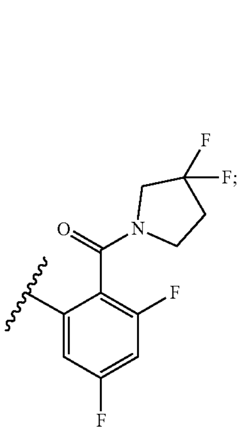
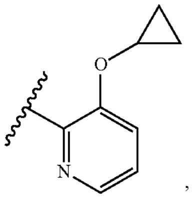
,
-continued
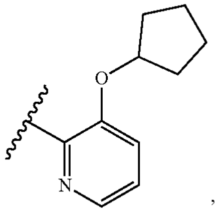
,
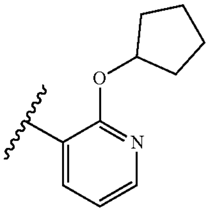
,
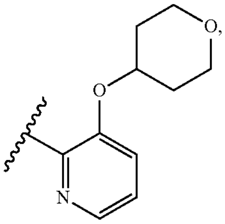
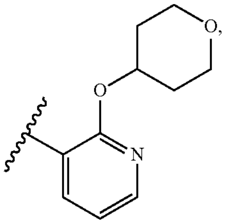
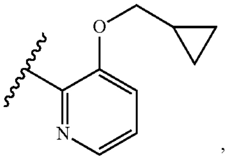
,
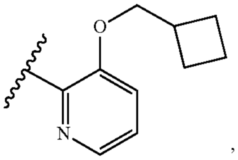
,
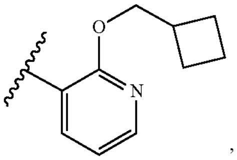
,
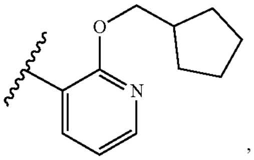
,
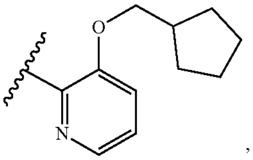
,
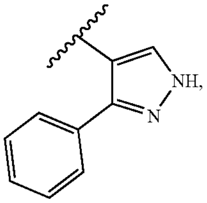
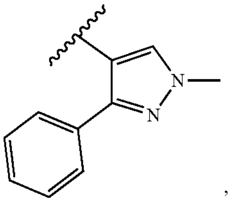
,
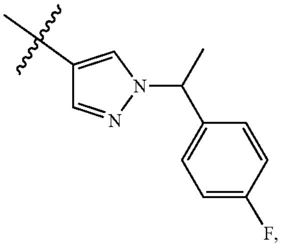
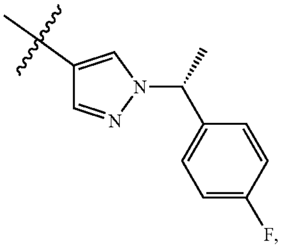
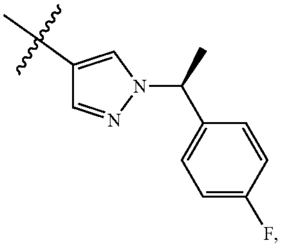

-continued

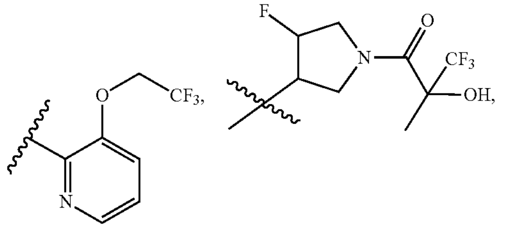

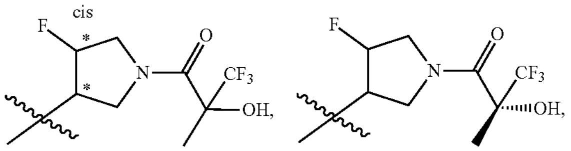

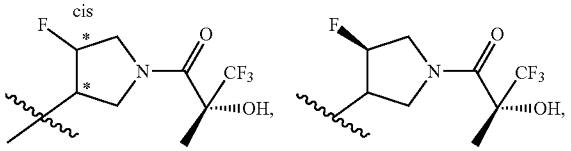

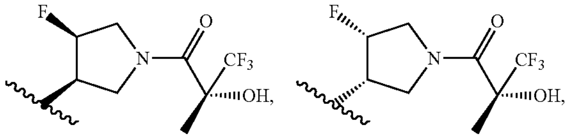

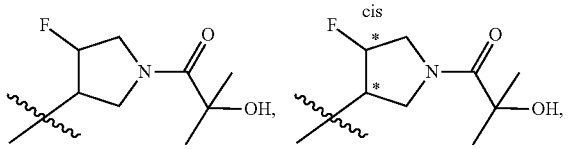

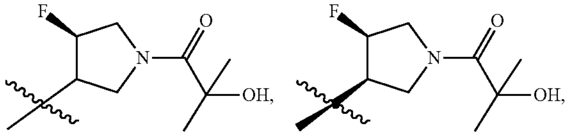

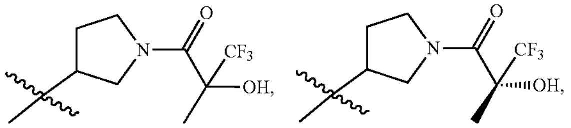

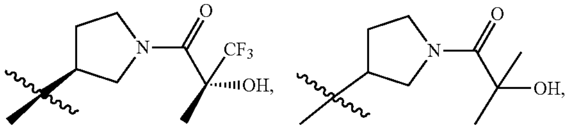

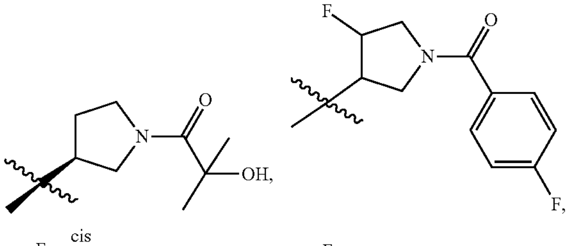

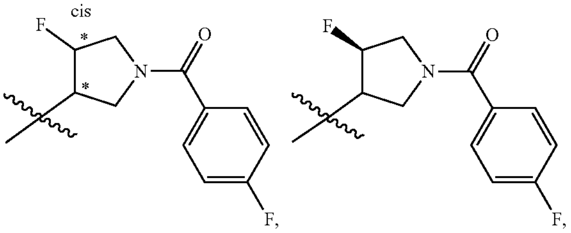

and

-continued

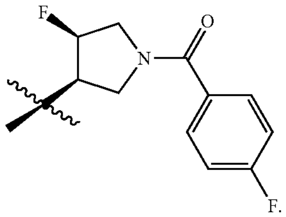

In an embodiment of the present disclosure, in the 9- or 10-membered aromatic fused bicyclic ring and 8- to 10-membered bicyclic heteroaryl, when the non-aromatic ring is 3- to 6-membered saturated or partially unsaturated monocyclic heterocycloalkyl, the monocyclic heterocycloalkyl is selected from the following structures:

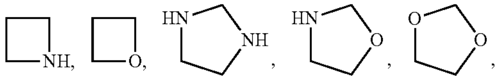

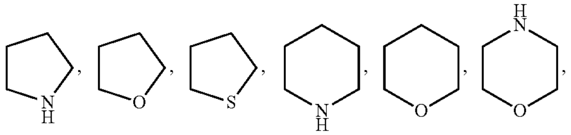

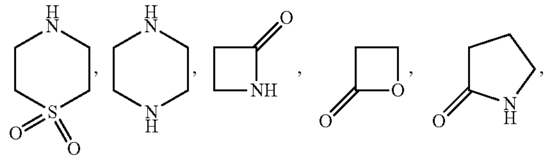

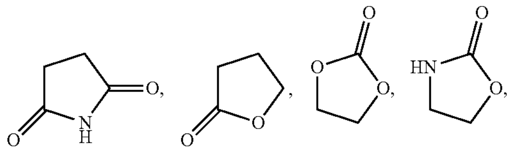

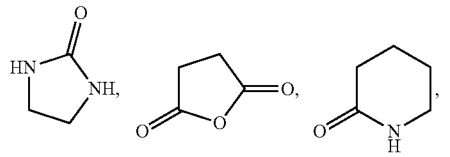

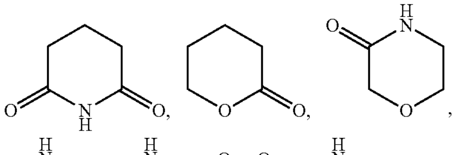

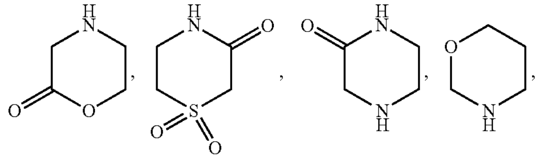

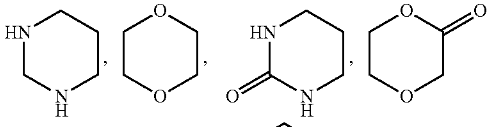

and

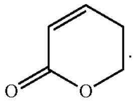

In an embodiment of the present disclosure, L is a bond.

In an embodiment of the present disclosure, L is selected from the following structures:

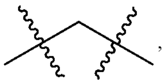 , 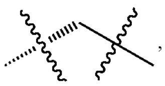 , 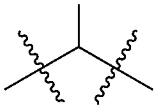 ,

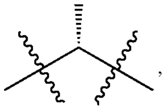 , 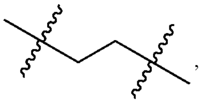 ,

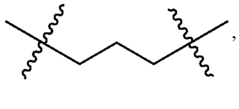 , 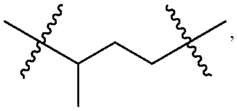 ,

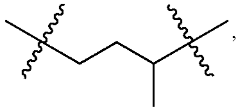 , 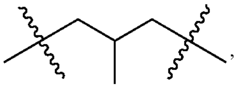 ,

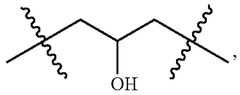 , 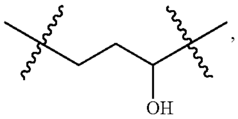 ,

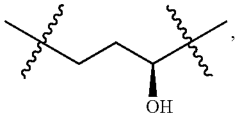 , 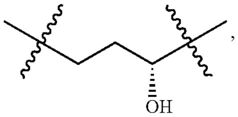 ,

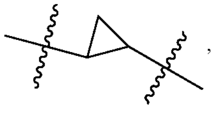 , 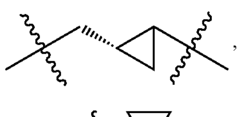 ,

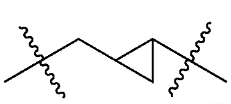 , 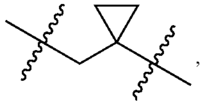 ,

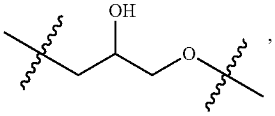 ,

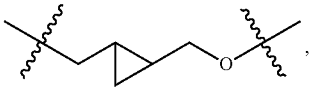 ,

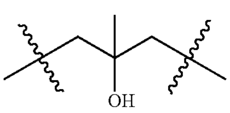 , and 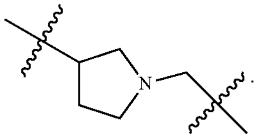 .

In an embodiment of the present disclosure, $R_3$ and $R_4$ form together with the carbon atom adjacent thereto a $C_{3-8}$ cycloalkyl ring, which is selected from cyclopropyl, cyclobutyl, cyclopentyl, cyclopentenyl, cyclohexyl, cyclohexenyl, cyclohexadienyl, cycloheptyl, cycloheptatrienyl, cyclooctyl, cyclobutanone, cyclobutane-1,2-dione, cyclopentanone, cyclopentane-1,3-dione, cyclohexanone, and cyclohexane-1,3-dione; the $C_{3-8}$ cycloalkyl ring is unsubstituted or substituted with 1, 2, 3 or 4 substituents each independently selected from group S.

In an embodiment of the present disclosure, $R_5$ and $R_6$ form together with the carbon atom adjacent thereto a $C_{3-8}$ cycloalkyl ring, which is selected from cyclopropyl, cyclobutyl, cyclopentyl, cyclopentenyl, cyclohexyl, cyclohexenyl, cyclohexadienyl, cycloheptyl, cycloheptatrienyl, cyclooctyl, cyclobutanone, cyclobutane-1,2-dione, cyclopentanone, cyclopentane-1,3-dione, cyclohexanone, and cyclohexane-1,3-dione; the $C_{3-8}$ cycloalkyl ring is unsubstituted or substituted with 1, 2, 3 or 4 substituents each independently selected from group S.

In an embodiment of the present disclosure, $R_4$ and $R_5$ form together with the carbon atom adjacent thereto a $C_{3-8}$ cycloalkyl ring, which is selected from cyclopropyl, cyclobutyl, cyclopentyl, cyclopentenyl, cyclohexyl, cyclohexenyl, cyclohexadienyl, cycloheptyl, cycloheptatrienyl, cyclooctyl, cyclobutanone, cyclobutane-1,2-dione, cyclopentanone, cyclopentane-1,3-dione, cyclohexanone, and cyclohexane-1,3-dione; the $C_{3-8}$ cycloalkyl ring is unsubstituted or substituted with 1, 2, 3 or 4 substituents each independently selected from group S.

In an embodiment of the present disclosure, $R_{21}$ and $R_{22}$ form together with the carbon atom adjacent thereto a $C_{3-8}$ cycloalkyl ring, which is selected from cyclopropyl, cyclobutyl, cyclopentyl, cyclopentenyl, cyclohexyl, cyclohexenyl, cyclohexadienyl, cycloheptyl, cycloheptatrienyl, cyclooctyl, cyclobutanone, cyclobutane-1,2-dione, cyclopentanone, cyclopentane-1,3-dione, cyclohexanone, and cyclohexane-1,3-dione; the $C_{3-8}$ cycloalkyl ring is unsubstituted or substituted with 1, 2, 3 or 4 substituents each independently selected from group S.

In an embodiment of the present disclosure, $R_{31}$ and $R_{32}$ form together with the carbon atom adjacent thereto a $C_{3-8}$ cycloalkyl ring, which is selected from cyclopropyl, cyclobutyl, cyclopentyl, cyclopentenyl, cyclohexyl, cyclohexenyl, cyclohexadienyl, cycloheptyl, cycloheptatrienyl, cyclooctyl, cyclobutanone, cyclobutane-1,2-dione, cyclopentanone, cyclopentane-1,3-dione, cyclohexanone, and cyclohexane-1,3-dione; the $C_{3-8}$ cycloalkyl ring is unsubstituted or substituted with 1, 2, 3 or 4 substituents each independently selected from group S.

In an embodiment of the present disclosure, $R_{21}$ and $R_{31}$ form together with the carbon atom adjacent thereto a $C_{3-8}$ cycloalkyl ring, which is selected from cyclopropyl, cyclobutyl, cyclopentyl, cyclopentenyl, cyclohexyl, cyclohexenyl, cyclohexadienyl, cycloheptyl, cycloheptatrienyl, cyclooctyl, cyclobutanone, cyclobutane-1,2-dione, cyclopentanone, cyclopentane-1,3-dione, cyclohexanone, and cyclohexane-1,3-dione; the $C_{3-8}$ cycloalkyl ring is unsubstituted or substituted with 1, 2, 3 or 4 substituents each independently selected from group S.

In an embodiment of the present disclosure, $R_{11}$ and $R_{31}$ form together with the atom adjacent thereto a $C_{3-8}$ cycloalkyl ring, which is selected from cyclopropyl, cyclobutyl, cyclopentyl, cyclopentenyl, cyclohexyl, cyclohexenyl, cyclohexadienyl, cycloheptyl, cycloheptatrienyl, cyclooctyl, cyclobutanone, cyclobutane-1,2-dione, cyclopentanone, cyclopentane-1,3-dione, cyclohexanone, and cyclohexane-1,3-dione; the $C_{3-8}$ cycloalkyl ring is unsubstituted or substituted with 1, 2, 3 or 4 substituents each independently selected from group S.

In an embodiment of the present disclosure, $R_{23}$ and $R_{24}$ form together with the carbon atom adjacent thereto a $C_{3-8}$ cycloalkyl ring, which is selected from cyclopropyl, cyclobutyl, cyclopentyl, cyclopentenyl, cyclohexyl, cyclohexenyl, cyclohexadienyl, cycloheptyl, cycloheptatrienyl, cyclooctyl, cyclobutanone, cyclobutane-1,2-dione, cyclopentanone, cyclopentane-1,3-dione, cyclohexanone, and cyclohexane-1,3-dione; the $C_{3-8}$ cycloalkyl ring is unsubstituted or substituted with 1, 2, 3 or 4 substituents each independently selected from group S.

In an embodiment of the present disclosure, $R_3$ and $R_4$ form together with the carbon atom adjacent thereto a 3- to 6-membered heterocycloalkyl ring, which is selected from aziridine, ethylene oxide, azetidine, oxetane, tetrahydrofuran, tetrahydrothiophene, tetrahydropyrrole, piperidine, piperazine, morpholine, thiomorpholine, thiomorpholine-1,1-dioxide and tetrahydropyran; the 3- to 6-membered heterocycloalkyl ring is unsubstituted or substituted with 1, 2, 3 or 4 substituents each independently selected from group S.

In an embodiment of the present disclosure, $R_5$ and $R_6$ form together with the carbon atom adjacent thereto a 3- to 6-membered heterocycloalkyl ring, which is selected from aziridine, ethylene oxide, azetidine, oxetane, tetrahydrofuran, tetrahydrothiophene, tetrahydropyrrole, piperidine, piperazine, morpholine, thiomorpholine, thiomorpholine-1,1-dioxide and tetrahydropyran; the 3- to 6-membered heterocycloalkyl ring is unsubstituted or substituted with 1, 2, 3 or 4 substituents each independently selected from group S.

In an embodiment of the present disclosure, $R_4$ and $R_5$ form together with the carbon atom adjacent thereto a 3- to 6-membered heterocycloalkyl ring, which is selected from aziridine, ethylene oxide, azetidine, oxetane, tetrahydrofuran, tetrahydrothiophene, tetrahydropyrrole, piperidine, piperazine, morpholine, thiomorpholine, thiomorpholine-1,1-dioxide and tetrahydropyran; the 3- to 6-membered heterocycloalkyl ring is unsubstituted or substituted with 1, 2, 3 or 4 substituents each independently selected from group S.

In an embodiment of the present disclosure, $R_{21}$ and $R_{22}$ form together with the carbon atom adjacent thereto a 3- to 6-membered heterocycloalkyl ring, which is selected from aziridine, ethylene oxide, azetidine, oxetane, tetrahydrofuran, tetrahydrothiophene, tetrahydropyrrole, piperidine, piperazine, morpholine, thiomorpholine, thiomorpholine-1,1-dioxide and tetrahydropyran; the 3- to 6-membered heterocycloalkyl ring is unsubstituted or substituted with 1, 2, 3 or 4 substituents each independently selected from group S.

In an embodiment of the present disclosure, $R_{31}$ and $R_{32}$ form together with the carbon atom adjacent thereto a 3- to 6-membered heterocycloalkyl ring, which is selected from aziridine, ethylene oxide, azetidine, oxetane, tetrahydrofuran, tetrahydrothiophene, tetrahydropyrrole, piperidine, piperazine, morpholine, thiomorpholine, thiomorpholine-1,1-dioxide and tetrahydropyran; the 3- to 6-membered heterocycloalkyl ring is unsubstituted or substituted with 1, 2, 3 or 4 substituents each independently selected from group S.

In an embodiment of the present disclosure, $R_{21}$ and $R_{31}$ form together with the carbon atom adjacent thereto a 3- to 6-membered heterocycloalkyl ring, which is selected from aziridine, ethylene oxide, azetidine, oxetane, tetrahydrofuran, tetrahydrothiophene, tetrahydropyrrole, piperidine, piperazine, morpholine, thiomorpholine, thiomorpholine-1,1-dioxide and tetrahydropyran; the 3- to 6-membered heterocycloalkyl ring is unsubstituted or substituted with 1, 2, 3 or 4 substituents each independently selected from group S.

In an embodiment of the present disclosure, $R_{11}$ and $R_{31}$ are connected form together to form a 3- to 6-membered heterocycloalkyl ring, which is selected from aziridine, ethylene oxide, azetidine, oxetane, tetrahydrofuran, tetrahydrothiophene, tetrahydropyrrole, piperidine, piperazine, morpholine, thiomorpholine, thiomorpholine-1,1-dioxide and tetrahydropyran; the 3- to 6-membered heterocycloalkyl ring is unsubstituted or substituted with 1, 2, 3 or 4 substituents each independently selected from group S.

In an embodiment of the present disclosure, $R_{23}$ and $R_{24}$ form together with the carbon atom adjacent thereto a 3- to 6-membered heterocycloalkyl ring, which is selected from aziridine, ethylene oxide, azetidine, oxetane, tetrahydrofuran, tetrahydrothiophene, tetrahydropyrrole, piperidine, piperazine, morpholine, thiomorpholine, thiomorpholine-1,1-dioxide and tetrahydropyran; the 3- to 6-membered heterocycloalkyl ring is unsubstituted or substituted with 1, 2, 3 or 4 substituents each independently selected from group S.

In an embodiment of the present disclosure, $R_{24}$ and $R_{33}$ form together with the atom adjacent thereto a 3- to 6-membered nitrogen-containing heterocycloalkyl ring, which is selected from aziridine, azetidine, tetrahydropyrrole, piperidine, piperazine, morpholine, thiomorpholine and thiomorpholine-1,1-dioxide; the 3- to 6-membered nitrogen-containing heterocycloalkyl ring is unsubstituted or substituted with 1, 2, 3 or 4 substituents each independently selected from group S.

In an embodiment of the present disclosure, $R_{14}$ and $R_{33}$ form together with the atom adjacent thereto a 3- to 6-membered nitrogen-containing heterocycloalkyl ring, which is selected from aziridine, azetidine, tetrahydropyrrole, piperidine, piperazine, morpholine, thiomorpholine and thiomorpholine-1,1-dioxide; the 3- to 6-membered nitrogen-containing heterocycloalkyl ring is unsubstituted or substituted with 1, 2, 3 or 4 substituents each independently selected from group S.

In an embodiment of the present disclosure, the 3- to 6-membered heterocycloalkyl is selected from the following structures:

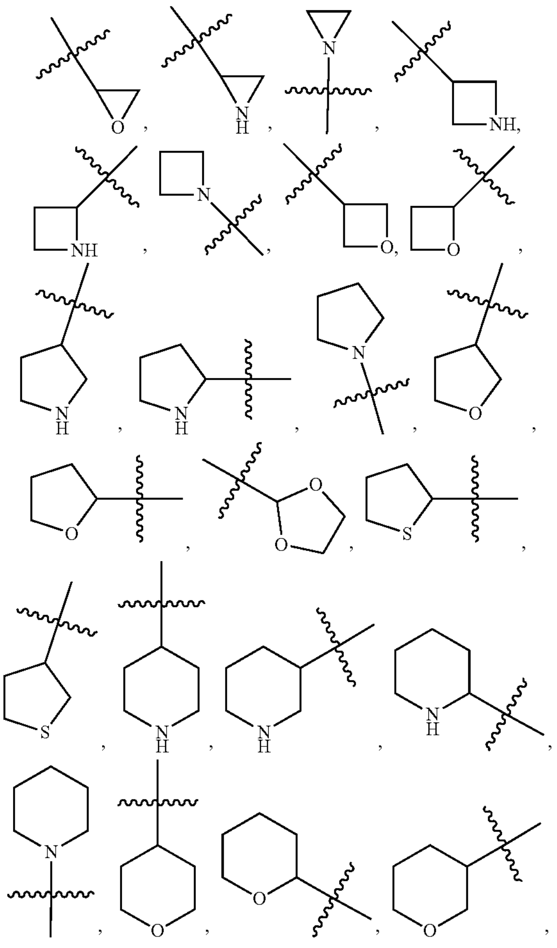

-continued

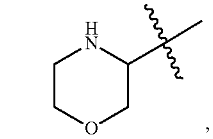 , 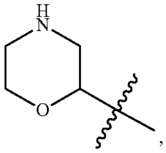 , 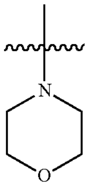 ,

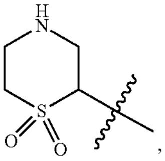 , 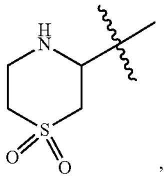 , 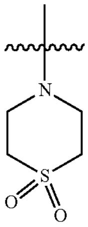 , 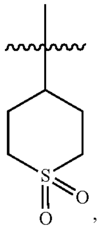 ,

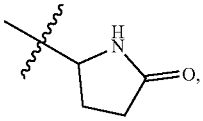 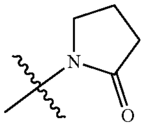 , 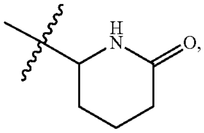

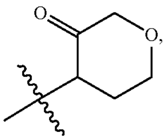 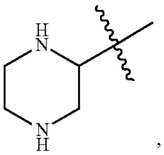 , and 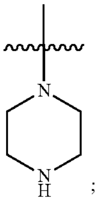 ;

the above 3- to 6-membered heterocycloalkyl is unsubstituted or substituted with 1, 2, 3 or 4 substituents each independently selected from group S.

In an embodiment of the present disclosure, the 3- to 8-membered nitrogen-containing heterocycloalkyl ring formed by $R_{a0}$ and $R_{b0}$ form together with the nitrogen atom adjacent thereto, or the 3- to 8-membered nitrogen-containing heterocycloalkyl ring formed by $R_{a0}'$ and $R_{b0}'$ form together with the nitrogen atom adjacent thereto is selected from the following structures:

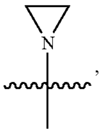 , 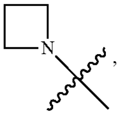 , 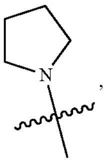 , 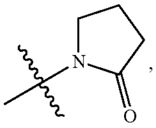 ,

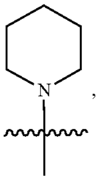 , 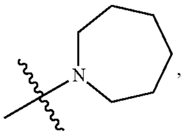 , 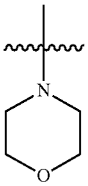 , 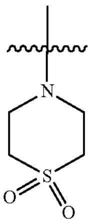 ,

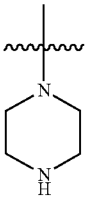 , and 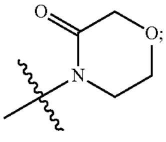

the above 3- to 8-membered nitrogen-containing heterocycloalkyl ring is unsubstituted or substituted with 1, 2, 3 or 4 substituents each independently selected from group S.

In an embodiment of the present disclosure, in each formula, $R_1$, $R_2$, $R_3$, $R_4$, $R_5$, $R_6$, A and B are each independently the corresponding groups in each specific compound in the embodiment.

In an embodiment of the present disclosure, the compound of formula (I) has a structure selected from table A.

TABLE A

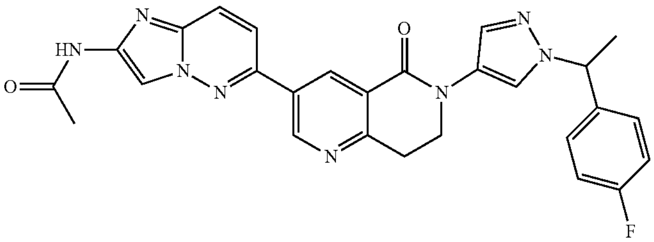 [SMILES: CC(=O)Nc1cn2nc(-c3cnc4c(c3)C(=O)N(c3cnn(C(C)c5ccc(F)cc5)c3)CC4)ccc2n1]

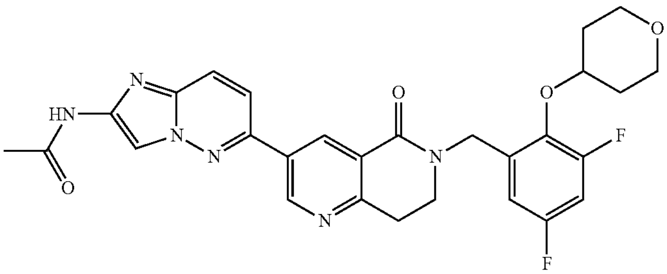 [SMILES: CC(=O)Nc1cn2nc(-c3cnc4c(c3)C(=O)N(Cc3cc(F)cc(F)c3OC3CCOCC3)CC4)ccc2n1]

TABLE A-continued
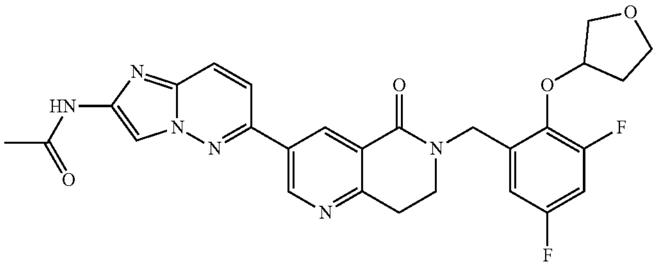 [SMILES: CC(=O)Nc1cn2nc(-c3cnc4c(c3)C(=O)N(Cc3cc(F)cc(F)c3OC3CCOC3)CC4)ccc2n1]
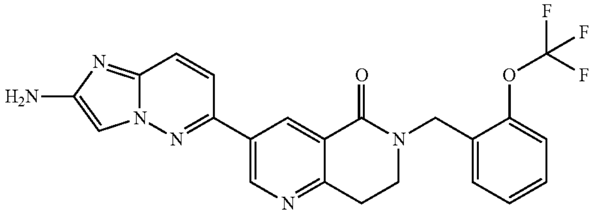 [SMILES: Nc1cn2nc(-c3cnc4c(c3)C(=O)N(Cc3ccccc3OC(F)(F)F)CC4)ccc2n1]
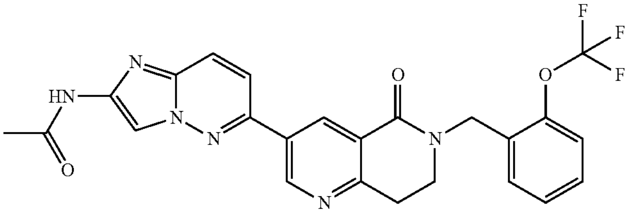 [SMILES: CC(=O)Nc1cn2nc(-c3cnc4c(c3)C(=O)N(Cc3ccccc3OC(F)(F)F)CC4)ccc2n1]
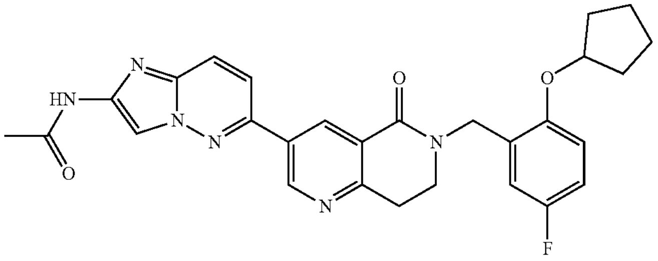 [SMILES: CC(=O)Nc1cn2nc(-c3cnc4c(c3)C(=O)N(Cc3cc(F)ccc3OC3CCCC3)CC4)ccc2n1]
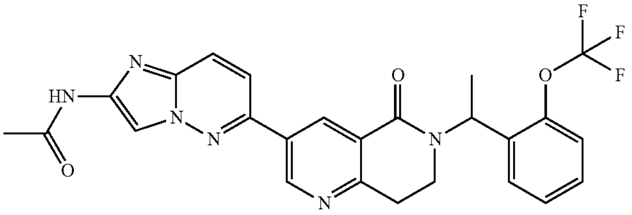 [SMILES: CC(=O)Nc1cn2nc(-c3cnc4c(c3)C(=O)N(C(C)c3ccccc3OC(F)(F)F)CC4)ccc2n1]
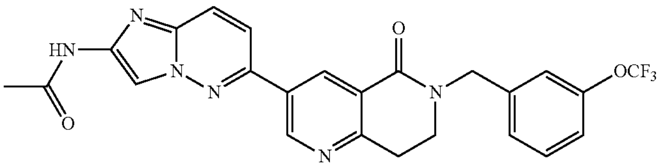 [SMILES: CC(=O)Nc1cn2nc(-c3cnc4c(c3)C(=O)N(Cc3cccc(OC(F)(F)F)c3)CC4)ccc2n1]
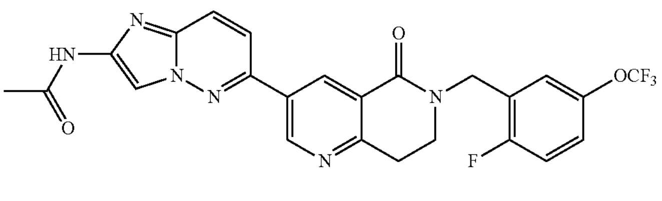 [SMILES: CC(=O)Nc1cn2nc(-c3cnc4c(c3)C(=O)N(Cc3cc(OC(F)(F)F)ccc3F)CC4)ccc2n1]

TABLE A-continued
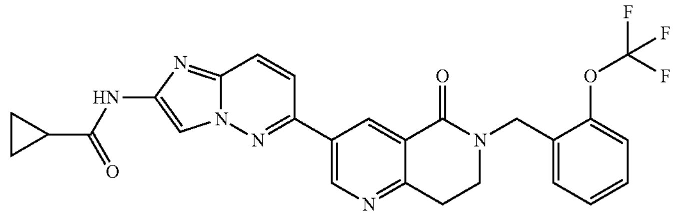 [SMILES: O=C(Nc1cn2nc(-c3cnc4c(c3)C(=O)N(Cc3ccccc3OC(F)(F)F)CC4)ccc2n1)C1CC1]
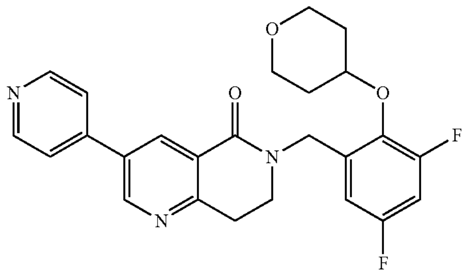 [SMILES: O=C1c2cc(-c3ccncc3)cnc2CCN1Cc1cc(F)cc(F)c1OC1CCOCC1]
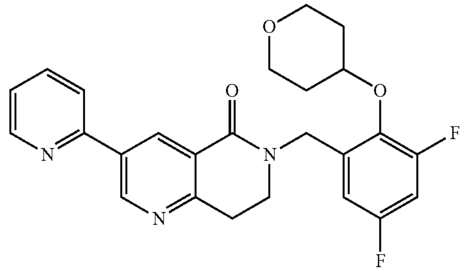 [SMILES: O=C1c2cc(-c3ccccn3)cnc2CCN1Cc1cc(F)cc(F)c1OC1CCOCC1]
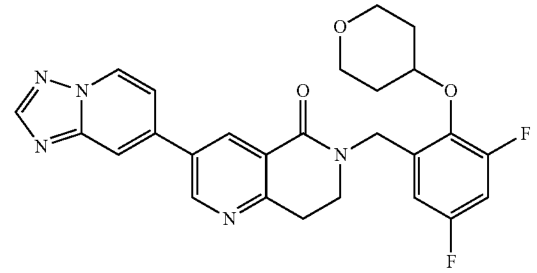 [SMILES: O=C1c2cc(-c3ccn4ncnc4c3)cnc2CCN1Cc1cc(F)cc(F)c1OC1CCOCC1]
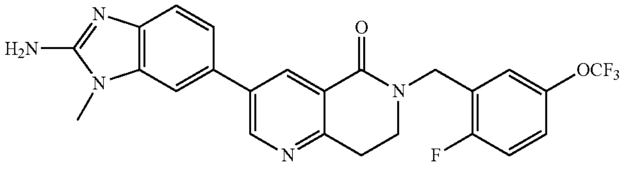 [SMILES: Cn1c(N)nc2ccc(-c3cnc4c(c3)C(=O)N(Cc3cc(OC(F)(F)F)ccc3F)CC4)cc21]
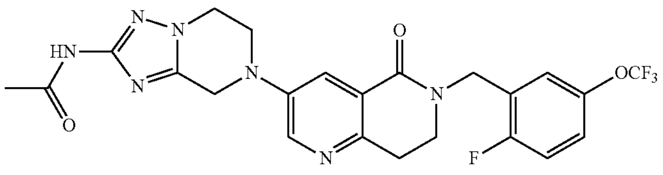 [SMILES: CC(=O)Nc1nc2n(n1)CCN(c1cnc3c(c1)C(=O)N(Cc1cc(OC(F)(F)F)ccc1F)CC3)C2]
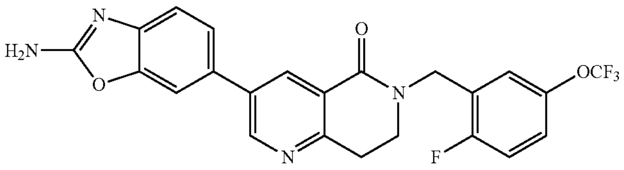 [SMILES: Nc1nc2ccc(-c3cnc4c(c3)C(=O)N(Cc3cc(OC(F)(F)F)ccc3F)CC4)cc2o1]

TABLE A-continued
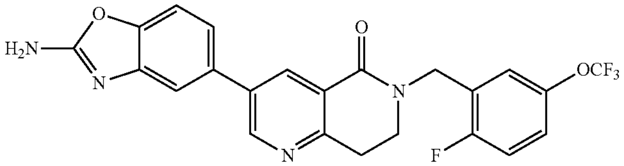 [SMILES: Nc1nc2cc(-c3cnc4c(c3)C(=O)N(Cc3cc(OC(F)(F)F)ccc3F)CC4)ccc2o1]
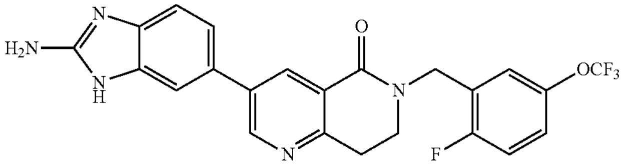 [SMILES: Nc1nc2ccc(-c3cnc4c(c3)C(=O)N(Cc3cc(OC(F)(F)F)ccc3F)CC4)cc2[nH]1]
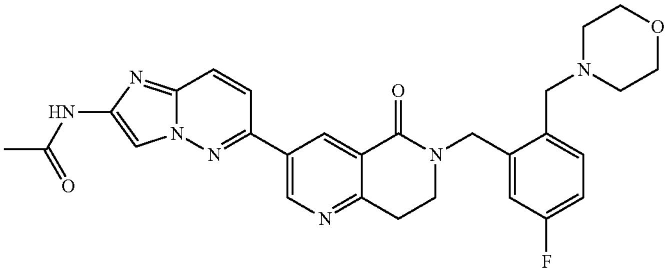
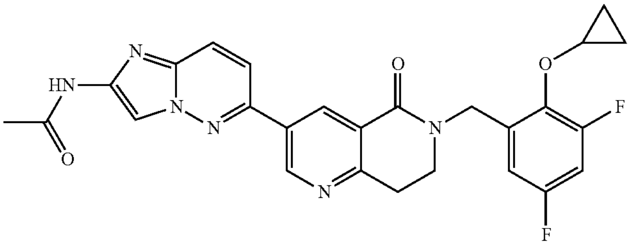 [SMILES: CC(=O)Nc1cn2nc(-c3cnc4c(c3)C(=O)N(Cc3cc(F)cc(F)c3OC3CC3)CC4)ccc2n1]
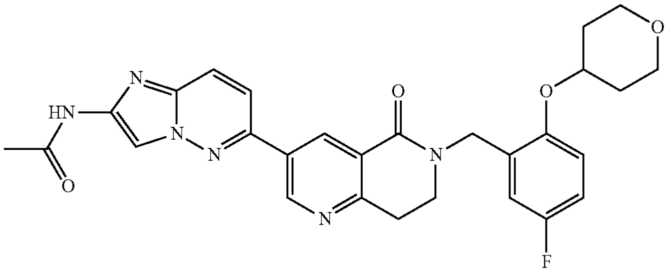 [SMILES: CC(=O)Nc1cn2nc(-c3cnc4c(c3)C(=O)N(Cc3cc(F)ccc3OC3CCOCC3)CC4)ccc2n1]
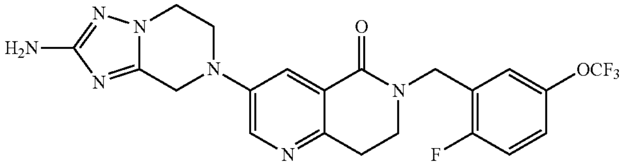 [SMILES: Nc1nc2n(n1)CCN(c1cnc3c(c1)C(=O)N(Cc1cc(OC(F)(F)F)ccc1F)CC3)C2]
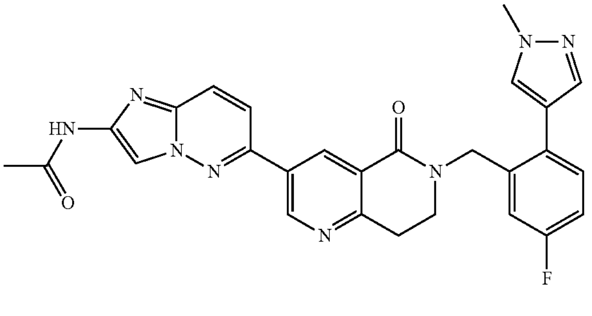 [SMILES: CC(=O)Nc1cn2nc(-c3cnc4c(c3)C(=O)N(Cc3cc(F)ccc3-c3cnn(C)c3)CC4)ccc2n1]

TABLE A-continued
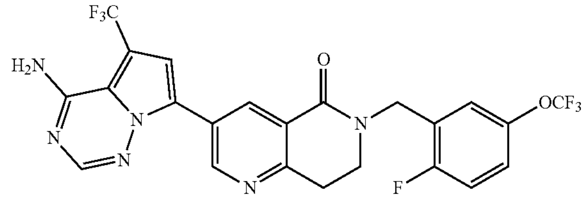 [SMILES: Nc1ncnn2c(-c3cnc4c(c3)C(=O)N(Cc3cc(OC(F)(F)F)ccc3F)CC4)cc(C(F)(F)F)c12]
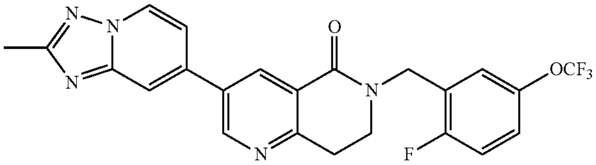 [SMILES: Cc1nc2cc(-c3cnc4c(c3)C(=O)N(Cc3cc(OC(F)(F)F)ccc3F)CC4)ccn2n1]
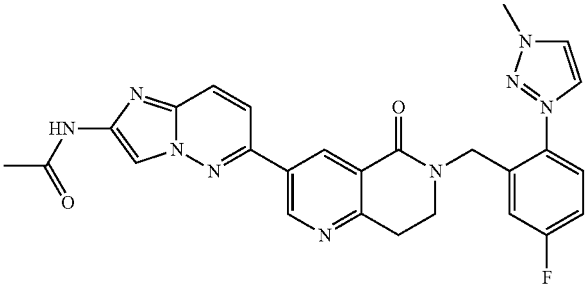
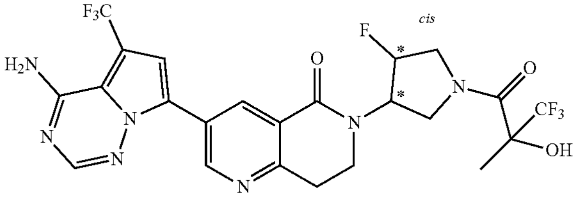 [SMILES: CC(O)(C(=O)N1CC(F)C(N2CCc3ncc(-c4cc(C(F)(F)F)c5c(N)ncnn45)cc3C2=O)C1)C(F)(F)F]
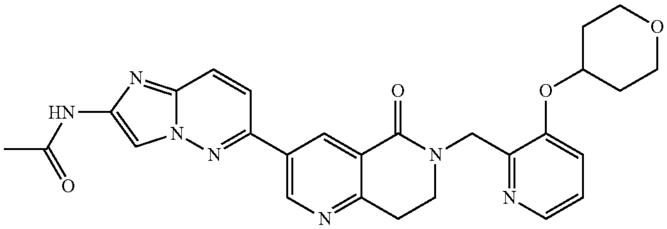 [SMILES: CC(=O)Nc1cn2nc(-c3cnc4c(c3)C(=O)N(Cc3ncccc3OC3CCOCC3)CC4)ccc2n1]
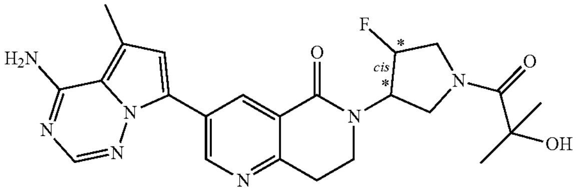 [SMILES: Cc1cc(-c2cnc3c(c2)C(=O)N(C2CN(C(=O)C(C)(C)O)CC2F)CC3)n2ncnc(N)c12]
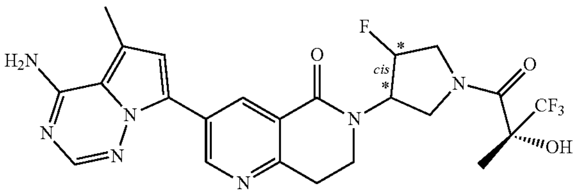 [SMILES: Cc1cc(-c2cnc3c(c2)C(=O)N(C2CN(C(=O)[C@@](C)(O)C(F)(F)F)CC2F)CC3)n2ncnc(N)c12]

TABLE A-continued
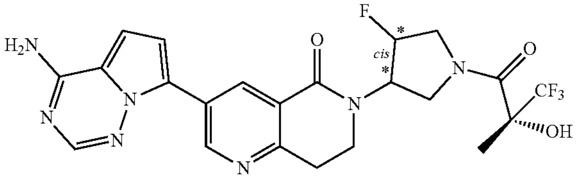 [SMILES: C[C@@](O)(C(=O)N1CC(F)C(N2CCc3ncc(-c4ccc5c(N)ncnn45)cc3C2=O)C1)C(F)(F)F]
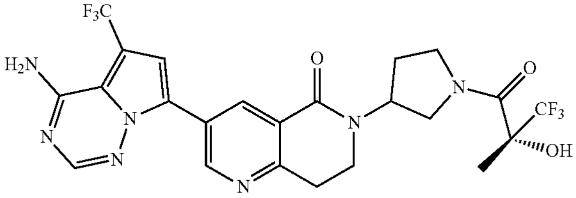 [SMILES: C[C@@](O)(C(=O)N1CCC(N2CCc3ncc(-c4cc(C(F)(F)F)c5c(N)ncnn45)cc3C2=O)C1)C(F)(F)F]
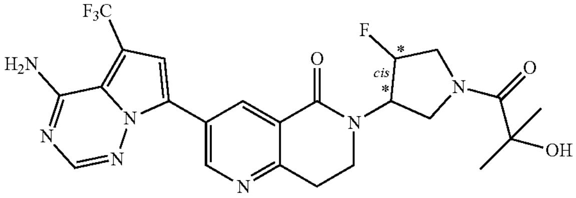 [SMILES: CC(C)(O)C(=O)N1CC(F)C(N2CCc3ncc(-c4cc(C(F)(F)F)c5c(N)ncnn45)cc3C2=O)C1]
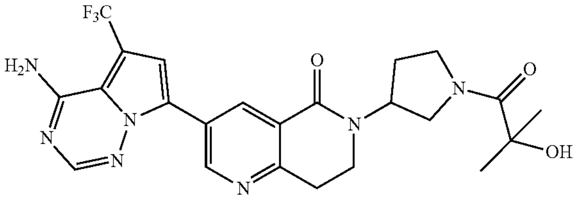 [SMILES: CC(C)(O)C(=O)N1CCC(N2CCc3ncc(-c4cc(C(F)(F)F)c5c(N)ncnn45)cc3C2=O)C1]
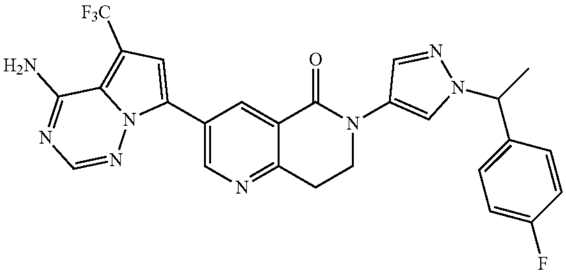 [SMILES: CC(c1ccc(F)cc1)n1cc(N2CCc3ncc(-c4cc(C(F)(F)F)c5c(N)ncnn45)cc3C2=O)cn1]
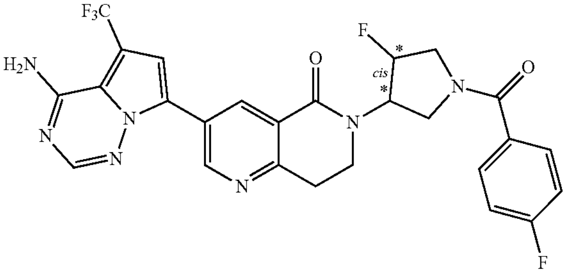 [SMILES: Nc1ncnn2c(-c3cnc4c(c3)C(=O)N(C3CN(C(=O)c5ccc(F)cc5)CC3F)CC4)cc(C(F)(F)F)c12]
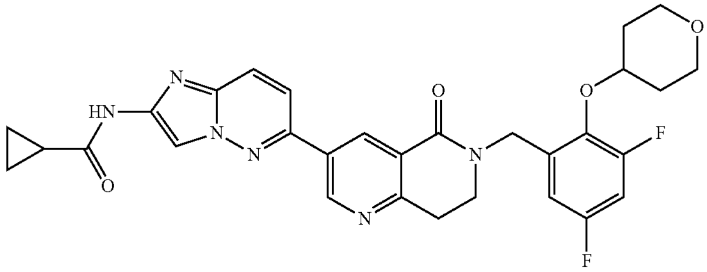 [SMILES: O=C(Nc1cn2nc(-c3cnc4c(c3)C(=O)N(Cc3cc(F)cc(F)c3OC3CCOCC3)CC4)ccc2n1)C1CC1]

TABLE A-continued
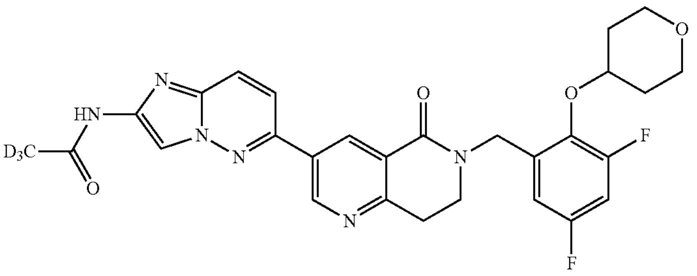 [SMILES: [2H]C([2H])([2H])C(=O)Nc1cn2nc(-c3cnc4c(c3)C(=O)N(Cc3cc(F)cc(F)c3OC3CCOCC3)CC4)ccc2n1]
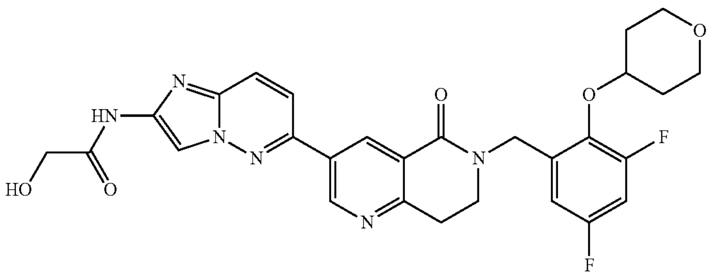 [SMILES: O=C(CO)Nc1cn2nc(-c3cnc4c(c3)C(=O)N(Cc3cc(F)cc(F)c3OC3CCOCC3)CC4)ccc2n1]
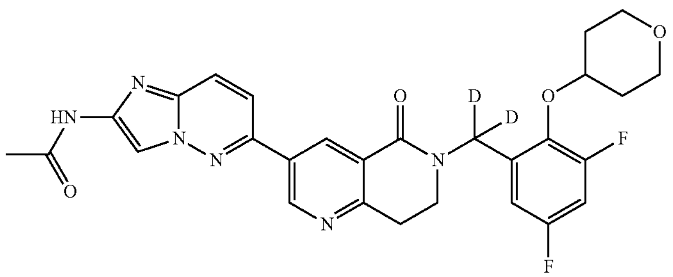 [SMILES: [2H]C([2H])(c1cc(F)cc(F)c1OC1CCOCC1)N1CCc2ncc(-c3ccc4nc(NC(C)=O)cn4n3)cc2C1=O]
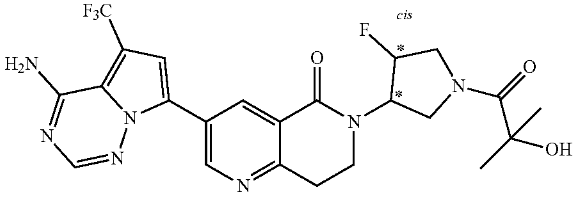 [SMILES: CC(C)(O)C(=O)N1CC(F)C(N2CCc3ncc(-c4cc(C(F)(F)F)c5c(N)ncnn45)cc3C2=O)C1]
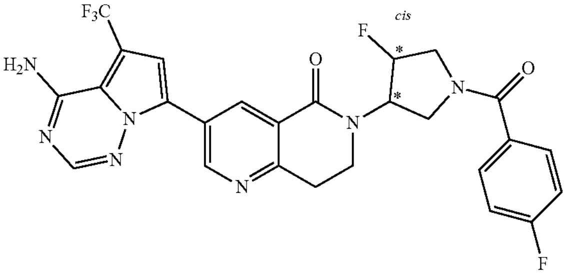 [SMILES: Nc1ncnn2c(-c3cnc4c(c3)C(=O)N(C3CN(C(=O)c5ccc(F)cc5)CC3F)CC4)cc(C(F)(F)F)c12]
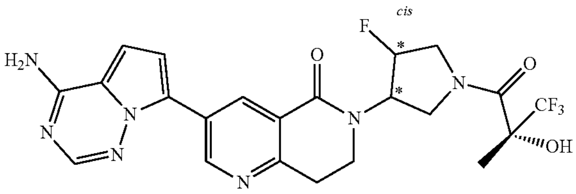

TABLE A-continued
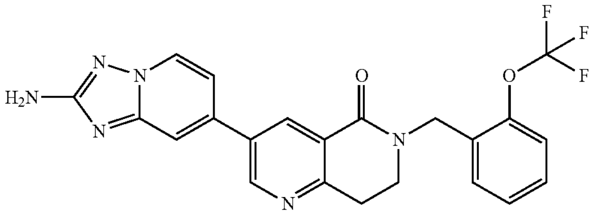 [SMILES: Nc1nc2cc(-c3cnc4c(c3)C(=O)N(Cc3ccccc3OC(F)(F)F)CC4)ccn2n1]
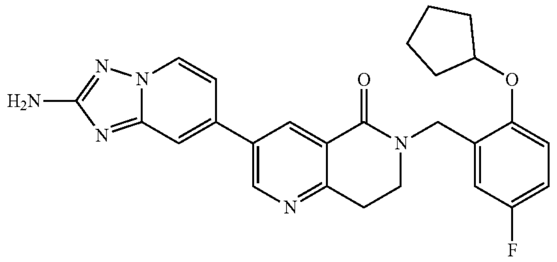 [SMILES: Nc1nc2cc(-c3cnc4c(c3)C(=O)N(Cc3cc(F)ccc3OC3CCCC3)CC4)ccn2n1]
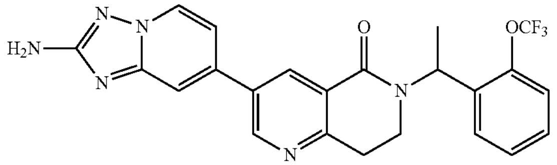 [SMILES: CC(c1ccccc1OC(F)(F)F)N1CCc2ncc(-c3ccn4nc(N)nc4c3)cc2C1=O]
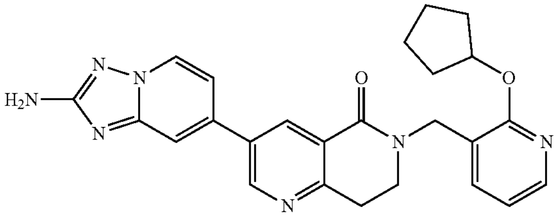 [SMILES: Nc1nc2cc(-c3cnc4c(c3)C(=O)N(Cc3cccnc3OC3CCCC3)CC4)ccn2n1]
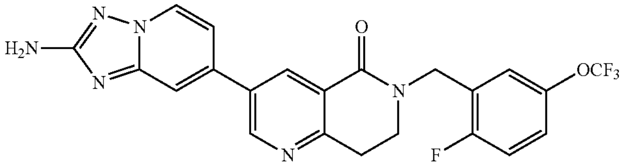 [SMILES: Nc1nc2cc(-c3cnc4c(c3)C(=O)N(Cc3cc(OC(F)(F)F)ccc3F)CC4)ccn2n1]
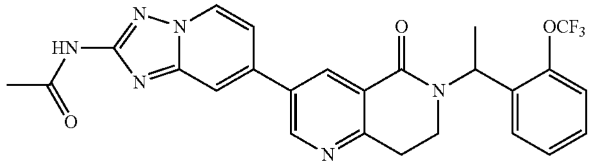 [SMILES: CC(=O)Nc1nc2cc(-c3cnc4c(c3)C(=O)N(C(C)c3ccccc3OC(F)(F)F)CC4)ccn2n1]
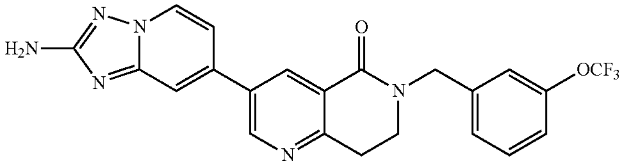 [SMILES: Nc1nc2cc(-c3cnc4c(c3)C(=O)N(Cc3cccc(OC(F)(F)F)c3)CC4)ccn2n1]

TABLE A-continued
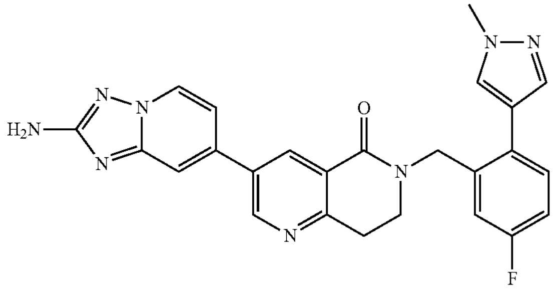 [SMILES: Cn1cc(-c2ccc(F)cc2CN2CCc3ncc(-c4ccn5nc(N)nc5c4)cc3C2=O)cn1]
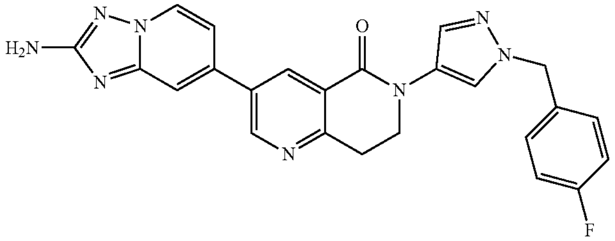 [SMILES: Nc1nc2cc(-c3cnc4c(c3)C(=O)N(c3cnn(Cc5ccc(F)cc5)c3)CC4)ccn2n1]
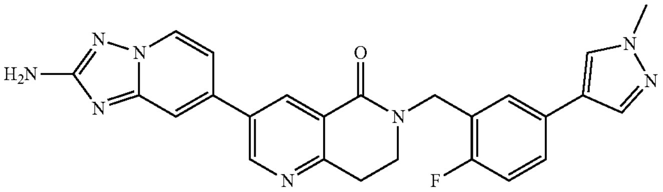 [SMILES: Cn1cc(-c2ccc(F)c(CN3CCc4ncc(-c5ccn6nc(N)nc6c5)cc4C3=O)c2)cn1]
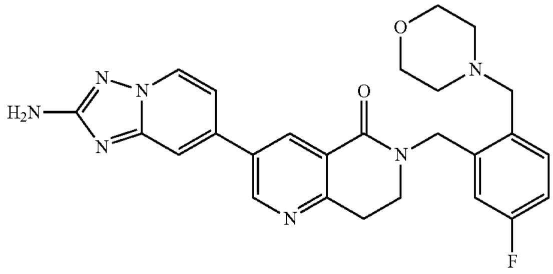 [SMILES: Nc1nc2cc(-c3cnc4c(c3)C(=O)N(Cc3cc(F)ccc3CN3CCOCC3)CC4)ccn2n1]
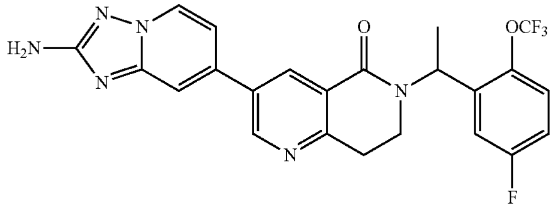 [SMILES: CC(c1cc(F)ccc1OC(F)(F)F)N1CCc2ncc(-c3ccn4nc(N)nc4c3)cc2C1=O]
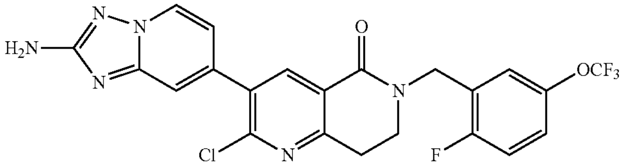 [SMILES: Nc1nc2cc(-c3cc4c(nc3Cl)CCN(Cc3cc(OC(F)(F)F)ccc3F)C4=O)ccn2n1]
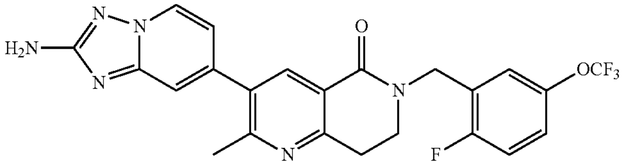 [SMILES: Cc1nc2c(cc1-c1ccn3nc(N)nc3c1)C(=O)N(Cc1cc(OC(F)(F)F)ccc1F)CC2]

TABLE A-continued
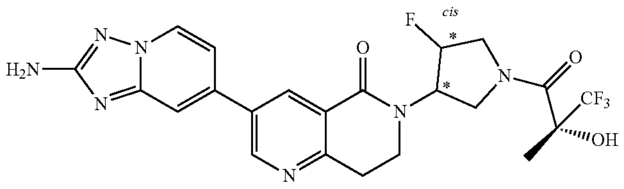 [SMILES: C[C@@](O)(C(=O)N1CC(F)C(N2CCc3ncc(-c4ccn5nc(N)nc5c4)cc3C2=O)C1)C(F)(F)F]
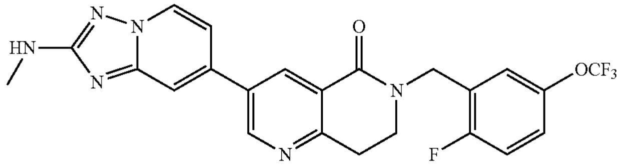 [SMILES: CNc1nc2cc(-c3cnc4c(c3)C(=O)N(Cc3cc(OC(F)(F)F)ccc3F)CC4)ccn2n1]
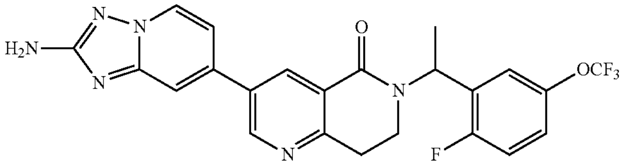 [SMILES: CC(c1cc(OC(F)(F)F)ccc1F)N1CCc2ncc(-c3ccn4nc(N)nc4c3)cc2C1=O]
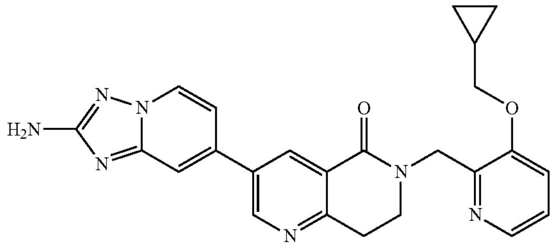 [SMILES: Nc1nc2cc(-c3cnc4c(c3)C(=O)N(Cc3ncccc3OCC3CC3)CC4)ccn2n1]
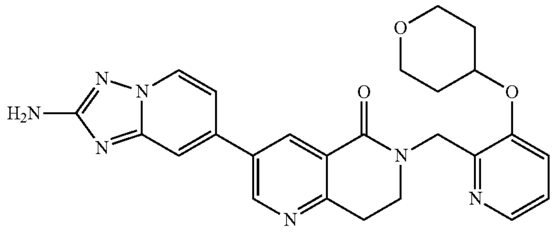 [SMILES: Nc1nc2cc(-c3cnc4c(c3)C(=O)N(Cc3ncccc3OC3CCOCC3)CC4)ccn2n1]
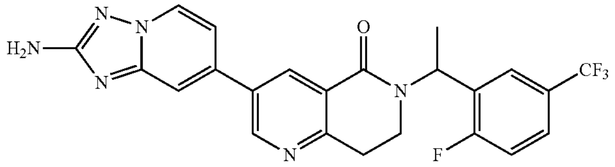 [SMILES: CC(c1cc(C(F)(F)F)ccc1F)N1CCc2ncc(-c3ccn4nc(N)nc4c3)cc2C1=O]
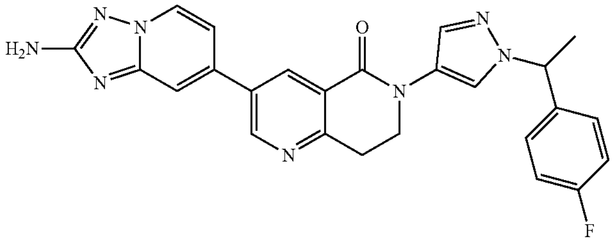

TABLE A-continued
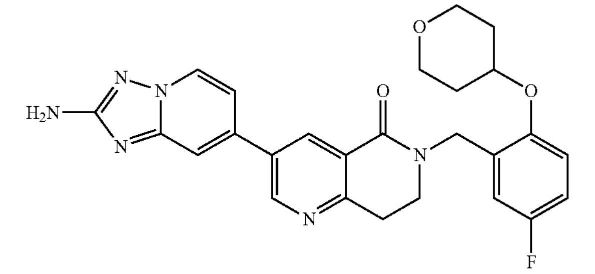
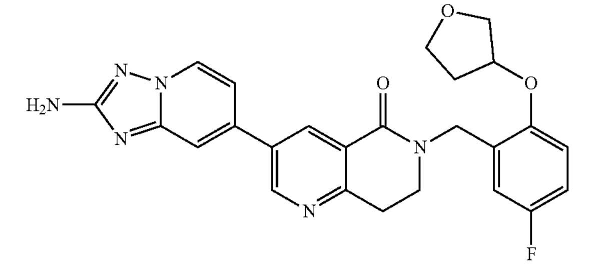 [SMILES: Nc1nc2cc(-c3cnc4c(c3)C(=O)N(Cc3cc(F)ccc3OC3CCOC3)CC4)ccn2n1]
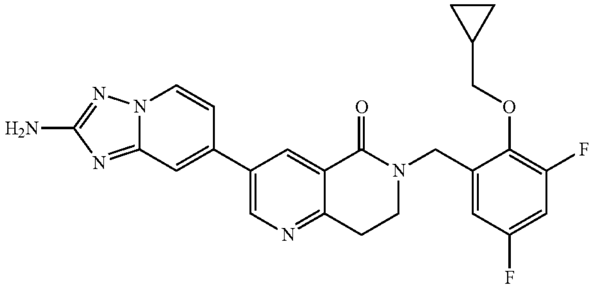 [SMILES: Nc1nc2cc(-c3cnc4c(c3)C(=O)N(Cc3cc(F)cc(F)c3OCC3CC3)CC4)ccn2n1]
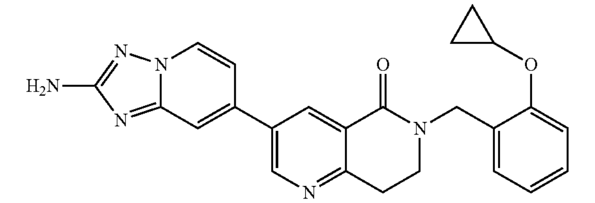 [SMILES: Nc1nc2cc(-c3cnc4c(c3)C(=O)N(Cc3ccccc3OC3CC3)CC4)ccn2n1]
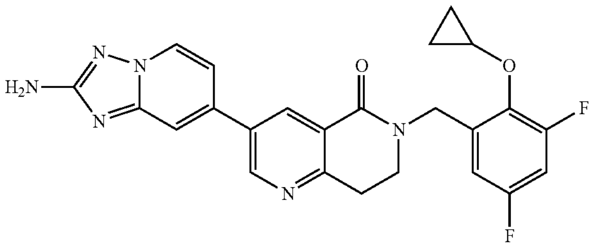 [SMILES: Nc1nc2cc(-c3cnc4c(c3)C(=O)N(Cc3cc(F)cc(F)c3OC3CC3)CC4)ccn2n1]
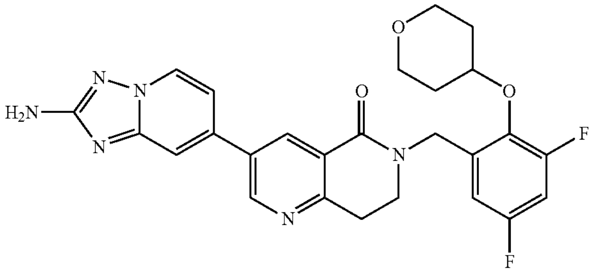 [SMILES: Nc1nc2cc(-c3cnc4c(c3)C(=O)N(Cc3cc(F)cc(F)c3OC3CCOCC3)CC4)ccn2n1]

TABLE A-continued
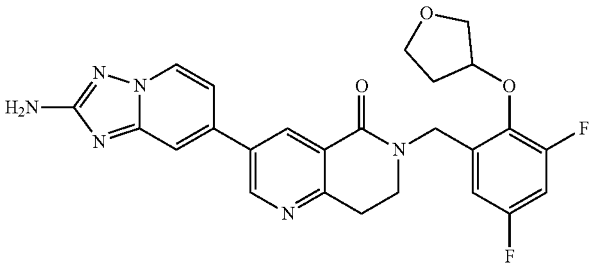 [SMILES: Nc1nc2cc(-c3cnc4c(c3)C(=O)N(Cc3cc(F)cc(F)c3OC3CCOC3)CC4)ccn2n1]
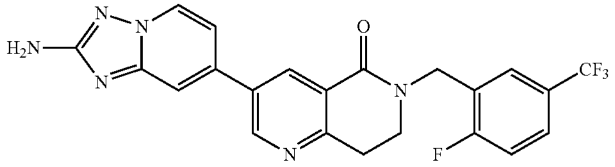 [SMILES: Nc1nc2cc(-c3cnc4c(c3)C(=O)N(Cc3cc(C(F)(F)F)ccc3F)CC4)ccn2n1]
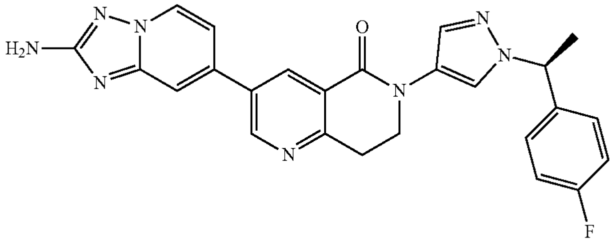 [SMILES: C[C@@H](c1ccc(F)cc1)n1cc(N2CCc3ncc(-c4ccn5nc(N)nc5c4)cc3C2=O)cn1]
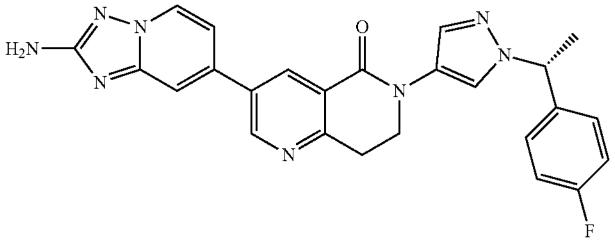 [SMILES: C[C@H](c1ccc(F)cc1)n1cc(N2CCc3ncc(-c4ccn5nc(N)nc5c4)cc3C2=O)cn1]
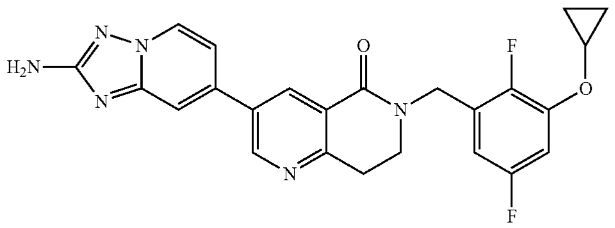 [SMILES: Nc1nc2cc(-c3cnc4c(c3)C(=O)N(Cc3cc(F)cc(OC5CC5)c3F)CC4)ccn2n1]
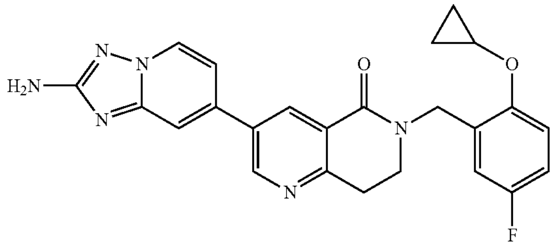 [SMILES: Nc1nc2cc(-c3cnc4c(c3)C(=O)N(Cc3cc(F)ccc3OC3CC3)CC4)ccn2n1]
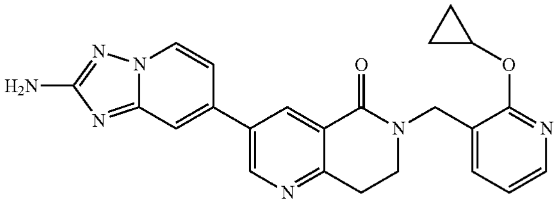 [SMILES: Nc1nc2cc(-c3cnc4c(c3)C(=O)N(Cc3cccnc3OC3CC3)CC4)ccn2n1]

TABLE A-continued
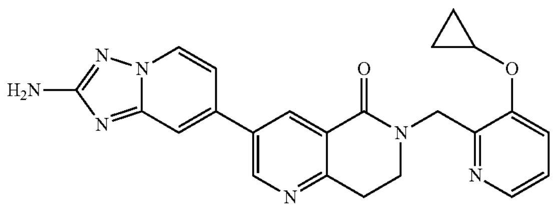
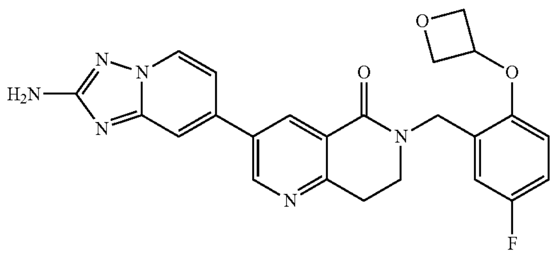 [SMILES: Nc1nc2cc(-c3cnc4c(c3)C(=O)N(Cc3cc(F)ccc3OC3COC3)CC4)ccn2n1]
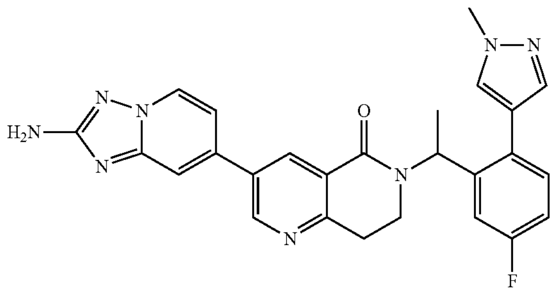 [SMILES: CC(c1cc(F)ccc1-c1cnn(C)c1)N1CCc2ncc(-c3ccn4nc(N)nc4c3)cc2C1=O]
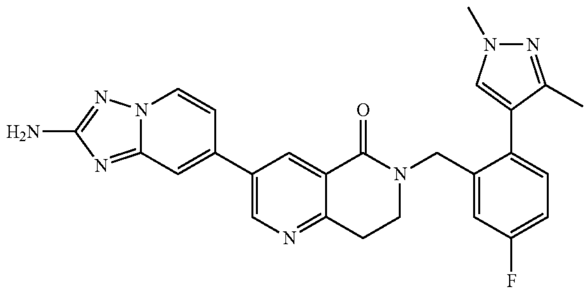 [SMILES: Cc1nn(C)cc1-c1ccc(F)cc1CN1CCc2ncc(-c3ccn4nc(N)nc4c3)cc2C1=O]
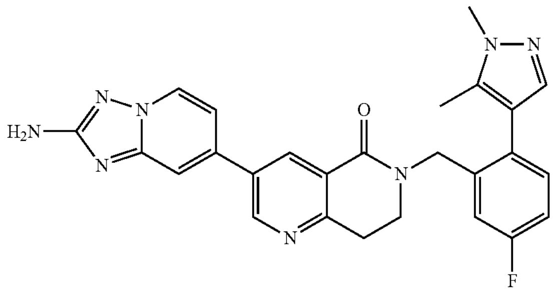 [SMILES: Cc1c(-c2ccc(F)cc2CN2CCc3ncc(-c4ccn5nc(N)nc5c4)cc3C2=O)cnn1C]
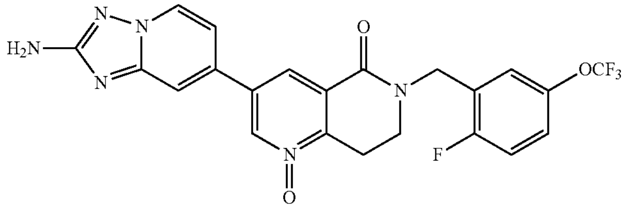 [SMILES: Nc1nc2cc(-c3cc4c([n+]([O-])c3)CCN(Cc3cc(OC(F)(F)F)ccc3F)C4=O)ccn2n1]

TABLE A-continued
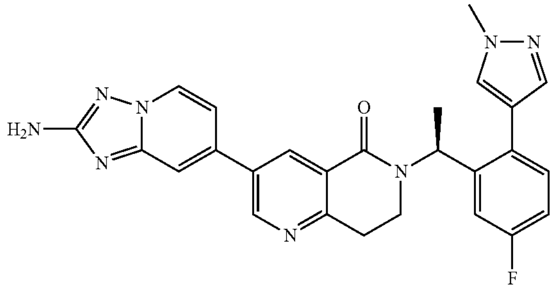 [SMILES: C[C@@H](c1cc(F)ccc1-c1cnn(C)c1)N1CCc2ncc(-c3ccn4nc(N)nc4c3)cc2C1=O]
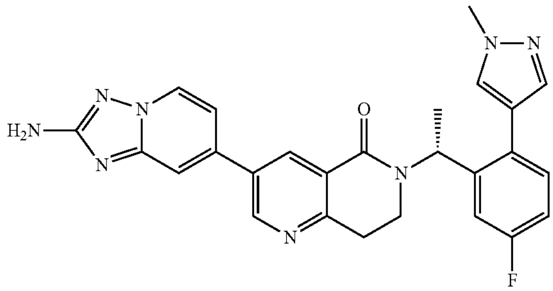
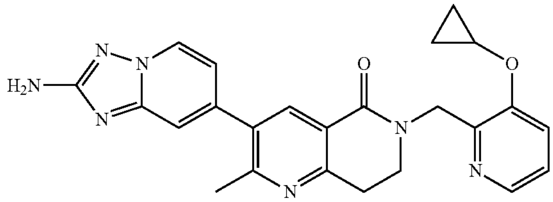 [SMILES: Cc1nc2c(cc1-c1ccn3nc(N)nc3c1)C(=O)N(Cc1ncccc1OC1CC1)CC2]
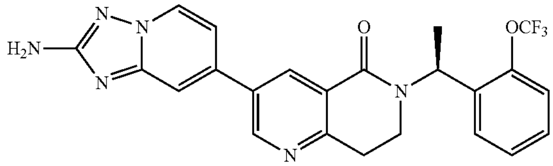 [SMILES: C[C@@H](c1ccccc1OC(F)(F)F)N1CCc2ncc(-c3ccn4nc(N)nc4c3)cc2C1=O]
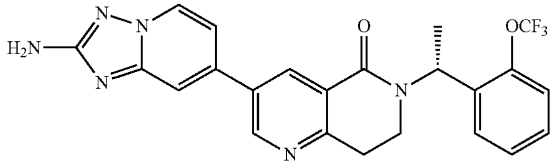
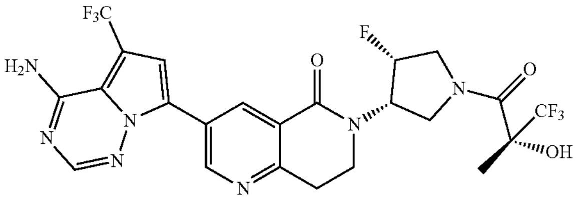 [SMILES: C[C@@](O)(C(=O)N1C[C@@H](F)[C@@H](N2CCc3ncc(-c4cc(C(F)(F)F)c5c(N)ncnn45)cc3C2=O)C1)C(F)(F)F]
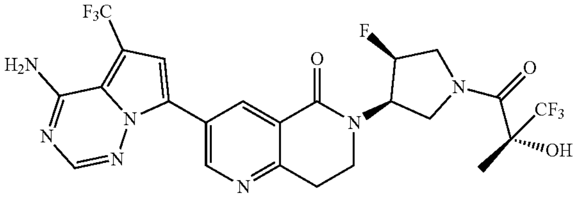 [SMILES: C[C@@](O)(C(=O)N1C[C@@H](N2CCc3ncc(-c4cc(C(F)(F)F)c5c(N)ncnn45)cc3C2=O)[C@@H](F)C1)C(F)(F)F]

TABLE A-continued

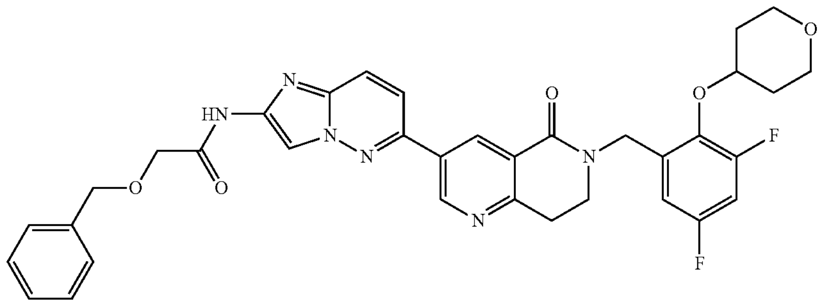 [SMILES: O=C(COCc1ccccc1)Nc1cn2nc(-c3cnc4c(c3)C(=O)N(Cc3cc(F)cc(F)c3OC3CCOCC3)CC4)ccc2n1]

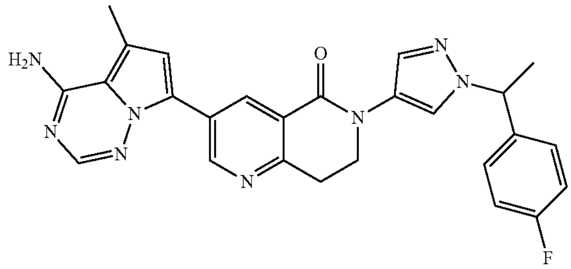 [SMILES: Cc1cc(-c2cnc3c(c2)C(=O)N(c2cnn(C(C)c4ccc(F)cc4)c2)CC3)n2ncnc(N)c12]

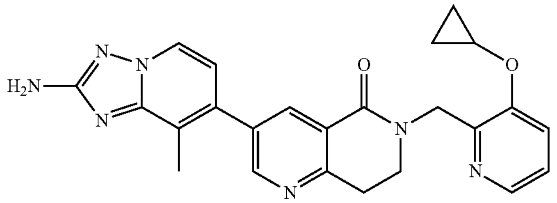 [SMILES: Cc1c(-c2cnc3c(c2)C(=O)N(Cc2ncccc2OC2CC2)CC3)ccn2nc(N)nc12]

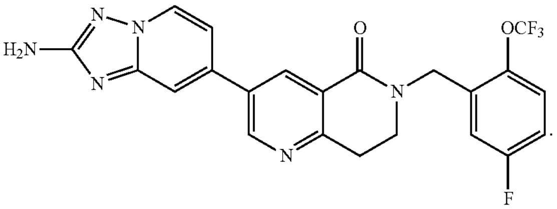 [SMILES: Nc1nc2cc(-c3cnc4c(c3)C(=O)N(Cc3cc(F)ccc3OC(F)(F)F)CC4)ccn2n1 ; "."]

In an embodiment of the present disclosure, the compound of formula (I) is selected from the compounds prepared in the embodiments of the present application. For example, the compound is selected from compounds Z1 to Z85, Z93, Z94, Z96, Z97, Z98, and Z102.

In a second aspect, the present disclosure provides a pharmaceutical composition, wherein the pharmaceutical composition comprises the compound or the pharmaceutically acceptable salt, stereoisomer, solvate or prodrug thereof described in the first aspect of the present disclosure; and a pharmaceutically acceptable carrier.

In a third aspect, the present disclosure provides a use of the compound or the pharmaceutically acceptable salt, the stereoisomer, the solvate or the prodrug thereof described in the first aspect of the present disclosure, or the pharmaceutical composition described in the second aspect of the present disclosure in the manufacture of a medicament for preventing and/or treating of diseases.

In an embodiment of the present disclosure, the diseases are selected from the group of stroke, inflammatory bowel disease, ulcerative colitis, Crohn's disease, psoriasis, rheumatoid arthritis, NASH and heart failure.

In a fourth aspect, the present disclosure provides a use of the compound or the pharmaceutically acceptable salt, the stereoisomer, the solvate or the prodrug thereof described in the first aspect of the present disclosure, or the pharmaceutical composition described in the second aspect of the present disclosure in the manufacture of a selective inhibitor of RIPK1, wherein the selective inhibitor of RIPK1 is used to treat RIPK1-related diseases or conditions.

In an embodiment of the present disclosure, the RIPK1-related diseases or conditions include, but are not limited to, inflammatory disease, such as Crohn's disease and ulcerative colitis, inflammatory bowel disease, asthma, graft versus host disease, and chronic obstructive pulmonary disease; autoimmune disease, such as Graves disease, rheumatoid arthritis, systemic lupus erythematosus, and psoriasis; destructive bone disease, such as bone resorption disease, osteoarthritis, osteoporosis, and multiple myeloma-associated bone disease; proliferative disease, such as acute myeloid leukemia, and chronic myelocytic leukemia; angiogenesis disorder, such as angiogenesis disorder, including solid tumor, ocular neoangiogenesis and hemangioma of infant; infectious disease, such as septicemia, septic shock and shigellosis; neurodegenerative disease, such as Alzheimer's disease, Parkinson disease, amyotrophic lateral sclerosis, cerebral ischemia or neurodegenerative disease caused by traumatic injury; tumor and viral disease, such as metastatic melanoma, Kaposi's sarcoma, multiple myeloma, HIV infection and CMV retinitis, and AIDS.

In an embodiment of the present disclosure, the RIPK1-related diseases or conditions include, but are not limited to, pancreatitis (acute or chronic), asthma, allergy, adult respiratory distress syndrome, chronic obstructive pulmonary disease, glomerulonephritis, rheumatoid arthritis, systemic lupus erythematosus, scleroderma, chronic thyroiditis, Graves disease, autoimmune gastritis, diabetes, autoimmune hemolytic anemia, autoimmune neutropenia, thrombocytopenia, atopic dermatitis, chronic active hepatitis, myasthenia gravis, amyotrophic lateral sclerosis, multiple sclerosis, inflammatory bowel disease, ulcerative colitis, Crohn's disease, psoriasis, graft versus host disease, inflammation caused by endotoxin, tuberculosis, atherosclerosis, muscle degeneration, cachexia, psoriatic arthritis, Reiter's syndrome, gout, traumatic arthritis, rubella arthritis, acute synovitis, pancreatic β cell disease; disease characterized by infiltration of large numbers of neutrophils; rheumatoid spondylitis, gouty arthritis and other arthritic conditions, cerebral malaria, chronic lung inflammation, silicosis, pulmonary sarcoma, bone resorption disease, allograft rejection, fever and myalgia caused by infection, cachexia secondary to infection, luteoid formation, scar tissue formation, ulcerative colitis, fever, influenza, osteoporosis, osteoarthritis, acute myeloid leukemia, chronic myelogenous leukemia, metastatic melanoma, Kaposi's sarcoma, multiple myeloma, septicemia, septic shock and shigellosis; Alzheimer's disease, Parkinson disease, neurodegenerative disease caused by cerebral ischemia or traumatic injury; angiogenesis disorder, including solid tumor, ocular neoangiogenesis and hemangioma of infant; viral disease, including acute hepatitis infection (including hepatitis A, hepatitis B and hepatitis C), HIV infection and CMV retinitis, AIDS, ARC or malignant tumor and herpes; stroke, myocardial ischemia, stroke heart attack, organ ischemia, vascular proliferation, heart and kidney reperfusion injury, thrombosis, cardiac hypertrophy, thrombin-induced platelet aggregation, endotoxemia and/or toxic shock syndrome, conditions related to prostaglandin endoperoxidase synthase-2, and pemphigus vulgaris.

In an embodiment of the present disclosure, the RIPK1-related diseases or conditions are selected from stroke, inflammatory bowel disease, Crohn's disease and ulcerative colitis, allograft rejection, rheumatoid arthritis, psoriasis, ankylosing spondylitis, psoriatic arthritis and pemphigus vulgaris. Alternatively, the conditions are preferably selected from ischemia reperfusion injury, including cerebral ischemia reperfusion injury caused by stroke, and myocardial ischemia reperfusion injury caused by myocardial infarction.

It should be understood that, within the scope of the present disclosure, each of the above-mentioned technical features of the present disclosure and each of the technical features specifically described hereinafter (e.g., examples) may be combined with each other to constitute a new or preferred technical solution. Due to space limitations, it will not be repeated herein.

Definitions

As used herein, the term "heteroatom" is selected from nitrogen, oxygen or sulfur, wherein the nitrogen can be optionally substituted, and the sulfur is also optionally substituted, for example oxidized, i.e. forming $S(O)_{t3}$ (where t3 is an integer of 0 to 2).

As used herein, when a group such as an alkyl group is in the middle of a structural formula, the group denotes an alkylene group; for example, alkyl for alkylene, etc.

As used herein, the term "alkyl" refers to a chain (straight or branched) saturated aliphatic hydrocarbon group. The term "alkyl" may be straight or branched alkyl containing 1 to 20 carbon atoms ($C_{1-20}$ alkyl), preferably alkyl containing 1 to 12 carbon atoms ($C_{1-12}$ alkyl), and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimetylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-etylhexyl, 4-ethyhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, various branched isomers thereof, etc. More preferably, the term "alkyl" is lower alkyl containing 1 to 6 carbon atoms ($C_{1-6}$ alkyl), and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. More preferably, the term "alkyl" is lower alkyl containing 1 to 3 carbon atoms ($C_{1-3}$ alkyl), and non-limiting examples include methyl, ethyl, n-propyl, isopropyl, etc. Alkyl may be substituted or non-substituted; and when alkyl is substituted, the substituents are preferably one or more groups as described in the present application.

As used herein, the terms "cycloalkyl" and "cycloalkyl ring" can be used interchangeably, and refer to a saturated or partially unsaturated monocyclic or polycyclic cyclic hydrocarbon group. The term "cycloalkyl" may be cycloalkyl containing 3 to 20 carbon atoms ($C_{3-20}$ cycloalkyl), preferably cycloalkyl containing 3 to 12 carbon atoms ($C_{3-12}$ cycloalkyl), more preferably cycloalkyl containing 3 to 10 carbon atoms ($C_{3-10}$ cycloalkyl), and more preferably cycloalkyl containing 3 to 6 carbon atoms ($C_{3-6}$ cycloalkyl). The ring carbon atoms of the cycloalkyl may be optionally substituted with 1, 2, or 3 oxo groups to form a cyclic ketone structure.

When the cycloalkyl is monocyclic cycloalkyl, monocyclic cycloalkyl containing 3 to 8 ring carbon atoms (i.e., 3- to 8-membered or $C_{3-8}$ cycloalkyl) is preferred; "$C_{3-8}$ monocyclic cycloalkyl" and "$C_{3-8}$ cycloalkyl" can be used interchangeably herein; monocyclic cycloalkyl containing 3 to 6 ring carbon atoms (i.e., 3- to 6-membered or $C_{3-6}$ cycloalkyl) is more preferred; non-limiting examples of monocyclic cycloalkyl (or $C_{3-6}$ cycloalkyl) include cyclopropyl, cyclobutyl, cyclopentyl, cyclopentenyl, cyclohexyl, cyclohexenyl, cyclohexadienyl, cycloheptyl, cycloheptatrienyl, cyclooctyl, cyclobutanone, cyclobutane-1,2-dione, cyclopentanone, cyclopentane-1,3-dione, cyclohexanone, cyclohexane-1,3-dione, etc.

Typically, cycloalkyl containing 3 to 6 carbon atoms ($C_{3-6}$ cycloalkyl) refers to monocyclic cycloalkyl ($C_{3-6}$monocyclic cycloalkyl). As used herein, "3- to 6-membered monocyclic", "3- to 6-membered monocyclic cycloalkyl", "$C_{3-6}$ monocyclic cycloalkyl" and "$C_{3-6}$ cycloalkyl" can be used interchangeably, and refer to a saturated or partially unsaturated full-carbon monocyclic ring containing 3 to 6 ring atoms. The ring carbon atoms of the monocyclic ring may be optionally substituted with 1, 2, or 3 oxo groups to form a cyclic ketone structure. Examples of 3- to 6-membered monocyclic ring include (but are not limited to): cyclopropyl ring, cyclobutyl ring, cyclopentyl ring, cyclopentenyl ring, cyclohexyl ring, cyclohexenyl ring, cyclohexadienyl ring, cyclobutanone, cyclobutane-1,2-dione, cyclopentanone, cyclopentane-1,3-dione, cyclohexanone, cyclohexane-1,3-dione, etc.

In the case of polycyclic cycloalkyl, the polycyclic cycloalkyl includes spirocycloalkyl, fused cycloalkyl and bridged cycloalkyl.

As used herein, the term "spirocycloalkyl" refers to a saturated or partially unsaturated polycyclic cyclic hydrocarbon group, wherein the rings in the system share one carbon atom (called spiro atom). The term "saturated spirocycloalkyl" refers to spirocycloalkyl containing no unsaturated bonds. The term "partially unsaturated spirocycloalkyl" refers to spirocycloalkyl that may contain one or more double bonds in each monocyclic ring, but none of the rings has a fully conjugated π-electron system. The term "spirocycloalkyl" may be spirocycloalkyl containing 5 to 20 ring carbon atoms (i.e. 5- to 20-membered or $C_{5-20}$ spirocycloalkyl), in which the 3- to 8-membered (i.e. containing 3 to 8 ring carbon atoms or $C_{3-8}$) monocyclic rings share a carbon atom (called spiro atom). 6- to 14-membered spirocycloalkyl is preferred, and 7- to 11-membered spirocycloalkyl is more preferred. According to the number of shared spiro atoms between rings, spirocycloalkyl can be divided into monospirocycloalkyl, bispirocycloalkyl or polyspirocycloalkyl; monospirocycloalkyl and bispirocycloalkyl are preferred; and 7-membered (4-membered monocyclic/4-membered monocyclic), 8-membered (4-membered monocyclic/5-membered monocyclic), 9-membered (4-membered monocyclic/6-membered monocyclic, 5-membered monocyclic/5-membered monocyclic), 10-membered (5-membered monocyclic/6-membered monocyclic) or 11-membered (6-membered monocyclic/6-membered monocyclic) monospirocycloalkyl is more preferred. Non-limiting examples of spirocycloalkyl (or 7- to 11-membered spirocycloalkyl) include:

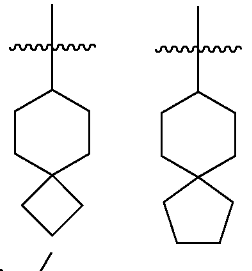

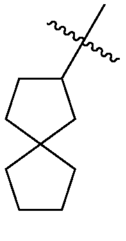

and

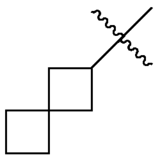

-continued

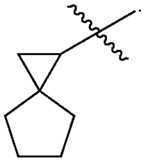

.

As used herein, the term "fused cycloalkyl" refers to a saturated or partially unsaturated polycyclic cyclic hydrocarbon group, wherein each ring in the system shares an adjacent pair of carbon atoms with another ring in the system. The term "saturated fused cycloalkyl" refers to fused cycloalkyl containing no unsaturated bonds. The term "partially unsaturated fused cycloalkyl" refers to fused cycloalkyl in which one or more rings may contain one or more double bonds, but none of the rings has a fully conjugated π-electron system. The term "fused cycloalkyl" may be fused cycloalkyl containing 5 to 20 ring carbon atoms (i.e., 5- to 20-membered or $C_{5-20}$). 6- to 14-membered fused cycloalkyl is preferred, and 6- to 10-membered fused cycloalkyl is more preferred. According to the number of constituent rings, it can be divided into bicyclic, tricyclic, tetracyclic or polycyclic fused cycloalkyl, preferably bicyclic or tricyclic, and more preferably 8-membered (5-membered monocyclic ring fused to 5-membered monocyclic ring), 9-membered (5-membered monocyclic ring fused to 6-membered monocyclic ring) or 10-membered (6-membered monocyclic ring fused to 6-membered monocyclic ring) bicyclic fused cycloalkyl. Non-limiting examples of fused cycloalkyl (or 6- to 10-membered fused cycloalkyl) include:

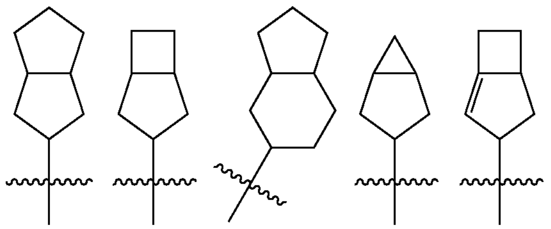

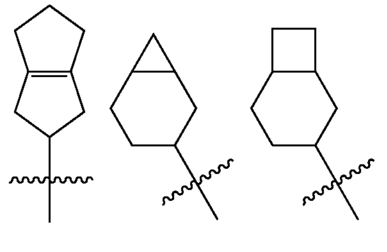

and

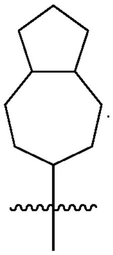

.

As used herein, the term "bridged cycloalkyl" refers to a saturated or partially unsaturated polycyclic cyclic hydrocarbon group, wherein any two rings in the system share two carbon atoms that are not directly connected. The term "saturated bridged cycloalkyl" refers to bridged cycloalkyl containing no unsaturated bonds. The term "partially unsaturated bridged cycloalkyl" refers to bridged cycloalkyl containing one or more double bonds, but none of the rings has a fully conjugated π-electron system. The term "bridged cycloalkyl" may be bridged cycloalkyl containing 5 to 20 ring carbon atoms (i.e., 5- to 20-membered or $C_{5-20}$). 6- to 14-membered bridged cycloalkyl is preferred, and 7- to 10-membered bridged cycloalkyl is more preferred. According to the number of constituent rings, it can be divided into bicyclic, tricyclic, tetracyclic or polycyclic bridged cycloalkyl, preferably bicyclic, tricyclic or tetracyclic, and more preferably bicyclic or tricyclic. Non-limiting examples of bridged cycloalkyl include:

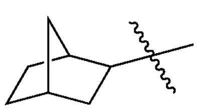

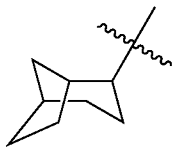

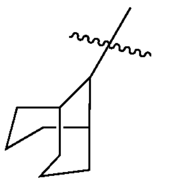

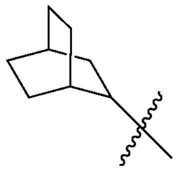

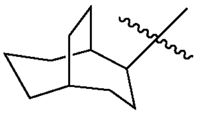

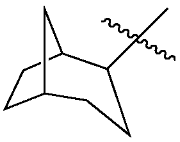

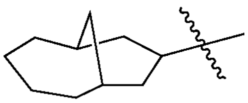

and

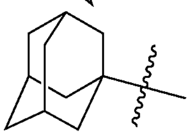

.

The cycloalkyl ring can be fused to aryl, heteroaryl or heterocycloalkyl ring, wherein the ring connected to the parent structure is a cycloalkyl ring, and non-limiting examples include indanyl, tetrahydronaphthyl, benzocycloheptanyl, etc. Cycloalkyl may be optionally substituted or non-substituted; and when cycloalkyl is substituted, the substituents are preferably one or more groups as described in the present application.

As used herein, the term "$C_{2-8}$ alkenyl" refers to alkyl as defined above composed of 2 to 8 carbon atoms and at least one carbon-carbon double bond, preferably $C_{2-6}$alkenyl composed of 2 to 6 carbon atoms and 1 to 2 carbon-carbon double bonds, and more preferably $C_{2-4}$ alkenyl composed of 2 to 4 carbon atoms and 1 to 2 carbon-carbon double bonds, such as vinyl, 1-propenyl, 2-propenyl, 1-, 2- or 3-butenyl, etc. Alkenyl may be substituted or non-substituted; and when alkenyl is substituted, the substituents are preferred one or more groups as described in the present application.

As used herein, the term "$C_{2-8}$ alkynyl" refers to alkyl as defined above composed of 2 to 8 carbon atoms and at least one carbon-carbon triple bond, preferably $C_{2-6}$ alkynyl composed of 2 to 6 carbon atoms and 1 to 2 carbon-carbon triple bonds, and more preferably $C_{2-4}$ alkynyl composed of 2 to 4 carbon atoms and 1 to 2 carbon-carbon triple bonds, such as ethynyl, 1-propynyl, 2-propynyl, 1-, 2- or 3-butynyl, etc. Alkynyl may be substituted or non-substituted; and when alkynyl is substituted, the substituents are preferred one or more groups as described in the present application.

As used herein, the term "heterocycloalkyl" and "heterocycloalkyl ring" can be used interchangeably, and refer to a saturated or partially unsaturated monocyclic or polycyclic cyclic hydrocarbon group, wherein one or more (preferably 1 to 4, 1 to 3, or 1 to 2) ring atoms are the heteroatoms selected from nitrogen, oxygen or $S(O)_{t3}$ (where t3 is an integer of 0 to 2), with the ring part of —O—O—, —O—S— or —S—S— being excluded, and the rest of the ring atoms being carbon atoms. The term "heterocycloalkyl" may be heterocycloalkyl containing 3 to 20 ring atoms (i.e., 3- to 20-membered heterocycloalkyl), preferably 3- to 12-membered heterocycloalkyl, more preferably 3- to 10-membered heterocycloalkyl, and more preferably 3- to 6-membered heterocycloalkyl, wherein one or more (preferably 1 to 4) ring atoms are the heteroatoms selected from nitrogen, oxygen or $S(O)_{t3}$ (where t3 is an integer of 0 to 2), with the ring part of —O—O—, —O—S— or —S—S— being excluded, and the rest of the ring atoms being carbon atoms. Nitrogen atoms may be substituted or unsubstituted (i.e., N or NR, R being hydrogen or any of the substituents already defined herein). The ring carbon atoms of the heterocycloalkyl may be optionally substituted with 1, 2, or 3 oxo groups to form a cyclic ketone, cyclic lactone or cyclolactam structure.

As used herein, with regard to "3- to 20-membered heterocycloalkyl", "3- to 12-membered heterocycloalkyl", "3- to 10-membered heterocycloalkyl" or "3- to 6-membered heterocycloalkyl", when these heterocycloalkyl groups are 3-membered heterocycloalkyl groups and contain only one heteroatom as a ring atom, the heteroatom is not a nitrogen atom.

In some embodiments of the present disclosure, "heterocycloalkyl" refers to monocyclic heterocycloalkyl, wherein the monocyclic heterocycloalkyl is saturated or partially unsaturated, preferably monocyclic heterocycloalkyl containing 3 to 8 ring atoms (i.e., 3- to 8-membered), of which 1, 2, or 3 are heteroatoms, more preferably monocyclic heterocycloalkyl containing 3 to 6 ring atoms (i.e., 3- to 6-membered), of which 1, 2, or 3 are heteroatoms, and most preferably monocyclic heterocycloalkyl containing 5 or 6 ring atoms (i.e., 5- or 6-membered), of which 1, 2, or 3 are heteroatoms. As used herein, the term "3- to 6-membered heterocycloalkyl" and "3- to 6-membered monocyclic heterocycloalkyl" can be used interchangeably, and the term "5- or 6-membered heterocycloalkyl" and "5- or 6-membered monocyclic heterocycloalkyl" can be used interchangeably. When the heteroatom is a nitrogen atom, the nitrogen atom may be substituted or unsubstituted (i.e., N or NR, R being hydrogen or other substituents already defined herein). When the heteroatom is a sulfur atom, the sulfur atom may be optionally oxidized (i.e., $S(O)_{t3}$, t3 is an integer of 0 to 2). The ring carbon atoms of the monocyclic heterocycloalkyl may be optionally substituted with 1, 2, or 3 oxo groups to form a cyclic ketone, cyclic lactone or cyclolactam structure. Non-limiting examples of monocyclic heterocycloalkyl include: aziridine, ethylene oxide, azetidine, azetidine-2-one, oxetane, oxetane-2-one, oxazolidine, pyrrolidine-2-one, pyrrolidine-2,5-dione, 1,3-dioxolane, dihydrofuran-2(3H)-one, dihydrofuran-2,5-dione, piperidine-2-one, piperidine-2,6-dione, tetrahydro-2H-pyran-2-one, imidazolidine, tetrahydrofuran, tetrahydrothiophene, tetrahydropyrrole, 1,3-dioxolane-2-one, oxazolidine-2-one, imidazolidine-2-one, piperidine, piperazine, piperazine-2-one, morpholine, morpholine-3-one, morpholine-2-one, thiomorpholine-3-one 1,1-dioxide, thiomorpholine, thiomorpholine-1,1-dioxide, tetrahydropyran, 1,2-dihydroazetidine, 1,2-dihydrooxetadiene, 2,5-dihydro-1H-pyrrole, 2,5-dihydrofuran, 2,3-dihydrofuran, 2,3-dihydro-1H-pyrrole, 3,4-dihydro-2H-pyran, 1,2,3,4-tetrahydropyridine, 3,6-dihydro-2H-pyran, 1,2,3,6-tetrahydropyridine, 1,3-oxazinane, hexahydropyrimidine, 1,4-dioxane, tetrahydropyrimidine-2(1H)-one, 1,4-dioxane-2-one, 5,6-dihydro-2H-pyran-2-one, 5,6-dihydropyrimidine-4(3H)-one, 3,4-dihydropyridine-2

(1H)-one, 5,6-dihydropyridine-2(1H)-one, 5,6-dihydropyrimidine-4(1H)-one, pyrimidine-4(3H)-one, pyrimidine-4(1H)-one, 4,5-dihydro-1H-imidazole, 2,3-dihydro-1H-imidazole, 2,3-dihydroxazole, 1,3-dioxolene, 2,3-dihydrothiophene, 2,5-dihydrothiophene, 3,4-dihydro-2H-1,4-oxazine, 3,4-dihydro-2H-1,4-thiazide 1,1-dioxide, 1,2,3,4-tetrahydropyrazine, 1,3-dihydro-2H-pyrrole-2-one, 1,5-dihydro-2H-pyrrole-2-one, 1H-pyrrole-2,5-dione, furan-2(3H)-one, furan-2(5H)-one, 1,3-dioxolene-2-one, oxazole-2(3H)-one, 1,3-dihydro-2H-imidazole-2-one, furan-2,5-dione, 3,6-dihydropyridine-2(1H)-one, pyridine-2,6-(1H,3H)-dione, 5,6-dihydro-2H-pyran-2-one, 3,6-dihydro-2H-pyran-2-one, 3,4-dihydro-2H-1,3-oxazine, 3,6-dihydro-2H-1,3-oxazine, 1,2,3,4-tetrahydropyrimidine, etc.

Typically, 3- to 6-membered heterocycloalkyl refers to 3- to 6-membered monocyclic heterocycloalkyl. As used herein, "3- to 6-membered monocyclic heterocyclic ring" or "3- to 6-membered monocyclic heterocycloalkyl" can be used interchangeably, and refers to 3- to 6-membered, preferably 4- to 6-membered, and more preferably 5- to 6-membered, saturated or partially unsaturated monocyclic ring, in which 1, 2 or 3 carbon atoms are substituted with heteroatoms selected from nitrogen, oxygen or $S(O)_{t5}$ (where t5 is an integer of 0 to 2), with the ring part of —O—O—, —O—S— or —S—S— being excluded, and the rest of the ring atoms being carbon atoms. The ring carbon atoms of the monocyclic heterocyclic ring may be optionally substituted with 1, 2, or 3 oxo groups to form a cyclic ketone, cyclic lactone or cyclolactam structure. Examples of 3- to 6-membered monocyclic heterocyclic ring include (but are not limited to) aziridine, ethylene oxide, azetidine, oxetane, tetrahydrofuran, tetrahydrothiophene, tetrahydropyrrole, piperidine, pyrroline, oxazolidine, piperazine, dioxolane, dioxane, morpholine, thiomorpholine, thiomorpholine-1,1-dioxide, tetrahydropyran, 1,2-dihydroazetidine, 1,2-dihydrooxetadiene, 2,5-dihydro-1H-pyrrole, 2,5-dihydrofuran, 2,3-dihydrofuran, 2,3-dihydro-1H-pyrrole, 3,4-dihydro-2H-pyran, 1,2,3,4-tetrahydropyridine, 3,6-dihydro-2H-pyran, 1,2,3,6-tetrahydropyridine, etc.

In an embodiment of the present disclosure, the monocyclic heterocycloalkyl is 3- to 6-membered monocyclic heterocycloalkyl or 4- to 6-membered monocyclic heterocycloalkyl, and non-limiting examples of the 3- to 6-membered monocyclic heterocycloalkyl or 4- to 6-membered monocyclic heterocycloalkyl include:

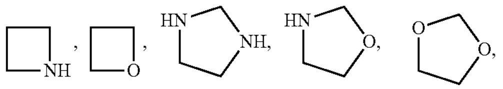
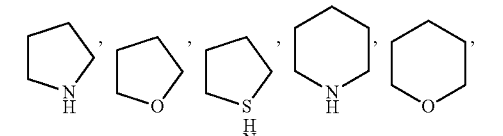
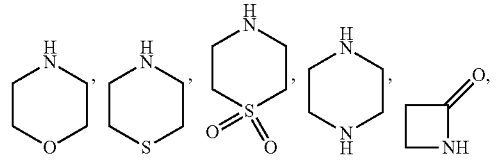
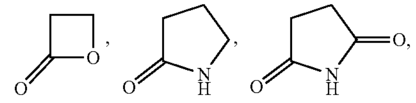

-continued

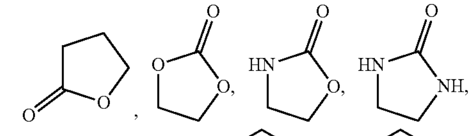
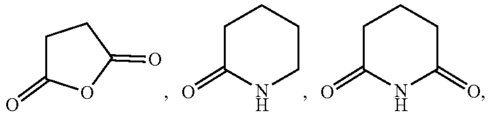
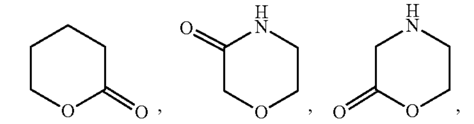
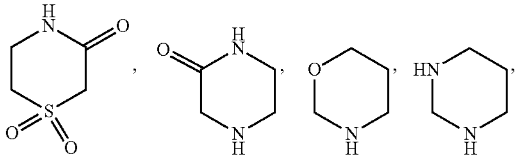
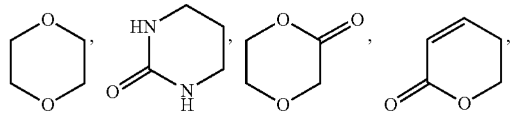
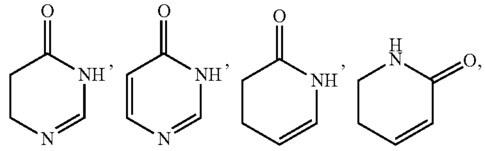
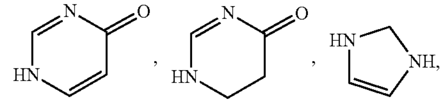
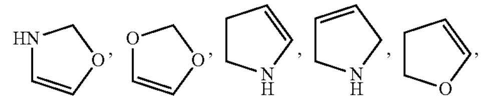
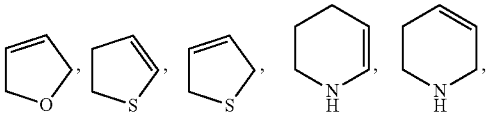
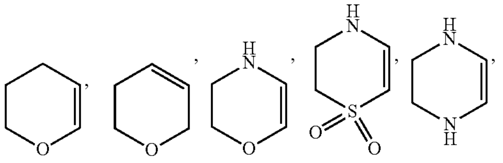
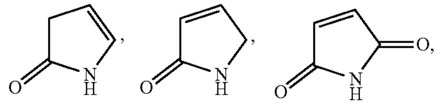
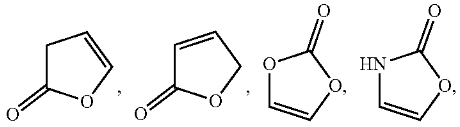
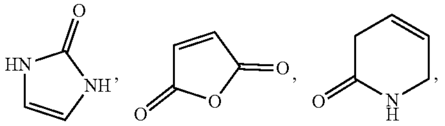
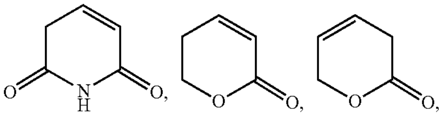

-continued

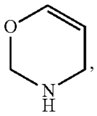, 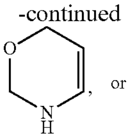, or 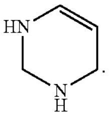.

The above-mentioned two ring atoms connected to the monocyclic heterocycloalkyl, including C—C and N—C, can be optionally fused with cycloalkyl, heterocycloalkyl, aryl or heteroaryl as defined in the present disclosure, such as monocyclic cycloalkyl ring, monocyclic heterocycloalkyl ring, monoaryl ring, and 5- or -6-membered monocyclic heteroaryl ring, to form a fused polycyclic ring, and the two ring atoms connected to the monocyclic heterocycloalkyl, which are together with other rings to form fused rings, are preferably C—C.

As used herein, "3- to 6-membered nitrogen-containing heterocycloalkyl" means that one of the ring atoms of the 3- to 6-membered heterocycloalkyl must be nitrogen atom, and the rest of the ring atoms are all carbon atoms, or 0, 1 or 2 of the rest of the ring atoms is each independently heteroatom selected from nitrogen, oxygen or sulfur. Preferably, the "3- to 6-membered nitrogen-containing heterocycloalkyl" is connected to the rest of the molecule via the nitrogen atom that must be contained in the molecule.

In some embodiments of the present disclosure, "heterocycloalkyl" refers to polycyclic heterocycloalkyl, including spiroheterocycloalkyl, fused heterocycloalkyl and bridged heterocycloalkyl.

As used herein, the term "spiroheterocycloalkyl" refers to saturated or partially unsaturated polycyclic heterocycloalkyl, wherein one atom (called a spiro atom) is shared between the monocyclic rings in the system, and one or more (for example, 1 to 4, or 1 to 3, or 1 to 2) of the ring atoms are heteroatoms selected from nitrogen, oxygen or $S(O)_{t4}$ (wherein t4 is an integer of 0 to 2), and the rest of the ring atoms are carbon. The term "saturated spiroheterocycloalkyl" refers to a spiroheterocycloalkyl system containing no unsaturated bonds. The term "partially unsaturated spiroheterocycloalkyl" means that one or more rings in the spiroheterocycloalkyl system may contain one or more double bonds, but none of the rings has a fully conjugated π-electron system. The term "spiroheterocycloalkyl" may be a spiroheterocycloalkyl containing 5 to 20 ring atoms (i.e., 5- to 20-membered), wherein one atom (called a spiro atom) is shared between 3- to 8-membered monocyclic rings (i.e., containing 3 to 8 ring atoms), and the spiroheterocycloalkyl is preferably 6- to 14-membered spiroheterocycloalkyl, and more preferably 7- to 11-membered spiroheterocycloalkyl; and one or more of the ring atoms are heteroatoms selected from nitrogen, oxygen or $S(O)_{t4}$ (wherein t4 is an integer of 0 to 2), and the rest of the ring atoms are carbon. When the heteroatom is a nitrogen atom, the nitrogen atom may be substituted or unsubstituted (i.e., N or NR, R being hydrogen or other substituents already defined herein). Each monocyclic ring can contain one or more double bonds, but none of the rings has a fully conjugated π-electron system. According to the number of shared spiro atoms between the rings, the spiroheterocycloalkyl is divided into monospiroheterocycloalkyl, bisspiroheterocycloalkyl or polyspiroheterocycloalkyl, preferably monospiroheterocycloalkyl and bisspiroheterocycloalkyl. More preferably, 7-membered (4-membered monocyclic ring/4-membered monocyclic ring), 8-membered (4-membered monocyclic ring/5-membered monocyclic ring), 9-membered (4-membered monocyclic ring/6-membered monocyclic ring, 5-membered monocyclic ring/5-membered monocyclic ring), 10-membered (5-membered monocyclic ring/6-membered monocyclic ring), or 11-membered (6-membered monocyclic ring/6-membered monocyclic ring) monospiroheterocycloalkyl. The non-limiting examples of spiroheterocycloalkyl include:

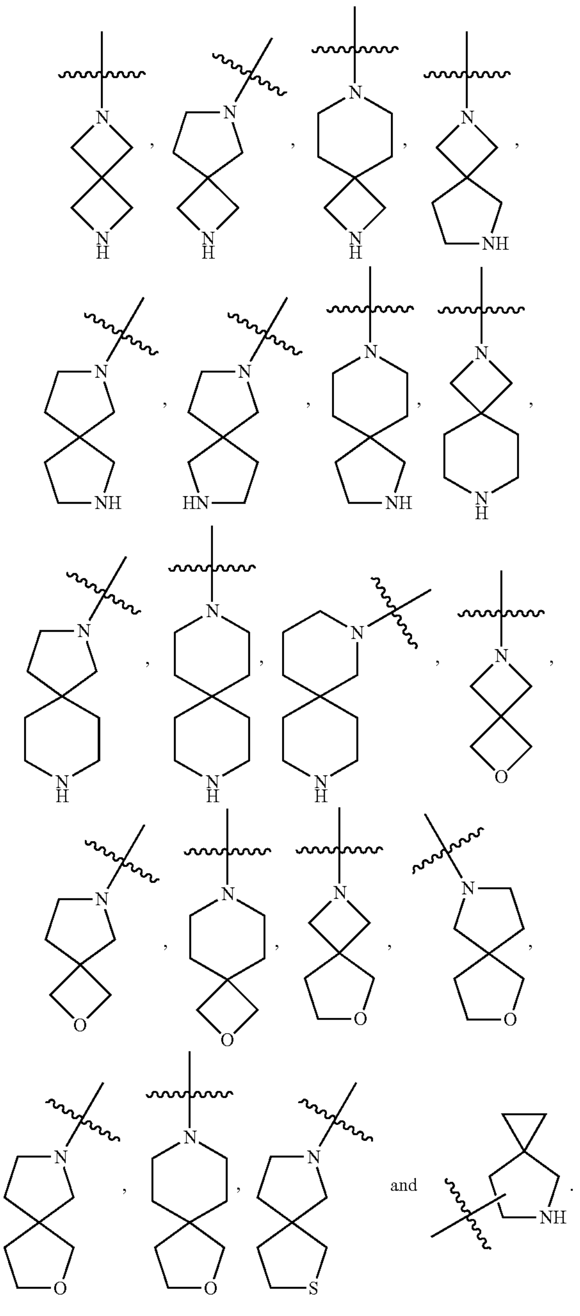

As used herein, the term "fused heterocycloalkyl" refers to saturated or partially unsaturated polycyclic heterocycloalkyl, wherein each ring in the system shares an adjacent pair of atoms with other rings in the system, and one or more (for example, 1 to 4, or 1 to 3, or 1 to 2) of the ring atoms in the system are heteroatoms selected from nitrogen, oxygen or $S(O)_{t4}$ (wherein t4 is an integer of 0 to 2), and the rest of the ring atoms are carbon. The term "saturated fused heterocycloalkyl" refers to a fused heterocycloalkyl system containing no unsaturated bonds. The term "partially unsaturated fused heterocycloalkyl" means that one or more rings in the fused heterocycloalkyl system may contain one or more double bonds, but none of the rings has a fully conjugated π-electron system. The term "fused heterocycloalkyl" may be a fused heterocycloalkyl containing 5 to 20 ring atoms (i.e., 5- to 20-membered), preferably 6- to 14-membered fused heterocycloalkyl, more preferably 6- to 10-membered fused heterocycloalkyl, and more preferably 8- to 10-membered fused heterocycloalkyl; and one or more of the ring atoms in the system are heteroatoms selected from nitrogen, oxygen or $S(O)_{t4}$ (wherein t4 is an integer of 0 to 2), and the rest of the ring atoms are carbon. When the heteroatom is a nitrogen atom, the nitrogen atom may be substituted or unsubstituted (i.e., N or NR, R being hydrogen or other substituents already defined herein). According to the number of constituent rings, it can be divided into bicyclic, tricyclic, tetracyclic or polycyclic fused heterocycloalkyl, preferably bicyclic or tricyclic, and more preferably 8-membered (5-membered monocyclic ring fused with 5-membered monocyclic ring), 9-membered (5-membered monocyclic ring fused with 6-membered monocyclic ring) or 10-membered (6-membered monocyclic ring fused with 6-membered monocyclic ring) bicyclic fused heterocycloalkyl. The non-limiting examples of fused heterocycloalkyl include:

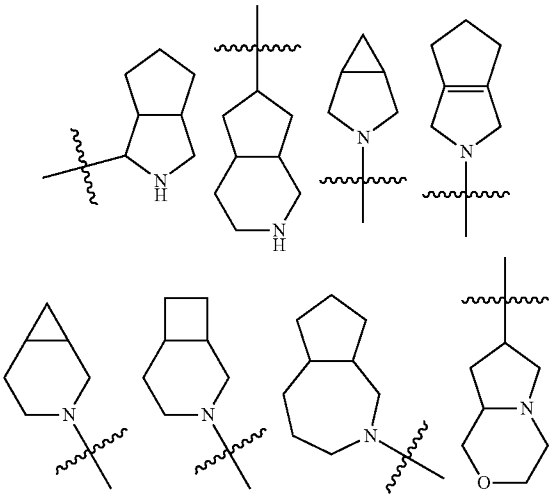

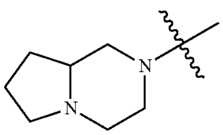

and

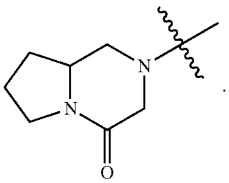

.

As used herein, the term "bridged heterocycloalkyl" refers to saturated or partially unsaturated polycyclic heterocycloalkyl, wherein any two rings in the system share two atoms that are not directly connected, and one or more (for example, 1 to 4, or 1 to 3, or 1 to 2) of the ring atoms are heteroatoms selected from nitrogen, oxygen or $S(O)_{t3}$ (wherein t3 is an integer of 0 to 2), and the rest of the ring atoms are carbon. The term "saturated bridged heterocycloalkyl" refers to a bridged heterocycloalkyl system containing no unsaturated bonds. The term "partially unsaturated bridged heterocycloalkyl" means that one or more rings in the bridged heterocycloalkyl system may contain one or more double bonds, but none of the rings has a fully conjugated π-electron system. The term "bridged heterocycloalkyl" may be a bridged heterocycloalkyl containing 5 to 20 ring atoms (i.e., 5- to 20-membered), preferably 6- to 14-membered bridged heterocycloalkyl, and more preferably 7- to 10-membered bridged heterocycloalkyl; and one or more (for example, 1 to 4, or 1 to 3, or 1 to 2) of the ring atoms are heteroatoms selected from nitrogen, oxygen or $S(O)_{t3}$ (wherein t3 is an integer of 0 to 2), and the rest of the ring atoms are carbon. According to the number of constituent rings, it can be divided into bicyclic, tricyclic, tetracyclic or polycyclic bridged heterocycloalkyl, preferably bicyclic, tricyclic or tetracyclic, and more preferably bicyclic or tricyclic. The non-limiting examples of bridged heterocycloalkyl include:

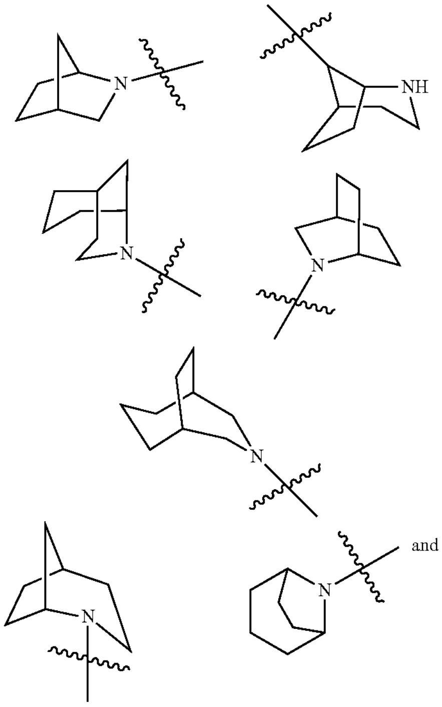

and

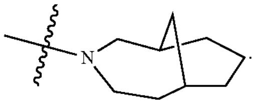

.

In the present disclosure, the above-mentioned various heterocycloalkyl groups may be optionally substituted or unsubstituted; when substituted, the substituents are preferably one or more groups as described in the present application.

As used herein, in "spiroheterocycloalkyl", "bridged heterocycloalkyl" or "fused heterocycloalkyl", when the ring containing a heteroatom is a 3-membered ring and contains only one heteroatom as a ring atom, the heteroatom is not a nitrogen atom.

As used herein, the terms "aryl", "aryl ring" and "aromatic ring" are used interchangeably and refer to fully unsaturated aliphatic hydrocarbon groups. It can be an all-carbon monocyclic ring containing 6 to 14 ring atoms (i.e., 6- to 14-membered or $C_{6-14}$), an all-carbon polycyclic ring (the rings are connected via covalent bonds, not by means of fusion) or an all-carbon fused polycyclic ring (that is, a ring that shares adjacent pairs of carbon atoms) group, wherein at least one ring in the ring system is aromatic, that is, it has a conjugated π-electron system. Preferably, aryl containing 6 to 10 ring carbon atoms (i.e., 6- to 10-membered or $C_{6-10}$). Each ring in the ring system contains 5 or 6 ring atoms.

In some embodiments of the present disclosure, "aryl" refers to a monoaryl or polyaryl ring, non-limiting examples of which include: phenyl, biphenyl, etc.

In some embodiments of the present disclosure, "aryl" refers to an aromatic fused polycyclic ring, which is a polycyclic group in which monoaryl ring is fused with one or more monoaryl rings, non-limiting examples of which include: naphthyl, anthracenyl, etc.

In some embodiments of the present disclosure, aryl ring described herein (e.g., monoaryl ring, preferably phenyl) may be fused with one or more non-aromatic rings to form a polycyclic group, wherein the ring connected to the parent structure is an aromatic ring or a non-aromatic ring, and the non-aromatic ring includes but is not limited to: a 3- to 6-membered monocyclic heterocycloalkyl ring, preferably a 5- or -6-membered monocyclic heterocycloalkyl ring (the ring carbon atoms of the monocyclic heterocycloalkyl ring may be substituted by 1 to 2 oxo groups to form a cyclolactam or cyclic lactone structure); a 3- to 6-membered monocyclic cycloalkyl ring, preferably a 5- or 6-membered monocyclic cycloalkyl ring (the ring carbon atoms of the monocyclic cycloalkyl ring may be substituted by 1 or 2 oxo groups to form a cyclic ketone structure), etc. The polycyclic group in which the above-mentioned monoaryl ring is fused with one or more non-aromatic rings can be connected to other groups or the parent structure via a nitrogen atom or carbon atom, and the ring connected to the parent structure is a monoaryl ring or non-aromatic ring.

As used herein, the phenyl is fused with a 5- or -6-membered monocyclic heterocycloalkyl ring to form a 9- or 10-membered bicyclic ring, which means that two adjacent substituent groups on the phenyl taken together with the ring atoms connecting them form a fused 5- or -6-membered monocyclic heterocycloalkyl ring, wherein the 5- or -6-membered monocyclic heterocycloalkyl ring is as defined herein, and the formed 9- or 10-membered bicyclic ring can also be called a 9- or 10-membered phenylheterocycloalkyl ring.

As used herein, the phenyl is fused with a 5- or -6-membered monocyclic cycloalkyl ring to form a 9- or 10-membered bicyclic ring, which means that two adjacent substituent groups on the phenyl taken together with the ring atoms connecting them form a fused 5- or -6-membered monocyclic cycloalkyl ring, wherein the 5- or -6-membered monocyclic cycloalkyl ring is as defined herein, and the formed 9- or 10-membered bicyclic ring can also be called a 9- or 10-membered phenylcycloalkyl ring.

In the present disclosure, the above-mentioned various aryl groups may be substituted or unsubstituted; when substituted, the substituents are preferably one or more groups as described in the present application.

As used herein, the term "heteroaryl", "heteroaryl ring" and "heteroaromatic ring" are used interchangeably and refer to fully unsaturated aliphatic hydrocarbon groups containing heteroatoms. It may be a monocyclic or fused polycyclic ring (that is, a ring that shares adjacent pairs of carbon atoms or heteroatoms) group which may contain 5 to 14 ring atoms (i.e., 5- to 14-membered), preferably 5 to 10 ring atoms (i.e., 5- to 10-membered), more preferably 5, 6, 8, 9 or 10 ring atoms, in which 1 to 4 heteroatoms are contained therein as ring atoms, and the heteroatoms are selected from oxygen, sulfur and nitrogen. The nitrogen and sulfur atoms can be optionally oxidized, and nitrogen atoms can be optionally quaternized. The heteroaryl preferably has 6, 10 or 14 π electrons shared in the ring system. At least one ring in the ring system is aromatic.

In some embodiments of the present disclosure, "heteroaryl" refers to monocyclic heteroaryl ring (preferably 5- or -6-membered monocyclic heteroaryl ring), non-limiting examples of which include: thiophene, N-alkylpyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine, pyrazine, etc.

In some embodiments of the present disclosure, "heteroaryl" refers to fused polyheteroaryl ring (preferably 8- to 10-membered bicyclic heteroaryl ring). The fused polyheteroaryl ring includes both a polycyclic group (preferably a 9- or 10-membered bicyclic heteroaryl ring) in which a monoaryl ring (preferably phenyl) is fused with a monocyclic heteroaryl ring (preferably a 5- or -6-membered monocyclic heteroaryl ring), and a polycyclic group (preferably a 8- to 10-membered bicyclic heteroaryl ring) in which a monocyclic heteroaryl (preferably a 5- or -6-membered monocyclic heteroaryl) is fused with a monocyclic heteroaryl (preferably a 5- or -6-membered monocyclic heteroaryl).

In some embodiments of the present disclosure, non-limiting examples of the monocyclic heteroaryl ring (preferably 5- or -6-membered monocyclic heteroaryl ring) that forms a fused polycyclic ring include:

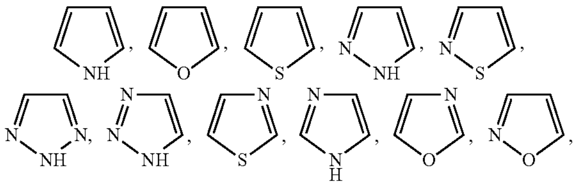
,

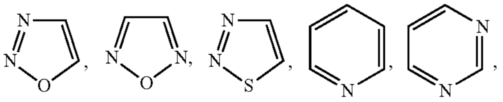
,

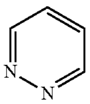
and
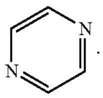
.

The above-mentioned any two ring atoms connected to the monocyclic heteroaryl ring, including C—C, N—C and N—N, can be fused with cycloalkyl, heterocycloalkyl, aryl or heteroaryl as defined in the present disclosure, such as monocyclic cycloalkyl ring, monocyclic heterocycloalkyl ring, monoaryl ring, and 5- or -6-membered monocyclic heteroaryl ring, to form a fused polycyclic ring. The two adjacent ring atoms of the monocyclic heteroaryl ring forming a fused ring with other rings are preferably C—C, and the monocyclic heteroaryl ring includes the following forms without limitation:

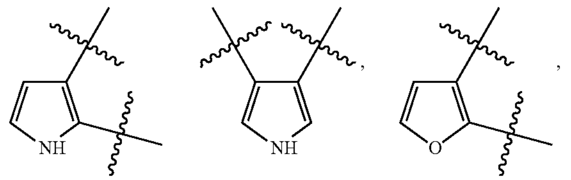
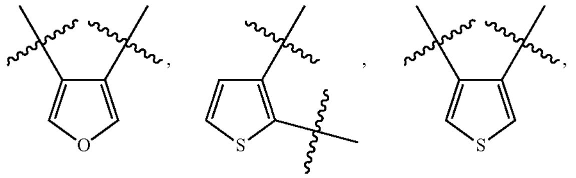
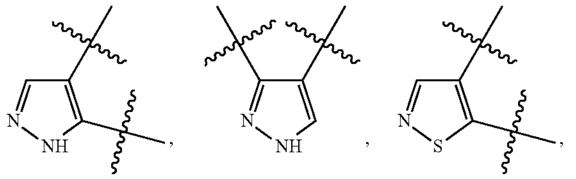
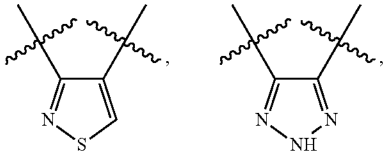
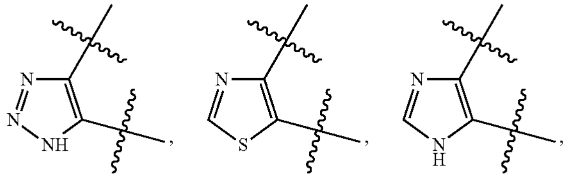
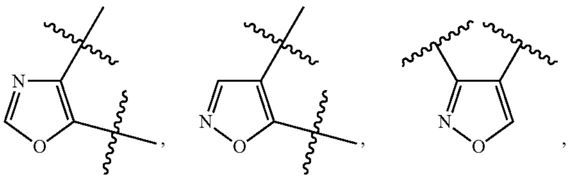
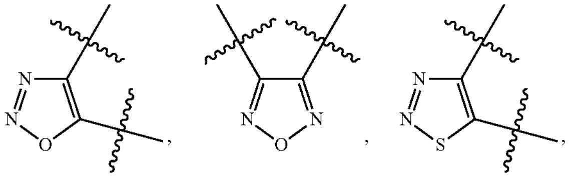
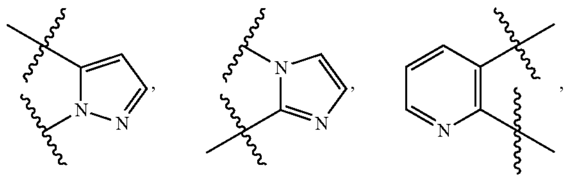
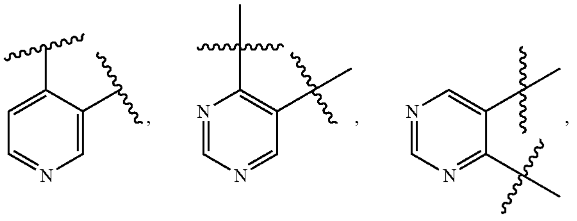

-continued

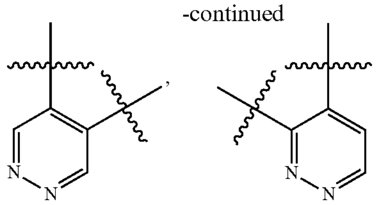

and

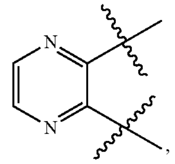

Non-limiting examples of fused polyheteroaryl rings include: benzo[d]isoxazole, 1H-indole, isoindole, 1H-benzo[d]imidazole, benzo[d]isothiazole, 1H-benzo[d][1,2,3]triazole, benzo[d]oxazole, benzo[d]thiazole, indazole, benzofuran, benzo[b]thiophene, quinoline, isoquinoline, quinazoline, quinoxaline, cinnoline, pyrido[3,2-d]pyrimidine, pyrido[2,3-d]pyrimidine, pyrido[3,4-d]pyrimidine, pyrido[4,3-d]pyrimidine, 1,8-naphthyridine, 1,7-naphthyridine, 1,6-naphthyridine, 1,5-naphthyridine, pyrazolo[1,5-a]pyrimidine, imidazolo[1,2-b]pyridazine, etc.

The above-mentioned monocyclic heteroaryl, or a polycyclic group in which a monoaryl ring is fused with a monocyclic heteroaryl ring, or a polycyclic group in which a monocyclic heteroaryl is fused with a monocyclic heteroaryl may be connected to other groups or the parent structure via a nitrogen atom or carbon atom. In the case of a polycyclic group, the ring connected to the parent structure is a heteroaryl ring, an aryl ring, a monocyclic cycloalkyl ring or a monocyclic heterocycloalkyl ring, non-limiting examples of which include:

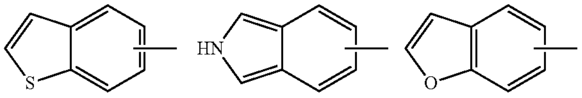
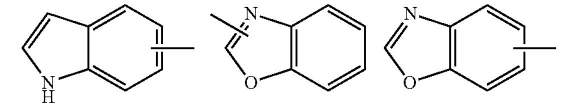
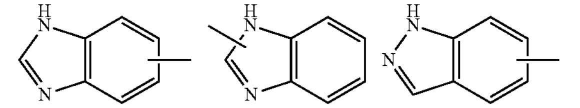
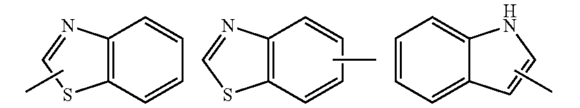
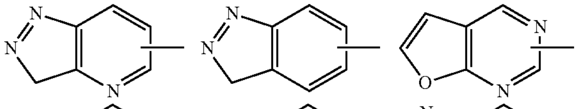
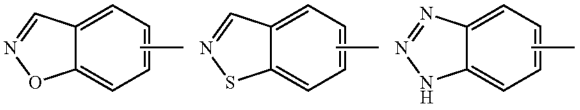
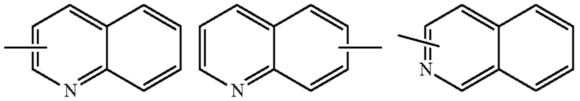

-continued

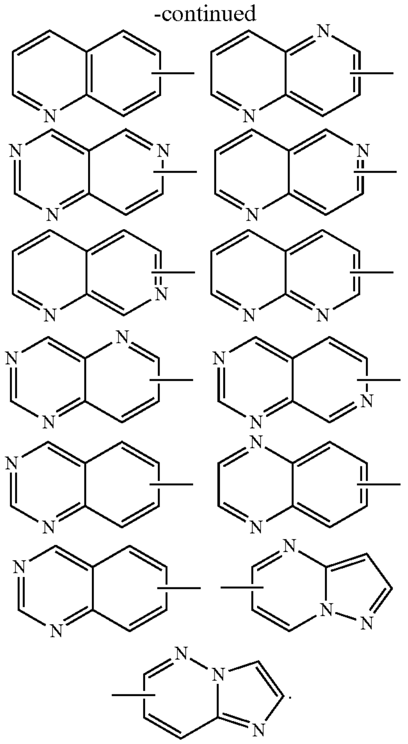

In some embodiments of the present disclosure, the heteroaryl ring as described in the present disclosure (e.g., monocyclic heteroaryl ring, preferably 5- or 6-membered monocyclic heteroaryl ring) may be fused with one or more non-aromatic rings to form a polycyclic group, wherein the ring connected to the parent structure is a heteroaryl ring or a non-aromatic ring, and the non-aromatic ring includes but is not limited to: a 3- to 6-membered (preferably a 5- or 6-membered) monocyclic heterocycloalkyl ring (the ring carbon atoms of the monocyclic heterocycloalkyl ring may be substituted by 1 to 2 oxo groups to form a cyclolactam or cyclic lactone structure); a 3- to 6-membered (preferably a 5- or -6-membered) monocyclic cycloalkyl ring (the ring carbon atoms of the monocyclic cycloalkyl ring may be substituted by 1 or 2 oxo groups to form a cyclic ketone structure), etc.

The polycyclic group in which the above-mentioned monocyclic heteroaryl ring is fused with one or more non-aromatic rings can be connected to other groups or the parent structure via a nitrogen atom or carbon atom, and the ring connected to the parent structure is a heteroaryl ring or a non-aromatic ring.

As used herein, the 5- or 6-membered monocyclic heteroaryl is fused with a 5- or -6-membered monocyclic heterocycloalkyl ring to form a 8- to 10-membered biheterocyclic ring, which means that two adjacent substituent groups on the 5- or 6-membered monocyclic heteroaryl together with the ring atoms connecting them form a fused 5- or -6-membered monocyclic heterocycloalkyl ring, and the 5- or -6-membered monocyclic heterocycloalkyl ring is as defined herein, and the formed 8- to 10-membered biheterocyclic ring can also be called a 8- to 10-membered heteroaryl heterocycloalkyl ring.

As used herein, the 5- or 6-membered monocyclic heteroaryl is fused with a 5- or -6-membered monocyclic cycloalkyl ring to form a 8- to 10-membered biheterocyclic ring, which means that two adjacent substituent groups on the 5- or 6-membered monocyclic heteroaryl together with the ring atoms connecting them form a fused 5- or -6-membered monocyclic cycloalkyl ring, wherein the 5- or -6-membered monocyclic cycloalkyl ring is as defined herein, and the formed 8- to 10-membered biheterocyclic ring can also be called a 8- to 10-membered heteroaryl cycloalkyl ring.

Non-limiting examples thereof include:

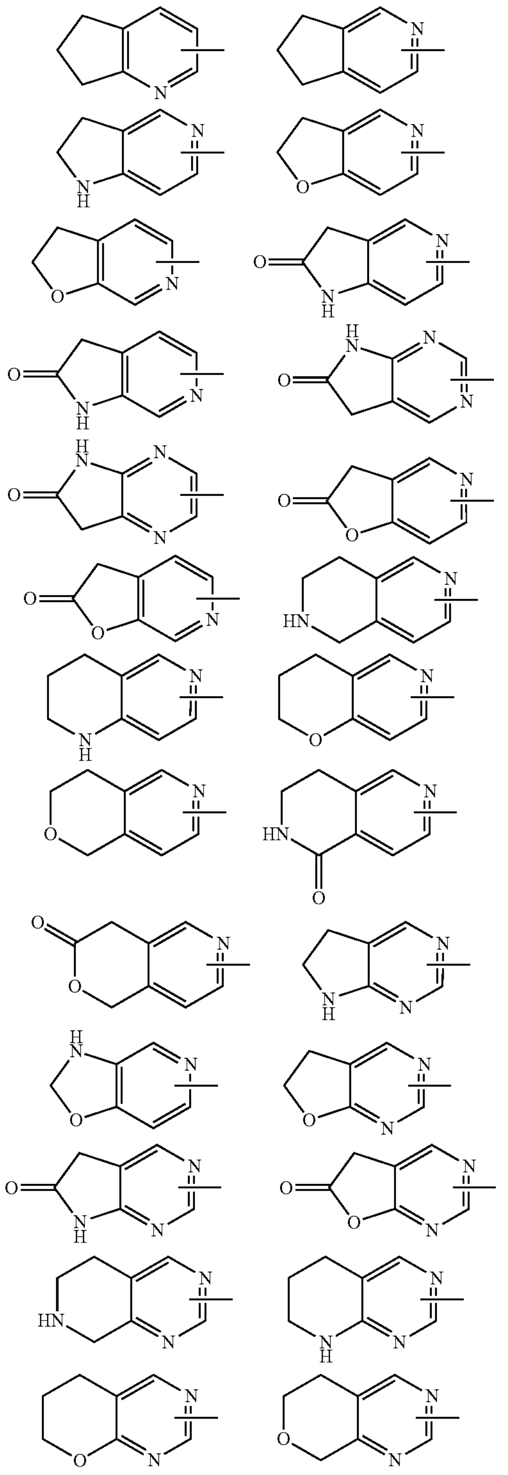

-continued
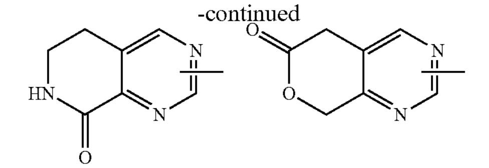
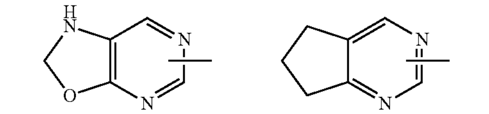
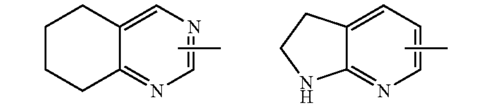
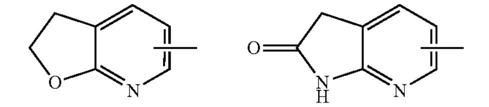
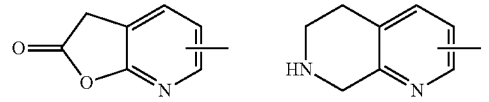
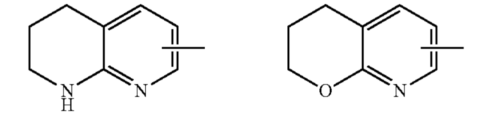
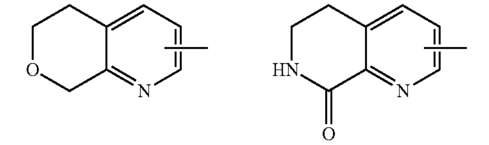
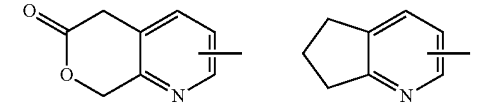
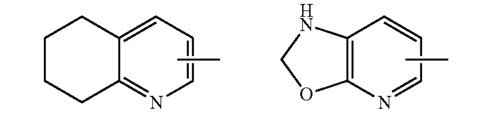
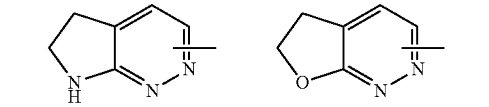
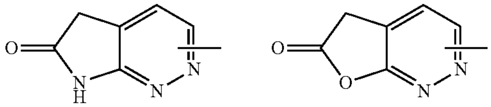
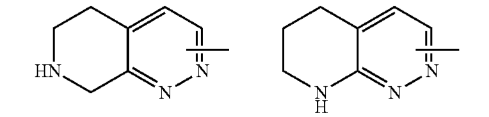
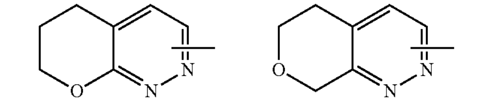
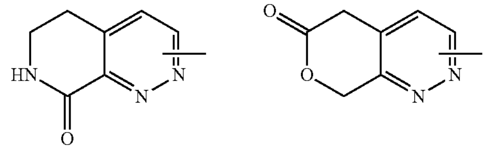
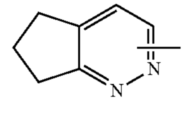
-continued
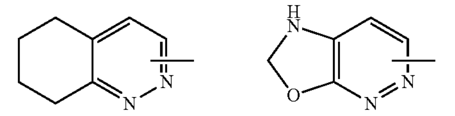
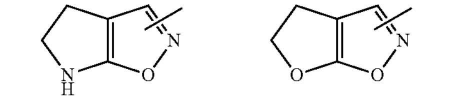
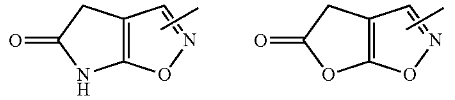
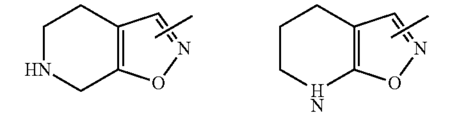
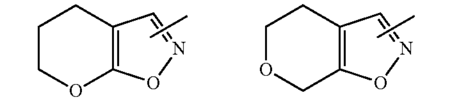
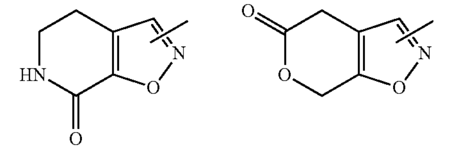
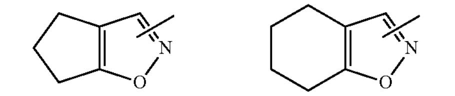
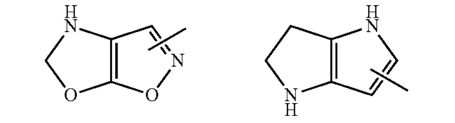
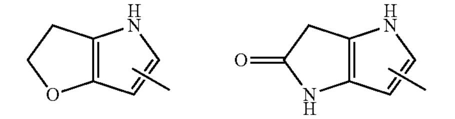
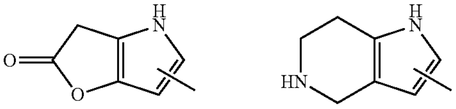
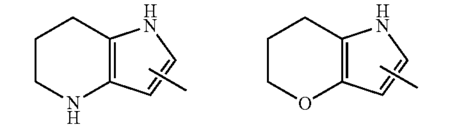
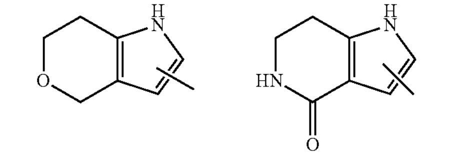
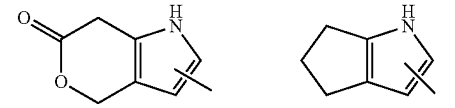
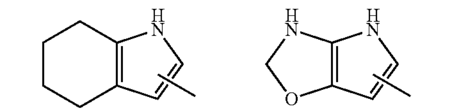
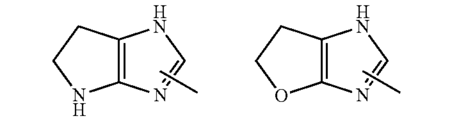

-continued
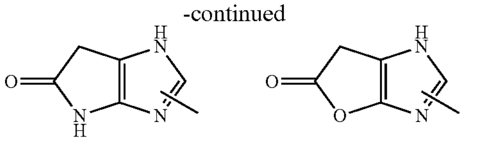
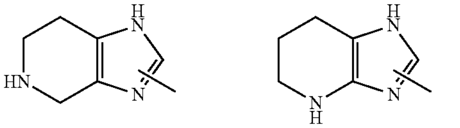
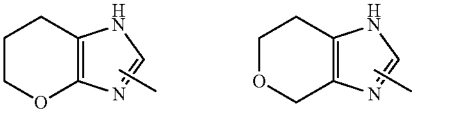
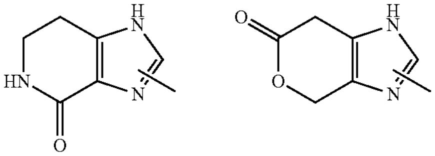
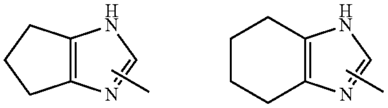
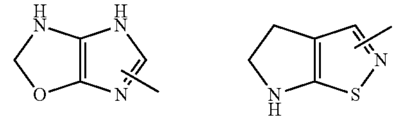
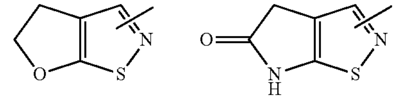
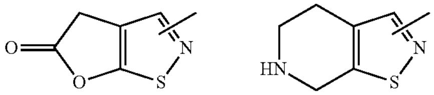
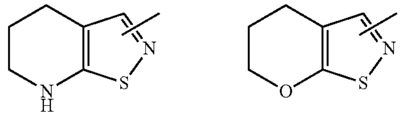
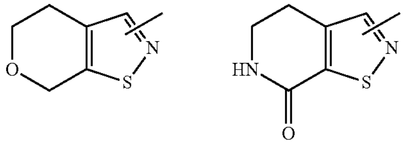
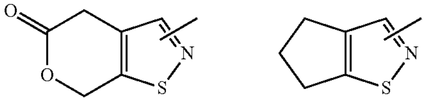
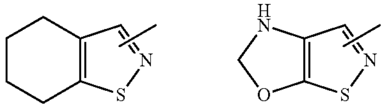
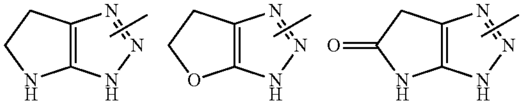
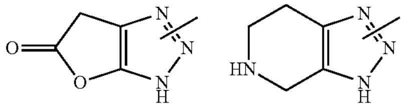
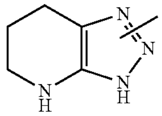
-continued
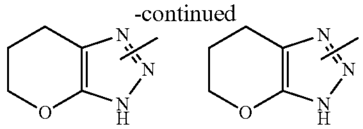
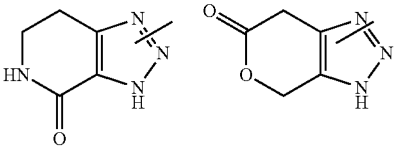
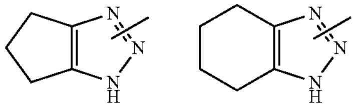
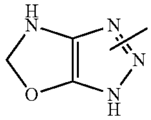
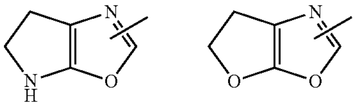
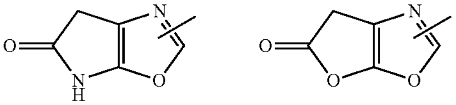
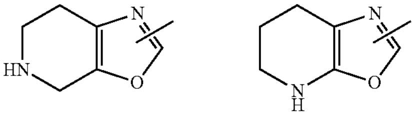
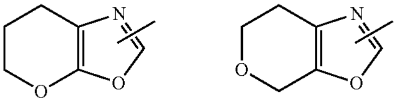
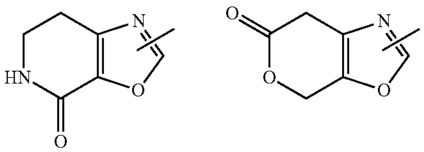
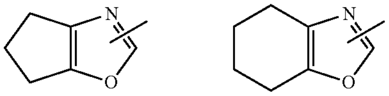
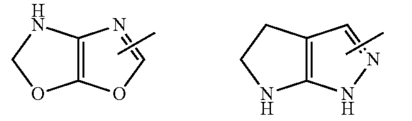
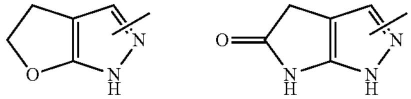
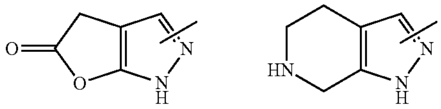
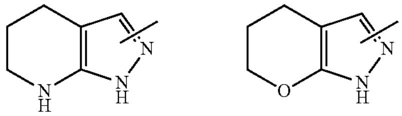
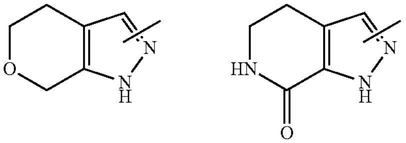

-continued
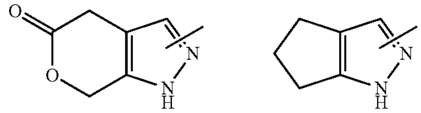
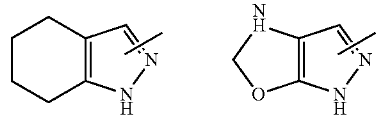
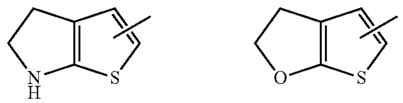
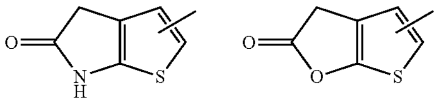
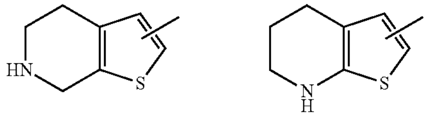
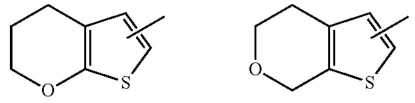
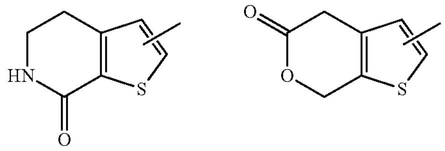
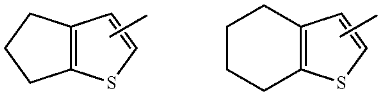
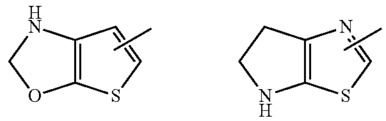
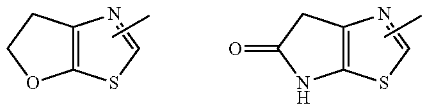
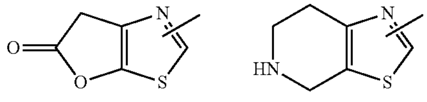
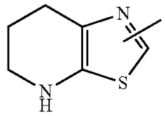
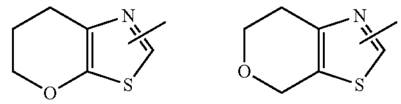
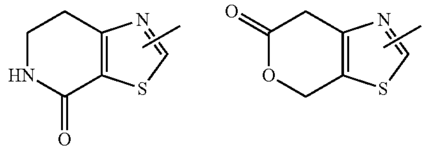
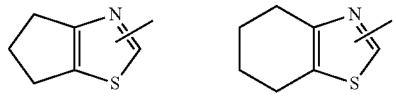
-continued
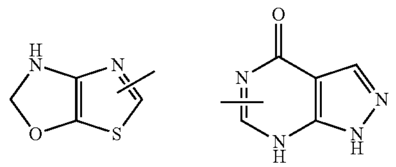
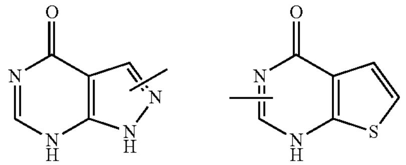
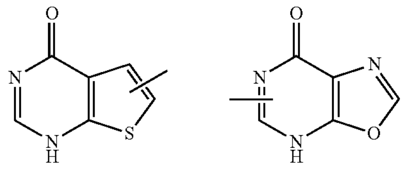
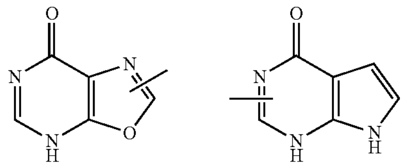
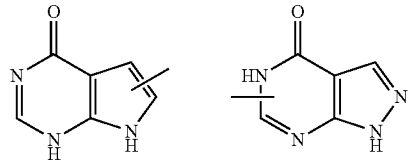
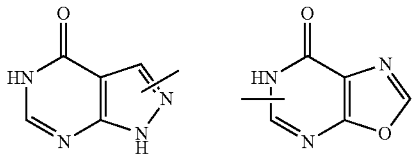
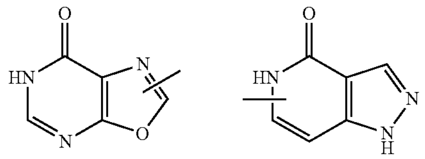
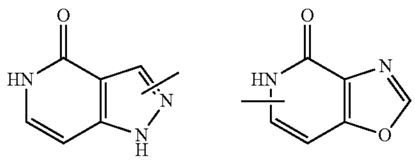
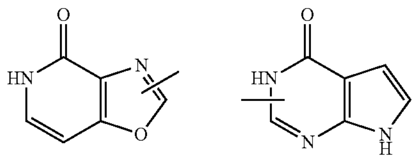
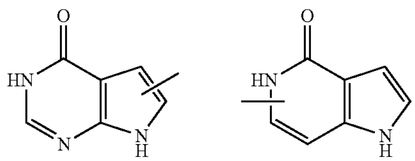

-continued

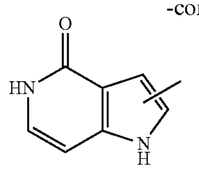

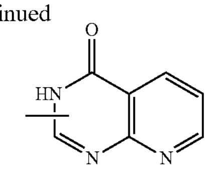

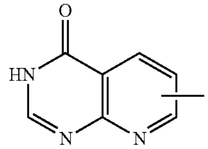

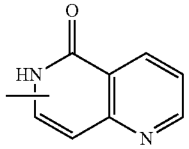

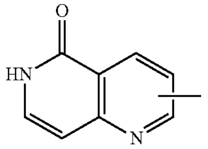

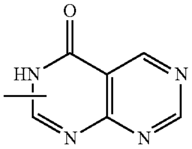

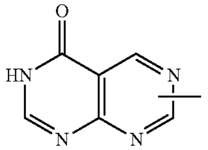

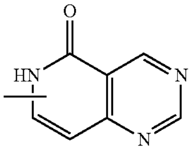

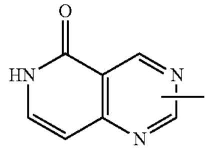

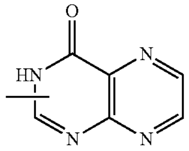

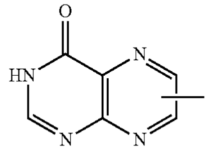

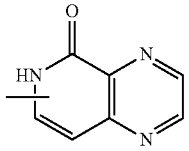

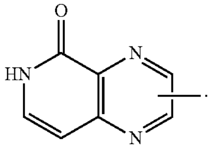.

In the present disclosure, the above-mentioned various heteroaryl groups may be substituted or unsubstituted; when substituted, the substituents are preferably one or more groups as described in the present application.

As used herein, the term "$C_{1-10}$ alkoxy" refers to —O—($C_{1-10}$ alkyl), wherein the definition of alkyl is as described above. $C_{1-6}$ alkoxy is preferred, and $C_{1-3}$ alkoxy is more preferred. Non-limiting examples include methoxy, ethoxy, propoxy, isopropoxy, butoxy, tert-butoxy, isobutoxy, pentoxy, etc. Alkoxy may be optionally substituted or non-substituted; and when alkoxy is substituted, the substituents are preferably one or more groups as described in the present application.

As used herein, "deuterated" refers to the substitution of one or more (such as 1, 2, 3, 4 or 5) or all hydrogens in a group with deuterium atoms.

For example, "deuterated $C_{1-10}$ alkyl" means that one or more (such as 1, 2, 3, 4 or 5) or all hydrogens in alkyl are substituted by deuterium atoms, wherein the definition of alkyl is as described above. Deuterated $C_{1-6}$ alkyl is preferred, and deuterated $C_{1-3}$ alkyl is more preferred. For example, deuterated methyl may be mono-deuterated methyl, di-deuterated methyl or per-deuterated methyl.

As used herein, "halo" refers to the substitution of one or more (e.g., 1, 2, 3, 4 or 5) hydrogens in a group with halogen.

For example, "halo $C_{1-10}$ alkyl" means that alkyl is substituted by one or more (such as 1, 2, 3, 4 or 5) halogens, wherein the definition of alkyl is as described above. Halo $C_{1-6}$ alkyl is preferred, and halo $C_{1-3}$ alkyl is more preferred. Examples of halo $C_{1-8}$ alkyl include (but are not limited to) monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, etc.

For another example, "halo $C_{1-10}$ alkoxy" means that alkoxy is substituted by one or more (such as 1, 2, 3, 4 or 5) halogens, wherein the definition of alkoxy is as described above. Halo $C_{1-6}$ alkoxy is preferred, and halo $C_{1-3}$ alkoxy is more preferred. Examples includes (but not limited to) trifluoromethoxy, trifluoroethoxy, monofluoromethoxy, monofluoroethoxy, difluoromethoxy, difluoroethoxy, etc.

For another example, "halo $C_{3-8}$ cycloalkyl" means that cycloalkyl is substituted by one or more (such as 1, 2, 3, 4 or 5) halogens, wherein the definition of cycloalkyl is as described above. Halo $C_{3-6}$ cycloalkyl is preferred. Examples includes (but not limited to) trifluorocyclopropyl, monofluorocyclopropyl, monofluorocyclohexyl, difluorocyclopropyl, difluorocyclohexyl, etc.

As used herein, the term "hydroxyl" refers to —OH.

As used herein, the term "hydroxymethyl" refers to —$CH_2OH$, and "hydroxyethyl" refers to —$CH_2CH_2OH$ or —$CHOHCH_3$.

As used herein, the term "cyanomethyl" refers to —$CH_2CN$, "cyanoethyl" refers to —$CH_2CH_2CN$ or —$CHCNCH_3$.

As used herein, the term "halogen" refers to fluorine, chlorine, bromine or iodine.

As used herein, the term "amino" refers to —$NH_2$.

As used herein, the term "cyano" refers to —CN.

As used herein, the term "nitro" refers to —$NO_2$.

As used herein, the term "benzyl" refers to —$CH_2$-benzene.

As used herein, the term "oxo" refers to =O.

As used herein, the term "carboxyl" refers to —C(O)OH.

As used herein, the term "carboxylate group" refers to —C(O)O(alkyl) or —C(O)O(cycloalkyl).

As used herein, the term "acetyl" refers to —$COCH_3$.

As used herein, the wavy line on the group, no matter what form it appears, means that it is the place where it is connected to the rest of the molecule. If there is no wavy line on the group, it means that any position in the group may be connected to other positions of the molecule.

"Optional" or "optionally" means that the event or circumstance subsequently described may but need not to occur, and the description includes the occasions where the events or circumstances occur or do not occur. For example, "heterocycloalkyl optionally substituted by alkyl" means that alkyl may but does not have to be present. This description includes the cases where the heterocycloalkyl group is substituted by an alkyl group and the heterocycloalkyl group is not substituted by an alkyl group.

"Substituted" means that one or more hydrogen atoms in the group, preferably up to 5, more preferably 1 to 3 hydrogen atoms, are independently to each other, substituted by a corresponding number of substituents. It goes without saying that the substituents are only in their possible chemical positions, and those skilled in the art can determine (by experiment or theory) possible or impossible substitutions without too much effort. For example, an amino group or a hydroxyl group having free hydrogen may be unstable when combined with a carbon atom having an unsaturated (e.g., olefinic) bond.

Unless otherwise defined, when a group described in the present disclosure is substituted by a substituent, it means that all the same groups appearing in the present disclosure can be substituted by a substituent, which means that the group can be substituted when it exists alone, and it can also be substituted when the group and other groups exist in combination. For example, R is —$C_{1-6}$ alkyl, $C_{6-10}$ aryl, $C_{3-6}$ monocyclic cycloalkyl, —C(O)$C_{1-6}$ alkyl, —$C_{1-4}$ alkyl —$C_{6-10}$ aryl or —$S(O)_2$—$C_{3-6}$ monocyclic cycloalkyl, wherein the $C_{1-6}$ alkyl, $C_{6-10}$ aryl, and $C_{3-6}$ monocyclic cycloalkyl are optionally substituted, and the description also includes the case where $C_{1-6}$ alkyl, $C_{6-10}$ aryl and $C_{3-6}$ monocyclic cycloalkyl of —C(O)$C_{1-6}$ alkyl, —$C_{1-4}$ alkyl —$C_{6-10}$ aryl and —$S(O)_2$—$C_{3-6}$ monocyclic cycloalkyl are optionally substituted.

Unless otherwise defined, the " . . . same or different, and are each independently . . . " as described in the present disclosure means that when there are more than one identical substituent groups in the general formula, the groups may be the same or different, and are of independent species to each other. For example, L is $(CR_{L1}R_{L2})_s$; when s is 2, that is, L is $(CR_{L1}R_{L2})$—$(CR_{L1}R_{L2})$, the two $R_{L1}$ or $R_{L2}$ may be the same or different, and are of independent species to each other; for example, L may be $C(CH_3)(CN)$—$C(CH_2CH_3)(OH)$, $C(CH_3)(CN)$—$C(CH_3)(OH)$ or $C(CN)(CH_2CH_3)$—$C(OH)(CH_2CH_3)$.

Unless otherwise defined, the "substituents independently selected from . . . " as described in the present disclosure means that when more than one hydrogen on the group is substituted by substituents, the types of the substituents may be the same or different, and the selected substituents are of independent species to each other.

As used herein, $C_{1-10}$ may preferably be $C_{1-6}$; more preferably $C_{1-4}$; more preferably $C_{1-3}$. For example, $C_{1-10}$ alkyl may preferably be $C_{1-6}$ alkyl; more preferably $C_{1-4}$ alkyl; more preferably $C_{1-3}$ alkyl. For example, $C_{1-10}$ alkoxy may preferably be $C_{1-6}$ alkoxy; more preferably $C_{1-4}$ alkoxy; more preferably $C_{1-3}$ alkoxy.

As used herein, $C_{3-20}$ may preferably be $C_{3-10}$; more preferably $C_{3-8}$; more preferably $C_{3-6}$; more preferably $C_{3-5}$. For example, $C_{3-20}$ cycloalkyl may preferably be $C_{3-8}$ cycloalkyl; more preferably $C_{3-6}$ cycloalkyl; more preferably $C_{3-6}$ cycloalkyl.

In an embodiment of the present disclosure, in any group, the 3- to 20-membered heterocycloalkyl is 3- to 6-membered heterocycloalkyl, 6- to 10-membered fused heterocycloalkyl, 7- to 11-membered spiroheterocycloalkyl or 7- to 10-membered bridged heterocycloalkyl, wherein, the 3- to 6-membered heterocycloalkyl, 6- to 10-membered fused heterocycloalkyl, 7- to 11-membered spiroheterocycloalkyl, and 7- to 10-membered bridged heterocycloalkyl each independently have 1, 2, or 3 heteroatoms selected from N, O and S as ring atoms.

In an embodiment of the present disclosure, in any group, the $C_{3-6}$ cycloalkyl is selected from: cyclopropyl, cyclobutyl, cyclopentyl and cyclohexyl.

In an embodiment of the present disclosure, in any group, the 3- to 6-membered heterocycloalkyl is selected from: aziridine, ethylene oxide, azetidine, oxetane, tetrahydrofuran, tetrahydrothiophene, tetrahydropyrrole, piperidine, piperazine, morpholine, thiomorpholine, thiomorpholine-1,1-dioxide and tetrahydropyran.

In an embodiment of the present disclosure, in any group, the 3- to 6-membered heterocycloalkyl or 3- to 6-membered monocyclic heterocycloalkyl is selected from the following structures:

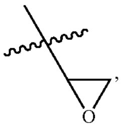, 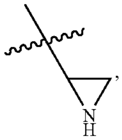, 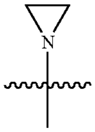, 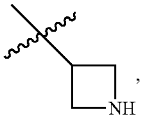,

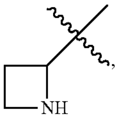, 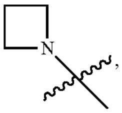, 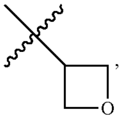, 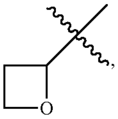,

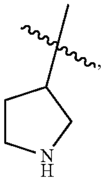, 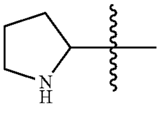, 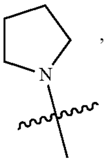, 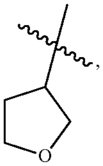,

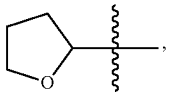, 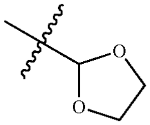, 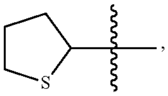,

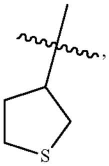, 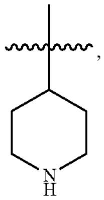, 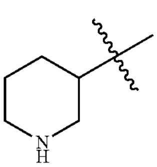,

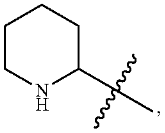, 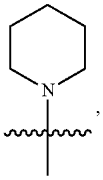, 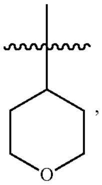, 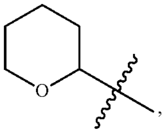,

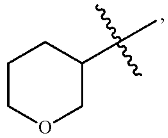, 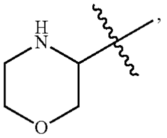, 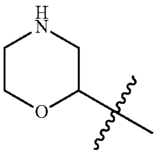,

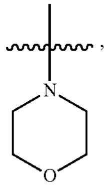, 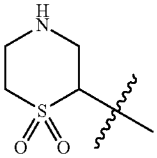, 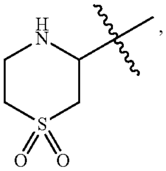,

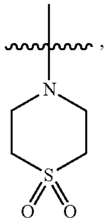, 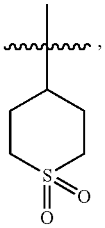, 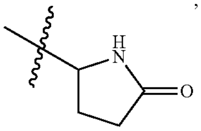,

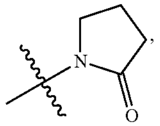, 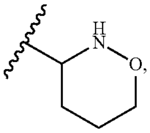, 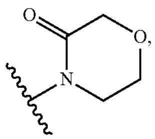,

-continued

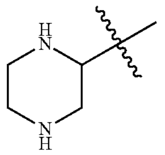

and

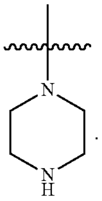

In an embodiment of the present disclosure, in any group, the 5- or -6-membered monocyclic heteroaryl is selected from: thiophene, N-alkylpyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine and pyrazine.

In an embodiment of the present disclosure, in any group, the 5- or -6-membered monocyclic heteroaryl is selected from:

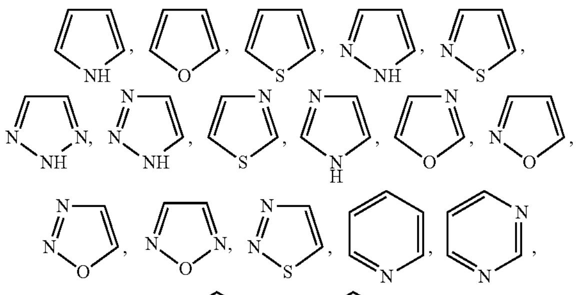

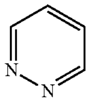

and

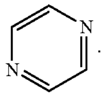

In an embodiment of the present disclosure, in any group, the 8- to 10-membered bicyclic heteroaryl is selected from: benzoxazole, benzisoxazole, benzimidazole, benzothiazole, benzisothiazole, benzotriazole, benzofuran, benzothiophene, indole, indazole, isoindole, quinoline, isoquinoline, quinazoline, quinoxaline, cinnoline, pyridopyrimidine and naphthyridine.

"Pharmaceutical composition" means a mixture containing one or more of the compounds described herein or physiologically/pharmaceutically acceptable salts or prodrugs thereof, and other chemical components, as well as other components such as physiological/pharmaceutically acceptable carriers and excipients. The purpose of the pharmaceutical composition is to promote the administration to the organism, facilitate the absorption of the active ingredients and then exert the biological activity.

The "pharmaceutically acceptable salt" includes pharmaceutically acceptable acid addition salts and pharmaceutically acceptable base addition salts.

"Pharmaceutically acceptable acid addition salt" refers to a salt formed with an inorganic acid or an organic acid that can retain the biological effectiveness of the free base without other side effects.

"Pharmaceutically acceptable base addition salts" include, but are not limited to, salts of inorganic bases such as sodium, potassium, calcium and magnesium salts; and include, but not limited to salts of organic bases, such as ammonium, triethylamine, lysine and arginine salts.

The "solvate" mentioned in the present disclosure refers to a complex formed by the compound of the present disclosure and a solvent. They are obtained either by reacting in a solvent or precipitating or crystallizing out of the solvent. For example, a complex formed from the compound with water is called a "hydrate". The solvate of the compound represented by formula (I) of the present disclosure falls within the scope of the present disclosure.

The compound represented by formula (I) of the present disclosure may contain one or more chiral centers and exist in different optically active forms. When a compound contains a chiral center, the compound contains enantiomers. The present disclosure includes these two isomers and mixtures of the isomers, such as racemic mixtures. Enantiomers can be resolved by methods known in the art, such as crystallization and chiral chromatography. When the compound represented by formula (I) contains more than one chiral center, diastereomers may exist. The present disclosure includes the resolved optically pure specific isomers and mixtures of diastereomers. Diastereoisomers can be resolved by methods known in the art, such as crystallization and preparative chromatography. The "stereoisomers" in the present disclosure include (but are not limited to) enantiomers, diastereomers, etc.

The present disclosure includes prodrugs of the aforementioned compounds. Prodrugs include known amino protecting groups and carboxyl protecting groups, which are hydrolyzed under physiological conditions or released through enzymatic reactions to obtain a parent compound. Specific preparation methods of prodrugs can refer to Saulnier, M. G.; Frennesson, D. B.; Deshpande, M. S.; Hansel, S. B and Vysa, D. M. Bioorg. Med. Chem Lett. 1994, 4, 1985-1990; and Greenwald, R. B.; Choe, Y. H.; Conover, C. D.; Shum, K.; Wu, D.; Royzen, M. J. Med. Chem. 2000, 43, 475.

Generally, the compound of the present disclosure or pharmaceutically acceptable salts thereof, or solvates thereof, or stereoisomers thereof, or prodrugs can be administered with one or more pharmaceutically acceptable carriers in a suitable dosage form. These dosage forms are suitable for oral, rectal, topical, intraoral, and other parenteral administration (for example, subcutaneous, intramuscular, and intravenous administration, etc.). For example, dosage forms suitable for oral administration include capsules, tablets, granules, syrups, etc. The compounds of the present disclosure contained in these preparations may be solid powders or granules; solutions or suspensions in aqueous or non-aqueous liquids; water-in-oil or oil-in-water emulsions, etc. The above-mentioned dosage forms can be prepared from the active compound and one or more carriers or excipients through general pharmacological methods. The above-mentioned carrier needs to be compatible with the active compound or other excipients. For solid preparations, commonly used non-toxic carriers include but are not limited to mannitol, lactose, starch, magnesium stearate, cellulose, glucose, sucrose, etc. Carriers for liquid preparations include water, physiological saline, aqueous dextrose, ethylene glycol, polyethylene glycol, etc. The active compound can form a solution or a suspension with the aforementioned carriers.

The composition of the present disclosure is formulated, quantified and administered in a manner that conforms to medical practice standards. The "therapeutically effective amount" of the compound to be administered is determined by factors such as the specific condition to be treated, the individual to be treated, the cause of the condition, the target of the drug, and the mode of administration.

As used herein, "therapeutically effective amount" refers to the amount of the compound of the present disclosure that will cause an individual's biological or medical response, such as reducing or inhibiting enzyme or protein activity or improving symptoms, alleviating symptoms, slowing or delaying disease progression, or preventing disease.

The therapeutically effective amount of the compound of the present disclosure, or a pharmaceutically acceptable salt thereof, or a solvate thereof, or a stereoisomer thereof contained in the pharmaceutical composition of the present disclosure is preferably 0.1 mg-5 g/kg (body weight).

As used herein, "pharmaceutically acceptable carrier" refers to a non-toxic, inert, solid or semi-solid substance or liquid filling agent, diluent, encapsulating material or auxiliary preparation or any type of excipient, which is compatible with the patient, preferably a mammal, and more preferably a human, and is suitable for delivering the active agent to the target without terminating the activity of the agent.

As used herein, "patient" refers to an animal, preferably a mammal, and more preferably a human. The term "mammal" refers to warm-blooded vertebral mammals, including cats, dogs, rabbits, bears, foxes, wolves, monkeys, deer, rats, pigs, and humans.

As used herein, "treating" refers to reducing, delaying progression of, attenuating, preventing, or maintaining an existing disease or condition (e.g., cancer). Treatment also includes curing one or more symptoms of a disease or condition, preventing the development thereof, or alleviating the disease or condition to a certain degree.

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

For example, the compound of the present disclosure has the structure as shown for compound 7, which can be prepared by the following method comprising: preparing compound 3 from compound 1; preparing compound 5 by reacting compound 4 with an alkenylation reagent; preparing compound 6 by reacting compound 5 with $NH_2$-L-$R_0$; and preparing compound 7 by reacting compound 6 with compound 3.

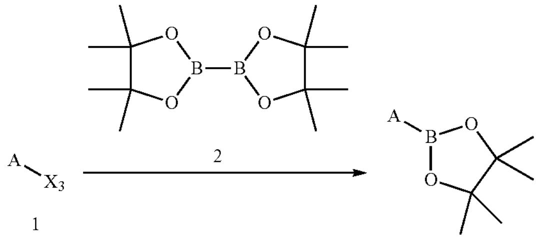
1
2
3

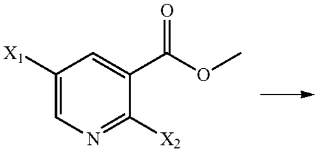
4

-continued

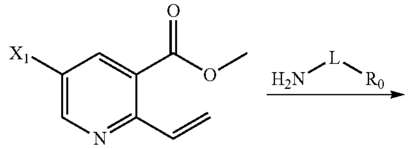
5

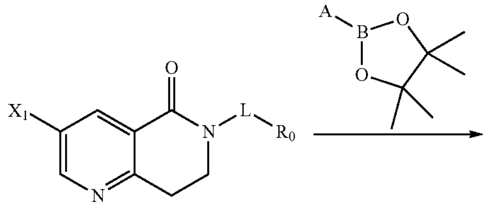
6

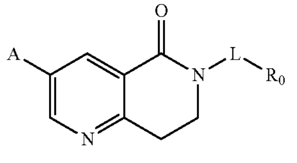
7 in each formula, $X_1$, $X_2$ and $X_3$ are each independently leaving groups (for example, fluorine, bromine, iodine, etc.), wherein A, L and $R_0$ are each defined as above.

DETAILED DESCRIPTION OF THE PREFERRED EMBODIMENT

The following examples further illustrate the present disclosure in combination with specific embodiments. It should be understood that these examples are only used to illustrate the present disclosure and not to limit the scope of the present disclosure. Experimental methods without specified condition in following examples are performed under normal conditions or conditions suggested by manufactures. Unless otherwise specified, percent and portion are calculated by weight. Unless otherwise specified, terms used herein have the same meaning familiar to those skilled in the art. Besides, methods and materials that similar or equivalent to the contents described can be applied in present disclosure.

As used herein, room temperature refers to about 20-25° C. The raw materials, reagents, solvents used in the present disclosure can all be obtained in the market. Preparation method of raw material or reagents in some examples are not indicated, even if the referenced preparation method is not explicitly stated, they can be obtained by referring to the preparation method in other examples.

Description of abbreviations: EtOAc: ethyl acetate, PE: petroleum ether, ACN: acetonitrile, IPA: isopropanol, DEA: diethylamine, DIPEA: N,N-diisopropylethylamine, FA; formic acid, Hex: hexane, EtOH: ethanol, HATU: 2-(7-azabenzotriazole)-N,N,N',N'-tetramethyluronium hexafluorophosphate, DMA: dimethyl acetylamide, DME: dimethyl ether, $H_2O$: water, MeOH: methanol, DCM: dichloromethane, i-PrOH: isopropyl alcohol, $Pd_2(dba)_3$: tris(dibenzylideneacetone)dipalladium, BINAP: (±)-2,2'-Bis(diphenylphosphino)-1,1'-binaphthyl, THF: tetrahydrofuran, TFA: trifluoroacetic acid; DMF: dimethylformamide; NIS: N-iodosuccinimide, PyBOP: benzotriazole-1-yl-oxytripyrrolidinophosphonium hexafluorophosphate; S-phos Pd G2:

chloro (2-dicyclohexylphosphino-2',6'-dimethoxy-1,1'-biphenyl)(2'-amino-1,1'-biphenyl-2-yl)palladium (II).

The alkaline HPLC method used in the following examples is as follows: column model: xbridge $C_{18}$ 19*150 mm, 5 μm; system: 10 mmol/L, $NH_4HCO_3$ aqueous solution; flow rate: 15 mL/min; gradient: 20%-45% ACN—$NH_4HCO_3$; column temperature: room temperature.

Example 1: Preparation of N-(6-(6-(1-(1-(1-(4-fluorophenyl)ethyl)-1H-pyrazol-4-yl)-5-oxo-5,6,7,8-tetrahydro-1,6-naphthyridin-3-yl)imidazo[1,2-b]pyridazin-2-yl)acetamide (Z1)

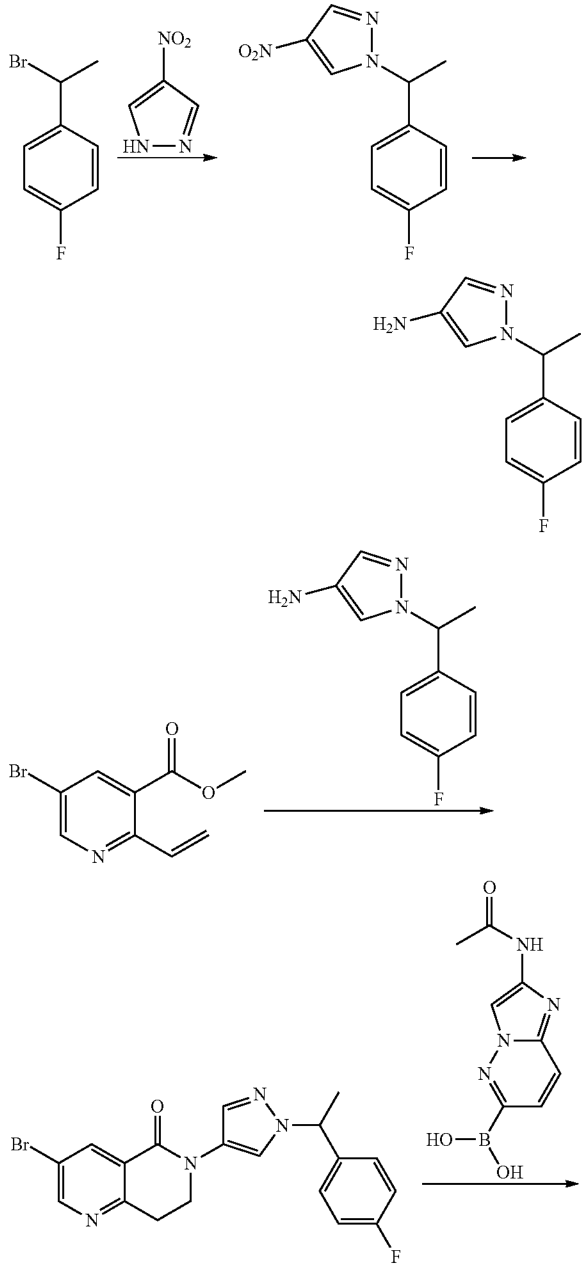

-continued

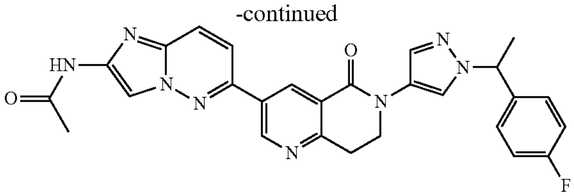

Z1

Step 1: Under the protection of nitrogen, anhydrous N,N-dimethylformamide (30 mL) and potassium carbonate (819.80 mg, 5.940 mmol) were added into a round bottom flask with three necks (50 mL), finally, 1-(1-bromoethyl)-4-fluorobenzene (1.0 g, 4.950 mmol) and 4-nitro-1H-pyrazole (0.5594 g, 4.950 mmol) were added, the mixture was stirred under room temperature for two hours. Ethyl acetate (80 mL) was added into the mixture, the mixture was washed with saturated ammonium chloride and sodium chloride twice (60 mL*2) successively, the ethyl acetate phase was dried over anhydrous sodium sulphate, filtered, the filtrate was spin-dried to obtain 1-(1-(4-fluorophenyl) ethyl)-4-nitro-1H-pyrazole (0.8378 g, yield (hereinafter referred to as Y): 72%). ES-API: $[M+H]^+$=236.1.

Step 2: Methanol (40 mL) and 1-(1-(4-fluorophenyl) ethyl)-4-nitro-1H-pyrazole (0.8378 g, 3.564 mmol) were added into a round bottom flask with single neck, then palladium on carbon (0.5 g) was added into the flask. Under the protection of hydrogen, the mixture was stirred under room temperature for 12 hours. After the reaction was completed, the reacted mixture was filtered, the filtrate was spin-dried to obtain 1-(1-(4-fluorophenyl)ethyl)-1H-pyrazol-4-amine (680.0 mg, 3.3156 mmol, Y: 37%). ES-API: $[M+H]^+$=206.1.

Step 3: Methyl 5-bromo-2-vinylnicotinate (280 mg, 1.157 mmol) and 1-(1-(4-fluorophenyl) ethyl)-1H-pyrazol-4-amine (680.0 mg, 3.3156 mmol) were mixed in DMA (5 mL) in a microwave bottle. The reaction was subjected to microwave radiation at 150° C. for three hours, then cooled to room temperature, ethyl acetate (50 mL) was added, the reaction mixture was washed with water (45 mL*3) and saturated sodium chloride solution (45 mL*3), the combined organic layers were concentrated, purified on silica gel by automatic fast chromatography (EtOAc/PE 0-50%) to obtain 3-bromine-6-(1-(1-(1-(4-fluorophenyl)ethyl)-1H-pyrazol-4-yl)-7,8-dihydro-1,6-naphthyridin-5 (6H)-one (388.05 mg, Y: 81%). ES-API: $[M+H]^+$=415.0.

Step 4: Under the protection of nitrogen, 3-bromo-6-(1-(1-(1-(4-fluorophenyl)ethyl)-1H-pyrazol-4-yl)-7,8-dihydro-1,6-naphthyridin-5(6H)-one (164.3 mg, 0.397 mmol), (2-acetylaminoimidazo[1,2-b]pyridazin-6-yl)boronic acid (174.68 mg, 0.794 mmol), sodium carbonate (84.16 mg, 0.794 mmol), and 1,1'-bis(diphenylphosphino)ferrocene-palladium(II) dichloride dichloromethane complex (49.60 mg, 0.05955 mmol) were dissolved in 1,4-dioxane (12 mL) and $H_2O$ (3 mL), the mixture was replaced with nitrogen for three times, subjected to microwave radiation at 90° C. for 35 minutes. The reaction mixture was cooled to room temperature, concentrated, the crude product was purified by alkaline HPLC to obtain light yellow solid N-(6-(6-(1-(1-(1-(4-fluorophenyl)ethyl)-1H-pyrazol-4-yl)-5-oxo-5,6,7,8-tetrahydro-1,6-naphthyridin-3-yl)imidazo[1,2-b]pyridazin-2-yl)acetamide (Z1, 75.0 mg, Y: 36%). ES-API: $[M+H]^+$ =511.2. $^1H$ NMR (400 MHz, DMSO-d6) δ 10.88 (s, 1H), 9.23 (s, 1H), 8.74 (d, J=1.7 Hz, 1H), 8.27 (d, J=10.2 Hz, 2H), 8.05 (d, J=9.4 Hz, 1H), 7.90-7.79 (m, 2H), 7.33-7.24 (m, 2H), 7.11 (t, J=8.8 Hz, 2H), 5.60 (q, J=6.9 Hz, 1H), 4.05 (t, J=6.5 Hz, 2H), 2.05 (s, 3H), 1.75 (d, J=7.0 Hz, 3H).

Example 2: Preparation of N-(6-(6-(3,5-difluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)acetamide (Z2)

mixture was cooled to room temperature, methanol was carefully added into the mixture dropwise, until there was no bubble generated, ethyl acetate (80 mL) was added into the mixture, the mixture was washed with saturated ammonium chloride and sodium chloride twice (60 mL*2) successively, the ethyl acetate phase was dried over anhydrous sodium sulphate, filtered, the filtrate was spin-dried to obtain (3,5-

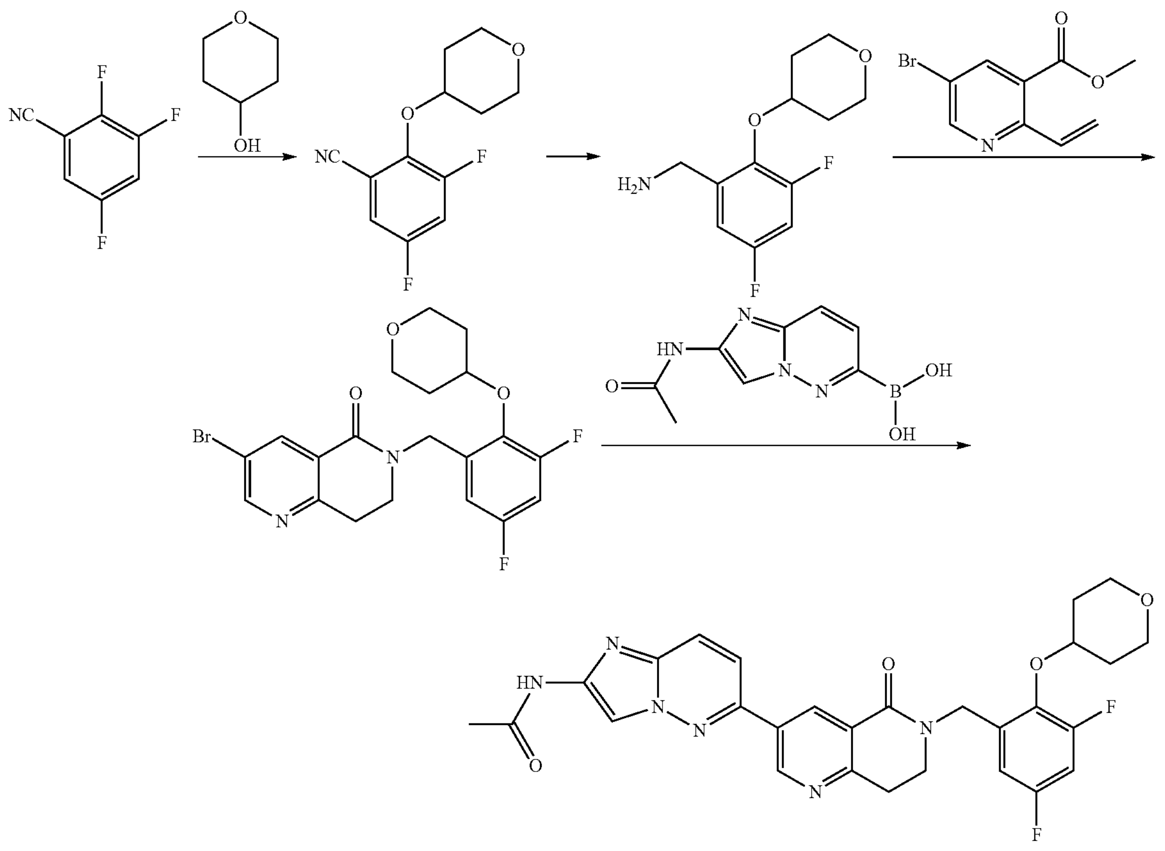

Z2

Step 1: Under the protection of nitrogen, tetrahydrofuran (30 mL) and tetrahydro-2H-pyran-4-ol (1.30 g, 12.74 mmol) were added into a round bottom flask with three necks at 0° C., then sodium hydride (305.73 mg, 7.643 mmol) was added, 2,3,5-trifluorobenzonitrile (1.0 g, 6.369 mmol) was added into the mixture and then the mixture was slowly heated to 55° C. and reacted for 12 hours. After the reaction was completed, the mixture was cooled to 0° C., ethyl acetate (80 mL) was added into it, the mixture was washed with saturated ammonium chloride and sodium chloride twice (60 mL*2) successively, the ethyl acetate phase was dried over anhydrous sodium sulphate, filtered, the filtrate was spin-dried to obtain 3,5-difluoro-2-((tetrahydro-2H-pyran-4-yl)oxy)benzonitrile (1.65 g, raw product). ES-API: $[M+H]^+$=240.1.

Step 2: Under the protection of nitrogen, tetrahydrofuran (80 mL) and 3,5-difluoro-2-((tetrahydro-2H-pyran-4-yl)oxy)benzonitrile (1.65 g, the crude product) was added into a round bottom flask with single neck, then borane-tetrahydrofuran complex was added (30 mL, 2M, 60 mmol). The mixture was slowly heated from room temperature to boiling and reacted overnight. After the reaction was completed, the difluoro-2-((tetrahydro-2H-pyran-4-yl)oxy)phenyl)methylamine (1.16 g, Y:75%). ES-API: $[M+H]^+$=244.1.

Step 3: Methyl 5-bromo-2-vinylnicotinate (280 mg, 1.157 mmol) and (3,5-difluoro-2-((tetrahydro-2H-pyran-4-yl)oxy)phenyl)methylamine (843.45 mg, 3.471 mmol) were mixed in DMA (5 mL) in a microwave bottle. The reaction was subjected to microwave radiation at 150° C. for 3 hours and then cooled to room temperature, ethyl acetate (50 mL) was added into the mixture, the mixture was washed with water (45 mL*3) and saturated sodium chloride solution (45 mL*3), the combined organic layers were concentrated, purified on silica gel by automatic fast chromatography (EtOAc/PE 0-50%) to obtain 3-bromo-6-(3,5-difluoro-2-((tetrahydro-2H-pyran-4-yl)oxy)benzyl)-7,8-dihydro-1,6-naphthyridin-5(6H)-one (540 mg, crude). ES-API: $[M+H]^+$=453.1.

Step 4: Under the protection of nitrogen, 3-bromo-6-(3,5-difluoro-2-((tetrahydro-2H-pyran-4-yl)oxy)benzyl)-7,8-dihydro-1,6-naphthyridin-5(6H)-one (180 mg, crude), (2-acetylaminoimidazo[1,2-b]pyridazin-6-yl)boronic acid (174.68 mg, 0.794 mmol), sodium carbonate (84.16 mg, 0.794 mmol), and 1,1'-bis(diphenylphosphino)ferrocene-palladium(II)dichloride dichloromethane complex (49.60 mg, 0.05955 mmol) were dissolved in dioxane (12 mL) and $H_2O$ (3 mL), the mixture was replaced with nitrogen for three times, subjected to microwave radiation at 90° C. for 35 minutes. The reaction mixture was cooled to room temperature, concentrated, the crude product was purified by alkaline HPLC to obtain light yellow solid N-(6-(6-(3,5-difluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)acetamide (Z2, 8.0 mg, Y: 7.8%). ES-API: $[M+H]^+$=549.2. $^1$H NMR (500 MHz, MeOD) δ 8.41 (s, 1H), 8.04 (s, 1H), 7.65 (s, 1H), 7.05 (d, J=9.4 Hz, 1H), 6.77 (d, J=9.3 Hz, 1H), 5.99 (dd, J=15.8, 8.0 Hz, 2H), 4.03 (s, 2H), 3.49 (s, 1H), 2.84 (t, J=6.7 Hz, 2H), 2.64 (t, J=10.0 Hz, 2H), 2.50 (s, 2H), 2.43 (t, J=6.5 Hz, 2H), 1.39 (s, 3H), 1.17 (s, 2H), 0.98 (d, J=10.2 Hz, 2H).

Example 3: Preparation of N-(6-(6-(3,5-difluoro-2-((tetrahydrofuran-3-yl)oxy)benzyl)-5-oxo-5,6,7,8-tetrahydro-1,6-naphthyridin-3-yl)imidazo[1,2-b]pyridazin-2-yl)acetamide (Z3)

with saturated ammonium chloride and sodium chloride twice (60 mL*2) successively, the ethyl acetate phase was dried over anhydrous sodium sulphate, filtered, the filtrate was spin-dried to obtain 3,5-difluoro-2-((tetrahydrofuran-3-yl)oxy)benzonitrile (1.50 g, the crude product). ES-API: $[M+H]^+$=226.1

Step 2: Under the protection of nitrogen, tetrahydrofuran (80 mL) and 3,5-difluoro-2-((tetrahydrofuran-3-yl)oxy)benzonitrile (1.50 g, the crude product) were added into a 500 mL round bottom flask with single neck, finally borane-tetrahydrofuran complex (30 mL, 2M, 60 mmol) was added. The mixture was slowly heated from room temperature to boiling and reacted overnight. After the reaction was completed, the mixture was cooled to room temperature, methanol was carefully added into the mixture dropwise, until there was no bubble generated, ethyl acetate (80 mL) was added into the mixture, the mixture was washed with saturated ammonium chloride and sodium chloride twice (60 mL*2) successively, the ethyl acetate phase was dried over anhydrous sodium sulphate, filtered, the filtrate was spin-dried to obtain (3,5-difluoro-2-((tetrahydrofuran-3-yl)oxy)phenyl)methylamine (0.773 g, Y:53%). ES-API: $[M+H]^+$=230.1.

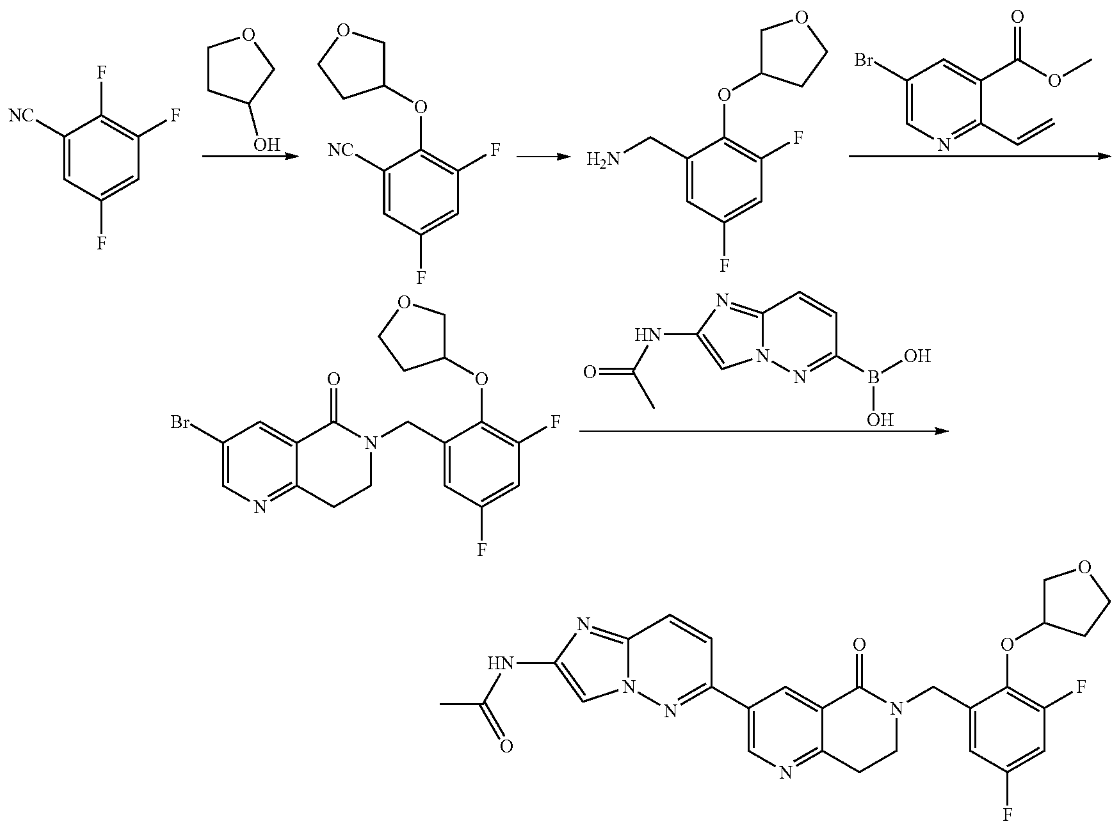

Z3

Step 1: Under the protection of nitrogen, tetrahydrofuran (30 mL) and tetrahydrofuran-3-ol (1.12 g, 12.74 mmol) were added into a 50 mL round bottom flask with three necks at 0° C., then sodium hydride (305.73 mg, 7.643 mmol) was added, finally, 2,3,5-trifluorobenzonitrile (1.0 g, 6.369 mmol) was added into the mixture, the mixture was slowly heated to 55° C. and reacted for 12 hours. After the reaction was completed, the mixture was cooled to 0° C., ethyl acetate (80 mL) was added into it, the mixture was washed Step 3: Methyl 5-bromo-2-vinylnicotinate (280 mg, 1.157 mmol) and (3,5-difluoro-2-((tetrahydrofuran-3-yl)oxy)phenyl)methylamine (773 mg, 3.375 mmol) were mixed in DMA (5 mL) in a microwave bottle. The reaction was subjected to microwave radiation at 150° C. for 3 hours and then cooled to room temperature, ethyl acetate (50 mL) was added into the mixture, the mixture was washed with water (45 mL*3) and saturated sodium chloride solution (45 mL*3), the combined organic layers were concentrated, purified on silica gel by automatic fast chromatography (EtOAc/PE 0-50%) to obtain 3-bromo-6-(3,5-difluoro-2-((tetrahydrofuran-3-yl)oxy)benzyl)-7,8-dihydro-1,6-naphthyridin-5(6H)-one (335 mg, Y:66%). ES-API: $[M+H]^+$= 439.1.

Step 4: Under the protection of nitrogen, 3-bromo-6-(3,5-difluoro-2-((tetrahydrofuran-3-yl)oxy)benzyl)-7,8-dihydro-1,6-naphthyridin-5(6H)-one (120 mg, 0.2733 mmol), (2-acetylaminoimidazo[1,2-b]pyridazin-6-yl)boronic acid (120.0 mg, 0.5454 mmol), sodium carbonate (90 mg, 0.8490 mmol), and 1,1'-bis(diphenylphosphino)ferrocene-palladium(II)dichloride dichloromethane complex (35.0 mg, 0.04278 mmol) were dissolved in dioxane (12 mL) and $H_2O$ (3 mL), the mixture was replaced with nitrogen for three times, subjected to microwave radiation at 90° C. for 35 minutes. The reaction mixture was cooled to room temperature, concentrated, the crude product was purified by alkaline HPLC to obtain light yellow solid N-(6-(6-(3,5-difluoro-2-((tetrahydrofuran-3-yl)oxy)benzyl)-5-oxo-5,6,7,8-tetrahydro-1,6-naphthyridin-3-yl)imidazo[1,2-b]pyridazin-2-yl)acetamide (Z3, 21.0 mg, Y: 21.5%). ES-API: $[M+H]^+$= 535.1. $^1$H NMR (400 MHz, DMSO-d6) δ 10.88 (s, 1H), 9.23 (d, J=2.2 Hz, 1H), 8.72 (d, J=2.2 Hz, 1H), 8.28 (s, 1H), 8.05 (d, J=9.5 Hz, 1H), 7.85 (d, J=9.5 Hz, 1H), 7.30-7.16 (m, 1H), 6.92 (d, J=8.1 Hz, 1H), 4.94 (s, 1H), 4.69 (s, 2H), 3.90 (q, J=7.9 Hz, 1H), 3.88-3.82 (m, 1H), 3.73 (dd, J=14.4, 6.6 Hz, 1H), 3.65 (dd, J=13.6, 5.4 Hz, 3H), 3.19 (t, J=6.7 Hz, 2H), 2.10-2.01 (m, 5H).

Example 4: Preparation of 3-(2-amino-imidazo[1,2-b]pyridazin-6-yl)-6-(2-trifluoromethoxy-benzyl)-7,8-dihydro-6H-[1,6]naphthyridin-5-one (Z4)

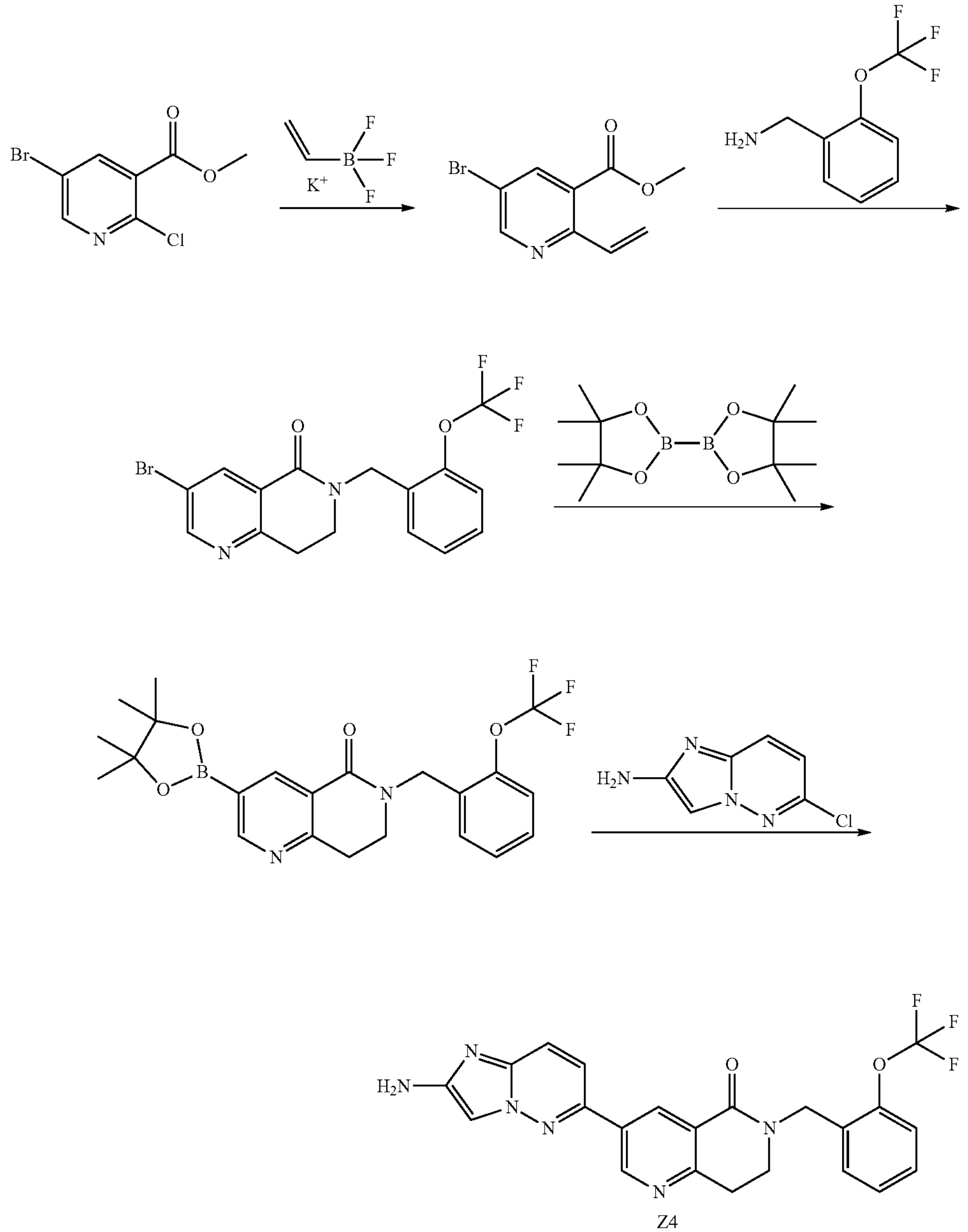

Z4

Step 1: Preparation of methyl 5-bromo-2-vinylnicotinate: Under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol) and [1,1-bis(diphenylphosphino)ferrocene] dichloropalladium(II) (585 mg, 0.798 mmol) were dissolved in EtOH (200 mL), the mixture was replaced with nitrogen for three times, reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 52%). ES-API: $[M+H]^+$=242.1

Step 2: Preparation of 3-bromo-6-(2-(trifluoromethoxy) benzyl)-7,8-dihydro-1,6-naphthyridin-5(6H)-one: Methyl 5-bromo-2-vinylnicotinate (150 mg, 0.620 mmol) and ((2-(trifluoromethoxy)phenyl)methylamine (178 mg, 0.929 mmol) were mixed in DMA (5 mL) in a microwave bottle. The reaction was subjected to microwave radiation at 180° C. for one hour and then cooled to room temperature, ethyl acetate (15 mL) was added into the mixture, the mixture was washed with water (10 mL*3) and saturated sodium chloride solution (10 mL*3), the combined organic layers were concentrated, purified on silica gel by automatic fast chromatography (EtOAc/PE 0-50%) to obtain 3-bromo-6-(2-(trifluoromethoxy)benzyl)-7,8-dihydro-1,6-naphthyridin-5 (6H)-one (135 mg, Y: 54%). ES-API: $[M+H]^+$=401.0.

Step 3: Preparation of 3-(4,4,5,5-tetramethyl-1,3,2-dioxaborolan-2-yl)-6-(2-(trifluoromethoxy)benzyl)-7,8-dihydro-1,6-naphthyridin-5(6H)-one: 3-Bromo-6-(2-(trifluoromethoxy)benzyl)-7,8-dihydro-1,6-naphthyridin-5(6H)-one (110 mg, 0.274 mmol), bis(pinacolato)diboron (104 mg, 0.411 mmol), potassium acetate (67 mg, 0.685 mmol), [1,1'-bis(diphenylphosphino)ferrocene]dichloropalladium (II) (10 mg, 0.014 mmol) and 1,4-dioxane (20 mL) were added into a 100 mL round bottom flask, the mixture was replaced with nitrogen for three times, reacted at 98° C. overnight, cooled to room temperature, filtered with suction, the filter cake was washed with ethyl acetate for three times to obtain the filtrate, the filtrate was concentrated to obtain crude product 3-(4,4,5,5-tetramethyl-1,3,2-dioxaborolan-2-yl)-6-(2-(trifluoromethoxy)benzyl)-7,8-dihydro-1,6-naphthyridin-5(6H)-one (100 mg, Y: 99%). ES-API: $[M+H]^+$ =367.1.

Step 4: preparation of N-(6-(5-oxo-6-(2-(trifluoromethoxy)benzyl)-5,6,7,8-tetrahydro-1,6-naphthyridin-3-yl)imidazo[1,2-b]pyridazin-2-yl acetamide: Under the protection of nitrogen, 6-chloroimidazo[1,2-b]pyridazin-2-amine (19 mg, 0.114 mmol), 3-(4,4,5,5-tetramethyl-1,3,2-dioxaborolan-2-yl)-6-(2-(trifluoromethoxy)benzyl)-7,8-dihydro-1,6-naphthyridin-5(6H)-one (50 mg, 0.137 mmol), sodium carbonate (18 mg, 0.171 mmol), 1,1'-bis(diphenylphosphino)ferrocene-palladium(II)dichloride dichloromethane complex (2 mg, 0.002 mmol) were dissolved into DME/$H_2O$/EtOH (7:3:2) (2 mL), the mixture was replaced with nitrogen for three times, subjected to microwave radiation at 120° C. for 30 minutes. The reaction mixture was cooled to room temperature, concentrated, the crude product was purified by acid HPLC to obtain yellow powder 3-(2-amino-imidazo[1,2-b]pyridazin-6-yl)-6-(2-trifluoromethoxy-benzyl)-7,8-dihydro-6H-[1,6]naphthyridin-5-one (Z4, 6.2 mg, Y: 10%). ES-API: $[M+H]^+$=455.0. $^1H$ NMR (400 MHz, DMSO-d6) δ 9.24 (d, J=2.0 Hz, 1H), 8.75 (d, J=2.4 Hz, 1H), 7.76 (d, J=8.8 Hz, 1H), 7.66 (d, J=9.2 Hz, 1H), 7.49-7.37 (m, 5H), 5.65 (s, 2H), 4.83 (m, 2H), 3.65 (t, J1=6.8 Hz, J2=13.6 Hz, 2H), 3.21 (t, J1=6.8 Hz, J2=13.2 Hz, 2H).

Example 5: Preparation of N-(6-(5-oxo-6-(2-(trifluoromethoxy)benzyl)-5,6,7,8-tetrahydro-1,6-naphthyridin-3-yl)imidazo[1,2-b]pyridazin-2-yl)acetamide (Z5)

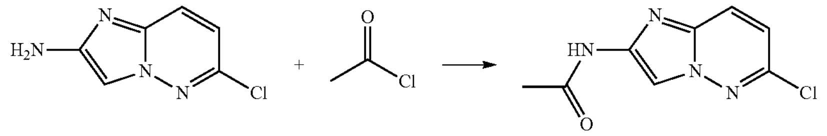

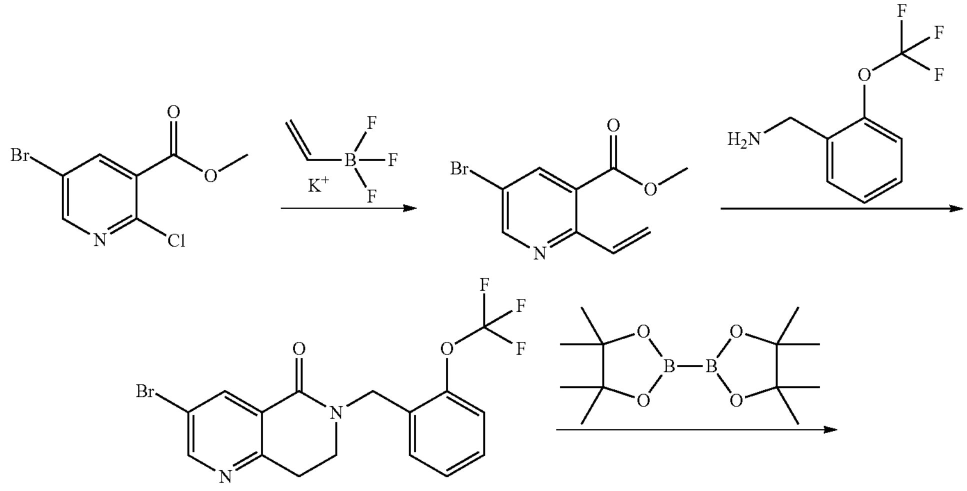

-continued

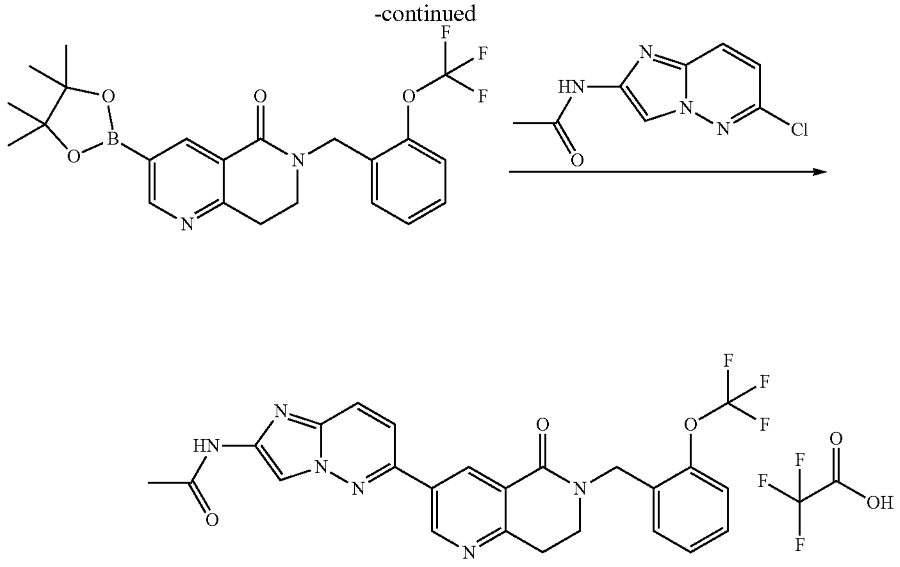

Z5

Step 1: Preparation of N-(6-chloroimidazo[1,2-b]pyridazin-2-yl)acetamide: Acetyl chloride (128 mg, 1.625 mmol) was slowly added into a solution of 2-amino-6-chloroimidazo[1,2-b]pyridazine (250 mg, 1.483 mmol) in N,N-dimethylacetamide (5 mL), the mixture was stirred at room temperature for one hour. LCMS showed the reaction was completed, the reaction solution was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (281 mg, Y: 90%). ES-API: $[M+H]^+$=211.0.

Step 2: Preparation of methyl 5-bromo-2-vinylnicotinate: Under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved into EtOH (200 mL), the mixture was replaced with nitrogen for three times, and reacted at 80° C. for one hour, the reaction mixture was cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 3: Preparation of 3-bromo-6-(2-(trifluoromethoxy)benzyl)-7,8-dihydro-1,6-naphthyridin-5(6H)-one: Methyl 5-bromo-2-vinylnicotinate (150 mg, 0.620 mmol) and ((2-(trifluoromethoxy)phenyl)methylamine (178 mg, 0.929 mmol) were mixed in DMA (4 mL) in a microwave bottle. The reaction was subjected to microwave radiation at 180° C. for one hour and then cooled to room temperature, ethyl acetate (15 mL) was added into the mixture, the mixture was washed with water (10 mL*3) and saturated sodium chloride solution (10 mL*3), the combined organic layers were concentrated, purified on silica gel by automatic fast chromatography (EtOAc/PE 0-50%) to obtain 3-bromo-6-(2-(trifluoromethoxy)benzyl)-7,8-dihydro-1,6-naphthyridin-5(6H)-one (135 mg, Y: 54%). ES-API: $[M+H]^+$=401.0

Step 4: Preparation of 3-(4,4,5,5-tetramethyl-1,3,2-dioxaborolan-2-yl)-6-(2-(trifluoromethoxy)benzyl)-7,8-dihydro-1,6-naphthyridin-5(6H)-one: 3-bromo-6-(2-(trifluoromethoxy)benzyl)-7,8-dihydro-1,6-naphthyridin-5(6H)-one (110 mg, 0.274 mmol), bis(pinacolato)diboron (104 mg, 0.411 mmol), potassium acetate (67 mg, 0.685 mmol), [1,1'-bis(diphenylphosphino)ferrocene]dichloropalladium (II) (10 mg, 0.014 mmol) and 1,4-dioxane (20 mL) were added into a 100 mL round bottom flask, the mixture was replaced with nitrogen for three times, reacted at 98° C. overnight, cooled to room temperature, filtered with suction, washed with ethyl acetate for three times to obtain the filtrate, the filtrate was concentrated to obtain crude product 3-(4,4,5,5-tetramethyl-1,3,2-dioxaborolan-2-yl)-6-(2-(trifluoromethoxy)benzyl)-7,8-dihydro-1,6-naphthyridin-5(6H)-one (100 mg, Y: 99%). ES-API: $[M+H]^+$=367.1.

Step 5: Preparation of N-(6-(5-oxo-6-(2-(trifluoromethoxy)benzyl)-5,6,7,8-tetrahydro-1,6-naphthyridin-3-yl)imidazo[1,2-b]pyridazin-2-yl acetamide: Under the protection of nitrogen, N-(6-chloroimidazo[1,2-b]pyridazin-2-yl)acetamide (24 mg, 0.114 mmol), 3-(4,4,5,5-tetramethyl-1,3,2-dioxaborolan-2-yl)-6-(2-(trifluoromethoxy)benzyl)-7,8-dihydro-1,6-naphthyridin-5(6H)-one (50 mg, 0.137 mmol), sodium carbonate (18 mg, 0.171 mmol), 1,1'-bis(diphenylphosphino)ferrocene-palladium(II)dichloride dichloromethane complex (2 mg, 0.002 mmol) were dissolved in DME/$H_2O$/EtOH (7:3:2) (2 mL), the mixture was replaced with nitrogen for three times, the reaction was subjected to microwave radiation at 120° C. for 30 minutes, then cooled to room temperature, the crude product was purified by acid HPLC to obtain yellow powder N-(6-(5-oxo-6-(2-(trifluoromethoxy)benzyl)-5,6,7,8-tetrahydro-1,6-naphthyridin-3-yl)imidazo[1,2-b]pyridazin-2-yl acetamide (Z5, 8.2 mg, Y: 12%). ES-API: $[M+H]^+$=497.1. $^1$H NMR (400 MHz, DMSO-d6) δ 10.96 (s, 1H), 9.30 (d, J=2.4 Hz, 1H), 8.80 (d, J=2.4 Hz, 1H), 8.35 (s, 1H), 8.12 (d, J=9.2 Hz, 1H), 7.92 (d, J=9.2 Hz, 1H), 7.49-7.37 (m, 4H), 4.84 (s, 2H), 3.66 (t, J1=6.8 Hz, J2=13.2 Hz, 2H), 3.23 (t, J1=6.4 Hz, J2=13.2 Hz, 2H), 2.11 (s, 3H).

Example 6: Preparation of N-(6-(6-(2-(cyclopentyloxy)-5-fluorobenzyl)-5-oxo-5,6,7,8-tetrahydro-1,6-naphthyridin-3-yl)imidazol[1,2-b]pyridazin-2-yl) acetamide (Z6)

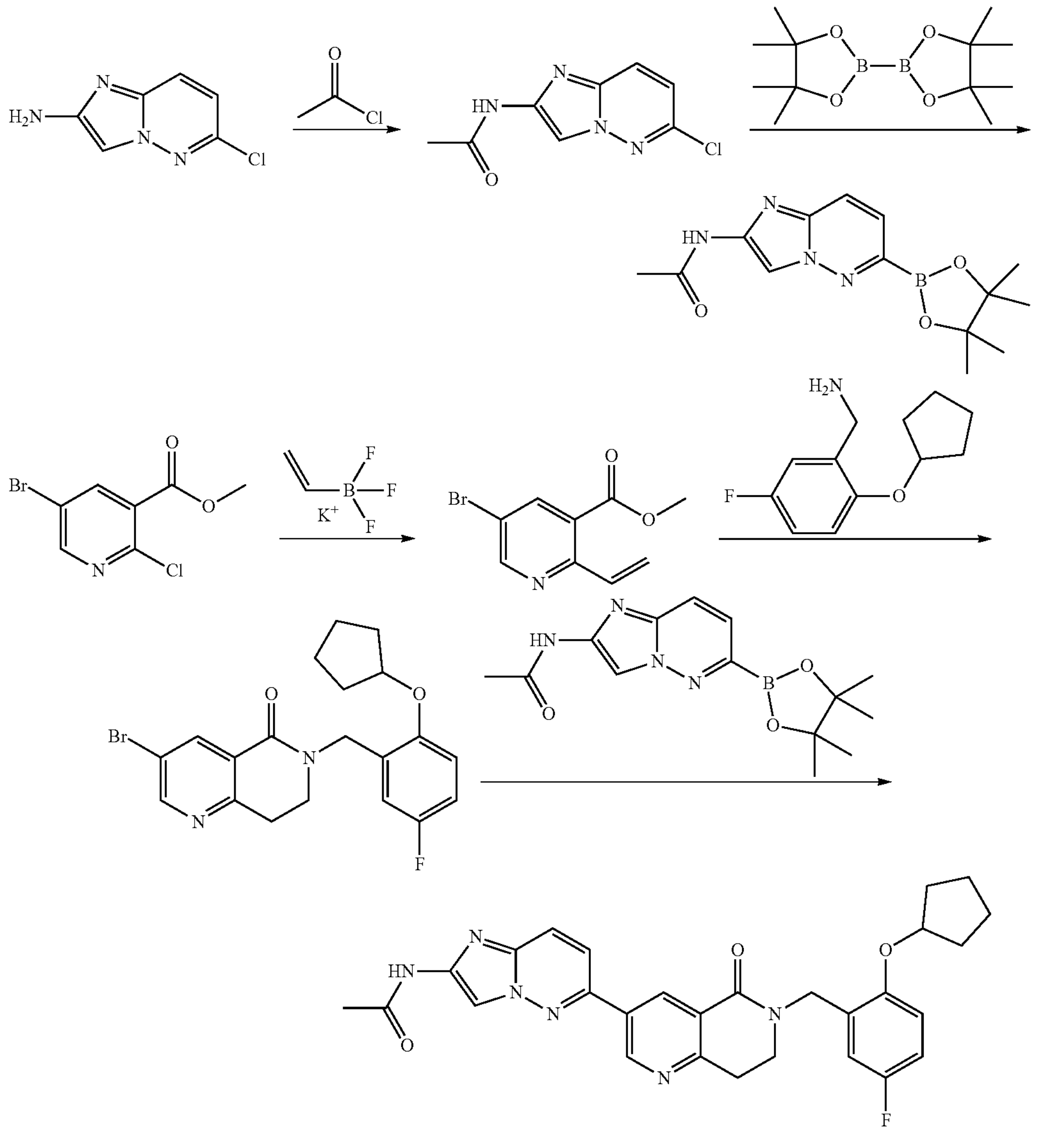

Z6

Step 1: Preparation of N-(6-chloroimidazo[1,2-b] pyridazin-2-yl)acetamide: Acetyl chloride (512 mg, 6.525 mmol) was slowly added into a solution of 2-amino-6-chloroimidazo[1,2-b]pyridazine (1 g, 5.932 mmol) in N,N-dimethylacetamide (20 mL), the mixture was stirred at room temperature for one hour. LCMS showed the reaction was completed, the reacted mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (1.15 g, Y: 92%). ES-API: $[M+H]^+$=211.0.

Step 2: Preparation of N-(6-(4,4,5,5-tetramethyl-1,3,2-dioxaborolan-2-yl)imidazo[1,2-b]pyridazin-2-yl)acetamide: N-(6-chloroimidazo[1,2-b]pyridazin-2-yl)acetamide (1.15 g, 5.46 mmol), bis(pinacolato)diboron (1.66 mg, 6.55 mmol), potassium acetate (1.34 g, 13.65 mmol), [1,1'-bis (diphenylphosphino)ferrocene]dichloropalladium(II) (400 mg, 0.546 mmol) and 1,4-dioxane (40 mL) were added into a 100 mL round bottom flask, the mixture was replaced with nitrogen for three times, reacted at 98° C. overnight, cooled to room temperature, filtered with suction, the filter cake was washed with ethyl acetate for three times to obtain the filtrate, the filtrate was concentrated to obtain crude product N-(6-(4,4,5,5-tetramethyl-1,3,2-dioxaborolan-2-yl)imidazo [1,2-b]pyridazin-2-yl)acetamide (1.201 g, Y: 99%). ES-API: $[M+H]^+$=221.0.

Step 3: Preparation of methyl 5-bromo-2-vinylnicotinate: Under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, reacted at 80° C. for one hour, then cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 4: Preparation of 3-bromo-6-(2-(cyclopentyloxy)-5-fluorobenzyl)-7,8-dihydro-1,6-naphthyridin-5(6H)-one: Methyl 5-bromo-2-vinylnicotinate (500 mg, 2.066 mmol) and (2-(cyclopentyloxy)-5-fluorophenyl)methylamine (648 mg, 3.098 mmol) were mixed in DMA (10 mL) in a microwave bottle. The reaction was subjected to microwave radiation for one hour at 180° C. and then cooled to room temperature, ethyl acetate (15 mL) was added into the mixture, the mixture was washed with water (10 mL*3) and saturated sodium chloride solution (10 mL*3), the combined organic layers were concentrated, purified on silica gel by automatic fast chromatography (EtOAc/PE 0-50%) to obtain 3-bromo-6-(2-(cyclopentyloxy)-5-fluorobenzyl)-7,8-dihydro-1,6-naphthyridin-5(6H)-one (300 mg, Y: 35%). ES-API: $[M+H]^+$=419.0.

Step 5: Preparation of N-(6-(6-(2-(cyclopentyloxy)-5-fluorobenzyl)-5-oxo-5,6,7,8-tetrahydro-1,6-naphthyridin-3-yl)imidazo[1,2-b]pyridazin-2-yl)acetamide: Under the protection of nitrogen, 3-bromo-6-(2-(cyclopentyloxy)-5-fluorobenzyl)-7,8-dihydro-1,6-naphthyridin-5(6H)-one (50 mg, 0.119 mmol), N-(6-(4,4,5,5-tetramethyl-1,3,2-dioxaborolan-2-yl)imidazo[1,2-b]pyridazin-2-yl)acetamide (66 mg, 0.298 mmol), sodium carbonate (38 mg, 0.357 mmol), 1,1'-bis(diphenylphosphino)ferrocene-palladium(II)dichloride dichloromethane complex (5 mg, 0.006 mmol) were dissolved into dioxane (5 mL) and $H_2O$ (1 mL), the mixture was replaced with nitrogen for three times, the reaction solution was heated in oil bath at 95° C. for four hours, then cooled to room temperature, concentrated, the crude product was purified by alkaline HPLC to obtain light yellow solid N-(6-(6-(2-(cyclopentyloxy)-5-fluorobenzyl)-5-oxo-5,6,7,8-tetrahydro-1,6-naphthyridin-3-yl)imidazo[1,2-b]pyridazin-2-yl)acetamide (Z6, 7.8 mg, Y: 10%). ES-API: $[M+H]^+$=515.2. $^1$H NMR (400 MHz, DMSO-d6) δ 10.89 (s, 1H), 9.22 (d, J=2.4 Hz, 1H), 8.73 (d, J=1.6 Hz, 1H), 8.29 (s, 1H), 8.05 (d, J=9.6 Hz, 1H), 7.85 (d, J=9.2 Hz, 1H), 7.03-6.93 (m, 3H), 4.80-4.77 (m, 1H), 4.60 (s, 2H), 3.59 (t, J1=6.8 Hz, J2=13.6 Hz, 2H), 3.15 (t, J1=6.4 Hz, J2=13.2 Hz, 2H), 2.05 (s, 3H), 1.84-1.80 (m, 2H), 1.67-1.58 (m, 4H), 1.51-1.47 (m, 2H).

Example 7: Preparation of N-(6-(5-oxo-6-(1-(2-(trifluoromethoxy)phenyl)ethyl)-5,6,7,8-tetrahydro-1,6-naphthyridin-3-yl)imidazo[1,2-b]pyridazin-2-yl)acetamide (Z7)

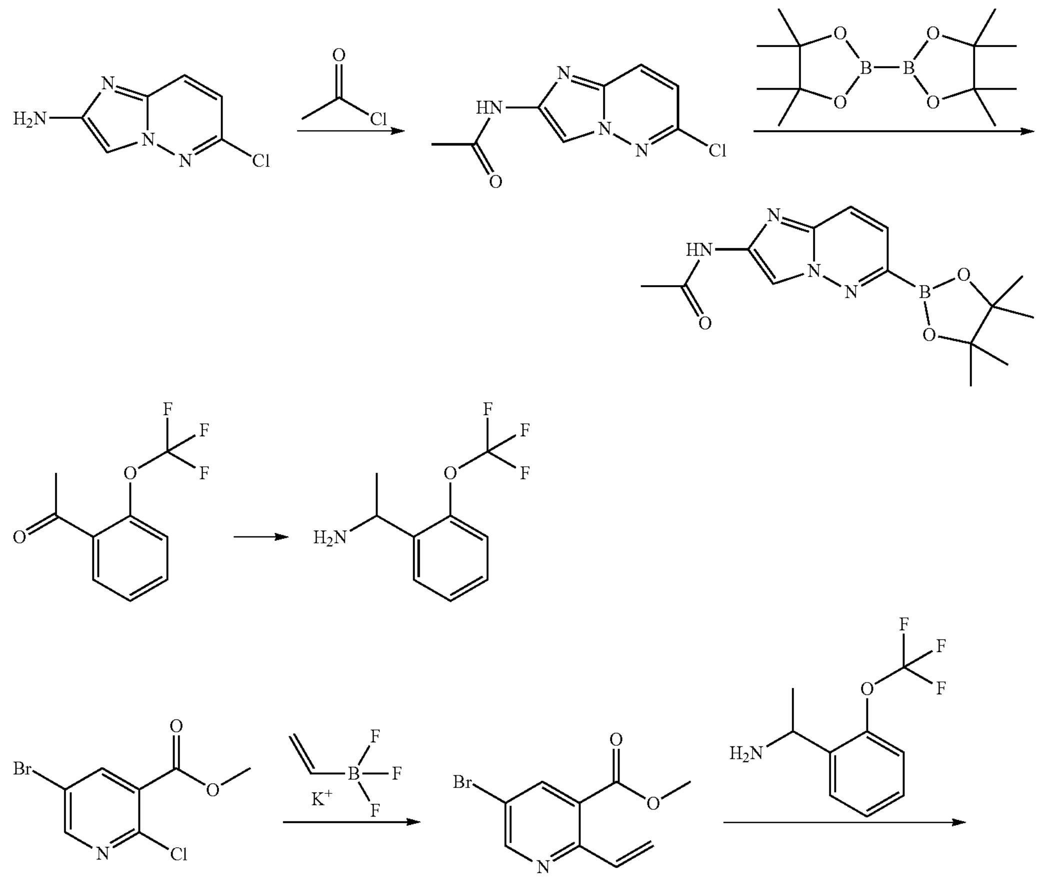

-continued

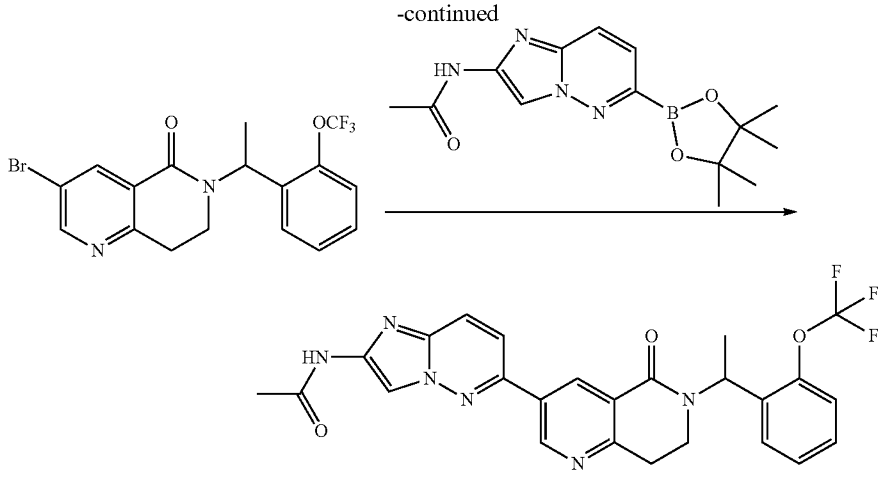

Z7

Step 1: Preparation of N-(6-chloroimidazo[1,2-b]pyridazin-2-yl)acetamide: Acetyl chloride (512 mg, 6.525 mmol) was slowly added into a solution of 2-amino-6-chloroimidazo[1,2-b]pyridazine (1 g, 5.932 mmol) in N,N-dimetylacetamide (20 mL), the reaction mixture was stirred at room temperature for one hour, LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (1.15 g, Y: 92%). ES-API: [M+H]*=211.0.

Step 2: Preparation of N-(6-(4,4,5,5-tetramethyl-1,3,2-dioxaborolan-2-yl)imidazo[1,2-b]pyridazin-2-yl)acetamide: N-(6-chloroimidazo[1,2-b]pyridazin-2-yl)acetamide (1.15 g, 5.46 mmol), bis(pinacolato)diboron (1.66 mg, 6.55 mmol), potassium acetate (1.34 g, 13.65 mmol), [1,1'-bis(diphenylphosphino)ferrocene]dichloropalladium(II) (400 mg, 0.546 mmol) and 1,4-dioxane (40 mL) were added into a 100 mL round bottom flask, the mixture was replaced with nitrogen for three times, reacted at 98° C. overnight, cooled to room temperature, filtered with suction, the filter cake was wash with ethyl acetate for three times to obtain the filtrate, the filtrate was concentrated to obtain crude product N-(6-(4,4,5,5-tetramethyl-1,3,2-dioxaborolan-2-yl)imidazo[1,2-b]pyridazin-2-yl)acetamide (1.201 g, Y: 99%). ES-API: $[M+H]^+$=221.0.

Step 3: Preparation of 1-(2-(trifluoromethoxy)phenyl)ethyl-1-amine: Ammonium acetate (28.3 g, 367.377 mmol) was added into a solution of 1-(2-(trifluoromethoxy)phenyl)ethyl-1-one (5 g, 24.492 mmol) in MeOH (70 mL) and CAN (70 mL), the mixture was heated to 65° C. and reacted for two hours, the reaction mixture was cooled to room temperature, sodium cyanoborohydride (2.309 g, 36.738 mmol) was added into the reaction mixture, the reaction mixture was stirred at 65° C. overnight, LCMS showed the reaction was completed, the reaction mixture was concentrated to dryness, the residue was dissolved in EtOAc (50 mL), washed with water (20 mL*3) and saturated sodium chloride solution (15 mL*3), the combined organic layers were concentrated, purified by preparative thin layer chromatography plate (EtOAc/PE=1:4) to obtain 1-(2-(trifluoromethoxy)phenyl)ethyl-1-amine (1.9 g, Y: 38%). ES-API: $[M+H]^+$=206.1.

Step 4: Preparation of methyl 5-bromo-2-vinylnicotinate: Under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-vinylnicotinate (5.186 g, Y: 54%). ES-API: $[M+H]^+$=242.1.

Step 5: Preparation of 3-bromo-6-(1-(2-(trifluoromethoxy)phenyl)ethyl)-7,8-dihydro-1,6-naphthyridin-5(6H)-one: Methyl 5-bromo-2-vinylnicotinate (780 mg, 3.222 mmol) and 1-(2-(trifluoromethoxy)phenyl)ethyl-1-amine (1.653 g, 8.055 mmol) were mixed in DMA (10 mL) in a microwave bottle. The reaction was subjected to microwave radiation at 150° C. for 8 hours and then cooled to room temperature, ethyl acetate (30 mL) was added into the mixture, the mixture was washed with water (15 mL*3) and saturated sodium chloride (15 mL*3), the combined organic layers were concentrated, purified on silica gel by automatic fast chromatography (EtOAc/PE 0-50%) to obtain 3-bromo-6-(1-(2-(trifluoromethoxy)phenyl)ethyl)-7,8-dihydro-1,6-naphthyridin-5(6H)-one (769 mg, Y: 57%). ES-API: $[M+H]^+$=415.0.

Step 6: Preparation of N-(6-(5-oxo-6-(1-(2-(trifluoromethoxy)phenyl)ethyl)-5,6,7,8-tetrahydro-1,6-naphthyridin-3-yl)imidazo[1,2-b]pyridazin-2-yl)acetamide: Under the protection of nitrogen, 3-bromo-6-(1-(2-(trifluoromethoxy)phenyl)ethyl)-7,8-dihydro-1,6-naphthyridin-5(6H)-one (50 mg, 0.120 mmol), N-(6-(4,4,5,5-tetramethyl-1,3,2-dioxaborolan-2-yl)imidazo[1,2-b]pyridazin-2-yl)acetamide (79 mg, 0.360 mmol), sodium carbonate (38 mg, 0.360 mmol), 1,1'-bis(diphenylphosphino)ferrocene-palladium(II)dichloride dichloromethane complex (5 mg, 0.006 mmol) were dissolved in dioxane (5 mL) and $H_2O$ (1 mL), the mixture was replaced with nitrogen for three times, the reacted solution was heated in oil bath at 95° C. for four hours, cooled to room temperature, concentrated, the crude product was purified by alkaline HPLC to obtain light yellow solid N-(6-(5-oxo-6-(1-(2-(trifluoromethoxy)phenyl)ethyl)-5,6,7,8-tetrahydro-1,6-naphthyridin-3-yl)imidazo[1,2-b]pyridazin-2-yl)acetamide (Z7, 17.67 mg, Y: 29%). ES-API: $[M+H]^+$=511.0. $^1$H NMR (400 MHz, DMSO-d6) δ 10.88 (s, 1H), 9.20 (d, J=2.0 Hz, 1H), 8.73 (d, J=1.6 Hz, 1H), 8.30 (s, 1H), 8.05 (d, J=7.2 Hz, 1H), 7.85 (d, J=7.2 Hz, 1H), 7.66-7.65 (m, 1H), 7.46-7.38 (m, 3H), 6.13-6.09 (m, 1H), 3.56-3.50 (m, 1H), 3.11-3.00 (m, 2H), 2.94-2.87 (m, 1H), 2.05 (s, 3H), 1.51 (d, J=5.6 Hz, 3H).

Example 8: Preparation of N-(6-(5-oxo-6-(3-(trifluoromethoxy)benzyl)-5,6,7,8-tetrahydro-1,6-naphthyridin-3-yl)imidazo[1,2-b]pyridazin-2-yl)acetamide (Z8)

Step 2: Preparation of N-(6-(4,4,5,5-tetramethyl-1,3,2-dioxaborolan-2-yl)imidazo[1,2-b]pyridazin-2-yl)acetamide: N-(6-chloroimidazo[1,2-b]pyridazin-2-yl)acetamide (1.15 g, 5.46 mmol), bis(pinacolato)diboron (1.66 mg, 6.55 mmol), potassium acetate (1.34 g, 13.65 mmol), [1,1'-bis(diphenylphosphino)ferrocene]dichloropalladium(II) (400 mg, 0.546 mmol) and 1,4-dioxane (40 ml) were added into a 100 mL round bottom flask, the mixture was replaced with nitrogen for three times, reacted at 98° C. overnight, cooled to room temperature, filtered with suction, the filter cake was washed with ethyl acetate for three times to obtain the filtrate, the filtrate was concentrated to obtain crude product N-(6-(4,4,5,5-tetramethyl-1,3,2-dioxaborolan-2-yl)imidazo[1,2-b]pyridazin-2-yl)acetamide (1.201 g, Y: 99%). ES-API: $[M+H]^+$=221.0.

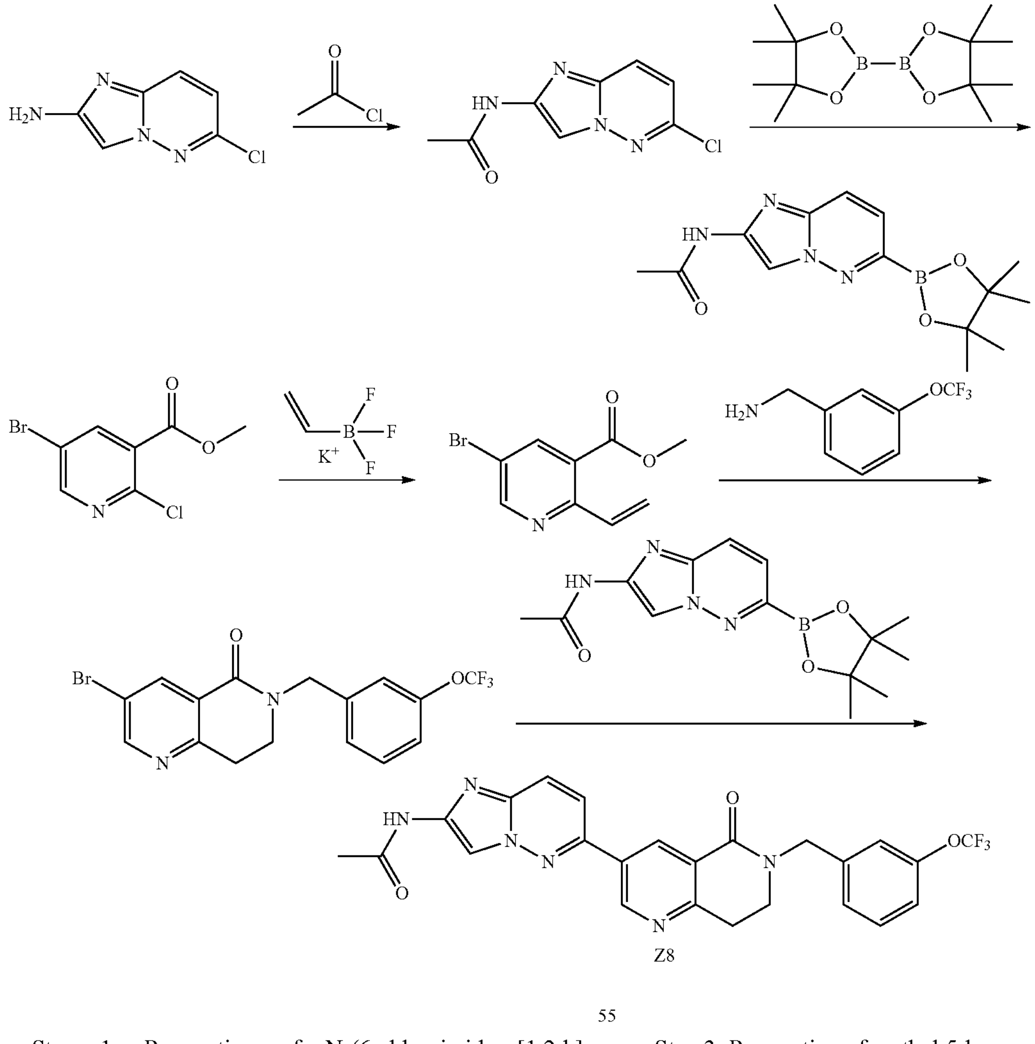

Z8

Step 1: Preparation of N-(6-chloroimidazo[1,2-b]pyridazin-2-yl)acetamide: Acetyl chloride (512 mg, 6.525 mmol) was slowly added into a solution of 2-amino-6-chloroimidazo[1,2-b]pyridazine (1 g, 5.932 mmol) in N,N-dimethylacetamide (20 mL), the reaction mixture was stirred at room temperature for one hour. LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (1.15 g, Y: 92%). ES-API: $[M+H]^+$=211.0.

Step 3: Preparation of methyl 5-bromo-2-vinylnicotinate: Under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 54%). ES-API: $[M+H]^+=242.1$.

Step 4: Preparation of 3-bromo-6-(3-(trifluoromethoxy)benzyl)-7,8-dihydro-1,6-naphthyridin-5(6H)-one: Methyl 5-bromo-2-vinylnicotinate (150 mg, 0.620 mmol) and (3-(trifluoromethoxy)phenyl)methylamine (296 mg, 1.549 mmol) were mixed in DMA (4 mL) in a microwave bottle. The reaction was subjected to microwave radiation at 150° C. for 2 hours and then cooled to room temperature, ethyl acetate (15 mL) was added into the mixture, the mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(3-(trifluoromethoxy)benzyl)-7,8-dihydro-1,6-naphthyridin-5(6H)-one (159 mg, Y: 64%). ES-API: $[M+H]^+=401.0$.

Step 5: Preparation of N-(6-(5-oxo-6-(3-(trifluoromethoxy)benzyl)-5,6,7,8-tetrahydro-1,6-naphthyridin-3-yl)imidazo[1,2-b]pyridazin-2-yl acetamide: Under the protection of nitrogen, 3-bromo-6-(3-(trifluoromethoxy)benzyl)-7,8-dihydro-1,6-naphthyridin-5(6H)-one (50 mg, 0.125 mmol), N-(6-(4,4,5,5-tetramethyl-1,3,2-dioxaborolan-2-yl)imidazo[1,2-b]pyridazin-2-yl)acetamide (83 mg, 0.375 mmol), sodium carbonate (40 mg, 0.375 mmol), 1,1'-bis(diphenylphosphino)ferrocene-palladium(II)dichloride dichloromethane complex (5 mg, 0.006 mmol) were dissolved in dioxane (5 mL) and $H_2O$ (1 mL), the mixture was replaced with nitrogen for three times, the reacted solution was heated in oil bath at 95° C. for four hours, cooled to room temperature, concentrated, the crude product was purified by alkaline HPLC to obtain light yellow solid N-(6-(5-oxo-6-(3-(trifluoromethoxy)benzyl)-5,6,7,8-tetrahydro-1,6-naphthyridin-3-yl)imidazo[1,2-b]pyridazin-2-yl)acetamide (Z8, 16.9 mg, Y: 29%). ES-API: $[M+H]^+=497.0$. $^1H$ NMR (400 MHz, DMSO-d6) δ 10.96 (s, 1H), 9.31 (d, J=2.0 Hz, 1H), 8.82 (d, J=1.6 Hz, 1H), 8.37 (s, 1H), 8.13 (d, J=8.0 Hz, 1H), 7.93 (d, J=7.6 Hz, 1H), 7.53-7.48 (m, 1H), 7.45-7.38 (m, 2H), 7.33-7.28 (m, 1H), 4.83 (s, 2H), 3.70 (t, J1=5.2 Hz, J2=10.8 Hz, 2H), 3.23 (t, J1=5.2 Hz, J2=10.8 Hz, 2H), 2.13 (s, 3H).

Example 9: Preparation of N-(6-(6-(2-fluoro-5-(trifluoromethoxy)benzyl)-5-oxo-5,6,7,8-tetrahydro-1,6-naphthyridin-3-yl)imidazo[1,2-b]pyridazin-2-yl)acetamide (Z9)

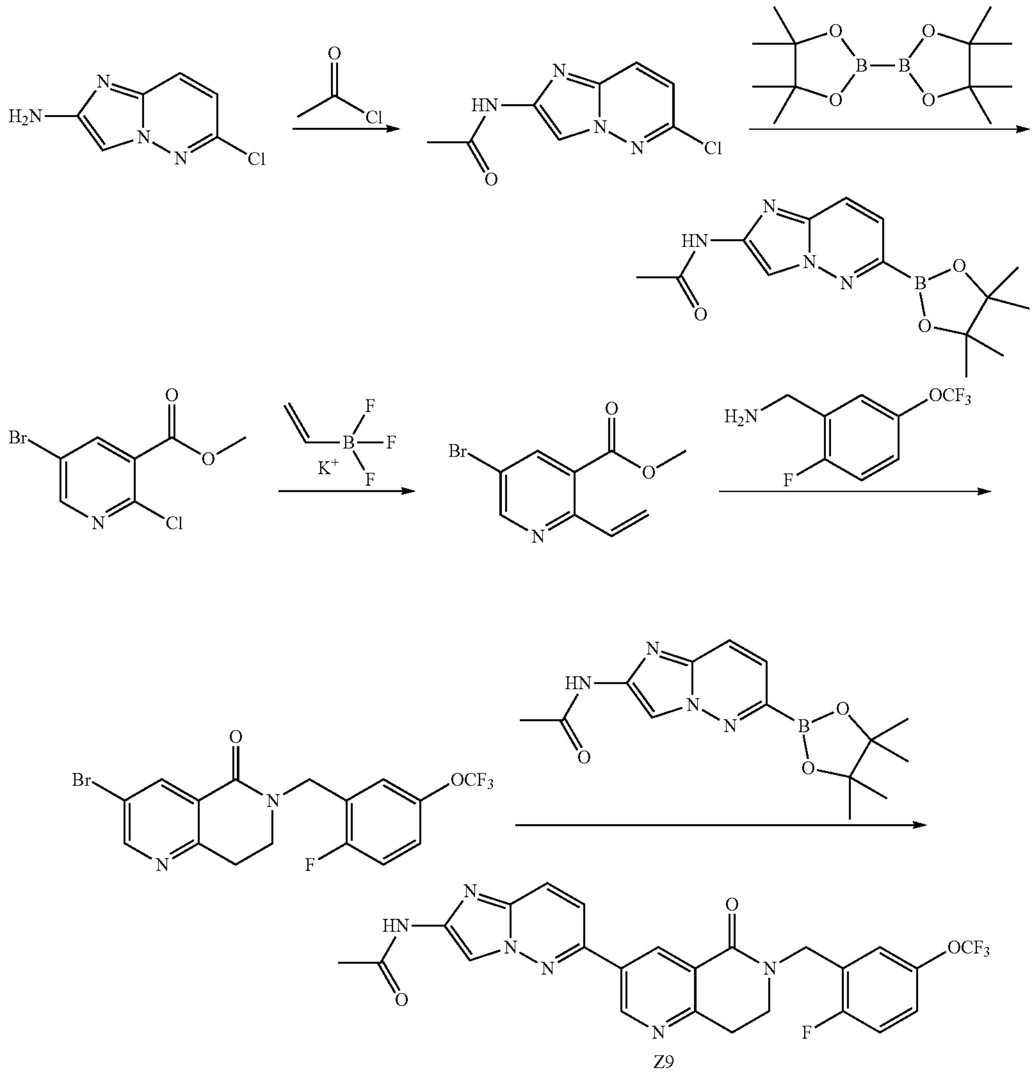

Z9

Step 1: Preparation of N-(6-chloroimidazo[1,2-b]pyridazin-2-yl)acetamide: Acetyl chloride (512 mg, 6.525 mmol) was slowly added into a solution of 2-amino-6-chloroimidazo[1,2-b]pyridazine (1 g, 5.932 mmol) in N,N-dimethylacetamide (20 mL), the reaction solution was stirred for at room temperature for one hour, LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (1.15 g, Y: 92%). ES-API: $[M+H]^+$=211.0.

Step 2: Preparation of N-(6-(4,4,5,5-tetramethyl-1,3,2-dioxaborolan-2-yl)imidazo[1,2-b]pyridazin-2-yl)acetamide: N-(6-chloroimidazo[1,2-b]pyridazin-2-yl)acetamide (1.15 g, 5.46 mmol), bis(pinacolato)diboron (1.66 mg, 6.55 mmol), potassium acetate (1.34 g, 13.65 mmol), [1,1'-bis(diphenylphosphino)ferrocene]dichloropalladium(II) (400 mg, 0.546 mmol) and 1,4-dioxane (40 mL) were added into a 100 mL round bottom flask, the mixture was replaced with nitrogen for three times, reacted at 98° C. overnight, cooled to room temperature, filtered with suction, the filter cake was washed with ethyl acetate for three times to obtain the filtrate, the filtrate was concentrated to obtain crude product N-(6-(4,4,5,5-tetramethyl-1,3,2-dioxaborolan-2-yl)imidazo[1,2-b]pyridazin-2-yl)acetamide (1.201 g, Y: 99%). ES-API: $[M+H]^+$=221.0.

Step 3: Preparation of methyl 5-bromo-2-vinylnicotinate: Under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 4: Preparation of 3-bromo-6-(2-fluoro-5-(trifluoromethoxy)benzyl)-7,8-dihydro-1,6-naphthyridin-5(6H)-one: Methyl 5-bromo-2-vinylnicotinate (280 mg, 1.157 mmol) and ((2-fluoro-5-(trifluoromethoxy)phenyl)methylamine (726 mg, 3.471 mmol) were mixed in DMA (5 mL) in a microwave bottle. The reaction was subjected to microwave radiation at 150° C. for 3 hours and then cooled to room temperature, ethyl acetate (15 mL) was added into the mixture, the mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-fluoro-5-(trifluoromethoxy)benzyl)-7,8-dihydro-1,6-naphthyridin-5(6H)-one (300 mg, Y: 62%). ES-API: $[M+H]^+$=419.0.

Step 5: Preparation of N-(6-(6-(2-fluoro-5-(trifluoromethoxy)benzyl)-5-oxo-5,6,7,8-tetrahydro-1,6-naphthyridin-3-yl)imidazo[1,2-b]pyridazin-2-yl)acetamide: Under the protection of nitrogen, 3-bromo-6-(2-fluoro-5-(trifluoromethoxy)benzyl)-7,8-dihydro-1,6-naphthyridin-5(6H)-one (50 mg, 0.119 mmol), N-(6-(4,4,5,5-tetramethyl-1,3,2-dioxaborolan-2-yl)imidazo[1,2-b]pyridazin-2-yl)acetamide (79 mg, 0.358 mmol), sodium carbonate (38 mg, 0.358 mmol), 1,1'-bis(diphenylphosphino)ferrocene-palladium(II) dichloride dichloromethane complex (5 mg, 0.006 mmol) were dissolved into dioxane (5 mL) and $H_2O$ (1 mL), the mixture was replaced with nitrogen for three times, the reacted solution was heated in oil bath at 95° C. for three hours, cooled to room temperature, concentrated, the crude product was purified by alkaline HPLC to obtain light yellow solid N-(6-(6-(2-fluoro-5-(trifluoromethoxy)benzyl)-5-oxo-5,6,7,8-tetrahydro-1,6-naphthyridin-3-yl)imidazo[1,2-b]pyridazin-2-yl)acetamide (Z9, 10.11 mg, Y: 25%). ES-API: $[M+H]^+$=515.0. $^1H$ NMR (400 MHz, DMSO-d6) δ 10.95 (s, 1H), 9.31 (d, J=2.0 Hz, 1H), 8.80 (d, J=1.6 Hz, 1H), 8.36 (s, 1H), 8.12 (d, J=7.6 Hz, 1H), 7.93 (d, J=7.6 Hz, 1H), 7.46-7.45 (m, 1H), 7.41-7.40 (m, 2H), 4.83 (s, 2H), 3.74 (t, J1=5.6 Hz, J2=11.2 Hz, 2H), 3.24 (t, J1=5.2 Hz, J2=10.4 Hz, 2H), 2.12 (s, 3H).

Example 10: Preparation of N-(6-(5-oxo-6-(2-(trifluoromethoxy)benzyl)-5,6,7,8-tetrahydro-1,6-naphthyridin-3-yl)imidazo[1,2-b]pyridazin-2-yl)cyclopropanecarboxamide (Z10)

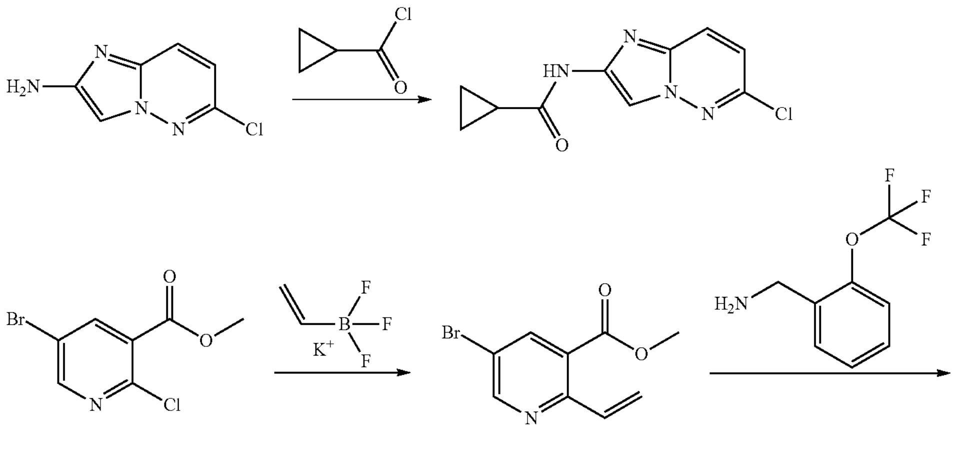

-continued

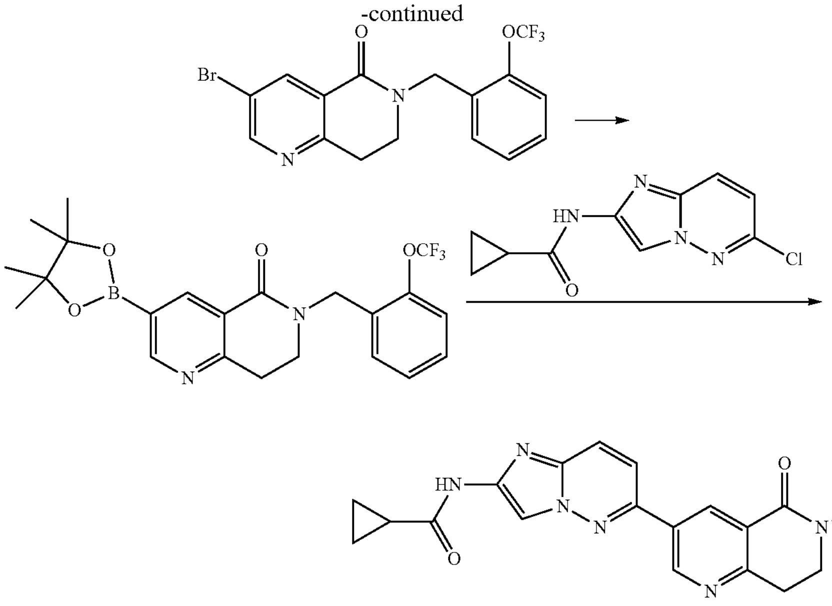

Z10

Step 1: Preparation of N-(6-chloroimidazo[1,2-b]pyridazin-2-yl)cyclopropanecarboxamide: cyclopropane carbonyl chloride (175 mg, 1.670 mmol) was slowly added into a solution of 2-amino-6-chloroimidazo[1,2-b]pyridazine (256 mg, 1.519 mmol) in N,N-dimethylacetamide (5 mL), the reaction solution was stirred at room temperature for three hours, LCMS showed the reaction was completed, ethyl acetate (20 mL) was added, the reaction mixture was washed with water (15 mL*3) and saturated sodium chloride solution (15 mL*3), the combined organic layers were concentrated to obtain white product N-(6-chloroimidazo[1,2-b]pyridazin-2-yl)cyclopropanecarboxamide (191 mg, Y: 53%). ES-API: $[M+H]^+$=237.1.

Step 2: Preparation of methyl 5-bromo-2-vinylnicotinate: Under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 3: Preparation of 3-bromo-6-(3-(trifluoromethoxy)benzyl)-7,8-dihydro-1,6-naphthyridin-5(6H)-one: Methyl 5-bromo-2-vinylnicotinate (150 mg, 0.620 mmol) and (3-(trifluoromethoxy)phenyl)methylamine (296 mg, 1.549 mmol) were mixed in DMA (4 mL) in a microwave bottle. The reaction was subjected to microwave radiation at 150° C. for 2 hours and then cooled to room temperature, ethyl acetate (15 mL) was added into the mixture, the mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(3-(trifluoromethoxy)benzyl)-7,8-dihydro-1,6-naphthyridin-5(6H)-one (159 mg, Y: 64%). ES-API: $[M+H]^+$=401.0

Step 4: Preparation of 3-(4,4,5,5-tetramethyl-1,3,2-dioxaborolan-2-yl)-6-(2-(trifluoromethoxy)benzyl)-7,8-dihydro-1,6-naphthyridin-5(6H)-one: 3-bromo-6-(3-(trifluoromethoxy)benzyl)-7,8-dihydro-1,6-naphthyridin-5(6H)-one (96 mg, 0.239 mmol), bis(pinacolato)diboron (91 mg, 0.359 mmol), potassium acetate (59 mg, 0.598 mmol), [1,1'-bis(diphenylphosphino)ferrocene]dichloropalladium (II) (9 mg, 0.012 mmol) and 1,4-dioxane (20 mL) were added into a 100 mL round bottom flask, the mixture was replaced with nitrogen for three times, reacted at 95° C. overnight, cooled to room temperature, filtered with suction, the filter cake was washed with ethyl acetate for three times to obtain the filtrate, the filtrate was concentrated to obtain crude product 3-(4,4,5,5-tetramethyl-1,3,2-dioxaborolan-2-yl)-6-(2-(trifluoromethoxy)benzyl)-7,8-dihydro-1,6-naphthyridin-5(6H)-one (88 mg, Y: 99%). ES-API: $[M+H]^+$=367.1.

Step 5: Preparation of N-(6-(5-oxo-6-(2-(trifluoromethoxy)benzyl)-5,6,7,8-tetrahydro-1,6-naphthyridin-3-yl)imidazo[1,2-b]pyridazin-2-yl)cyclopropanecarboxamide: Under the protection of nitrogen, N-(6-chloroimidazo[1,2-b]pyridazin-2-yl)cyclopropanecarboxamide (31 mg, 0.132 mmol), 3-(4,4,5,5-tetramethyl-1,3,2-dioxaborolan-2-yl)-6-(2-(trifluoromethoxy)benzyl)-7,8-dihydro-1,6-naphthyridin-5(6H)-one (44 mg, 0.120 mmol), sodium carbonate (32 mg, 0.300 mmol), 1,1'-bis(diphenylphosphino)ferrocene-palladium(II)dichloride dichloromethane complex (5 mg, 0.006 mmol) were dissolved in 1,4-dioxane (5 mL) and $H_2O$ (1 mL), the mixture was replaced with nitrogen for three times, the reacted solution was heated 95° C. in oil bath for three hours. The reaction mixture was cooled to room temperature, concentrated, the crude product was purified by alkaline HPLC to obtain light yellow solid N-(6-(5-oxo-6-(2-(trifluoromethoxy)benzyl)-5,6,7,8-tetrahydro-1,6-naphthyridin-3-yl)imidazo[1,2-b]pyridazin-2-yl)cyclopropanecarboxamide (Z10, 8.63 mg, Y: 14%). ES-API: $[M+H]^+$=523.0. $^1H$ NMR (400 MHz, DMSO-d6) δ 11.24 (s, 1H), 9.31 (d, J=2.0 Hz, 1H), 8.81 (d, J=1.6 Hz, 1H), 8.34 (s, 1H), 8.13 (d, J=7.6 Hz, 1H), 7.93 (d, J=7.6 Hz, 1H), 7.51-7.39 (m, 4H), 4.86 (s, 2H), 3.68 (t, J1=5.2 Hz, J2=10.8 Hz, 2H), 3.24 (t, J1=5.2 Hz, J2=10.8 Hz, 2H), 2.00-1.97 (m, 1H), 0.88-0.84 (m, 4H).

Example 11: Preparation of 6-(3,5-difluoro-2-((tetrahydro-2H-pyran-4-yl)oxy)benzyl)-3-(pyridin-4-yl)-7,8-dihydro-1,6-naphthyridin-5(6H)-one (Z11)

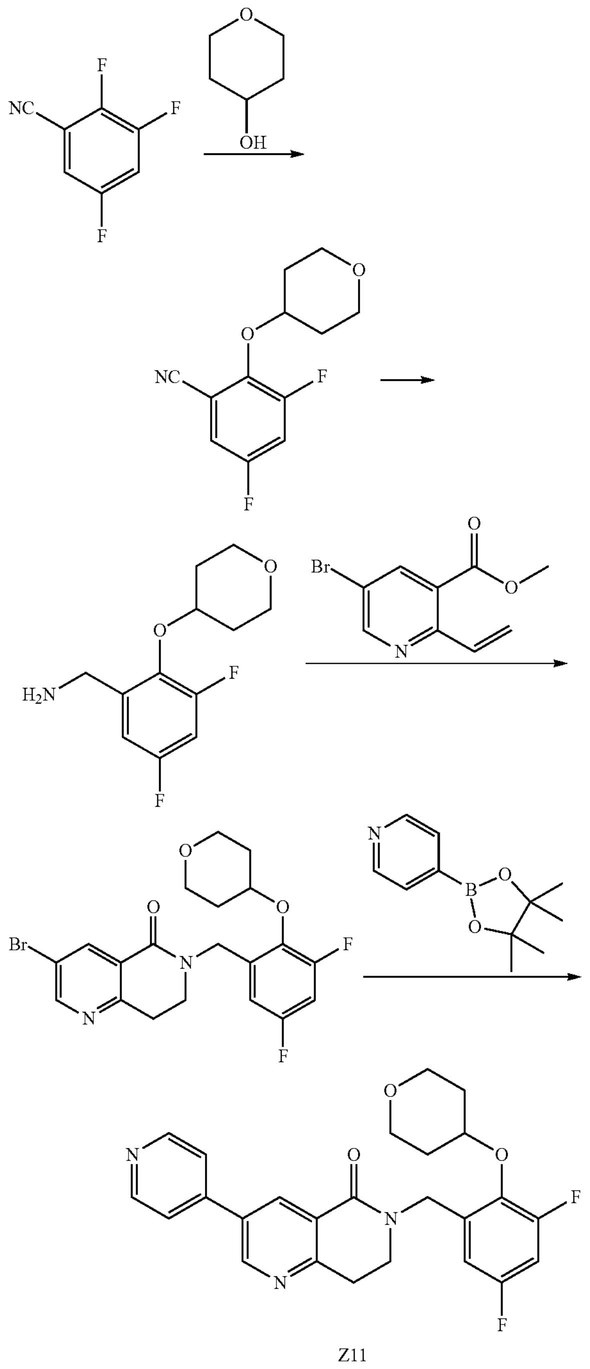

Z11

Step 1: Preparation of 3,5-difluoro-2-((tetrahydro-2H-pyran-4-yl)oxy)benzonitrile: Under ice water bath, sodium hydride (1.4 g, 36.04 mmol) was added into a solution of tetrahydro-2H-pyran-4-ol (3.346 g, 32.76 mmol) in THF (30 mL) in batches, the reaction mixture was stirred at 0° C. for one hour, 2,3,5-trifluorobenzonitrile (2.537 g, 16.38 mmol) was added into the reaction mixture, the reaction mixture was stirred at 55° C. for 12 hours, LCMS showed the reaction was completed, under ice water bath, water (50 mL) was added for quenching the reaction, extracted with EtOAc (30 mL*3), the organic phase was combined and washed with saturated sodium chloride solution (15 mL*3), the combined organic layers were concentrated, purified on silica gel by automatic fast chromatography to obtain crude product 3,5-difluoro-2-((tetrahydro-2H-pyran-4-yl)oxy)benzonitrile (3.918 g, Y: 99%). ES-API: $[M+H]^+$=240.1.

Step 2: Preparation of (3,5-difluoro-2-((tetrahydro-2H-pyran-4-yl)oxy)phenyl)methylamine: $BH_3$-THF (21 mL, 20.901 mmol) was added into a solution of 3,5-difluoro-2-((tetrahydro-2H-pyran-4-yl)oxy)benzonitrile (1 g, 4.18 mmol) in THF (30 mL), the reaction mixture was heated and refluxed overnight, LCMS showed the reaction was completed, the reaction mixture was cooled to room temperature, MeOH was slowly added for quenching the reaction, the reaction mixture was concentrated, the residue was dissolved in 1 N HCl (aq) (20 mL), extracted with DCM/i-PrOH (30 mL*3). The organic phases were combined, concentrated to obtain light yellow transparent liquid (3,5-difluoro-2-((tetrahydro-2H-pyran-4-yl)oxy)phenyl)methylamine (1.017 g, Y: 70%). ES-API: $[M+H]^+$=244.1.

Step 3: Preparation of 3-bromo-6-(3,5-difluoro-2-((tetrahydro-2H-pyran-4-yl)oxy)benzyl)-7,8-dihydro-1,6-naphthyridin-5(6H)-one: Methyl 5-bromo-2-vinylnicotinate (172 mg, 0.710 mmol) and (3,5-difluoro-2-((tetrahydro-2H-pyran-4-yl)oxy)phenyl)methylamine (345 mg, 1.420 mmol) were mixed in DMA (5 mL) in a microwave bottle. The reaction was subjected to microwave radiation at 180° C. for one hour, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(3,5-difluoro-2-((tetrahydro-2H-pyran-4-yl)oxy)benzyl)-7,8-dihydro-1,6-naphthyridin-5(6H)-one (268 mg, Y: 53%). ES-API: $[M+H]^+$=453.1

Step 4: Preparation of 6-(3,5-difluoro-2-((tetrahydro-2H-pyran-4-yl)oxy)benzyl)-3-(pyridin-4-yl)-7,8-dihydro-1,6-naphthyridin-5(6H)-one: Under the protection of nitrogen, 3-bromo-6-(3,5-difluoro-2-((tetrahydro-2H-pyran-4-yl)oxy)benzyl)-7,8-dihydro-1,6-naphthyridin-5(6H)-one (30 mg, 0.066 mmol), 4-(4,4,5,5-tetramethyl-1,3,2-dioxaborolan-2-yl)pyridine (20 mg, 0.100 mmol) and potassium phosphate (35 mg, 0.165 mmol), tetrakis(triphenylphosphine)palladium (4 mg, 0.0033 mmol) were dissolved in 1,4-dioxane (5 mL) and $H_2O$ (1 mL), the mixture was replaced with nitrogen for three times, the reaction solution was heated in oil bath at 95° C. overnight, cooled to room temperature, concentrated, the crude product was purified by alkaline HPLC to obtain white solid 6-(3,5-difluoro-2-((tetrahydro-2H-pyran-4-yl)oxy)benzyl)-3-(pyridine-4-yl)-7,8-dihydro-1,6-naphthyridin-5(6H)-one (Z11, 4.0 mg, Y: 13%). ES-API: $[M+H]^+$=452.1

Example 12: Preparation of 6-(3,5-difluoro-2-((tetrahydro-2H-pyran-4-yl)oxy)benzyl)-3-(pyridin-2-yl)-7,8-dihydro-1,6-naphthyridin-5(6H)-one (Z12)

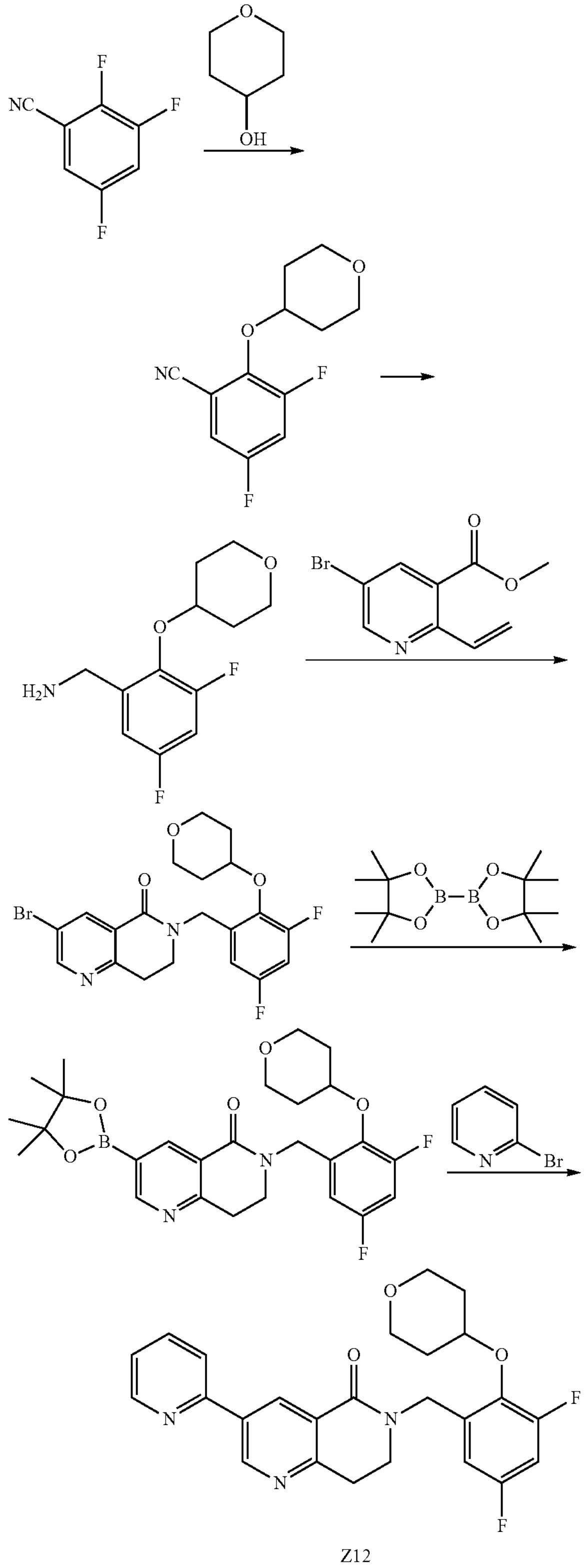

Z12

Step 1: Preparation of 3,5-difluoro-2-((tetrahydro-2H-pyran-4-yl)oxy)benzonitrile: Under ice water bath, sodium hydride (1.4 g, 36.04 mmol) was added into a solution of tetrahydro-2H-pyran-4-ol (3.346 g, 32.76 mmol) in THF (30 mL) in batches, the reaction mixture was stirred at 0° C. for one hour, 2,3,5-trifluorobenzonitrile (2.537 g, 16.38 mmol) was added into the reaction mixture, the reaction mixture was stirred at 55° C. for 12 hours, LCMS showed the reaction was completed, under ice water bath, water (50 mL) was added for quenching the reaction, extracted with EtOAc (30 mL*3), the organic phase was combined and washed with saturated sodium chloride solution (15 mL*3), the combined organic layers were concentrated, purified on silica gel by automatic fast chromatography to obtain crude product 3,5-difluoro-2-((tetrahydro-2H-pyran-4-yl)oxy)benzonitrile (3.918 g, Y: 99%). ES-API: $[M+H]^+$=240.1.

Step 2: Preparation of (3,5-difluoro-2-((tetrahydro-2H-pyran-4-yl)oxy)phenyl)methylamine: $BH_3$-THF (21 mL, 20.901 mmol) was added into a solution of 3,5-difluoro-2-((tetrahydro-2H-pyran-4-yl)oxy)benzonitrile (1 g, 4.18 mmol) in THF (30 mL), the reaction mixture was heated and refluxed overnight, LCMS showed the reaction was completed, the reaction mixture was cooled to room temperature, MeOH was slowly added for quenching the reaction, the reaction mixture was concentrated, the residue was dissolved in 1 N HCl (aq) (20 mL), extracted with DCM/i-PrOH (30 mL*3), the organic phase was combined and dried to obtain light yellow liquid (3,5-difluoro-2-((tetrahydro-2H-pyran-4-yl)oxy)phenyl)methylamine (1.017 g, Y: 70%). ES-API: $[M+H]^+$=244.1.

Step 3: Preparation of 3-bromo-6-(3,5-difluoro-2-((tetrahydro-2H-pyran-4-yl)oxy)benzyl)-7,8-dihydro-1,6-naphthyridin-5(6H)-one: Methyl 5-bromo-2-vinylnicotinate (172 mg, 0.710 mmol) and (3,5-difluoro-2-((tetrahydro-2H-pyran-4-yl)oxy)phenyl)methylamine (345 mg, 1.420 mmol) were mixed in DMA (5 mL) in a microwave bottle. The reaction was subjected to microwave radiation at 180° C. for one hour, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(3,5-difluoro-2-((tetrahydro-2H-pyran-4-yl)oxy)benzyl)-7,8-dihydro-1,6-naphthyridin-5(6H)-one (268 mg, Y: 53%). ES-API: $[M+H]^+$=453.1.

Step 4: Preparation of 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one: 3-bromo-6-(3,5-difluoro-2-((tetrahydro-2H-pyran-4-yl)oxy)benzyl)-7,8-dihydro-1,6-naphthyridin-5(6H)-one (238 mg, 0.527 mmol), bis(pinacolato)diboron (201 mg, 0.790 mmol), potassium acetate (129 mg, 1.318 mmol), [1,1'-bis(diphenylphosphino)ferrocene]dichloropalladium(II) (19 mg, 0.026 mmol) and 1,4-dioxane (20 mL) were added into a 100 mL round bottom flask, the mixture was replaced with nitrogen for three times, reacted at 95° C. overnight, cooled to room temperature, filtered with suction, the filter cake was washed with ethyl acetate for three times to obtain the filtrate, the filtrate was concentrated to obtain crude product 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one (220 mg, Y: 99%). ES-API: $[M+H]^+$=419.2.

Step 5: Preparation of 6-(3,5-difluoro-2-((tetrahydro-2H-pyran-4-yl)oxy)benzyl)-3-(pyridin-2-yl)-7,8-dihydro-1,6-naphthyridin-5(6H)-one: Under the protection of nitrogen, 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one (55 mg, 0.132 mmol), 2-bromopyridine (21 mg, 0.132 mmol), sodium carbonate (35 mg, 0.329 mmol), 1,1'-bis(diphenylphosphino)ferrocene-palladium(II)dichloride dichloromethane complex (5.4 mg, 0.0066 mmol) were dissolved in 1,4-dioxane (5 mL) and $H_2O$ (1 mL), the mixture was replaced with nitrogen for three times, the reaction solution was heated in oil bath at 100° C. overnight, cooled to room temperature, concentrated, the crude product was purified by alkaline HPLC to obtain black viscous solid product 6-(3,5-difluoro-2-((tetrahydro-2H-pyran-4-yl)oxy)benzyl)-3-(pyridine-2-yl)-7,8-dihydro-1,6-naphthyridin-5(6H)-one (Z12, 20.72 mg, Y: 35%). ES-API: $[M+H]^+$=452.1. $^1$H NMR (400 MHz, DMSO-d6) δ 9.33 (d, J=2.0 Hz, 1H), 8.86 (d, J=1.6 Hz, 1H), 8.74 (d, J=3.2 Hz, 1H), 8.14 (d, J=2.8 Hz, 1H), 7.97-7.94 (m, 1H), 7.46-7.44 (m, 1H), 7.29-7.24 (m, 1H), 6.98 (d, J=6.8 Hz, 1H), 4.81 (s, 2H), 4.33-4.27 (m, 1H), 3.92-3.88 (m, 2H), 3.69 (t, J1=5.6 Hz, J2=10.8 Hz, 2H), 3.41-3.36 (m, 2H), 3.23 (t, J1=4.8 Hz, J2=10.4 Hz, 2H), 1.97-1.94 (m, 2H), 1.74-1.67 (m, 2H).

Example 13: Preparation of 3-([1,2,4]triazolo[1,5-a]pyridin-7-yl)-6-(3,5-difluoro-2-((tetrahydro-2H-pyran-4-yl)oxy)benzyl)-7,8-dihydro-1,6-naphthyridin-5(6H)-one (Z13)

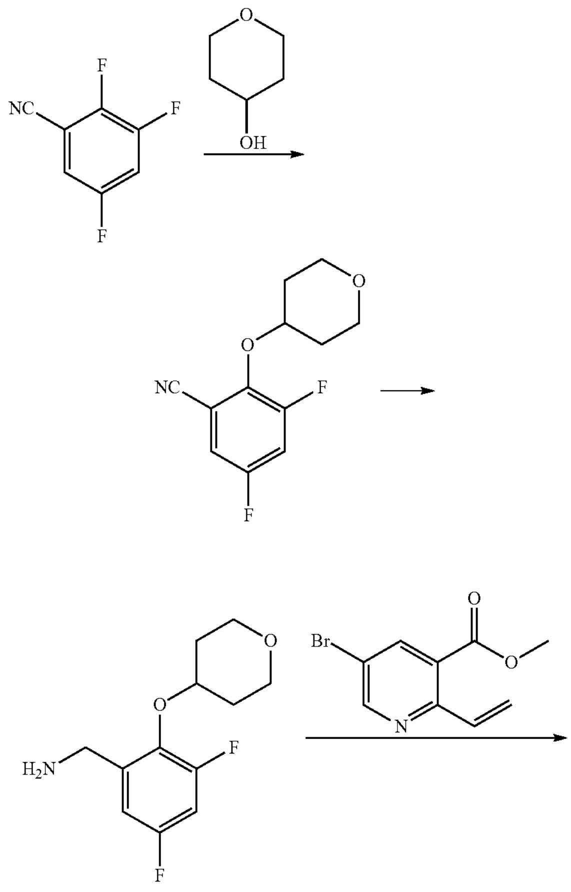

-continued

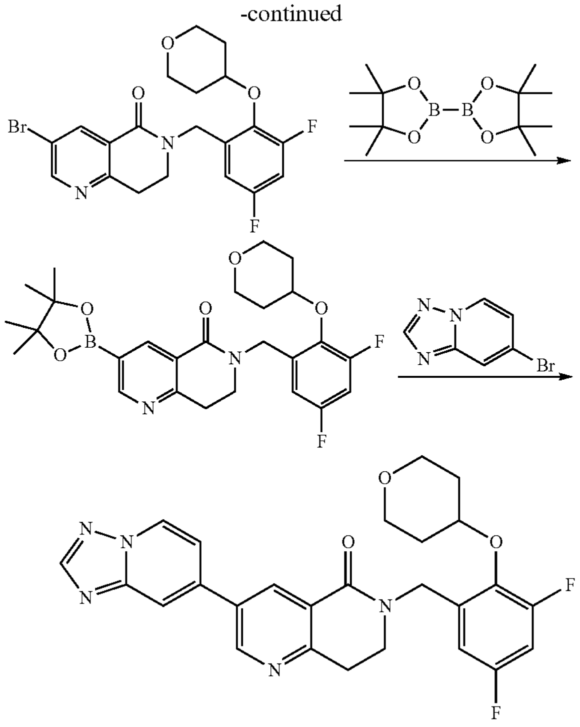

Z13

Step 1: Preparation of 3,5-difluoro-2-((tetrahydro-2H-pyran-4-yl)oxy)benzonitrile: Under ice water bath, sodium hydride (1.4 g, 36.04 mmol) was added into a solution of tetrahydro-2H-pyran-4-ol (3.346 g, 32.76 mmol) in THF (30 mL) in batches, the reaction mixture was stirred at 0° C. for one hour, 2,3,5-trifluorobenzonitrile (2.537 g, 16.38 mmol) was added into the reaction mixture, the reaction mixture was stirred at 55° C. for 12 hours, LCMS showed the reaction was completed, under ice water bath, water (50 mL) was added for quenching the reaction, extracted with EtOAc (30 mL*3), the organic phases were combined and washed with saturated sodium chloride solution (15 mL*3), the combined organic layers were concentrated, purified on silica gel by automatic fast chromatography to obtain crude product 3,5-difluoro-2-((tetrahydro-2H-pyran-4-yl)oxy)benzonitrile (3.918 g, Y: 99%). ES-API: $[M+H]^+$=240.1.

Step 2: Preparation of (3,5-difluoro-2-((tetrahydro-2H-pyran-4-yl)oxy)phenyl)methylamine: $BH_3$-THF (21 mL, 20.901 mmol) was added into a solution of 3,5-difluoro-2-((tetrahydro-2H-pyran-4-yl)oxy)benzonitrile (1 g, 4.18 mmol) in THF (30 mL), the reaction mixture was heated and refluxed overnight. LCMS showed the reaction was completed, the reaction mixture was cooled to room temperature, MeOH was slowly added for quenching the reaction, the reaction mixture was concentrated, the residue was dissolved in 1 N HCl (aq) (20 mL), extracted with DCM/i-PrOH (30 mL*3), the organic phase was combined, dried to obtain light yellow transparent liquid (3,5-difluoro-2-((tetrahydro-2H-pyran-4-yl)oxy)phenyl)methylamine (1.017 g, Y: 70%). ES-API: $[M+H]^+$=244.1.

Step 3: Preparation of 3-bromo-6-(3,5-difluoro-2-((tetrahydro-2H-pyran-4-yl)oxy)benzyl)-7,8-dihydro-1,6-naphthyridin-5(6H)-one: Methyl 5-bromo-2-vinylnicotinate (172 mg, 0.710 mmol) and (3,5-difluoro-2-((tetrahydro-2H-pyran-4-yl)oxy)phenyl)methylamine (345 mg, 1.420 mmol) were mixed in DMA (5 mL) in a microwave bottle. The reaction was subjected to microwave radiation at 180° C. for one hour, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(3,5-difluoro-2-((tetrahydro-2H-pyran-4-yl)oxy)benzyl)-7,8-dihydro-1,6-naphthyridin-5(6H)-one (268 mg, Y: 53%). ES-API: $[M+H]^+=453.1$.

Step 4: Preparation of 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one: 3-bromo-6-(3,5-difluoro-2-((tetrahydro-2H-pyran-4-yl)oxy)benzyl)-7,8-dihydro-1,6-naphthyridin-5(6H)-one (238 mg, 0.527 mmol), bis(pinacolato)diboron (201 mg, 0.790 mmol), potassium acetate (129 mg, 1.318 mmol), [1,1'-bis(diphenylphosphino)ferrocene]dichloropalladium(II) (19 mg, 0.026 mmol) and 1,4-dioxane (20 mL) were added into a 100 mL round bottom flask, the mixture was replaced with nitrogen for three times, reacted at 95° C. overnight, cooled to room temperature, filtered with suction, the filter cake was washed with ethyl acetate for three times to obtain the filtrate, the filtrate was concentrated to obtain crude product 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one (220 mg, Y: 99%). ES-API: $[M+H]^+=419.2$.

Step 5: Preparation of 3-([1,2,4]triazolo[1,5-a]pyridin-7-yl)-6-(3,5-difluoro-2-((tetrahydro-2H-pyran-4-yl)oxy)benzyl)-7,8-dihydro-1,6-naphthyridin-5(6H)-one: Under the protection of nitrogen, 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one (55 mg, 0.132 mmol), 7-bromo-[1,2,4]triazolo[1,5-a]pyridine (26 mg, 0.132 mmol), sodium carbonate (35 mg, 0.329 mmol), 1,1'-bis(diphenylphosphino)ferrocene-palladium(II) dichloride dichloromethane complex (5.4 mg, 0.0066 mmol) were dissolved in 1,4-dioxane (5 mL) and $H_2O$ (1 mL), the mixture was replaced with nitrogen for three times, the reaction solution was heated in oil bath at 100° C. overnight, cooled to room temperature, concentrated, the crude product was purified by alkaline HPLC to obtain white solid product 3-([1,2,4]triazolo[1,5-a]pyridine-7-yl)-6-(3,5-difluoro-2-((tetrahydro-2H-pyran-4-yl)oxy)benzyl)-7,8-dihydro-1,6-naphthyridin-5(6H)-one (Z13, 8.68 mg, Y: 13%). ES-API: $[M+H]^+=492.1$. $^1H$ NMR (400 MHz, DMSO-d6) δ 9.17 (d, J=2.0 Hz, 1H), 9.08 (d, J=6.0 Hz, 1H), 8.60 (d, J=2.0 Hz, 1H), 8.57 (s, 1H), 8.34 (d, J=0.8 Hz, 1H), 7.67 (dd, J1=1.2 Hz, J2=5.6 Hz, 1H), 7.30-7.25 (m, 1H), 6.98 (d, J=7.2 Hz, 1H), 4.82 (s, 2H), 4.32-4.28 (m, 1H), 3.92-3.88 (m, 2H), 3.71 (t, J1=5.2 Hz, J2=10.4 Hz, 2H), 3.43-3.37 (m, 2H), 3.25 (t, J1=5.2 Hz, J2=10.4 Hz, 2H), 1.98-1.95 (m, 2H), 1.75-1.67 (m, 2H).

Example 14: Preparation of 3-(2-amino-1-methyl-1H-benzo[d]imidazol-6-yl)-6-(2-fluoro-5-(trifluoromethoxy)benzyl)-7,8-dihydro-1,6-naphthyridin-5(6H)-one (Z14)

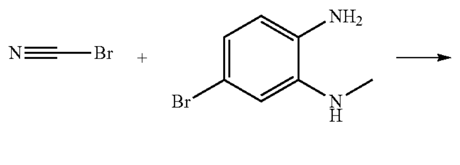

-continued

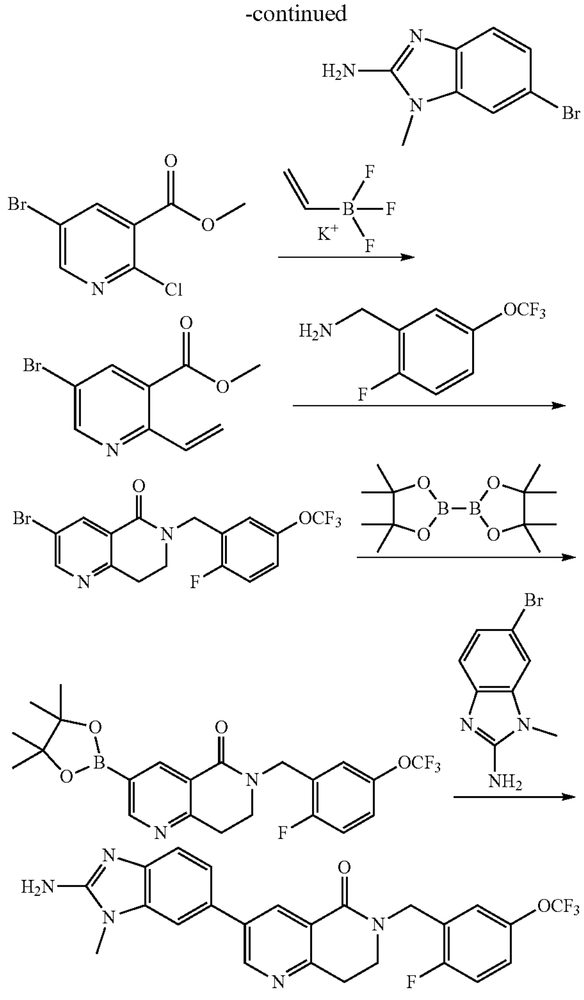

Z14

Step 1: Preparation of 6-bromo-1-methyl-1H-benzo[d]imidazol-2-amine: cyanogen bromide (1.05 g, 9.905 mmol), 4-bromo-2-methylaminoaniline (1 g, 4.952 mmol) was dissolved in methanol (10 mL) solution, the mixture was stirred at room temperature for one hour, LCMS showed the reaction was completed, the reaction mixture was added into EtOAc (100 mL), sat.$NaHCO_3$(aq) (100 mL) and $H_2O$ (20 mL) in batches, the organic phase was separated, washed with saturated sodium chloride solution (20 mL*3), dried, and the combined organic layers were concentrated to obtain crude product 6-bromo-1-methyl-1H-benzo[d]imidazol-2-amine (769 mg, Y: 69%). ES-API: $[M+H]^+=226.0$.

Step 2: Preparation of methyl 5-bromo-2-vinylnicotinate: Under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 54%). ES-API: $[M+H]^+=242.1$.

Step 3: Preparation of 3-bromo-6-(2-(trifluoromethoxy)benzyl)-7,8-dihydro-1,6-naphthyridin-5(6H)-one: Methyl 5-bromo-2-vinylnicotinate (280 mg, 1.157 mmol) and ((2-fluoro-5-(trifluoromethoxy)phenyl)methylamine (726 mg, 3.471 mmol) were mixed in DMA (5 mL) in a microwave bottle. The reaction was subjected to microwave radiation at 150° C. for three hours, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-fluoro-5-(trifluoromethoxy)benzyl)-7,8-dihydro-1,6-naphthyridin-5(6H)-one (300 mg, Y: 62%). ES-API: $[M+H]^+$=419.0.

Step 4: Preparation of 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one: 3-bromo-6-(2-fluoro-5-(trifluoromethoxy)benzyl)-7,8-dihydro-1,6-naphthyridin-5(6H)-one (200 mg, 0.477 mmol), bis(pinacolato)diboron (244 mg, 0.955 mmol), potassium acetate (117 mg, 1.193 mmol), [1,1'-bis(diphenylphosphino)ferrocene]dichloropalladium(II) (35 mg, 0.0477 mmol) and 1,4-dioxane (10 mL) were added into a 100 mL round bottom flask, the mixture was replaced with nitrogen for three times, reacted at 95° C. overnight, cooled to room temperature, filtered with suction, the filter cake was washed with ethyl acetate for three times to obtain the filtrate, the filtrate was concentrated to obtain crude product 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (222 mg, Y: 99%). ES-API: $[M+H]^+$=385.1.

Step 5: Preparation of 3-(2-amino-1-methyl-1H-benzo[d]imidazol-6-yl)-6-(2-fluoro-5-(trifluoromethoxy)benzyl)-7,8-dihydro-1,6-naphthyridin-5(6H)-one: Under the protection of nitrogen, 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (111 mg, 0.239 mmol), 6-bromo-1-methyl-1H-benzo[d]imidazol-2-amine (27 mg, 0.120 mmol), sodium carbonate (32 mg, 0.300 mmol), 1,1'-bis(diphenylphosphino)ferrocene-palladium(II)dichloride dichloromethane complex (5 mg, 0.006 mmol) were dissolved in 1,4-dioxane (5 mL) and $H_2O$ (1 mL), the mixture was replaced with nitrogen for three times, the reaction solution was heated in oil bath at 95° C. for two hours, cooled to room temperature, concentrated, the crude product was purified by alkaline HPLC to obtain the light yellow solid product 3-(2-amino-1-methyl-1H-benzo[d]imidazol-6-yl)-6-(2-fluoro-5-(trifluoromethoxy)benzyl)-7,8-dihydro-1,6-naphthyridin-5(6H)-one (Z14, 47.33 mg, Y: 81%). ES-API: $[M+H]^+$=486.1. $^1H$ NMR (400 MHz, DMSO-d6) δ 8.96 (d, J=2.0 Hz, 1H), 8.42 (d, J=1.6 Hz, 1H), 7.56 (s, 1H), 7.43-7.39 (m, 3H), 7.34 (dd, J1=1.2 Hz, J2=6.8 Hz, 1H), 7.22 (d, J=6.4 Hz, 1H), 6.55 (s, 2H), 4.81 (s, 2H), 3.71 (t, J1=5.2 Hz, J2=10.4 Hz, 2H), 3.58 (s, 3H), 3.16 (t, J1=5.2 Hz, J2=10.4 Hz, 2H).

Example 15: Preparation of N-(7-(6-(2-fluoro-5-(trifluoromethoxy)benzyl)-5-oxo-5,6,7,8-tetrahydro-1,6-naphthyridin-3-yl)-5,6,7,8-tetrahydro-[1,2,4]triazolo[1,5-a]pyrazin-2-yl)acetamide (Z15)

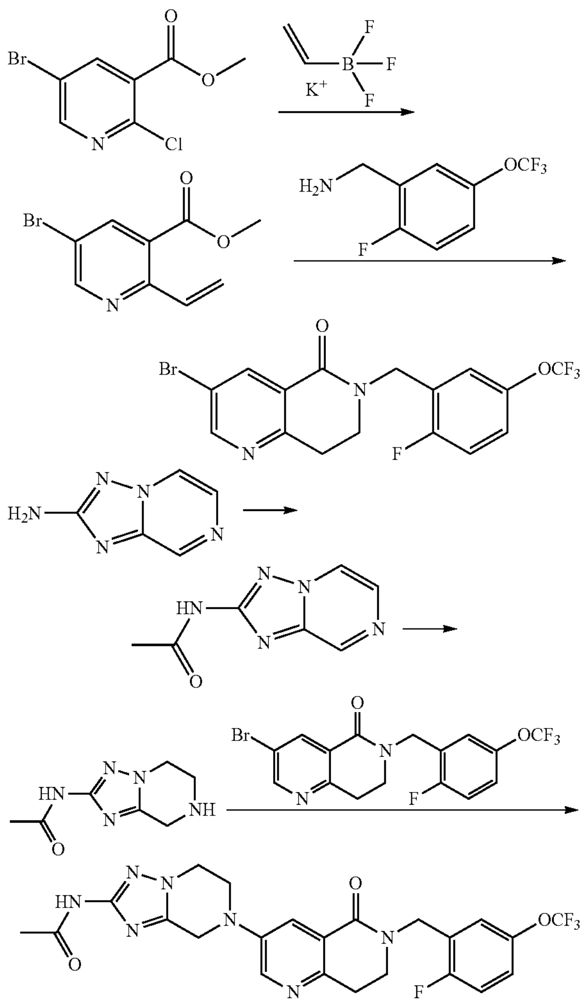

Z15

Step 1: Preparation of methyl 5-bromo-2-vinylnicotinate: Under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 54%). ES-API: $[M+H]^+$=242.1

Step 2: Preparation of 3-bromo-6-(2-fluoro-5-(trifluoromethoxy)benzyl)-7,8-dihydro-1,6-naphthyridin-5(6H)-one: Methyl 5-bromo-2-vinylnicotinate (280 mg, 1.157 mmol) and ((2-fluoro-5-(trifluoromethoxy)phenyl)methylamine (726 mg, 3.471 mmol) were mixed in DMA (5 mL)

in a microwave bottle. The reaction was subjected to microwave radiation at 150° C. for three hours and then cooled to room temperature, ethyl acetate (15 mL) was added into the mixture, the mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-fluoro-5-(trifluoromethoxy)benzyl)-7,8-dihydro-1,6-naphthyridin-5(6H)-one (300 mg, Y: 62%). ES-API: $[M+H]^+$=419.0.

Step 3: Preparation of N-([1,2,4]triazolo[1,5-a]pyrazin-2-yl)acetamide: acetic anhydride (3.775 g, 36.98 mmol) was added into a solution of [1,2,4]triazolo[1,5-a]pyrazin-2-amine (2.5 g, 18.5 mmol) in toluene (50 mL), the reaction mixture was heated and refluxed overnight, cooled to room temperature, filtered to obtain N-([1,2,4]triazolo[1,5-a]pyrazin-2-yl)acetamide (2.14 g, Y: 65%). ES-API: $[M+H]^+$=178.1.

Step 4: Preparation of N-(5,6,7,8-tetrahydro-[1,2,4]triazolo[1,5-a]pyrazin-2-yl)acetamide: Under the protection of hydrogen, $PtO_2$ (192 mg, 0.847 mmol) was added into a solution of N-([1,2,4]triazolo[1,5-a]pyrazin-2-yl)acetamide (1 g, 5.650 mmol) in EtOH (20 mL), the reaction mixture reacted under the protection of hydrogen at room temperature for 3 days, filtered, concentrated to obtain N-(5,6,7,8-tetrahydro-[1,2,4]triazolo[1,5-a]pyrazin-2-yl)acetamide (1.02 g, Y: 99%). ES-API: $[M+H]^+$=182.1.

Step 5: Preparation of N-(7-(6-(2-fluoro-5-(trifluoromethoxy)benzyl)-5-oxo-5,6,7,8-tetrahydro-1,6-naphthyridin-3-yl)-5,6,7,8-tetrahydro-[1,2,4]triazolo[1,5-a]pyrazin-2-yl)acetamide: Under the protection of nitrogen, N-(5,6,7,8-tetrahydro-[1,2,4]triazolo[1,5-a]pyrazin-2-yl)acetamide (18 mg, 0.099 mmol), 3-bromo-6-(2-fluoro-5-(trifluoromethoxy)benzyl)-7,8-dihydro-1,6-naphthyridin-5(6H)-one (42 mg, 0.099 mmol), sodium tert-butoxide (24 mg, 0.248 mmol), $Pd_2(dba)_3$ (6 mg, 0.0099 mmol) and BINAP (6 mg, 0.0099 mmol) were dissolved in toluene (5 mL), the mixture was replaced with nitrogen for three times, the reaction solution was heated in oil bath at 110° C. overnight, cooled to room temperature, concentrated, the crude product was purified by alkaline HPLC to obtain white solid product N-(7-(6-(2-fluoro-5-(trifluoromethoxy)benzyl)-5-oxo-5,6,7,8-tetrahydro-1,6-naphthyridin-3-yl)-5,6,7,8-tetrahydro-[1,2,4]triazolo[1,5-a]pyrazin-2-yl)acetamide (Z15, 4.8 mg, Y: 9%). ES-API: $[M+H]^+$=520.2.

Example 16: Preparation of 3-(2-aminobenzo[d]oxazol-6-yl)-6-(2-fluoro-5-(trifluoromethoxy)benzyl)-7,8-dihydro-1,6-naphthyridin-5(6H)-one (Z16)

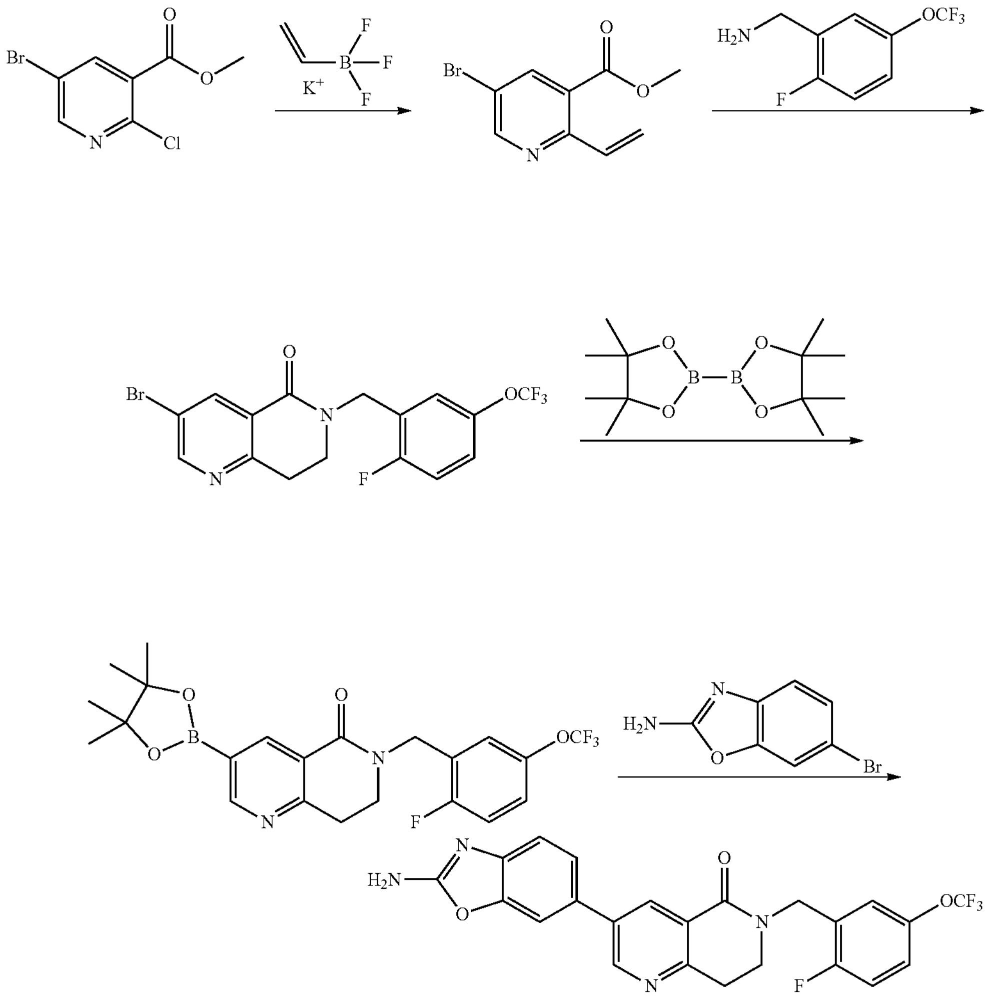

Z16

Step 1: Preparation of methyl 5-bromo-2-vinylnicotinate: under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 2: Preparation of 3-bromo-6-(2-(trifluoromethoxy) benzyl)-7,8-dihydro-1,6-naphthyridin-5(6H)-one: methyl 5-bromo-2-vinylnicotinate (280 mg, 1.157 mmol) and ((2-fluoro-5-(trifluoromethoxy)phenyl)methylamine (726 mg, 3.471 mmol) were mixed in DMA (5 mL) in a microwave bottle. The reaction was subjected to microwave radiation at 150° C. for three hours, then cooled to room temperature, ethyl acetate (50 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-fluoro-5-(trifluoromethoxy)benzyl)-7,8-dihydro-1,6-naphthyridin-5(6H)-one (300 mg, Y: 62%). ES-API: $[M+H]^+$= 419.0.

Step 3: Preparation of 6-(2-fluoro-5-(trifluoromethoxy) benzyl)-3-(4,4,5,5-tetramethyl-1,3,2-dioxaborinan-2-yl)-7,8-dihydro-1,6-naphthyridin-5(6H)-one: 3-bromo-6-(2-fluoro-5-(trifluoromethoxy)benzyl)-7,8-dihydro-1,6-naphthyridin-5(6H)-one (200 mg, 0.477 mmol), bis (pinacolato)diboron (244 mg, 0.955 mmol), potassium acetate (117 mg, 1.193 mmol), [1,1'-bis(diphenylphosphino) ferrocene]dichloropalladium(II) (35 mg, 0.0477 mmol) and 1,4-dioxane (10 mL) were added into a 100 mL round bottom flask, the mixture was replaced with nitrogen for three times, reacted at 95° C. overnight, cooled to room temperature, filtered with suction, the filter cake was washed with ethyl acetate for three times to obtain the filtrate, the filtrate was concentrated to obtain crude product 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (222 mg, Y: 99%). ES-API: $[M+H]^+$=385.1.

Step 4: Preparation of 3-(2-aminobenzo[d]oxazol-6-yl)-6-(2-fluoro-5-(trifluoromethoxy)benzyl)-7,8-dihydro-1,6-naphthyridin-5(6H)-one: under the protection of nitrogen, 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (50 mg, 0.107 mmol), 6-bromobenzo[d]oxazol-2-amine (34 mg, 0.161 mmol), sodium carbonate (28 mg, 0.268 mmol), 1,1'-bis(diphenylphosphino)ferrocene-palladium(II)dichloride dichloromethane complex (9 mg, 0.0107 mmol) were dissolved in 1,4-dioxane (5 mL) and $H_2O$ (1 mL), the mixture was replaced with nitrogen for three times, the reaction solution was heated in oil bath at 95° C. for two hours, cooled to room temperature, concentrated, the crude product was purified by alkaline HPLC to obtain off-white solid product 3-(2-aminobenzo[d]oxazol-6-yl)-6-(2-fluoro-5-(trifluoromethoxy)benzyl)-7,8-dihydro-1,6-naphthyridin-5(6H)-one (Z16, 20.98 mg, Y: 43%). ES-API: $[M+H]^+$=473.1. $^1H$ NMR (400 MHz, DMSO-d6) δ 8.96 (d, J=1.6 Hz, 1H), 8.39 (d, J=1.6 Hz, 1H), 7.79 (d, J=0.8 Hz, 1H), 7.56 (s, 2H), 7.50 (dd, J1=0.8 Hz, J2=6.4 Hz, 1H), 7.44-7.40 (m, 3H), 7.31 (d, J=6.4 Hz, 1H), 4.81 (s, 2H), 3.72 (t, J1=5.2 Hz, J2=10.4 Hz, 2H), 3.18 (t, J1=5.6 Hz, J2=11.2 Hz, 2H).

Example 17: Preparation of 3-(2-aminobenzo[d]oxazol-5-yl)-6-(2-fluoro-5-(trifluoromethoxy)benzyl)-7,8-dihydro-1,6-naphthyridin-5(6H)-one (Z17)

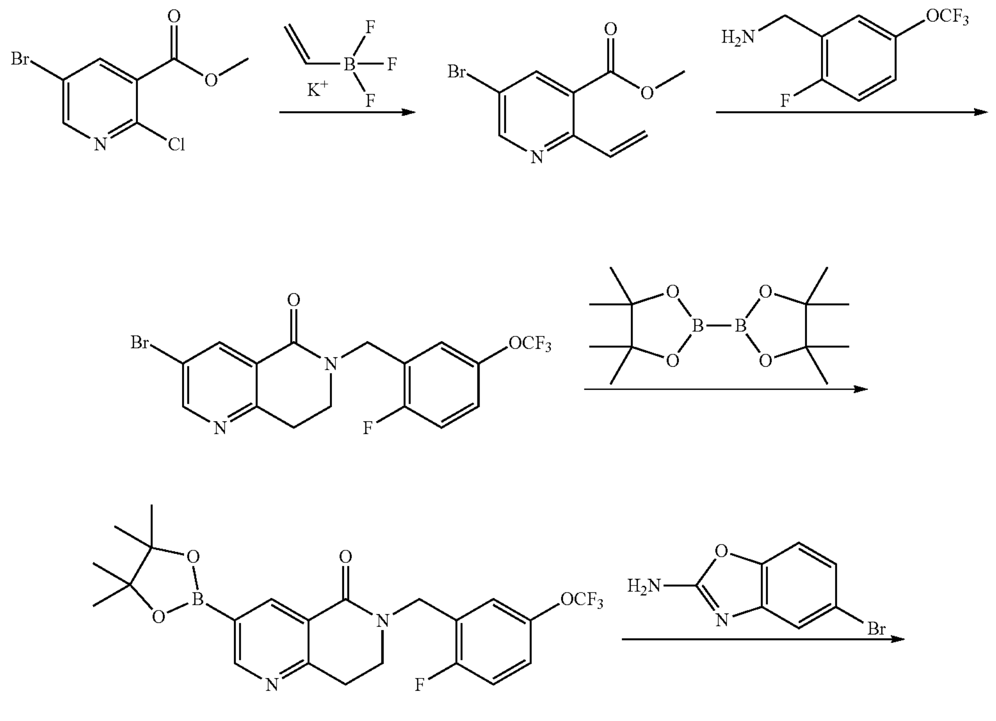

-continued

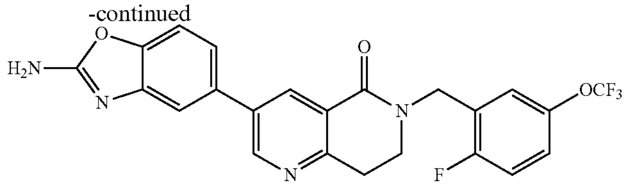

Z17

Step 1: Preparation of methyl 5-bromo-2-vinylnicotinate: under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 2: Preparation of 3-bromo-6-(2-(trifluoromethoxy)benzyl)-7,8-dihydro-1,6-naphthyridin-5(6H)-one: methyl 5-bromo-2-vinylnicotinate (280 mg, 1.157 mmol) and ((2-fluoro-5-(trifluoromethoxy)phenyl)methylamine (726 mg, 3.471 mmol) were mixed in DMA (5 mL) in a microwave bottle. The reaction was subjected to microwave radiation at 150° C. for three hours, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-fluoro-5-(trifluoromethoxy)benzyl)-7,8-dihydro-1,6-naphthyridin-5(6H)-one (300 mg, Y: 62%). ES-API: $[M+H]^+$=419.0.

Step 3: Preparation of 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one: 3-bromo-6-(2-fluoro-5-(trifluoromethoxy)benzyl)-7,8-dihydro-1,6-naphthyridin-5(6H)-one (200 mg, 0.477 mmol), bis(pinacolato)diboron (244 mg, 0.955 mmol), potassium acetate (117 mg, 1.193 mmol), [1,1'-bis(diphenylphosphino)ferrocene]dichloropalladium(II) (35 mg, 0.0477 mmol) and 1,4-dioxane (10 mL) were added into a 100 mL round bottom flask, the mixture was replaced with nitrogen for three times, reacted at 95° C. overnight, cooled to room temperature, filtered with suction, the filter cake was washed with ethyl acetate for three times to obtain the filtrate, the filtrate was concentrated to obtain crude product 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (222 mg, Y: 99%). ES-API: $[M+H]^+$=385.1.

Step 4: Preparation of 3-(2-aminobenzo[d]oxazol-5-yl)-6-(2-fluoro-5-(trifluoromethoxy)benzyl)-7,8-dihydro-1,6-naphthyridin-5(6H)-one: Under the protection of nitrogen, 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (50 mg, 0.107 mmol), 5-bromobenzo[d]oxazol-2-amine (34 mg, 0.161 mmol), sodium carbonate (28 mg, 0.268 mmol), 1,1'-bis(diphenylphosphino)ferrocene-palladium(II)dichloride dichloromethane complex (9 mg, 0.0107 mmol) were dissolved in 1,4-dioxane (5 mL) and $H_2O$ (1 mL), the mixture was replaced with nitrogen for three times, the reaction solution was heated in oil bath at 95° C. for two hours, cooled to room temperature, concentrated, the crude product was purified by alkaline HPLC to obtain off-white solid product 3-(2-aminobenzo[d]oxazol-5-yl)-6-(2-fluoro-5-(trifluoromethoxy)benzyl)-7,8-dihydro-1,6-naphthyridin-5(6H)-one (Z17, 13.82 mg, Y: 27%). ES-API: $[M+H]^+$=473.1. $^1H$ NMR (400 MHz, DMSO-d6) δ 8.94 (d, J=1.6 Hz, 1H), 8.37 (d, J=1.6 Hz, 1H), 7.55-7.53 (m, 3H), 7.46-7.39 (m, 4H), 7.32 (dd, J1=1.6 Hz, J2=6.8 Hz, 1H), 4.81 (s, 2H), 3.72 (t, J1=5.2 Hz, J2=10.4 Hz, 2H), 3.18 (t, J1=5.2 Hz, J2=10.4 Hz, 2H).

Example 18: Preparation of 3-(2-amino-1H-benzo[d]imidazol-6-yl)-6-(2-fluoro-5-(trifluoromethoxy)benzyl)-7,8-dihydro-1,6-naphthyridin-5(6H)-one (Z18)

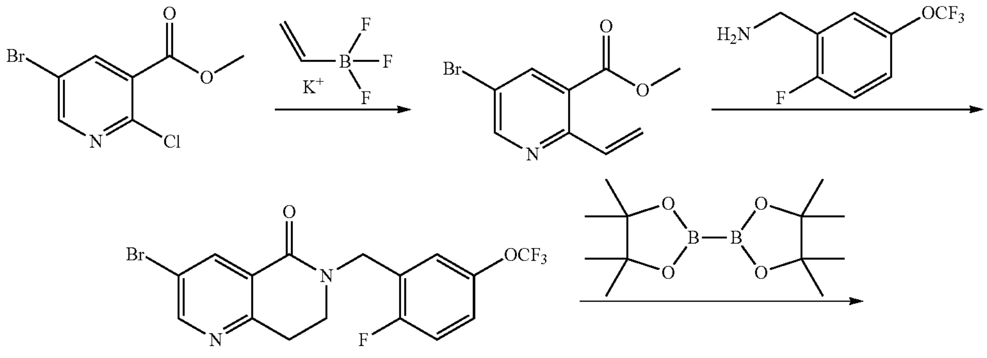

-continued

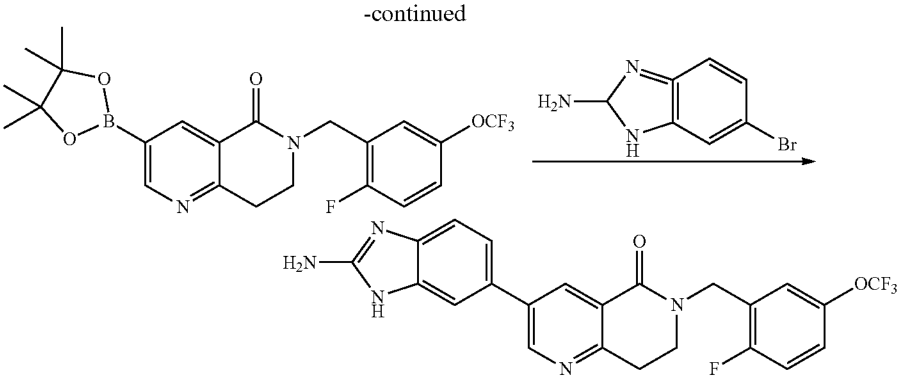

Z18

Step 1: Preparation of methyl 5-bromo-2-vinylnicotinate: under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 2: Preparation of 3-bromo-6-(2-(trifluoromethoxy)benzyl)-7,8-dihydro-1,6-naphthyridin-5(6H)-one: methyl 5-bromo-2-vinylnicotinate (280 mg, 1.157 mmol) and ((2-fluoro-5-(trifluoromethoxy)phenyl)methylamine (726 mg, 3.471 mmol) were mixed in DMA (5 mL) in a microwave bottle. The reaction was subjected to microwave radiation at 150° C. for three hours, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-fluoro-5-(trifluoromethoxy)benzyl)-7,8-dihydro-1,6-naphthyridin-5(6H)-one (300 mg, Y: 62%). ES-API: $[M+H]^+$=419.0.

Step 3: Preparation of 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one: 3-Bromo-6-(2-fluoro-5-(trifluoromethoxy)benzyl)-7,8-dihydro-1,6-naphthyridin-5(6H)-one (200 mg, 0.477 mmol), bis(pinacolato)diboron (244 mg, 0.955 mmol), potassium acetate (117 mg, 1.193 mmol), [1,1'-bis(diphenylphosphino)ferrocene]dichloropalladium(II) (35 mg, 0.0477 mmol) and 1,4-dioxane (10 mL) were added into a 100 mL round bottom flask, the mixture was replaced with nitrogen for three times, reacted at 95° C. overnight, cooled to room temperature, filtered with suction, the filter cake was washed with ethyl acetate for three times to obtain the filtrate, the filtrate was concentrated to obtain crude product 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (222 mg, Y: 99%). ES-API: $[M+H]^+$=385.1.

Step 4: Preparation of 3-(2-amino-1H-benzo[d]imidazol-6-yl)-6-(2-fluoro-5-(trifluoromethoxy)benzyl)-7,8-dihydro-1,6-naphthyridin-5(6H)-one: under the protection of nitrogen, 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (30 mg, 0.064 mmol), 6-bromo-2,7a-dihydro-1H-benzo[d]imidazol-2-amine (20 mg, 0.097 mmol), sodium carbonate (17 mg, 0.160 mmol), 1,1'-bis(diphenylphosphino)ferrocene-palladium(II)dichloride dichloromethane complex (5 mg, 0.0064 mmol) were dissolved in 1,4-dioxane (5 mL) and $H_2O$ (1 mL), the mixture was replaced with nitrogen for three times, the reaction solution was heated in oil bath at 95° C. for two hours, cooled to room temperature, concentrated, the crude product was purified by alkaline HPLC to obtain off-white solid product 3-(2-amino-1H-benzo[d]imidazol-6-yl)-6-(2-fluoro-5-(trifluoromethoxy)benzyl)-7,8-dihydro-1,6-naphthyridin-5(6H)-one (Z18, 11.39 mg, Y: 38%). ES-API: $[M+H]^+$=472.0. $^1H$ NMR (400 MHz, DMSO-d6) δ 10.80 (bs, 1H), 8.91 (d, J=1.6 Hz, 1H), 8.34 (d, J=1.6 Hz, 1H), 7.44-7.39 (m, 4H), 7.24-7.20 (m, 2H), 6.29 (s, 2H), 4.81 (s, 2H), 3.71 (t, J1=5.6 Hz, J2=11.2 Hz, 2H), 3.17 (t, J1=5.2 Hz, J2=10.8 Hz, 2H).

Example 19: Preparation of 3-bromo-6-(5-fluoro-2-(morpholinomethyl)benzyl)-7,8-dihydro-1,6-naphthyridin-5(6H)-one (Z19)

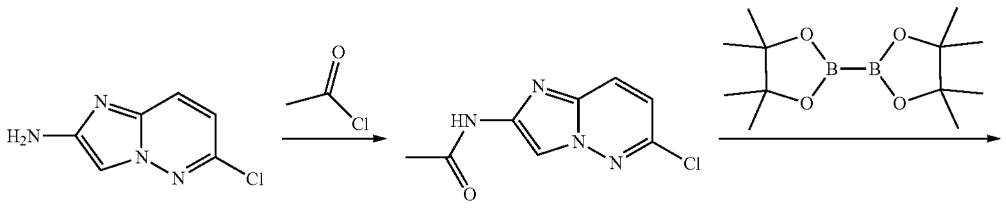

-continued

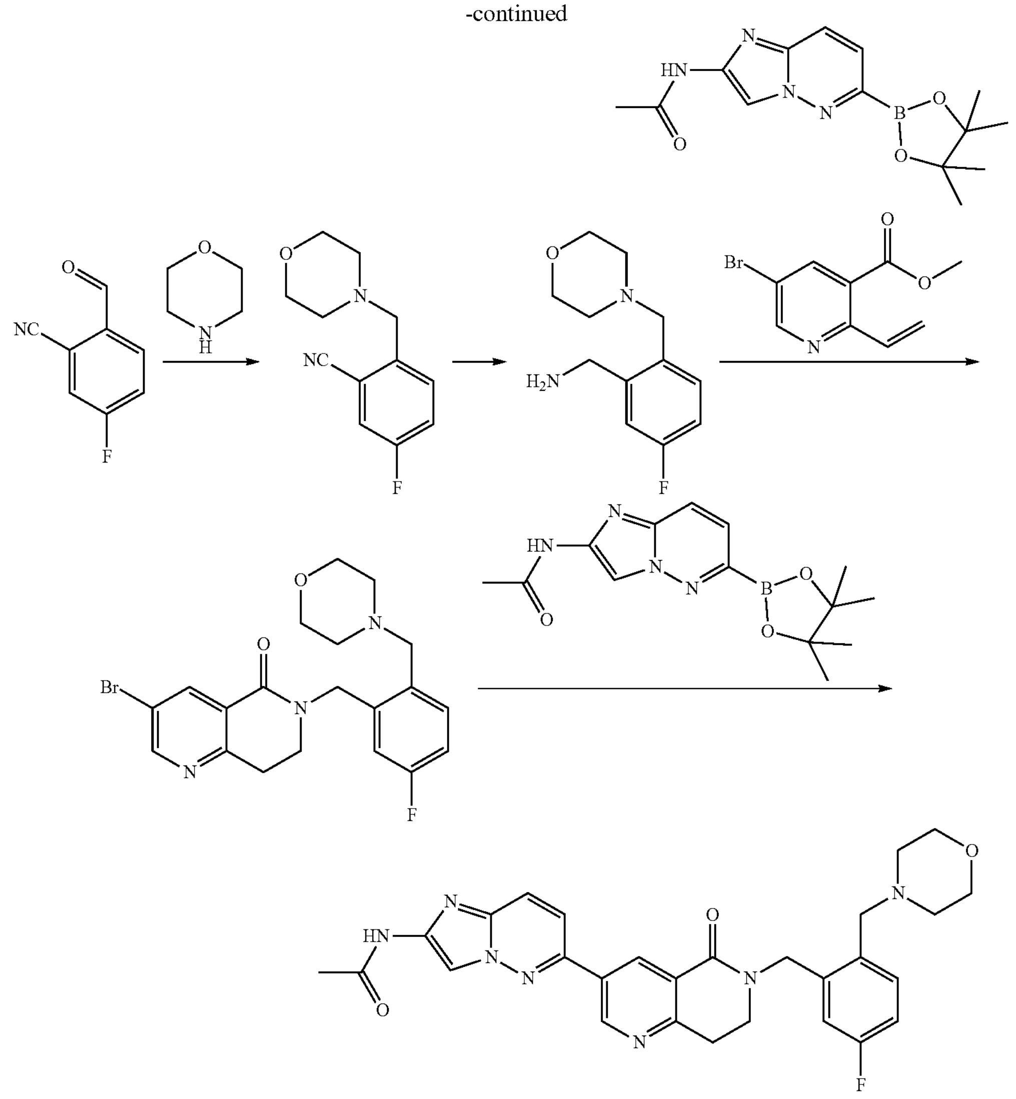

Z19

Step 1: Preparation of N-(6-chloroimidazo[1,2-b]pyridazin-2-yl)acetamide: acetyl chloride (512 mg, 6.525 mmol) was added into a solution of 2-amino-6-chloroimidazo[1,2-b]pyridazine (1 g, 5.932 mmol) in N,N-dimethylacetamide (20 mL), the reaction mixture was stirred at room temperature for one hour, LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (1.15 g, Y: 92%). ES-API: $[M+H]^+$=211.0.

Step 2: Preparation of N-(6-(4,4,5,5-tetramethyl-1,3,2-dioxaborolan-2-yl)imidazo[1,2-b]pyridazin-2-yl)acetamide: N-(6-chloroimidazo[1,2-b]pyridazin-2-yl)acetamide (1.15 g, 5.46 mmol), bis(pinacolato)diboron (1.66 mg, 6.55 mmol), potassium acetate (1.34 g, 13.65 mmol), [1,1'-bis(diphenylphosphino)ferrocene]dichloropalladium(II) (400 mg, 0.546 mmol) and 1,4-dioxane (40 mL) were added into a 100 mL round bottom flask, the mixture was replaced with nitrogen for three times, reacted at 98° C. overnight, cooled to room temperature, filtered with suction, the filter cake was washed with ethyl acetate for three times to obtain the filtrate, the filtrate was concentrated to obtain crude product N-(6-(4,4,5,5-tetramethyl-1,3,2-dioxaborolan-2-yl)imidazo[1,2-b]pyridazin-2-yl)acetamide (1.201 g, Y: 99%). ES-API: $[M+H]^+$=221.0.

Step 3: Preparation of 5-fluoro-2-(morpholinomethyl)benzonitrile: 5-fluoro-2-formylbenzonitrile (1 g, 6.711 mmol), morpholine (642 mg, 7.383 mmol), $NaBH(OAc)_3$ (2.134 g, 10.067 mmol) were dissolved in EtOH (40 mL), the reaction mixture was stirred for 20 hours under the protection of nitrogen, after the reaction was completed, 1N NaOH (aq) (20 mL) was used for quenching the reaction, the reaction mixture was added into EtOAc (30 mL) and $H_2O$ (30 mL) in batches, the organic phase was separated and washed with $H_2O$ (10 mL) and sodium chloride (10 mL*2), dried and concentrated to obtain crude product 5-fluoro-2-(morpholinomethyl)benzonitrile (1.187 g, Y: 80%). ES-API: $[M+H]^+$=221.1.

Step 4: Preparation of (5-fluoro-2-(morpholinomethyl)phenyl)methylamine: Raney-Ni (240 mg, 2.698 mmol) was added into a solution of 5-fluoro-2-(morpholinomethyl)benzonitrile (1.187 g, 5.395 mmol) in EtOH (20 mL), the reaction mixture was stirred overnight under the protection of hydrogen. After the reaction was completed, the mixture was filtered to obtain crude product (5-fluoro-2-(morpholinomethyl)phenyl)methylamine (236 mg, Y: 20%). ES-API: $[M+H]^+$=225.1.

Step 5: Preparation of 3-bromo-6-(5-fluoro-2-(morpholinomethyl)benzyl)-7,8-dihydro-1,6-naphthyridin-5(6H)-one: methyl 5-bromo-2-vinylnicotinate (127 mg, 0.527 mmol) and (5-fluoro-2-(morpholinomethyl)phenyl)methylamine (236 mg, 1.054 mmol) were mixed in DMA (3 mL) in a microwave bottle. The reaction was subjected to microwave radiation at 150° C. for three hours, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(5-fluoro-2-(morpholinomethyl)benzyl)-7,8-dihydro-1,6-naphthyridin-5(6H)-one (178 mg, Y: 78%). ES-API: $[M+H]^+$=434.1.

Step 5: Preparation of N-(6-(6-(5-fluoro-2-(morpholinomethyl)benzyl)-5-oxo-5,6,7,8-tetrahydro-1,6-naphthyridin-3-yl)imidazo[1,2-b]pyridazin-2-yl acetamide: under the protection of nitrogen, N-(6-(4,4,5,5-tetramethyl-1,3,2-dioxaborolan-2-yl)imidazo[1,2-b]pyridazin-2-yl)acetamide (50 mg, 0.166 mmol), 3-bromo-6-(5-fluoro-2-(morpholinomethyl)benzyl)-7,8-dihydro-1,6-naphthyridin-5(6H)-one (72 mg, 0.166 mmol), sodium carbonate (44 mg, 0.415 mmol), 1,1'-bis(diphenylphosphino)ferrocene-palladium(II) dichloride dichloromethane complex (7 mg, 0.0083 mmol) were dissolved in 1,4-dioxane (5 mL) and $H_2O$ (1 mL), the mixture was replaced with nitrogen for three times, the reaction solution was reacted and heated in oil bath at 95° C. for two hours. The reaction mixture was cooled to room temperature, concentrated, the crude product was purified by alkaline HPLC to obtain light yellow solid product 3-bromo-6-(5-fluoro-2-(morpholinomethyl)benzyl)-7,8-dihydro-1,6-naphthyridin-5(6H)-one (Z19, 10 mg, Y: 11%). ES-API: $[M+H]^+$=530.2. $^1H$ NMR (400 MHz, DMSO-d6) δ 10.88 (s, 1H), 9.24 (d, J=2.0 Hz, 1H), 8.76 (d, J=1.6 Hz, 1H), 8.30 (s, 1H), 8.06 (d, J=7.6 Hz, 1H), 7.86 (d, J=7.6 Hz, 1H), 7.27-7.25 (m, 1H), 7.05-6.99 (m, 2H), 4.88 (s, 2H), 3.60 (t, J1=5.6 Hz, J2=10.8 Hz, 2H), 3.45-3.44 (m, 6H), 3.16 (t, J1=5.2 Hz, J2=10.8 Hz, 2H), 2.29 (s, 4H), 2.05 (s, 3H).

Example 20: Preparation of N-(6-(6-(2-cyclopropoxy-3,5-difluorobenzyl)-5-oxo-5,6,7,8-tetrahydro-1,6-naphthyridin-3-yl)imidazo[1,2-b]pyridazin-2-yl)acetamide (Z20)

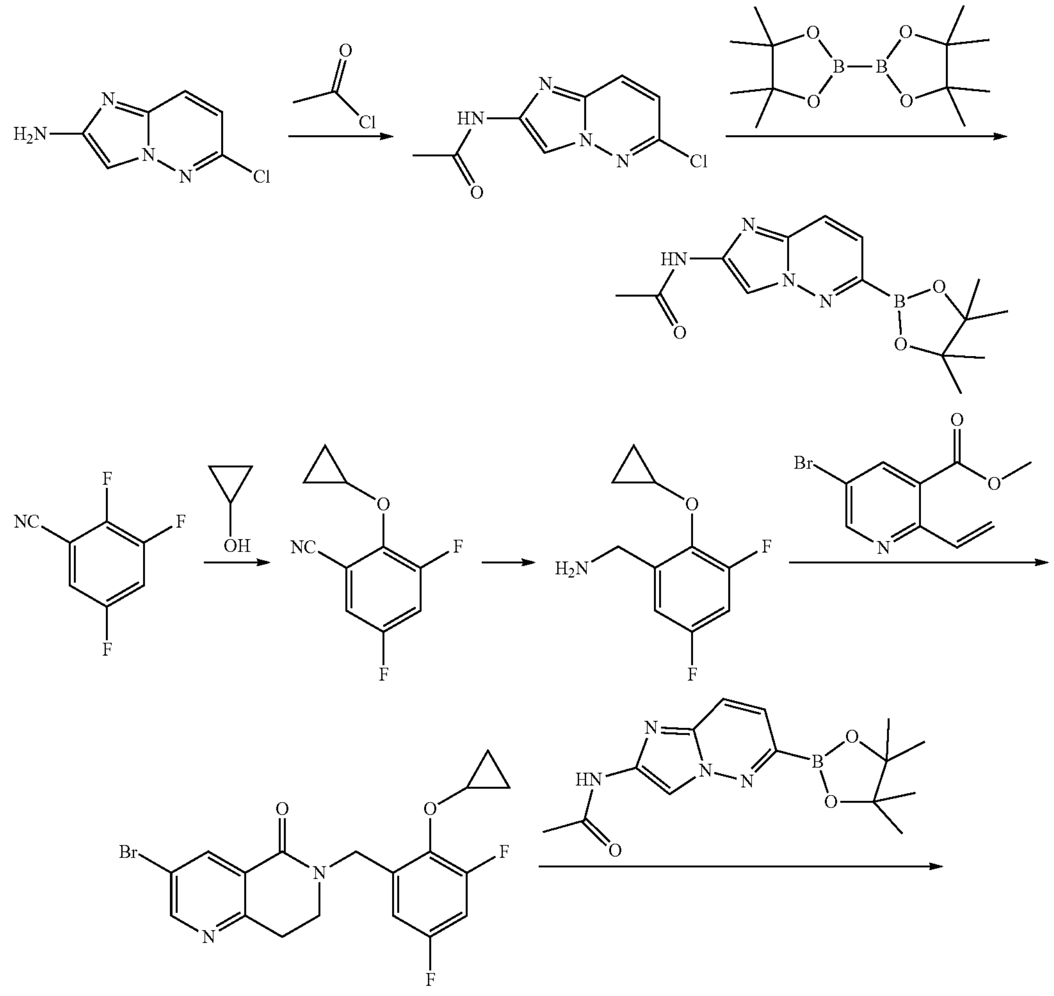

-continued

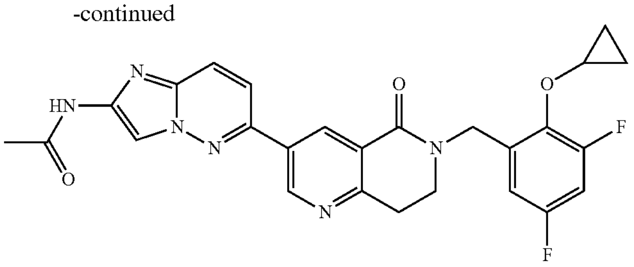

Z20

Step 1: Preparation of N-(6-chloroimidazo[1,2-b]pyridazin-2-yl)acetamide: acetyl chloride (512 mg, 6.525 mmol) was slowly added in a solution of 2-amino-6-chloroimidazo[1,2-b]pyridazine (1 g, 5.932 mmol) in N,N-dimethylacetamide (20 mL), the reaction mixture was stirred at room temperature for one hour, LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (1.15 g, Y: 92%). ES-API: $[M+H]^+$=211.0.

Step 2: Preparation of N-(6-(4,4,5,5-tetramethyl-1,3,2-dioxaboran-2-yl)imidazo[1,2-b]pyridazin-2-yl)acetamide: N-(6-chloroimidazo[1,2-b]pyridazin-2-yl) acetamide (1.15 g, 5.46 mmol), bis (pinacolato) diboron (1.66 mg, 6.55 mmol), potassium acetate (1.34 g, 13.65 mmol), [1,1'-bis (diphenylphosphino)ferrocene]dichloropalladium(II) (400 mg, 0.546 mmol) and 1,4-dioxane (40 mL) were added to a 100 mL round bottom flask, the mixture was replaced with nitrogen for three times, reacted at 98° C. overnight, cooled to room temperature, filtered with suction, the filter cake was washed with ethyl acetate for three times to obtain the filtrate, the filtrate was concentrated to obtain crude product N-(6-(4,4,5,5-tetramethyl-1,3,2-dioxaborolan-2-yl)imidazo [1,2-b]pyridazin-2-yl)acetamide (1.201 g, Y: 99%). ES-API: $[M+H]^+$=221.0.

Step 3: Preparation of 2-cyclopropoxy-3,5-difluorobenzonitrile: 2,3,5-trifluorobenzonitrile (1.57 g, 10 mmol), cyclopropanol (581 g, 10 mmol), $Cs_2CO_3$ (8.15 g, 25 mmol) were mixed in DMF (60 mL), the mixture was heated to 75° C. and stirred for 7 hours, LCMS showed the reaction was completed, water (50 mL) was added for quenching the reaction, extracted with EtOAc (30 mL*3), the combined organic phases were concentrated, the residue was purified on silica gel by automatic fast chromatography to obtain crude product 2-cyclopropoxy-3,5-difluorobenzonitrile (1.952 g, Y: 99%). ES-API: $[M+H]^+$=196.1.

Step 4: Preparation of (2-cyclopropoxy-3,5-difluorophenyl)methylamine: $BH_3$-THF (30 mL, 30 mmol) was added into a solution of 2-cyclopropoxy-3,5-difluorobenzonitrile (1.952 g, 10 mmol) in THF (30 mL), the reaction mixture was heated and refluxed overnight, LCMS showed the reaction was completed, the reaction mixture was cooled to room temperature, MeOH was slowly added for quenching the reaction, the reaction mixture was concentrated, the residue was dissolved in 1 N HCl(aq) (20 mL), extracted with DCM/i-PrOH (30 mL*3), the organic phase was combined, concentrated to obtain light yellow transparent liquid (2-cyclopropoxy-3,5-difluorophenyl)methylamine (1.474 g, Y: 74%). ES-API: $[M+H]^+$=200.1.

Step 5: Preparation of 3-bromo-6-(2-cyclopropoxy-3,5-difluorobenzyl)-7,8-dihydro-1,6-naphthyridin-5(6H)-one: methyl 5-bromo-2-vinylnicotinate (136 mg, 0.564 mmol) and (2-cyclopropoxy-3,5-difluorophenyl)methylamine (337 mg, 1.693 mmol) was mixed in DMA (6 mL) in a microwave bottle. The reaction was subjected to microwave radiation at 180° C. for one hour, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-cyclopropoxy-3,5-difluorobenzyl)-7,8-dihydro-1,6-naphthyridin-5(6H)-one (231 mg, Y: 99%). ES-API: $[M+H]^+$=409.1.

Step 6: Preparation of N-(6-(6-(2-cyclopropoxy-3,5-difluorobenzyl)-5-oxo-5,6,7,8-tetrahydro-1,6-naphthyridin-3-yl)imidazo[1,2-b]pyridazin-2-yl)acetamide: under the protection of nitrogen, N-(6-(4,4,5,5-tetramethyl-1,3,2-dioxaborolan-2-yl)imidazo[1,2-b]pyridazin-2-yl)acetamide (33 mg, 0.110 mmol), 3-bromo-6-(2-cyclopropoxy-3,5-difluorobenzyl)-7,8-dihydro-1,6-naphthyridin-5(6H)-one (30 mg, 0.074 mmol), sodium carbonate (29 mg, 0.275 mmol), 1,1'-bis(diphenylphosphino)ferrocene-palladium(II)dichloride dichloromethane complex (4.5 mg, 0.0055 mmol) were dissolved in 1,4-dioxane (5 mL) and $H_2O$ (1 mL), the mixture was replaced with nitrogen for three times, the reaction solution was stirred in oil bath at 95° C. for 2 hours. The reaction mixture was cooled to room temperature, concentrated, the crude product was purified by alkaline HPLC to obtain N-(6-(6-(2-cyclopropoxy-3,5-difluorobenzyl)-5-oxo-5,6,7,8-tetrahydro-1,6-naphthyridin-3-yl)imidazo[1,2-b]pyridazin-2-yl)acetamide (Z20, 20 mg, Y: 54%). ES-API: $[M+H]^+$=505.1. $^1$H NMR (400 MHz, DMSO-d6) δ 10.95 (s, 1H), 9.31 (d, J=2.0 Hz, 1H), 8.80 (d, J=2.0 Hz, 1H), 8.36 (s, 1H), 8.13 (d, J=7.6 Hz, 1H), 7.93 (d, J=7.6 Hz, 1H), 7.32-7.28 (m, 1H), 7.00 (d, J=6.4 Hz, 1H), 4.71 (s, 2H), 4.23-4.20 (m, 1H), 3.69 (t, J1=5.2 Hz, J2=10.8 Hz, 2H), 3.24 (t, J1=5.2 Hz, J2=10.8 Hz, 2H), 2.13 (s, 3H), 0.84 (s, 2H), 0.65-0.61 (s, 2H).

Example 21: Preparation of N-(6-(6-(5-fluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)acetamide (Z21)

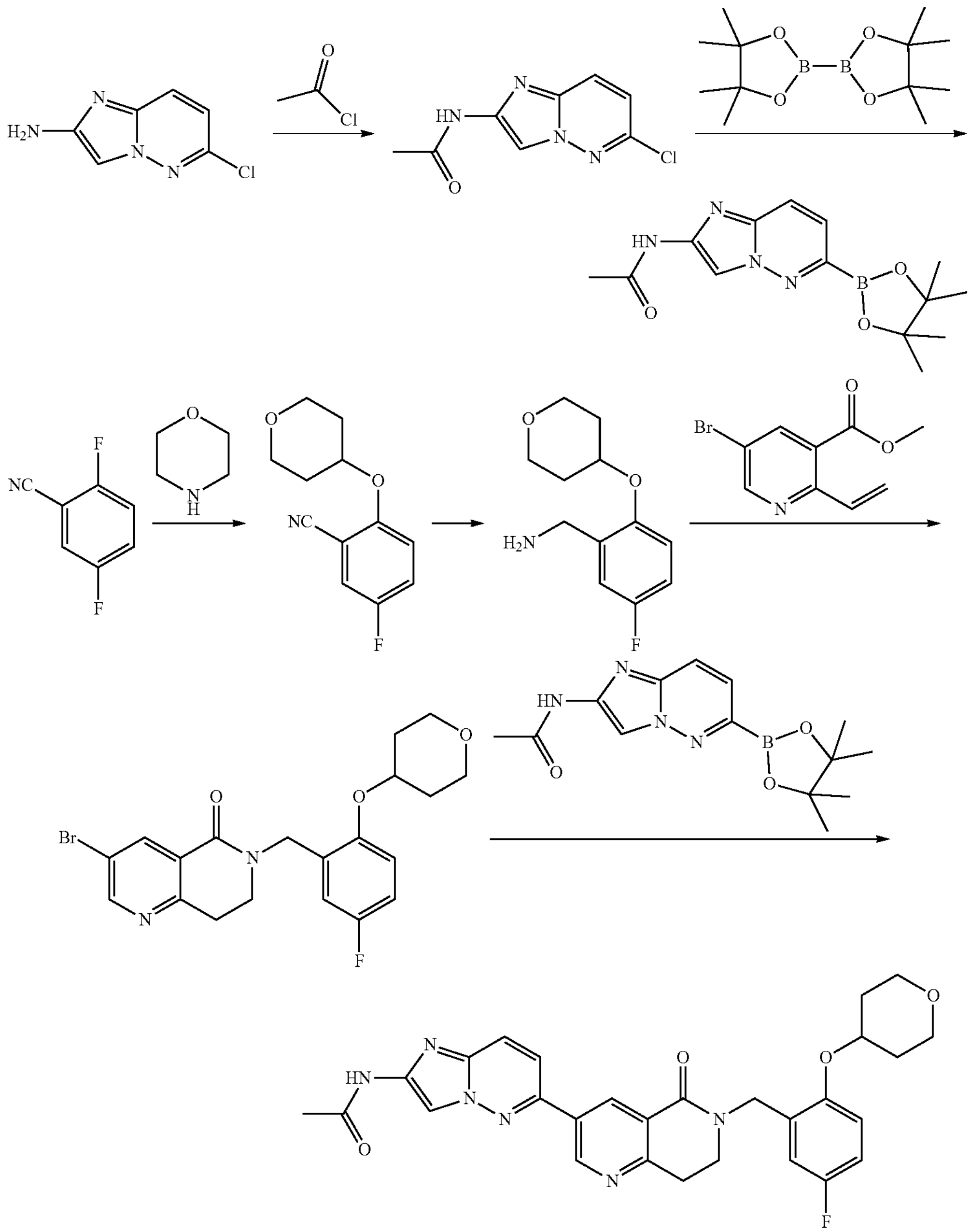

Z21

Step 1: Preparation of N-(6-chloroimidazo[1,2-b]pyridazin-2-yl)acetamide: acetyl chloride (512 mg, 6.525 mmol) was slowly added in a solution of 2-amino-6-chloro-imidazo[1,2-b]pyridazine (1 g, 5.932 mmol) in N,N-dimethylacetamide (20 mL), the reaction mixture was stirred at room temperature for one hour, LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (1.15 g, Y: 92%). ES-API: $[M+H]^+$=211.0.

Step 2: Preparation of N-(6-(4,4,5,5-tetramethyl-1,3,2-dioxaborolan-2-yl)imidazo[1,2-b]pyridazin-2-yl)acetamide: N-(6-chloroimidazo[1,2-b]pyridazin-2-yl)acetamide (1.15 g, 5.46 mmol), bis(pinacolato)diboron (1.66 mg, 6.55 mmol), potassium acetate (1.34 g, 13.65 mmol), [1,1'-bis(diphenylphosphino)ferrocene]dichloropalladium(II) (400 mg, 0.546 mmol) and 1,4-dioxane (40 mL) were added into a 100 mL round bottom flask, the mixture was replaced with nitrogen for three times, reacted at 98° C. overnight, cooled to room temperature, filtered with suction, the filter cake was washed with ethyl acetate for three times to obtain the filtrate, the filtrate was concentrated to obtain crude product N-(6-(4,4,5,5-tetramethyl-1,3,2-dioxaborolan-2-yl)imidazo[1,2-b]pyridazin-2-yl)acetamide (1.201 g, Y: 99%). ES-API: $[M+H]^+=221.0$.

Step 3: Preparation of 5-fluoro-2-((tetrahydro-2H-pyran-4-yl)oxy)benzonitrile: under ice water bath, sodium hydride (1 g, 25 mmol) was added into a solution of tetrahydro-2H-pyran-4-ol (20.043 g, 20 mmol) in THF (30 mL) in batches, the reaction mixture was stirred at 0° C. for one hour, 2,5-difluorobenzonitrile (1.39 g, 10 mmol) was added into the reaction mixture, the reaction mixture was stirred at 55° C. for 12 hours. LCMS showed the reaction was completed, under ice water bath, water (50 mL) was added for quenching the reaction, extracted with EtOAc (30 mL*3), the organic phases were combined and washed with saturated sodium chloride solution (15 mL*3), the combined organic layers were concentrated, purified on silica gel by automatic fast chromatography to obtain crude product 5-fluoro-2-((tetrahydro-2H-pyran-4-yl)oxy)benzonitrile (2.21 g, Y: 99%). ES-API: $[M+H]^+=222.1$.

Step 4: Preparation of (5-fluoro-2-(((tetrahydro-2H-pyran-4-yl)oxy)phenyl)methylamine: $BH_3$-THF (30 mL, 30 mmol) was added into a solution of 5-fluoro-2-((tetrahydro-2H-pyran-4-yl)oxy)benzonitrile (2.21 g, 10 mmol) in THF (30 mL), the reaction mixture was heated and refluxed overnight, LCMS showed the reaction was completed, the reaction mixture was cooled to room temperature. MeOH was slowly added for quenching the reaction, the reaction mixture was concentrated, the residue was dissolved in 1 N HCl (aq) (20 mL), extracted with DCM/i-PrOH (30 mL*3), the organic phases were combined, concentrated to obtain light yellow transparent liquid (5-fluoro-2-(((tetrahydro-2H-pyran-4-yl)oxy)phenyl)methylamine (1.718 g, Y: 76%). ES-API: $[M+H]^+=226.1$.

Step 5: Preparation of 3-bromo-6-(5-fluoro-2-((tetrahydro-2H-pyran-4-yl)oxy)benzyl)-7,8-dihydro-1,6-naphthyridin-5(6H)-one: methyl 5-bromo-2-vinylnicotinate (163 mg, 0.676 mol) and (5-fluoro-2-(((tetrahydro-2H-pyran-4-yl)oxy)phenyl)methylamine (456 mg, 2.027 mmol) were mixed in DMA (6 mL) in a microwave bottle. The reaction was subjected to microwave radiation at 180° C. for one hour, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(5-fluoro-2-((tetrahydro-2H-pyran-4-yl)oxy)benzyl)-7,8-dihydro-1,6-naphthyridin-5(6H)-one (295 mg, Y: 99%). ES-API: $[M+H]^+=435.1$.

Step 6: Preparation of N-(6-(6-(5-fluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)acetamide: under the protection of nitrogen, N-(6-(4,4,5,5-tetramethyl-1,3,2-dioxaborolan-2-yl)imidazo[1,2-b]pyridazin-2-yl)acetamide (53 mg, 0.173 mmol), 3-bromo-6-(5-fluoro-2-((tetrahydro-2H-pyran-4-yl)oxy)benzyl)-7,8-dihydro-1,6-naphthyridin-5(6H)-one (50 mg, 0.115 mmol), sodium carbonate (30 mg, 0.288 mmol), 1,1'-bis(diphenylphosphino)ferrocene-palladium(II)dichloride dichloromethane complex (7 mg, 0.0087 mmol) were dissolved in 1,4-dioxane (5 mL) and $H_2O$ (1 mL), the mixture was replaced with nitrogen for three times, the reaction solution was stirred in oil bath at 95° C. for 2 hours. The reaction mixture was cooled to room temperature, concentrated, the crude product was purified by alkaline HPLC to obtain light yellow solid N-(6-(6-(5-fluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)acetamide (Z21, 34.78 mg, Y: 57%). ES-API: $[M+H]^+=531.1$. $^1H$ NMR (400 MHz, DMSO-d6) δ 10.95 (s, 1H), 9.30 (d, J=1.6 Hz, 1H), 8.81 (d, J=1.6 Hz, 1H), 8.36 (s, 1H), 8.12 (d, J=8.0 Hz, 1H), 7.92 (d, J=7.6 Hz, 1H), 7.15-7.06 (m, 3H), 4.74 (s, 2H), 4.63-4.60 (m, 1H), 3.88-3.84 (m, 2H), 3.70 (t, J1=5.6 Hz, J2=10.8 Hz, 2H), 3.51-3.47 (m, 2H), 3.24 (t, J1=5.2 Hz, J2=10.4 Hz, 2H), 2.13 (s, 3H), 1.99-1.96 (m, 2H), 1.66-1.59 (m, 2H).

Example 22: Preparation of 3-(2-amino-5,6-dihydro-[1,2,4]triazolo[1,5-a]pyrazin-7(8H)-yl)-6-(2-fluoro-5-(trifluoromethoxy)benzyl)-7,8-dihydro-1,6-naphthyridin-5(6H)-one (Z22)

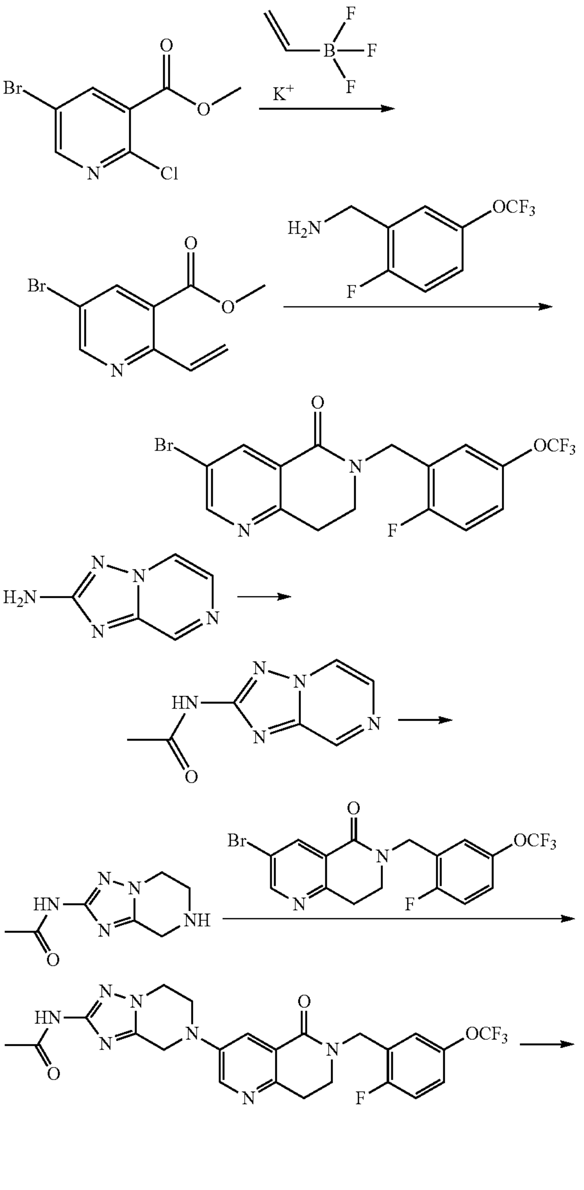

-continued

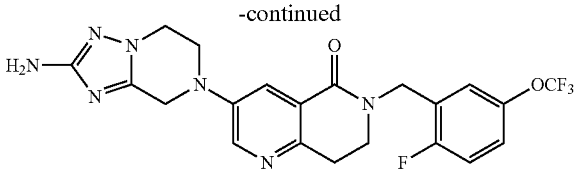

Z22

Step 1: Preparation of methyl 5-bromo-2-vinylnicotinate: under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, then cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 2: Preparation of 3-bromo-6-(2-fluoro-5-(trifluoromethoxy)benzyl)-7,8-dihydro-1,6-naphthyridin-5(6H)-one: methyl 5-bromo-2-vinylnicotinate (280 mg, 1.157 mmol) and ((2-fluoro-5-(trifluoromethoxy)phenyl)methylamine (726 mg, 3.471 mmol) were mixed in DMA (5 mL) in a microwave bottle. The reaction was subjected to microwave radiation at 150° C. for three hours, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-fluoro-5-(trifluoromethoxy)benzyl)-7,8-dihydro-1,6-naphthyridin-5(6H)-one (300 mg, Y: 62%). ES-API: $[M+H]^+$=419.0.

Step 3: Preparation of N-([1,2,4]triazolo[1,5-a]pyrazin-2-yl)acetamide: acetic anhydride (3.775 g, 36.98 mmol) was added into a solution of [1,2,4]triazolo[1,5-a]pyrazin-2-amine (2.5 g, 18.5 mmol) in toluene (50 mL), the reaction mixture was heated and refluxed overnight, cooled to room temperature, filtered to obtain N—([1,2,4]triazolo[1,5-a]pyrazin-2-yl)acetamide (2.14 g, Y: 65%). ES-API: $[M+H]^+$=178.1.

Step 4: Preparation of N-(5,6,7,8-tetrahydro-[1,2,4]triazolo[1,5-a]pyrazin-2-yl)acetamide: under the protection of hydrogen, $PtO_2$ (192 mg, 0.847 mmol) was added into a solution of N—([1,2,4]triazolo[1,5-a]pyrazin-2-yl)acetamide (1 g, 5.650 mmol) in EtOH (20 mL), the reaction mixture was reacted in room temperature for three days, filtered and concentrated to obtain N-(5,6,7,8-tetrahydro-[1,2,4]triazolo[1,5-a]pyrazin-2-yl)acetamide (1.02 g, Y: 99%). ES-API: $[M+H]^+$=182.1.

Step 5: Preparation of N-(7-(6-(2-fluoro-5-(trifluoromethoxy)benzyl)-5-oxo-5,6,7,8-tetrahydro-1,6-naphthyridin-3-yl)-5,6,7,8-tetrahydro-[1,2,4]triazolo[1,5-a]pyrazin-2-yl)acetamide: under the protection of nitrogen, N-(5,6,7,8-tetrahydro-[1,2,4]triazolo[1,5-a]pyrazin-2-yl)acetamide (18 mg, 0.099 mmol), 3-bromo-6-(2-fluoro-5-(trifluoromethoxy)benzyl)-7,8-dihydro-1,6-naphthyridin-5(6H)-one (42 mg, 0.099 mmol), sodium tert-butoxide (24 mg, 0.248 mmol), $Pd_2(dba)_3$ (6 mg, 0.0099 mmol) and BINAP (6 mg, 0.0099 mmol) were dissolved in toluene (5 mL), the mixture was replaced with nitrogen for three times, the reaction solution was heated in oil bath at 110° C. for overnight, cooled to room temperature, concentrated, the crude product was purified by alkaline HPLC to obtain white solid N-(7-(6-(2-fluoro-5-(trifluoromethoxy)benzyl)-5-oxo-5,6,7,8-tetrahydro-1,6-naphthyridin-3-yl)-5,6,7,8-tetrahydro-[1,2,4]triazolo[1,5-a]pyrazin-2-yl)acetamide (4.8 mg, Y: 9%). ES-API: $[M+H]^+$=520.2.

Step 6: Preparation of 3-(2-amino-5,6-dihydro-[1,2,4]triazolo[1,5-a]pyrazin-7(8H)-yl)-6-(2-fluoro-5-(trifluoromethoxy)benzyl)-7,8-dihydro-1,6-naphthyridin-5(6H)-one: 6N NaOH(aq.) (2.0 mg, 0.0462 mmol) was added into a solution of N-(7-(6-(2-fluoro-5-(trifluoromethoxy)benzyl)-5-oxo-5,6,7,8-tetrahydro-1,6-naphthyridin-3-yl)-5,6,7,8-tetrahydro-[1,2,4]triazolo[1,5-a]pyrazin-2-yl)acetamide (4.8 mg, 0.00924 mmol) in methanol (5 mL), the reaction mixture was heated and refluxed overnight. After the reaction was completed, the reaction mixture was concentrated, the crude product was purified by alkaline HPLC to obtain white solid 3-(2-amino-5,6-dihydro-[1,2,4]triazolo[1,5-a]pyrazin-7(8H)-yl)-6-(2-fluoro-5-(trifluoromethoxy)benzyl)-7,8-dihydro-1,6-naphthyridin-5(6H)-one (Z22, 1.98 mg, Y: 45%). ES-API: $[M+H]^+$=478.1.

Example 23: Preparation of N-(6-(6-(5-fluoro-2-(1-methyl-1H-pyrazol-4-yl)benzyl)-5-oxo-5,6,7,8-tetrahydro-1,6-naphthyridin-3-yl)imidazo[1,2-b]pyridazin-2-yl)acetamide (Z23)

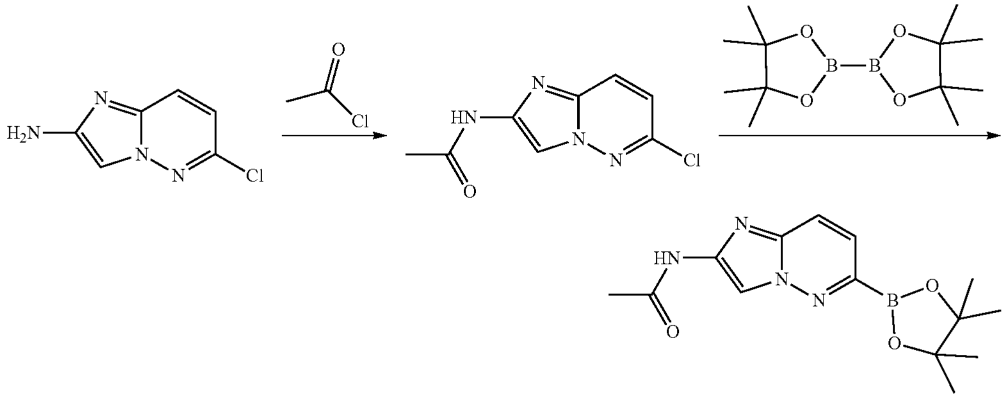

-continued

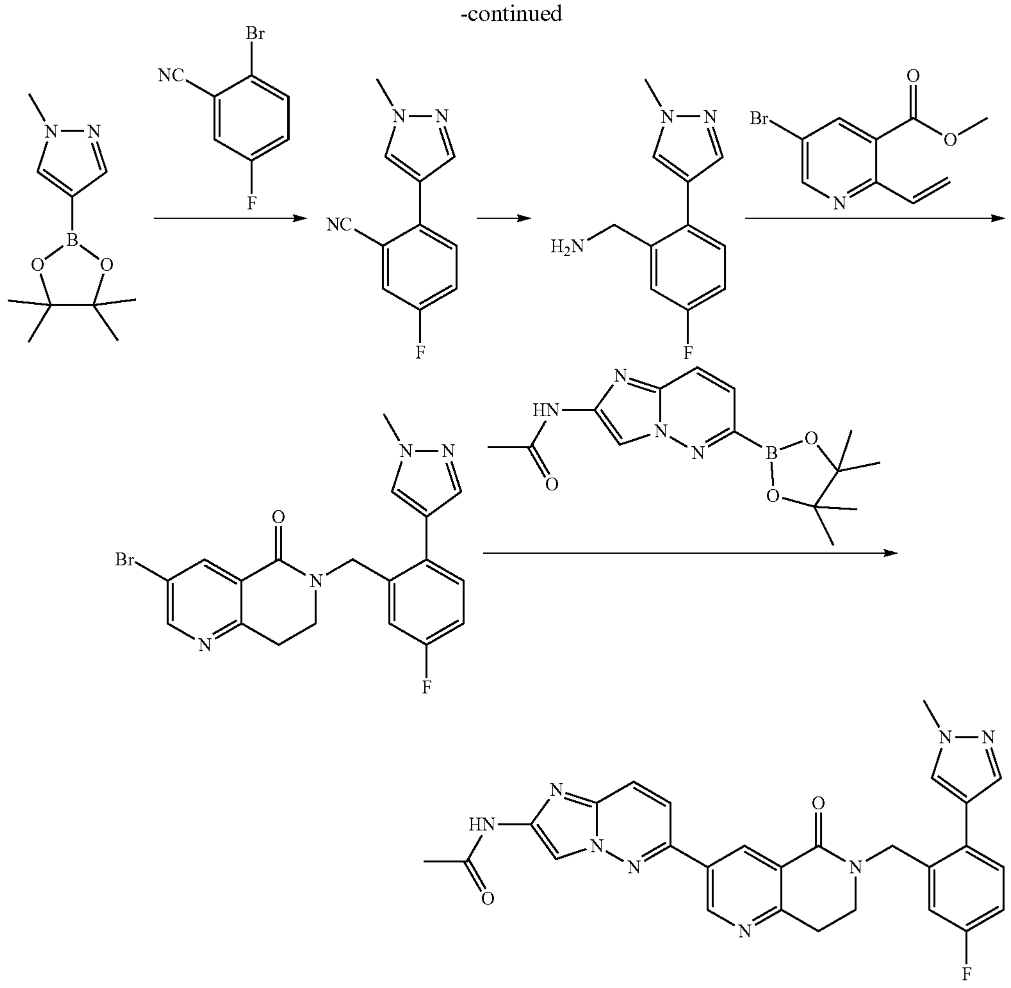

Z23

Step 1: Preparation of N-(6-chloroimidazo[1,2-b]pyridazin-2-yl) acetamide: Acetyl chloride (512 mg, 6.525 mmol) was slowly added into a solution of 2-amino-6-chloroimidazo[1,2-b]pyridazine (1 g, 5.932 mmol) in N,N-dimethylacetamide (20 mL), the reaction mixture was stirred at room temperature for one hour. LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (1.15 g, Y: 92%). ES-API: $[M+H]^+$=211.0.

Step 2: Preparation of N-(6-(4,4,5,5-tetramethyl-1,3,2-dioxaborolan-2-yl)imidazo[1,2-b]pyridazin-2-yl)acetamide: N-(6-chloroimidazo[1,2-b]pyridazin-2-yl)acetamide (1.15 g, 5.46 mmol), bis(pinacolato)diboron (1.66 mg, 6.55 mmol), potassium acetate (1.34 g, 13.65 mmol), [1,1'-bis(diphenylphosphino)ferrocene]dichloropalladium(II) (400 mg, 0.546 mmol) and 1,4-dioxane (40 mL) were added into a 100 mL round bottom flask, the mixture was replaced with nitrogen for three times, reacted at 98° C. overnight, cooled to room temperature, filtered with suction, the filter cake was washed with ethyl acetate for three times to obtain the filtrate, the filtrate was concentrated to obtain crude product N-(6-(4,4,5,5-tetramethyl-1,3,2-dioxaborolan-2-yl)imidazo[1,2-b]pyridazin-2-yl)acetamide (1.201 g, Y: 99%). ES-API: $[M+H]^+$=221.0.

Step 3: Preparation of 5-fluoro-2-(1-methyl-1H-pyrazol-4-yl)benzonitrile: under the protection of nitrogen, 1-methyl-4-(4,4,5,5-tetramethyl-1,3,2-dioxaborinan-2-yl)-1H-pyrazol (1.144 g, 5.5 mmol), 2-bromo-5-fluorobenzonitrile (1 g, 5.0 mmol), sodium carbonate (1.325 g, 12.5 mmol), tetrakis(triphenylphosphine) (289 mg, 0.25 mmol) were dissolved in EtOH (10 mL), toluene (10 mL) and $H_2O$ (2 mL), the mixture was replaced with nitrogen for three times, the reaction mixture was heated and refluxed overnight, LCMS showed the reaction was completed. The reaction mixture was concentrated, the residue was purified on silica gel by automatic fast chromatography to obtain crude product 5-fluoro-2-(1-methyl-1H-pyrazol-4-yl)benzonitrile (1.15 g, Y: 99%). ES-API: $[M+H]^+$=202.1.

Step 4: Preparation of (5-fluoro-2-(1-methyl-1H-pyrazol-4-yl)phenyl)methylamine: Under the protection of hydrogen, Raney-Ni (115 mg) was added into a solution of 5-fluoro-2-(1-methyl-1H-pyrazol-4-yl)benzonitrile (1.15 g, 5.721 mmol) in EtOH (20 mL), the reaction mixture was stirred at room temperature overnight under the protection of hydrogen, LCMS showed the reaction was completed, filtered, concentrated, the residue was purified on silica gel by automatic fast chromatography to obtain (5-fluoro-2-(1-methyl-1H-pyrazol-4-yl)phenyl)methylamine (661 mg, Y: 56%). ES-API: $[M+H]^+$=206.1.

Step 5: Preparation of 3-bromo-6-(5-fluoro-2-(1-methyl-1H-pyrazol-4-yl)benzyl)-7,8-dihydro-1,6-naphthyridin-5(6H)-one: Methyl 5-bromo-2-vinylnicotinate (50 mg, 0.207 mol) and 5-fluoro-2-(1-methyl-1H-pyrazol-4-yl)phenyl) methylamine (127 mg, 0.62 mmol) were mixed in DMA (3 mL) in a microwave bottle. The reaction was subjected to microwave radiation for 1 hour at 180° C. and then cooled to room temperature, ethyl acetate (15 mL) was added into the mixture, the mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(5-fluoro-2-(1-methyl-1H-pyrazol-4-yl)benzyl)-7,8-dihydro-1,6-naphthyridin-5(6H)-one (86 mg, Y: 99%). ES-API: $[M+H]^+=415.1$.

Step 6: Preparation of N-(6-(6-(5-fluoro-2-(1-methyl-1H-pyrazol-4-yl)benzyl)-5-oxo-5,6,7,8-tetrahydro-1,6-naphthyridin-3-yl)imidazo[1,2-b]pyridazin-2-yl)acetamide: Under the protection of nitrogen, N-(6-(4,4,5,5-tetramethyl-1,3,2-dioxaborolan-2-yl)imidazo[1,2-b]pyridazin-2-yl)acetamide (188 mg, 0.621 mmol), 3-bromo-6-(5-fluoro-2-(1-methyl-1H-pyrazol-4-yl)benzyl)-7,8-dihydro-1,6-naphthyridin-5(6H)-one (86 mg, 0.207 mmol), sodium carbonate (55 mg, 0.518 mmol), 1,1'-bis(diphenylphosphino)ferrocene-palladium(II)dichloride dichloromethane complex (8 mg, 0.010 mmol) were dissolved in dioxane (5 mL) and $H_2O$ (1 mL), the mixture was replaced with nitrogen for three times, the reaction mixture was stirred in oil bath at 95° C. for two hours, cooled to room temperature, concentrated, the crude product was purified by alkaline HPLC to obtain white solid N-(6-(6-(5-fluoro-2-(1-methyl-1H-pyrazol-4-yl)benzyl)-5-oxo-5,6,7,8-tetrahydro-1,6-naphthyridin-3-yl)imidazo[1,2-b]pyridazin-2-yl)acetamide (Z23, 22.32 mg, Y: 23%). ES-API: $[M+H]^+=511.1$. $^1H$ NMR (400 MHz, DMSO-d6) δ 10.95 (s, 1H), 9.31 (d, J=2.0 Hz, 1H), 8.81 (d, J=1.6 Hz, 1H), 8.37 (s, 1H), 8.13 (d, J=7.6 Hz, 1H), 7.99 (s, 1H), 7.93 (d, J=7.6 Hz, 1H), 7.67 (s, 1H), 7.44-7.41 (m, 1H), 7.18-7.14 (m, 1H), 7.14-7.09 (m, 1H), 4.86 (s, 2H), 3.90 (s, 3H), 3.62 (t, J1=5.2 Hz, J2=10.4 Hz, 2H), 3.23 (t, J1=5.2 Hz, J2=10.4 Hz, 2H), 2.13 (s, 3H).

Example 24: Preparation of 3-(4-amino-5-(trifluoromethyl)pyrrolo[2,1-f][1,2,4]triazin-7-yl)-6-(2-fluoro-5-(trifluoromethoxy)benzyl)-7,8-dihydro-1,6-naphthyridin-5(6H)-one (Z24)

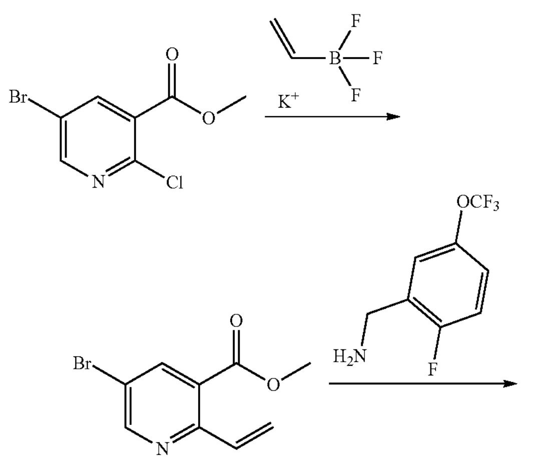

-continued

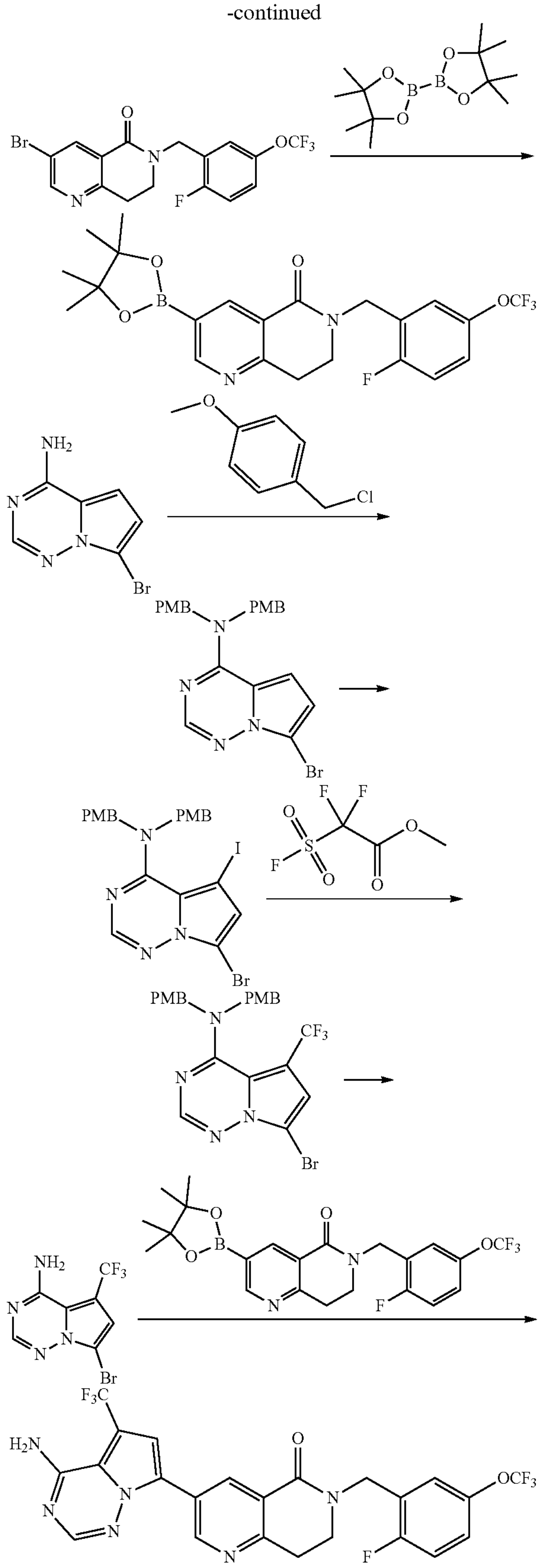

Z24

Step 1: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in 200 mL EtOH, the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, the residue was purified on silica gel by automatic fast chromatography (EtOAc/PE 0-20%) to obtain methyl 5-bromo-2-vinylnicotinate (5.186 g, Y: 55%). ES-API: $[M+H]^+$=242.1.

Step 2: Preparation of 3-bromo-6-(2-(trifluoromethoxy) benzyl)-7,8-dihydro-1,6-naphthyridin-5(6H)-one: methyl 5-bromo-2-vinylnicotinate (280 mg, 1.157 mmol) and ((2-fluoro-5-(trifluoromethoxy)phenyl)methylamine (726 mg, 3.471 mmol) were mixed in DMA (5 mL) in a microwave bottle. The reaction was subjected to microwave radiation at 150° C. for three hours and then cooled to room temperature, ethyl acetate (15 mL) was added into the mixture, the mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-fluoro-5-(trifluoromethoxy)benzyl)-7,8-dihydro-1,6-naphthyridin-5(6H)-one (300 mg, Y: 62%). ES-API: $[M+H]^+$=419.0.

Step 3: Preparation of 6-(2-fluoro-5-(trifluoromethoxy) benzyl)-3-(4,4,5,5-tetramethyl-1,3,2-dioxaborinan-2-yl)-7,8-dihydro-1,6-naphthyridin-5(6H)-one: 3-bromo-6-(2-fluoro-5-(trifluoromethoxy)benzyl)-7,8-dihydro-1,6-naphthyridin-5(6H)-one (200 mg, 0.477 mmol), bis (pinacolato)diboron (244 mg, 0.955 mmol), potassium acetate (117 mg, 1.193 mmol), [1,1'-bis(diphenylphosphino) ferrocene]dichloropalladium(II) (35 mg, 0.0477 mmol) and 1,4-dioxane (10 mL) were added into a 100 mL round bottom flask, the mixture was replaced with nitrogen for three times, and reacted at 95° C. overnight, cooled to room temperature, filtered with suction, the filter cake was washed with ethyl acetate for three times to obtain the filtrate, the filtrate was concentrated to obtain crude product 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (222 mg, Y: 99%). ES-API: $[M+H]^+$=385.1.

Step 4: Preparation of 7-bromo-N,N-bis(4-methoxybenzyl)pyrrolo[2,1-f][1,2,4]triazin-4-amine: $Cs_2CO_3$ (3.827 g, 11.738 mmol) was added into a solution of 7-bromopyrrolo [2,1-f][1,2,4]triazin-4-amine (1 g, 4.695 mmol) and 1-(chloromethyl)-4-methoxybenzene (1.618 g, 10.329 mmol) in DMF (25 mL) at once, the reaction mixture was stirred at room temperature overnight. After the reaction was completed, the reaction mixture was added into $H_2O$ (60 mL), extracted with EtOAc (25*4 mL), the organic phases were combined and washed with saturated sodium chloride solution (25 mL*3), the organic phase was dried, concentrated, the residue was purified on silica gel by automatic fast chromatography to obtain 7-bromo-N,N-bis(4-methoxybenzyl)pyrrolo[2,1-f][1,2,4]triazin-4-amine (1.473 g, Y: 69%). ES-API: $[M+H]^+$=453.1.

Step 5: Preparation of 7-bromo-5-iodo-N,N-bis(4-methoxybenzyl)pyrrolo[2,1-f][1,2,4]triazin-4-amine: three drops of TFA were added into a solution of 7-bromo-N,N-bis(4-methoxybenzyl)pyrrolo[2,1-f][1,2,4]triazin-4-amine (1.473 g, 3.249 mmol) and NIS (731 mg, 3.249 mmol) in DMF (7 mL), the reaction mixture was stirred at room temperature overnight. After the reaction was completed, the reaction mixture was poured into ice water and 1.5 M $Na_2HPO_4$(1:1), yellow insoluble substance was precipitated, filtered, the filter cake was beaten with ethyl acetate, then was beaten with methanol to obtain white powder product 7-bromo-5-iodo-N,N-bis(4-methoxybenzyl)pyrrolo[2,1-f] [1,2,4]triazin-4-amine (1.88 g, Y: 99%). ES-API: $[M+H]^+$=579.0.

Step 6: Preparation of 7-bromo-N,N-bis(4-methoxybenzyl)-5-(trifluoromethyl)pyrrolo[2,1-f][1,2,4]triazin-4-amine: under the protection of nitrogen, 7-bromo-5-iodo-N,N-bis(4-methoxybenzyl)pyrrolo[2,1-f][1,2,4]triazin-4-amine (600 mg, 1.036 mmol), CuI (216 mg, 1.14 mmol) and DMF (9 mL) were added into pressure-resistant bottle (10 mL) successively, the mixture was replaced with nitrogen for three times, the reaction mixture was added into methyl 2,2-difluoro-2-(fluorosulfonyl)acetate (795 mg, 4.143 mmol), the reaction bottle was placed in 80° C. oil bath pot, and reacted for three hours. After the reaction was completed, the mixture was cooled to room temperature, insoluble substance was filtered, the filter cake was washed with ethyl acetate for three times, concentrated to obtain 7-bromo-N,N-bis(4-methoxybenzyl)-5-(trifluoromethyl) pyrrolo[2,1-f][1,2,4]triazin-4-amine (720 mg, Y: 99%). ES-API: $[M+H]^+$=521.0.

Step 7: Preparation of 7-bromo-5-(trifluoromethyl)pyrrolo[2,1-f][1,2,4]triazin-4-amine: 7-bromo-N,N-bis(4-methoxybenzyl)-5-(trifluoromethyl)pyrrolo[2,1-f][1,2,4]triazin-4-amine (720 mg, 1.385 mmol) and TFA (6 mL) were added into a 20 mL sealed tube, the reaction mixture was heated to 110° C. in oil bath pot for four hours. After the reaction was completed, the mixture was cooled to room temperature. The residue was concentrated, purified on silica gel by automatic fast chromatography to obtain 7-bromo-5-(trifluoromethyl)pyrrolo[2,1-f][1,2,4]triazin-4-amine (233 mg, Y: 60%). ES-API: $[M+H]^+$=281.0.

Step 8: Preparation of 3-(4-amino-5-(trifluoromethyl)pyrrolo[2,1-f][1,2,4]triazin-7-yl)-6-(2-fluoro-5-(trifluoromethoxy)benzyl)-7,8-dihydro-1,6-naphthyridin-5(6H)-one: under the protection of nitrogen, 7-bromo-5-(trifluoromethyl)pyrrolo[2,1-f][1,2,4]triazin-4-amine (40 mg, 0.142 mmol), 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (133 mg, 0.284 mmol), potassium phosphate (90 mg, 0.426 mmol), 1,1'-bis(diphenylphosphino)ferrocene-palladium(II)dichloride dichloromethane complex (12 mg, 0.0142 mmol) were dissolved in DMF (3 mL) and $H_2O$ (0.5 mL), the mixture was replaced with nitrogen for three times, the reaction mixture was heated and reacted in oil bath at 100° C. for three hours. After the reaction was completed, the mixture was cooled to room temperature, concentrated, the crude product was purified by alkaline HPLC to obtain off-white solid product 3-(4-amino-5-(trifluoromethyl)pyrrolo[2,1-f][1,2,4]triazin-7-yl)-6-(2-fluoro-5-(trifluoromethoxy)benzyl)-7-7,8-dihydro-1,6-naphthyridin-5(6H)-one (Z24, 4.60 mg, Y: 6%). ES-API: $[M+H]^+$=541.1. $^1$H NMR (400 MHz, DMSO-d6) δ 9.22 (d, J=2.0 Hz, 1H), 8.96 (d, J=1.6 Hz, 1H), 8.21 (s, 1H), 7.76 (s, 1H), 7.45 (d, J=3.6 Hz, 1H), 7.40 (d, J=5.2 Hz, 2H), 4.81 (s, 2H), 3.73 (t, J1=5.2 Hz, J2=10.4 Hz, 2H), 3.21 (t, J1=5.6 Hz, J2=11.2 Hz, 2H).

Example 25: Preparation of 6-(2-fluoro-5-(trifluoromethoxy)benzyl)-3-(2-methyl-[1,2,4]triazolo[1,5-a]pyridin-7-yl)-7,8-dihydro-1,6-naphthyridin-5(6H)-one (Z25)

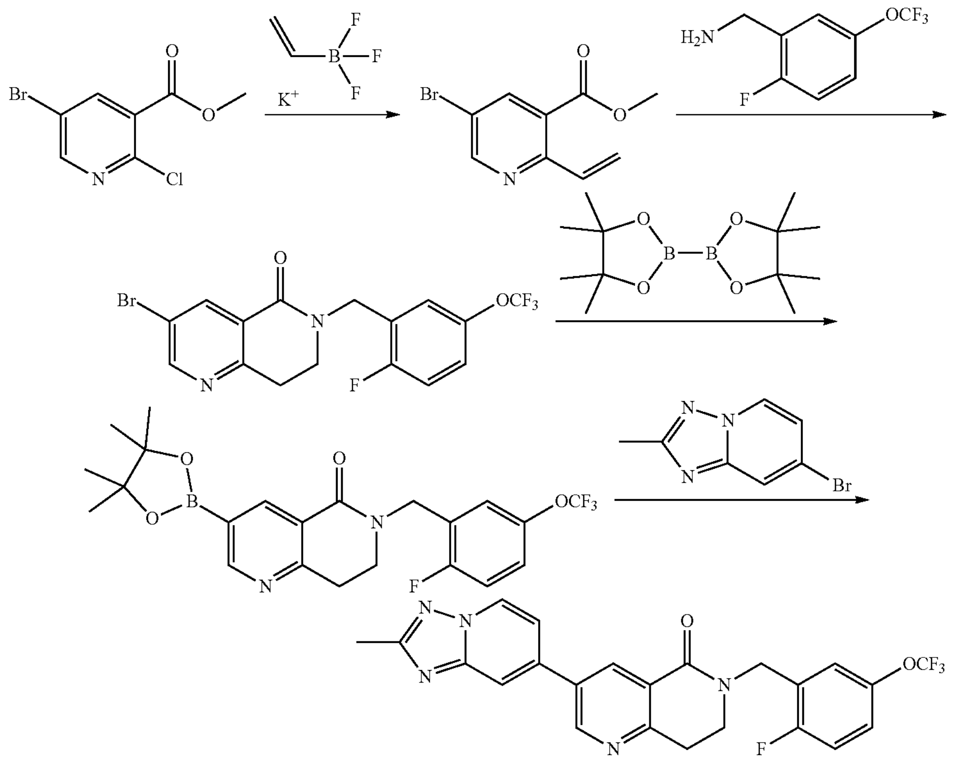

Z25

Step 1: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in 200 mL EtOH, the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 2: Preparation of 3-bromo-6-(2-(trifluoromethoxy)benzyl)-7,8-dihydro-1,6-naphthyridin-5(6H)-one: methyl 5-bromo-2-vinylnicotinate (280 mg, 1.157 mmol) and ((2-fluoro-5-(trifluoromethoxy)phenyl)methylamine (726 mg, 3.471 mmol) were mixed in DMA (5 mL) in a microwave bottle. The reaction was subjected to microwave radiation at 150° C. for three hours, cooled to room temperature, the reaction mixture was added into 15 mL ethyl acetate, then the mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-fluoro-5-(trifluoromethoxy)benzyl)-7,8-dihydro-1,6-naphthyridin-5(6H)-one (300 mg, Y: 62%). ES-API: $[M+H]^+$=419.0.

Step 3: Preparation of 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one: 3-bromo-6-(2-fluoro-5-(trifluoromethoxy)benzyl)-7,8-dihydro-1,6-naphthyridin-5(6H)-one (200 mg, 0.477 mmol), bis(pinacolato)diboron (244 mg, 0.955 mmol), potassium acetate (117 mg, 1.193 mmol), [1,1'-bis(diphenylphosphino)ferrocene]dichloropalladium(II) (35 mg, 0.0477 mmol) and 1,4-dioxane (10 mL) were added into a 100 mL round bottom flask, the mixture was replaced with nitrogen for three times, and reacted at 95° C. overnight, cooled to room temperature, filtered with suction, the filter cake was washed with ethyl acetate for three times to obtain the filtrate, the filtrate was concentrated to obtain crude product 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (222 mg, Y: 99%). ES-API: $[M+H]^+$=385.1.

Step 4: Preparation of 6-(2-fluoro-5-(trifluoromethoxy)benzyl)-3-(2-methyl-[1,2,4]triazolo[1,5-a]pyridin-7-yl)-7,8-dihydro-1,6-naphthyridin-5(6H)-one: under the protection of nitrogen, 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (150 mg, 0.322 mmol), 7-bromo-2-methyl-[1,2,4]triazolo[1,5-a]pyridine (34 mg, 0.161 mmol), sodium carbonate (43 mg, 0.403 mmol), 1,1'-bis(diphenylphosphino)ferrocene-palladium(II)dichloride dichloromethane complex (7 mg, 0.008 mmol) were dissolved in dioxane (5 mL) and $H_2O$ (1 mL), the mixture was replaced with nitrogen for three times, the reaction mixture was heated and reacted at 95° C. in oil bath for three hours, cooled to room temperature, concentrated, the crude product was purified by alkaline HPLC to obtain off-white solid 6-(2-fluoro-5-(trifluoromethoxy)benzyl)-3-(2-methyl-[1,2,4]triazolo[1,5-a]pyridin-7-yl)-7,8-dihydro-1,6-naphthyridin-5(6H)-one (Z25, 26.0 mg, Y: 34%). ES-API: $[M+H]^+$=472.1. $^1$H NMR (400 MHz, DMSO-d6) δ 9.15 (d, J=2.4 Hz, 1H), 8.95 (d, J=5.6 Hz, 1H), 8.57 (d, J=1.6 Hz, 1H), 8.18 (d, J=1.2 Hz, 1H), 7.57 (dd, J1=1.6 Hz, J2=5.6 Hz, 1H), 7.44 (d, J=3.6 Hz, 1H), 7.40 (d, J=5.2 Hz, 2H), 4.83 (s, 2H), 3.74 (t, J1=5.6 Hz, J2=10.8 Hz, 2H), 3.23 (t, J1=5.6 Hz, J2=10.8 Hz, 2H), 2.51 (s, 3H).

Example 26: Preparation of N-(6-(6-(5-fluoro-2-(1-methyl-1H-1,2,4-triazol-3-yl)benzyl)-5-oxo-5,6,7,8-tetrahydro-1,6-naphthyridin-3-yl)imidazo[1,2-b]pyridazin-2-yl)acetamide (Z26)

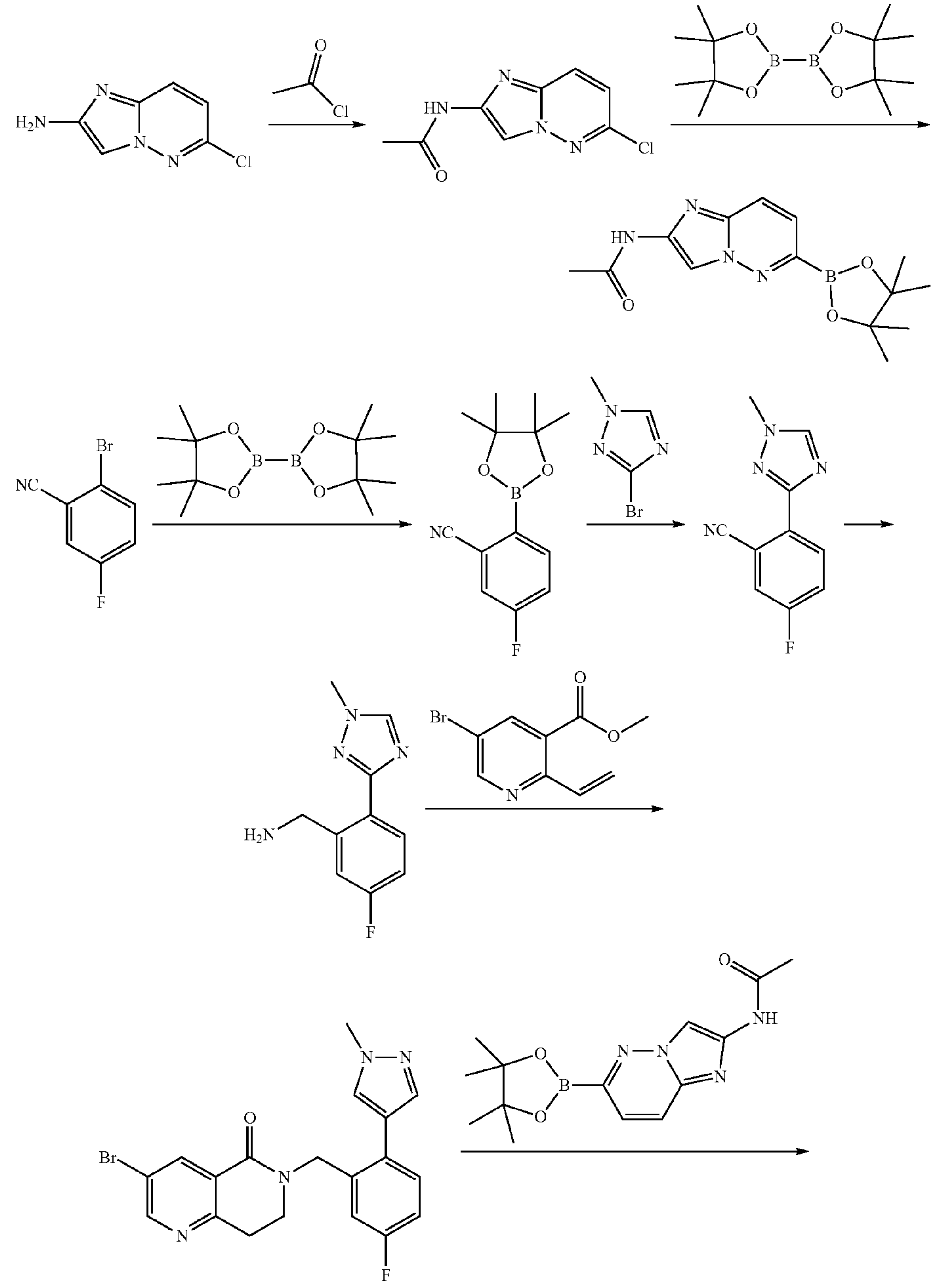

-continued

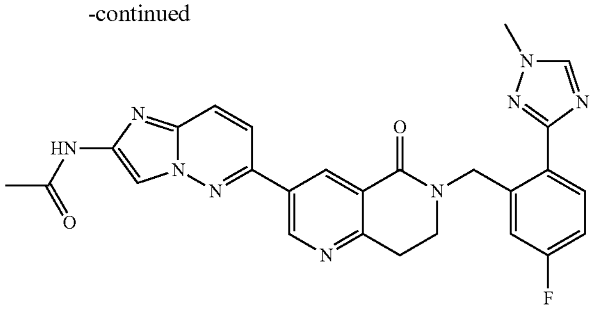

Z26

Step 1: Preparation of N-(6-chloroimidazo[1,2-b]pyridazin-2-yl)acetamide: acetyl chloride (512 mg, 6.525 mmol) was slowly added into a solution of 2-amino-6-chloroimidazo[1,2-b]pyridazine (1 g, 5.932 mmol) in N,N-dimethylacetamide (20 mL), the reaction mixture was stirred at room temperature for one hour. LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (1.15 g, Y: 92%). ES-API: $[M+H]^+$=211.0.

Step 2: Preparation of N-(6-(4,4,5,5-tetramethyl-1,3,2-dioxaborolan-2-yl)imidazo[1,2-b]pyridazin-2-yl)acetamide: N-(6-chloroimidazo[1,2-b]pyridazin-2-yl)acetamide (1.15 g, 5.46 mmol), bis(pinacolato)diboron (1.66 mg, 6.55 mmol), potassium acetate (1.34 g, 13.65 mmol), [1,1'-bis(diphenylphosphino)ferrocene]dichloropalladium(II) (400 mg, 0.546 mmol) and 1,4-dioxane (40 mL) were added into a 100 mL round bottom flask, the mixture was replaced with nitrogen for three times, reacted at 98° C. overnight, cooled to room temperature, filtered with suction, the filter cake was washed with ethyl acetate for three times to obtain the filtrate, the filtrate was concentrated to obtain crude product N-(6-(4,4,5,5-tetramethyl-1,3,2-dioxaborolan-2-yl)imidazo[1,2-b]pyridazin-2-yl)acetamide (1.201 g, Y: 99%). ES-API: $[M+H]^+$=221.0.

Step 3: Preparation of 5-fluoro-2-(4,4,5,5-tetramethyl-1,3,2-dioxaborinan-2-yl)benzonitrile: 2-bromo-5-fluorobenzonitrile (2 g, 10 mmol), bis(pinacolato)diboron (5.12 g, 20 mmol), potassium acetate (2.45 g, 25 mmol), [1,1'-bis(diphenylphosphino)ferrocene]dichloropalladium(II) (358 mg, 0.5 mmol) and 1,4-dioxane (40 mL) were added into a 100 mL round bottom flask, the mixture was replaced with nitrogen for three times, and reacted at 95° C. overnight, cooled to room temperature, filtered with suction, the filter cake was washed with ethyl acetate for three times to obtain the filtrate, the filtrate was concentrated to obtain crude product 5-fluoro-2-(4,4,5,5-tetramethyl-1,3,2-dioxaborinan-2-yl)benzonitrile (2.47 g, Y: 99%). ES-API: $[M+H]^+$=166.0.

Step 4: Preparation of 5-fluoro-2-(1-methyl-1H-1,2,4-triazol-3-yl)benzonitrile: under the protection of nitrogen, 5-fluoro-2-(4,4,5,5-tetramethyl-1,3,2-dioxaborinan-2-yl)benzonitrile (2.47 g, 10 mmol), 3-bromo-1-methyl-1H-1,2,4-triazole (1 g, 6.173 mmol), sodium carbonate (1.64 g, 15.433 mmol), 1,1'-bis(diphenylphosphino)ferrocene-palladium(II)dichloride dichloromethane complex (252 mg, 0.309 mmol) were dissolved in dioxane (15 mL) and $H_2O$ (3 mL), the mixture was replaced with nitrogen for three times, the reaction mixture was heated to 95° C. overnight, LCMS showed the reaction was completed. The reaction mixture was concentrated, the residue was purified on silica gel by automatic fast chromatography to obtain crude product 5-fluoro-2-(1-methyl-1H-1,2,4-triazol-3-yl)benzonitrile (91 mg, Y: 14%). ES-API: $[M+H]^+$=203.1.

Step 5: Preparation of (5-fluoro-2-(1-methyl-1H-1,2,4-triazol-3-yl)phenyl)methylamine: under the protection of hydrogen, Raney-Ni (10 mg) was added into a solution of 5-fluoro-2-(1-methyl-1H-1,2,4-triazol-3-yl)benzonitrile (91 mg, 0.45 mmol) in EtOH (10 mL), the reaction mixture was stirred at room temperature overnight under the protection of hydrogen, LCMS showed the reaction was completed, filtered, concentrated, the residue was purified on silica gel by automatic fast chromatography to obtain (5-fluoro-2-(1-methyl-1H-1,2,4-triazol-3-yl)phenyl)methylamine (40 mg, Y: 43%). ES-API: $[M+H]^+$=207.1.

Step 6: Preparation of 3-bromo-6-(5-fluoro-2-(1-methyl-1H-1,2,4-triazol-3-yl)benzyl)-7,8-dihydro-1,6-naphthyridin-5(6H)-one: methyl 5-bromo-2-vinylnicotinate (23 mg, 0.097 mol) and (5-fluoro-2-(1-methyl-1H-1,2,4-triazol-3-yl)phenyl)methylamine (40 mg, 0.194 mmol) were mixed in DMA (2 mL) in a microwave bottle. The reaction was subjected to microwave radiation at 180° C. for 1.5 hours, cooled to room temperature, the reaction mixture was added into ethyl acetate (15 mL), then the mixture was washed with water (15 mL*3) and saturated sodium chloride solution (15 mL*3), the combined organic layers were concentrated, purified on silica gel by automatic fast chromatography (EtOAc/PE 0-50%) to obtain crude product 3-bromo-6-(5-fluoro-2-(1-methyl-1H-1,2,4-triazol-3-yl)benzyl)-7,8-dihydro-1,6-naphthyridin-5(6H)-one (60 mg). ES-API: $[M+H]^+$=416.0.

Step 7: Preparation of N-(6-(6-(5-fluoro-2-(1-methyl-1H-1,2,4-triazol-3-yl)benzyl)-5-oxo-5,6,7,8-tetrahydro-1,6-naphthyridin-3-yl)imidazo[1,2-b]pyridazin-2-yl)acetamide: under the protection of nitrogen, N-(6-(4,4,5,5-tetramethyl-1,3,2-dioxaborolan-2-yl)imidazo[1,2-b]pyridazin-2-yl)acetamide (44 mg, 0.145 mmol), 3-bromo-6-(5-fluoro-2-(1-methyl-1H-1,2,4-triazol-3-yl)benzyl)-7,8-dihydro-1,6-naphthyridin-5(6H)-one (60 mg, 0.145 mmol), sodium carbonate (38 mg, 0.363 mmol), 1,1'-bis(diphenylphosphino)ferrocene-palladium(II)dichloride dichloromethane complex (6 mg, 0.00725 mmol) were dissolved in dioxane (5 mL) and $H_2O$ (1 mL), the mixture was replaced with nitrogen for three times, the reaction mixture was stirred at 95° C. in oil bath for 2 hours, cooled to room temperature, concentrated, the crude product was purified by alkaline HPLC to obtain white solid product N-(6-(6-(5-fluoro-2-(1-methyl-1H-1,2,4-triazol-3-yl)benzyl)-5-oxo-5,6,7,8-tetrahydro-1,6-naphthyridin-3-yl)imidazo[1,2-b]pyridazin-2-yl)acetamide (Z26, 0.71 mg, Y: 1%). ES-API: $[M+H]^+$=512.4.

Example 27: Preparation of 3-(4-amino-5-(trifluoromethyl)pyrrolo[2,1-f][1,2,4]triazin-7-yl)-6-(((3S,4R)-4-fluoro-1-((R)-3,3,3-trifluoro-2-hydroxy-2-methylpropionyl)pyrrolidin-3-yl)-7,8-dihydro-1,6-naphthyridin-5(6H)-one (Z27-1) and 3-(4-amino-5-(trifluoromethyl)pyrrolo[2,1-f][1,2,4]triazin-7-yl)-6-(((3R,4S)-4-fluoro-1-((R)-3,3,3-trifluoro-2-hydroxy-2-methylpropionyl)pyrrolidin-3-yl)-7,8-dihydro-1,6-naphthyridin-5(6H)-one (Z27-2)
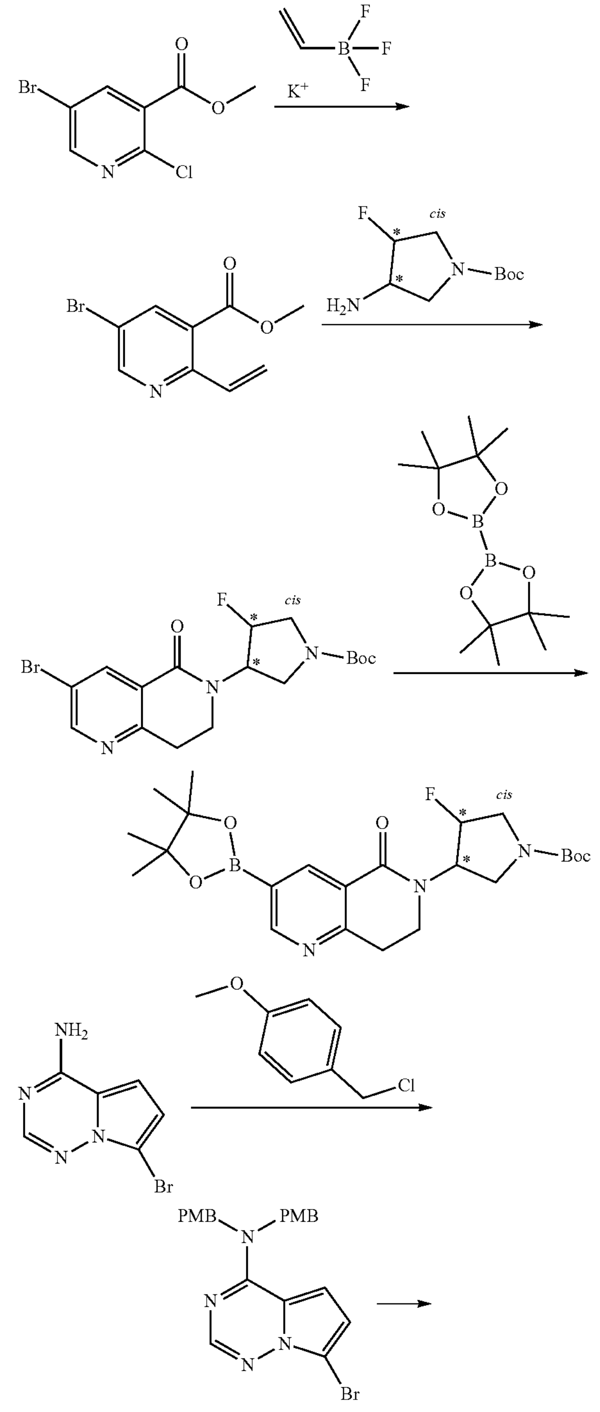
-continued
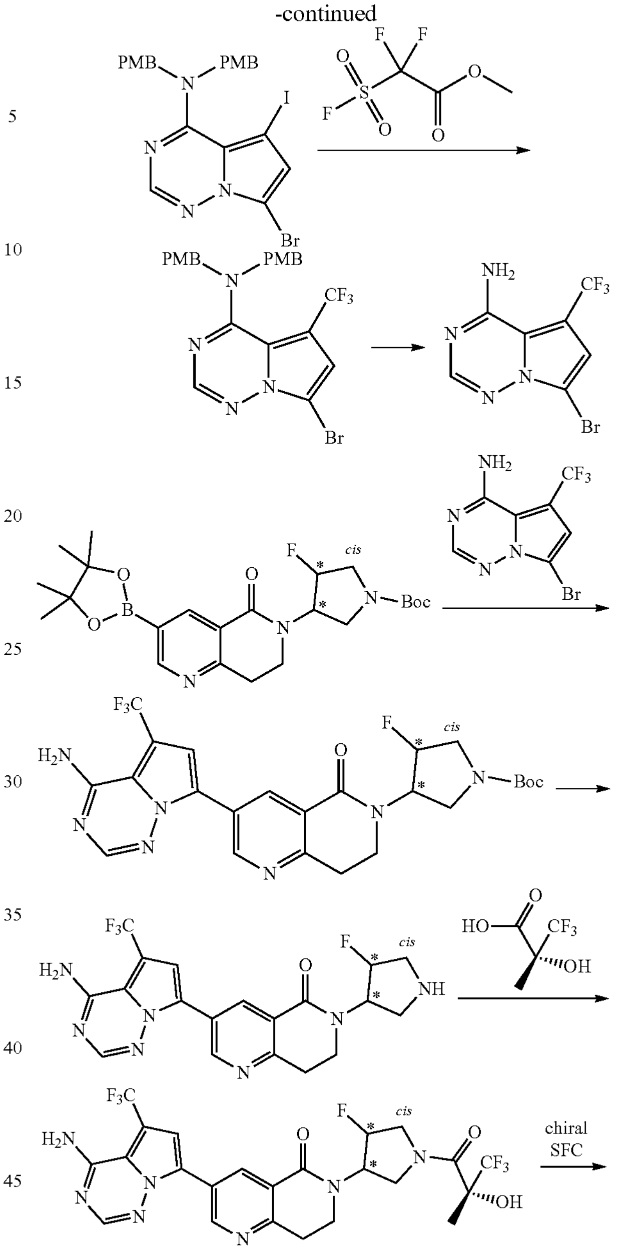
Z27
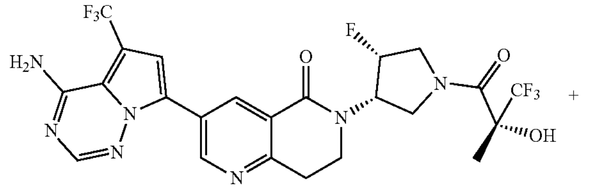
Z27-1
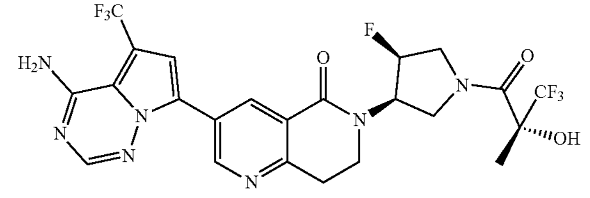
Z27-2

Step 1: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in 300 mL ethyl acetate and water (300 mL), separated, the organic phase was concentrated, purified on silica gel by automatic fast chromatography (EtOAc/PE 0-20%) to obtain methyl 5-bromo-2-vinylnicotinate (5.186 g, Y: 55%). ES-API: $[M+H]^+$=242.1.

Step 2: Preparation of tert-butyl cis-3-(3-bromo-5-oxo-7,8-dihydro-1,6-naphthyridin-6(5H)-yl)-4-fluoropyrrolidine-1-carboxylate: methyl 5-bromo-2-vinylnicotinate (842 mg, 3.494 mmol) and tert-butyl cis-3-amino-4-fluoropyrrolidine-1-carboxylate (2.138 g, 10.481 mmol) were mixed in DMA (10 mL) in a microwave bottle. The reaction was subjected to microwave radiation at 180° C. for 1.5 hours, cooled to room temperature, the reaction mixture was added in ethyl acetate (35 mL), then the mixture was washed with water (20 mL*3) and saturated sodium chloride solution (15 mL*3), the combined organic layers were concentrated, purified on silica gel by automatic fast chromatography (EtOAc/PE 0-50%) to obtain tert-butyl cis-3-(3-bromo-5-oxo-7,8-dihydro-1,6-naphthyridin-6(5H)-yl)-4-fluoropyrrolidine-1-carboxylate (461 mg, Y: 32%). ES-API: $[M+H]^+$=414.1.

Step 3: Preparation of tert-butyl cis-3-fluoro-4-(5-oxo-3-(4,4,5,5-tetramethyl-1,3,2-dioxaborinan-2-yl)-7,8-dihydro-1,6-naphthyridin-6(5H)-yl)pyrrolidine-1-carboxylate: tert-butyl cis-3-(3-bromo-5-oxo-7,8-dihydro-1,6-naphthyridin-6(5H)-yl)-4-fluoropyrrolidine-1-carboxylate (230 mg, 0.557 mmol), bis(pinacolato)diboron (285 mg, 1.114 mmol), potassium acetate (136 mg, 1.393 mmol), [1,1'-bis(diphenylphosphino)ferrocene]dichloropalladium(II) (20 mg, 0.028 mmol) and 1,4-dioxane (10 mL) were added into a 50 mL round bottom flask, the mixture was replaced with nitrogen for three times, reacted at 95° C. overnight, cooled to room temperature, filtered with suction, the filter cake was washed with ethyl acetate for three times to obtain the filtrate, the filtrate was concentrated to obtain crude product tert-butyl cis-3-fluoro-4-(5-oxo-3-(4,4,5,5-tetramethyl-1,3,2-dioxaborinan-2-yl)-7,8-dihydro-1,6-naphthyridin-6(5H)-yl)pyrrolidine-1-carboxylate (257 mg, Y: 99%). ES-API: $[M+H]^+$=462.2.

Step 4: Preparation of 7-bromo-N,N-bis(4-methoxybenzyl)pyrrolo[2,1-f][1,2,4]triazin-4-amine: $Cs_2CO_3$ (3.827 g, 11.738 mmol) was added into a solution of 7-bromopyrrolo[2,1-f][1,2,4]triazin-4-amine (1 g, 4.695 mmol), 1-(chloromethyl)-4-methoxybenzene (1.618 g, 10.329 mmol) in DMF (25 mL), the reaction mixture was stirred at room temperature overnight. After the reaction was completed, the reaction mixture was added into $H_2O$ (60 mL), extracted with EtOAc (25*4 mL), the combined organic layers were washed with saturated sodium chloride solution (25 mL*3), dried, concentrated, then the residue was purified on silica gel by automatic fast chromatography to obtain 7-bromo-N,N-bis(4-methoxybenzyl)pyrrolo[2,1-f][1,2,4]triazin-4-amine (1.473 g, Y: 69%). ES-API: $[M+H]^+$=453.1.

Step 5: Preparation of 7-bromo-5-iodo-N,N-bis(4-methoxybenzyl)pyrrolo[2,1-f][1,2,4]triazin-4-amine: three drops of TFA were added into a solution of 7-bromo-N,N-bis(4-methoxybenzyl)pyrrolo[2,1-f][1,2,4]triazin-4-amine (1.473 g, 3.249 mmol) and NIS (731 mg, 3.249 mmol) in DMF (7 mL), the reaction mixture was stirred at room temperature overnight. After the reaction was completed, the reaction mixture was poured into ice water and 1.5 M $Na_2HPO_4$ (1:1) (1.5 mL), yellow insoluble substance was precipitate, filtered, the filter cake was beaten with ethyl acetate, then beaten with methanol to obtain white powder product 7-bromo-5-iodo-N,N-bis(4-methoxybenzyl)pyrrolo[2,1-f][1,2,4]triazin-4-amine (1.88 g, Y: 99%). ES-API: $[M+H]^+$=579.0.

Step 6: Preparation of 7-bromo-N,N-bis(4-methoxybenzyl)-5-(trifluoromethyl)pyrrolo[2,1-f][1,2,4]triazin-4-amine: under the protection of nitrogen, 7-bromo-5-iodo-N,N-bis(4-methoxybenzyl)pyrrolo[2,1-f][1,2,4]triazin-4-amine (600 mg, 1.036 mmol), CuI (216 mg, 1.14 mmol), DMF (9 mL) were added into a 10 mL pressure bottle successively, the mixture was replaced with nitrogen for three times, methyl 2,2-difluoro-2-(fluorosulfonyl)acetate (795 mg, 4.143 mmol) was added to the reaction mixture, the pressure bottle was placed in oil bath pot at 80° C. for three hours. After the reaction was completed, the mixture was cooled to room temperature, insoluble substance was filtered, the filter cake was washed with ethyl acetate for three times, concentrated to obtain 7-bromo-N,N-bis(4-methoxybenzyl)-5-(trifluoromethyl)pyrrolo[2,1-f][1,2,4]triazin-4-amine (720 mg, Y: 99%). ES-API: $[M+H]^+$=521.0.

Step 7: Preparation of 7-bromo-5-(trifluoromethyl)pyrrolo[2,1-f][1,2,4]triazin-4-amine: 7-bromo-N,N-bis(4-methoxybenzyl)-5-(trifluoromethyl)pyrrolo[2,1-f][1,2,4]triazin-4-amine (720 mg, 1.385 mmol) and TFA (6 mL) were put in a sealed tube (20 mL), the reaction mixture was heated and reacted at 110° C. in oil bath pot for four hours. After the reaction was completed, the mixture was cooled to room temperature. The concentrated residue was purified on silica gel by automatic fast chromatography to obtain 7-bromo-5-(trifluoromethyl)pyrrolo[2,1-f][1,2,4]triazin-4-amine (233 mg, Y: 60%). ES-API: $[M+H]^+$=281.0.

Step 8: Preparation of tert-butyl cis-3-(3-(4-amino-5-(trifluoromethyl)pyrrolo[2,1-f][1,2,4]triazin-7-yl)-5-oxo-7,8-dihydro-1,6-naphthyridin-6(5H)-yl)-4-fluoropyrrolidine-1-carboxylate: under the protection of nitrogen, 7-bromo-5-(trifluoromethyl)pyrrolo[2,1-f][1,2,4]triazin-4-amine (200 mg, 0.714 mmol), tert-butyl cis-3-fluoro-4-(5-oxo-3-(4,4,5,5-tetramethyl-1,3,2-dioxaborinan-2-yl)-7,8-dihydro-1,6-naphthyridin-6(5H)-yl)pyrrolidine-1-carboxylate (567 mg, 1.230 mmol), sodium carbonate (151 mg, 1.428 mmol), 1,1'-bis(diphenylphosphino)ferrocene-palladium(II)dichloride dichloromethane complex (30 mg, 0.0357 mmol) were dissolved in dioxane (20 mL) and $H_2O$ (4 mL), the mixture was replaced with nitrogen for three times, the reaction mixture was heated and reacted at 95° C. in oil bath pot for three hours. After the reaction was completed, the mixture was cooled to room temperature, concentrated, the residue was purified on silica gel by automatic fast chromatography to obtain crude product tert-butyl cis-3-(3-(4-amino-5-(trifluoromethyl)pyrrolo[2,1-f][1,2,4]triazin-7-yl)-5-oxo-7,8-dihydro-1,6-naphthyridin-6(5H)-yl)-4-fluoropyrrolidine-1-carboxylate. ES-API: $[M+H]^+$=536.2.

Step 9: Preparation of cis-3-(4-amino-5-(trifluoromethyl)pyrrolo[2,1-f][1,2,4]triazin-7-yl)-6-(4-fluoropyrrolidin-3-yl)-7,8-dihydro-1,6-naphthyridin-5(6H)-one: TFA(1 mL, 12.682 mmol) was added to a solution of tert-butyl cis-3-(3-(4-amino-5-(trifluoromethyl)pyrrolo[2,1-f][1,2,4]triazin-7-yl)-5-oxo-7,8-dihydro-1,6-naphthyridin-6(5H)-yl)-4-fluoropyrrolidine-1-carboxylate (295 mg, 0.551 mmol) in DCM (5 mL), stirred at room temperature for three hours. After the reaction was completed, the mixture was concentrated to obtain crude product cis-3-(4-amino-5-(trifluoromethyl)pyrrolo[2,1-f][1,2,4]triazin-7-yl)-6-(4-fluoropyrrolidin-3-yl)-7,8-dihydro-1,6-naphthyridin-5(6H)-one (306 mg, Y: 99%)). ES-API: $[M+H]^+$=436.1.

Step 10: Preparation of cis-3-(4-amino-5-(trifluoromethyl)pyrrolo[2,1-f][1,2,4]triazin-7-yl)-6-(4-fluoro-1-((R)-3,3,3-trifluoro-2-hydroxy-2-methylpropionyl)pyrrolidin-3-yl)-7,8-dihydro-1,6-naphthyridin-5(6H)-one: (R)-3,3,3-trifluoro-2-hydroxy-2-methylpropionic acid (54 mg, 0.345 mmol), cis-3-(4-amino-5-(trifluoromethyl)pyrrolo[2,1-f][1,2,4]triazin-7-yl)-6-(4-fluoropyrrolidin-3-yl)-7,8-dihydro-1,6-naphthyridin-5(6H)-one (150 mg, 0.345 mmol), PyBOP (180 mg, 0.345 mmol), DIPEA (136 mg, 1.035 mmol) and DMF (5 mL) were added into a 25 mL round bottom flask, the mixture was and reacted at room temperature overnight. After the reaction was completed, the reaction mixture was purified by alkaline HPLC to obtain white solid product: cis-3-(4-amino-5-(trifluoromethyl)pyrrolo[2,1-f][1,2,4]triazin-7-yl)-6-(4-fluoro-1-((R)-3,3,3-trifluoro-2-hydroxy-2-methylpropionyl)pyrrolidin-3-yl)-7,8-dihydro-1,6-naphthyridin-5(6H)-one (Z27, 68 mg, Y:34%). ES-API: $[M+H]^+$=576.1. $^1$H NMR (400 MHz, DMSO-d6) δ 9.23-9.22 (m, 1H), 8.97-8.96 (m, 1H), 8.21 (s, 1H), 7.76 (s, 1H), 7.11-7.07 (m, 1H), 5.45-5.19 (m, 2H), 4.44-4.22 (m, 1H), 4.13-3.97 (m, 1H), 3.83-3.70 (m, 4H), 3.19-3.15 (m, 2H), 1.58-1.55 (m, 3H).

Step 11: Separation of 3-(4-amino-5-(trifluoromethyl)pyrrolo[2,1-f][1,2,4]triazin-7-yl)-6-(4-fluoro-1-((R)-3,3,3-trifluoro-2-hydroxy-2-methylpropionyl)pyrrolidin-3-yl)-7,8-dihydro-1,6-naphthyridin-5(6H)-one: the compound Z27 obtained in the above step was chiral separated with SFC (column: Chiralpak IG 250 mm*4.6 mm 5 um; mobile phase: CAN/IPA=70:30; flow rate: 1 mL/min; column temperature: room temperature) to obtain following two compounds with different configurations:

a compound with retention time of 4.5 min was collected: the structure of which was arbitrarily defined as 3-(4-amino-5-(trifluoromethyl)pyrrolo[2,1-f][1,2,4]triazin-7-yl)-6-(((3S,4R)-4-fluoro-1-((R)-3,3,3-trifluoro-2-hydroxy-2-methylpropionyl)pyrrolidin-3-yl)-7,8-dihydro-1,6-naphthyridin-5(6H)-one (Z27-1, 20 mg, Y: 20%), ES-API: $[M+H]^+$=576.2;

a compound with retention time of 8.1 min was collected: the structure of which was arbitrarily defined as 3-(4-amino-5-(trifluoromethyl)pyrrolo[2,1-f][1,2,4]triazin-7-yl)-6-(((3R,4S)-4-fluoro-1-((R)-3,3,3-trifluoro-2-hydroxy-2-methylpropionyl)pyrrolidin-3-yl)-7,8-dihydro-1,6-naphthyridin-5(6H)-one (Z27-2, 19.6 mg, Y: 20%), ES-API: $[M+H]^+$=576.1. $^1$H NMR (400 MHz, DMSO-d6) δ 9.22-9.21 (m, 1H), 8.97-8.95 (m, 1H), 8.21 (s, 1H), 7.76 (s, 1H), 7.10 (d, J=10.8 Hz, 1H), 5.43-5.12 (m, 2H), 4.43-4.26 (m, 1H), 4.12-3.96 (m, 1H), 3.87-3.65 (m, 4H), 3.27-3.10 (m, 2H), 1.56 (d, J=9.6 Hz, 3H).

Example 28: Preparation of N-(6-(5-oxo-6-((3-((tetrahydro-2H-pyran-4-yl)oxy)pyridyl-2-yl)methyl)-5,6,7,8-tetrahydro-1,6-naphthyridin-3-yl)imidazo[1,2-b]pyridazin-2-yl)acetamide (Z28)

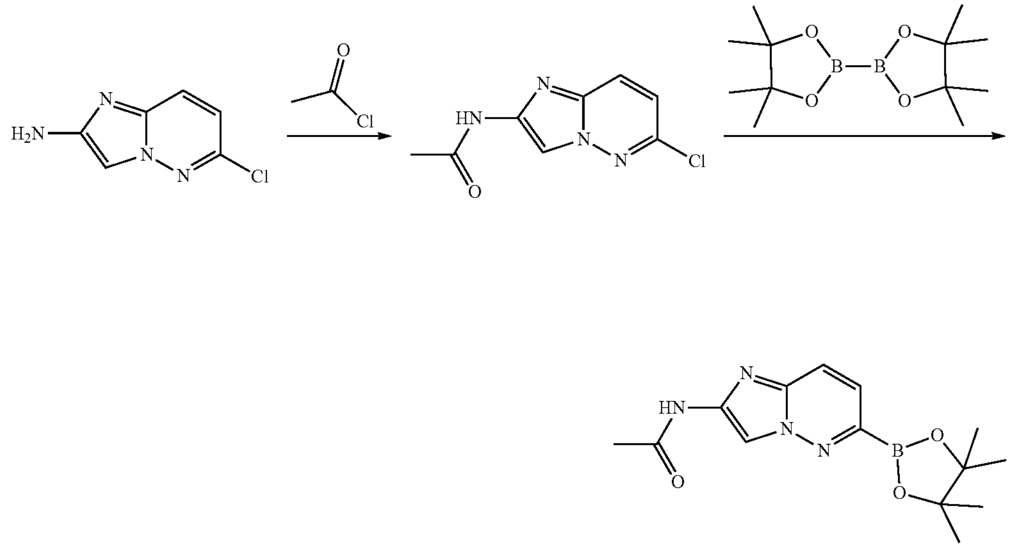

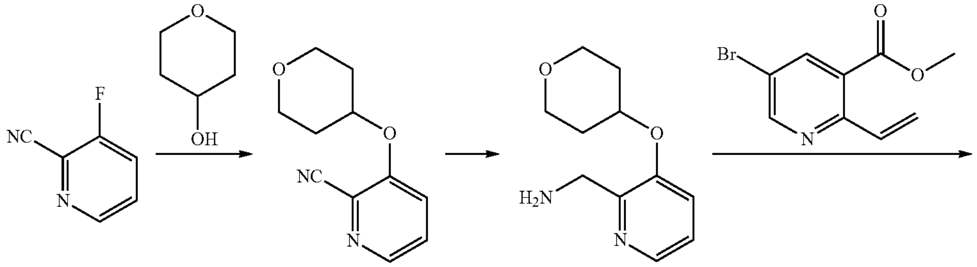

-continued

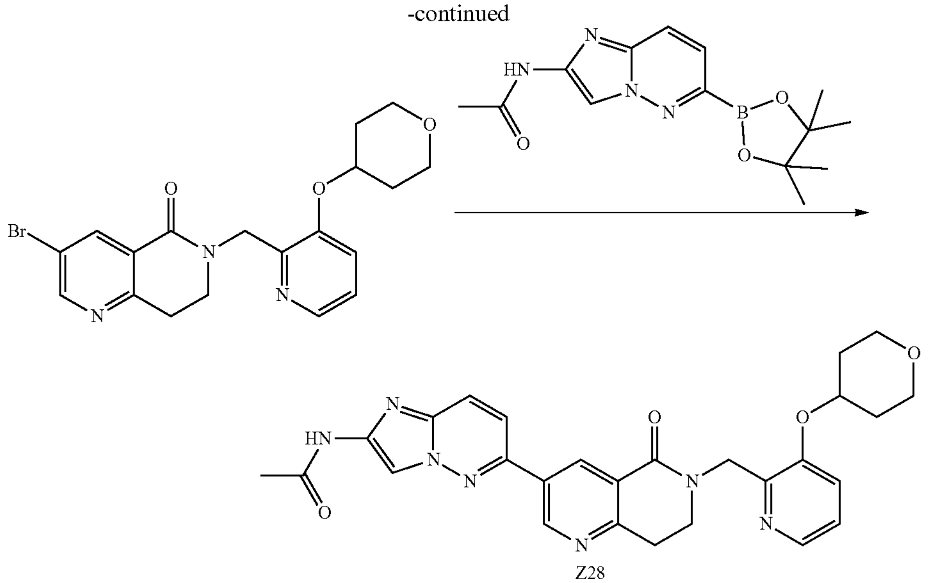

Z28

Step 1: Preparation of N-(6-chloroimidazo[1,2-b]pyridazin-2-yl)acetamide: acetyl chloride (512 mg, 6.525 mmol) was slowly added into a solution of 2-amino-6-chloroimidazo[1,2-b]pyridazine (1 g, 5.932 mmol) in N,N-dimethylacetamide (20 mL), the reaction mixture was stirred at room temperature for one hour. LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide (1.15 g, Y: 92%). ES-API: $[M+H]^+$=211.0.

Step 2: Preparation of N-(6-(4,4,5,5-tetramethyl-1,3,2-dioxaborolan-2-yl)imidazo[1,2-b]pyridazin-2-yl)acetamide: N-(6-chloroimidazo[1,2-b]pyridazin-2-yl)acetamide (1.15 g, 5.46 mmol), bis(pinacolato)diboron (1.66 mg, 6.55 mmol), potassium acetate (1.34 g, 13.65 mmol), [1,1'-bis(diphenylphosphino)ferrocene]dichloropalladium(II) (400 mg, 0.546 mmol) and 1,4-dioxane (40 mL) were added into a 100 mL round bottom flask, the mixture was replaced with nitrogen for three times, reacted at 98° C. overnight, cooled to room temperature, filtered with suction, the filter cake was washed with ethyl acetate for three times to obtain the filtrate, the filtrate was concentrated to obtain crude product N-(6-(4,4,5,5-tetramethyl-1,3,2-dioxaborolan-2-yl)imidazo[1,2-b]pyridazin-2-yl)acetamide (1.201 g, Y: 99%). ES-API: $[M+H]^+$=221.0.

Step 3: Preparation of 3-((tetrahydro-2H-pyran-4-yl)oxy)pyridinoline: under ice water bath, NaH (655 mg, 16.380 mmol) was added into a solution of tetrahydro-2H-pyran-4-ol (1.253 g, 12.285 mmol) in THF (60 mL) in batches, the reaction mixture was stirred at 0° C. for one hour. Then 3-fluoropicolinonitrile (1 g, 8.19 mmol) was added, the reaction mixture was stirred at room temperature for four hours. After the reaction was completed, water (20 mL) was added for quenching the reaction, then the mixture was extracted with EtOAc (15 mL*3), the combined organic phases were washed with saturated sodium chloride solution (15 mL*3), concentrated, purified on silica gel by automatic fast chromatography to obtain crude product 3-((tetrahydro-2H-pyran-4-yl)oxy)pyridinoline (1.96 g, Y: 100%). ES-API: $[M+H]^+$=205.1.

Step 4: Preparation of (3-((tetrahydro-2H-pyran-4-yl)oxy]pyridyl-2-yl)methylamine: Raney-Ni (200 mg) was added into a solution of 3-((tetrahydro-2H-pyran-4-yl)oxy)pyridinoline (1.96 g, 9.608 mmol) in EtOH (30 mL), the reaction mixture was stirred at room temperature under the protection of hydrogen overnight. LCMS showed the reaction was completed, filtered, concentrated to obtain light yellow transparent liquid (3-((tetrahydro-2H-pyran-4-yl)oxy]pyridyl-2-yl)methylamine (881 mg, Y: 44%). ES-API: $[M+H]^+$=209.1.

Step 5: Preparation of 3-bromo-6-(((3-((tetrahydro-2H-pyran-4-yl)oxy)pyridyl-2-yl)methyl)-7,8-dihydro-1,6-naphthyridin-5(6H)-one: methyl 5-bromo-2-vinylnicotinate (100 mg, 0.415 mmol) and (3-((tetrahydro-2H-pyran-4-yl)oxy]pyridyl-2-yl)methylamine (173 mg, 0.83 mmol) were mixed in DMA (3 mL) in a microwave bottle. The reaction was subjected to microwave radiation at 180° C. for one hour, cooled to room temperature, the reaction mixture was added into 15 mL ethyl acetate, then the mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(((3-((tetrahydro-2H-pyran-4-yl)oxy)pyridyl-2-yl)methyl)-7,8-dihydro-1,6-naphthyridin-5(6H)-one (176 mg, Y: 57%). ES-API: $[M+H]^+$=418.0.

Step 6: Preparation of N-(6-(5-oxo-6-((3-((tetrahydro-2H-pyran-4-yl)oxy)pyridyl-2-yl)methyl)-5,6,7,8-tetrahydro-1,6-naphthyridin-3-yl)imidazo[1,2-b]pyridazin-2-yl)acetamide: under the protection of nitrogen, N-(6-(4,4,5,5-tetramethyl-1,3,2-dioxaborolan-2-yl)imidazo[1,2-b]pyridazin-2-yl)acetamide (72 mg, 0.240 mmol), 3-bromo-6-(((3-((tetrahydro-2H-pyran-4-yl)oxy)pyridyl-2-yl)methyl)-7,8-dihydro-1,6-naphthyridin-5(6H)-one (50 mg, 0.120 mmol), sodium carbonate (32 mg, 0.300 mmol), 1,1'-bis(diphenylphosphino)ferrocene-palladium(II)dichloride dichloromethane complex (5 mg, 0.006 mmol) were dissolved in dioxane (5 mL) and $H_2O$ (1 mL), the mixture was replaced with nitrogen for three times, the reaction mixture was stirred at 95° C. in oil bath for 2 hours, cooled to room temperature, concentrated, the crude product was purified by alkaline HPLC to obtain light yellow solid N-(6-(5-oxo-6-

((3-((tetrahydro-2H-pyran-4-yl)oxy)pyridyl-2-yl)methyl)-5,6,7,8-tetrahydro-1,6-naphthyridin-3-yl)imidazo[1,2-b]pyridazin-2-yl)acetamide (Z28, 33.95 mg, Y: 82%). ES-API: $[M+H]^+$=514.2. $^1$H NMR (400 MHz, DMSO-d6) δ 10.95 (s, 1H), 9.29 (d, J=1.6 Hz, 1H), 8.76 (d, J=2.0 Hz, 1H), 8.35 (s, 1H), 8.11 (d, J=7.6 Hz, 1H), 8.06 (dd, J1=1.2 Hz, J2=4.0 Hz, 1H), 7.91 (d, J=7.6 Hz, 1H), 7.52 (d, J=6.4 Hz, 1H), 7.28-7.26 (m, 1H), 4.91 (s, 2H), 4.75-4.70 (m, 1H), 3.88-3.84 (m, 2H), 3.77 (t, J1=5.6 Hz, J2=10.8 Hz, 2H), 3.54-3.49 (m, 2H), 3.24 (t, J1=5.2 Hz, J2=10.8 Hz, 2H), 2.12 (s, 3H), 1.99-1.96 (m, 2H), 1.68-1.61 (m, 2H).

Example 29 cis-3-(4-amino-5-methylpyrrolo[2,1-f][1,2,4]triazin-7-yl)-6-(4-fluoro-1-(2-hydroxy-2-methylpropionyl)pyrrolidinepyridyl-3-yl)-7,8-dihydro-1,6-naphthyridin-5(6H-one (Z29)

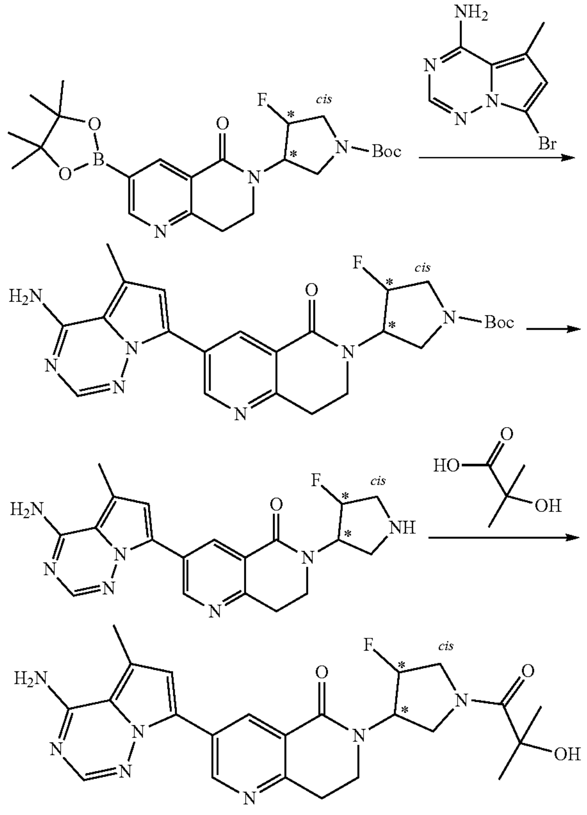

Z29

Step 1: under the protection of nitrogen, 7-bromo-5-methylpyrrolo[2,1-f][1,2,4]triazin-4-amine (320 mg, 1.416 mmol), tert-butyl cis-3-fluoro-4-(5-oxo-3-(4,4,5,5-tetramethyl-1,3,2-dioxaborinan-2-yl)-7,8-dihydro-1,6-naphthyridin-6(5H)-yl)pyrrolidin-1-carboxylate (referring to the preparation method in Example 27, 1304 mg, 2.832 mmol), sodium carbonate (375 mg, 3.540 mmol), 1,1'-bis(diphenylphosphino)ferrocene-palladium(II)dichloride dichloromethane complex (58 mg, 0.0708 mmol) were dissolved in dioxane (15 mL) and $H_2O$ (3 mL), the mixture was replaced with nitrogen for three times, the reaction mixture was heated and reacted at 95° C. in oil bath for two hours. After the reaction was completed, the mixture was cooled to room temperature, concentrated, the residue was purified on silica gel by automatic fast chromatography to obtain tert-butyl cis-3-(3-(4-amino-5-methylpyrrolo[2,1-f][1,2,4]triazin-7-yl)-5-oxo-7,8-dihydro-1,6-naphthyridin-6(5H)-yl)-4-fluoropyrrolidine-1-carboxylate (490 mg, Y: 72%). ES-API: $[M+H]^+$=482.2.

Step 5: TFA (1.822 mL, 23.43 mmol) was added into a solution of tert-butyl cis-3-(3-(4-amino-5-methylpyrrolo[2,1-f][1,2,4]triazin-7-yl)-5-oxo-7,8-dihydro-1,6-naphthyridin-6(5H)-yl)-4-fluoropyrrolidine-1-carboxylate (490 mg, 1.019 mmol) in DCM (10 mL), stirred at room temperature for three hours. After the reaction was completed, concentrated to obtain crude product cis-3-(4-amino-5-methylpyrrolo[2,1-f][1,2,4]triazin-7-yl)-6-(4-fluoropyrrolidin-3-yl)-7,8-dihydro-1,6-naphthyridin-5(6H)-one (388 mg, Y: 100%)). ES-API: $[M+H]^+$=382.1.

Step 6: 2-Hydroxy-2-methylpropionic acid (21 mg, 0.210 mmol), cis-3-(4-amino-5-methylpyrrolo[2,1-f][1,2,4]triazin-7-yl)-6-(4-fluoropyrrolidin-3-yl)-7,8-dihydro-1,6-naphthyridin-5(6H)-one (80 mg, 0.210 mmol), PyBOP (109 mg, 0.210 mmol), DIPEA (81 mg, 0.630 mmol) and DMF (2 mL) were added into a 25 mL round bottom flask, and reacted at room temperature overnight. After the reaction was completed, the reaction mixture was purified by alkaline HPLC to obtain white solid cis-3-(4-amino-5-methylpyrrolo[2,1-f][1,2,4]triazin-7-yl)-6-(4-fluoro-1-(2-Hydroxy-2-methylpropionyl)pyrrolidinepyridyl-3-yl)-7,8-dihydro-1,6-naphthyridin-5(6H)-one (Z29, 46.7 mg, Y: 48%). ES-API: $[M+H]^+$=468.2. $^1$H NMR (400 MHz, DMSO-d6) δ 9.19 (s, 1H), 8.95 (s, 1H), 7.88 (s, 1H), 7.35-7.06 (m, 3H), 5.41-5.11 (m, 3H), 4.40-4.29 (m, 1H), 4.06-3.96 (m, 1H), 3.78-3.62 (m, 4H), 3.18-3.07 (m, 2H), 2.54 (s, 3H), 1.35-1.32 (m, 6H).

Example 30 Cis-3-(4-amino-5-methylpyrrolo[2,1-f][1,2,4]triazin-7-yl)-6-(4-fluoro-1-((R)-3,3,3-trifluoro-2-hydroxy-2-methylpropionyl)pyrrolidin-3-yl)-7,8-dihydro-1,6-naphthyridin-5(6H)-one (Z30)

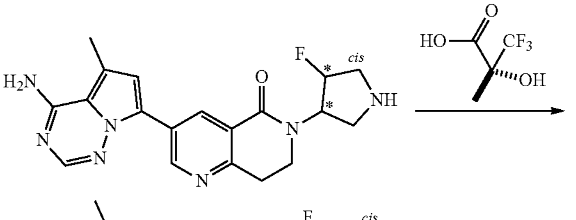

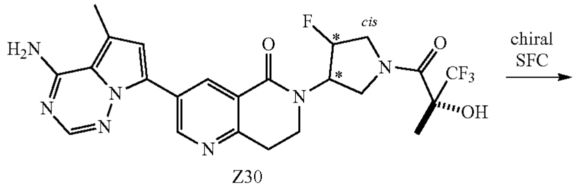

Z30

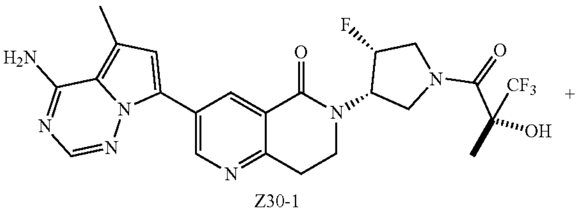

Z30-1

-continued

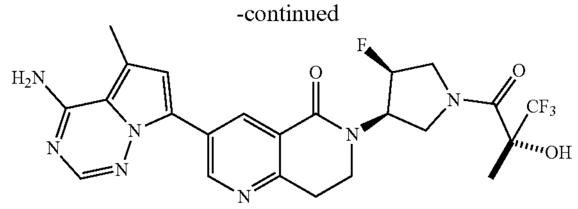

Z30-2

Step 6: (R)-3,3,3-trifluoro-2-hydroxy-2-methylpropionic acid (33 mg, 0.210 mmol), cis-3-(4-amino-5-methylpyrrolo[2,1-J][1,2,4]triazin-7-yl)-6-(4-fluoropyrrolidin-3-yl)-7,8-dihydro-1,6-naphthyridin-5(6H)-one (referring to the preparation method in Example 29, 80 mg, 0.210 mmol), PyBOP (109 mg, 0.210 mmol), DIPEA (81 mg, 0.630 mmol) and DMF (2 mL) were added into a 25 mL round bottom flask, and reacted at room temperature overnight. After the reaction was completed, the reaction mixture was purified by alkaline HPLC to obtain white solid: cis-3-(4-amino-5-methylpyrrolo[2,1-f][1,2,4]triazin-7-yl)-6-(4-fluoro-1-((R)-3,3,3-trifluoro-2-hydroxy-2-methylpropionyl)pyrrolidin-3-yl)-7,8-dihydro-1,6-naphthyridin-5(6H)-one (Z30, 54.5 mg, Y: 50%). ES-API: $[M+H]^+=522.2$. $^1H$ NMR (400 MHz, DMSO-d6) δ9.19 (t, J=2.0 Hz, 1H), 8.95-8.93 (m, 1H), 7.88 (s, 1H), 7.11-7.07 (m, 1H), 7.05 (s, 1H), 5.44-5.17 (m, 2H), 4.42-4.22 (m, 1H), 4.08-3.96 (m, 1H), 3.79-3.66 (m, 4H), 3.16-3.09 (m, 2H), 2.53 (s, 3H), 1.57-1.54 (m, 3H).

Step 7: The compound Z30 obtained above was chiral separated with SFC (column: Daicel CHIRALPAK IG 250*20 mm, 5 μm; mobile phase: ACN/IPA=70:30 (V/V); flow rate: 15 mL/min; injection volume: 400 μL; column temperature: room temperature; running time: 32 min) to obtain two compounds with different configurations:

Compound Z30-1 (retention time: 7.440 min): the structure of which was arbitrarily defined as 3-(4-amino-5-methylpyrrolo[2,1-f][1,2,4]triazin-7-yl)-6-((3S, 4R)-4-fluoro-1-((R)-3,3,3-trifluoro-2-hydroxy-2-methylpropionyl)pyrrolidin-3-yl)-7,8-dihydro-1,6-naphthyridin-5(61)-one (19.15 mg). ES-API: $[M+H]^+=522.2$;

Compound Z30-2 (retention time: 11.628 min): the structure of which was arbitrarily defined as 3-(4-amino-5-methylpyrrolo[2,1-f][1,2,4]triazin-7-yl)-6-((3R, 4S)-4-fluoro-1-((R)-3,3,3-trifluoro-2-hydroxy-2-methylpropionyl)pyrrolidin-3-yl)-7,8-dihydro-1,6-naphthyridin-5(6H)-one (10.33 mg). ES-API: $[M+H]^+=522.2$.

Example 31 3-(4-aminopyrrolo[2,1-f][1,2,4]triazin-7-yl)-6-(4-fluoro-1-((R)-3,3,3-trifluoro-2-hydroxy-2-methylpropionyl)pyrrolidin-3-yl)-7,8-dihydro-1,6-naphthyridin-5(6H-one (Z31)

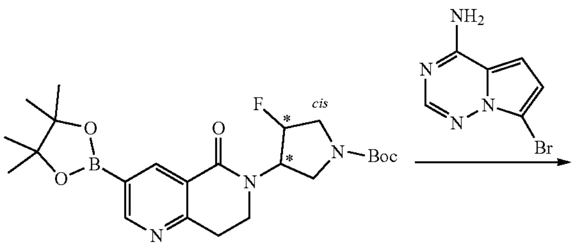

-continued

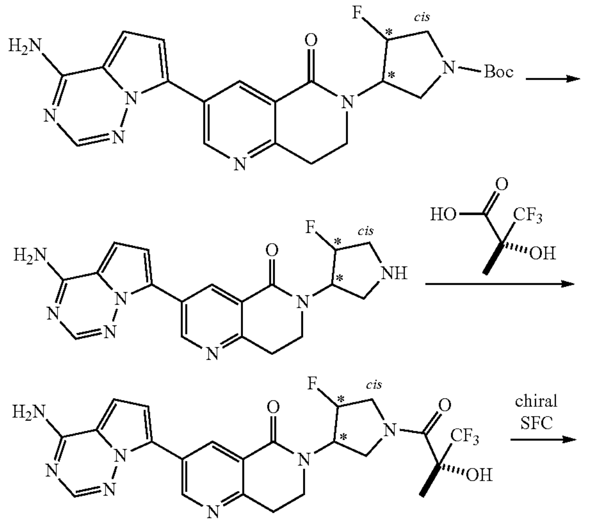

Z31

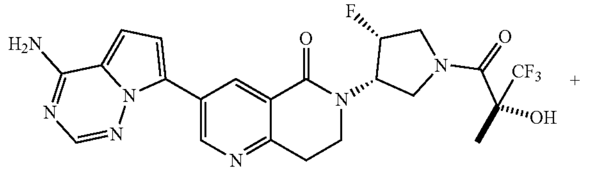

Z31-1

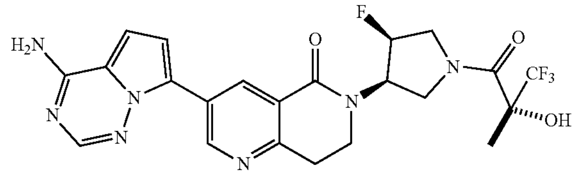

Z31-2

Step 1: Under the protection of nitrogen, 7-bromopyrrolo[2,1-f][1,2,4]triazin-4-amine (150 mg, 0.708 mmol), tert-butyl cis-3-fluoro-4-(5-oxo-3-(4,4,5,5-tetramethyl-1,3,2-dioxaborinan-2-yl)-7,8-dihydro-1,6-naphthyridin-6(5H)-yl)pyrrolidin-1-carboxylate (refers to preparation method in Example 27, 652 mg, 1.416 mmol), sodium carbonate (188 mg, 1.770 mmol), 1,1'-bis(diphenylphosphino)ferrocene-palladium(II)dichloride dichloromethane complex (29 mg, 0.0354 mmol) were dissolved in dioxane (10 mL) and $H_2O$ (2 mL), the mixture was replaced with nitrogen for three times, the reaction mixture heated and reacted at 95° C. in oil bath for two hours. After the reaction was completed, the mixture was cooled to room temperature, concentrated, the residue was purified on silica gel by automatic fast chromatography to obtain crude product tert-butyl cis-3-(3-(4-aminopyrrolo[2,1-f][1,2,4]triazin-7-yl)-5-oxo-7,8-dihydro-1,6-naphthyridin-6(5H)-yl)-4-fluoropyrrolidine-1-carboxylate (430 mg, Y: 99%). ES-API: $[M+H]^*=468.2$.

Step 2: TFA(1.67 mL, 21.183 mmol) was added into a solution of tert-butyl cis-3-(3-(4-aminopyrrolo[2,1-f][1,2,4]triazin-7-yl)-5-oxo-7,8-dihydro-1,6-naphthyridin-6(5H)-yl)-4-fluoropyrrolidin-1-carboxylate (430 mg, 0.921 mmol) in DCM (9 mL), stirred at room temperature for three hours, after the reaction was completed, the mixture was concentrated to obtain crude product, purified by combiflash to obtain cis-3-(4-aminopyrrolo[2,1-f][1,2,4]triazin-7-yl)-6-(4-fluoropyrrolidin-3-yl)-7,8-dihydro-1,6-naphthyridin-5(6H)-one (256 mg, Y: 76%)). ES-API: $[M+H]^+=368.1$.

Step 3: (R)-3,3,3-trifluoro-2-hydroxy-2-methylpropionic Acid (34 mg, 0.218 mmol), cis-3-(4-aminopyrrolo[2,1-f][1,2,4]triazin-7-yl)-6-(4-fluoropyrrolidin-3-yl)-7,8-dihydro-1,6-naphthyridin-5(6H)-one (80 mg, 0.218 mmol), PyBOP (113 mg, 0.218 mmol), DIPEA (84 mg, 0.654 mmol) and DMF (3 mL) were added into a 25 mL round bottom flask, reacted at room temperature overnight. After the reaction was completed, the reaction mixture was purified by alkaline HPLC to obtain white solid cis-3-(4-aminopyrrolo[2,1-f][1,2,4]triazin-7-yl)-6-(4-fluoro-1-((R)-3,3,3-trifluoro-2-hydroxy-2-methylpropionyl)pyrrolidin-3-yl)-7,8-dihydro-1,6-naphthyridin-5(6H)-one (Z31, 65.93 mg, Y:60%). ES-API: $[M+H]^+$=508.1. $^1H$ NMR (400 MHz, DMSO-d6) δ9.25-9.24 (m, 1H), 8.98-8.97 (m, 1H), 8.00 (s, 1H), 7.89 (bs, 2H), 7.24 (d, J=3.6 Hz, 1H), 7.11 (s, 1H), 7.06 (d, J=3.6 Hz, 1H), 5.45-5.18 (m, 2H), 4.44-4.23 (m, 1H), 4.11-3.97 (m, 1H), 3.83-3.67 (m, 4H), 3.21-3.07 (m, 2H), 1.58-1.55 (m, 3H).

Step 4: The compound 100 obtained above was chiral separated with SFC (column: Daicel CHIRALPAK IC 250*20 mm, 5 μm; mobile phase: Hex/EtOH=40:60 (V/V); flow rate: 15 mL/min; injection volume: 300 μL; column temperature: room temperature; running time: 26 min) to obtain two compounds with different configurations:

Compound Z31-1 (retention time: 10.683 min): the structure of which was arbitrarily defined as 3-(4-aminopyrrolo[2,1-f][1,2,4]triazin-7-yl)-6-(((3S, 4R)-4-fluoro-1-((R)-3,3,3-trifluoro-2-hydroxy-2-methylpropionyl)pyrrolidin-3-yl)-7,8-dihydro-1,6-naphthyridin-5(6H)-one (17.20 mg). ES-API: $[M+H]^+$=508.1.

Compound Z31-2 (retention time: 12.489 min): the structure of which was arbitrarily defined as 3-(4-aminopyrrolo[2,1-f][1,2,4]triazin-7-yl)-6-(((3R, 4S)-4-fluoro-1-((R)-3,3,3-trifluoro-2-hydroxy-2-methylpropionyl)pyrrolidin-3-yl)-7,8-dihydro-1,6-naphthyridin-5(6H)-one (18.85 mg). ES-API: $[M+H]^+$=508.1.

Example 32 Preparation of 3-(4-amino-5-(trifluoromethyl)pyrrolo[2,1-f][1,2,4]triazin-7-yl)-6-(((S)-1-((R)-3,3,3-trifluoro-2-hydroxy-2-methylpropionyl)pyrrolidin-3-yl)-7,8-dihydro-1,6-naphthyridin-5(6H)-one (Z32)

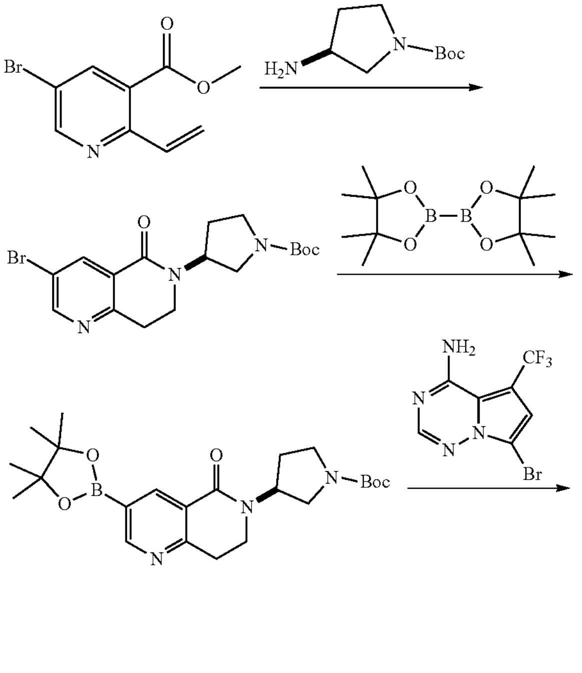

-continued

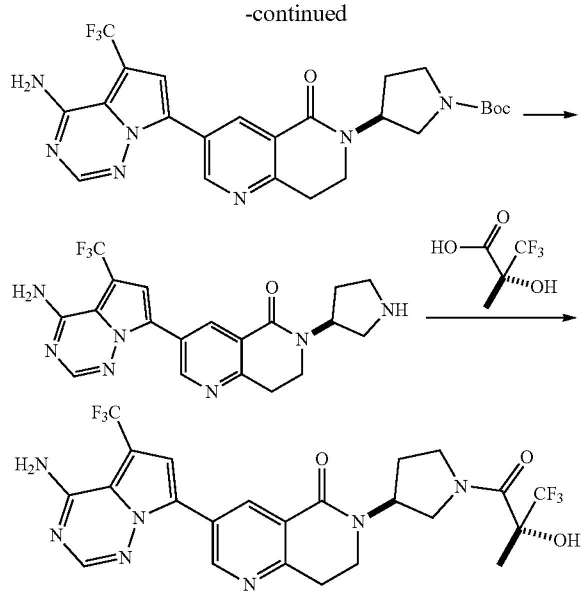

Z32

Step 1: Methyl 5-bromo-2-vinylnicotinate (544 mg, 2.248 mmol) and tert-butyl (S)-3-aminopyrrolidine-1-carboxylate (837 mg, 4.496 mmol) were mixed in DMA (6 mL) in a microwave bottle. The reaction was subjected to microwave radiation at 180° C. for 1.5 hours, cooled to room temperature, the reaction mixture was added into 15 mL ethyl acetate, then the mixture was washed with water (15 mL*3) and saturated sodium chloride solution (15 mL*3), the combined organic layers were concentrated, purified on silica gel by automatic fast chromatography (EtOAc/PE 0-50%) to obtain tert-butyl (S)-3-(3-bromo-5-oxo-7,8-dihydro-1,6-naphthyridin-6(5H)-yl)pyrrolidine-1-carboxylate (596 mg, Y: 67%). ES-API: $[M+H]^+$=396.1.

Step 2: Tert-butyl (S)-3-(3-bromo-5-oxo-7,8-dihydro-1,6-naphthyridin-6(5H)-yl)pyrrolidine-1-carboxylate (551 mg, 1.395 mmol), bis(pinacolato)diboron (714 mg, 2.790 mmol), potassium acetate (342 mg, 3.488 mmol), [1,1'-bis(diphenylphosphino)ferrocene]dichloropalladium(II) (51 mg, 0.070 mmol) and 1,4-dioxane (20 mL) were added into a 100 mL round bottom flask, the mixture was replaced with nitrogen for three times, and reacted at 95° C. overnight, cooled to room temperature, filtered with suction, the filter cake was washed with ethyl acetate for three times to obtain the filtrate, the filtrate was concentrated to obtain crude product tert-butyl (S)-3-(5-oxo-3-(4,4,5,5-tetramethyl-1,3,2-dioxaborolan-2-yl)-7,8-dihydro-1,6-naphthyridin-6(5H)-yl)pyrrolidine-1-carboxylate (667 mg, Y: 100%). ES-API: $[M+H]^+$=444.2.

Step 3: Under the protection of nitrogen, 7-bromo-5-(trifluoromethyl)pyrrolo[2,1-f][1,2,4]triazin-4-amine (281 mg, 1.004 mmol), tert-butyl (S)-3-(5-oxo-3-(4,4,5,5-tetramethyl-1,3,2-dioxaborolan-2-yl)-7,8-dihydro-1,6-naphthyridin-6(5H)-yl)pyrrolidine-1-carboxylate (667 mg, 1.506 mmol), sodium carbonate (266 mg, 2.510 mmol), 1,1'-bis(diphenylphosphino)ferrocene-palladium(II)dichloride dichloromethane complex (41 mg, 0.050 mmol) were dissolved in dioxane (20 mL) and $H_2O$ (4 mL), the mixture was replaced with nitrogen for three times, the reaction mixture was heated to 95° C. in oil bath for two hours. After the reaction was completed, the mixture was cooled to room temperature, concentrated, the crude product was purified on silica gel by automatic fast chromatography to obtain off-white solid tert-butyl (S)-3-(3-(4-amino-5-(trifluoromethyl)pyrrolo[2,1-f][1,2,4]triazin-7-yl)-5-oxo-7,8-dihydro-1,6-naphthyridin-6(5H)-yl)pyrrolidine-1-carboxylate (318 mg, Y: 61%). ES-API: $[M+H]^+$=518.2.

Step 4: TFA (1.11 mL, 14.147 mmol) was added into a solution of tert-butyl (S)-3-(3-(4-amino-5-(trifluoromethyl)pyrrolo[2,1-f][1,2,4]triazin-7-yl)-5-oxo-7,8-dihydro-1,6-naphthyridin-6(5H)-yl)pyrrolidine-1-carboxylate (318 mg, 0.615 mmol) in DCM (6 mL), stirred at room temperature for two hours. After the reaction was completed, the mixture was concentrated to obtain crude product (S)-3-(4-amino-5-(trifluoromethyl)pyrrolo[2,1-f][1,2,4]triazin-7-yl)-6-(pyrrolidin-3-yl)-7,8-dihydro-1,6-naphthyridin-5(6H)-one (241 mg, Y: 94%). ES-API: $[M+H]^+$=418.2.

Step 9: (R)-3,3,3-trifluoro-2-hydroxy-2-methylpropionic acid (30 mg, 0.192 mmol), (S)-3-(4-amino-5-(trifluoromethyl)pyrrolo[2,1-f][1,2,4]triazin-7-yl)-6-(pyrrolidin-3-yl)-7,8-dihydro-1,6-naphthyridin-5(6H)-one (80 mg, 0.192 mmol), PyBOP (100 mg, 0.192 mmol), DIPEA (74 mg, 0.576 mmol) and DMF (2.5 mL) were added into a 25 mL round bottom flask, reacted at room temperature overnight. After the reaction was completed, the reaction mixture was purified by alkaline HPLC to obtain white solid 3-(4-amino-5-(trifluoromethyl)pyrrolo[2,1-f][1,2,4]triazin-7-yl)-6-(((S)-1-((R)-3,3,3-trifluoro-2-hydroxy-2-methylpropionyl)pyrrolidin-3-yl)-7,8-dihydro-1,6-naphthyridin-5(6H)-one (Z32, 33.5 mg, Y:31%). ES-API: $[M+H]^+$=558.1. 1H NMR (400 MHz, DMSO-d6) δ 9.20-9.19 (m, 1H), 8.94-8.93 (m, 1H), 8.21 (s, 1H), 7.75 (s, 1H), 6.97 (s, 1H), 5.16-5.12 (m, 1H), 4.16-4.12 (m, 1H), 3.77-3.70 (m, 1H), 3.67-3.61 (m, 3H), 3.49-3.42 (m, 1H), 3.18-3.15 (m, 2H), 2.14-2.02 (m, 2H), 1.53 (s, 3H).

Example 33: Preparation of cis-3-(4-amino-5-(trifluoromethyl)pyrrolo[2,1-f][1,2,4]triazin-7-yl)-6-(4-fluoro-1-(2-hydroxy-2-methylpropionyl)pyrrolidin-3-yl)-7,8-dihydro-1,6-naphthyridin-5(6H)-one (Z33)

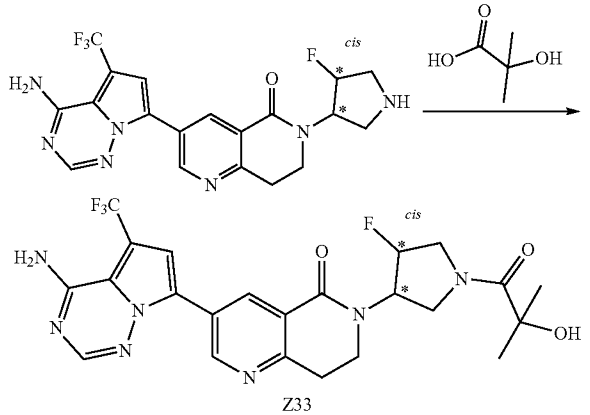

Z33

2-Hydroxy-2-methylpropionic acid (12 mg, 0.115 mmol), cis-3-(4-amino-5-(trifluoromethyl)pyrrolo[2,1-f][1,2,4]triazin-7-yl)-6-(4-fluoropyrrolidin-3-yl)-7,8-dihydro-1,6-naphthyridin-5(6H)-one (referring to the preparation method in Example 27, 50 mg, 0.115 mmol), PyBOP (60 mg, 0.115 mmol), DIPEA (45 mg, 0.345 mmol) and DMF (2 mL) were added into a 25 mL round bottom flask, and reacted at room temperature overnight. After the reaction was completed, the reaction mixture was purified by alkaline HPLC to obtain white solid: cis-3-(4-amino-5-(trifluoromethyl)pyrrolo[2,1-f][1,2,4]triazin-7-yl)-6-(4-fluoro-1-(2-hydroxy-2-methylpropionyl)pyrrolidin-3-yl)-7,8-dihydro-1,6-naphthyridin-5(6H)-one (Z33, 21.1 mg, Y:35%). ES-API: $[M+H]^+$=522.2. $^1$H NMR (400 MHz, DMSO-d6) δ9.22 (s, 1H), 8.97 (s, 1H), 8.21 (s, 1H), 7.76 (s, 1H), 5.41-5.11 (m, 3H), 4.40-4.29 (m, 1H), 4.06-3.95 (m, 1H), 3.82-3.61 (m, 4H), 3.22-3.09 (m, 2H), 1.34 (d, J=12.4 Hz, 6H).

Example 34 Preparation of (S)-3-(4-amino-5-(trifluoromethyl)pyrrolo[2,1-f][1,2,4]triazin-7-yl)-6-(1-(2-hydroxy-2-methylpropionyl)pyrrolidin-3-yl)-7,8-dihydro-1,6-naphthyridin-5(6H)-one (Z34)

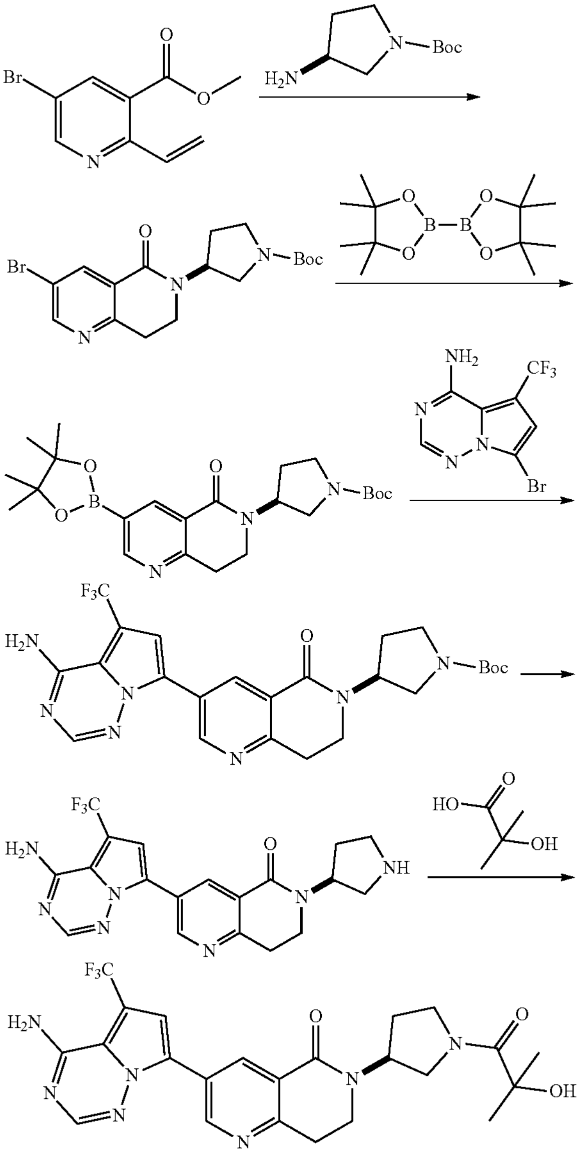

Z34

Step 1: Preparation of tert-butyl (S)-3-(3-bromo-5-oxo-7,8-dihydro-1,6-naphthyridin-6(5H)-yl)pyrrolidine-1-carboxylate: methyl 5-bromo-2-vinylnicotinate (544 mg, 2.248 mmol) and tert-butyl (S)-3-aminopyrrolidine-1-carboxylate (837 mg, 4.496 mmol) were mixed in DMA (6 mL) in a microwave bottle. The reaction was subjected to microwave radiation at 180° C. for 1.5 hours, cooled to room temperature, the reaction mixture was added into 15 mL ethyl acetate, then the mixture was washed with water (15 mL*3) and saturated sodium chloride solution (15 mL*3), the combined organic layers were concentrated, purified on silica gel by automatic fast chromatography (EtOAc/PE 0-50%) to obtain tert-butyl (S)-3-(3-bromo-5-oxo-7,8-dihydro-1,6-naphthyridin-6(5H)-yl)pyrrolidine-1-carboxylate (596 mg, Y: 67%). ES-API: $[M+H]^+$=396.1.

Step 2: Preparation of tert-butyl (S)-3-(5-oxo-3-(4,4,5,5-tetramethyl-1,3,2-dioxaborolan-2-yl)-7,8-dihydro-1,6-naphthyridin-6(5H)-yl)pyrrolidine-1-carboxylate: tert-butyl (S)-3-(3-bromo-5-oxo-7,8-dihydro-1,6-naphthyridin-6(5H)-yl) pyrrolidine-1-carboxylate (551 mg, 1.395 mmol), bis (pinacolato)diboron (714 mg, 2.790 mmol), potassium acetate (342 mg, 3.488 mmol), [1,1'-bis(diphenylphosphino) ferrocene]dichloropalladium(II) (51 mg, 0.070 mmol) and 1,4-dioxane (20 mL) were added into a 100 mL round bottom flask, the mixture was replaced with nitrogen for three times, and reacted at 95° C. overnight, cooled to room temperature, filtered with suction, the filter cake was washed with ethyl acetate for three times to obtain the filtrate, the filtrate was concentrated to obtain crude product tert-butyl (S)-3-(5-oxo-3-(4,4,5,5-tetramethyl-1,3,2-dioxaborolan-2-yl)-7,8-dihydro-1,6-naphthyridin-6(5H)-yl)pyrrolidine-1-carboxylate (667 mg, Y: 100%). ES-API: $[M+H]^+$=444.2.

Step 3: Preparation of tert-butyl (S)-3-(3-(4-amino-5-(trifluoromethyl)pyrrolo[2,1-f][1,2,4]triazin-7-yl)-5-ox-7,8-dihydro-1,6-naphthyridin-6(5H)-yl)pyrrolidine-1-carboxylate: under the protection of nitrogen, 7-bromo-5-(trifluoromethyl)pyrrolo[2,1-f][1,2,4]triazin-4-amine (281 mg, 1.004 mmol), tert-butyl (S)-3-(5-oxo-3-(4,4,5,5-tetramethyl-1,3,2-dioxaborolan-2-yl)-7,8-dihydro-1,6-naphthyridin-6(5H)-yl)pyrrolidine-1-carboxylate (667 mg, 1.506 mmol), sodium carbonate (266 mg, 2.510 mmol), [1,1'-bis (diphenylphosphino)ferrocene]palladium(II)dichloride dichloromethane complex (41 mg, 0.050 mmol) were dissolved in dioxane (20 mL) and $H_2O$ (4 mL), the mixture was replaced with nitrogen for three times, the reaction mixture was heated to 95° C. in boil bath for two hours. After the reaction was completed, the mixture was cooled to room temperature, concentrated, the crude product was purified to obtain off-white solid tert-butyl (S)-3-(3-(4-amino-5-(trifluoromethyl)pyrrolo[2,1-f][1,2,4]triazin-7-yl)-5-oxo-7,8-dihydro-1,6-naphthyridin-6(5H)-yl)pyrrolidine-1-carboxylate (318 mg, Y: 61%). ES-API: $[M+H]^+$=518.2.

Step 4 Preparation of (S)-3-(4-amino-5-(trifluoromethyl) pyrrolo[2,1-f][1,2,4]triazin-7-yl)-6-(pyrrolidin-3-yl)-7,8-dihydro-1,6-naphthyridin-5(6H)-one: TFA(1.11 mL, 14.147 mmol) was added into a solution of tert-butyl (S)-3-(3-(4-amino-5-(trifluoromethyl)pyrrolo[2,1-f][1,2,4]triazin-7-yl)-5-ox-7,8-dihydro-1,6-naphthyridin-6(5H)-yl)pyrrolidine-1-carboxylate (318 mg, 0.615 mmol) in DCM (6 mL), stirred at room temperature for two hours. After the reaction was completed, the mixture was concentrated to obtain crude product (S)-3-(4-amino-5-(trifluoromethyl)pyrrolo[2,1-f][1,2,4]triazin-7-yl)-6-(pyrrolidin-3-yl)-7,8-dihydro-1,6-naphthyridin-5(6H)-one (241 mg, Y: 94%). ES-API: $[M+H]^+$=418.2.

Step 5: Preparation of (S)-3-(4-amino-5-(trifluoromethyl) pyrrolo[2,1-f][1,2,4]triazin-7-yl)-6-(1-(2-hydroxy-2-methylpropionyl)pyrrolidin-3-yl)-7,8-dihydro-1,6-naphthyridin-5(6H)-one: 2-hydroxy-2-methylpropionic acid (20 mg, 0.192 mmol), (S)-3-(4-amino-5-(trifluoromethyl)pyrrolo[2,1-f][1,2,4]triazin-7-yl)-6-(pyrrolidin-3-yl)-7,8-dihydro-1,6-naphthyridin-5(6H)-one (80 mg, 0.192 mmol), PyBOP (100 mg, 0.192 mmol), DIPEA (74 mg, 0.576 mmol) and DMF (2.5 mL) were added into a 25 mL round bottom flask, reacted at room temperature overnight. After the reaction was completed, the reaction mixture was purified by alkaline HPLC to obtain white solid (S)-3-(4-amino-5-(trifluoromethyl)pyrrolo[2,1-f][1,2,4]triazin-7-yl)-6-(1-(2-hydroxy-2-methylpropionyl)pyrrolidin-3-yl)-7,8-dihydro-1,6-naphthyridin-5(6H)-one (Z34, 23.6 mg, Y: 24%). ES-API: $[M+H]^+$=504.2. $^1H$ NMR (400 MHz, DMSO-d6) δ 9.19 (d, J=2.0 Hz, 1H), 8.94 (s, 1H), 8.21 (s, 1H), 7.74 (s, 1H), 5.24-5.13 (m, 2H), 4.11-4.07 (m, 1H), 3.81-3.74 (m, 1H), 3.64-3.57 (m, 3H), 3.49-3.43 (m, 1H), 3.17-3.16 (m, 2H), 2.13-2.01 (m, 2H), 1.31-1.30 (m, 6H).

Example 35 3-(4-amino-5-(trifluoromethyl)pyrrolo [2,1-f][1,2,4]triazin-7-yl)-6-(1-(1-(4-fluorophenyl)) ethyl)-1H-pyrazol-4-yl)-7,8-dihydro-1,6-naphthyridin-5(6H)-one (Z35)

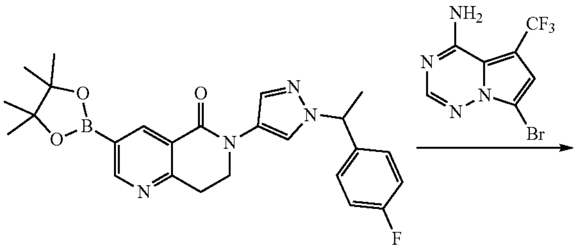

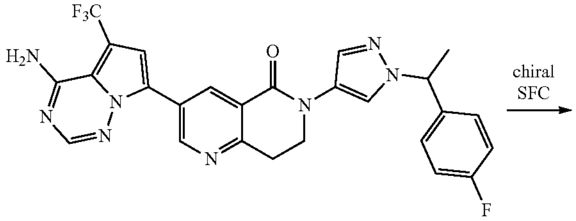

Z35

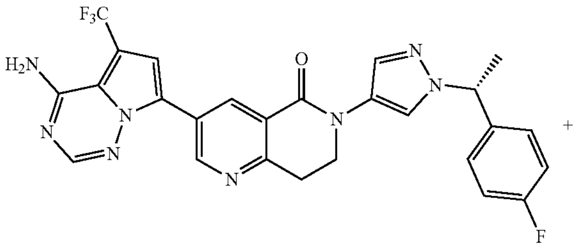

Z35-1

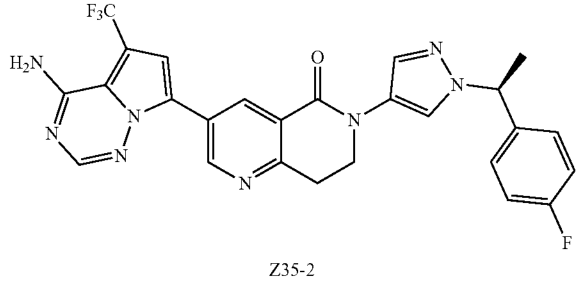

Z35-2

Step 6: Under the protection of nitrogen, 7-bromo-5-(trifluoromethyl)pyrrolo[2,1-f][1,2,4]triazin-4-amine (60 mg, 0.214 mmol), 6-(1-(1-(1-(4-fluorophenyl)ethyl)-1H-pyrazol-4-yl)-3-(4,4,5,5-tetramethyl-1,3,2-dioxaborinan-2-yl)-7,8-dihydro-1,6-naphthyridin-5(6H)-one (198 mg, 0.428 mmol), sodium carbonate (57 mg, 0.535 mmol), 1,1'-bis (diphenylphosphino)ferrocene-palladium(II)dichloride dichloromethane complex (9 mg, 0.0107 mmol) was dissolved in dioxane (8 mL) and $H_2O$ (2 mL), the mixture was replaced with nitrogen for three times, the reaction mixture was heated to 95° C. in oil for two hours. After the reaction was completed, the mixture was cooled to room temperature, concentrated, the residue was purified on silica gel by automatic fast chromatography to obtain 3-(4-amino-5-(trifluoromethyl)pyrrolo[2,1-f][1,2,4]triazin-7-yl)-6-(1-(1-(4-fluorophenyl))ethyl)-1H-pyrazol-4-yl)-7,8-dihydro-1,6-naphthyridin-5(6H)-one (Z35, 16.2 mg, Y: 15%). ES-API: $[M+H]^+$=537.2. 1H NMR (400 MHz, DMSO-d6) δ9.22 (d, J=2.0 Hz, 1H), 9.03 (d, J=2.0 Hz, 1H), 8.33 (s, 1H), 8.21 (s, 1H), 7.88 (s, 1H), 7.77 (s, 1H), 7.36-7.33 (m, 2H), 7.20-7.16 (m, 2H), 5.68-5.63 (m, 1H), 4.10 (t, J=5.6 Hz, 2H), 3.31-3.30 (m, 2H), 1.82 (d, J=5.6 Hz, 3H).

Step 7: The compound Z35 obtained above was chiral separated with SFC (column: Daicel CHIRALPAK IC 250*20 mm, 5 um; mobile phase: Hex/EtOH=40:60 (V/V); flow rate: 15 mL/min; injection volume: 400 μL; column temperature: room temperature; running time: 28 min) to obtain two compounds with different configurations:

Compound Z35-1 (retention time: 9.818 min): the structure of which was arbitrarily defined as (R)-3-(4-amino-5-(trifluoromethyl)pyrrolo[2,1-f][1,2,4]triazin-7-yl)-6-(1-(1-(4-fluorophenyl))ethyl)-1H-pyrazol-4-yl)-7,8-dihydro-1,6-naphthyridin-5(6H)-one (3.27 mg). ES-API: $[M+H]^+$=537.2;

Compound Z35-2 (retention time: 12.380 min): the structure of which was arbitrarily defined as (S)-3-(4-amino-5-(trifluoromethyl)pyrrolo[2,1-f][1,2,4]triazin-7-yl)-6-(1-(1-(4-fluorophenyl))ethyl)-1H-pyrazol-4-yl)-7,8-dihydro-1,6-naphthyridin-5(6H)-one (2.42 mg). ES-API: $[M+H]^+$=537.2.

Example 36 Preparation of cis-3-(4-amino-5-(trifluoromethyl)pyrrolo[2,1-f][1,2,4]triazin-7-yl)-6-(4-fluoro-1-(4-fluorobenzoyl)pyrrolidin-3-yl)-7,8-dihydro-1,6-naphthyridin-5(6H)-one (Z36)

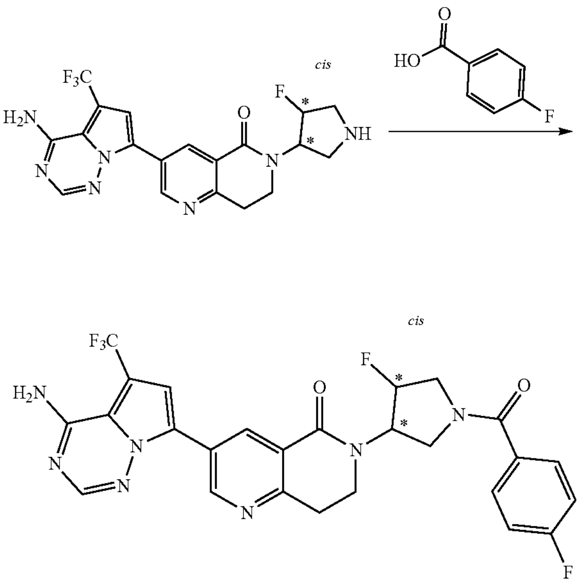

Z36

4-Fluorobenzoic acid (16 mg, 0.115 mmol), cis-3-(4-amino-5-(trifluoromethyl)pyrrolo[2,1-f][1,2,4]triazin-7-yl)-6-(4-fluoropyrrolidin-3-yl)-7,8-dihydro-1,6-naphthyridin-5 (6H)-one (referring to the preparation method in Example 27, 50 mg, 0.115 mmol), PyBOP (60 mg, 0.115 mmol), DIPEA (45 mg, 0.345 mmol) and DMF (2 mL) were added into a 25 mL round bottom flask, and reacted at room temperature overnight. After the reaction was completed, the reaction mixture was purified by alkaline HPLC to obtain white solid: cis-3-(4-amino-5-(trifluoromethyl)pyrrolo[2,1-f][1,2,4]triazin-7-yl)-6-(4-fluoro-1-(4-fluorobenzoyl)pyrrolidin-3-yl)-7,8-dihydro-1,6-naphthyridin-5(6H)-one (Z36, 19.06 mg, Y:30%). ES-API: $[M+H]^+$=558.1. 1H NMR (400 MHz, DMSO-d6) δ9.21 (d, J=8.0 Hz, 1H), 8.96 (d, J=15.2 Hz, 1H), 8.21 (d, J=7.6 Hz, 1H), 7.77-7.71 (m, 2H), 7.68-7.65 (m, 1H), 7.33-7.29 (m, 2H), 5.50-5.15 (m, 2H), 4.10-3.73 (m, 6H), 3.24-3.10 (m, 2H).

Example 37 Preparation of N-(6-(6-(3,5-difluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)cyclopropanecarboxamide (Z37)

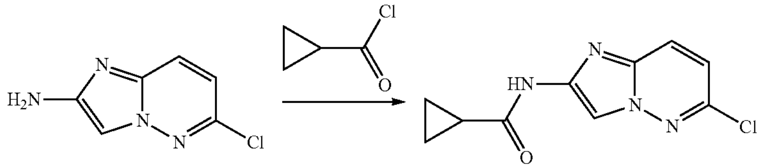

-continued

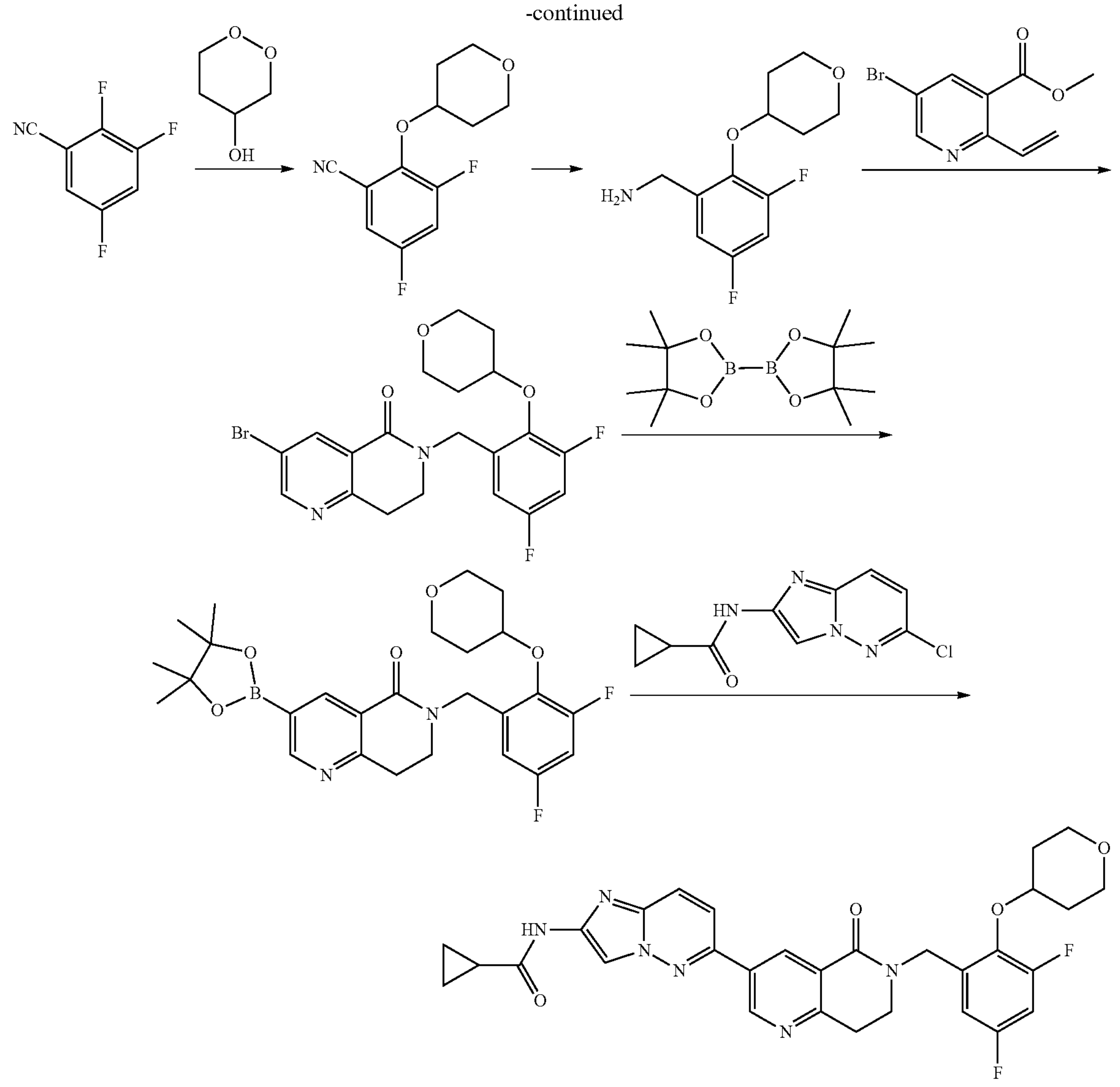

Z37

Step 1: Cyclopropanecarbonyl chloride (175 mg, 1.67 mmol) was slowly added into a solution of 2-amino-6-chloroimidazo[1,2-b]pyridazine (256 mg, 1.519 mmol) in N,N-dimethylacetamide (5 mL), the reaction mixture was stirred at room temperature for three hours. LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl) cyclopropanecarboxamide (191 mg, Y: 53%). ES-API: $[M+H]^+$= 237.1.

Step 2: Under ice water bath, sodium hydride (918 mg, 22.930 mmol) was added into a solution of tetrahydro-2H-pyran-4-ol (3.898 g, 38.216 mmol) in THF (30 mL) in batches, the reaction mixture was stirred at 0° C. for one hour. 2,3,5-Trifluorobenzonitrile (3 g, 19.108 mmol) was added into reaction mixture, the reaction mixture was stirred at 55° C. for 12 hours. LCMS showed the reaction was completed, water (50 mL) was added for quenching the reaction under ice water bath, then the mixture was extracted with EtOAc (30 mL*3), the combined organic phases were washed with saturated sodium chloride solution (15 mL*3), concentrated, purified on silica gel by automatic fast chromatography to obtain crude product 3,5-difluoro-2-((tetrahydro-2H-pyran-4-yl)oxy)benzonitrile (3.385 g, Y: 74%). ES-API: $[M+H]^+$=240.1.

Step 3: $BH_3$-THF (20 mL, 18.828 mmol) was added into a solution of 3,5-difluoro-2-((tetrahydro-2H-pyran-4-yl) oxy)benzonitrile (1.5 g, 6.276 mmol) in THF (30 mL), the reaction mixture was heated and refluxed overnight. LCMS showed the reaction was completed, the reaction mixture was cooled to room temperature, MeOH was slowly added for quenching the reaction, the reaction mixture was concentrated, the residue was dissolved in 1 N HCl (aq) (20 mL), extracted with DCM/i-PrOH (30 mL*3), the combined organic phases were dried to obtain light yellow transparent liquid (3,5-difluoro-2-((tetrahydro-2H-pyran-4-yl)oxy)phenyl)methylamine (1.418 g, Y: 93%). ES-API: $[M+H]^+$= 244.1.

Step 4: Methyl 5-bromo-2-vinylnicotinate (400 mg, 1.660 mol) and (3,5-difluoro-2-((tetrahydro-2H-pyran-4-yl)oxy)phenyl)methylamine (807 mg, 3.320 mmol) were mixed in DMA (6 mL) in a microwave bottle. The reaction was subjected to microwave radiation at 180° C. for one hour, cooled to room temperature, the reaction mixture was added into 15 mL ethyl acetate, then the mixture was washed with water (15 mL*3) and saturated sodium chloride solution (15 mL*3), the combined organic layers were concentrated, purified on silica gel by automatic fast chromatography (EtOAc/PE 0-50%) to 3-bromo-6-(3,5-difluoro-2-((tetrahydro-2H-pyran-4-yl)oxy)benzyl)-7,8-dihydro-1,6-naphthyridin-5(6H)-one (514 mg, Y: 69%). ES-API: $[M+H]^+$=453.1.

Step 5: 3-Bromo-6-(3,5-difluoro-2-((tetrahydro-2H-pyran-4-yl)oxy)benzyl)-7,8-dihydro-1,6-naphthyridin-5(6H)-one (514 mg, 1.137 mmol), bis(pinacolato)diboron (582 mg, 2.274 mmol), potassium acetate (279 mg, 2.843 mmol), [1,1'-bis(diphenylphosphino)ferrocene]dichloropalladium(II) (42 mg, 0.057 mmol) and 1,4-dioxane (12 mL) were added into a 100 mL round bottom flask, the mixture was replaced with nitrogen for three times, and reacted at 95° C. overnight, cooled to room temperature, filtered with suction, the filter cake was washed with ethyl acetate for three times to obtain the filtrate, the filtrate was concentrated to obtain crude product 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one (568 mg, Y: 100%). ES-API: $[M+H]^+$=501.2.

Step 6: Under the protection of nitrogen, 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one (95 mg, 0.190 mmol), N-(6-chloroimidazo[1,2-b]pyridazin-2-yl) cyclopropanecarboxamide (22 mg, 0.095 mmol), sodium carbonate (25 mg, 0.238 mmol), 1,1'-bis(diphenylphosphino)ferrocene-palladium(II)dichloride dichloromethane complex (4 mg, 0.0048 mmol) was dissolved in dioxane (5 mL) and $H_2O$ (1 mL), the mixture was replaced with nitrogen for three times, the reaction mixture was stirred at 95° C. in oil bath for two hours, cooled to room temperature, concentrated, the crude product was purified by alkaline HPLC to obtain white solid N-(6-(6-(3,5-difluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl) cyclopropanecarboxamide (Z37, 27.9 mg, Y: 51%). ES-API: $[M+H]^+$=575.2. $^1$H NMR (400 MHz, DMSO-d6) δ 11.24 (s, 1H), 9.30 (d, J=2.0 Hz, 1H), 8.79 (d, J=2.5 Hz, 1H), 8.34 (s, 1H), 8.13 (d, J=9.5 Hz, 1H), 7.93 (d, J=9.5 Hz, 1H), 7.30-7.25 (m, 1H), 6.99-6.97 (m, 1H), 4.81 (s, 2H), 4.32-4.27 (m, 1H), 3.92-3.88 (m, 2H), 3.70 (t, J1=6.5 Hz, J2=13.0 Hz, 2H), 3.41-3.38 (m, 2H), 3.25 (t, J1=6.5 Hz, J2=13.0 Hz, 2H), 1.99-1.94 (m, 3H), 1.74-1.66 (m, 2H), 0.88-0.82 (m, 4H).

Example 38 Preparation of N-(6-(6-(3,5-difluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)acetamide-2,2,2-$d_3$ (Z38)

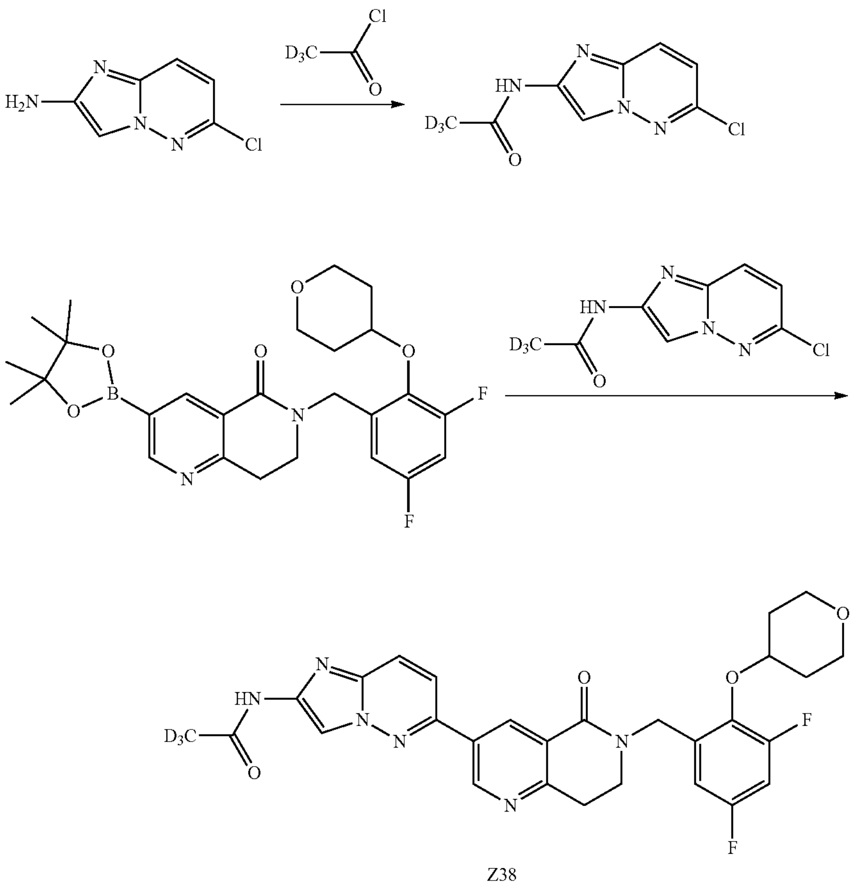

Z38

Step 1: Acetyl-$d_3$ chloride (266 mg, 3.263 mmol) was slowly added into a solution of 2-amino-6-chloroimidazo[1,2-b]pyridazine (500 mg, 2.966 mmol) in N,N-dimethylacetamide (10 mL), the reaction mixture was stirred at room temperature for one hour. LCMS showed the reaction was completed, the reaction mixture was adjusted to pH=8.0 by saturated sodium bicarbonate solution, white insoluble substance was precipitated, filtered, the filter cake was washed with water twice to obtain white product N-(6-chloroimidazo[1,2-b]pyridazin-2-yl)acetamide-2,2,2-$d_3$ (366 mg, Y: 55%). ES-API: $[M+H]^+$=214.1.

Step 2: Under the protection of nitrogen, 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one (95 mg, 0.190 mmol), N-(6-chloroimidazo[1,2-b]pyridazin-2-yl)acetamide-2,2,2-$d_3$ (20 mg, 0.095 mmol), sodium carbonate (25 mg, 0.238 mmol), 1,1'-bis(diphenylphosphino)ferrocene-palladium(II)dichloride dichloromethane complex (4 mg, 0.0048 mmol) were dissolved in dioxane (5 mL) and $H_2O$ (1 mL), the mixture was replaced with nitrogen for three times, the reaction mixture was stirred at 95° C. in oil bath for two hours, cooled to room temperature, concentrated, the crude product was purified by alkaline HPLC to obtain white solid product N-(6-(6-(3,5-difluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)acetamide-2,2,2-$d_3$ (Z38, 6.2 mg, Y: 12%). ES-API: $[M+H]^+$=552.2. $^1H$ NMR (400 MHz, DMSO-d6) δ 10.96-10.93 (m, 1H), 9.30 (d, J=2.5 Hz, 1H), 8.80 (d, J=2.0 Hz, 1H), 8.36 (s, 1H), 8.12 (d, J=9.5 Hz, 1H), 7.93 (d, J=9.5 Hz, 1H), 7.30-7.25 (m, 1H), 6.99-6.97 (m, 1H), 4.82 (s, 2H), 4.32-4.27 (m, 1H), 3.92-3.88 (m, 2H), 3.70 (t, J1=6.5 Hz, J2=13.0 Hz, 2H), 3.41-3.36 (m, 2H), 3.29-3.24 (m, 2H), 1.97-1.94 (m, 2H), 1.74-1.67 (m, 2H).

Example 39 N-(6-(6-(3,5-difluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)-2-hydroxylacetamide (Z39) and ethyl 2-((6-(6-(3,5-difluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)amino)-2-oxoacetate (Z96)

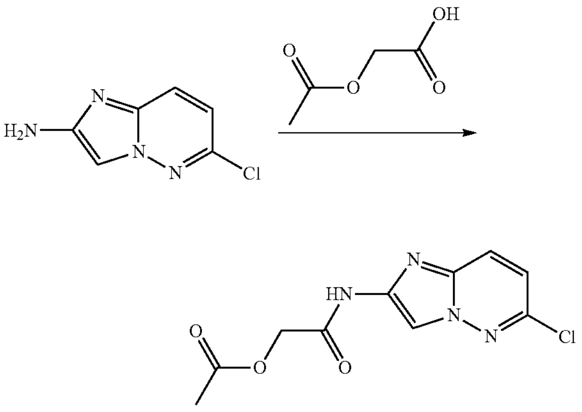

-continued

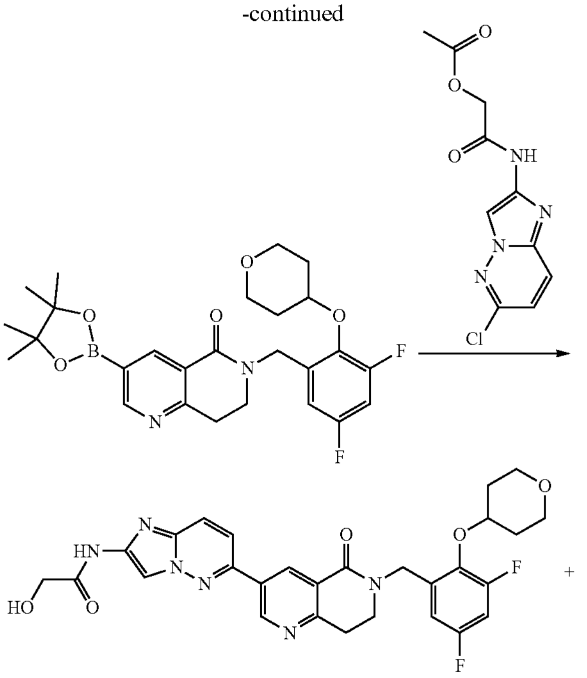

Z39

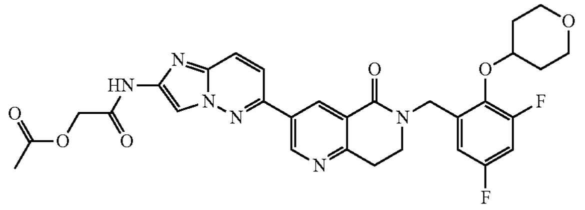

Z96

Step 1: HATU (858 mg, 2.259 mmol) was added into a solution of 2-amino-6-chloroimidazo[1,2-b]pyridazine (266 mg, 1.581 mmol), 2-acetoxyacetic acid (178 mg, 1.506 mmol), DIPEA (971 mg, 7.530 mmol) in N,N-dimethylacetamide (7 mL), the reaction mixture was stirred at room temperature overnight. LCMS showed the reaction was completed, the reaction mixture was added into water (30 mL), then extracted with EtOAc (20 mL*3), the combined organic phases were washed with saturated sodium chloride solution (15 mL*3), the combined organic layers were concentrated, purified on silica gel by automatic fast chromatography to obtain white product 2-((6-chloroimidazo[1,2-b]pyridazin-2-yl)amino)-2-oxo ethyl acetate (266 mg, Y: 60%). ES-API: $[M+H]^+$=269.0.

Step 6: Under the protection of nitrogen, 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one (95 mg, 0.190 mmol), 2-((6-chloroimidazo[1,2-b]pyridazin-2-yl)amino)-2-oxoethyl acetate (25 mg, 0.095 mmol), sodium carbonate (25 mg, 0.238 mmol), [1,1'-bis(diphenylphosphino)ferrocene-palladium(II)dichloride dichloromethane complex (4 mg, 0.0048 mmol) were dissolved in dioxane (5 mL) and $H_2O$ (1 mL), the mixture was replaced with nitrogen for three times, the reaction mixture was stirred at 95° C. in oil bath overnight, cooled to room temperature, concentrated, the crude product was purified by alkaline HPLC to obtain off-white solid product: N-(6-(6-(3,5-difluoro-2-((tetrahydro-2H-pyran-4-yl)oxy)benzyl)-5-oxo-5,6,7,8-tetrahydro-1,6-naphthyridin- 3-yl)imidazo[1,2-b]pyridazin-2-yl)-2-hydroxyacetamide (Z39, 34.42 mg, Y: 64%). ES-API: $[M+H]^+$=565.2. $^1$H NMR (400 MHz, DMSO-d6) δ9.32 (d, J=2.5 Hz, 1H), 8.81 (d, J=2.0 Hz, 1H), 8.42 (s, 1H), 8.15 (d, J=9.5 Hz, 1H), 7.96 (d, J=9.5 Hz, 1H), 7.30-7.26 (m, 1H), 7.00-6.98 (m, 1H), 5.57-5.55 (m, 1H), 4.82 (s, 2H), 4.32-4.27 (m, 1H), 4.11 (s, 2H), 3.92-3.88 (m, 2H), 3.71 (t, J1=7.0 Hz, J2=13.5 Hz, 2H), 3.41-3.36 (m, 2H), 3.26 (t, J1=6.5 Hz, J2=13.0 Hz, 2H), 1.97-1.94 (m, 2H), 1.74-1.67 (m, 2H).

In addition a brown solid was obtained by reaction: ethyl 2-((6-(6-(3,5-difluoro-2-((tetrahydro-2H-pyran-4-yl)oxy) benzyl)-5-oxo-5,6,7,8-tetrahydro-1,6-naphthyridin-3-yl) imidazo[1,2-b]pyridazin-2-yl)amino)-2-oxoacetate (Z96, 14.85 mg, Y: 26%). ES-API: $[M+H]^+$=607.2. $^1$H NMR (400 MHz, DMSO-d6) δ11.20 (s, 1H), 9.31 (d, J=2.5 Hz, 1H), 8.81 (d, J=2.0 Hz, 1H), 8.37 (s, 1H), 8.16 (d, J=9.5 Hz, 1H), 7.96 (d, J=9.5 Hz, 1H), 7.30-7.26 (m, 1H), 6.99-6.98 (m, 1H), 4.82 (s, 2H), 4.76 (s, 2H), 4.31-4.28 (m, 1H), 3.92-3.89 (m, 2H), 3.71 (t, J1=6.5 Hz, J2=13.5 Hz, 2H), 3.41-3.36 (m, 2H), 3.26 (t, J1=6.5 Hz, J2=13.0 Hz, 2H), 2.14 (s, 3H), 1.97-1.94 (m, 2H), 1.74-1.67 (m, 2H).

Example 40

Compound Z40 can be prepared by referring to the method in the above Examples.

| Example | Compound | Structure | MS $[M + H]^+$ |
|---|---|---|---|
| 40 | Z40 | 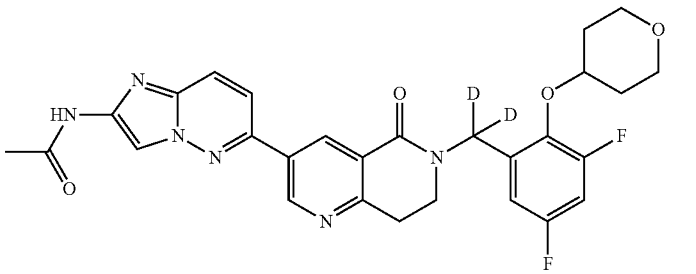 [SMILES: [2H]C([2H])(c1cc(F)cc(F)c1OC1CCOCC1)N1CCc2ncc(-c3ccc4nc(NC(C)=O)cn4n3)cc2C1=O] | 551.2 |

Example 44 Preparation of 3-(2-amino-[1,2,4]triazolo[1,5-a]pyridyl-7-yl)-6-(2-(trifluoromethoxy) benzyl)-7,8-dihydro-1,6-naphthyridin-5(6H)-one (Z44)

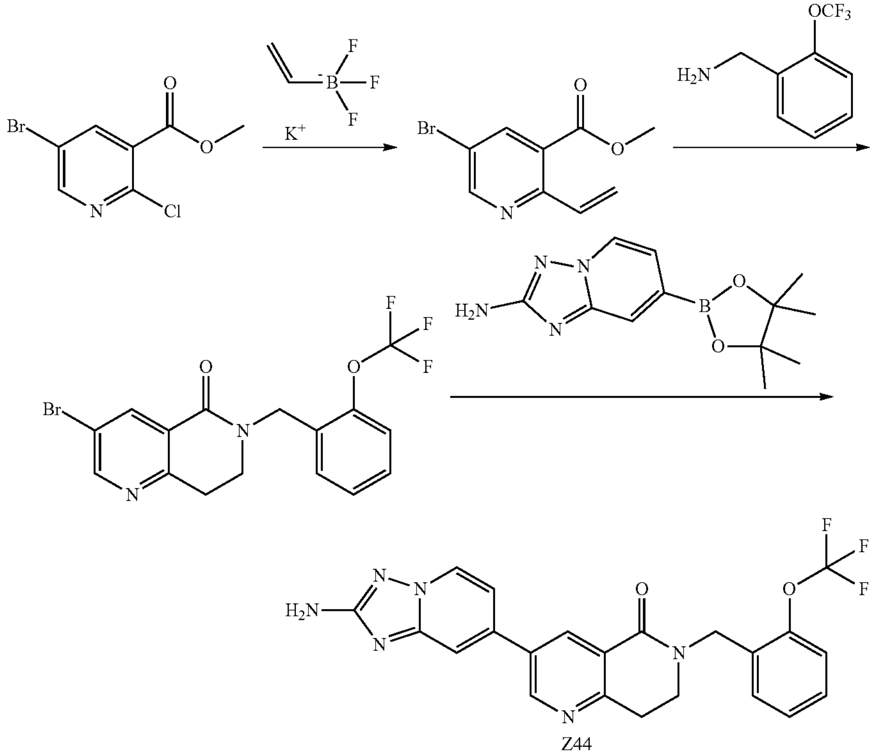

Z44

Step 1: Preparation of methyl 5-bromo-2-vinylnicotinate: under the protection of nitrogen, 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 55%). ES-API: $[M+H]^+$=242.1.

Step 2: Preparation of 3-bromo-6-(2-(trifluoromethoxy)benzyl)-7,8-dihydro-1,6-naphthyridin-5(6H)-one: methyl 5-bromo-2-vinylnicotinate (450 mg, 1.859 mmol) and (2-(trifluoromethoxy)phenyl)methylamine (710 mg, 3.719 mmol) were mixed in DMA (10 mL) in a microwave bottle. The reaction was subjected to microwave radiation at 180° C. for one hour, cooled to room temperature, the reaction mixture was added into 20 mL ethyl acetate, then the mixture was washed with water (15 mL*3) and saturated sodium chloride solution (15 mL*3), the combined organic layers were concentrated, purified on silica gel by automatic fast chromatography to obtain 3-bromo-6-(2-(trifluoromethoxy)benzyl)-7,8-dihydro-1,6-naphthyridin-5(6H)-one (180 mg, Y: 22%). ES-API: $[M+H]^+$=401.0.

Step 3: Preparation of 3-(2-amino-[1,2,4]triazolo[1,5-a]pyridyl-7-yl)-6-(2-(trifluoromethoxy)benzyl)-7,8-dihydro-1,6-naphthyridin5(6H)-one: under the protection of nitrogen, 3-bromo-6-(2-(trifluoromethoxy)benzyl)-7,8-dihydro-1,6-naphthyridin-5(6H)-one (80 mg, 0.200 mmol), 7-(4,4,5,5-tetramethyl-1,3,2-dioxaborolan-2-yl)-[1,2,4]triazolo[1,5-a]pyridyl-2-amine (53 mg, 0.300 mmol), sodium carbonate (53 mg, 0.500 mmol), 1,1'-bis(diphenylphosphino)ferrocene-palladium(II)dichloride dichloromethane complex (8 mg, 0.01 mmol) were dissolved in dioxane (10 mL) and $H_2O$ (2 mL), the mixture was replaced with nitrogen for three times, and reacted at 95° C. for 1.5 hours, cooled to room temperature, the reaction mixture was added into EtOAc (30 mL), washed with water (15 mL*3) and saturated sodium chloride solution (15 mL*3), the combined organic layers were concentrated, the residue was purified by alkaline HPLC to obtain white solid 3-(2-amino-[1,2,4]triazolo[1,5-a]pyridyl-7-yl)-6-(2-(trifluoromethoxy)benzyl)-7,8-dihydro-1,6-naphthyridin-5(6H)-one (Z44, 30 mg, Y: 27%). ES-API: $[M+H]^+$=455.1. $^1H$ NMR (400 MHz, DMSO-d6) δ 9.10 (d, J=2.4 Hz, 1H), 8.65 (d, J=6.8 Hz, 1H), 8.52 (d, J=2.4 Hz, 1H), 7.80 (d, J=1.2 Hz, 1H), 7.50-7.38 (m, 4H), 7.30 (dd, J1=2.0 Hz, J2=7.2 Hz, 1H), 6.12 (s, 2H), 4.84 (s, 2H), 3.67 (t, J1=6.8 Hz, J2=13.6 Hz, 2H), 3.21 (t, J1=6.8 Hz, J2=13.6 Hz, 2H).

Example 45 Preparation of 3-(2-amino-[1,2,4]triazolo[1,5-a]pyridyl-7-yl)-6-(2-(cyclopentyloxy)-5-fluorobenzyl)-7,8-dihydro-1,6-naphthyridin-5(6H)-one (Z45)

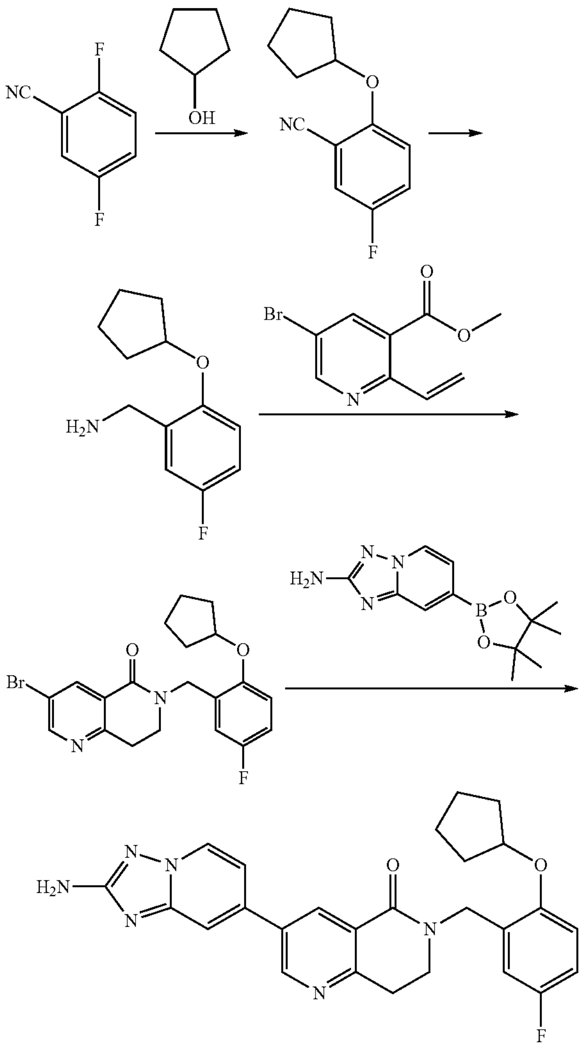

Z45

Step 1: Preparation of 2-(cyclopentyloxy)-5-fluorobenzonitrile: under ice water bath, sodium hydride (533 mg, 13.317 mmol) was added into a solution of cyclopentanol (1.15 g, 13.317 mmol) in THF (30 mL) in batches, the reaction mixture was stirred at 0° C. for one hour. 2,5-Difluorobenzonitrile (1.18 g, 8.478 mmol) was added into reaction mixture, the reaction mixture was stirred at room temperature overnight. LCMS showed the reaction was completed, saturated ammonium chloride (50 mL) was added for quenching the reaction under ice water bath, then the mixture was extracted with EtOAc (30 mL*3), the combined organic phases were washed with saturated sodium chloride solution (15 mL*3) the combined organic layers were concentrated to obtain crude product 2-(cyclopentyloxy)-5-fluorobenzonitrile (1.74 g, Y: 99%). ES-API: $[M+H]^+$=206.1.

Step 2: Preparation of (2-(cyclopentyloxy)-5-fluorophenyl)methylamine: under room temperature, $BH_3$-THF (17 mL, 16.957 mmol) was added into a solution of 2-(cyclopentyloxy)-5-fluorobenzonitrile (1.74 g, 8.478 mmol) in THF (20 mL), the reaction mixture was stirred at room temperature overnight. LCMS showed the reaction was completed, the reaction mixture was cooled to room temperature, MeOH was slowly added dropwise for quenching the reaction. The reaction mixture was concentrated, the residue was dissolved in 1 N HCl (aq) (20 mL), extracted with DCM/i-PrOH (30 mL*3), the organic phases were combined, concentrated to dryness to obtain light yellow transparent liquid (2-(cyclopentyloxy)-5-fluorophenyl) methylamine (860 mg, Y: 48%). ES-API: $[M+H]^+$=210.1.

Step 3: Preparation of 3-bromo-6-(2-(cyclopentyloxy)-5-fluorobenzyl)-7,8-dihydro-1,6-naphthyridin-5(6H)-one: methyl 5-bromo-2-vinylnicotinate (500 mg, 2.066 mmol) and (2-(cyclopentyloxy)-5-fluorophenyl)methylamine (648 mg, 3.098 mmol) were mixed in DMA (10 mL) in a microwave bottle. The reaction was subjected to microwave radiation at 180° C. for one hour, cooled to room temperature, the reaction mixture was added into 15 mL ethyl acetate, then the mixture was washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-(cyclopentyloxy)-5-fluorobenzyl)-7,8-dihydro-1,6-naphthyridin-5(6H)-one (300 mg, Y: 35%). ES-API: $[M+H]^+$=419.0.

Step 4: Preparation of 3-(2-amino-[1,2,4]triazolo[1,5-a]pyridyl-7-yl)-6-(2-(cyclopentyloxy)-5-fluorobenzyl)-7,8-dihydro-1,6-naphthyridin-5(6H)-one: under the protection of nitrogen, 3-bromo-6-(2-(cyclopentyloxy)-5-fluorobenzyl)-7,8-dihydro-1,6-naphthyridin-5(6H)-one (100 mg, 0.238 mmol), 7-(4,4,5,5-tetramethyl-1,3,2-dioxaborolan-2-yl)-[1,2,4]triazolo[1,5-a]pyridyl-2-amine (106 mg, 0.596 mmol), sodium carbonate (76 mg, 0.714 mmol), 1,1'-bis(diphenylphosphino)ferrocene-palladium(II)dichloride dichloromethane complex (10 mg, 0.0119 mmol) were dissolved in dioxane (2 mL) and $H_2O$ (0.5 mL) the mixture was replaced with nitrogen for three times, the reaction mixture was heated to 95° C. in oil bath for 1.5 hours, cooled to room temperature, concentrated, the crude product was purified by alkaline HPLC to obtain off-white solid 3-(2-amino-[1,2,4]triazolo[1,5-a]pyridyl-7-yl)-6-(2-(cyclopentyloxy)-5-fluorobenzyl)-7,8-dihydro-1,6-naphthyridin-5(6H)-one (Z45, 32.31 mg, Y: 29%). ES-API: $[M+H]^+$=473.1. $^1$H NMR (400 MHz, DMSO-d6) δ 9.08 (d, J=2.0 Hz, 1H), 8.64 (d, J=7.2 Hz, 1H), 8.50 (d, J=2.4 Hz, 1H), 7.79 (d, J=1.2 Hz, 1H), 7.29 (dd, J1=2.4 Hz, J2=7.2 Hz, 1H), 7.09-6.99 (m, 3H), 6.10 (s, 2H), 4.87-4.84 (m, 1H), 4.66 (s, 2H), 3.65 (t, J1=6.8 Hz, J2=13.6 Hz, 2H), 3.19 (t, J1=6.8 Hz, J2=13.6 Hz, 2H), 1.92-1.87 (m, 2H), 1.75-1.63 (m, 4H), 1.58-1.55 (m, 2H).

Example 46 Preparation of 3-(2-amino-[1,2,4]triazolo[1,5-a]pyridyl-7-yl)-6-(1-(2-(trifluoromethoxy)phenyl)ethyl)-7,8-dihydro-1,6-naphthyridin-5(6H)-one (Z46)

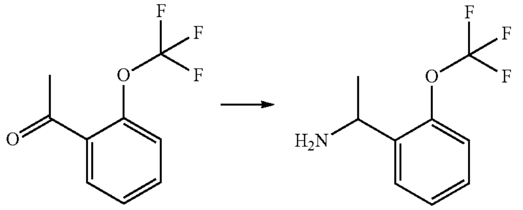

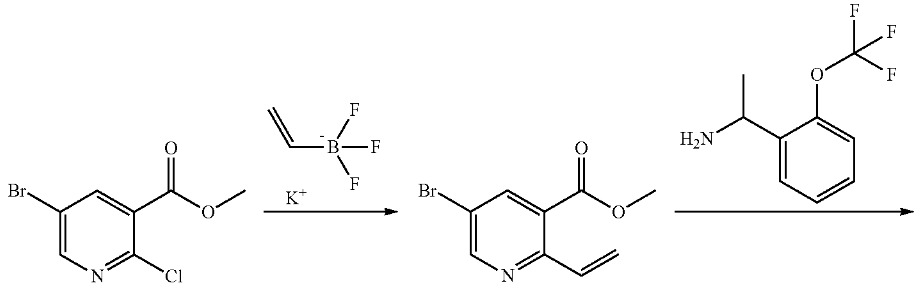

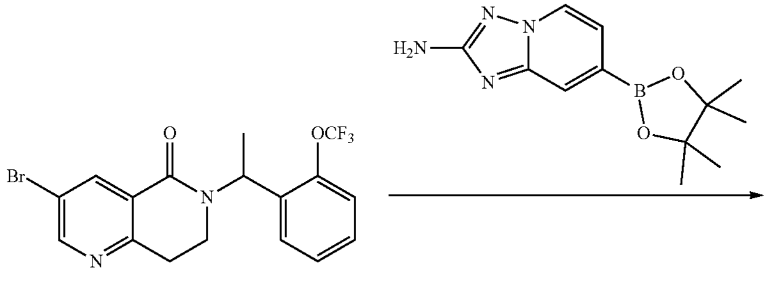

-continued

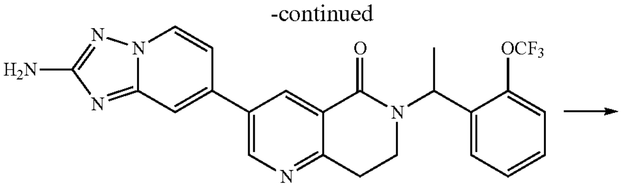

Z46

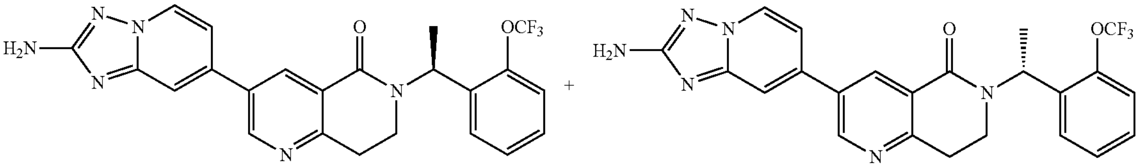

Z46-1

Z46-2

Step 1: Preparation of 1-(2-(trifluoromethoxy)phenyl)ethyl-1-amine: $NH_4OAc$ (28.3 g, 367.377 mmol) was added into a solution of 1-(2-(trifluoromethoxy)phenyl)ethyl-1-one (5 g, 24.492 mmol) in methanol (70 mL) and acetonitrile (70 mL), the reaction mixture was heated to 65° C. for two hours, cooled to room temperature, $NaBH_3CN$ (2.309 g, 36.738 mmol) was added into the above solution, the reaction mixture was heated to 65° C. and stirred overnight. After the reaction was completed, the mixture was cooled to room temperature, the solvent was spun off under reduced pressure, the residue was dissolved in EtOH (50 mL), then the mixture was washed with water (25 mL*3) and saturated sodium chloride solution (25 mL*3), the combined organic layers were concentrated, purified on silica gel by automatic fast chromatography to obtain 1-(2-(trifluoromethoxy)phenyl)ethyl-1-amine (1.9 g, Y: 38%). ES-API: $[M+H]^+$=206.1.

Step 2: Preparation of methyl 5-bromo-2-vinylnicotinate: under the protection of nitrogen, 5-Bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 3: Preparation of 3-bromo-6-(1-(2-(trifluoromethoxy)phenyl)ethyl)-7,8-dihydro-1,6-naphthyridin-5(6H)-one: methyl 5-bromo-2-vinylnicotinate (780 mg, 3.222 mmol) and 1-(2-(trifluoromethoxy)phenyl)ethyl-1-amine (1.653 g, 8.055 mmol) were mixed in DMA (10 mL) in a microwave bottle. The reaction was subjected to microwave radiation at 150° C. for 8 hours, cooled to room temperature, the reaction mixture was added into ethyl acetate (50 mL), then the mixture was washed with water (25 mL*3) and saturated sodium chloride solution (25 mL*3), the combined organic layers were concentrated, purified on silica gel by automatic fast chromatography to obtain 3-bromo-6-(1-(2-(trifluoromethoxy)phenyl)ethyl)-7,8-dihydro-1,6-naphthyridin-5(6H)-one (769 mg, Y: 57%). ES-API: $[M+H]^+$=415.0.

Step 4: Preparation of 3-(2-amino-[1,2,4]triazolo[1,5-a]pyridyl-7-yl)-6-(1-(2-(trifluoromethoxy)phenyl)ethyl)-7,8-dihydro-1,6-naphthyridin-5(6H)-one: under the protection of nitrogen, 3-bromo-6-(1-(2-(trifluoromethoxy)phenyl)ethyl)-7,8-dihydro-1,6-naphthyridin-5(6H)-one (385 mg, 0.927 mmol), 7-(4,4,5,5-tetramethyl-1,3,2-dioxaborolan-2-yl)-[1,2,4]triazolo[1,5-a]pyridyl-2-amine (413 mg, 2.318 mmol), sodium carbonate (295 mg, 2.781 mmol), 1,1'-bis(diphenylphosphino)ferrocene-palladium(II)dichloride dichloromethane complex (38 mg, 0.046 mmol) was dissolved in dioxane (15 mL) and $H_2O$ (3 mL), the mixture was replaced with nitrogen for three times, and reacted at 95° C. for 1.5 hours, cooled to room temperature, the reaction mixture was added into EtOAc (20 mL), washed with water (15 mL*3) and saturated sodium chloride solution (15 mL*3), the combined organic layers were concentrated, the residue was purified by alkaline HPLC to obtain white compound 3-(2-amino-[1,2,4]triazolo[1,5-a]pyridyl-7-yl)-6-(1-(2-(trifluoromethoxy)phenyl)ethyl)-7,8-dihydro-1,6-naphthyridin-5(6H)-one (Z46, 154.5 mg, Y: 36%). ES-API: $[M+H]^+$=469.1.

Step 5: Preparation of (R or S)-3-(2-amino-[1,2,4]triazolo[1,5-a]pyridyl-7-yl)-6-(1-(2-(trifluoromethoxy)phenyl)ethyl)-7,8-dihydro-1,6-naphthyridin-5(6H)-one: the compound Z46 obtained above was chiral separated with SFC (column: IC (4.6*250 mm 5 um); mobile phase: MeOH (0.2% Methanolamino); flow rate: 1.0 mL/min; column temperature: 40° C.;) to obtain two compounds with different configurations:

Compound Z46-1 (retention time: 11.663 min): the structure of which was arbitrarily defined as (S)-3-(2-amino-[1,2,4]triazolo[1,5-a]pyridyl-7-yl)-6-(1-(2-(trifluoromethoxy)phenyl)ethyl)-7,8-dihydro-1,6-naphthyridin-5(6H)-one (72.04 mg, Y: 47%), ES-API: $[M+H]^+$=469.1;

Compound Z46-2 (retention time: 13.761 min): the structure of which was arbitrarily defined as (R)-3-(2-amino-[1,2,4]triazolo[1,5-a]pyridyl-7-yl)-6-(1-(2-(trifluoromethoxy)phenyl)ethyl)-7,8-dihydro-1,6-naphthyridin-5(6H)-one (70.65 mg, Y: 46%), ES-API: $[M+H]^+$=469.1.

Example 47 Preparation of 3-(2-amino-[1,2,4]triazole[1,5-a]pyridyl-7-yl)-6-((2-(cyclopentyloxy)pyridyl-3-yl)methyl)-7,8-dihydro-1,6-naphthyridin-5(6H)-one (Z47)

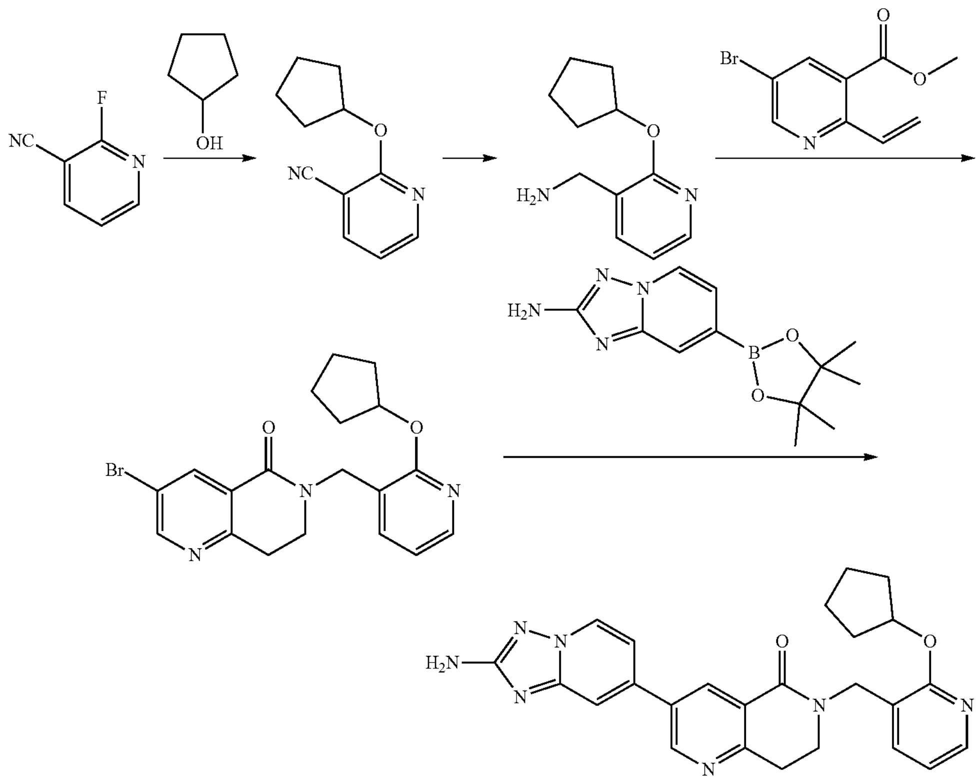

Z47

Step 1: Preparation of 2-(cyclopentyloxy)nicotinonitrile: under ice water bath, sodium hydride (1.4 g, 36.04 mmol) was added into a solution of cyclopentanol (2.822 g, 32.76 mmol) in THF (30 mL) in batches, the reaction mixture was stirred at 0° C. for one hour. 2-Fluoronicotinonitrile (2 g, 16.38 mmol) was added into reaction mixture, the reaction mixture was stirred at room temperature overnight. LCMS showed the reaction was completed, saturated ammonium chloride solution (50 mL) was added for quenching the reaction under ice water bath, the mixture was extracted with EtOAc (30 mL*3), the combined organic phases were washed with saturated sodium chloride solution (15 mL*3), concentrated, the residue was purified on silica gel by automatic fast chromatography to obtain crude product 2-(cyclopentyloxy)nicotinonitrile (1.907 g, Y: 62%). ES-API: $[M+H]^+=189.1$.

Step 2: Preparation of (2-(cyclopentyloxy)pyridyl-3-yl)methylamine: $BH_3$-THF (50 mL, 50.656 mmol) was added into a solution of 2-(cyclopentyloxy)nicotinonitrile (1.907 g, 10.131 mmol) in THF (30 mL) at room temperature, the reaction mixture was heated and refluxed overnight. LCMS showed the reaction was completed, the reaction mixture was cooled to room temperature, MeOH was slowly added dropwise for quenching the reaction. The reaction mixture was concentrated, the residue was dissolved in 1 N HCl (aq) (20 mL), extracted with DCM/i-PrOH (30 mL*3), the combined organic phase was concentrated to dryness to obtain light yellow transparent liquid (2-(cyclopentyloxy)pyridyl-3-yl)methylamine (2.0 g, Y: 83%). ES-API: $[M+H]^+=193.1$.

Step 3: Preparation of 3-bromo-6-((2-(cyclopentyloxy)pyridyl-3-yl)methyl)-7,8-dihydro-1,6-naphthyridin-5(6H)-one: methyl 5-bromo-2-vinylnicotinate (100 mg, 0.413 mmol) and (2-(cyclopentyloxy)pyridyl-3-yl)methylamine (238 mg, 1.239 mmol) were mixed in DMA (5 mL) in a microwave bottle. The reaction was subjected to microwave radiation at 180° C. for one hour, then cooled to room temperature, ethyl acetate (15 mL) was added, the reaction mixture was washed with water (15 mL*3) and saturated sodium chloride solution (15 mL*3), the combined organic layers were concentrated, purified on silica gel by automatic fast chromatography to obtain 3-bromo-6-((2-(cyclopentyloxy)pyridyl-3-yl)methyl)-7,8-dihydro-1,6-naphthyridin-5(6H)-one (31 mg, Y: 19%). ES-API: $[M+H]^+=402.1$.

Step 4: Preparation of 3-(2-amino-[1,2,4]triazole[1,5-a]pyridyl-7-yl)-6-((2-(cyclopentyloxy)pyridyl-3-yl)methyl)-7,8-dihydro-1,6-naphthyridin-5(6H)-one: under the protection of nitrogen, 3-bromo-6-((2-(cyclopentyloxy)pyridyl-3-yl)methyl)-7,8-dihydro-1,6-naphthyridin-5(6H)-one (31 mg, 0.077 mmol), 7-(4,4,5,5-tetramethyl-1,3,2-dioxaborolan-2-yl)-[1,2,4]triazolo[1,5-a]pyridyl-2-amine (34 mg, 0.193 mmol), sodium carbonate (24 mg, 0.231 mmol), [1,1'-bis(diphenylphosphino)ferrocene-palladium(II)dichloride dichloromethane complex (3 mg, 0.0039 mmol) were dissolved in dioxane (6 mL) and $H_2O$ (1.5 mL), the mixture was replaced with nitrogen for three times, the reaction mixture was heated to 95° C. in oil bath for 1.5 hours, cooled to room temperature, concentrated, the crude product was purified by alkaline HPLC to obtain off-white solid 3-(2-amino-[1,2,4]triazole[1,5-a]pyridyl-7-yl)-6-((2-(cyclopentyloxy)pyridyl-3-yl)methyl)-7,8-dihydro-1,6-naphthyridin-5(6H)-one (Z47, 14.2 mg, Y: 41%). ES-API: $[M+H]^+$=456.1. $^1$H NMR (400 MHz, DMSO-d6) δ 9.08 (d, J=2.4 Hz, 1H), 8.63 (d, J=6.8 Hz, 1H), 8.48 (d, J=2.4 Hz, 1H), 8.07 (dd, J1=1.6 Hz, J2=4.8 Hz, 1H), 7.78 (d, J=1.6 Hz, 1H), 7.62 (dd, J1=1.6 Hz, J2=7.2 Hz, 1H), 7.28 (dd, J1=2.0 Hz, J2=7.2 Hz, 1H), 6.94-6.91 (m, 1H), 6.11 (bs, 2H), 5.45-5.41 (m, 1H), 4.63 (s, 2H), 3.66 (t, J1=6.4 Hz, J2=13.2 Hz, 2H), 3.19 (t, J1=6.4 Hz, J2=13.6 Hz, 2H), 1.93-1.88 (m, 2H), 1.72-1.53 (m, 6H).

Example 48 Preparation of 3-(2-amino-[1,2,4]triazolo[1,5-a]pyridyl-7-yl)-6-(2-fluoro-5-(trifluoromethoxy)benzyl)-7,8-dihydro-1,6-naphthyridin-5(6H)-one (Z48)

filtered with suction, the filter cake was washed with ethyl acetate for three times to obtain the filtrate, the filtrate was concentrated to obtain crude product 7-(4,4,5,5-tetramethyl-1,3,2-dioxaborolan-2-yl)-[1,2,4]triazolo[1,5-a]pyridyl-2-amine (2.6 g, Y: 78%). ES-API: $[M+H]^+$=179.1.

Step 2: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) was dissolved in 200 mL EtOH, the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 3: Preparation of 3-bromo-6-(2-fluoro-5-(trifluoromethoxy)benzyl)-7,8-dihydro-1,6-naphthyridin-5(6H)-

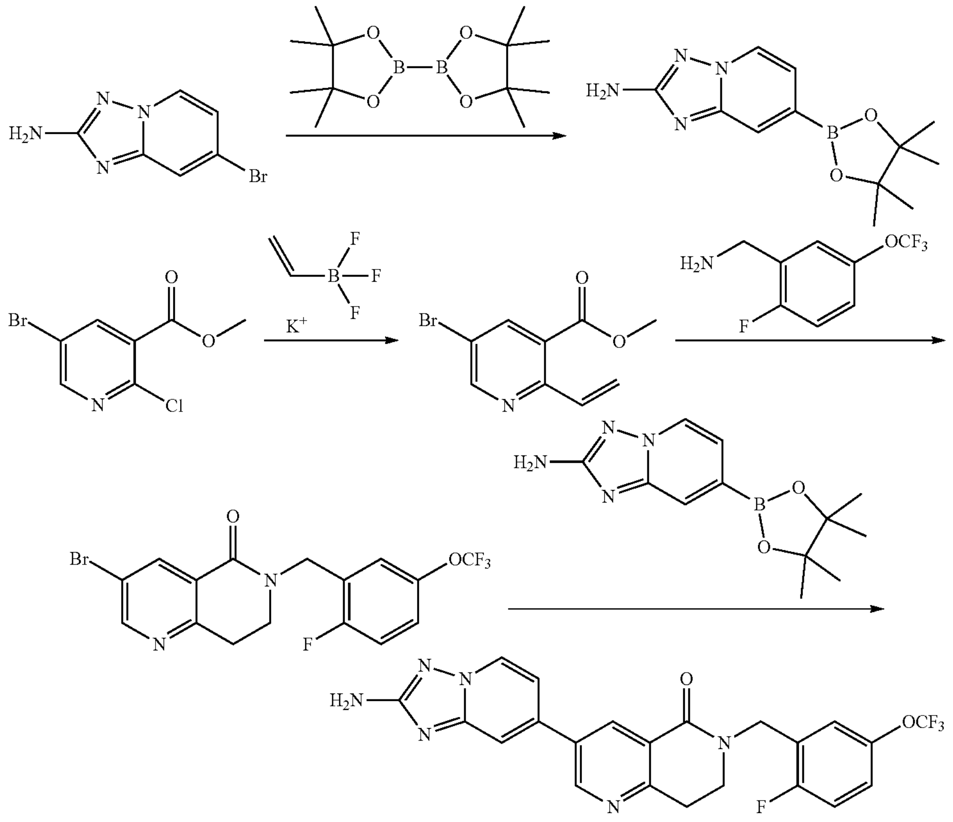

Z48

Step 1: Preparation of 7-(4,4,5,5-tetramethyl-1,3,2-dioxaborolan-2-yl)-[1,2,4]triazolo[1,5-a]pyridyl-2-amine: 7-bromo-[1,2,4]triazolo[1,5-a]pyridyl-2-amine (4.0 g, 18.78 mmol), bis(pinacolato)diboron (5.723 g, 22.53 mmol), potassium acetate (4.601 g, 46.95 mmol), [1,1'-bis(diphenylphosphino)ferrocene-palladium(II)dichloride dichloromethane complex (767 mg, 0.939 mmol) and 1,4-dioxane (50 mL) were added into a 250 mL round bottom flask, the mixture was replaced with nitrogen for three times, and reacted at 90° C. overnight, cooled to room temperature, one: methyl 5-bromo-2-vinylnicotinate (2.5 g, 10.328 mmol) and (2-fluoro-5-(trifluoromethoxy)phenyl)methylamine (4.32 g, 20.656 mmol) were mixed in DMA (75 mL) in a microwave bottle. The reaction was subjected to microwave radiation at 150° C. for three hours, then cooled to room temperature, ethyl acetate (100 mL) was added, the reaction mixture was washed with water (30 mL*3) and saturated sodium chloride solution (30 mL*3), the combined organic layers were concentrated, purified on silica gel by automatic fast chromatography (EtOAc/PE 0-20%) to obtain 3-bromo-6-(2-fluoro-5-(trifluoromethoxy)benzyl)-7,8-dihydro-1,6-naphthyridin-5(6H)-one (2.356 g, Y: 54%). ES-API: $[M+H]^+$=419.1.

Step 4: Preparation of 3-(2-amino-[1,2,4]triazolo[1,5-a]pyridyl-7-yl)-6-(2-fluoro-5-(trifluoromethoxy)benzyl)-7,8-dihydro-1,6-naphthyridin-5(6H)-one: under the protection of nitrogen, 3-bromo-6-(2-fluoro-5-(trifluoromethoxy)benzyl)-7,8-dihydro-1,6-naphthyridin-5(6H)-one (1.885 g, 4.499 mmol), 7-(4,4,5,5-tetramethyl-1,3,2-dioxaborolan-2-yl)-[1,2,4]triazolo[1,5-a]pyridyl-2-amine (1.602 g, 8.998 mmol), sodium carbonate (1.192 g, 11.248 mmol), 1,1'-bis(diphenylphosphino)ferrocene-palladium(II)dichloride dichloromethane complex (184 mg, 0.225 mmol) were dissolved in dioxane (30 mL) and $H_2O$ (6 mL), the mixture was replaced with nitrogen for three times, and reacted at 95° C. overnight, cooled to room temperature, the reaction mixture was added into EtOAc (50 mL), then washed with water (30 mL*3) and saturated sodium chloride solution (30 mL*3), purified on silica gel by automatic fast chromatography (EtOAc/PE 0-100%, followed by DCM/MeOH 0-4%) to obtain light yellow compound 3-(2-amino-[1,2,4]triazolo[1,5-a]pyridyl-7-yl)-6-(2-fluoro-5-(trifluoromethoxy)benzyl)-7,8-dihydro-1,6-naphthyridin-5(6H)-one (Z48, 1.426 g, Y: 67%) with 95% purity. ES-API: $[M+H]^+$=473.0. $^1H$ NMR (400 MHz, DMSO-d6) δ 9.10 (d, J=2.4 Hz, 1H), 8.64 (d, J=6.8 Hz, 1H), 8.52 (d, J=2.4 Hz, 1H), 7.80 (d, J=1.6 Hz, 1H), 7.40-7.45 (m, 3H), 7.30 (dd, J1=2.0 Hz, J2=6.8 Hz, 1H), 6.10 (s, 2H), 4.82 (s, 2H), 3.73 (t, J=6.8 Hz, 2H), 3.21 (t, J=6.8 Hz, 2H).

Example 49 Preparation of N-(7-(5-oxo-6-(1-(2-(trifluoromethoxy)phenyl)ethyl)-5,6,7,8-tetrahydro-1,6-naphthyridin-3-yl)-[1,2,4]triazolo[1,5-a]pyridyl-2-yl)acetamide (Z49)

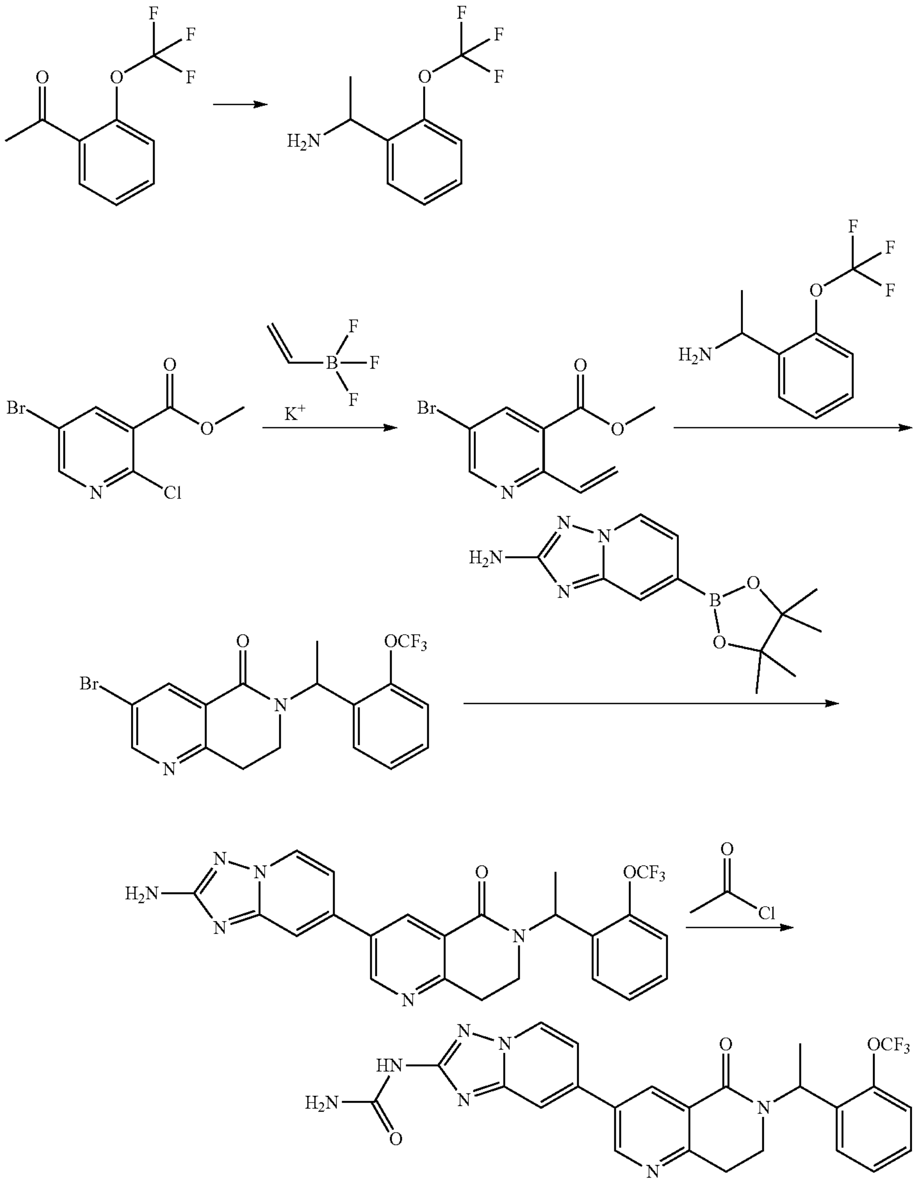

Z49

Step 1: Preparation of 1-(2-(trifluoromethoxy)phenyl) ethyl-1-amine: $NH_4OAc$ (28.3 g, 367.377 mmol) was added into a solution of 1-(2-(trifluoromethoxy)phenyl)ethyl-1-one (5 g, 24.492 mmol) in methanol (70 mL) and acetonitrile (70 mL), the reaction mixture was heated to 65° C. and reacted for two hours, cooled to room temperature, $NaBH_3CN$ (2.309 g, 36.738 mmol) was added to above solution, the reaction mixture was heated to 65° C. and stirred overnight. After the reaction was completed, the mixture was cooled to room temperature, the solvent was spun off under reduced pressure, the residue was dissolved in EtOH (50 mL), washed with water (25 mL*3) and saturated sodium chloride solution (25 mL*3), the combined organic layers were concentrated, purified on silica gel by automatic fast chromatography to obtain 1-(2-(trifluoromethoxy)phenyl)ethyl-1-amine (1.9 g, Y: 38%). ES-API: $[M+H]^+$=206.1.

Step 2: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 3: Preparation of 3-bromo-6-(1-(2-(trifluoromethoxy)phenyl)ethyl)-7,8-dihydro-1,6-naphthyridin-5 (6H)-one: methyl 5-bromo-2-vinylnicotinate (780 mg, 3.222 mmol) and 1-(2-(trifluoromethoxy)phenyl)ethyl-1-amine (1.653 g, 8.055 mmol) were mixed in DMA (10 mL) in a microwave bottle. The reaction was subjected to microwave radiation at 150° C. for eight hours, then cooled to room temperature, ethyl acetate (50 mL) was added, the reaction mixture was washed with water (25 mL*3) and saturated sodium chloride solution (25 mL*3), the combined organic layers were concentrated, purified on silica gel by automatic fast chromatography to obtain 3-bromo-6-(1-(2-(trifluoromethoxy)phenyl)ethyl)-7,8-dihydro-1,6-naphthyridin-5 (6H)-one (769 mg, Y: 57%). ES-API: $[M+H]^+$=415.0.

Step 4: Preparation of 3-(2-amino-[1,2,4]triazolo[1,5-a] pyridyl-7-yl)-6-(1-(2-(tri(trifluoromethoxy)phenyl)ethyl)-7,8-dihydro-1,6-naphthyridin-5(6H)-one: under the protection of nitrogen, 3-bromo-6-(1-(2-(trifluoromethoxy)phenyl) ethyl)-7,8-dihydro-1,6-naphthyridin-5(6H)-one (385 mg, 0.927 mmol), 7-(4,4,5,5-tetramethyl-1,3,2-dioxaborolan-2-yl)-[1,2,4]triazolo[1,5-a]pyridyl-2-amine (413 mg, 2.318 mmol), sodium carbonate (295 mg, 2.781 mmol), [1,1'-bis (diphenylphosphino)ferrocene-palladium(II)dichloride dichloromethane complex (38 mg, 0.046 mmol) were dissolved in dioxane (15 mL) and $H_2O$ (3 mL), the mixture was replaced with nitrogen for three times, and reacted at 95° C. for 1.5 hours, cooled to room temperature, the reaction mixture was added into EtOAc (20 mL), washed with water (15 mL*3) and saturated sodium chloride solution (15 mL*3), the combined organic layers were concentrated, the residue was purified by alkaline HPLC to obtain white product 3-(2-amino-[1,2,4]triazolo[1,5-a]pyridyl-7-yl)-6-(1-(2-(tri(trifluoromethoxy)phenyl)ethyl)-7,8-dihydro-1,6-naphthyridin-5(6H)-one (154.5 mg, Y: 36%). ES-API: $[M+H]^+$=469.1.

Step 5: Preparation of N-(7-(5-oxo-6-(1-(2-(trifluoromethoxy)phenyl)ethyl)-5,6,7,8-tetrahydro-1,6-naphthyridin-3-yl)-[1,2,4]triazolo[1,5-a]pyridyl-2-yl)acetamide: 3-(2-Amino-[1,2,4]triazolo[1,5-a]pyridyl-7-yl)-6-(1-(2-(tri (trifluoromethoxy)phenyl)ethyl)-7,8-dihydro-1,6-naphthyridin-5(6H)-one (43 mg, 0.092 mmol), acetyl chloride (50 mg, 0.643 mmol), 4-dimethylaminopyridine (11 mg, 0.092 mmol) was dissolved in acetonitrile (10 mL), the reaction mixture was heated to 50° C. and reacted overnight, cooled to room temperature, concentrated to dryness under reduced pressure, the residue was purified by alkaline HPLC to obtain white compound N-(7-(5-oxo-6-(1-(2-(trifluoromethoxy)phenyl)ethyl)-5,6,7,8-tetrahydro-1,6-naphthyridin-3-yl)-[1,2,4]triazolo[1,5-a]pyridyl-2-yl)acetamide (Z49, 5.3 mg, Y: 16%). ES-API: $[M+H]^+$=511.1. $^1H$ NMR (400 MHz, DMSO-d6) δ 10.85 (s, 1H), 9.12 (d, J=2.0 Hz, 1H), 8.95 (d, J=5.2 Hz, 1H), 8.58 (d, J=2.0 Hz, 1H), 8.14 (s, 1H), 7.73 (dd, J1=2.0 Hz, J2=6.4 Hz, 1H), 7.56 (dd, J1=1.2 Hz, J2=5.6 Hz, 1H), 7.51-7.47 (m, 2H), 7.40-7.38 (m, 1H), 6.19-6.15 (m, 1H), 3.64-3.58 (m, 1H), 3.20-3.08 (m, 2H), 3.00-2.93 (m, 1H), 2.16 (s, 3H), 1.58 (d, J=5.6 Hz, 3H).

Example 50 Preparation of 3-(2-amino-[1,2,4]triazolo[1,5-a]pyridyl-7-yl)-6-(3-(trifluoromethoxy) benzyl)-7,8-dihydro-1,6-naphthyridin5(6H)-one (Z50)

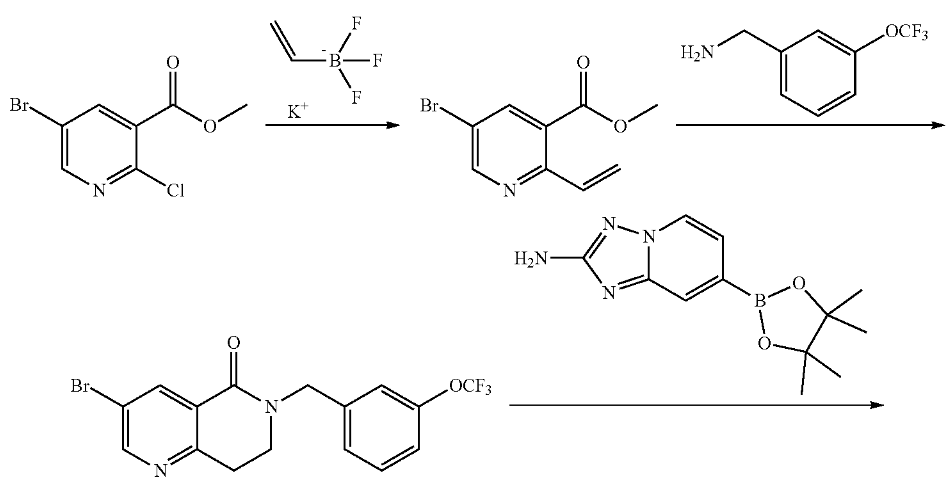

-continued

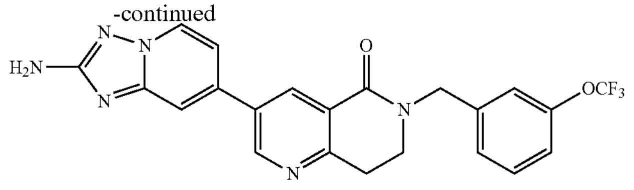

Z50

Step 1: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 55%). ES-API: $[M+H]^+$=242.1.

Step 2: Preparation of 3-bromo-6-(3-(trifluoromethoxy)benzyl)-7,8-dihydro-1,6-naphthyridin-5(6H)-one: Methyl 5-bromo-2-vinylnicotinate (280 mg, 1.157 mmol) and (3-(trifluoromethoxy)phenyl)methylamine (726 mg, 3.471 mmol) were mixed in DMA (5 mL) in a microwave bottle. The reaction was subjected to microwave radiation at 150° C. for three hours, then cooled to room temperature, ethyl acetate (20 mL) was added, the reaction mixture was washed with water (15 mL*3) and saturated sodium chloride solution (15 mL*3), the combined organic layers were concentrated, purified on silica gel by automatic fast chromatography to obtain 3-bromo-6-(3-(trifluoromethoxy)benzyl)-7,8-dihydro-1,6-naphthyridin-5(6H)-one (300 mg, Y: 62%). ES-API: $[M+H]^+$=401.1.

Step 3: Preparation of 3-(2-amino-[1,2,4]triazolo[1,5-a]pyridyl-7-yl)-6-(3-(trifluoromethoxy)benzyl)-7,8-dihydro-1,6-naphthyridin-5(6H)-one: under the protection of nitrogen, 3-bromo-6-(3-(trifluoromethoxy)benzyl)-7,8-dihydro-1,6-naphthyridin-5(6H)-one (50 mg, 0.125 mmol), 7-(4,4,5,5-tetramethyl-1,3,2-dioxaborolan-2-yl)-[1,2,4]triazolo[1,5-a]pyridyl-2-amine (56 mg, 0.313 mmol), sodium carbonate (40 mg, 0.375 mmol), [1,1'-bis(diphenylphosphino)ferrocene-palladium(II)dichloride dichloromethane complex (5 mg, 0.00625 mmol) were dissolved in dioxane (6 mL) and $H_2O$ (1.2 mL), the mixture was replaced with nitrogen for three times, and reacted at 95° C. overnight, cooled to room temperature, the reaction mixture was added into EtOAc (30 mL), washed with water (15 mL*3) and saturated sodium chloride solution (15 mL*3), the combined organic layers were concentrated, the residue was purified by alkaline HPLC to obtain white product 3-(2-amino-[1,2,4]triazolo[1,5-a]pyridyl-7-yl)-6-(3-(trifluoromethoxy)benzyl)-7,8-dihydro-1,6-naphthyridin-5(6H)-one (Z50, 16.14 mg, Y: 29%). ES-API: $[M+H]^+$=455.0. $^1$H NMR (400 MHz, DMSO-d6) δ 9.10 (d, J=2.0 Hz, 1H), 8.65 (d, J=5.6 Hz, 1H), 8.54 (d, J=1.6 Hz, 1H), 7.81 (s, 1H), 7.51 (t, J1=6.4 Hz, J2=12.4 Hz, 1H), 7.41 (d, J=6.0 Hz, 1H), 7.37 (s, 1H), 7.31-7.30 (m, 2H), 6.11 (s, 2H), 4.82 (s, 2H), 3.68 (t, J1=6.0 Hz, J2=11.2 Hz, 2H), 3.20 (t, J1=5.6 Hz, J2=10.8 Hz, 2H).

Example 51 Preparation of 3-(2-amino-[1,2,4]triazolo[1,5-a]pyridyl-7-yl)-6-(5-fluoro-2-(1-methyl-1H-pyrazol-4-yl)benzyl)-7,8-dihydro-1,6-naphthyridin-5(6H)-one (Z51)

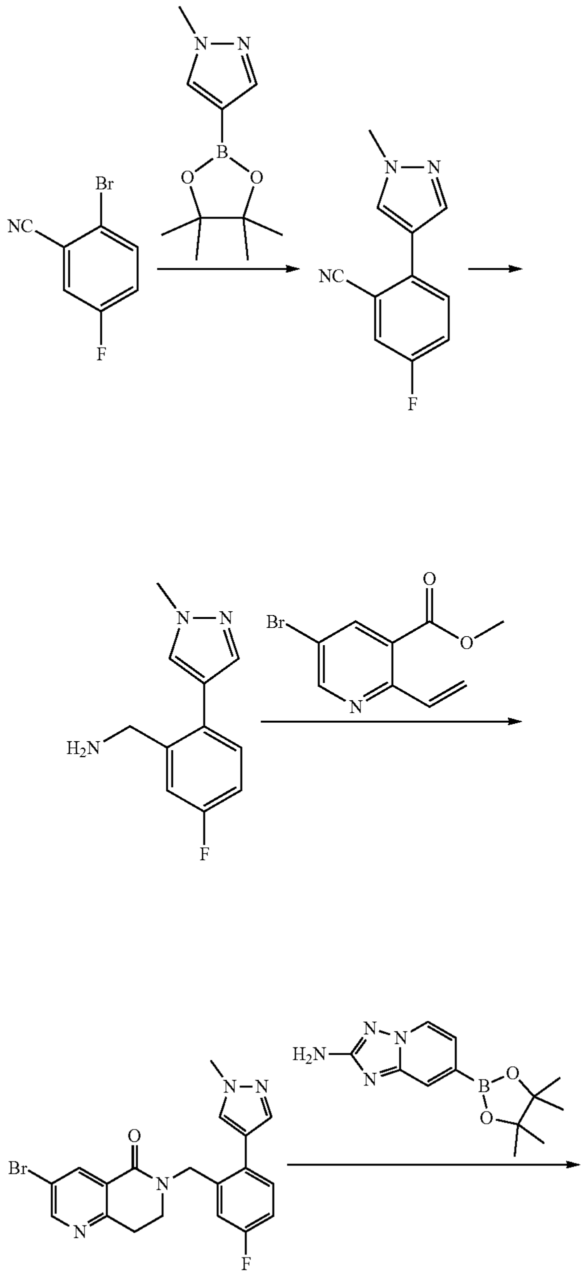

-continued

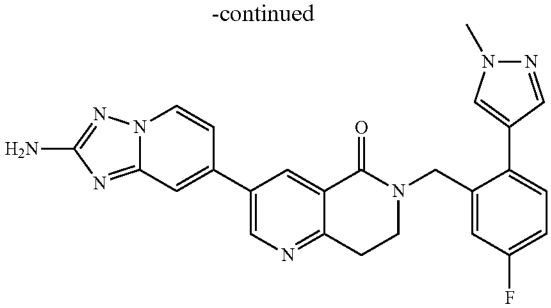

Z51

Step 1: Preparation of 5-fluoro-2-(1-methyl-1H-pyrazol-4-yl)benzonitrile: under the protection of nitrogen, 2-bromo-5-fluorobenzonitrile (2.187 g, 10.934 mmol), 1-methyl-4-(4,4,5,5-tetramethyl-1,3,2-dioxaborinan-2-yl)-1H-pyrazole (3.411 g, 16.401 mmol), sodium carbonate (2.898 g, 27.335 mmol), [1,1'-bis(diphenylphosphino)ferrocene-palladium (II)dichloride dichloromethane complex (446 mg, 0.547 mmol) were dissolved in dioxane (40 mL) and $H_2O$ (8 mL), the mixture was replaced with nitrogen for three times, the reaction mixture was heated to 100° C. in oil bath overnight, cooled to room temperature, the reaction mixture was added into ethyl acetate (30 mL), washed with water (20 mL*3) and saturated sodium chloride solution (20 mL*3), the combined organic layers were concentrated, purified on silica gel by automatic fast chromatography to obtain 5-fluoro-2-(1-methyl-1H-pyrazol-4-yl)benzonitrile (1.1 g, Y: 50%). ES-API: $[M+H]^+$=202.1.

Step 2: Preparation of (5-fluoro-2-(1-methyl-1H-pyrazol-4-yl)phenyl)methylamine: $BH_3$-THF (15.2 mL, 15.219 mmol) was added into a solution of 5-fluoro-2-(1-methyl-1H-pyrazol-4-yl)benzonitrile (1.021 g, 5.073 mmol) in THF (30 mL) at room temperature, the reaction mixture was heated to 50° C. and stirred overnight. LCMS showed the reaction was completed, the reaction mixture cooled to room temperature, MeOH was slowly added into the mixture dropwise for quenching the reaction, the reaction mixture was concentrated, the residue was dissolved in 1 N HCl (aq) (20 mL), extracted with DCM/i-PrOH (30 mL*3), the combined organic phase was concentrated to dryness to obtain light yellow transparent liquid (5-fluoro-2-(1-methyl-1H-pyrazol-4-yl)phenyl)methylamine (260 mg, Y: 25%). ES-API: $[M+H]^+$=206.1.

Step 3: Preparation of 3-bromo-6-(5-fluoro-2-(1-methyl-1H-pyrazol-4-yl)benzyl)-7,8-dihydro-1,6-naphthyridin-5(6H)-one: methyl 5-bromo-2-vinylnicotinate (252 mg, 1.041 mmol) and (5-fluoro-2-(1-methyl-1H-pyrazol-4-yl)phenyl)methylamine (257 mg, 1.249 mmol) were mixed in DMA (5 mL) in a microwave bottle. The reaction was subjected to microwave at 150° C. for two hours, cooled to room temperature, the reaction mixture was added into ethyl acetate (15 mL), then washed with water (15 mL*3) and saturated sodium chloride solution (15 mL*3), the combined organic layers were concentrated, purified on silica gel by automatic fast chromatography to obtain 3-bromo-6-(5-fluoro-2-(1-methyl-1H-pyrazol-4-yl)benzyl)-7,8-dihydro-1,6-naphthyridin-5(6H)-one (410 mg, Y: 95%). ES-API: $[M+H]^+$=415.1.

Step 4: Preparation of 3-(2-amino-[1,2,4]triazolo[1,5-a]pyridyl-7-yl)-6-(5-fluoro-2-(1-methyl-1H-pyrazol-4-yl)benzyl)-7,8-dihydro-1,6-naphthyridin-5(6H)-one: under the protection of nitrogen, 3-bromo-6-(5-fluoro-2-(1-methyl-1H-pyrazol-4-yl)benzyl)-7,8-dihydro-1,6-naphthyridin-5(6H)-one (70 mg, 0.169 mmol), 7-(4,4,5,5-tetramethyl-1,3,2-dioxaborolan-2-yl)-[1,2,4]triazolo[1,5-a]pyridyl-2-amine (60 mg, 0.338 mmol), sodium carbonate (45 mg, 0.423 mmol), [1,1'-bis(diphenylphosphino)ferrocene-palladium (II)dichloride dichloromethane complex (7 mg, 0.00845 mmol) were dissolved in dioxane (10 mL) and $H_2O$ (2 mL), the mixture was replaced with nitrogen for three times, the reaction mixture was heated to 95° C. in oil bath overnight, cooled to room temperature, concentrated, the crude product was purified by alkaline HPLC to obtain white solid product 3-(2-amino-[1,2,4]triazolo[1,5-a]pyridyl-7-yl)-6-(5-fluoro-2-(1-methyl-1H-pyrazol-4-yl)benzyl)-7,8-dihydro-1,6-naphthyridin-5(6H)-one (Z51, 18.9 mg, Y: 24%). ES-API: $[M+H]^+$=469.1. $^1H$ NMR (400 MHz, DMSO-d6) δ 9.03 (d, J=2.4 Hz, 1H), 8.58 (d, J=5.2 Hz, 1H), 8.44 (d, J=2.0 Hz, 1H), 7.92 (s, 1H), 7.73 (d, J=0.8 Hz, 1H), 7.59 (d, J=0.8 Hz, 1H), 7.37-7.34 (m, 1H), 7.23 (dd, J1=1.6 Hz, J2=5.6 Hz, 1H), 7.10-7.06 (m, 1H), 7.01 (dd, J1=2.4 Hz, J2=8.4 Hz, 1H), 6.03 (s, 2H), 4.77 (s, 2H), 3.82 (s, 3H), 3.53 (t, J1=5.6 Hz, J2=10.8 Hz, 2H), 3.13 (t, J1=5.2 Hz, J2=10.4 Hz, 2H).

Example 52 Preparation of 3-(2-amino-[1,2,4]triazolo[1,5-a]pyridyl-7-yl)-6-(1-(4-fluorobenzyl)-1H-pyrazol-4-yl)-7,8-dihydro-1,6-naphthyridin-5(6H)-one (Z52)

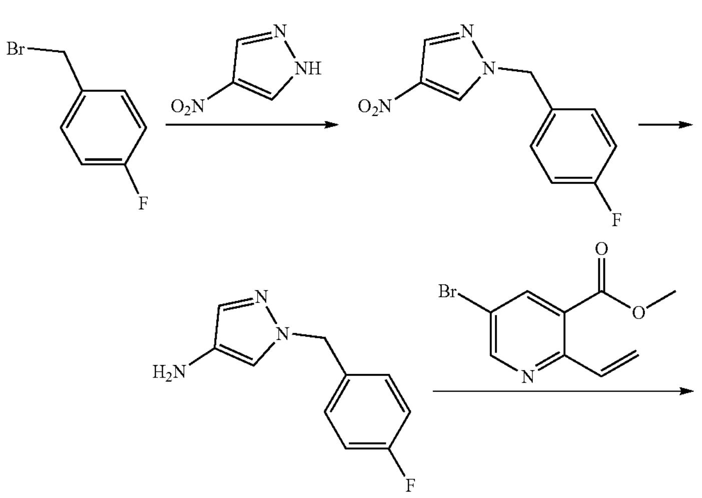

-continued

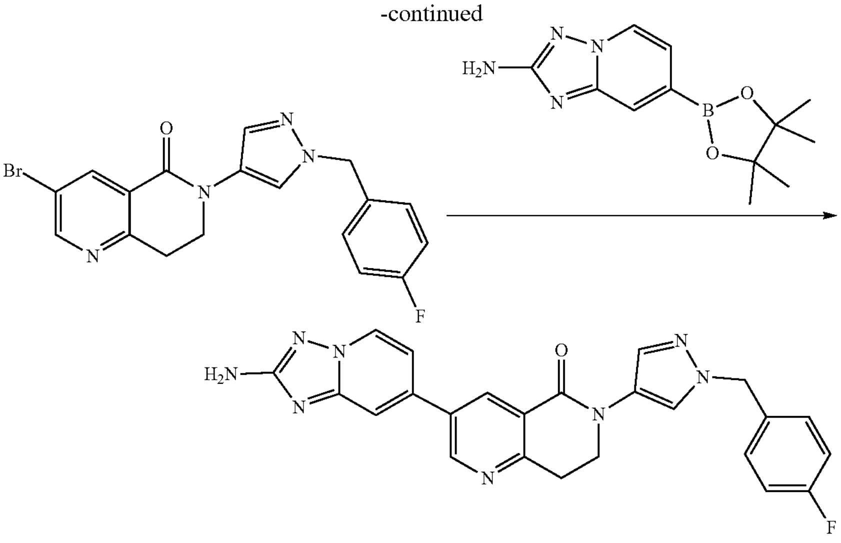

Z52

Step 1: Preparation of 1-(4-fluorobenzyl)-4-nitro-1H-pyrazole: 1-(bromomethyl)-4-fluorobenzene (1.672 g, 8.843 mmol), 4-nitro-1H-pyrazole (1 g, 8.843 mmol), potassium carbonate (2.44 g, 17.686 mmol) were dissolved in acetone (40 mL), the reaction mixture was heated and refluxed for two hours, cooled to room temperature, the solution was concentrated to dryness, the residue was purified on silica gel by automatic fast chromatography to obtain 1-(4-fluorobenzyl)-4-nitro-1H-pyrazole (1.348 g, Y: 69%). ES-API: $[M+H]^+$=222.1.

Step 2: Preparation of 1-(4-fluorobenzyl)-1H-pyrazol-4-amine: Pd/C (270 mg, 1.219 mmol) was added into a solution of 1-(4-fluorobenzyl)-4-nitro-1H-pyrazole (1.348 g, 6.094 mmol) in EtOH (30 mL), the reaction mixture was stirred overnight under the protection of hydrogen. After the reaction was completed, filtered, concentrated to dryness. Residue was purified by combiflash to obtain 1-(4-fluorobenzyl)-1H-pyrazol-4-amine (1.163 g, Y: 99%). ES-API: $[M+H]^+$=192.1.

Step 3: Preparation of 3-bromo-6-(1-(4-fluorobenzyl)-1H-pyrazol-4-yl)-7,8-dihydro-1,6-naphthyridin-5(6H)-one: methyl 5-bromo-2-vinylnicotinate (250 mg, 1.033 mmol) and 1-(4-fluorobenzyl)-1H-pyrazol-4-amine (395 mg, 2.066 mmol) were mixed in DMA (6 mL) in a microwave bottle. The reaction was subjected to microwave radiation at 150° C. for 2 hours, cooled to room temperature, the reaction mixture was added into ethyl acetate (15 mL), then washed with water (15 mL*3) and saturated sodium chloride solution (15 mL*3), the combined organic layers were concentrated, purified on silica gel by automatic fast chromatography to obtain 3-bromo-6-(1-(4-fluorobenzyl)-1H-pyrazol-4-yl)-7,8-dihydro-1,6-naphthyridin-5(6H)-one (164 mg, Y: 40%). ES-API: $[M+H]^+$=401.0.

Step 4: Preparation of 3-(2-amino-[1,2,4]triazolo[1,5-a]pyridyl-7-yl)-6-(1-(4-fluorobenzyl)-1H-pyrazol-4-yl)-7,8-dihydro-1,6-naphthyridin-5(6H)-one: under the protection of nitrogen, 3-bromo-6-(1-(4-fluorobenzyl)-1H-pyrazol-4-yl)-7,8-dihydro-1,6-naphthyridin-5(6H)-one (80 mg, 0.199 mmol), 7-(4,4,5,5-tetramethyl-1,3,2-dioxaborolan-2-yl)-[1,2,4]triazolo[1,5-a]pyridyl-2-amine (71 mg, 0.398 mmol), sodium carbonate (53 mg, 0.498 mmol), 1,1'-bis(diphenylphosphino)ferrocene-palladium(II)dichloride dichloromethane complex (8 mg, 0.00995 mmol) were dissolved in dioxane (5 mL) and $H_2O$ (1 mL), the mixture was replaced with nitrogen for three times, the reaction mixture was heated to 95° C. in oil bath for 3 hours, cooled to room temperature, concentrated, the crude product was purified by alkaline HPLC to obtain white solid 3-(2-amino-[1,2,4]triazolo[1,5-a]pyridyl-7-yl)-6-(1-(4-fluorobenzyl)-1H-pyrazol-4-yl)-7,8-dihydro-1,6-naphthyridin-5(6H)-one (Z52, 22.76 mg, Y: 25%). ES-API: $[M+H]^+$=455.1. $^1H$ NMR (400 MHz, DMSO-d6) δ 9.10 (d, J=2.0 Hz, 1H), 8.65 (d, J=5.6 Hz, 1H), 8.53 (d, J=1.6 Hz, 1H), 8.34 (s, 1H), 7.85 (s, 1H), 7.80 (d, J=1.2 Hz, 1H), 7.35-7.33 (m, 2H), 7.29 (dd, J1=1.6 Hz, J2=5.6 Hz, 1H), 7.21-7.17 (m, 2H), 6.10 (s, 2H), 5.34 (s, 2H), 4.10 (t, J1=5.6 Hz, J2=11.2 Hz, 2H), 3.31 (t, J1=2.8 Hz, J2=5.6 Hz, 2H).

Example 53 Preparation of 3-(2-amino-[1,2,4]triazolo[1,5-a]pyridyl-7-yl)-6-(2-fluoro-5-(1-methyl-1H-pyrazol-4-yl)benzyl)-7,8-dihydro-1,6-naphthyridin-5(6H)-one (Z53)

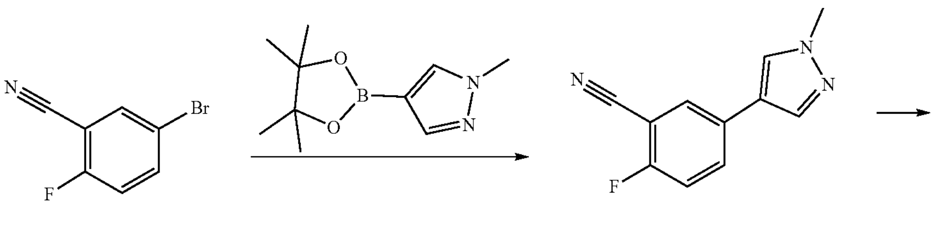

-continued

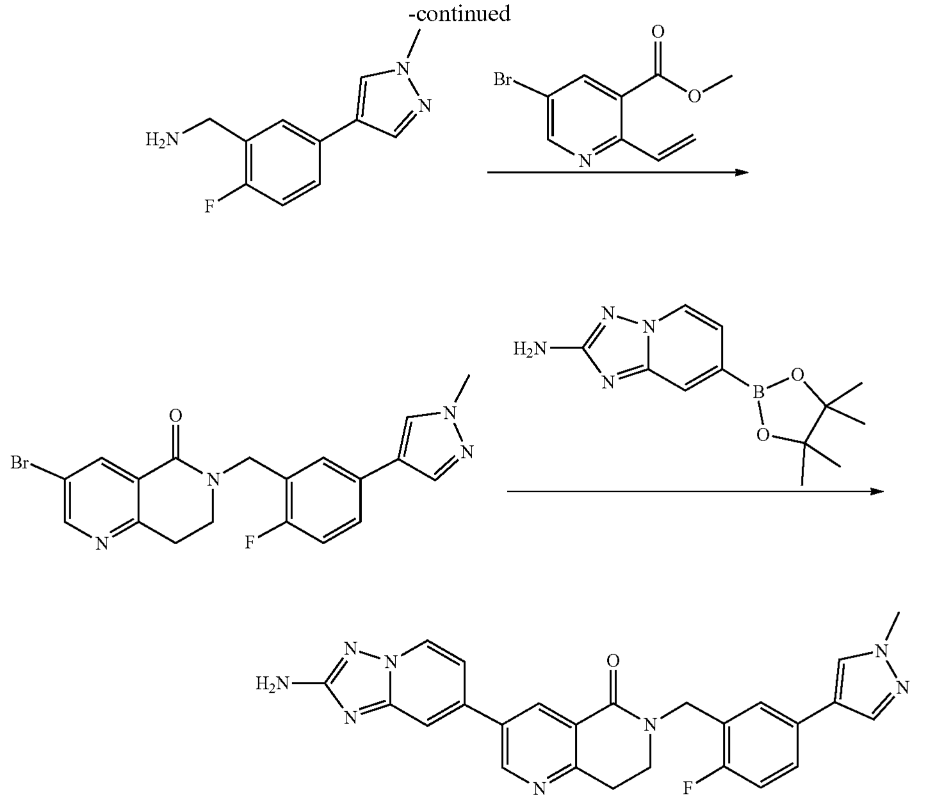

Z53

Step 1: Preparation of 2-fluoro-5-(1-methyl-1H-pyrazol-4-yl)benzonitrile: under the protection of nitrogen, 5-bromo-2-fluorobenzonitrile (2.0 g, 10 mmol), 1-methyl-4-(4,4,5,5-tetramethyl-1,3,2-dioxaborinan-2-yl)-1H-pyrazol (3.12 g, 15 mmol), potassium phosphate (6.368 g, 30 mmol), 1,1'-bis(diphenylphosphino)ferrocene-palladium(II)dichloride dichloromethane complex (408 mg, 0.5 mmol) were dissolved in dioxane (40 mL) and $H_2O$ (15 mL), the mixture was replaced with nitrogen for three times, the reaction mixture was heated to 105° C. in oil bath overnight, cooled to room temperature, the reaction mixture was added into ethyl acetate (30 mL), washed with water (20 mL*3) and saturated sodium chloride solution (20 mL*3), the combined organic layers were concentrated, purified on silica gel by automatic fast chromatography to obtain 2-fluoro-5-(1-methyl-1H-pyrazol-4-yl)benzonitrile (1.823 g, Y: 91%). ES-API: $[M+H]^+$=202.1.

Step 2: Preparation of ((2-fluoro-5-(1-methyl-1H-pyrazol-4-yl)phenyl)methylamine: Raney-Ni (239 mg, 2.791 mmol) was added into a solution of 2-fluoro-5-(1-methyl-1H-pyrazol-4-yl)benzonitrile (1.123 g, 5.582 mmol) in EtOH (20 mL). The reaction mixture was stirred overnight under the protection of hydrogen. After the reaction was completed, filtered, concentrated to dryness. The residue was purified by combiflash to obtain ((2-fluoro-5-(1-methyl-1H-pyrazol-4-yl)phenyl)methylamine (675 mg, Y: 59%). ES-API: $[M+H]^+$=206.1.

Step 3: Preparation of 3-bromo-6-(2-fluoro-5-(1-methyl-1H-pyrazol-4-yl)benzyl)-7,8-dihydro-1,6-naphthyridin-5(6H)-one: methyl 5-bromo-2-vinylnicotinate (50 mg, 0.207 mmol) and ((2-fluoro-5-(1-methyl-1H-pyrazol-4-yl)phenyl) methylamine (85 mg, 0.415 mmol) were mixed in DMA (2 mL) in a microwave bottle. The reaction was subjected to microwave radiation at 150° C. for 3 hours, cooled to room temperature, the reaction mixture added into ethyl acetate (15 mL), washed with water (15 mL*3) and saturated sodium chloride solution (15 mL*3), the combined organic layers were concentrated, purified on silica gel by automatic fast chromatography to obtain 3-bromo-6-(2-fluoro-5-(1-methyl-1H-pyrazol-4-yl)benzyl)-7,8-dihydro-1,6-naphthyridin-5(6H)-one (60 mg, Y: 70%). ES-API: $[M+H]^+$=415.1.

Step 4: Preparation of 3-(2-amino-[1,2,4]triazolo[1,5-a]pyridyl-7-yl)-6-(2-fluoro-5-(1-methyl-1H-pyrazol-4-yl)benzyl)-7,8-dihydro-1,6-naphthyridin-5(6H)-one: under the protection of nitrogen, 3-bromo-6-(2-fluoro-5-(1-methyl-1H-pyrazol-4-yl)benzyl)-7,8-dihydro-1,6-naphthyridin-5(6H)-one (60 mg, 0.145 mmol), 7-(4,4,5,5-tetramethyl-1,3,2-dioxaborolan-2-yl)-[1,2,4]triazolo[1,5-a]pyridyl-2-amine (51 mg, 0.289 mmol), sodium carbonate (38 mg, 0.363 mmol), [1,1'-bis(diphenylphosphino)ferrocene-palladium (II)dichloride dichloromethane complex (6 mg, 0.00725 mmol) were dissolved in dioxane (6 mL) and $H_2O$ (1.2 mL), the mixture was replaced with nitrogen for three times, the reaction mixture was heated to 95° C. in oil bath for 1.5 hours, cooled to room temperature, concentrated, the crude product was purified by alkaline HPLC to obtain white solid 3-(2-amino-[1,2,4]triazolo[1,5-a]pyridyl-7-yl)-6-(2-fluoro-5-(1-methyl-1H-pyrazol-4-yl)benzyl)-7,8-dihydro-1,6-naphthyridin-5(6H)-one (Z53, 25.41 mg, Y: 38%). ES-API: $[M+H]^+$=469.1. $^1H$ NMR (400 MHz, DMSO-d6) δ 9.09 (d, J=2.0 Hz, 1H), 8.64 (d, J=6.0 Hz, 1H), 8.53 (d, J=1.6 Hz, 1H), 8.11 (s, 1H), 7.82 (s, 1H), 7.80 (d, J=1.2 Hz, 1H), 7.55-7.52 (m, 2H), 7.30 (dd, J1=1.2 Hz, J2=5.6 Hz, 1H), 7.25-7.21 (m, 1H), 6.10 (s, 2H), 4.82 (s, 2H), 3.84 (s, 3H), 3.72 (t, J1=4.8 Hz, J2=10.4 Hz, 2H), 3.22 (t, J1=5.2 Hz, J2=10.4 Hz, 2H).

Example 54 Preparation of 3-(2-amino-[1,2,4]triazolo[1,5-a]pyridyl-7-yl)-6-(5-fluoro-2-(morpholinomethyl)benzyl)-7,8-dihydro-1,6-naphthyridin-5(6H)-one (Z54)

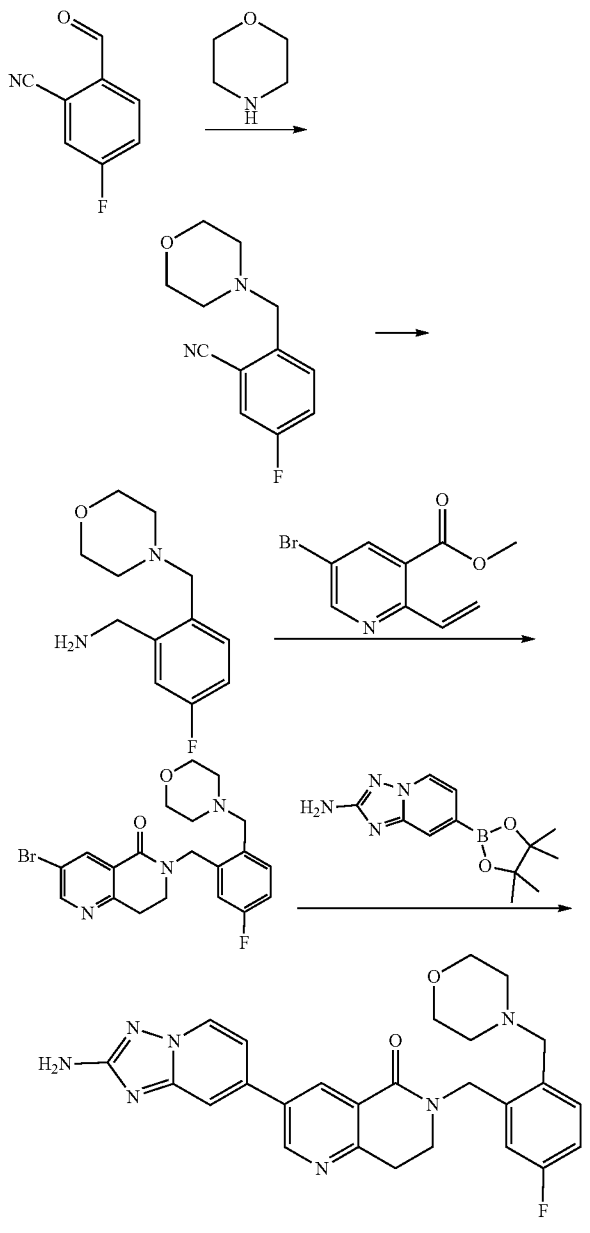

Z54

Step 1: Preparation of 5-fluoro-2-(morpholinomethyl)benzonitrile: under the protection of nitrogen, 5-fluoro-2-formylbenzonitrile (1 g, 6.711 mmol), morpholine (642 mg, 7.383 mmol), $NaBH(OAc)_3$ (2.134 g, 10.067 mmol) were dissolved in EtOH (40 mL). Under the protection of nitrogen, the reaction mixture was stirred overnight. After the reaction was completed, 1N NaOH(aq) (20 mL) was used for quenching the reaction, the reaction mixture was poured into EtOAc (30 mL) and $H_2O$ (30 mL) in batches, the organic phase was separated, washed with water (10 mL) and saturated sodium chloride solution (10 mL*2), dried, concentrated to obtain crude product 5-fluoro-2-(morpholinomethyl)benzonitrile (1.187 g, Y: 80%). ES-API: $[M+H]^+$=221.1.

Step 2: Preparation of (5-fluoro-2-(morpholinomethyl)phenyl)methylamine: Raney-Ni (240 mg, 2.698 mmol) was added into a solution of 5-fluoro-2-(morpholinomethyl)benzonitrile (1.187 g, 5.395 mmol) in EtOH (20 mL), the reaction mixture was stirred overnight under the protection of hydrogen. After the reaction was completed, the mixture was filtered to obtain crude product (5-fluoro-2-(morpholinomethyl)phenyl)methylamine (236 mg, Y: 20%). ES-API: $[M+H]^+$=225.1.

Step 3: Preparation of 3-bromo-6-(5-fluoro-2-(morpholinomethyl)benzyl)-7,8-dihydro-1,6-naphthyridin-5(6H)-one: methyl 5-bromo-2-vinylnicotinate (127 mg, 0.527 mmol) and (5-fluoro-2-(morpholinomethyl)phenyl)methylamine (236 mg, 1.054 mmol) were mixed in DMA (3 mL) in a microwave bottle. The reaction was subjected in microwave radiation at 150° C. for 3 hours, cooled to room temperature, the reaction mixture was added into ethyl acetate (15 mL), washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(5-fluoro-2-(morpholinomethyl)benzyl)-7,8-dihydro-1,6-naphthyridin-5(6H)-one (178 mg, Y: 78%). ES-API: $[M+H]^+$=434.1.

Step 4: Preparation of 3-(2-amino-[1,2,4]triazolo[1,5-a]pyridyl-7-yl)-6-(5-fluoro-2-(morpholinomethyl)benzyl)-7,8-dihydro-1,6-naphthyridin-5(6H)-one: under the protection of nitrogen, 7-(4,4,5,5-tetramethyl-1,3,2-dioxaborolan-2-yl)-[1,2,4]triazolo[1,5-a]pyridyl-2-amine (73 mg, 0.411 mmol), 3-bromo-6-(5-fluoro-2-(morpholinomethyl)benzyl)-7,8-dihydro-1,6-naphthyridin-5(6H)-one (89 mg, 0.206 mmol), sodium carbonate (55 mg, 0.515 mmol), 1,1'-bis(diphenylphosphino)ferrocene-palladium(II)dichloride dichloromethane complex (8.5 mg, 0.0103 mmol) were dissolved in dioxane (6 mL) and $H_2O$ (1 mL), the mixture was replaced with nitrogen for three times, the reaction mixture was heated to 95° C. in oil bath for 3 hours, cooled to room temperature, concentrated, the crude product was purified by alkaline HPLC to obtain white solid 3-(2-amino-[1,2,4]triazolo[1,5-a]pyridyl-7-yl)-6-(5-fluoro-2-(morpholinomethyl)benzyl)-7,8-dihydro-1,6-naphthyridin-5(6H)-one (Z54, 27.5 mg, Y: 28%). ES-API: $[M+H]^+$=488.2. 1H NMR (400 MHz, DMSO-d6) δ 9.10 (d, J=2.0 Hz, 1H), 8.65 (d, J=7.2 Hz, 1H), 8.54 (d, J=2.0 Hz, 1H), 7.80 (d, J=1.2 Hz, 1H), 7.34-7.08 (m, 3H), 6.10 (s, 2H), 4.94 (s, 2H), 3.66 (t, J1=6.0 Hz, J2=12.0 Hz, 2H), 3.52 (s, 6H), 3.20 (t, J1=6.8 Hz, J2=12.4 Hz, 2H), 2.35 (s, 4H).

Example 55 Preparation of 3-(2-amino-[1,2,4]triazolo[1,5-a]pyridyl-7-yl)-6-(1-(5-fluoro-2-(trifluoromethoxy)phenyl)ethyl)-7,8-dihydro-1,6-naphthyridin-5(6H)-one (Z55)

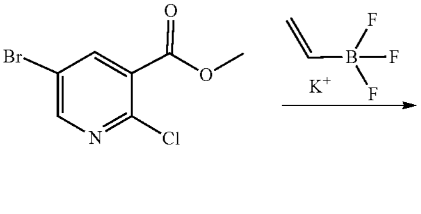

-continued

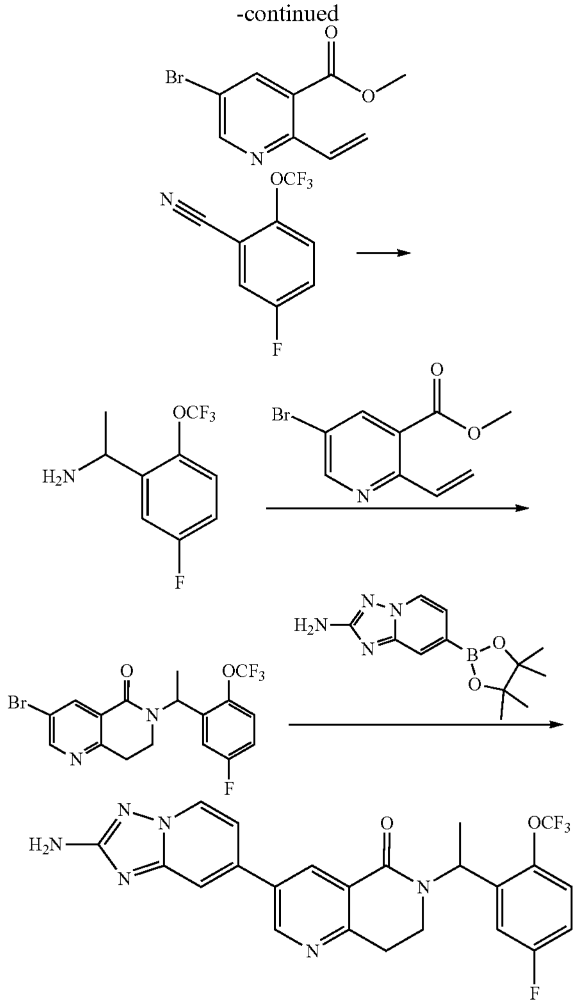

Z55

Step 1: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, the reaction mixture was heated to 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 2: Preparation of 1-(5-fluoro-2-(trifluoromethoxy)phenyl)ethyl-1-amine: under ice water bath, a solution of methylmagnesium iodide in tetrahydrofuran (3.252 mL, 9.756 mmol) was slowly added into a solution of 5-fluoro-2-(trifluoromethoxy)benzonitrile (1.0 g, 4.878 mmol) in THF (40 mL). Ice water bath was removed, the reaction mixture was stirred for one hour under the protection of nitrogen, then heated to 60° C. and stirred for one hour, the mixture was cooled to 0° C., a solution of lithium aluminum hydride in tetrahydrofuran (9.756 mL, 9.756 mmol) was added into reaction mixture, the reaction mixture was stirred at room temperature for 30 min, stirred at 60° C. for one hour, finally, stirred at room temperature overnight. LCMS showed the reaction was completed, the reaction mixture was cooled to 0° C., $H_2O$ (0.5 mL), 10% NaOH(aq) (0.5 mL) and $H_2O$ (2 mL) were added for quenching the reaction, white insoluble substance was precipitated, filtered, the filtrate was concentrated, the residue was purified by combiflash to obtain yellow liquid 1-(5-fluoro-2-(trifluoromethoxy)phenyl)ethyl-1-amine (234 mg, Y: 22%). ES-API: $[M+H]^+$=224.0.

Step 3: Preparation of 3-bromo-6-(1-(5-fluoro-2-(trifluoromethoxy)phenyl)ethyl)-7,8-dihydro-1,6-naphthyridin-5(6H)-one: methyl 5-bromo-2-vinylnicotinate (113 mg, 0.469 mmol) and 1-(5-fluoro-2-(trifluoromethoxy)phenyl)ethyl-1-amine (209 mg, 0.937 mmol) were mixed in DMA (4 mL) in a microwave bottle. The reaction was subjected to microwave radiation at 150° C. for 3 hours, cooled to room temperature, the reaction mixture was added into ethyl acetate (20 mL), washed with water (15 mL*3) and saturated sodium chloride solution (15 mL*3), the combined organic layers were concentrated, purified on silica gel by automatic fast chromatography (EtOAc/PE 0-20%) to obtain 3-bromo-6-(1-(5-fluoro-2-(trifluoromethoxy)phenyl)ethyl)-7,8-dihydro-1,6-naphthyridin-5(6H)-one (112 mg, Y: 55%). ES-API: $[M+H]^+$=433.0.

Step 4: Preparation of 3-(2-amino-[1,2,4]triazolo[1,5-a]pyridyl-7-yl)-6-(1-(5-fluoro-2-(trifluoromethoxy)phenyl)ethyl)-7,8-dihydro-1,6-naphthyridin-5(6H)-one: under the protection of nitrogen, 3-bromo-6-(1-(5-fluoro-2-(trifluoromethoxy)phenyl)ethyl)-7,8-dihydro-1,6-naphthyridin-5(6H)-one (112 mg, 0.259 mmol), (7-(4,4,5,5-tetramethyl-1,3,2-dioxaborolan-2-yl)-[1,2,4]triazolo[1,5-a]pyridyl-2-amine (115 mg, 0.648 mmol), sodium carbonate (69 mg, 0.648 mmol), 1,1'-bis(diphenylphosphino)ferrocene-palladium(II)dichloride dichloromethane complex (10 mg, 0.013 mmol) were dissolved in dioxane (10 mL) and $H_2O$ (2 mL), the mixture was replaced with nitrogen for three times, and reacted at 95° C. for 3 hours, cooled to room temperature, the reaction mixture was added into EtOAc (20 mL), washed with water (15 mL*3) and saturated sodium chloride solution (15 mL*3), the combined organic phases were concentrated, the residue was purified by alkaline HPLC to obtain white solid 3-(2-amino-[1,2,4]triazolo[1,5-a]pyridyl-7-yl)-6-(1-(5-fluoro-2-(trifluoromethoxy)phenyl)ethyl)-7,8-dihydro-1,6-naphthyridin-5(6H)-one (Z55, 34.9 mg, Y: 28%). S-API: $[M+H]^+$=487.1. $^1H$ NMR (400 MHz, DMSO-d6) δ 9.07 (d, J=1.6 Hz, 1H), 8.63 (d, J=5.6 Hz, 1H), 8.50 (d, J=2.4 Hz, 1H), 7.78 (d, J=0.8 Hz, 1H), 7.58 (dd, J1=2.4 Hz, J2=7.6 Hz, 1H), 7.46-7.44 (m, 1H), 7.36-7.32 (m, 1H), 7.28 (dd, J1=2.0 Hz, J2=6.0 Hz, 1H), 6.13-6.09 (m, 3H), 3.65-3.60 (m, 1H), 3.25-3.20 (m, 1H), 3.13-3.07 (m, 1H), 3.00-2.94 (m, 1H), 1.57 (d, J=5.6 Hz, 3H).

Example 56 Preparation of 3-(2-amino-[1,2,4]triazolo[1,5-a]pyridyl-7-yl)-6-(2-fluoro-5-(trifluoromethoxy)benzyl)-5-oxo-5,6,7,8-tetrahydro-1,6-naphthyridin-1-oxide (Z83) and 3-(2-amino-[1,2,4]triazolo[1,5-a]pyridyl-7-yl)-2-fluoro-6-(2-fluoro-5-(trifluoromethoxy)benzyl)-7,8-dihydro-1,6-naphthyridin-5(6H)-one (Z56)

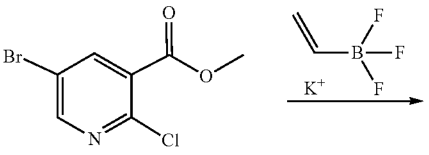

-continued

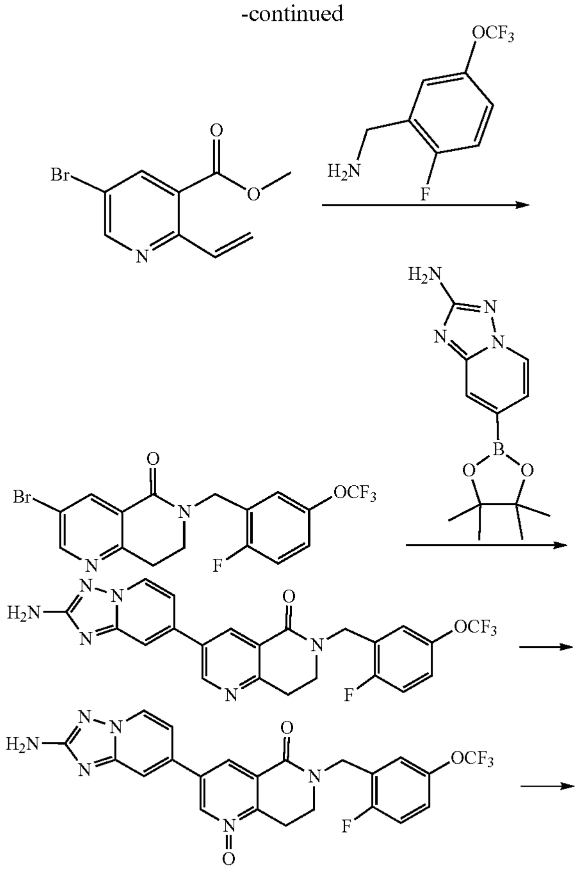

Z83

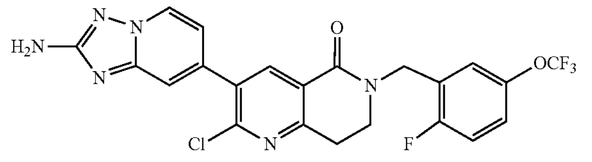

Z56

Step 1: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 55%). ES-API: $[M+H]^+$=242.1.

Step 2: Preparation of 3-bromo-6-(2-fluoro-5-(trifluoromethoxy)benzyl)-7,8-dihydro-1,6-naphthyridin-5(6H)-one: methyl 5-bromo-2-vinylnicotinate (2.5 g, 10.328 mmol) and (2-fluoro-5-(trifluoromethoxy)phenyl)methylamine (4.32 g, 20.656 mmol) were mixed in DMA (75 mL) in a microwave bottle. The reaction was subjected to microwave radiation at 150° C. for 3 hours, cooled to room temperature, the reaction mixture was added into 100 mL ethyl acetate, washed with water (30 mL*3) and saturated sodium chloride solution (30 mL*3), the combined organic layers were concentrated, purified on silica gel by automatic fast chromatography (EtOAc/PE 0-20%) to obtain 3-bromo-6-(2-fluoro-5-(trifluoromethoxy)benzyl)-7,8-dihydro-1,6-naphthyridin-5(6H)-one (2.356 g, Y: 62%). ES-API: $[M+H]^+$=419.1.

Step 3: Preparation of 3-(2-amino-[1,2,4]triazolo[1,5-a]pyridyl-7-yl)-6-(2-fluoro-5-(trifluoromethoxy)benzyl)-7,8-dihydro1,6-naphthyridin-5(6H)-one: under the protection of nitrogen, 3-bromo-6-(2-fluoro-5-(trifluoromethoxy)benzyl)-7,8-dihydro-1,6-naphthyridin-5(6H)-one (1.885 g, 4.499 mmol), 7-(4,4,5,5-tetramethyl-1,3,2-dioxaborolan-2-yl)-[1,2,4]triazolo[1,5-a]pyridyl-2-amine (1.602 g, 8.998 mmol), sodium carbonate (1.192 g, 11.248 mmol), 1,1'-bis(diphenylphosphino)ferrocene-palladium(II)dichloride dichloromethane complex (184 mg, 0.225 mmol) were dissolved in dioxane (30 mL) and $H_2O$ (6 mL), the mixture was replaced with nitrogen for three times, and reacted at 95° C. overnight, cooled to room temperature, the reaction mixture was added into EtOAc (50 mL), washed with water (30 mL*3) and saturated sodium chloride solution (30 mL*3), the combined organic phases were concentrated, purified on silica gel by automatic fast chromatography (EtOAc/PE 0-100%, followed by DCM/MeOH 0-4%) to obtain light yellow compound 3-(2-amino-[1,2,4]triazolo[1,5-a]pyridyl-7-yl)-6-(2-fluoro-5-(trifluoromethoxy)benzyl)-7,8-dihydro-1,6-naphthyridin-5(6H)-one (1.426 g, Y: 67%) with 95% purity. ES-API: $[M+H]^+$=473.0. $^1$H NMR (400 MHz, DMSO-d6) δ 9.10 (d, J=2.4 Hz, 1H), 8.64 (d, J=6.8 Hz, 1H), 8.52 (d, J=2.4 Hz, 1H), 7.80 (d, J=1.6 Hz, 1H), 7.40-7.45 (m, 3H), 7.30 (dd, J1=2.0 Hz, J2=6.8 Hz, 1H), 6.10 (s, 2H), 4.82 (s, 2H), 3.73 (t, J=6.8 Hz, 2H), 3.21 (t, J=6.8 Hz, 2H).

Step 4: Preparation of: 3-(2-amino-[1,2,4]triazolo[1,5-a]pyridyl-7-yl)-6-(2-fluoro-5-(trifluoromethoxy)benzyl)-5-oxo-5,6,7,8-tetrahydro-1,6-naphthyridin-1-oxide: 3-meta-chloroperoxybenzoic acid (165 mg, 0.954 mmol) was added into a solution of 3-(2-amino-[1,2,4]triazolo[1,5-a]pyridyl-7-yl)-6-(2-fluoro-5-(trifluoromethoxy)benzyl)-7,8-dihydro1,6-naphthyridin-5(6H)-one (300 mg, 0.636 mmol) in DCM (15 mL), the reaction mixture was stirred at room temperature overnight. After the reacted was completed, the reaction mixture was concentrated, the residue was purified by combiflash to obtain 3-(2-amino-[1,2,4]triazolo[1,5-a]pyridyl-7-yl)-6-(2-fluoro-5-(trifluoromethoxy)benzyl)-5-oxo-5,6,7,8-tetrahydro-1,6-naphthyridin-1-oxide (Z83, 277 mg, Y: 89%). ES-API: $[M+H]^+$=489.0. 1H NMR (400 MHz, DMSO-d6) δ 9.00 (d, J=1.2 Hz, 1H), 8.63 (d, J=5.6 Hz, 1H), 8.10 (d, J=1.2 Hz, 1H), 7.83 (d, J=1.2 Hz, 1H), 7.45 (d, J=4.0 Hz, 1H), 7.40 (d, J=5.6 Hz, 2H), 7.30 (dd, J1=1.6 Hz, J2=5.6 Hz, 1H), 6.13 (s, 2H), 4.79 (s, 2H), 3.72 (t, J1=5.6 Hz, J2=11.6 Hz, 2H), 3.23 (t, J1=5.6 Hz, J2=11.2 Hz, 2H).

Step 5: Preparation of 3-(2-amino-[1,2,4]triazolo[1,5-a]pyridyl-7-yl)-2-chloro-6-(2-fluoro-5-(trifluoromethoxy)benzyl)-7,8-dihydro-1,6-naphthyridin-5(6H)-one: 3-(2-amino-[1,2,4]triazolo[1,5-a]pyridyl-7-yl)-6-(2-fluoro-5-(trifluoromethoxy)benzyl)-5-oxo-5,6,7,8-tetrahydro-1,6-naphthyridin-1-oxide (277 mg, 0.568 mmol) were dissolved in phosphorus oxychloride (8 mL), the reaction mixture was heated to 80° C. and stirred overnight. After the reaction was completed, the reaction mixture was concentrated, the residue was purified by combiflash to obtain 3-(2-amino-[1,2,4]triazolo[1,5-a]pyridyl-7-yl)-2-chloro-6-(2-fluoro-5-(trifluoromethoxy)benzyl)-7,8-dihydro-1,6-naphthyridin-5(6H)-one (Z56, 267 mg, Y: 93%). ES-API: $[M+H]^+$=507.1.

Example 57 Preparation of 3-(2-amino-[1,2,4]triazolo[1,5-a]pyridyl-7-yl)-6-(2-fluoro-5-(trifluoromethoxy)benzyl)-2-methyl-7,8-dihydro-1,6-naphthyridin-5(6H)-one (Z57)

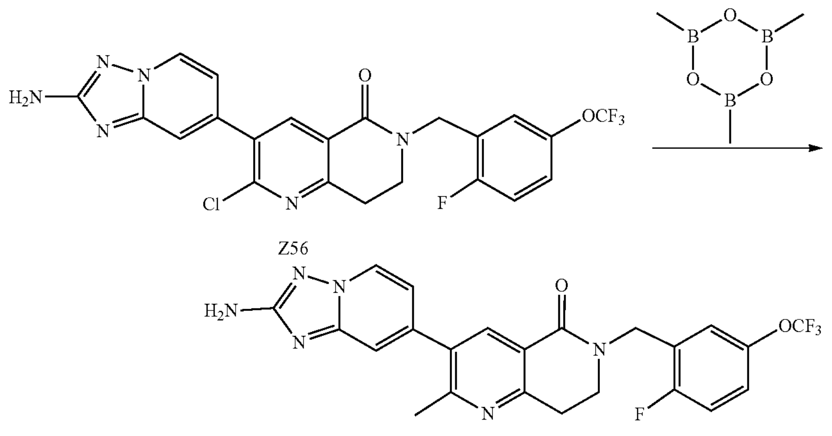

Z56

Z57

Under the protection of nitrogen, 3-(2-amino-[1,2,4]triazolo[1,5-a]pyridyl-7-yl)-2-chloro-6-(2-fluoro-5-(trifluoromethoxy)benzyl)-7,8-dihydro-1,6-naphthyridin-5(6H)-one (150 mg, 0.296 mmol), 2,4,6-trimethyl-1,3,5,2,4,6-trioxytriborane (112 mg, 0.889 mmol), cesium carbonate (241 mg, 0.740 mmol), [1,1'-bis(diphenylphosphino)ferrocene-palladium(II)dichloride dichloromethane complex (24 mg, 0.0296 mmol) were dissolved in dioxane (8 mL) and $H_2O$ (2 mL), the mixture was replaced with nitrogen for three times, the reaction mixture was heated to 110° C. in oil bath for 6 hours. After the reaction was completed, the mixture was cooled to room temperature, concentrated, the crude product was purified by alkaline HPLC to obtain off-white solid 3-(2-amino-[1,2,4]triazolo[1,5-a]pyridyl-7-yl)-6-(2-fluoro-5-(trifluoromethoxy)benzyl)-2-methyl-7,8-dihydro-1,6-naphthyridin-5(6H)-one (Z57, 3.7 mg, Y: 3%). ES-API: $[M+H]^+$=487.0.

Example 58 Preparation of cis-3-(2-amino-[1,2,4]triazolo[1,5-a]pyridyl-7-yl)-6-(4-fluoro-1-((R)-3,3,3-trifluoro-2-hydroxy-2-methylpropionyl)pyrrolidin-3-yl)-7,8-dihydro-1,6-naphthyridin-5(6H)-one (Z58)

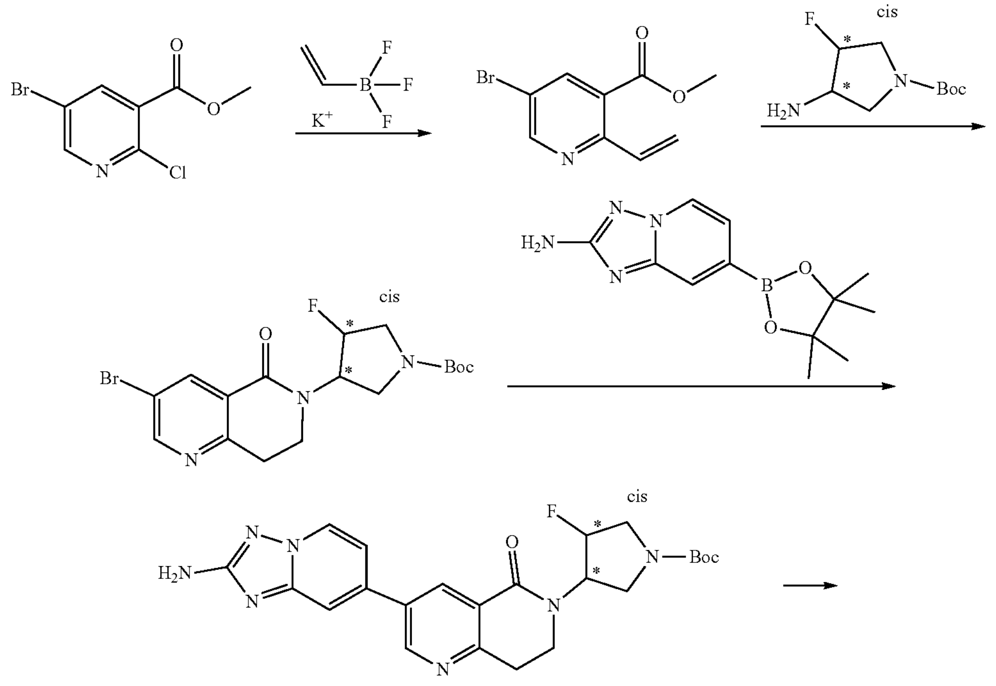

-continued

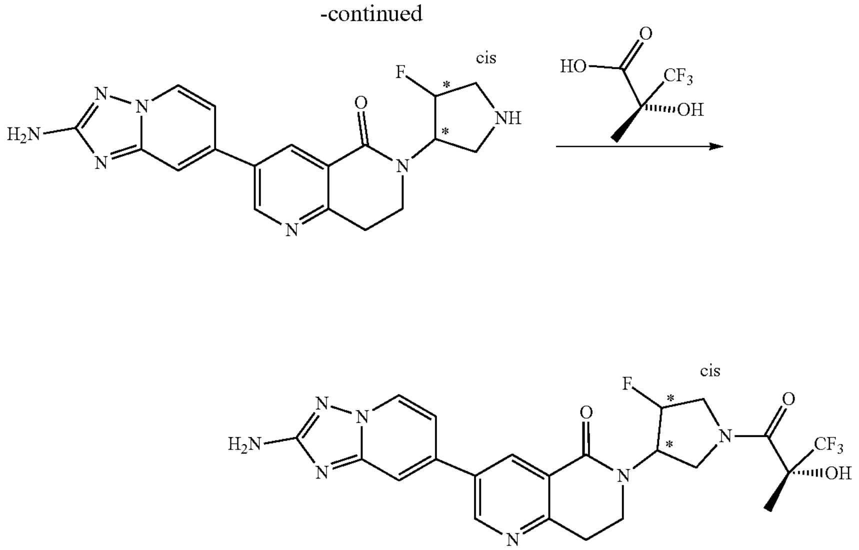

Z58

Step 1: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 55%). ES-API: $[M+H]^+$=242.1.

Step 2: Preparation of tert-butyl cis-3-(3-bromo-5-oxo-7,8-dihydro-1,6-naphthyridin-6(5H)-yl)-4-fluoropyrrolidine-1-formate: methyl 5-bromo-2-vinylnicotinate (842 mg, 3.494 mmol) and tert-butyl cis-3-amino-4-fluoropyrrolidine-1-carboxylate (2.138 g, 10.481 mmol) were mixed in DMA (10 mL) in a microwave bottle. The reaction was subjected to microwave radiation at 180° C. for 1.5 hours, cooled to room temperature, the reaction mixture was added into ethyl acetate (35 mL), washed with water (20 mL*3) and saturated sodium chloride solution (15 mL*3), the combined organic layers were concentrated, purified on silica gel by automatic fast chromatography (EtOAc/PE 0-50%) to obtain tert-butyl cis-3-(3-bromo-5-oxo-7,8-dihydro-1,6-naphthyridin-6(5H)-yl)-4-fluoropyrrolidine-1-formate (461 mg, Y: 32%). ES-API: $[M+H]^+$=414.1.

Step 3: Preparation of tert-butyl cis-3-(3-(2-amino-[1,2,4]triazolo[1,5-a]pyridyl-7-yl)-5-oxo-7,8-dihydro-1,6-naphthyridin-6(5H)-yl)-4-fluoropyrrolidine-1-carboxylate: tert-butyl cis-3-(3-bromo-5-oxo-7,8-dihydro-1,6-naphthyridin-6(5H)-yl)-4-fluoropyrrolidine-1-formate (230 mg, 0.557 mmol), 7-(4,4,5,5-tetramethyl-1,3,2-dioxaborolan-2-yl)-[1,2,4]triazolo[1,5-a]pyridyl-2-amine (362 mg, 1.392 mmol), sodium carbonate (148 mg, 1.392 mmol), 1,1'-bis(diphenylphosphino)ferrocene-palladium(II)dichloride dichloromethane complex (23 mg, 0.027 mmol), 1,4-dioxane (10 mL) and $H_2O$ (2 mL) were added into a 50 mL round bottom flask, the mixture was replaced with nitrogen for three times, and reacted at 95° C. for three hours, cooled to room temperature, filtered with suction, the filter cake was washed with ethyl acetate for three times to obtain the filtrate, the filtrate was concentrated to obtain crude product tert-butyl cis-3-(3-(2-amino-[1,2,4]triazolo[1,5-a]pyridyl-7-yl)-5-oxo-7,8-dihydro-1,6-naphthyridin-6(5H)-yl)-4-fluoropyrrolidine-1-carboxylate (351 mg, Y: 99%). ES-API: $[M+H]^+$=468.2.

Step 4: Preparation of cis-3-(2-amino-[1,2,4]triazolo[1,5-a]pyridyl-7-yl)-6-(4-fluoropyrrolidin-3-yl)-7,8-dihydro-1,6 naphthyridin-5(6H)-one: TFA (0.4 mL, 5.19 mmol) was added into a solution of tert-butyl cis-3-(3-(2-amino-[1,2,4]triazolo[1,5-a]pyridyl-7-yl)-5-oxo-7,8-dihydro-1,6-naphthyridin-6(5H)-yl)-4-fluoropyrrolidine-1-carboxylate (104 mg, 0.222 mmol) in DCM (2 mL), stirred at room temperature for one hour. After the reaction was completed, the mixture was concentrated to obtain crude product, the crude product was purified by combiflash to obtain cis-3-(2-amino-[1,2,4]triazolo[1,5-a]pyridyl-7-yl)-6-(4-fluoropyrrolidin-3-yl)-7,8-dihydro-1,6 naphthyridin-5(6H)-one (81 mg, Y: 99%). ES-API: $[M+H]^+$=368.1.

Step 5: Preparation of cis-3-(2-amino-[1,2,4]triazolo[1,5-a]pyridyl-7-yl)-6-(4-fluoro-1-((R)-3,3,3-trifluoro-2-hydroxy-2-methylpropionyl)pyrrolidin-3-yl)-7,8-dihydro-1,6-naphthyridin-5(6H)-one: (R)-3,3,3-trifluoro-2-hydroxy-2-methylpropionic acid (35.1 mg, 0.222 mmol), cis-3-(2-amino-[1,2,4]triazolo[1,5-a]pyridyl-7-yl)-6-(4-fluoropyrrolidin-3-yl)-7,8-dihydro-1,6-naphthyridin-5(6H)-one (81 mg, 0.222 mmol), PyBOP (116 mg, 0.222 mmol), DIPEA (86 mg, 0.666 mmol) and DMF (2 mL) were added into a 25 mL round bottom flask, and reacted at room temperature overnight. After the reaction was completed, the reaction mixture was purified by alkaline HPLC to obtain white solid cis-3-(2-amino-[1,2,4]triazolo[1,5-a]pyridyl-7-yl)-6-(4-fluoro-1-((R)-3,3,3-trifluoro-2-hydroxy-2-methylpropionyl)pyrrolidin-3-yl)-7,8-dihydro-1,6-naphthyridin-5(6H)-one (Z58, 47.76 mg, Y:42%). ES-API: $[M+H]^+$=508.1. $^1H$ NMR (400 MHz, DMSO-d6) δ 9.11 (s, 1H), 8.65 (d, J=5.6 Hz, 1H), 8.52 (s, 1H), 7.80 (s, 1H), 7.30 (dd, J1=1.6 Hz, J2=6.0 Hz, 1H), 7.11-7.08 (m, 1H), 6.10 (s, 2H), 5.44-5.15 (m, 2H), 4.43-4.23 (m, 1H), 4.12-3.98 (m, 1H), 3.84-3.70 (m, 4H), 3.20-3.15 (m, 2H), 1.57 (d, J=10.4 Hz, 3H).

Example 59 Preparation of 6-(2-fluoro-5-(trifluoromethoxy)benzyl)-3-(2-(methylamino)-[1,2,4]triazolo[1,5-a]pyridyl-7-yl)-7,8-dihydro-1,6-naphthyridin-5(6H)-one

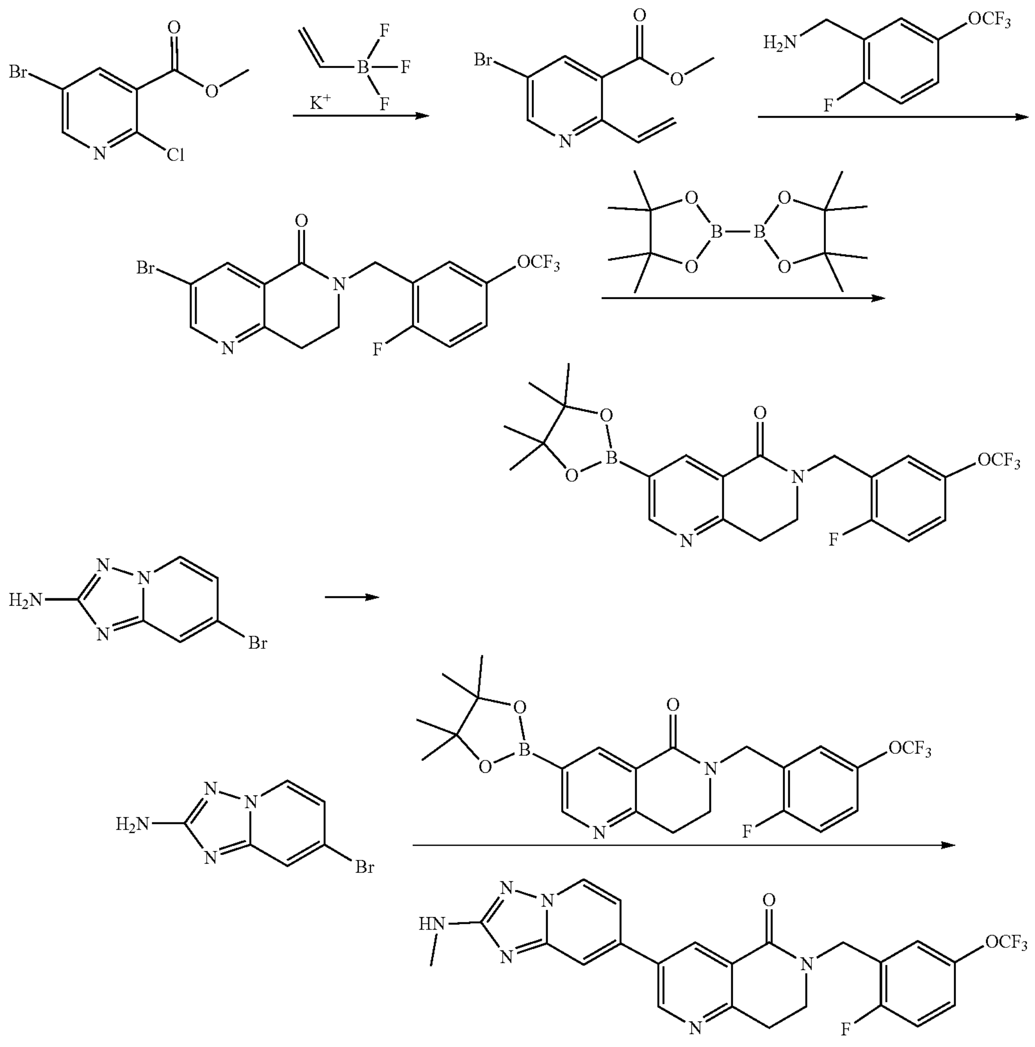

Z59

Step 1: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 55%). ES-API: $[M+H]^+$=242.1.

Step 2: Preparation of 3-bromo-6-(2-(trifluoromethoxy)benzyl)-7,8-dihydro-1,6-naphthyridin-5(6H)-one: methyl 5-bromo-2-vinylnicotinate (280 mg, 1.157 mmol) and ((2-fluoro-5-(trifluoromethoxy)phenyl)methylamine (726 mg, 3.471 mmol) were mixed in DMA (5 mL) in a microwave bottle. The reaction was subjected to microwave radiation at 150° C. for three hours, cooled to room temperature, the reaction mixture was added into ethyl acetate (15 mL), washed with water (15 mL*3) and saturated sodium chloride solution (15 mL*3), the combined organic layers were concentrated, purified on silica gel by automatic fast chromatography (EtOAc/PE 0-50%) to obtain 3-bromo-6-(2-fluoro-5-(trifluoromethoxy)benzyl)-7,8-dihydro-1,6-naphthyridin-5(6H)-one (300 mg, Y: 62%). ES-API: $[M+H]^+$=419.0.

Step 3: Preparation of 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one: 3-bromo-6-(2-fluoro-5-(trifluoromethoxy)benzyl)-7,8-dihydro-1,6-naphthyridin-5(6H)-one (200 mg, 0.477 mmol), bis(pinacolato)diboron (244 mg, 0.955 mmol), potassium acetate (117 mg, 1.193 mmol), [1,1'-bis(diphenylphosphino)

ferrocene]dichloropalladium(II) (35 mg, 0.0477 mmol) and 1,4-dioxane (10 mL) were added into a 100 mL round bottom flask, the mixture was replaced with nitrogen for three times, and reacted at 95° C. overnight, cooled to room temperature, filtered with suction, the filter cake was washed with ethyl acetate for three times to obtain the filtrate, the filtrate was concentrated to obtain crude product 6-(2-fluoro-5-(trifluoromethoxy)benzyl)-3-(4,4,5,5-tetramethyl-1,3,2-dioxaborinan-2-yl)-7,8-dihydro-1,6 naphthyridin-5(6H)-one (222 mg, Y: 99%). ES-API: $[M+H]^+$=385.1.

Step 4: Preparation of 7-bromo-N-methyl-[1,2,4]triazolo [1,5-a]pyridyl-2-amine: 7-bromo-[1,2,4]triazolo[1,5-a] pyridyl-2-amine (187 mg, 0.880 mmol), paraformaldehyde (264 mg, 8.80 mmol), sodium methanolate (190 mg, 3.52 mmol) were dissolved in methanol (5 mL), the reaction mixture was stirred at 80° C. for 2 hours, cooled to room temperature, the reaction mixture was added into sodium borohydride (167.2 mg, 4.40 mmol), heated to 80° C. and stirred for 2 hours. After the reaction was completed, the mixture was cooled to 0° C., acetone was slowly added for quenching the reaction, the reaction mixture was concentrated to dryness, the residue was dissolved in EtOAc (30 mL), washed with water (15 mL*2) and saturated sodium chloride solution (15 mL*2), the organic phase was concentrated to obtain 7-bromo-N-methyl-[1,2,4]triazolo[1,5-a] pyridyl-2-amine (100 mg, Y: 50%). ES-API: $[M+H]^+$= 227.0.

Step 5: Preparation of: 6-(2-fluoro-5-(trifluoromethoxy) benzyl)-3-(2-(methylamino)-[1,2,4]triazolo[1,5-a]pyridyl- 7-yl)-7,8-dihydro-1,6-naphthyridin-5(6H)-one. under the protection of nitrogen, 7-bromo-N-methyl-[1,2,4]triazolo[1, 5-a]pyridyl-2-amine (100 mg, 0.442 mmol), 6-(2-fluoro-5-(trifluoromethoxy)benzyl)-3-(4,4,5,5-tetramethyl-1,3,2-dioxaborinan-2-yl)-7,8-dihydro-1,6-naphthyridin-5(6H)-one (412 mg, 0.885 mmol), sodium carbonate (117 mg, 1.105 mmol), [1,1'-bis(diphenylphosphino)ferrocene-palladium (II)dichloride dichloromethane complex (18 mg, 0.0221 mmol) were dissolved in dioxane (10 mL) and $H_2O$ (2 mL), the mixture was replaced with nitrogen for three times, the reaction mixture was heated to 95° C. in oil bath for 3 hours. After the reaction was completed, the mixture was cooled to room temperature, concentrated, the crude product was purified by alkaline HPLC to obtain off-white solid 6-(2-fluoro-5-(trifluoromethoxy)benzyl)-3-(2-(methyl amino)-[1, 2,4]triazolo[1,5-a]pyridyl-7-yl)-7,8-dihydro-1,6-naphthyridin-5(6H)-one (Z59, 15.61 mg, Y: 7%). ES-API: $[M+H]^+$= 487.1. $^1H$ NMR (400 MHz, DMSO-d6) δ 9.10 (d, J=1.6 Hz, 1H), 8.70 (d, J=5.6 Hz, 1H), 8.51 (d, J=1.6 Hz, 1H), 7.82 (s, 1H), 7.44 (d, J=4.0 Hz, 1H), 7.40 (d, J=5.2 Hz, 1H), 7.31 (dd, J1=1.6 Hz, J2=5.6 Hz, 2H), 6.56-6.53 (m, 1H), 4.82 (s, 2H), 3.73 (t, J1=5.6 Hz, J2=10.8 Hz, 2H), 3.21 (t, J1=5.2 Hz, J2=10.8 Hz, 2H), 2.85 (d, J=3.6 Hz, 3H).

Example 60 Preparation of 3-(2-amino-[1,2,4]triazolo[1,5-a]pyridyl-7-yl)-6-(1-(2-fluoro-5-(trifluoromethoxy)phenyl)ethyl)-7,8-dihydro-1,6-naphthyridin-5(6H)-one (Z60)

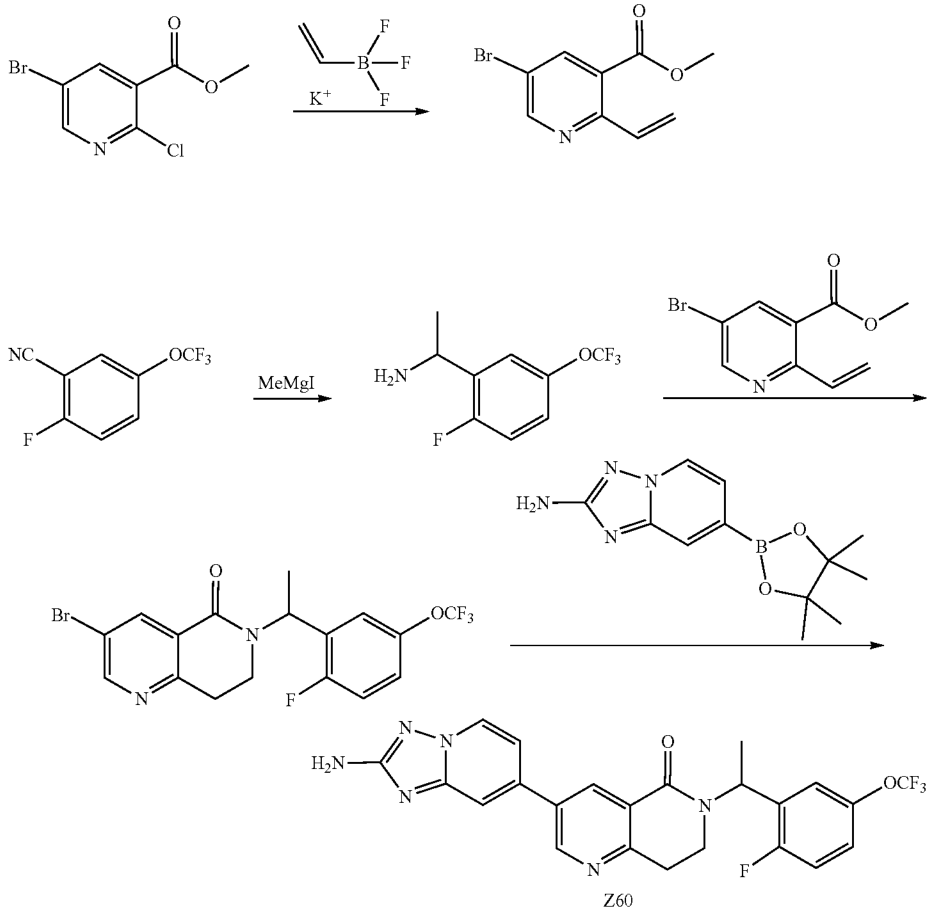

Z60

Step 1: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 2: Preparation of 1-(2-fluoro-5-(trifluoromethoxy) phenyl)ethyl-1-amine: under ice water bath, a solution of methylmagnesium iodide in tetrahydrofuran (4.878 mL, 14.634 mmol) was slowly added into a solution of 2-fluoro-5-(trifluoromethoxy)benzonitrile (1.5 g, 7.317 mmol) in THF (50 mL). Ice water bath was removed, the mixture was stirred for one hour under the protection of nitrogen, then heated to 60° C. and stirred for 1 hour. The mixture was cooled to 0° C., a solution of lithium aluminum hydride in tetrahydrofuran (14.634 mL, 14.634 mmol) was added into reaction mixture, the reaction mixture was stirred at room temperature for 30 min, stirred at 60° C. for one hour, finally, stirred at room temperature overnight. LCMS showed the reaction was completed, the reaction mixture was cooled to 0° C., $H_2O$ (0.75 mL), 10% NaOH(aq)(0.75 mL) and $H_2O$ (3 mL) were added for quenching the reaction, white insoluble substance was precipitated, filtered, the filtrate was concentrated, the residue was purified by combiflash to obtain yellow liquid 1-(2-fluoro-5-(trifluoromethoxy)phenyl)ethyl-1-amine (173 mg, Y: 11%). ES-API: $[M+H]^+$= 224.0.

Step 3: Preparation of 3-bromo-6-(1-(2-fluoro-5-(trifluoromethoxy)phenyl)ethyl)-7,8-dihydro-1,6-naphthyridin-5(6H)-one: methyl 5-bromo-2-vinylnicotinate (93 mg, 0.388 mmol) and 1-(2-fluoro-5-(trifluoromethoxy)phenyl)ethyl-1-amine (173 mg, 0.776 mmol) were mixed in DMA (2 mL) in a microwave bottle. The reaction was subjected to microwave radiation at 150° C. for three hours, cooled to room temperature, the reaction mixture was added into ethyl acetate (20 mL), washed with water (15 mL*3) and saturated sodium chloride solution (15 mL*3), the combined organic layers were concentrated, purified on silica gel by automatic fast chromatography (EtOAc/PE 0-20%) to obtain 3-bromo-6-(1-(2-fluoro-5-(trifluoromethoxy)phenyl)ethyl)-7,8-dihydro-1,6-naphthyridin-5(6H)-one (51 mg, Y: 30%). ES-API: $[M+H]^+$=388.0.

Step 4: Preparation of 3-(2-amino-[1,2,4]triazolo[1,5-a] pyridyl-7-yl)-6-(1-(2-fluoro-5-(trifluoromethoxy)phenyl) ethyl)-7,8-dihydro-1,6-naphthyridin-5(6H)-one: under the protection of nitrogen, 3-bromo-6-(1-(2-fluoro-5-(trifluoromethoxy)phenyl)ethyl)-7,8-dihydro-1,6-naphthyridin-5 (6H)-one (51 mg, 0.118 mmol), (7-(4,4,5,5-tetramethyl-1,3,2-dioxaborolan-2-yl)-[1,2,4]triazolo[1,5-a]pyridyl-2-amine (61 mg, 0.236 mmol), sodium carbonate (31 mg, 0.295 mmol), [1,1'-bis(diphenylphosphino)ferrocene-palladium (II)dichloride dichloromethane complex (5 mg, 0.0059 mmol) were dissolved in dioxane (5 mL) and $H_2O$ (1 mL), the mixture was replaced with nitrogen for three times, and reacted at 95° C. for 2 hours, cooled to room temperature, the reaction mixture was added into EtOAc (20 mL), washed with water (15 mL*3) and saturated sodium chloride solution (15 mL*3), the combined organic was concentrated, the residue was purified by alkaline HPLC to obtain white compound 3-(2-amino-[1,2,4]triazolo[1,5-a]pyridyl-7-yl)-6-(1-(2-fluoro-5-(trifluoromethoxy)phenyl)ethyl)-7,8-dihydro-1,6-naphthyridin-5(6H)-one (Z60, 23.8 mg, Y: 42%). ES-API: $[M+H]^+$=487.1. $^1$H NMR (400 MHz, DMSO-d6) δ 9.07 (d, J=1.6 Hz, 1H), 8.64 (d, J=5.6 Hz, 1H), 8.51 (d, J=2.4 Hz, 1H), 7.79 (d, J=0.8 Hz, 1H), 7.57-7.56 (m, 1H), 7.44-7.43 (m, 1H), 7.37 (t, J1=7.2 Hz, J2=14.8 Hz, 1H), 7.30 (dd, J1=1.6 Hz, J2=5.6 Hz, 1H), 6.10-6.05 (m, 3H), 3.69-3.63 (m, 1H), 3.30-3.27 (m, 1H), 3.17-3.11 (m, 1H), 3.06-2.99 (m, 1H), 1.60 (d, J=5.6 Hz, 3H).

Example 61 Preparation of 3-(2-amino-[1,2,4]triazolo[1,5-a]pyridyl-7-yl)-6-((3-(cyclopropylmethoxy)pyridyl-2-yl)methyl)-7,8-dihydro-1,6-naphthyridin-5(6H)-one (Z61)

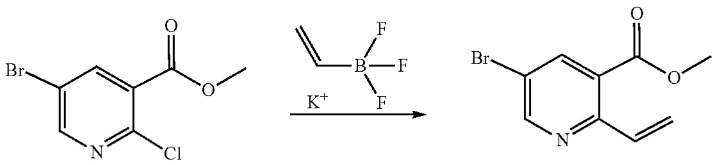

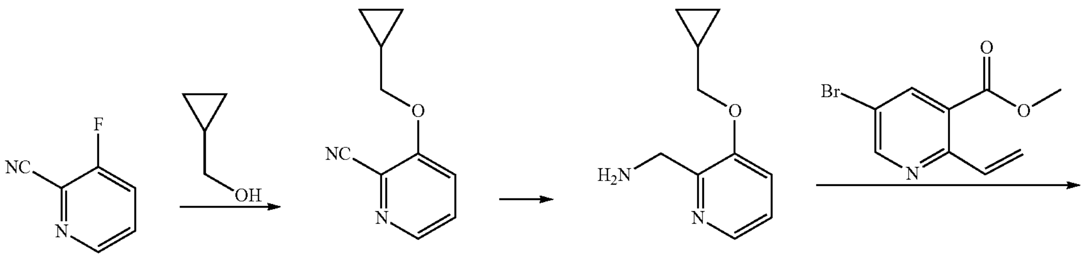

-continued

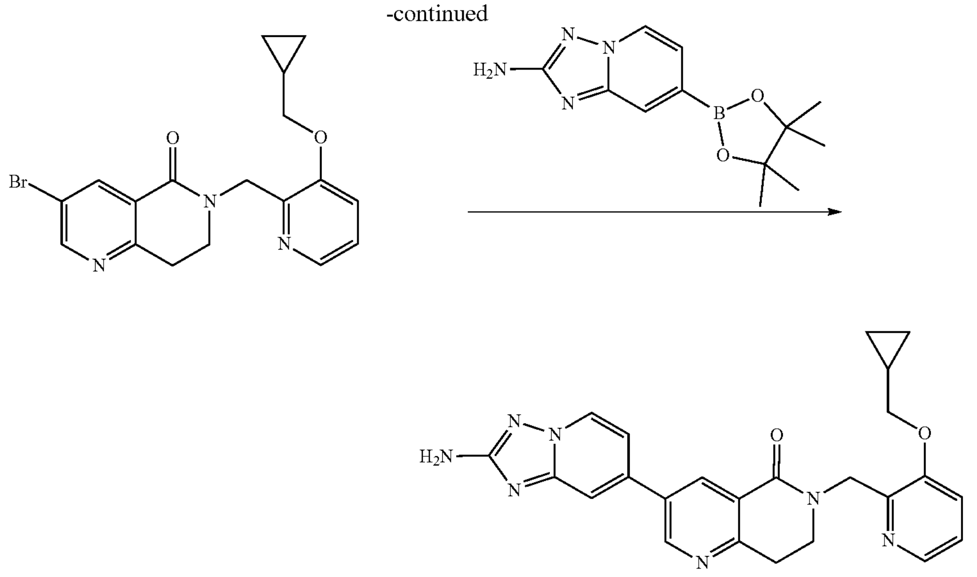

Z61

Step 1: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 2: Preparation of 3-(cyclopropylmethoxy)pyridinoline: under ice water bath, sodium hydride (655 mg, 16.380 mmol) was added into a solution of cyclopropylmethanol (889 mg, 12.285 mmol) in THF (30 mL), the reaction mixture was stirred at 0° C. for one hour. 3-Fluoropyridylcarbonitrile (1 g, 8.190 mmol) was added into reaction mixture, the reaction mixture was stirred at room temperature overnight. LCMS showed the reaction was completed, water (30 mL) was added for quenching the reaction under ice water bath, extracted with EtOAc (15 mL*3), the combined organic phases were washed with saturated sodium chloride solution (15 mL*3), concentrated to obtain crude product 3-(cyclopropylmethoxy)pyridinoline (1.648 g). ES-API: $[M+H]^+$=175.0.

Step 3: Preparation of (3-(cyclopropylmethoxy)pyridyl-2-yl)methylamine: Raney-Ni (165 mg, 1.855 mmol) was added into a solution of 3-(cyclopropylmethoxy)pyridinoline (1.648 g, 9.471 mmol) in EtOH (30 mL), the reaction mixture was stirred overnight under the protection of hydrogen. After the reaction was completed, the mixture was filtered, concentrated, the residue was purified by combiflash to obtain (3-(cyclopropylmethoxy)pyridyl-2-yl)methylamine (752 mg, Y: 45%). ES-API: $[M+H]^+$=179.1.

Step 4: Preparation of 3-bromo-6-((3-(cyclopropylmethoxy)pyridyl-2-yl)methyl)-7,8-dihydro-1,6-naphthyridin-5(6H)-one: methyl 5-bromo-2-vinylnicotinate (100 mg, 0.415 mmol) and (3-(cyclopropylmethoxy)pyridyl-2-yl)methylamine (148 mg, 0.830 mmol) were mixed in DMA (3 mL) in a microwave bottle. The reaction was subjected to microwave radiation at 180° C. for one hour, cooled to room temperature, the reaction mixture was added into ethyl acetate (30 mL), washed with water (15 mL*3) and saturated sodium chloride solution (15 mL*3), the combined organic layers were concentrated, purified on silica gel by automatic fast chromatography (EtOAc/PE 0-20%) to obtain 3-bromo-6-((3-(cyclopropylmethoxy)pyridyl-2-yl)methyl)-7,8-dihydro-1,6-naphthyridin-5(6H)-one (149 mg, Y: 93%). ES-API: $[M+H]^+$=388.0.

Step 5: Preparation of 3-(2-amino-[1,2,4]triazolo[1,5-a]pyridyl-7-yl)-6-((3-(cyclopropylmethoxy)pyridyl-2-yl)methyl)-7,8-dihydro-1,6-naphthyridin-5(6H)-one: under the protection of nitrogen, 3-bromo-6-((3-(cyclopropylmethoxy)pyridyl-2-yl)methyl)-7,8-dihydro-1,6-naphthyridin-5(6H)-one (50 mg, 0.129 mmol), (7-(4,4,5,5-tetramethyl-1,3,2-dioxaborolan-2-yl)-[1,2,4]triazolo[1,5-a]pyridyl-2-amine (67 mg, 0.258 mmol), sodium carbonate (34 mg, 0.323 mmol), [1,1'-bis(diphenylphosphino)ferrocene-palladium(II)dichloride dichloromethane complex (5 mg, 0.00645 mmol) were dissolved in dioxane (5 mL) and $H_2O$ (1 mL), the mixture was replaced with nitrogen for three times, and reacted at 95° C. for 2 hours, cooled to room temperature, the reaction mixture was added into EtOAc (20 mL), washed with water (15 mL*3) and saturated sodium chloride solution (15 mL*3), the combined organic were concentrated, the residue was purified by alkaline HPLC to obtain white compound 3-(2-amino-[1,2,4]triazolo[1,5-a]pyridyl-7-yl)-6-((3-(cyclopropylmethoxy)pyridyl-2-yl)methyl)-7,8-dihydro-1,6-naphthyridin-5(6H)-one (Z61, 33.0 mg, Y: 63%). ES-API: $[M+H]^+$=442.1. $^1$H NMR (400 MHz, DMSO-d6) δ 9.09 (d, J=2.0 Hz, 1H), 8.64 (d, J=5.6 Hz, 1H), 8.48 (d, J=2.0 Hz, 1H), 8.05 (dd, J1=0.8 Hz, J2=3.6 Hz, 1H), 7.79 (d, J=0.8 Hz, 1H), 7.41 (dd, J1=0.8 Hz, J2=6.8 Hz, 1H), 7.29 (dd, J1=1.6 Hz, J2=5.6 Hz, 1H), 7.27-7.24 (m, 1H), 6.10 (s, 2H), 4.91 (s, 2H), 3.95 (d, J=5.6 Hz, 2H), 3.79 (t, J1=5.2 Hz, J2=10.8 Hz, 2H), 3.23 (t, J1=5.6 Hz, J2=11.2 Hz, 2H), 1.28-1.24 (m, 1H), 0.59-0.55 (m, 2H), 0.38-0.35 (m, 2H).

Example 62 Preparation of 3-(2-amino-[1,2,4]triazolo[1,5-a]pyridin-7-yl)-6-((3-((tetrahydro-2H-pyran-4-yl)oxy)pyridin-2-yl)methyl)-7,8-dihydro-1,6-naphthyridin-5(6H)-one (Z62)

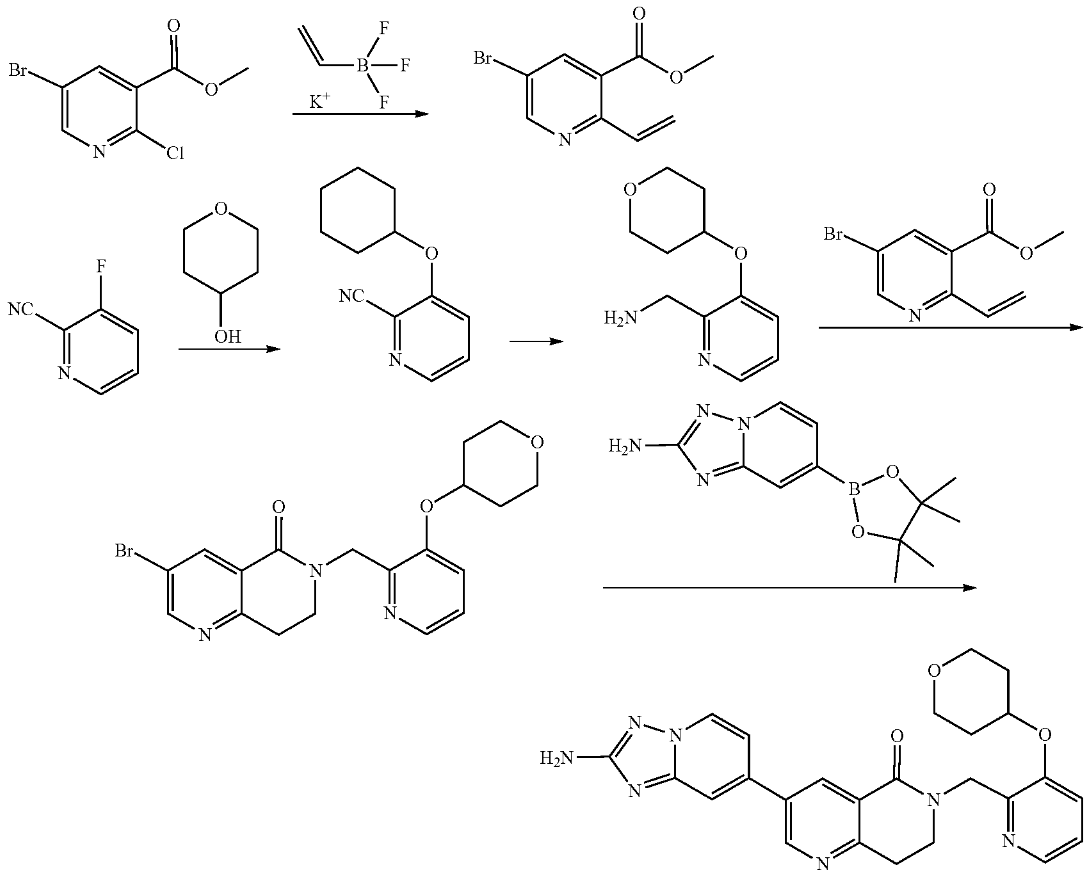

Z62

Step 1: Preparation of methyl 5-bromo-2-vinylnicotinate: Under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+$=242.1.

Step 2: Preparation of 3-((tetrahydro-2H-pyran-4-yl)oxy) pyridinoline: under ice water bath, sodium hydrogen (655 mg, 16.380 mmol) was added into a solution of tetrahydro-2H-pyran-4-ol (1.253 g, 12.285 mmol) in THF (30 mL) in batches, and the reaction mixture was stirred at 0° C. for one hour. 3-Fluoropyridylcarbonitrile (1 g, 8.19 mmol) was added to the reaction solution, and the reaction solution was stirred at room temperature overnight. LCMS showed that the reaction was completed, water (30 mL) was added for quenching the reaction in ice water bath, then EtOAc (15 mL*3) was added for extracting, the combined organic phases were washed with saturated sodium chloride solution (15 mL*3), and the combined organic phases were concentrated to obtain crude product 3-((tetrahydro-2H-pyran-4-yl) oxy) pyridinoline (1.96 g). ES-API:$[M+H]^+$=205.0.

Step 3: Preparation of (3-((tetrahydro-2H-pyran-4-yl) oxy)pyridin-2-yl)methanamine: Raney-Ni (200 mg, 2.248 mmol) was added into a solution of 3-((tetrahydro-2H-pyran-4-yl)oxy)pyridinoline (1.96 g, 9.608 mmol) in EtOH (30 mL), and the reaction solution was stirred overnight under the protection of hydrogen. After the reaction was completed, the residue was purified by combiflash to obtain (3-((tetrahydro-2H-pyran-4-yl)oxy)pyridin-2-yl)methanamine (881 mg, Y: 44%). ES-API:$[M+H]^+$=209.1.

Step 4: Preparation of 3-bromo-6-(((3-((tetrahydro-2H-pyran-4-yl)oxy)pyridin-2-yl)methyl)-7,8-dihydro-1,6-naphthyridin-5(6H)-one: methyl 5-bromo-2-vinylnicotinate (100 mg, 0.415 mmol) and (3-((tetrahydro-2H-pyran-4-yl)oxy] pyridin-2-yl)methanamine (173 mg, 0.830 mmol) were mixed in DMA (3 mL) in a microwave bottle. The reaction was subjected to microwave radiation at 180° C. for one hour, then the mixture was cooled to room temperature, added with ethyl acetate (30 mL), washed with water (15 mL*3) and saturated sodium chloride solution (15 mL*3).

The combined organic layers were concentrated and purified on silica gel by automatic fast chromatography (EtOAc/PE 0-20%) to obtain 3-bromo-6-((3-((tetrahydro-2H-pyran-4-yl)oxy)pyridin-2-yl)methyl)-7,8-dihydro-1,6-naphthyridin-5(6H)-one (176 mg, Y: 57%). ES-API:$[M+H]^+$=418.0.

Step 5: Preparation of 3-(2-amino-[1,2,4]triazolo[1,5-a]pyridin-7-yl)-6-((3-((tetrahydro-2H-pyran-4-yl)oxy)pyridin-2-yl)methyl)-7,8-dihydro-1,6-naphthyridin-5(6H)-one: under the protection of nitrogen, 3-bromo-6-((3-((tetrahydro-2H-pyran-4-yl)oxy)pyridin-2-yl)methyl)-7,8-dihydro-1,6-naphthyridin-5(6H)-one (50 mg, 0.120 mmol), (7-(4,4,5,5-tetramethyl-1,3,2-dioxaborolan-2-yl)-[1,2,4]triazolo[1,5-a]pyridin-2-amine (62 mg, 0.240 mmol), sodium carbonate (32 mg, 0.300 mmol), [1,1'-bis(diphenylphosphino)ferrocene-palladium(II)dichloride dichloromethane complex (5 mg, 0.006 mmol) was dissolved in dioxane (5 mL) and $H_2O$ (1 mL), the mixture was replaced with nitrogen for three times, and reacted at 95° C. for 2 hours. The reaction solution was cooled to room temperature and added with EtOAc (20 mL), then washed with water (15 mL*3) and saturated sodium chloride solution (15 mL*3), the combined organic layers were concentrated, and the residue was purified by alkaline HPLC to obtain white compound 3-(2-amino-[1,2,4]triazolo[1,5-a]pyridin-7-yl)-6-((3-((tetrahydro-2H-pyran-4-yl)oxy)pyridin-2-methyl)-7,8-dihydro-1,6-naphthyridin-5(6H)-one (Z62, 43.37 mg, Y: 82%). ES-API:[M+H]+=472.1. 1H NMR (400 MHz, DMSO-d6) δ 9.09 (d, J=1.6 Hz, 1H), 8.64 (d, J=5.2 Hz, 1H), 8.48 (d, J=2.4 Hz, 1H), 8.06 (dd, J1=1.2 Hz, J2=4.0 Hz, 1H), 7.79 (d, J=1.2 Hz, 1H), 7.54-7.52 (m, 1H), 7.30-7.26 (m, 2H), 6.11 (s, 2H), 4.91 (s, 2H), 4.75-4.71 (m, 1H), 3.89-3.85 (m, 2H), 3.77 (t, J1=5.6 Hz, J2=11.2 Hz, 2H), 3.55-3.50 (m, 2H), 3.22 (t, J1=5.6 Hz, J2=10.8 Hz, 2H), 2.00-1.96 (m, 2H), 1.68-1.62 (m, 2H).

Example 63 Preparation of 3-(2-amino-[1,2,4]triazolo[1,5-a]pyridyl-7-yl)-6-(1-(2-fluoro-5-(trifluoromethyl)phenyl)ethyl)-7,8-dihydro-1,6-naphthyridin-5(6H)-one (Z63)

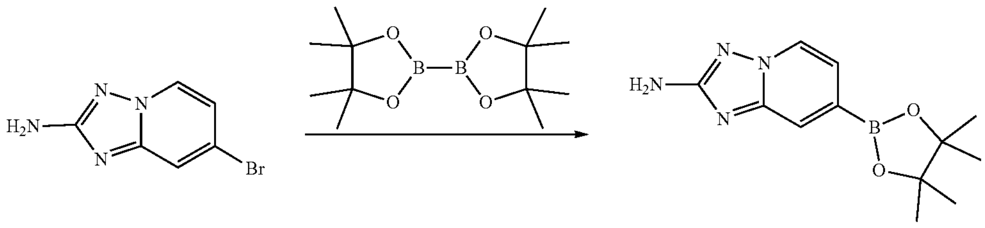

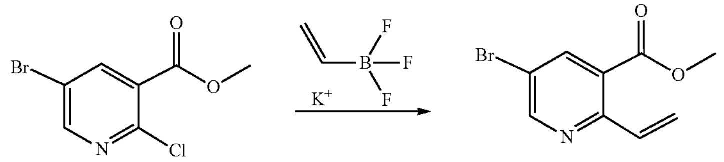

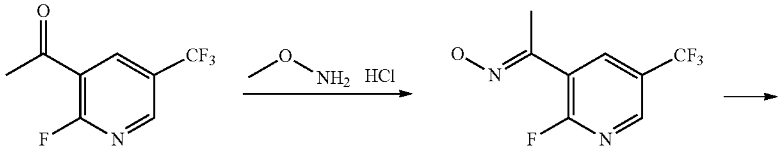

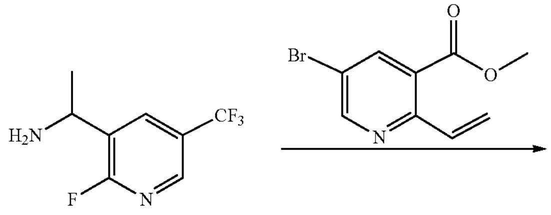

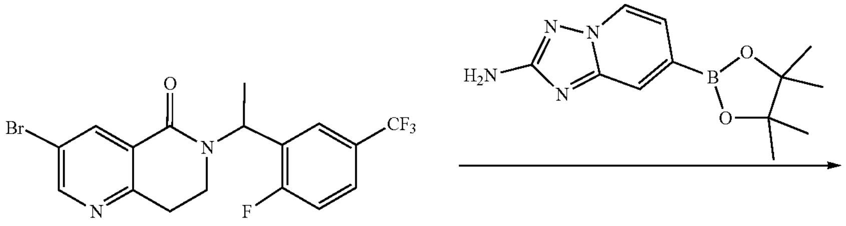

-continued

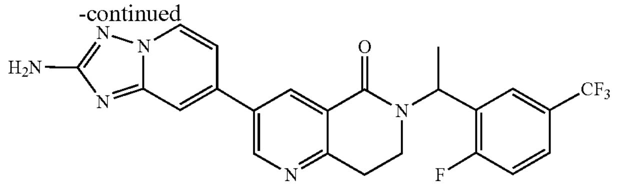

Z63

Step 1: Preparation of (7-(4,4,5,5-tetramethyl-1,3,2-dioxaborolan-2-yl)-[1,2,4]triazolo[1,5-a]pyridyl-2-amine: 7-bromo-[1,2,4]triazolo[1,5-a]pyridyl-2-amine (4.0 g, 18.78 mmol), bis(pinacolato)diboron (5.723 g, 22.53 mmol), potassium acetate (4.601 g, 46.95 mmol), [1,1'-bis(diphenylphosphino)ferrocene-palladium(II)dichloride dichloromethane complex (767 mg, 0.939 mmol) and 1,4-dioxane (50 mL) were added into a 250 mL round bottom flask, the mixture was replaced with nitrogen for three times, and reacted at 90° C. overnight, cooled to room temperature, filtered with suction, the filter cake was washed with ethyl acetate for three times to obtain the filtrate, the filtrate was concentrated to obtain crude product (7-(4,4,5,5-tetramethyl-1,3,2-dioxaborolan-2-yl)-[1,2,4]triazolo[1,5-a] pyridyl-2-amine (2.6 g, Y: 78%). ES-API: $[M-82+H]^+=$ 179.1.

Step 2: Preparation of methyl 5-bromo-2-vinylnicotinate: under the protection of nitrogen, methyl 5-bromo-2-chloronicotinate (10 g, 39.923 mmol), potassium vinyltrifluoroborate (5.348 g, 39.923 mmol), triethylamine (5.56 mL, 39.923 mmol), [1,1'-bis(diphenylphosphino)ferrocene]dichloropalladium(II) (585 mg, 0.798 mmol) were dissolved in EtOH (200 mL), the mixture was replaced with nitrogen for three times, and reacted at 80° C. for one hour, cooled to room temperature, filtered, the filtrate was spin-dried. Residue was dissolved in ethyl acetate (300 mL) and water (300 mL), separated, the organic phase was concentrated, purified on silica gel by automatic fast chromatography (EtOAc/PE 0-20%) to obtain methyl 5-bromo-2-vinylnicotinate (5.186 g, Y: 54%). ES-API: $[M+H]^+=242.1$.

Step 3: Preparation of: 1-(2-fluoro-5-(trifluoromethyl) phenyl)ethyl-1-one-O-methyloxime: o-methylhydroxylamine hydrochloride (2.33 g, 27.9 mmol) was added into a solution of 1-(2-fluoro-5-(trifluoromethyl)phenyl)ethyl-1-one (1.643 g, 7.97 mmol) in ethanol (20 mL) and pyridine (2 mL). The reaction mixture was heated and refluxed for one hour, cooled to room temperature, concentrated to dryness, the residue was added into water (20 mL) and ethyl acetate (20 mL), layered, the water phase was extracted with ethyl acetate (15 mL*3), washed with saturated sodium chloride solution (15 mL*3), dried over anhydrous sodium sulfate, filtered, the filtrate was concentrated to obtain crude product 1-(2-fluoro-5-(trifluoromethyl)phenyl)ethyl-1-one-O-methyloxime (1.62 g, Y: 85%). ES-API: $[M-82+H]^+=$ 236.1.

Step 4: Preparation of 1-(2-fluoro-5-(trifluoromethyl)phenyl)ethyl-1-amine: sodium borohydride (1.17 g, 31.0 mmol) was slowly added into a solution of zirconium chloride (1.8 g, 7.75 mmol) in tetrahydrofuran (35 mL), a solution of 1-(2-fluoro-5-(trifluoromethyl)phenyl)ethyl-1-one-O-methyloxime (1.457 g, 6.20 mmol) in tetrahydrofuran (7 mL) was added, the reaction mixture was stirred at room temperature overnight. After the reaction was completed, the reaction mixture was cooled to 0° C., water (16 mL) was slowly added, then extra aqueous ammonia was added. The reaction mixture was extracted with ethyl acetate (15 mL*3), the organic phase was washed with 1N dilute hydrochloric acid. The water phase was alkalized with sodium hydroxide, extracted with ethyl acetate (15 mL*3), the organic phase was wash with saturated sodium chloride solution (15 mL*3), dried over anhydrous sodium sulphate, filtered, concentrated to obtain 1-(2-fluoro-5-(trifluoromethyl)phenyl)ethyl-1-amine (477 mg, Y: 37%). ES-API: $[M-82+H]^+=$ 208.1.

Step 5: Preparation of 3-bromo-6-(1-(2-fluoro-5-(trifluoromethyl)phenyl)ethyl)-7,8-dihydro-1,6-naphthyridin-5 (6H)-one: methyl 5-bromo-2-vinylnicotinate (228 mg, 0.944 mmol) and 1-(2-fluoro-5-(trifluoromethyl)phenyl)ethyl-1-amine (391 mg, 1.888 mmol) were mixed in DMA (6 mL) in a microwave bottle. The reaction was subjected to microwave radiation at 180° C. for one hour, cooled to room temperature, the reaction mixture was added into ethyl acetate (30 mL), washed with water (15 mL*3) and saturated sodium chloride solution (15 mL*3), the combined organic layers were concentrated, purified on silica gel by automatic fast chromatography (EtOAc/PE 0-20%) to obtain 3-bromo-6-(1-(2-fluoro-5-(trifluoromethyl)phenyl)ethyl)-7,8-dihydro-1,6-naphthyridin-5(6H)-one (146 mg, Y: 30%). ES-API: $[M+H]^+=417.0$.

Step 6: Preparation of 3-(2-amino-[1,2,4]triazolo[1,5-a] pyridyl-7-yl)-6-(1-(2-fluoro-5-(trifluoromethyl)phenyl) ethyl)-7,8-dihydro-1,6-naphthyridin-5(6H)-one: under the protection of nitrogen, 3-bromo-6-(1-(2-fluoro-5-(trifluoromethyl)phenyl)ethyl)-7,8-dihydro-1,6-naphthyridin-5 (6H)-one (103 mg, 0.248 mmol), (7-(4,4,5,5-tetramethyl-1,3,2-dioxaborolan-2-yl)-[1,2,4]triazolo[1,5-a]pyridyl-2-amine (129 mg, 0.496 mmol), sodium carbonate (66 mg, 0.620 mmol), [1,1'-bis(diphenylphosphino)ferrocene-palladium(II)dichloride dichloromethane complex (10 mg, 0.0124 mmol) were dissolved in dioxane (8 mL) and $H_2O$ (2 mL), the mixture was replaced with nitrogen for three times, and reacted at 95° C. for 2 hours, cooled to room temperature, the reaction mixture was added into EtOAc (20 mL), wash with water (15 mL*3) and saturated sodium chloride solution (15 mL*3), the combined organic phases were concentrated, the residue was purified by alkaline HPLC to obtain white product 3-(2-amino-[1,2,4]triazolo[1,5-a] pyridyl-7-yl)-6-(1-(2-fluoro-5-(trifluoromethyl)phenyl) ethyl)-7,8-dihydro-1,6-naphthyridin-5(6H)-one (Z63, 63.0 mg, Y: 57%). ES-API: $[M+H]^+=471.1$. $^1H$ NMR (400 MHz, DMSO-d6) δ 9.07 (d, J=1.6 Hz, 1H), 8.64 (d, J=5.2 Hz, 1H), 8.51 (d, J=1.6 Hz, 1H), 7.89 (d, J=4.0 Hz, 1H), 7.82-7.80 (m, 2H), 7.47 (t, J1=7.6 Hz, J2=14.8 Hz, 1H), 7.30 (dd, J1=0.8 Hz, J2=5.2 Hz, 1H), 6.10 (s, 3H), 3.70-3.65 (m, 1H), 3.29-3.28 (m, 1H), 3.17-3.11 (m, 1H), 3.05-2.98 (m, 1H), 1.65 (d, J=5.2 Hz, 3H).

Example 64: Preparation of 3-(2-amino-[1,2,4]triazolo[1,5-a]pyridyl-7-yl)-6-(1-(1-(1-(4-fluorophenyl)ethyl)-1H-pyrazol-4-yl)-7,8-dihydro-1,6-naphthyridin-5(6H)-one (Z64) and two stereoisomer compounds thereof (Z73 and Z74)

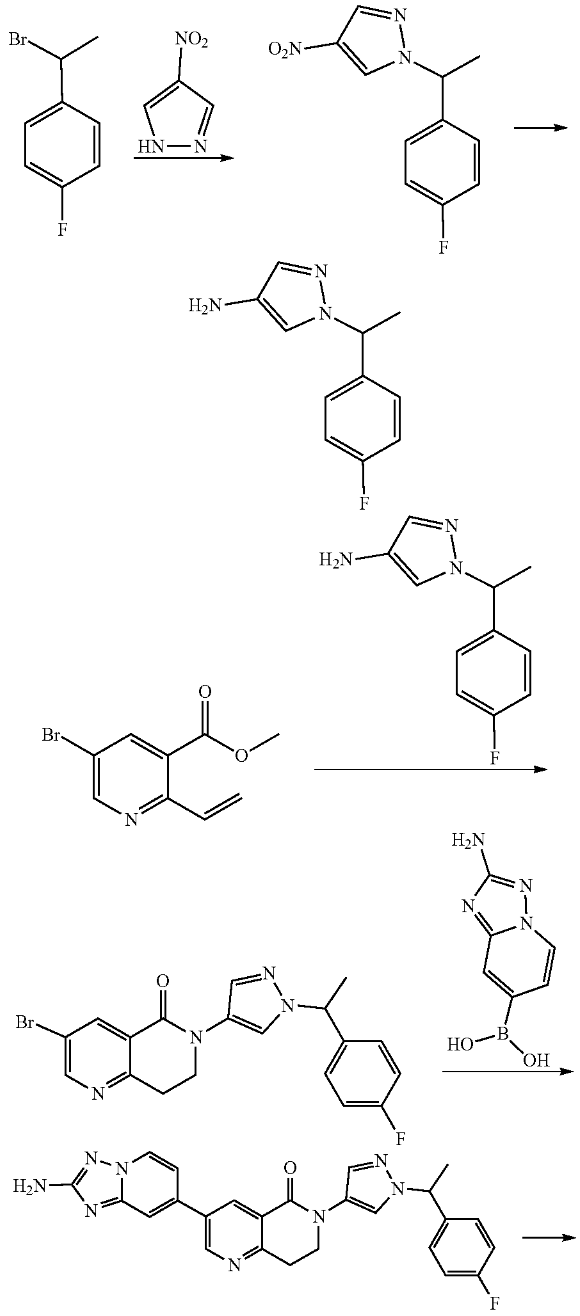

Z64

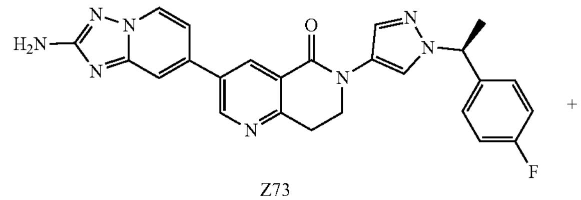

Z73

-continued

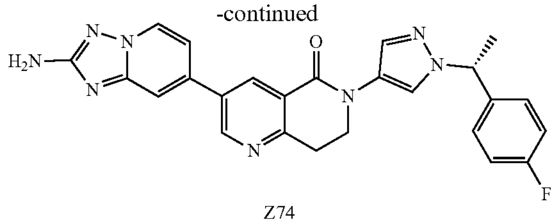

Z74

Step 1: Under the protection of nitrogen, N,N-dimethylformamide (20 mL) and 4-nitro-1H-pyrazole (500 mg, 4.425 mmol) were added into a 50 mL round bottom flask at room temperature, then potassium carbonate (733 mg, 5.311 mmol) was added, then 1-(1-bromoethyl)-4-fluorobenzene (0.9 g, 4.433 mmol) was added and reacted for 2 hours. After the reaction was completed, the reaction mixture was added into ethyl acetate (80 mL), washed with ammonium chloride and sodium chloride (60 mL*2), the ethyl acetate phase was dried over anhydrous sodium sulfate, filtered, the filtrate was spin-dried, purified on silica gel by automatic fast chromatography (EtOAc/PE 0-70%) to obtain 1-(1-(4-fluorophenyl)ethyl)-4-nitro-1H-pyrazole (750 mg, Y:72%). ES-API: $[M+H]^+$=236.1.

Step 2: Methanol (50 mL) and 1-(1-(4-fluorophenyl)ethyl)-4-nitro-1H-pyrazole (750 mg, 3.19 mmol) were added into a 100 mL round bottom flask, then palladium on carbon (0.5 g) was added. And the mixture was reacted at room temperature for 12 hours under the protection of hydrogen, after the reaction was completed, the mixture was filtered, the filtrate was spin-dried to obtain 1-(1-(4-fluorophenyl)ethyl)-1H-pyrazol-4-amine (0.61 g, Y:93%). ES-API: $[M+H]^+$=206.1.

Step 3: Methyl 5-bromo-2-vinylnicotinate (100 mg, 0.4132 mmol) and 1-(1-(4-fluorophenyl)ethyl)-1H-pyrazol-4-amine (300 mg, 1.463 mmol) were mixed in DMA (3 mL) in a microwave bottle. The reaction was subjected to microwave radiation at 150° C. for three hours, cooled to room temperature, the reaction mixture was added into ethyl acetate (50 mL), washed with water (45 mL*3) and saturated sodium chloride solution (45 mL*3), the combined organic layers were concentrated, purified on silica gel by automatic fast chromatography (EtOAc/PE 0-50%) to obtain 3-bromo-6-(1-(1-(1-(4-fluorophenyl)ethyl)-1H-pyrazol-4-yl)-7,8-dihydro-1,6-naphthyridin-5(6H)-)-one (120 mg, Y:70%). ES-API: $[M+H]^+$=415.

Step 4: Under the protection of nitrogen, 3-bromo-6-(1-(1-(1-(4-fluorophenyl)ethyl)-1H-pyrazol-4-yl)-7,8-dihydro-1,6-naphthyridin-5(6H)-)-one (120 mg, 0.0.289 mmol), (2-amino-[1,2,4]triazolo[1,5-a]pyridyl-7-yl)boronic acid (156 mg, 0.8764 mmol), sodium carbonate (100 mg, 0.9434 mmol), 1,1'-bis(diphenylphosphino)ferrocene-palladium(II) dichloride dichloromethane complex (40.0 mg, 0.0488 mmol) were dissolved in dioxane (12 mL) and $H_2O$ (3 mL), the mixture was replaced with nitrogen for three times, the reaction was subjected to microwave radiation at 90° C. for 35 min, cooled to room temperature, concentrated, the crude product was purified by alkaline HPLC to obtain white solid 3-(2-amino-[1,2,4]triazolo[1,5-a]pyridyl-7-yl)-6-(1-(1-(1-(4-fluorophenyl)ethyl)-1H-pyrazol-4-yl)-7,8-dihydro-1,6-naphthyridin-5(6H)-one (Z64, 23.0 mg, Y: 17%). ES-API: $[M+H]^+$=469.1. $^1H$ NMR (400 MHz, DMSO-d6) δ 9.11 (d, J=2.4 Hz, 1H), 8.66 (d, J=6.9 Hz, 1H), 8.53 (d, J=2.4 Hz, 1H), 8.33 (s, 1H), 7.89 (s, 1H), 7.80 (d, J=1.3 Hz, 1H), 7.45-7.27 (m, 3H), 7.18 (t, J=8.9 Hz, 2H), 6.11 (s, 2H), 5.67 (q, J=7.0 Hz, 1H), 4.11 (t, J=6.7 Hz, 2H), 3.31 (d, J=6.6 Hz, 2H), 1.82 (d, J=7.1 Hz, 3H).

Step 5: The compound Z64(10 mg, 0.02136 mmol) obtained in above step was chiral separated with SFC (column: R,R-WHELK-O1 (4.6*250 mm 5 um); mobile phase: hexane (0.1% DEA): EtOH (0.1% DEA)=10:90; wavelength: 254 nm; flow rate: 1.0 mL/min; column temperature: 40° C.;) to obtain two stereoisomer compounds:

Compound Z73 (2.0 mg; Y: 20%), the first peaking compound (retention time: 13.776 min), the structure of which was arbitrarily defined as (S)-3-(2-amino-[1,2,4]triazolo[1,5-a]pyridyl-7-yl)-6-(1-(1-(1-(4-fluorophenyl)ethyl)-1H-pyrazol-4-yl)-7,8-dihydro-1,6-naphthyridin-5(6H)-one, light white solid, ES-API: $[M+H]^+$=469.1.

Compound Z74(1.5 mg; Y: 15%), the second peaking compound, (retention time: 18.009 min); the structure of which was arbitrarily defined as (R)-3-(2-amino-[1,2,4]triazolo[1,5-a]pyridyl-7-yl)-6-(1-(1-(1-(4-fluorophenyl)ethyl)-1H-pyrazol-4-yl)-7,8-dihydro-1,6-naphthyridin-5(6H)-one; light white solid; ES-API: $[M+H]^+$= 469.1.

Example 80: Preparation of 3-(2-amino-[1,2,4]triazolo[1,5-a]pyridyl-7-yl)-6-(1-(5-fluoro-2-(1-methyl-1H-pyrazol-4-yl)phenyl)ethyl)-7,8-dihydro-1,6-naphthyridin-5(6H)-one (Z80) and two stereoisomer compounds thereof: (Z84 and Z85)

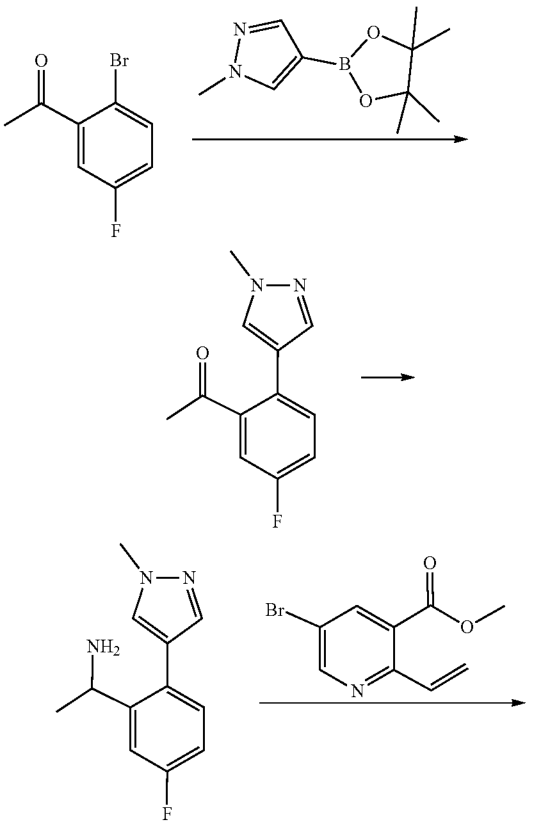

-continued

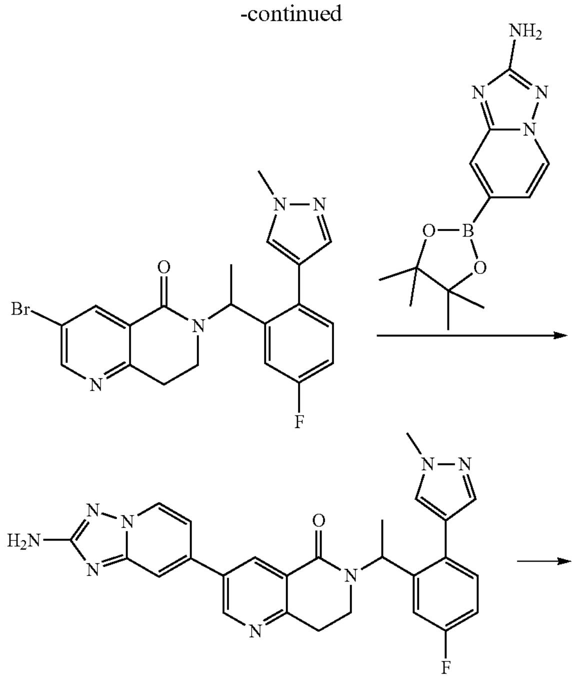

Z80

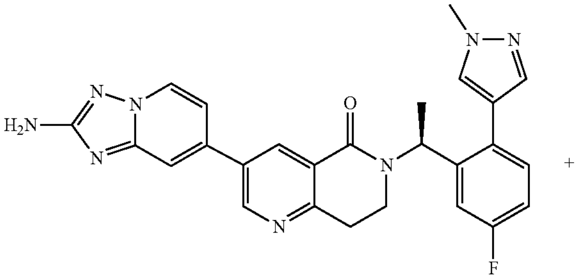

Z84

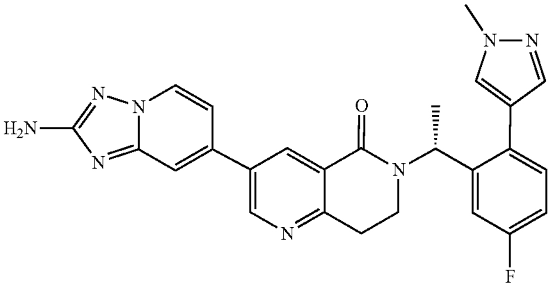

Z85

Step 1: Under the protection of nitrogen, dioxane (30 mL) and water (6 mL) were added into a 100 mL round bottom flask with single neck, 1-(2-bromo-5-fluorophenyl)ethyl-1-one (3.0 g, 13.89 mmol), 1-methyl-4-(4,4,5,5-tetramethyl-1,3,2-dioxaborinan-2-yl)-1H-pyrazol (3.46 g, 16.63 mmol), sodium carbonate (4.20 g, 39.62 mmol), [1,1'-bis(diphenylphosphino)ferrocene]dichloropalladium(II) (1.0 g, 1.363 mmol) were added into the mixture, the mixture was replaced with nitrogen for three times, heated to 100° C. in oil bath for 12 hours. LCMS showed the reaction was completed, the mixture was cooled to room temperature, added with ethyl acetate (80 mL), washed with saturated ammonium chloride and sodium chloride twice (60 mL*2), the ethyl acetate phase was dried over anhydrous sodium sulphate, filtered, the combined organic phases were concentrated, purified on silica gel by automatic fast chromatography (EtOAc/PE 0-50%) to obtain 1-(5-fluoro-2-(1-methyl-1H-pyrazol-4-yl)phenyl)ethyl-1-one (2.5 g, Y: 71%). ES-API: $[M+H]^+$=219.1.

Step 2: Under the protection of nitrogen, methanol ammonia solution (5 mL) and 1-(5-fluoro-2-(1-methyl-1H-pyrazol-4-yl)phenyl)ethyl-1-one (0.5 g, 2.293 mmol) were added into a 100 mL round bottom flask with single neck, then tetraisopropoxytitanium (3.256 g, 11.46 mmol) was added, and the mixture was reacted under the protection of nitrogen for 24 hours, the reaction mixture was cooled to 0° C., sodium borohydride (174 mg, 4.586 mmol) was added, heated to room temperature for 2 hours. After the reaction was completed, the reaction mixture was added into 4M sodium hydroxide solution (20 mL), filtered. Ethyl acetate (5 mL) was added into the filtrate, the mixture was washed with saturated sodium chloride solution (30 mL*2), the ethyl acetate phase was dried over anhydrous sodium sulphate, filtered, the combined organic phases were concentrated to obtain 1-(5-fluoro-2-(1-methyl-1H-pyrazol-4-yl)phenyl) ethyl-1-amine (315 mg, Y: 63%). ES-API: $[M+H]^+$=220.1.

Step 3: Methyl 5-bromo-2-vinylnicotinate (150 mg, 0.6198 mmol) and 1-(5-fluoro-2-(1-methyl-1H-pyrazol-4-yl)phenyl)ethyl-1-amine (315 mg, 1.507 mmol) were mixed in DMA (2.5 mL) in a microwave bottle. The reaction was subjected to microwave radiation at 150° C. for 3 hours, cooled to room temperature, the reaction mixture was added into ethyl acetate (50 mL), then washed with water (45 mL*3) and saturated sodium chloride solution (45 mL*3), the combined organic layers were concentrated, purified on silica gel by automatic fast chromatography (EtOAc/PE 0-50%) to obtain 3-bromo-6-(1-(5-(5-fluoro-2-(1-methyl-1H-pyrazol-4-yl)phenyl)ethyl)-7,8-dihydro-1,6-naphthyridin-5(6H)-one (120 mg, Y:50%). ES-API: $[M+H]^+$=429/431.

Step 4: Under the protection of nitrogen, 3-bromo-6-(1-(5-(5-fluoro-2-(1-methyl-1H-pyrazol-4-yl)phenyl)ethyl)-7,8-dihydro-1,6-naphthyridin-5(6H)-one (120 mg, 0.2792 mmol), 7-(4,4,5,5-tetramethyl-1,3,2-dioxaborolan-2-yl)-[1,2,4]triazolo[1,5-a]pyridyl-2-amine (146 mg, 0.5615 mmol), sodium carbonate (90 mg, 0.8490 mmol), [1,1'-bis(diphenylphosphino)ferrocene-palladium(II)dichloride dichloromethane complex (30.0 mg, 0.04088 mmol) were dissolved in dioxane (10 mL) and $H_2O$ (2 mL), the mixture was replaced with nitrogen for three times, subjected to microwave radiation at 90° C. for 35 min, cooled to room temperature, concentrated, the crude product was purified by alkaline HPLC to obtain light white solid 3-(2-amino-[1,2,4]triazolo[1,5-a]pyridyl-7-yl)-6-(1-(5-fluoro-2-(1-methyl-1H-pyrazol-4-yl)phenyl)ethyl)-7,8-dihydro-1,6-naphthyridin-5(6H)-one (Z80, 50.0 mg, Y: 37%). ES-API: $[M+H]^+$=483.3. $^1$H NMR (400 MHz, DMSO-d6) δ 9.04 (d, J=2.4 Hz, 1H), 8.64 (d, J=6.9 Hz, 1H), 8.37 (d, J=2.4 Hz, 1H), 7.76 (d, J=2.2 Hz, 2H), 7.45-7.37 (m, 2H), 7.33-7.23 (m, 2H), 7.19 (td, J=8.4, 2.7 Hz, 1H), 6.10 (s, 2H), 5.91 (q, J=6.7 Hz, 1H), 3.76 (s, 3H), 3.54-3.46 (m, 1H), 3.30-3.20 (m, 1H), 3.09-2.94 (m, 2H), 1.50 (d, J=7.0 Hz, 3H).

Step 5: The compound Z80(50 mg, 0.1659 mmol) obtained in the above step was chiral separated (column: Chiralpak IB 250 mm*4.6 mm Sum; mobile phase: ACN: EtOH:AMMN=90:10:0.2; flow rate: 1 mL/min; column temperature: room temperature) to obtain two stereoisomer compounds:

Compound Z84: the first peaking compound (retention time: 7.282 min), the structure of which was arbitrarily defined as (S)-3-(2-amino-[1,2,4]triazolo[1,5-a]pyridyl-7-yl)-6-(1-(5-fluoro-2-(1-methyl-1H-pyrazol-4-yl)phenyl)ethyl)-7,8-dihydro-1,6-naphthyridin-5(6H)-one (15.0 mg, Y: 25%). ES-API: $[M+H]^+$=483.3. $^1$H NMR (500 MHz, DMSO-d6) δ 9.09 (d, J=2.4 Hz, 1H), 8.70 (d, J=6.9 Hz, 1H), 8.43 (d, J=2.4 Hz, 1H), 7.82 (s, 2H), 7.50-7.41 (m, 2H), 7.39-7.30 (m, 2H), 7.24 (td, J=8.4, 2.7 Hz, 1H), 6.16 (s, 2H), 5.96 (q, J=6.9 Hz, 1H), 3.81 (s, 3H), 3.63-3.51 (m, 1H), 3.30 (dt, J=12.7, 6.4 Hz, 1H), 3.06 (dd, J=13.0, 6.5 Hz, 2H), 1.55 (d, J=7.0 Hz, 3H).

Compound Z85: the second peaking compound (retention time: 5.943 min), the structure of which was arbitrarily defined as (R)-3-(2-amino-[1,2,4]triazolo[1,5-a]pyridyl-7-yl)-6-(1-(5-fluoro-2-(1-methyl-1H-pyrazol-4-yl)phenyl)ethyl)-7,8-dihydro-1,6-naphthyridin5(6H)-one (15.0 mg, Y: 25%). ES-API: $[M+H]^+$=483.3. $^1$H NMR (500 MHz, DMSO-d6) δ 8.97 (d, J=2.4 Hz, 1H), 8.57 (d, J=6.9 Hz, 1H), 8.30 (d, J=2.4 Hz, 1H), 7.69 (d, J=2.2 Hz, 2H), 7.40-7.29 (m, 2H), 7.25-7.18 (m, 2H), 7.11 (td, J=8.4, 2.7 Hz, 1H), 6.03 (s, 2H), 5.83 (q, J=7.0 Hz, 1H), 3.69 (s, 3H), 3.48-3.39 (m, 1H), 3.17 (dt, J=12.6, 6.3 Hz, 1H), 2.94 (dd, J=13.0, 6.6 Hz, 2H), 1.42 (d, J=7.0 Hz, 3H).

Preparation of Amino Compound

Preparation Example 1: Preparation of (5-fluoro-2-(((tetrahydrofuran-3-yl)oxy)phenyl)methylamine

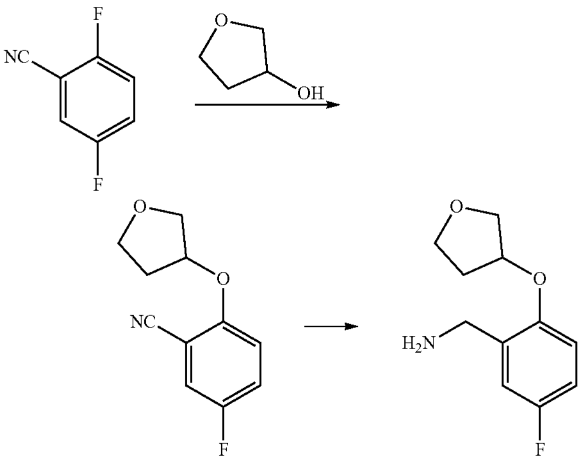

Step 1: Under the protection of nitrogen, at 0° C., dry tetrahydrofuran (50 mL) and tetrahydrofuran-3-ol (1.76 g, 20.0 mmol) were added into a 100 mL round bottom flask, then sodium hydride (0.6 g, 15.0 mmol) was added, and the reaction was reacted at 0° C. for one hour, then 2,5-difluorobenzonitrile (1.39 g, 10.0 mmol) was added, the mixture was slowly heated to 50° C. and reacted for 12 hours. After the reaction was completed, the mixture was cooled to 0° C., ethyl acetate (80 mL) was added into reaction mixture, the mixture was washed with saturated ammonium chloride and sodium chloride twice (70 mL*2), the ethyl acetate phase was dried over anhydrous sodium sulphate, filtered, the filtrate was spin-dried to obtain 5-fluoro-2-((tetrahydrofuran-3-yl)oxy)benzonitrile (2.35 g, crude). ES-API: $[M+H]^+$=208.0.

Step 2: Under the protection of nitrogen, tetrahydrofuran (50 mL) and 5-fluoro-2-((tetrahydrofuran-3-yl)oxy)benzonitrile (2.35 g, 10.0 mmol) were added into a 500 mL round bottom flask with single neck, then borane-tetrahydrofuran complex (50 mL, 1M, 50 mmol) was added, the mixture was heated from room temperature to boiling and reacted overnight. After the reaction was completed, the mixture was cooled to room temperature, methanol was carefully added until there was no bubble generated. The reaction mixture was added with ethyl acetate (80 mL), washed with saturate ammonium chloride and sodium chloride (70 mL*2) successively, the ethyl acetate phase was dried with anhydrous sodium sulphate, filtered, the filtrate was spin-dried to obtain (5-fluoro-2-(((tetrahydrofuran-3-yl)oxy)phenyl)methylamine (1.51 g, Y:71%), ES-API: $[M+H]^+$=212.1.

Preparation Example 2: Preparation of (2-(cyclopropylmethoxy)-3,5-difluorophenyl)methylamine

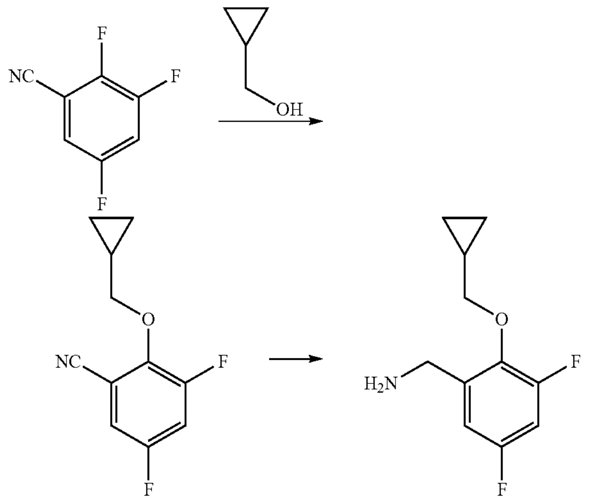

Step 1: Under the protection of nitrogen, at 0° C., tetrahydrofuran (50 mL) and cyclopropyl carbinol (800 mg, 11.09 mmol) were added into a 100 mL round bottom flask with three necks, sodium hydride (480.0 mg, 12.0 mmol) was added, then 2,3,5-trifluorobenzonitrile (1.57 g, 10.0 mmol) was added, the mixture was heated to 55° C. and reacted for 12 hours. After the reaction was completed, the mixture was cooled to 0° C., added with ethyl acetate (80 mL), washed with saturated ammonium chloride and sodium chloride twice (80 mL*2) successively, the ethyl acetate phase was dried with anhydrous sodium sulphate, filtered, the filtrate was spin-dried to obtain 2-((cyclopropylmethoxy)-3,5-difluorobenzonitrile (1.75 g, Y:83.7%). ES-API: $[M+H]^+$=210.1.

Step 2: Under the protection of nitrogen, tetrahydrofuran (50 mL) and 2-(cyclopropylmethoxy)-3,5-difluorobenzonitrile (1.75 g, 8.37 mmol) were added into a 500 mL round bottom flask with single neck, then borane-tetrahydrofuran complex (42 mL, 1M, 42 mmol) was added, the mixture was heated from room temperature to boiling and reacted overnight. After the reaction was completed, the mixture was cooled to room temperature, methanol was carefully added until there was no bubble generated. The reaction mixture was added with ethyl acetate (80 mL), washed with saturated ammonium chloride and sodium chloride twice (60 mL*2), the ethyl acetate phase was dried with anhydrous sodium sulphate, filtered, the filtrate was spin-dried to obtain (2-(cyclopropylmethoxy)-3,5-difluorophenyl)methylamine (0.593 g, Y:35%). ES-API: $[M+H]^+$=214.1.

Preparation Example 3: Preparation-of-2-cyclopropoxyphenyl)methylamine

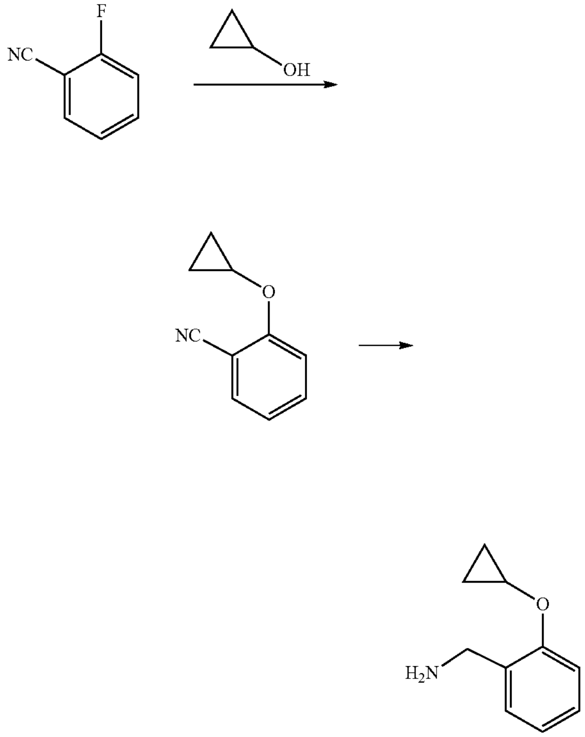

Step 1: Under the protection of nitrogen, at room temperature, N,N-dimethylformamide (30 mL) and cyclopropanol (1.16 g, 11.09 mmol) were added into a 100 mL round bottom flask with three necks, cesium carbonate (9.8 g, 30.0 mmol) was added, then 2-fluorobenzonitrile (1.21 g, 10.0 mmol) was added, heated to 75° C. and reacted for 7 hours. After the reaction was completed, the mixture was cooled to room temperature, added with ethyl acetate (80 mL), washed with saturated ammonium chloride and sodium chloride twice (80 mL*2) successively, the ethyl acetate phase was dried with anhydrous sodium sulphate, filtered, the filtrate was spin-dried to obtain 2-cyclopropyl benzonitrile (2.0 g, crude). ES-API: $[M+H]^+$=160.

Step 2: Under the protection of nitrogen, tetrahydrofuran (50 mL) and 2-cyclopropyl benzonitrile (2.0 g, 10.0 mmol) were added into a 500 mL round bottom flask with single neck, then borane-tetrahydrofuran complex (50 mL, 1M, 50 mmol) was added, the mixture was heated from room temperature to boiling and reacted overnight. After the reaction was completed, the mixture was cooled to room temperature, methanol was carefully added until there was no bubble generated, the reaction mixture was added with ethyl acetate (80 mL), washed with saturated ammonium chloride and sodium chloride twice (70 mL*2) successively, the ethyl acetate phase was dried with anhydrous sodium sulphate, filtered, the filtrate was spin-dried to obtain (2-cyclopropoxyphenyl)methylamine (0.80 g, Y:63%). ES-API: $[M+H]^+$=164.1.

Preparation Example 4: Preparation of (3-cyclopropoxy-2,5-difluorophenyl)methylamine

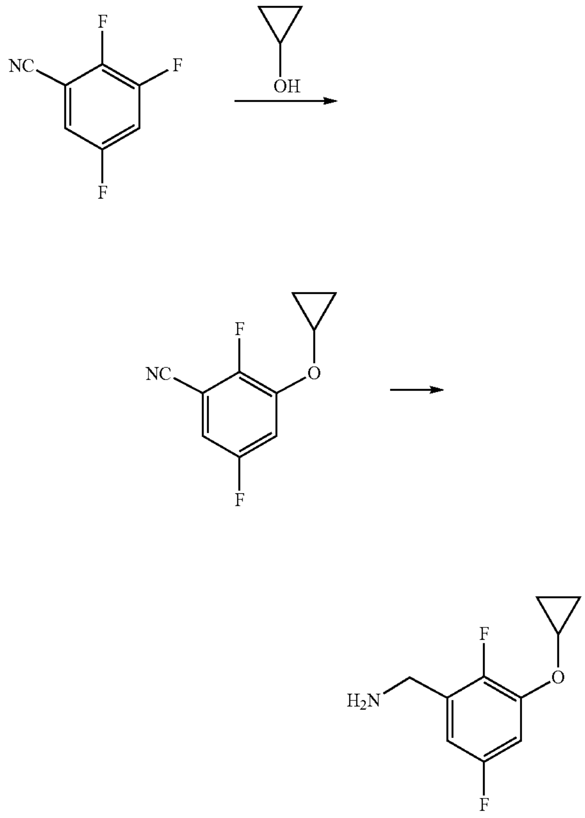

Step 1: Under the protection of nitrogen, at room temperature, N,N-dimethylformamide (25 mL) and cyclopropanol (554 mg, 9.552 mmol) were added into a 100 mL round bottom flask with three necks, cesium carbonate (6.21 g, 19.06 mmol) was added, 2,3,5-trifluorobenzonitrile (1.0 g, 6.370 mmol) was added, heated to 75° C. for 7 hours. After the reaction was completed, the mixture was cooled to room temperature, added with ethyl acetate (80 mL), washed with saturated ammonium chloride and sodium chloride twice (60 mL*2) successively, the ethyl acetate phase was dried with anhydrous sodium sulphate, filtered, the filtrate was spin-dried to obtain 3-cyclopropoxy-2,5-difluorobenzonitrile (1.52 g, crude). ES-API: $[M+H]^+$=196.05.

Step 2: Under the protection of nitrogen, tetrahydrofuran (50 mL) and 3-cyclopropoxy-2,5-difluorobenzonitrile (1.52 g, 6.37 mmol) were added into a 500 mL round bottom flask with single neck, then borane-tetrahydrofuran complex (30 mL, 1M, 30 mmol) was added, the mixture was heated from room temperature to boiling and reacted overnight. After the reaction was completed, the mixture was cooled to room temperature, methanol was carefully added until there was no bubble generated. The reaction mixture was added with ethyl acetate (80 mL), washed with saturated ammonium chloride and sodium chloride twice (70 mL*2) successively, the ethyl acetate phase was dried with anhydrous sodium sulphate, filtered, the filtrate was spin-dried to obtain (3-cyclopropoxy-2,5-difluorophenyl)methylamine (0.80 g, Y:64%). ES-API: $[M+H]^+$=200.1.

Preparation Example 5: Preparation of 5 (2-cyclopropoxy-5-fluorophenyl)methylamine

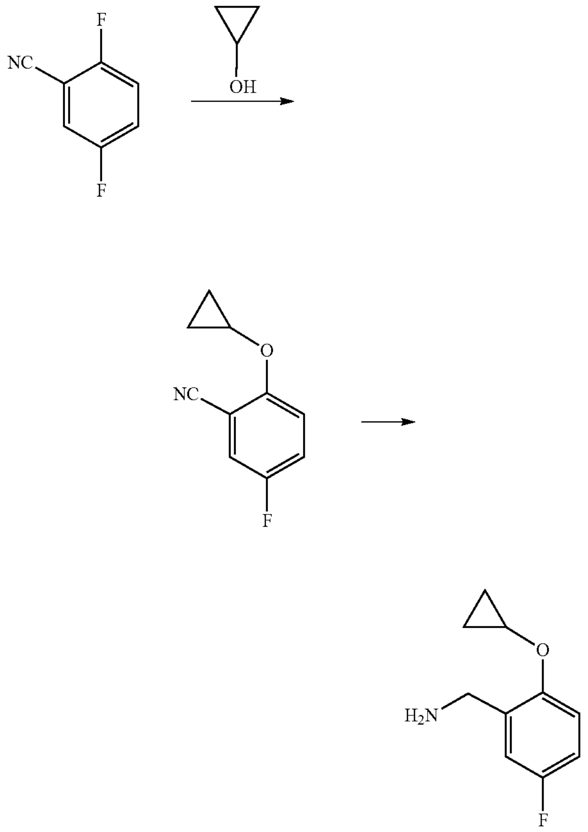

Step 1: Under the protection of nitrogen, at 0° C., tetrahydrofuran (50 mL) and cyclopropanol (0.87 g, 15.0 mmol) were added into a 100 mL round bottom flask with three necks, cesium carbonate (9.80 g, 30.0 mmol) was added, 2,5-difluorobenzonitrile (1.39 g, 10.0 mmol) was added, heated to 75° C. for 8 hours. After the reaction was completed, the mixture was cooled to room temperature, added with ethyl acetate (80 mL), washed with saturated ammonium chloride and sodium chloride twice (70 mL*2) successively, the ethyl acetate phase was dried with anhydrous sodium sulphate, filtered, the filtrate was spin-dried to obtain 2-cyclopropoxy-5-fluorobenzonitrile (1.55 g, Y: 87.5%). ES-API: $[M+H]^+$=178.1.

Step 2: Under the protection of nitrogen, tetrahydrofuran (50 mL) and 2-cyclopropoxy-5-fluorobenzonitrile (1.55 g, 8.757 mmol) were added into a 500 mL round bottom flask with single neck, then borane-tetrahydrofuran complex (43 mL, 1M, 43 mmol) was added, the mixture was heated from room temperature to boiling and reacted overnight. After the reaction was completed, the mixture was cooled to room temperature, methanol was carefully added until there was no bubble generated. The reaction mixture was added with ethyl acetate (80 mL), washed with saturated ammonium chloride and sodium chloride twice (70 mL*2), the ethyl acetate phase was dried with anhydrous sodium sulphate, filtered, the filtrate was spin-dried to obtain (2-cyclopropoxy-5-fluorophenyl)methylamine (1.08 g, Y:76%). ES-API: $[M+H]^+$=182.0.

Preparation Example 6: Preparation of (2-cyclopropoxypyridyl-3-yl)methylamine

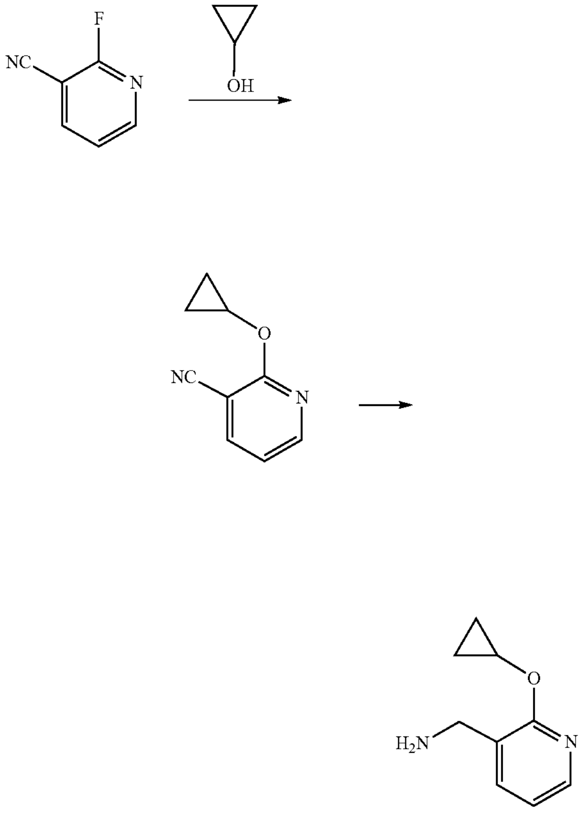

Step 1: Under the protection of nitrogen, at 0° C., tetrahydrofuran (50 mL) and cyclopropanol (0.87 g, 15.0 mmol) were added into a 100 mL round bottom flask with three necks, cesium carbonate (9.80 g, 30.0 mmol) was added, 2-fluoronicotinonitrile (1.39 g, 10.0 mmol) was added at room temperature, the mixture was heated to 75° C. for 8 hours. After the reaction was completed, the mixture was cooled to room temperature, added with ethyl acetate (80 mL), washed with saturated ammonium chloride and sodium chloride twice (70 mL*2) successively, the ethyl acetate phase was dried with anhydrous sodium sulphate, filtered, the filtrate was spin-dried to obtain 2-cyclopropoxynicotinonitrile (1.68 g, crude). ES-API: $[M+H]^+$=161.1.

Step 2: Under the protection of nitrogen, tetrahydrofuran (50 mL) and 2-cyclopropoxy-5-fluorobenzonitrile (1.68 g, 10.0 mmol) were added into a 500 mL round bottom flask with single neck, then borane-tetrahydrofuran complex (50 mL, 1M, 50 mmol) was added, the mixture was heated from room temperature to boiling and reacted overnight. After the reaction was completed, the mixture was cooled to room temperature, methanol was carefully added until there was no bubble generated. The reaction mixture was added with ethyl acetate (80 mL), washed with saturated ammonium chloride and sodium chloride twice (70 mL*2), the ethyl acetate phase was dried with anhydrous sodium sulphate, filtered, the filtrate was spin-dried to obtain oily liquid ((2-cyclopropoxypyridyl-3-yl)methylamine (0.42 g, Y:25%). ES-API: $[M+H]^+$=165.1.

Preparation Example 7: Preparation of (5-fluoro-2-(oxetan-3-yl-oxy)phenyl)methylamine

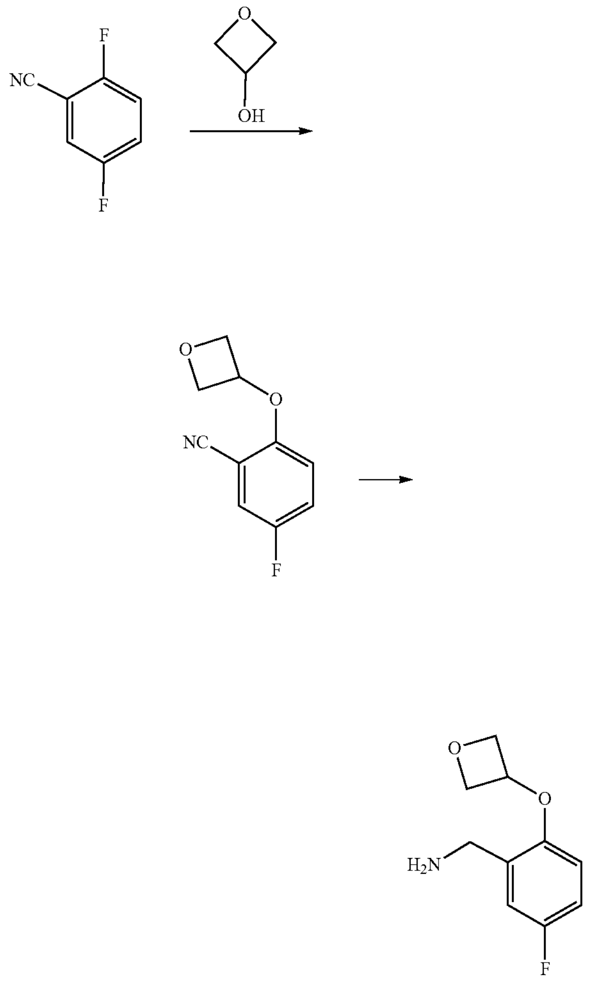

Step 1: Under the protection of nitrogen, at 0° C., tetrahydrofuran (50 mL) and oxetan-3-ol (0.74 g, 10.0 mmol) were added into a 100 mL round bottom flask with three necks, cesium carbonate (9.80 g, 30.0 mmol) was added, 2,5-difluorobenzonitrile (1.39 g, 10.0 mmol) was added at room temperature, the mixture was heated to 75° C. for 8 hours. After the reaction was completed, the mixture was cooled to room temperature, added with ethyl acetate (80 mL), washed with saturated ammonium chloride and sodium chloride twice (70 mL*2) successively, the ethyl acetate phase was dried with anhydrous sodium sulphate, filtered, the filtrate was spin-dried to obtain 5-fluoro-2-(oxetan-3-yloxy)benzonitrile (1.80 g, crude). ES-API: $[M+H]^+$=194.1.

Step 2: Under the protection of nitrogen, methanol (50 mL) and 5-fluoro-2-(oxetan-3-yl-oxy)benzonitrile (1.80 g, crude) were added into a 500 mL round bottom flask with single neck, then Raney-Ni (0.5 g) was added, and the mixture was reacted under the protection of hydrogen overnight. After the reaction was completed, celite was added to filtered, the filtrate was spin-dried to obtain 5-fluoro-2-(oxetan-3-yl-oxy)phenyl)methylamine (0.70 g, Y:87%), oily liquid. ES-API: $[M+H]^+$=198.1.

Preparation Example 8: Preparation of 1-(5-fluoro-2-(1-methyl-1H-pyrazol-4-yl)phenyl)ethyl-1-amine

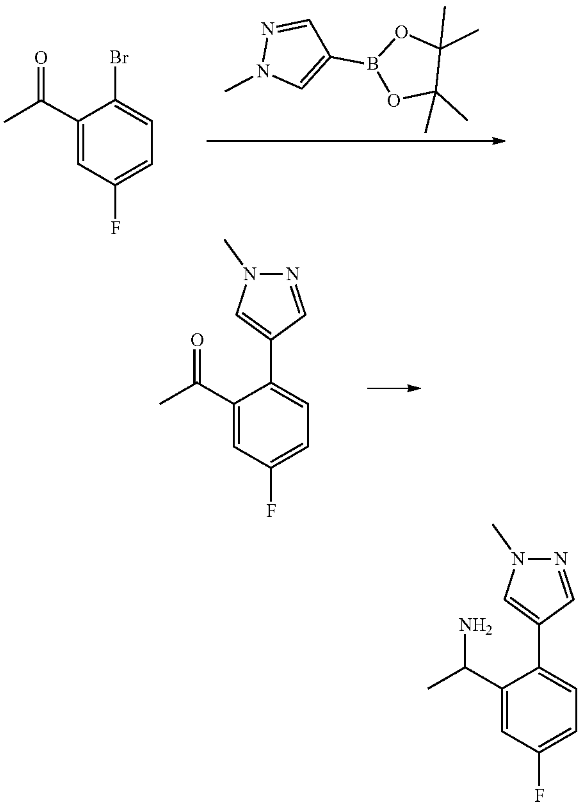

Step 1: Under the protection of nitrogen, dioxane (30 mL) and water (6 mL) were added into a 100 mL round bottom flask with three necks, 1-(2-bromo-5-fluorophenyl)ethyl-1-one (3.0 g, 13.89 mmol), 1-methyl-4-(4,4,5,5-tetramethyl-1,3,2-dioxaborinan-2-yl)-1H-pyrazol (3.46 g, 16.63 mmol), sodium carbonate (4.20 g, 39.62 mmol), [1,1'-bis(diphenylphosphino)ferrocene]dichloropalladium(II) (1.0 g, 1.363 mmol) were added into the solution, the mixture was heated to 100° C. in oil bath for 12 hours. LCMS showed the reaction was completed, the mixture was cooled to room temperature, added with ethyl acetate (80 mL), washed with saturated ammonium chloride and sodium chloride twice (60 mL*2) successively, the ethyl acetate phase was dried with anhydrous sodium sulphate, the combined organic layers were concentrated, purified on silica gel by automatic fast chromatography (EtOAc/PE 0-50%) to obtain 1-(5-fluoro-2-(1-methyl-1H-pyrazol-4-yl)phenyl)ethyl-1-one (2.5 g, Y: 71%). ES-API: $[M+H]^+$=219.1.

Step 2: Under the protection of nitrogen, methanol ammonia solution (5 mL) and 1-(5-fluoro-2-(1-methyl-1H-pyrazol-4-yl)phenyl)ethyl-1-one (0.5 g, 2.293 mmol) were added into a 100 mL round bottom flask with single neck, then tetraisopropyl titanate (3.256 g, 11.46 mmol) was added, and the mixture was reacted at room temperature under the protection of nitrogen for 24 hours. Then the mixture was cooled to 0° C., sodium borohydride (174 mg, 4.586 mmol) was added, the mixture was slowly heated to room temperature and reacted for 2 hours. After the reaction was completed, 4M sodium hydroxide aqueous solutions (20 mL) was added into the reaction mixture, the mixture was filtered, the filtrate was added with ethyl acetate (5 mL) and washed twice with saturated sodium chloride solution (30 mL*2), the ethyl acetate phase was dried over anhydrous sodium sulfate and filtered, and the combined organic layer was concentrated to obtain 1-(5-fluoro-2-(1-methyl-1H-pyrazol-4-yl)phenyl)ethyl-1-amine (315 mg, Y: 63%). ES-API: $[M+H]^+$=220.1.

Preparation Example 9: Preparation of (2-(1,3-dimethyl-1H-pyrazol-4-yl)-5-fluorophenyl)methylamine

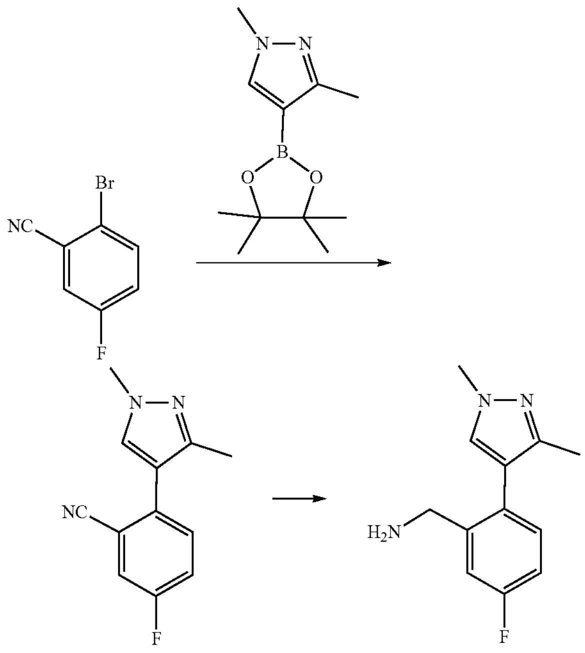

Step 1: Under the protection of nitrogen, dioxane (30 mL) and water (6 mL) were added into a microwave tube (30 mL), 2-bromo-5-fluorobenzonitrile (1.613 g, 8.107 mmol), 1,3-dimethyl-4-(4,4,5,5-tetramethyl-1,3,2-dioxaborinan-2-yl)-1H-pyrazole (1.50 g, 6.756 mmol), sodium carbonate (2.15 g, 20.268 mmol), [1,1'-bis(diphenylphosphino)ferrocene]dichloropalladium(II) (495 mg, 0.6756 mmol) were added into the solution, the mixture was replaced with nitrogen for three times, the reaction was subjected to microwave radiation at 100° C. for 35 minutes. LCMS showed the reaction was completed, the mixture was cooled to room temperature, added with ethyl acetate (80 mL), washed with saturated ammonium chloride and sodium chloride twice (60 mL*2) successively, the ethyl acetate phase was dried with anhydrous sodium sulphate, the combined organic layers were concentrated, purified on silica gel by automatic fast chromatography (EtOAc/PE 0-50%) to obtain 2-(1,3-2methyl-1H-pyrazol-4-yl)-5-fluorobenzonitrile (1.4 g, Y: 86%). ES-API: $[M+H]^+$=216.1.

Step 2: Under the protection of nitrogen, methanol (30 mL) and 2-(1,3-dimethyl-1H-pyrazol-4-yl)-5-fluorobenzonitrile (0.5 g, 2.325 mmol) were added into a 100 mL round bottom flask with single neck, then Raney-Ni (100 mg) was added, and the mixture was reacted under the protection of hydrogen for 12 hours, filtered, the filtrate was concentrated to obtain (2-(1,3-dimethyl-1H-pyrazol-4-yl)-5-fluorophenyl)methylamine (402 mg, Y: 76%). ES-API: $[M+H]^+$=220.1.

Preparation Example 10: Preparation of (2-(1,5-dimethyl-1H-pyrazol-4-yl)-5-fluorophenyl)methylamine

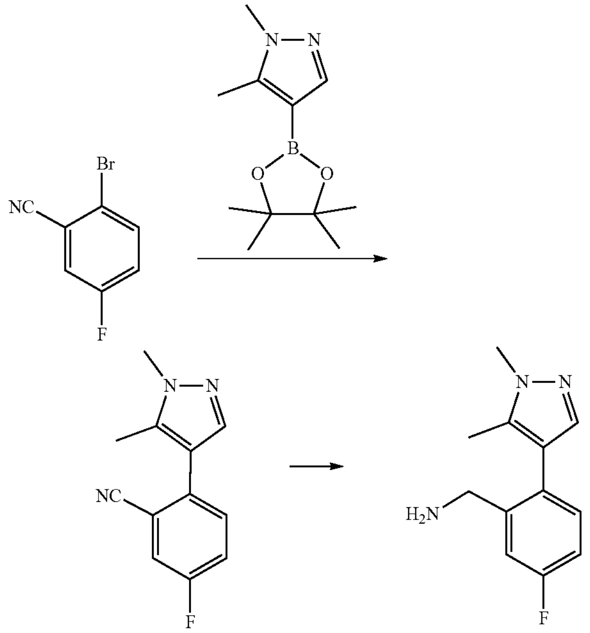

Step 1: Under the protection of nitrogen, dioxane (30 mL) and water (6 mL) were added into a microwave tube, 2-bromo-5-fluorobenzonitrile (1.613 g, 8.107 mmol), 1,5-dimethyl-4-(4,4,5,5-tetramethyl-1,3,2-dioxaborinan-2-yl)-1H-pyrazol (1.50 g, 6.756 mmol), sodium carbonate (2.15 g, 20.268 mmol), [1,1'-bis(diphenylphosphino)ferrocene]dichloropalladium(II) (495 mg, 0.6756 mmol) were added into the solution, the mixture was replaced with nitrogen for three times, the reaction was subjected to microwave radiation at 100° C. for 35 min. LCMS showed the reaction was completed, the mixture was cooled to room temperature, added with ethyl acetate (80 mL), washed with saturated ammonium chloride and sodium chloride twice (60 mL*2) successively, the ethyl acetate phase was dried with anhydrous sodium sulphate, the combined organic layers were concentrated, purified on silica gel by automatic fast chromatography (EtOAc/PE 0-50%) to obtain 2-(1,5-dimethyl-1H-pyrazol-4-yl)-5-fluorobenzonitrile (1.05 g, Y: 65%). ES-API: $[M+H]^+=216.1$.

Step 2: Under the protection of nitrogen, methanol (30 mL) and 2-(1,5-dimethyl-1H-pyrazol-4-yl)-5-fluorobenzonitrile (0.5 g, 2.325 mmol) were added into a 100 mL round bottom flask with single neck, then Raney-Ni (100 mg) was added, and reacted at room temperature for 12 hours, filtered, the filtrate was concentrated to obtain (2-(1,5-dimethyl-1H-pyrazol-4-yl)-5-fluorophenyl)methylamine (404 mg, Y: 80%). ES-API: $[M+H]^+=220.1$.

Example 65 to 72 and Example 75 to 82

Compounds 65 to 72 and compounds 75 to 82 can be prepared by referring to the methods of the above Examples, e.g. by referring to Example 48, the difference was that (2-fluoro-5-(trifluoromethoxy)phenyl methylamine was replaced with a different amino compound.

| Example | Amino compound | Structure and number of final products | MS $[M + H]^+$ |
|---|---|---|---|
| 65 | 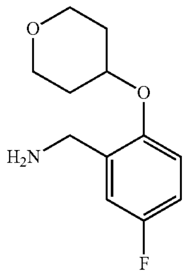 [SMILES: NCc1cc(F)ccc1OC1CCOCC1] | 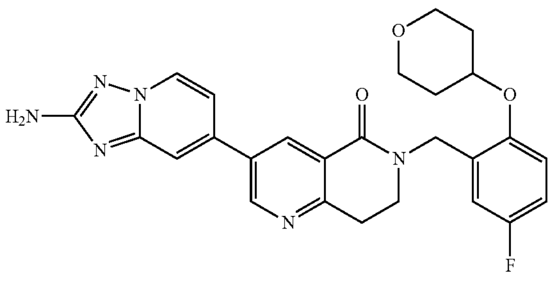 Z65 | 489.2 |
| 66 | 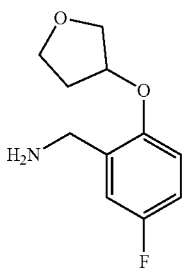 [SMILES: NCc1cc(F)ccc1OC1CCOC1] | 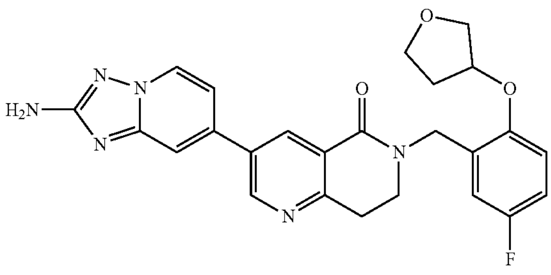 Z66 | 475.2 |

-continued
| Example | Amino compound | Structure and number of final products | MS $[M + H]^+$ |
|---|---|---|---|
| 67 | 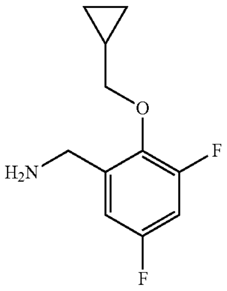 [SMILES: NCc1cc(F)cc(F)c1OCC1CC1] | 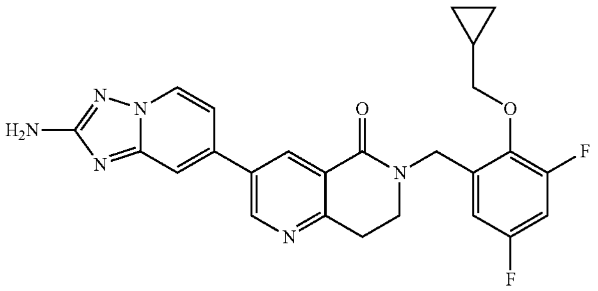 Z67 | 477.2 |
| 68 | 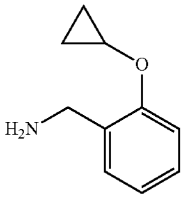 [SMILES: NCc1ccccc1OC1CC1] | 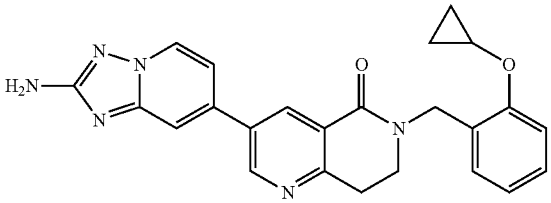 Z68 | 427.2 |
| 69 | 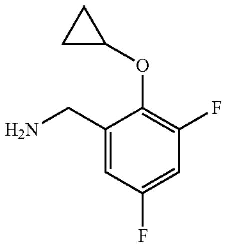 [SMILES: NCc1cc(F)cc(F)c1OC1CC1] | 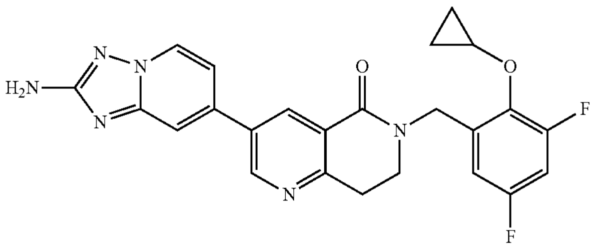 Z69 | 463.2 |
| 70 | 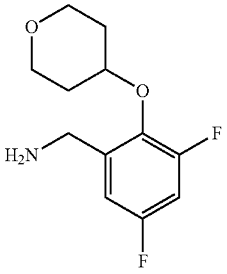 [SMILES: NCc1cc(F)cc(F)c1OC1CCOCC1] | 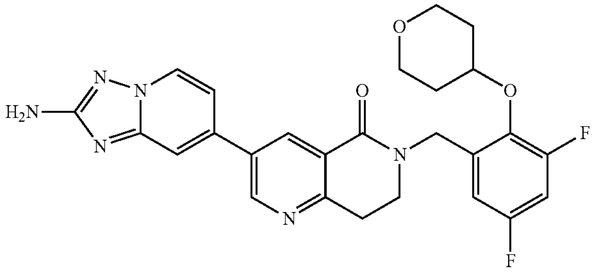 Z70 | 507.2 |
| 71 | 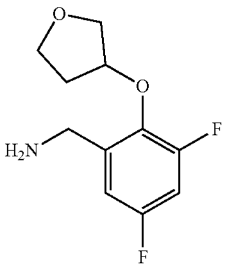 [SMILES: NCc1cc(F)cc(F)c1OC1CCOC1] | 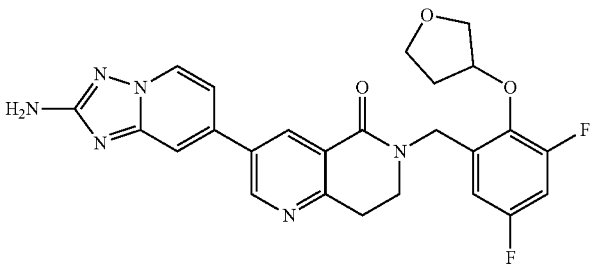 Z71 | 493.2 |

-continued
| Example | Amino compound | Structure and number of final products | MS $[M + H]^+$ |
| --- | --- | --- | --- |
| 72 | 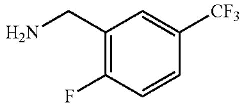 [SMILES: NCc1cc(C(F)(F)F)ccc1F] | 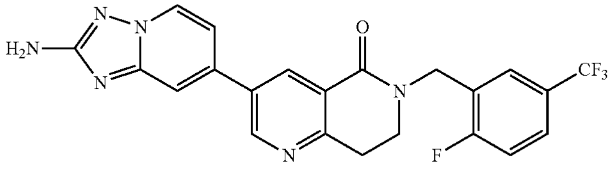 Z72 | 457 |
| 75 | 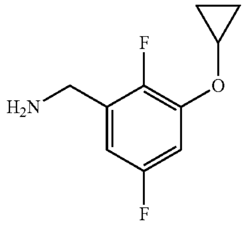 [SMILES: NCc1cc(F)cc(OC2CC2)c1F] | 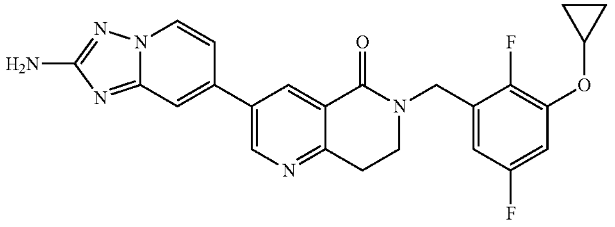 Z75 | 463.2 |
| 76 | 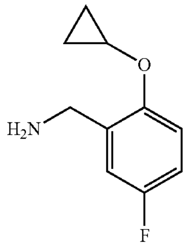 [SMILES: NCc1cc(F)ccc1OC1CC1] | 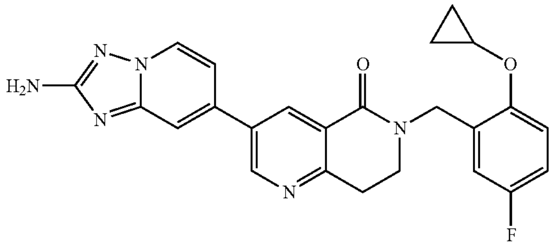 Z76 | 445.2 |
| 77 | 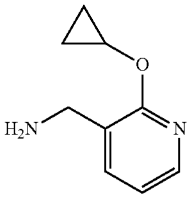 [SMILES: NCc1cccnc1OC1CC1] | 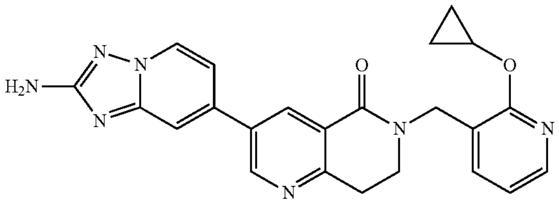 Z77 | 428.2 |
| 78 | 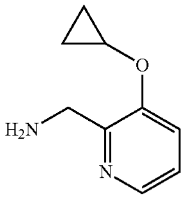 [SMILES: NCc1ncccc1OC1CC1] | 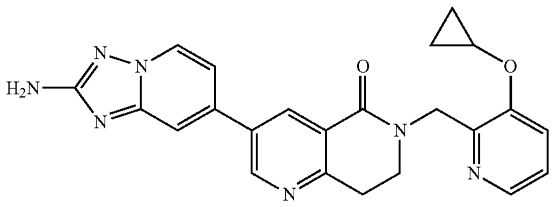 Z78 | 428.2 |
| 79 | 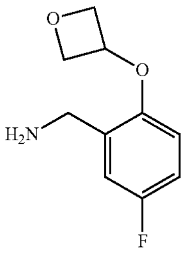 [SMILES: NCc1cc(F)ccc1OC1COC1] | 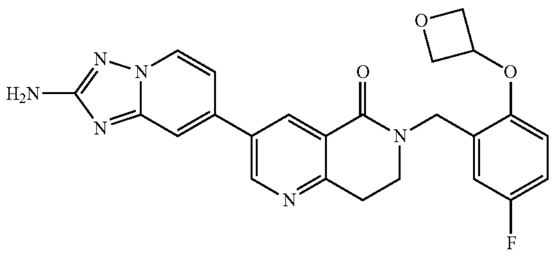 Z79 | 461.2 |

-continued

| Example | Amino compound | Structure and number of final products | MS [M + H]+ |
|---|---|---|---|
| 81 | 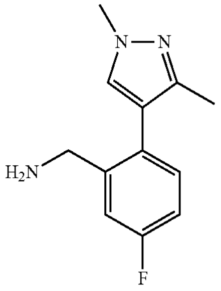 [SMILES: Cc1nn(C)cc1-c1ccc(F)cc1CN] | 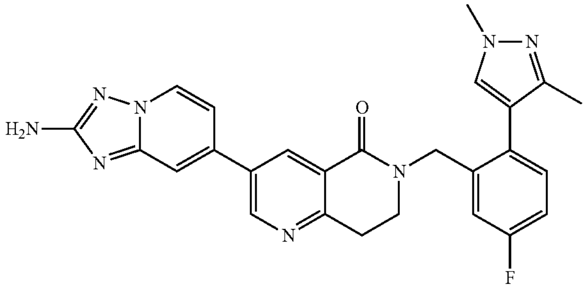 Z81 | 483.2 |
| 82 | 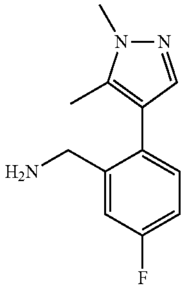 [SMILES: Cc1c(-c2ccc(F)cc2CN)cnn1C] | 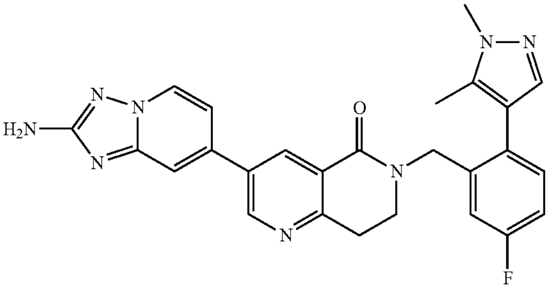 Z82 | 483.2 |

| Number | NMR |
|---|---|
| Z65 | $^1$H NMR (500 MHz, DMSO-d6) δ 9.02 (s, 1H), 8.57 (d, J = 6.9 Hz, 1H), 8.44 (s, 1H), 7.72 (s, 1H), 7.22 (d, J = 6.8 Hz, 1H), 7.11-6.93 (m, 3H), 6.03 (s, 2H), 4.65 (s, 2H), 4.54 (s, 1H), 3.85-3.72 (m, 2H), 3.62 (t, J = 6.6 Hz, 2H), 3.42 (t, J = 9.1 Hz, 2H), 3.14 (t, J = 6.5 Hz, 2H), 1.90 (d, J = 9.6 Hz, 2H), 1.64-1.47 (m, 2H) |
| Z66 | $^1$H NMR (500 MHz, DMSO-d6) δ 9.01 (d, J = 2.1 Hz, 1H), 8.57 (d, J = 7.0 Hz, 1H), 8.43 (d, J = 2.1 Hz, 1H), 7.72 (s, 1H), 7.22 (d, J = 7.1 Hz, 1H), 6.99 (ddd, J = 13.3, 10.5, 6.8 Hz, 3H), 6.03 (s, 2H), 4.99 (s, 1H), 4.67-4.54 (m, 2H), 3.82 (dd, J = 10.1, 4.4 Hz, 1H), 3.78-3.65 (m, 3H), 3.60 (t, J = 6.7 Hz, 2H), 3.12 (t, J = 6.6 Hz, 2H), 2.13 (td, J = 14.2, 8.2 Hz, 1H), 1.98-1.85 (m, 1H) |
| Z67 | $^1$H NMR (500 MHz, DMSO-d6) δ 9.03 (s, 1H), 8.57 (d, J = 7.0 Hz, 1H), 8.45 (s, 1H), 7.73 (s, 1H), 7.30-7.13 (m, 2H), 6.89 (d, J = 8.9 Hz, 1H), 6.03 (s, 2H), 4.76 (s, 2H), 3.82 (d, J = 7.2 Hz, 2H), 3.65 (t, J = 6.6 Hz, 2H), 3.16 (t, J = 6.5 Hz, 2H), 1.17 (d, J = 7.4 Hz, 1H), 0.49 (d, J = 7.6 Hz, 2H), 0.23 (d, J = 4.6 Hz, 2H) |
| Z68 | $^1$H NMR (500 MHz, DMSO-d6) δ 9.08 (d, J = 2.4 Hz, 1H), 8.64 (d, J = 7.0 Hz, 1H), 8.50 (d, J = 2.4 Hz, 1H), 7.79 (d, J = 1.3 Hz, 1H), 7.34-7.22 (m, 4H), 7.00-6.92 (m, 1H), 6.10 (s, 2H), 4.65 (s, 2H), 3.91 (tt, J = 6.0, 2.9 Hz, 1H), 3.62 (t, J = 6.7 Hz, 2H), 3.17 (t, J = 6.7 Hz, 2H), 0.80 (dt, J = 11.6, 5.8 Hz, 2H), 0.71-0.62 (m, 2H) |
| Z69 | $^1$H NMR (500 MHz, DMSO-d6) δ 9.02 (d, J = 2.4 Hz, 1H), 8.57 (d, J = 7.0 Hz, 1H), 8.44 (d, J = 2.3 Hz, 1H), 7.73 (d, J = 1.2 Hz, 1H), 7.29-7.18 (m, 2H), 6.91 (d, J = 8.8 Hz, 1H), 6.03 (s, 2H), 4.63 (s, 2H), 4.14 (dt, J = 9.0, 3.0 Hz, 1H), 3.61 (t, J = 6.7 Hz, 2H), 3.14 (t, J = 6.7 Hz, 2H), 0.76 (s, 2H), 0.59-0.48 (m, 2H) |
| Z70 | $^1$H NMR (500 MHz, DMSO-d6) δ 9.03 (d, J = 2.4 Hz, 1H), 8.57 (d, J = 6.9 Hz, 1H), 8.45 (d, J = 2.4 Hz, 1H), 7.73 (d, J = 1.2 Hz, 1H), 7.26-7.16 (m, 2H), 6.90 (d, J = 8.7 Hz, 1H), 6.03 (s, 2H), 4.74 (s, 2H), 4.27-4.18 (m, 1H), 3.83 (dt, J = 11.6, 3.9 Hz, 2H), 3.63 (t, J = 6.7 Hz, 2H), 3.31 (dd, J = 15.7, 6.4 Hz, 2H), 3.16 (t, J = 6.7 Hz, 2H), 1.88 (d, J = 10.9 Hz, 2H), 1.72-1.55 (m, 2H) |
| Z71 | $^1$H NMR (500 MHz, DMSO-d6) δ 9.03 (d, J = 2.4 Hz, 1H), 8.57 (d, J = 6.9 Hz, 1H), 8.44 (d, J = 2.4 Hz, 1H), 7.73 (d, J = 1.3 Hz, 1H), 7.22 (ddd, J = 11.8, 7.9, 2.5 Hz, 2H), 6.91 (d, J = 8.8 Hz, 1H), 6.03 (s, 2H), 4.93 (s, 1H), 4.68 (s, 2H), 3.96-3.81 (m, 2H), 3.73 (dd, J = 14.4, 6.5 Hz, 1H), 3.65 (dt, J = 13.5, 5.4 Hz, 3H), 3.16 (t, J = 6.7 Hz, 2H), 2.06 (td, J = 7.2, 3.7 Hz, 2H) |
| Z72 | $^1$H NMR (400 MHz, DMSO-d6) δ 9.09 (d, J = 2.1 Hz, 1H), 8.64 (d, J = 6.8 Hz, 1H), 8.51 (d, J = 2.0 Hz, 1H), 7.81 (d, J = 11.6 Hz, 3H), 7.50 (t, J = 9.1 Hz, 1H), 7.30 (d, J = 5.8 Hz, 1H), 6.10 (s, 2H), 4.86 (s, 2H), 3.76 (s, 2H), 3.20 (t, J = 6.6 Hz, 2H) |
| Z75 | $^1$H NMR (500 MHz, DMSO-d6) δ 9.09 (d, J = 2.4 Hz, 1H), 8.64 (d, J = 7.0 Hz, 1H), 8.51 (d, J = 2.4 Hz, 1H), 7.80 (d, J = 1.3 Hz, 1H), 7.30 (dd, J = 7.0, 1.9 Hz, 1H), 7.25 (ddd, J = 9.7, 6.6, 3.0 Hz, 1H), 6.85-6.76 (m, 1H), 6.09 (s, 2H), 4.78 (s, 2H), 4.04-3.96 (m, 1H), 3.71 (t, J = 6.7 Hz, 2H), 3.21 (t, J = 6.7 Hz, 2H), 0.88-0.80 (m, 2H), 0.76-0.67 (m, 2H) |

-continued

| Number | NMR |
|---|---|
| Z76 | $^1$H NMR(500 MHz, DMSO-d6) δ 9.08 (s, 1H), 8.64 (d, J = 6.8 Hz, 1H), 8.50 (s, 1H), 7.79 (s, 1H), 7.31 (s, 2H), 7.22-7.00 (m, 2H), 6.09 (s, 2H), 4.63 (s, 2H), 3.92 (s, 1H), 3.65 (d, J = 6.4 Hz, 2H), 3.19 (s, 2H), 0.79 (d, J = 4.9 Hz, 2H), 0.68 (s, 2H) |
| Z77 | $^1$H NMR 500 MHz, DMSO-d6) δ 9.08 (d, J = 2.4 Hz, 1H), 8.64 (d, J = 7.0 Hz, 1H), 8.49 (d, J = 2.3 Hz, 1H), 8.13 (dd, J = 4.9, 1.6 Hz, 1H), 7.79 (d, J = 1.1 Hz, 1H), 7.64 (d, J = 6.0 Hz, 1H), 7.29 (dd, J = 7.0, 1.9 Hz, 1H), 7.01 (dd, J = 7.2, 5.0 Hz, 1H), 6.10 (s, 2H), 4.60 (s, 2H), 4.39-4.29 (m, 1H), 3.67 (t, J = 6.7 Hz, 2H), 3.20 (t, J = 6.7 Hz, 2H), 0.82-0.71 (m, 2H), 0.67 (dd, J = 10.6, 5.0 Hz, 2H) |
| Z78 | $^1$H NMR (500 MHz, DMSO-d6) δ 9.08 (d, J = 2.4 Hz, 1H), 8.63 (d, J = 7.0 Hz, 1H), 8.47 (d, J = 2.4 Hz, 1H), 8.14-8.04 (m, 1H), 7.79 (d, J = 1.3 Hz, 1H), 7.68 (dd, J = 8.3, 1.0 Hz, 1H), 7.30 (ddd, J = 8.9, 7.6, 3.3 Hz, 2H), 6.08 (s, 2H), 4.81 (s, 2H), 4.03-3.94 (m, 1H), 3.74 (t, J = 6.7 Hz, 2H), 3.32 (s, 6H), 3.20 (t, J = 6.7 Hz, 2H), 0.82 (t, J = 6.5 Hz, 2H), 0.71 (d, J = 7.2 Hz, 2H) |
| Z79 | $^1$H NMR (500 MHz, DMSO-d6) δ 9.01 (d, J = 2.3 Hz, 1H), 8.57 (d, J = 7.0 Hz, 1H), 8.44 (d, J = 2.3 Hz, 1H), 7.72 (s, 1H), 7.22 (dd, J = 7.0, 1.8 Hz, 1H), 7.07 (dd, J = 9.1, 3.1 Hz, 1H), 6.99 (td, J = 8.6, 3.1 Hz, 1H), 6.59 (dd, J = 8.9, 4.4 Hz, 1H), 6.02 (s, 2H), 5.29-5.21 (m, 1H), 4.85 (t, J = 6.7 Hz, 2H), 4.69 (s, 2H), 4.50 (dd, J = 7.2, 5.0 Hz, 2H), 3.65 (t, J = 6.7 Hz, 2H), 3.15 (t, J = 6.7 Hz, 2H) |
| Z81 | $^1$H NMR (400 MHz, DMSO-d6) δ 9.01 (d, J = 2.4 Hz, 1H), 8.57 (d, J = 6.9 Hz, 1H), 8.43 (d, J = 2.4 Hz, 1H), 7.73 (s, 1H), 7.66 (s, 1H), 7.23 (dd, J = 7.0, 1.9 Hz, 1H), 7.19 (dd, J = 8.3, 6.0 Hz, 1H), 7.11-7.04 (m, 2H), 6.03 (s, 2H), 4.58 (s, 2H), 3.73 (s, 3H), 3.45 (t, J = 6.7 Hz, 2H), 3.09 (t, J = 6.7 Hz, 2H), 1.99 (s, 3H) |
| Z82 | $^1$H NMR (500 MHz, DMSO-d6) δ 9.01 (d, J = 2.4 Hz, 1H), 8.57 (d, J = 7.0 Hz, 1H), 8.42 (d, J = 2.3 Hz, 1H), 7.72 (d, J = 1.2 Hz, 1H), 7.34 (d, J = 8.8 Hz, 1H), 7.22 (dd, J = 7.0, 1.9 Hz, 1H), 7.17-7.13 (m, 1H), 7.09 (dd, J = 14.6, 6.3 Hz, 2H), 6.03 (s, 2H), 4.57 (s, 2H), 3.72 (s, 3H), 3.44 (t, J = 6.7 Hz, 2H), 3.09 (t, J = 6.7 Hz, 2H), 2.10 (s, 3H) |

Example 86 3-(2-amino-[1,2,4]triazolo[1,5-a]pyridyl-7-yl)-6-(((3-cyclopropoxypyridyl-2-yl)methyl)-2-methyl-7,8-dihydro-1,6-naphthyridin-5(6H)-one (Z93)

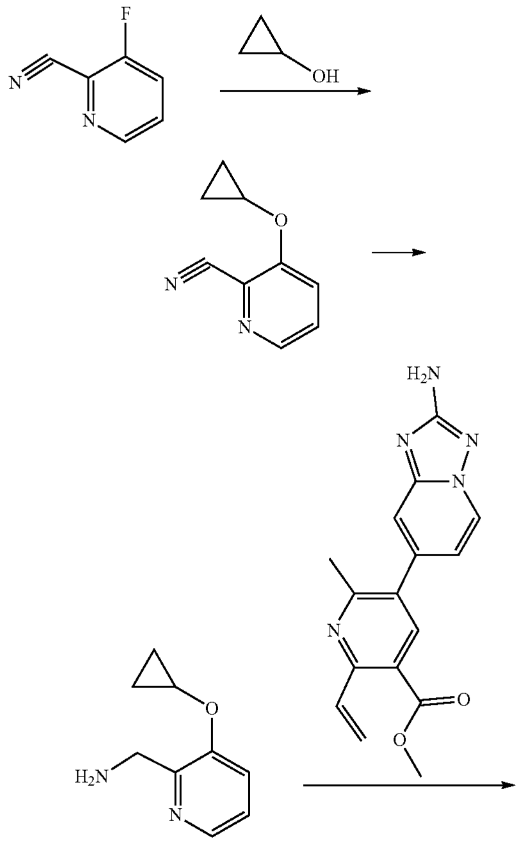

-continued

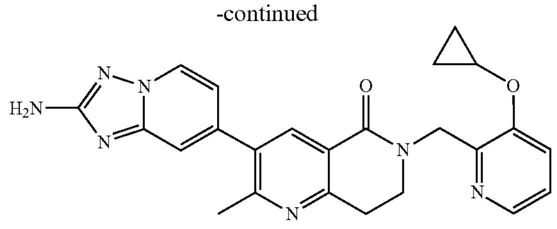

Z93

Step 1: Under the protection of nitrogen, dry N,N-dimethylformamide (50 mL) and cyclopropanol (1.0 g, 17.238 mmol) were added into a 100 mL round bottom flask with three necks, then cesium carbonate (12.33 g, 37.84 mmol) was added, 3-fluoropicolinonitrile (1.45 g, 11.88 mmol) was added at room temperature, the mixture was slowly heated to 75° C. for 8 hours. After the reaction was completed, the mixture was cooled to room temperature, added with ethyl acetate (80 mL), washed with saturated ammonium chloride and sodium chloride twice (70 mL*2) successively, the ethyl acetate phase was dried with anhydrous sodium sulphate, filtered, the filtrate was spin-dried to obtain 3-cyclopropylpyridinoline (1.98 g, crude product). ES-API: $[M+H]^+$=161.2.

Step 2: Under the protection of nitrogen, tetrahydrofuran (50 mL) and 3-cyclopropylpyridinoline (1.98 g, crude product) were added into a 500 mL round bottom flask with single neck, then borane-tetrahydrofuran complex (59 mL, 1M, 59 mmol) was added, the mixture was heated from room temperature to reflux and reacted overnight. After the reaction was completed, the mixture was cooled to room temperature, methanol was carefully added until there was no bubble generated. The reaction mixture was added with ethyl acetate (80 mL), washed with saturated ammonium chloride and sodium chloride twice (70 mL*2), the ethyl acetate phase was dried with anhydrous sodium sulphate, filtered, the filtrate was spin-dried to obtain oily liquid (3-cyclopropoxypyridyl-2-yl)methylamine (1.37 g, Y:70%). ES-API: $[M+H]^+$=165.2.

Step 3: Methyl 5-(2-amino-[1,2,4]triazolo[1,5-a]pyridyl-7-yl)-6-methyl-2-vinylnicotinate (65 mg, 0.210 mmol) and (3-cyclopropoxypyridyl-2-yl)methylamine (300 mg, 1.827 mmol) were mixed in DMA (2.5 mL) in a microwave bottle. The reaction was subjected to microwave radiation at 150° C. for 2 hours, cooled to room temperature, the reaction mixture was added with ethyl acetate (50 mL), then washed with water (45 mL*3) and saturated sodium chloride solution (45 mL*3), the combined organic layers were concentrated, purified on silica gel by automatic fast chromatography (EtOAc/PE 0-50%) to obtain 3-(2-amino-[1,2,4]triazolo[1,5-a]pyridyl-7-yl)-6-(((3-cyclopropoxypyridyl-2-yl)methyl)-2-methyl-7,8-dihydro-1,6-naphthyridin-5(6H)-one (Z93, 17.0 mg, Y:18.4%). ES-API: $[M+H]^+$=442.3. $^1H$ NMR (400 MHz, DMSO-d6) δ 8.61 (d, J=6.9 Hz, 1H), 8.08 (dd, J=4.7, 1.1 Hz, 1H), 7.98 (s, 1H), 7.67 (dd, J=8.3, 1.2 Hz, 1H), 7.41 (d, J=1.0 Hz, 1H), 7.31 (dd, J=8.3, 4.7 Hz, 1H), 6.93 (dd, J=6.9, 1.9 Hz, 1H), 6.07 (s, 2H), 4.77 (s, 2H), 4.01-3.93 (m, 1H), 3.72 (t, J=6.8 Hz, 2H), 3.15 (t, J=6.7 Hz, 2H), 2.52 (s, 3H), 0.82 (t, J=6.3 Hz, 2H), 0.72-0.61 (m, 2H).

Example 87 2-(Benzoxy)-N-(6-(6-(3,5-difluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)acetamide (Z94)

Step 1: HATU (858 mg, 2.259 mmol) was added into a solution of 2-amino-6-chloroimidazo[1,2-b]pyridazine (266 mg, 1.581 mmol), 2-(benzoxy)acetic acid (250 mg, 1.506 mmol), DIPEA (971 mg, 7.530 mmol) in N,N-dimethylacetamide (7 mL), the reaction mixture was stirred at room temperature overnight, LCMS showed the reaction was completed, the reaction mixture was added with water (50 mL), then extracted with EtOAc (30 mL*3), the combined organic phases were washed with saturated sodium chloride solution (15 mL*3), concentrated, the residue was purified on silica gel by automatic fast chromatography to obtain white product 2-(benzoxy)-N-(6-chloroimidazo[1,2-b]pyridazin-2-yl)acetamide (428 mg, Y: 90%). ES-API: $[M+H]^+$=317.1.

Step 6: Under the protection of nitrogen, 6-(3,5-difluoro-2-((tetrahydro-2H-pyran-4-yl)oxy)benzyl)-3-(4,4,5,5-tetramethyl-1,3,2-dioxaborolan-2-yl)-7,8-dihydro-1,6-naphthyridin-5(6H)-one (190 mg, 0.380 mmol), 2-(benzoxy)-N-(6-chloroimidazo[1,2-b]pyridazin-2-yl)acetamide (60 mg, 0.190 mmol), sodium carbonate (50 mg, 0.475 mmol), 1,1'-bis(diphenylphosphino)ferrocene-palladium(II)dichloride dichloromethane complex (8 mg, 0.0095 mmol) was dissolved in dioxane (5 mL) and $H_2O$ (1 mL), the mixture was replaced with nitrogen for three times, the reaction mixture was heated to 95° C. in oil bath for 2 hours, then

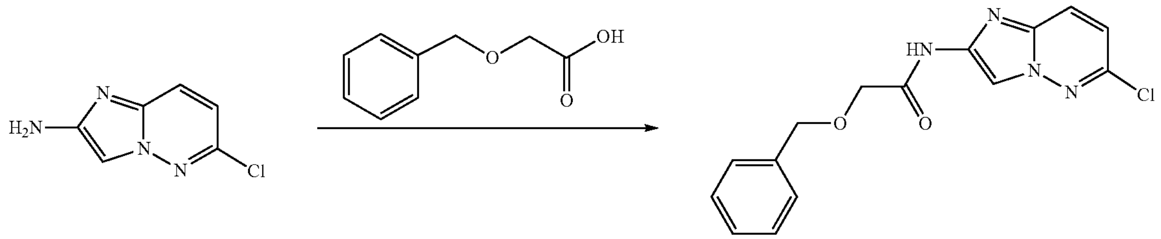 [SMILES: Nc1cn2nc(Cl)ccc2n1 ; O=C(O)COCc1ccccc1 ; O=C(COCc1ccccc1)Nc1cn2nc(Cl)ccc2n1]

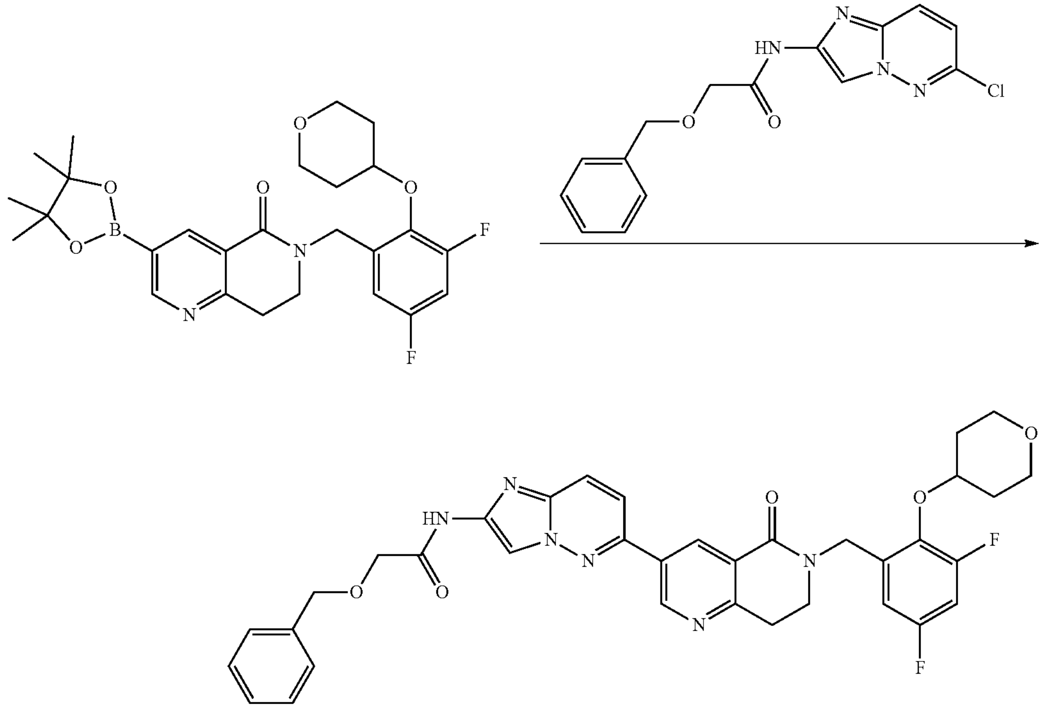

Z94 cooled to room temperature, concentrated, the crude product was purified by alkaline HPLC to obtain off-white solid 2-(benzox)-N-(6-(6-(3,5-difluoro-2-((tetrahydro-2H-pyran-4-yl)oxy)benzyl)-5-oxo-5,6,7,8-tetrahydro-1,6-naphthyridin-3-yl)imidazo[1,2-b]pyridazin-2-yl)acetamide (Z94, 37.7 mg, Y: 30%). ES-API: $[M+H]^+$=655.2. $^1H$ NMR (400 MHz, DMSO-d6) δ 10.82 (s, 1H), 9.32 (d, J=2.0 Hz, 1H), 8.81 (d, J=2.0 Hz, 1H), 8.43 (s, 1H), 8.15 (d, J=9.5 Hz, 1H), 7.96 (d, J=9.5 Hz, 1H), 7.42-7.37 (m, 4H), 7.33-7.26 (m, 2H), 6.99-6.98 (m, 1H), 4.82 (s, 2H), 4.63 (s, 2H), 4.32-4.27 (m, 1H), 4.24 (s, 2H), 3.92-3.88 (m, 2H), 3.71 (t, J1=7.0 Hz, J2=13.5 Hz, 2H), 3.41-3.36 (m, 2H), 3.26 (t, J1=6.5 Hz, J2=13.0 Hz, 2H), 1.97-1.94 (m, 2H), 1.74-1.67 (m, 2H).

Example 88 3-(4-amino-5-methylpyrrolo[2,1-f][1,2,4]triazin-7-yl)-6-(1-(1-(1-(4-fluorophenyl)ethyl)-1H-pyrazol-4-yl)-7,8-dihydro-1,6-naphthyridin-5(6H)-one (Z97)

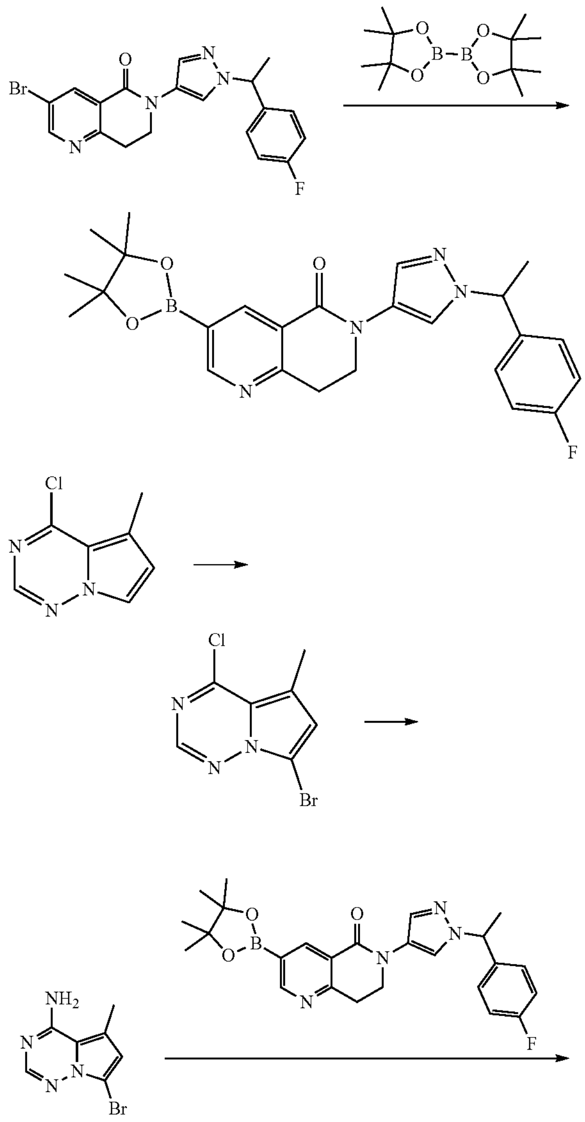

-continued

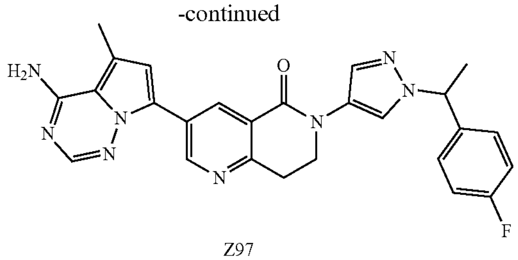

Z97

Step 5: 3-Bromo-6-(1-(1-(4-fluorophenyl)ethyl)-1H-pyrazol-4-yl)-7,8-dihydro-1,6-naphthyridin-5(6H)-one (177 mg, 0.428 mmol), bis(pinacolato)diboron (219 mg, 0.856 mmol), potassium acetate (104 mg, 1.070 mmol), [1,1'-bis(diphenylphosphino)ferrocene]dichloropalladium(II) (16 mg, 0.0214 mmol) and 1,4-dioxane (8 mL) were added into a 100 mL round bottom flask, the mixture was replaced with nitrogen for three times, and reacted at 100° C. overnight, cooled to room temperature, filtered with suction, the filter cake was washed with ethyl acetate for three times to obtain the filtrate, the filtrate was concentrated to obtain crude product 6-(1-(1-(1-(4-fluorophenyl)ethyl)-1H-pyrazol-4-yl)-3-(4,4,5,5-tetramethyl-1,3,2-dioxaborinan-2-yl)-7,8-dihydro-1,6-naphthyridin-5(6H)-one (198 mg, Y: 100%). ES-API: $[M+H]^+$=463.2.

Step 6: 4-Chloro-5-methylpyrrolo[2,1-f][1,2,4]triazine (200 mg, 1.313 mmol), N— bromosuccinimide (234 mg, 1.313 mmol), trifluoroacetic acid (0.4 mL) was dissolved in dichloromethane (4 mL). The reaction solution was stirred at room temperature for 3 hours. The solvent was concentrated to dryness and the residue was purified on silica gel by automated fast chromatography to obtain 7-bromo-4-chloro-5-methylpyrrolo[2,1-f][1,2,4]triazine (90 mg, Y: 28%). ES-API:$[M+H]^+$=245.9.

Step 7: Aqueous ammonia (0.5 mL, 3.67 mmol) was added into a solution of 7-bromo-4-chloro-5-methylpyrrolo[2,1-f][1,2,4]triazine (90 mg, 0.367 mmol) in dioxane (2 mL), the reaction mixture was stirred at room temperature overnight. The solution was concentrated to dryness to obtain compound 7-bromo-5-methylpyrrolo[2,1-f][1,2,4]triazin-4-amine (83 mg, Y: 99%). ES-API: $[M+H]^+$=227.0.

Step 8: Under the protection of nitrogen, 7-bromo-5-methylpyrrolo[2,1-f][1,2,4]triazin-4-amine (38 mg, 0.171 mmol), 6-(1-(1-(1-(4-fluorophenyl)ethyl)-1H-pyrazol-4-yl)-3-(4,4,5,5-tetramethyl-1,3,2-dioxaborinan-2-yl)-7,8-dihydro-1,6-naphthyridin-5(6H)-one (158 mg, 0.341 mmol), sodium carbonate (45 mg, 0.428 mmol), [1,1'-bis(diphenylphosphino)ferrocene-palladium(II)dichloride dichloromethane complex (14 mg, 0.0171 mmol) were dissolved in dioxane (10 mL) and $H_2O$ (2 mL), the mixture was replaced with nitrogen for three times, the reaction mixture was heated to 95° C. in oil bath for 2 hours. After the reaction was completed, the mixture was cooled to room temperature, concentrated, the residue was purified on silica gel by automatic fast chromatography to obtain 3-(4-amino-5-methylpyrrolo[2,1-f][1,2,4]triazin-7-yl)-6-(1-(1-(1-(4-fluorophenyl)ethyl)-1H-pyrazol-4-yl)-7,8-dihydro-1,6-naphthyridin-5(6H)-one (Z97, 7.6 mg, Y: 9%). ES-API: $[M+H]^+$=483.2. $^1H$ NMR (400 MHz, DMSO-d6) δ9.18 (d, J=3.0 Hz, 1H), 9.00 (d, J=3.0 Hz, 1H), 8.32 (s, 1H), 7.90 (s, 1H), 7.86 (s, 1H), 7.36-7.33 (m, 2H), 7.20-7.15 (m, 2H), 7.07 (s, 1H), 5.67-5.62 (m, 1H), 4.09 (t, J1=8.5 Hz, J2=17.0 Hz, 2H), 3.27 (t, J1=9.0 Hz, J2=17.0 Hz, 2H), 2.53 (s, 3H), 1.81 (d, J=8.5 Hz, 3H).

Example 89 3-(2-amino-8-methyl-[1,2,4]triazolo[1,5-a]pyridyl-7-yl)-6-((3-cyclopropoxypyridyl-2-yl)methyl)-7,8-dihydro-1,6-naphthyridin-5(6H)-one (Z98)

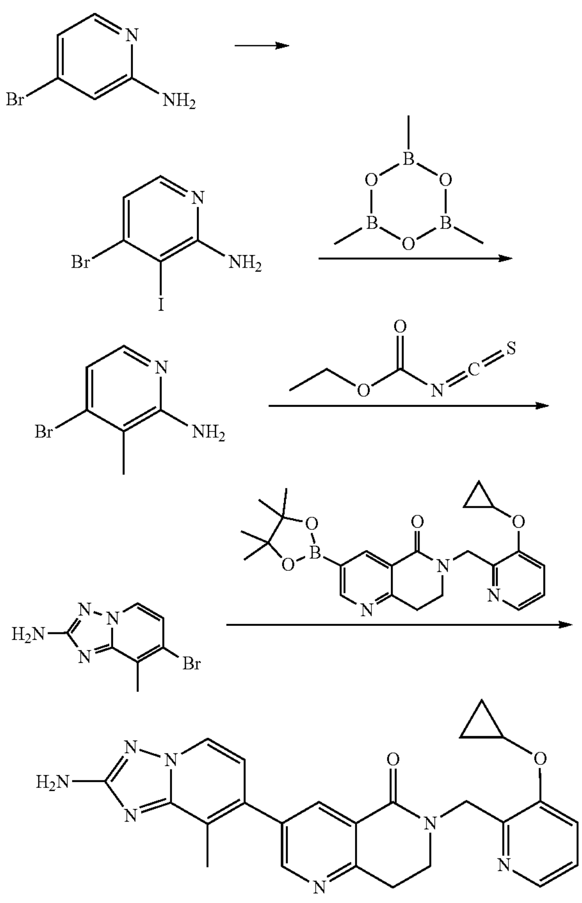

Z98

Step 1: HOAC (5 mL) and $H_5IO_6$ (1 g) were added into 4-bromopyridyl-2-amine (1.72 g, 10 mmol) in 30% $H_2SO_4$ (30 mL) solution, after dissolving completely, the reaction mixture was added with $I_2$ (1.5 g, 5.91 mmol) at once, the reaction mixture was heated to 80° C. and stirred for 1.5 hours. LCMS showed the reaction was completed, the mixture was cooled to room temperature, poured into 100 mL ice water, gray insoluble substance was precipitated, filtered, the filter cake was purified on silica gel by automatic fast chromatography to obtain 4-bromo-3-iodopyridyl-2-amine (702 mg, Y: 24%). ES-API: $[M+H]^+$=298.8.

Step 2: Under the protection of nitrogen, 4-bromo-3-iodopyridyl-2-amine (520 mg, 1.745 mmol), 2,4,6-3methyl-1,3,5,2,4,6-trioxytriborane (330 mg, 2.617 mmol), sodium carbonate (462 mg, 4.363 mmol), [1,1'-bis(diphenylphosphino)ferrocene-palladium(II)dichloride dichloromethane complex (143 mg, 0.1745 mmol) were dissolved in dioxane (12 mL) and $H_2O$ (3 mL), the mixture was replaced with nitrogen for three times, the reaction mixture was stirred at 80° C. in oil bath overnight, cooled to room temperature, concentrated, the crude product was purified on silica gel by automatic fast chromatography to obtain 4-bromo-3-methylpyridyl-2-amine (130 mg, Y: 40%). ES-API: $[M+H]^+$=187.0.

Step 3: 4-Bromo-3-methylpyridyl-2-amine (130 mg, 0.699 mmol) and O-ethyl carbonisothiocyanatidate (103 mg, 0.769 mmol) were dissolved in dry dioxane (5 mL) solution, the reaction mixture was stirred at room temperature for 4 hours, the mixture was spun-dried under reduced pressure, the residue was added into another solution (hydroxylamine hydrochloride (243 mg, 3.495 mmol), DIPEA (271 mg, 2.097 mmol) were dissolved in MeOH (3 mL) and ethanol (3 mL)), the reaction mixture was stirred at room temperature for one hour, heated to 60° C. for 3 hours. LCMS showed the reaction was completed, the mixture was cooled to room temperature, concentrated, the crude product was purified on silica gel by automatic fast chromatography to obtain 7-bromo-8-methyl-[1,2,4]triazole[1,5-a]pyridyl-2-amine (90 mg, Y: 57%). ES-API: $[M+H]^+$=227.0.

Step 4: Under the protection of nitrogen, 7-bromo-8-methyl-[1,2,4]triazole[1,5-a]pyridyl-2-amine (20 mg, 0.088 mmol), 6-((3-cyclopropoxypyridyl-2-yl)methyl)-3-(4,4,5,5-tetramethyl-1,3,2-dioxaborinan-2-yl)-7,8-dihydro-1,6 naphthyridin-5(6H)-one (56 mg, 0.132 mmol), sodium carbonate (23 mg, 0.220 mmol), 1,1'-bis(diphenylphosphino)ferrocene-palladium(II)dichloride dichloromethane complex (7 mg, 0.0088 mmol) were dissolved in dioxane (3 mL) and $H_2O$ (0.6 mL), the mixture was replaced with nitrogen for three times, the reaction mixture was stirred at 95° C. in oil bath for 2 hours, cooled to room temperature, concentrated, the crude product was purified by alkaline HPLC to obtain white solid 3-(2-amino-8-methyl-[1,2,4]triazole[1,5-a]pyridyl-7-yl)-6-((3-cyclopropoxypyridyl-2-yl)methyl)-7,8-dihydro-1,6-naphthyridin-5(6H)-one (Z98, 11.5 mg, Y: 29%). ES-API: $[M+H]^+$=442.1. $^1H$ NMR (400 MHz, DMSO-d6) δ8.70 (d, J=2.5 Hz, 1H), 8.56 (s, 1H), 8.18 (d, J=2.5 Hz, 1H), 8.09 (dd, J1=1.0 Hz, J2=5.0 Hz, 1H), 7.68 (dd, J1=1.5 Hz, J2=8.0 Hz, 1H), 7.33-7.231 (m, 2H), 6.01 (s, 2H), 4.79 (s, 2H), 4.00-3.97 (m, 1H), 3.74 (t, J1=7.0 Hz, J2=13.5 Hz, 2H), 3.21 (t, J1=7.0 Hz, J2=14.0 Hz, 2H), 2.17 (s, 3H), 0.84-0.81 (m, 2H), 0.71-0.68 (m, 2H).

Example 90 3-(2-amino-[1,2,4]triazolo[1,5-a]pyridyl-7-yl)-6-(5-fluoro-2-(trifluoromethoxy)benzyl)-7,8-dihydro-1,6-naphthyridin-5(6H)-one (Z102)

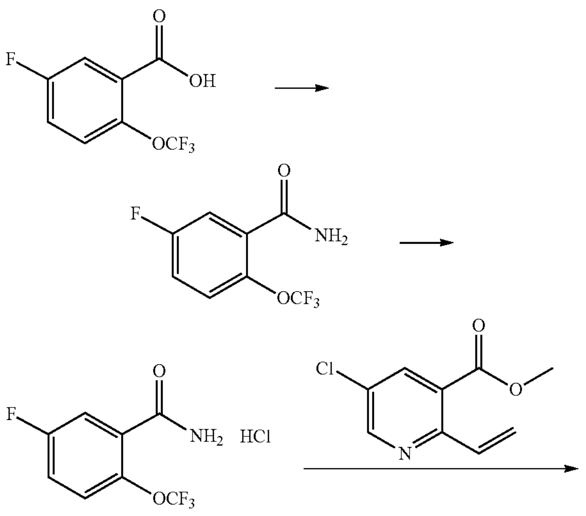

-continued

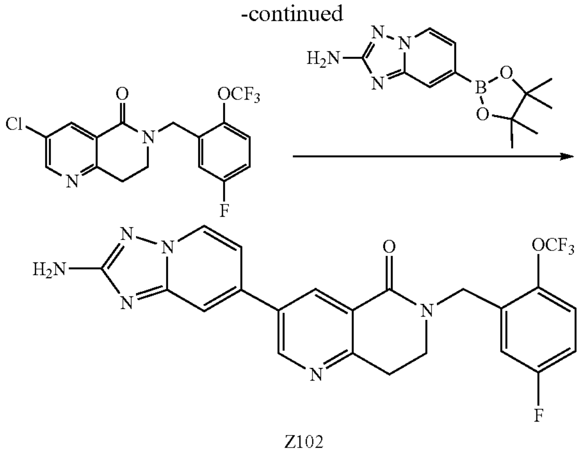

Z102

Step 1: 5-Fluoro-2-(trifluoromethoxy)benzoic acid (718 mg, 3.2 mmol), tetrahydrofuran (7 mL) were added into a 100 mL round bottom flask with single neck, cooled in ice bath, thionyl chloride was added dropwise (1.5 mL, 20.65 mmol), then a drop of DMF was added. The mixture was stirred at the room temperature for 4 hours, concentrated to remove solution, the residue was added with tetrahydrofuran (5 mL), cooled in ice water bath, aqueous ammonia (2 mL) was added dropwise. Then the mixture was stirred for 0.5 hour, added with ethyl acetate (30 mL), washed with water (30 mL) once, and washed with saturated sodium bicarbonate (30 mL) once, the organic phase was dried with anhydrous sodium sulfate and concentrated to obtain off-white solid 5-fluoro-2-(trifluoromethoxy)benzamide (540 mg, 2.42 mmol) with 75.5% yield. $[M+H]^+=224.1$.

Step 2: 5-Fluoro-2-(trifluoromethoxy)benzamide (540 mg, 2.42 mmol), tetrahydrofuran (5 mL) were added into a 100 mL round bottom flask, cooled in ice water, borane-tetrahydrofuran solution (10 mL, 1M, 10 mmol) was added dropwise, the mixture was heated to 75° C. in oil bath and stirred overnight, then cooled to room temperature, methanol was added for quenching the reaction, the mixture was concentrated to remove solution. The residue was added with methanol (5 mL), concentrated hydrochloric acid (1 mL), heated to 75° C. in an oil bath and stirred for one hour. The solvent was removed by concentration and evaporation, and the residue was beaten with n-heptane and dichloromethane in turn, filtered and dried to obtain white solid (5-fluoro-2-(trifluoromethoxy)phenyl)methanamine hydrochloride (310 mg, 1.26 mmol) with 52.2% yield. $[M+H]^+=210.1$.

Step 3: (5-fluoro-2-(trifluoromethoxy)phenyl)methylamine (300 mg, 1.22 mmol), methyl 5-chloro-2-vinylnicotinate (190 mg, 1.47 mmol), sulfolane (5 mL), acetic acid (220 mg, 3.67 mmol) were added into a 50 mL round bottom flask, the mixture was heated to 130° C. in oil bath and stirred for 12 hours, cooled to room temperature, extracted with methyl tert-butyl ether/water, the organic phase was concentrated and subjected to column chromatography (0-20% ethyl acetate/petroleum ether) to obtain yellow solid 3-chloro-6-(5-fluoro-2-(trifluoromethoxy)benzyl)-7,8-dihydro-1,6-naphthyridin-5(6H)-one (326 mg, 0.87 mmol) with 71.2% yield. $[M+H]^+=375.1$.

Step 4: 3-Chloro-6-(5-fluoro-2-(trifluoromethoxy)benzyl)-7,8-dihydro-1,6-naphthyridin-5(6H)-one (326 mg, 0.87 mmol), 7-(4,4,5,5-tetramethyl-1,3,2-dioxaborolan-2-yl)-[1,2,4]triazolo[1,5-a]pyridyl-2-amine (181 mg, 0.92 mmol), potassium carbonate (361 mg, 2.61 mmol), S-phos Pd G2 (20 mg, 0.028 mmol), 1,4-dioxane (12 mL), water (2 mL) were added into a 100 mL round bottom flask, and the mixture was replaced with nitrogen. The reaction was heated to 90° C. in an oil bath and stirred for 2 hours. The solvent was removed by concentration and evaporation, and the residue was added with water (50 mL), stirred at room temperature for 10 minutes, filtered, and the filter cake was beaten with methanol at room temperature for 0.5 hour, filtered and dried to obtain grey solid 3-(2-amino-[1,2,4]triazolo[1,5-a]pyridyl-7-yl)-6-(5-fluoro-2-(trifluoromethoxy)benzyl)-7,8-dihydro-1,6-naphthyridin-5(6H)-one (Z102, 280 mg, 0.59 mmol) with 68.1% yield. $[M+H]^+=473.1$. $^1$HNMR (DMSO-d6, 500 MHz): δ 9.11 (d, J=2.5 Hz, 1H), 8.65 (d, J=7.0 Hz, 1H), 8.52 (d, J=2.0 Hz, 1H), 7.80 (d, J=2.0 Hz, 1H), 7.51-7.48 (m, 1H), 7.34-7.28 (m, 3H), 6.10 (s, 2H), 4.82 (s, 2H), 3.70 (t, J=7.0 Hz, 2H), 3.23 (t, J=7.0 Hz, 2H).

Biological Test

The U937 cell line used in the following test examples is from ATCC, with the number of CRL-1593.2, batch number of 63479999, and the culture medium of RPMI-1640+10% FBS. The L929 cell line used in the following test examples is from ATCC, with the number of CCL-1, batch number of 70001022, and the culture medium of MEM+10% FBS+1% PS. The reagents used, and suppliers and article numbers thereof are as follows: RPMI-1640, Gibco, 11875-093; FBS, Gibco, 10099-141; Trypsin-EDTA, Gibco, 25200-072; PS, Gibco, 15140-122; CellTiter Glo, Progema, G7573; DMSO, VWR AMRESCO, 0231-500ML; TNF-α protein (human, recombinant), Peprotech, 300-01A; Q-VD-Oph, MCE, HY-12305; V-shaped bottom plate, Corning, 3894; 384 well low flange white flat bottom polystyrene TC-treated microplates, Corning, 3570; RIPK1, Eurofins, 16-022; MOPS, BDH, 441644J; EDTA, Sigma, E5134; myelin basic protein, Sigma, M1891-25.00 MG; magnesium acetate, Merck, DU008026; ATP (non-radioactive label), Sigma, A-7699; ATP (radioactive label), Hartmann Analytic, DU008054; phosphoric acid, Metlab, DU003000; Z-VAD: Shanghai Twochem Co., Ltd., YA02401.

Test Example 1: Inhibitory Activity of the Compound Against TNF-α Induced Programmed Cell Necrosis The compounds to be tested was dissolved in DMSO and diluted with DMSO to form a series of concentration gradients. 5000 U937 cells/well were seeded on a 384-well white plate, and the corresponding concentration of compound was added to each well to mix with the cells uniformly. At the same time, human TNF-α and Q-VD-Oph were added to induce programmed necrosis of the cells. The cells were placed at a 37° C., 5% $CO_2$ incubator for further incubation for 48 hours. CellTiter-Glo reagent was used for detection. After the reaction was fully lysed, the chemiluminescence readings was detected by a microplate reader. The test results were calculated using the formula for survival rate: SR (%)=(RLU compound−RLU blank)/(RLU high control−RLU blank)×100%. The survival rate and the final concentration of the corresponding compound were plotted as a curve, and fitted using a four-parameter model to calculate the inhibitory $IC_{50}$ of compounds on TNF-α-induced programmed cell necrosis. It can be seen from the experimental results that the exemplary compounds of the present disclosure have a relatively high inhibitory activity against U937 cells, with $IC_{50}$ values less than 500 nM (for example, 0.1 nM to 500 nM); some compounds even have $IC_{50}$ values less than 100 nM (for example, 0.1 nM to 100 nM) or less than 50 nM (for example, 0.1 nM to 50 nM). The experimental results of some of the compounds are as shown in Table 1:

TABLE 1

Inhibitory activity of compounds against U937 cells

| Compound No. | U937 $IC_{50}$ (μM) | Compound No. | U937 $IC_{50}$ (μM) |
|---|---|---|---|
| Z5 | 0.0467 | Z59 | 0.012 |
| Z6 | 0.0004 | Z60 | 0.162 |
| Z7 | 0.0039 | Z61 | 0.014 |
| Z8 | 0.0403 | Z62 | 0.013 |
| Z9 | 0.0104 | Z64 | 0.002 |
| Z1 | 0.0028 | Z65 | 0.0005 |
| Z10 | 0.0059 | Z66 | 0.0023 |
| Z2 | 0.000103 | Z67 | 0.0005 |
| Z3 | 0.0014 | Z68 | 0.0043 |
| Z11 | 0.0312 | Z69 | 0.0014 |
| Z13 | 0.0017 | Z70 | 0.0004 |
| Z14 | 0.0102 | Z71 | 0.0011 |
| Z16 | 0.0107 | Z72 | 0.082 |
| Z17 | 0.0575 | Z73 | 0.034 |
| Z18 | 0.0702 | Z74 | 0.0038 |
| Z19 | 0.0347 | Z76 | 0.0041 |
| Z20 | 0.0044 | Z77 | 0.1434 |
| Z21 | 0.0006 | Z78 | 0.0595 |
| Z23 | 0.0243 | Z79 | 0.0476 |
| Z24 | 0.0365 | Z80 | 0.0198 |
| Z27 | 0.0060 | Z82 | 0.0234 |
| Z27-2 | 0.0019 | Z85 | 0.0043 |
| Z28 | 0.0127 | Z33 | 0.3382 |
| Z31 | 0.0182 | Z37 | 0.0005 |
| Z36 | 0.0453 | Z32 | 0.0268 |
| Z44 | 0.042 | Z30 | 0.0091 |
| Z45 | 0.0002 | Z38 | 0.0013 |
| Z46 | 0.007 | Z35 | 0.0003 |
| Z46-1 | 0.0074 | Z94 | 0.0025 |
| Z46-2 | 0.9857 | Z39 | 0.0009 |
| Z47 | 0.003 | Z96 | 0.0017 |
| Z48 | 0.006 | Z31-1 | 0.0074 |
| Z49 | 0.026 | Z35-1 | 0.0003 |
| Z50 | 0.040 | Z35-2 | 0.0002 |
| Z51 | 0.024 | Z30-2 | 0.0034 |
| Z52 | 0.019 | Z97 | 0.0002 |
| Z54 | 0.012 | Z93 | 0.013 |
| Z55 | 0.008 | Z102 | 0.0211 |
| Z56 | 0.004 | Z98 | 0.4174 |
| Z57 | 0.002 | | |

Test Example 2: Inhibitory Activity of the Compound Against RIPK1 Enzyme

The compounds to be tested was dissolved in DMSO to prepare a 10 mM stock solution, which was diluted 3.16 times with DMSO into a series of concentration gradients, and then diluted 50 times with MOPS buffer solution (pH 7.0) to prepare a working solution, which were mixed well with 36 nM RIPK1 (final concentration), and 0.33 mg/ml substrate MBP. 10 mM magnesium ions and 155 μM phosphorous 33 isotope-labeled ATP were added to the reaction. The final concentration of DMSO was 2%. After 2 hours of reaction at room temperature, phosphoric acid was added to stop the reaction. The final reaction system was processed and then detected with a liquid scintillation counter. The percentage of activity which is calculated by subtracting the blank control from the test result and dividing same by the reading value of the control group, and the corresponding final compound concentration were plotted as a curve, and fitted using a four-parameter model to obtain the inhibitory $IC_{50}$ of the compound against RIPK1 enzymatic activity. It can be known from the experimental results that the exemplary compounds of the present disclosure have a relatively high inhibitory activity against RIPK1, with $IC_{50}$ values less than 200 nM (for example, 0.1 nM to 200 nM); some compounds even have $IC_{50}$ values less than 100 nM (for example, 0.1 nM to 100 nM) or less than 50 nM (for example, 0.1 nM to 50 nM). The experimental results of some of the compounds are as shown in Table 2:

TABLE 2

Inhibitory activity of compounds against RIPK1 enzyme

| Compound No. | RIPK1 enzyme $IC_{50}$ (nM) | Compound No. | RIPK1 enzyme $IC_{50}$ (nM) |
|---|---|---|---|
| Z48 | 39 | Z69 | 33 |
| Z10 | 56 | Z2 | 37 |
| Z51 | 72 | Z74 | 193 |
| Z82 | 50 | Z85 | 34 |

Test Example 3: Inhibitory Activity of the Compound Against TNF-α Induced Programmed Necrosis of L929 Cells The compounds to be tested was dissolved in DMSO and prepared as a 10 mM stock solution, which was diluted 3.16 times with DMSO to form a series of concentration gradients, and then diluted 100 times with culture medium to make a working solution. 10,000 L929 cells/well were seeded on a 384-well white plate, and the corresponding concentration of compound was added to each well to mix with the cells uniformly. At the same time, 30 ng/ml murine TNF-α and 15 μM Z-VAD were added to induce programmed necrosis of the cells. The final concentration of DMSO was 0.2%, and the cells were placed in a 37° C., 5% CO2 incubator for further incubation for 6 hours. CellTiter-Glo reagent was used for detection. After the reaction was fully lysed, the chemiluminescence readings was detected by a microplate reader. The test results were calculated using the formula for survival rate: SR (%)=(RLU compound−RLU blank)/(RLU high control-RLU blank)×100%. The survival rate and the final concentration of the corresponding compound were plotted as a curve, and fitted using a four-parameter model to calculate the inhibitory $IC_{50}$ of compounds on TNF-α-induced programmed cell necrosis. It can be known from the experimental results that the exemplary compounds of the present disclosure have a relatively high inhibitory activity against L929 cells, with $IC_{50}$ values less than 500 nM (for example, 0.1 nM to 500 nM); some compounds even have $IC_{50}$ values less than 100 nM (for example, 0.1 nM to 100 nM) or less than 50 nM (for example, 0.1 nM to 50 nM). The experimental results of some of the compounds are as shown in Table 3:

TABLE 3

Inhibitory activity of compounds against L929 cells

| Compound No. | L929 $IC_{50}$ (μM) | Compound No. | L929 $IC_{50}$ (μM) |
|---|---|---|---|
| Z44 | 0.0092 | Z69 | 0.0037 |
| Z45 | 0.0013 | Z10 | 0.0024 |
| Z46 | 0.0029 | Z2 | <0.0028 |
| Z47 | 0.0051 | Z74 | 0.0023 |
| Z5 | 0.0080 | Z85 | 0.0134 |
| Z48 | 0.0030 | | |

All documents mentioned in this application are hereby incorporated by reference as if each document were individually incorporated by reference. In addition, it should be understood that after reading the above teachings of the invention, those skilled in the art can make various changes or modifications to the invention, and these equivalent forms also fall within the scope defined by the appended claims of this application.

The invention claimed is:

1. A dihydronaphthyridinone compound, or a pharmaceutically acceptable salt, a stereoisomer, a solvate or a prodrug thereof, wherein the compound has a structure represented by formula (I):

(I)

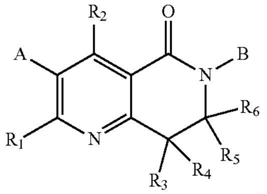

wherein, $R_1$ and $R_2$ are each independently hydrogen, halogen, substituted or unsubstituted $C_{1-6}$ alkyl, substituted or unsubstituted $C_{1-6}$ alkoxy or substituted or unsubstituted $NR_{a0}R_{b0}$, wherein $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl; the "substituted" in $R_1$ and $R_2$ means that 1, 2, 3 or 4 hydrogen atoms in the group are substituted with substituent(s) each independently selected from group S;

the definition for $R_3$, $R_4$, $R_5$ and $R_6$ are selected from one of the following groups:

(i) $R_3$, $R_4$, $R_5$ and $R_6$ are each independently hydrogen, halogen, substituted or unsubstituted $C_{1-6}$ alkyl, or substituted or unsubstituted $C_{3-8}$ cycloalkyl; the "substituted" means that 1, 2, 3 or 4 hydrogen atoms in the group are substituted with substituent(s) each independently selected from group S;

(ii) $R_3$ and $R_4$ form together with the carbon atom adjacent thereto a substituted or unsubstituted $C_{3-8}$ cycloalkyl ring or a substituted or unsubstituted 3- to 6-membered heterocycloalkyl ring; $R_5$ and $R_6$ are each independently hydrogen, halogen, substituted or unsubstituted $C_{1-6}$ alkyl, or substituted or unsubstituted $C_{3-8}$ cycloalkyl; the "substituted" means that 1, 2, 3 or 4 hydrogen atoms in the group are substituted with substituent(s) each independently selected from group S;

(iii) $R_3$ and $R_4$ are each independently hydrogen, halogen, substituted or unsubstituted $C_{1-6}$ alkyl, or substituted or unsubstituted $C_{3-8}$ cycloalkyl; $R_5$ and $R_6$ form together with the carbon atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

(iv) $R_4$ and $R_5$ form together with the carbon atom adjacent thereto a substituted or unsubstituted $C_{3-8}$ cycloalkyl ring or a substituted or unsubstituted 3- to 6-membered heterocycloalkyl ring; $R_3$ and $R_6$ are each independently hydrogen, halogen, substituted or unsubstituted $C_{1-6}$ alkyl, or substituted or unsubstituted $C_{3-8}$ cycloalkyl; the "substituted" means that 1, 2, 3 or 4 hydrogen atoms in the group are substituted with substituent(s) each independently selected from group S;

B is $-L-R_0$, wherein, $R_0$ is substituted or unsubstituted $C_{6-14}$ aryl, substituted or unsubstituted 5- to 14-membered heteroaryl or substituted or unsubstituted 5- to 14-membered heterocycloalkyl; the "substituted" in $R_0$ means that 1, 2, 3 or 4 hydrogen atoms in the group are substituted with substituent(s) each independently selected from group S;

L is a bond, $-(CR_{11}R_{12})_{t1}-(CR_{21}R_{22})_{t2}-(CR_{31}R_{32})_{t3}-(CR_{41}R_{42})_{t4}-(O)_{t5}-$ or $-(CR_{13}R_{14})_{t1}-(CR_{23}R_{24})_{t2}-(NR_{33})_{t3}-(CR_{43}R_{44})_{t4}-(O)_{t5}-$, wherein t1, t2, t3, t4 and t5 are each independently 0 or 1;

the definition for $R_{11}$, $R_{12}$, $R_{21}$, $R_{22}$, $R_{31}$, $R_{32}$, $R_{41}$ and $R_{42}$ are selected from one of the following groups:

(a2)

$R_{11}$, $R_{12}$, $R_{41}$ and $R_{42}$ are each independently hydrogen, deuterium, halogen, hydroxyl, hydroxymethyl, hydroxyethyl or $C_{1-3}$ alkyl;

$R_{21}$, $R_{22}$, $R_{31}$ and $R_{32}$ are each independently hydrogen, deuterium, halogen, hydroxyl, hydroxymethyl, hydroxyethyl or $C_{1-3}$ alkyl;

(b2)

$R_{11}$, $R_{12}$, $R_{41}$ and $R_{42}$ are each independently hydrogen, deuterium, halogen, hydroxyl, hydroxymethyl, hydroxyethyl or $C_{1-3}$ alkyl;

$R_{21}$ and $R_{22}$ form together with the carbon atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

$R_{31}$ and $R_{32}$ are each independently hydrogen, deuterium, halogen, hydroxyl, hydroxymethyl, hydroxyethyl or $C_{1-3}$ alkyl;

(c2)

$R_{11}$, $R_{12}$, $R_{41}$ and $R_{42}$ are each independently hydrogen, deuterium, halogen, hydroxyl, hydroxymethyl, hydroxyethyl or $C_{1-3}$ alkyl;

$R_{21}$ and $R_{22}$ are each independently hydrogen, deuterium, halogen, hydroxyl, hydroxymethyl, hydroxyethyl or $C_{1-3}$ alkyl;

$R_{31}$ and $R_{32}$ form together with the carbon atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

(d2)

$R_{11}$, $R_{12}$, $R_{41}$ and $R_{42}$ are each independently hydrogen, deuterium, halogen, hydroxyl, hydroxymethyl, hydroxyethyl or $C_{1-3}$ alkyl;

$R_{22}$ and $R_{32}$ are each independently hydrogen, deuterium, halogen, hydroxyl, hydroxymethyl, hydroxyethyl or $C_{1-3}$ alkyl;

$R_{21}$ and $R_{31}$ form together with the atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

(e2)

$R_{12}$, $R_{41}$ and $R_{42}$ are each independently hydrogen, deuterium, halogen, hydroxyl, hydroxymethyl, hydroxyethyl or $C_{1-3}$ alkyl;

$R_{21}$, $R_{22}$ and $R_{32}$ are each independently hydrogen, deuterium, halogen, hydroxyl, hydroxymethyl, hydroxyethyl or $C_{1-3}$ alkyl;

$R_{11}$ and $R_{31}$ form together with the atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

the definition for $R_{13}$, $R_{14}$, $R_{23}$, $R_{24}$, $R_{33}$, $R_{43}$ and $R_{44}$ are selected from one of the following groups:

(a3)

$R_{13}$, $R_{14}$, $R_{23}$, $R_{24}$, $R_{43}$ and $R_{44}$ are each independently hydrogen, deuterium, halogen, hydroxyl, hydroxymethyl, hydroxyethyl or $C_{1-3}$ alkyl;

$R_{33}$ is hydrogen, deuterium, hydroxymethyl, hydroxyethyl or $C_{1-3}$ alkyl;

(b3)

$R_{13}$, $R_{14}$, $R_{43}$ and $R_{44}$ are each independently hydrogen, deuterium, halogen, hydroxyl, hydroxymethyl, hydroxyethyl or $C_{1-3}$ alkyl;

$R_{23}$ and $R_{24}$ form together with the carbon atom adjacent thereto a substituted or unsubstituted $C_{3-8}$ cycloalkyl ring or a substituted or unsubstituted 3- to 6-membered heterocycloalkyl ring; the "substituted" means that 1, 2, 3 or 4 hydrogen atoms in the group are substituted with substituent(s) each independently selected from group S;

$R_{33}$ is hydrogen, deuterium, hydroxymethyl, hydroxyethyl or $C_{1-3}$ alkyl;

(c3)

$R_{13}$, $R_{14}$, $R_{23}$, $R_{43}$ and $R_{44}$ are each independently hydrogen, deuterium, halogen, hydroxyl, hydroxymethyl, hydroxyethyl or $C_{1-3}$ alkyl;

$R_{24}$ and $R_{33}$ form together with the atom adjacent thereto a substituted or unsubstituted 3- to 6-membered nitrogen-containing heterocycloalkyl ring; the "substituted" means that 1, 2, 3 or 4 hydrogen atoms in the group are substituted with substituent(s) each independently selected from group S;

(d3)

$R_{13}$, $R_{23}$, $R_{24}$, $R_{43}$ and $R_{44}$ are each independently hydrogen, deuterium, halogen, hydroxyl, hydroxymethyl, hydroxyethyl or $C_{1-3}$ alkyl;

$R_{14}$ and $R_{33}$ form together with the atom adjacent thereto a substituted or unsubstituted 3- to 6-membered nitrogen-containing heterocycloalkyl ring; the "substituted" means that 1, 2, 3 or 4 hydrogen atoms in the group are substituted with substituent(s) each independently selected from group S;

A is (i) substituted or unsubstituted 8- to 10-membered bicyclic heteroaryl, wherein the 8- to 10-membered bicyclic heteroaryl is formed by fusing a 5- or 6-membered monocyclic heteroaryl ring with a 5- or 6-membered monocyclic heteroaryl ring, wherein the "substituted" means that 1, 2, 3 or 4 hydrogen atoms in the group are substituted with substituent(s) each independently selected from group S;

(ii) substituted or unsubstituted 9- or 10-membered bicyclic heteroaryl; the 9- or 10-membered bicyclic heteroaryl is formed by fusing a benzene ring with a 5- or 6-membered monocyclic heteroaryl ring; wherein the 5- or 6-membered monocyclic heteroaryl ring is selected from:

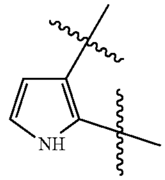,
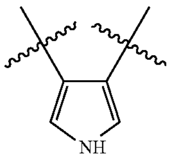,
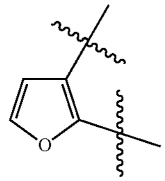,
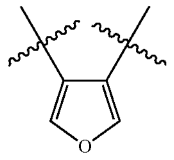,
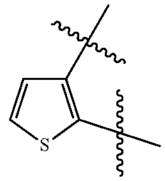,
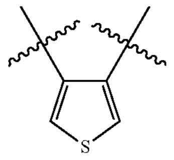,
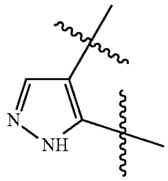,
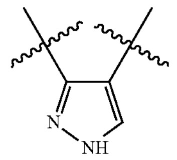,
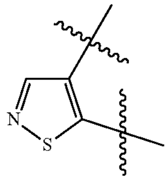,
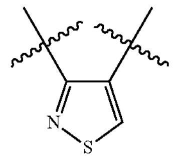,
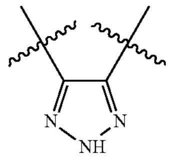,
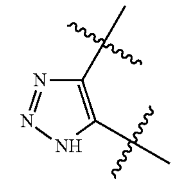,
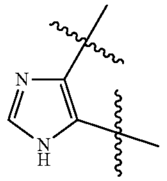,
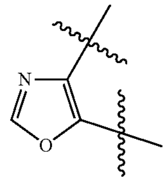,
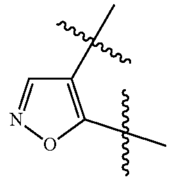,
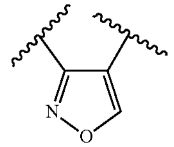, -continued

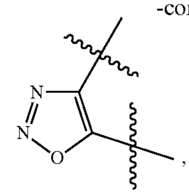 , 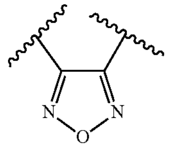 ,

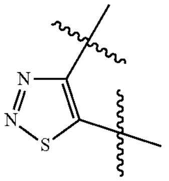 ,

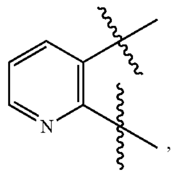 , 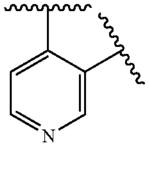 ,

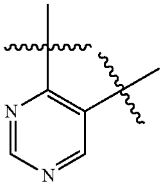 , 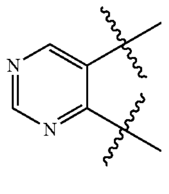 ,

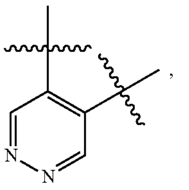 , 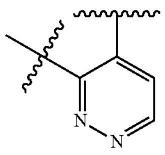 , and

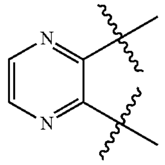 , wherein the attached two carbon atoms represented by " ~~~ " are adjacent pairs of carbon atoms shared when fused with other rings; the "substituted" means that 1, 2, 3 or 4 hydrogen atoms in the group are substituted with substituent(s) each independently selected from group S;

(iii) substituted or unsubstituted 8- to 10-membered bicyclic heteroaryl; the 8- to 10-membered bicyclic heteroaryl is formed by fusing a 5- or 6-membered monocyclic heteroaryl ring with a 5- or 6-membered monocyclic heterocycloalkyl ring, wherein the "substituted" means that 1, 2, 3 or 4 hydrogen atoms in the group are substituted with substituent(s) each independently selected from group S; or (iv) substituted or unsubstituted benzothiazole, wherein the "substituted" means that 1, 2, 3 or 4 hydrogen atoms in the group are substituted with substituent(s) each independently selected from group S';

in the above groups, the substituents from group S are selected from deuterium, halogen, nitro, oxo, $-C_{1-6}$ alkyl, -halo $C_{1-6}$ alkyl, -deuterated $C_{1-6}$ alkyl, $-S-C_{1-6}$ alkyl, —S-halo $C_{1-6}$alkyl, $-(CR_{a1}R_{b1})_u$-cyano, $-(CR_{a1}R_{b1})_u$-hydroxyl, $-(CR_{a1}R_{b1})_u-C_{1-6}$ alkoxy, $-(CR_{a1}R_{b1})_u$-halo $C_{1-6}$ alkoxy, $-(CR_{a1}R_{b1})_u$-deuterated $C_{1-6}$ alkoxy, $-(CR_{a1}R_{b1})_u$-halo $C_{1-6}$ alkyl, $-(CR_{a1}R_{b1})_u$-deuterated $C_{1-6}$ alkyl, $-(CR_{a1}R_{b1})_u$-3- to 6-membered heterocycloalkyl, $-(CR_{a1}R_{b1})_u-C_{3-8}$ cycloalkyl, $-(CR_{a1}R_{b1})_u$-phenyl, $-(CR_{a1}R_{b1})_u$-5- or 6-membered monocyclic heteroaryl, $-(CR_{a1}R_{b1})_u-O-(CR_{a2}R_{b2})_v$-halo $C_{1-6}$ alkyl, $-(CR_{a1}R_{b1})_u-O-(CR_{a2}R_{b2})_v-C_{3-8}$ cycloalkyl, $-(CR_{a1}R_{b1})_u-O-(CR_{a2}R_{b2})_v$-3- to 6-membered heterocycloalkyl, $-(CR_{a1}R_{b1})_u-O-(CR_{a2}R_{b2})$v-phenyl, $-(CR_{a1}R_{b1})_u-O-(CR_{a2}R_{b2})_v$-5- or 6-membered monocyclic heteroaryl, $-(CR_{a1}R_{b1})_u-S-(CR_{a2}R_{b2})_v$-phenyl, $-(CR_{a1}R_{b1})_u-SO_2-(CR_{a2}R_{b2})_v$-phenyl, $-(CR_{a1}R_{b1})_u-O-C(O)NR_{a0}R_{b0}$, $-(CR_{a1}R_{b1})_u-O-(CR_{a2}R_{b2})_v-C_{1-6}$ alkoxy, $-(CR_{a1}R_{b1})_u-O-(CR_{a2}R_{b2})_v$-hydroxyl, $-(CR_{a1}R_{b1})_u-SO_2C_{1-6}$ alkyl, $-(CR_{a1}R_{b1})_u-SO_2NR_{a0}R_{b0}$, $-(CR_{a1}R_{b1})_u-C(O)NR_{a0}R_{b0}$, $-(CR_{a1}R_{b1})_u-C(O)$phenyl, $-(CR_{a1}R_{b1})_u-C(O)C_{1-6}$ alkyl, $-C(O)OC_{1-6}$ alkyl, $-C(O)-(CR_{a2}R_{b2})_v$-hydroxyl, $-(CR_{a1}R_{b1})_u-NR_{a0}R_{b0}$, $-NR_{a0}C(O)-C_{1-6}$ alkyl, $-NR_{a0}C(O)$-deuterated $C_{1-6}$alkyl, $-NR_{a0}C(O)-(CR_{a1}R_{b1})_u$-hydroxyl, $-NR_{a0}C(O)-(CR_{a1}R_{b1})_u-O-(CR_{a2}R_{b2})_v-C(O)C_{1-6}$ alkyl, $-NR_{a0}C(O)-(CR_{a1}R_{b1})_u-O-(CR_{a2}R_{b2})_v$-phenyl, $-NR_{a0}C(O)-C_{3-8}$ cycloalkyl, $-NR_{a0}C(O)-(CR_{a1}R_{b1})_u-NR_{a0}R_{b0}$, and $-NR_{a0}C(O)$-halo $C_{1-6}$ alkyl, wherein the $C_{3-8}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$ alkyl; $R_{a1}$, $R_{b1}$, $R_{a2}$ and $R_{b2}$ are the same or different, and are each independently hydrogen, hydroxyl, $C_{1-3}$ alkyl or halo $C_{1-3}$ alkyl;

in the above groups, the substituents from group S' are selected from deuterium, halogen, nitro, oxo, $-C_{1-6}$ alkyl, -halo $C_{1-6}$ alkyl, -deuterated $C_{1-6}$ alkyl, $-S-C_{1-6}$ alkyl, —S-halo $C_{1-6}$alkyl, $-(CR_{a1}'R_{b1}')_u'$-cyano, $-(CR_{a1}'R_{b1}')_u'$-hydroxyl, $-(CR_{a1}'R_{b1}')_u'-C_{1-6}$ alkoxy, $-(CR_{a1}'R_{b1}')_u'$-halo $C_{1-6}$ alkoxy, $-(CR_{a1}'R_{b1}')_u'$-halo $C_{1-6}$ alkyl, $-(CR_{a1}'R_{b1}')_u'$-3- to 6-membered heterocycloalkyl, $-(CR_{a1}'R_{b1}')_u'-C_{3-8}$ cycloalkyl, $-(CR_{a1}'R_{b1}')_u'$- phenyl, $-(CR_{a1}'R_{b1}')_u'$-5- or 6-membered monocyclic heteroaryl, $-(CR_{a1}'R_{b}')_u'-O-(CR_{a2}'R_{b2}')_v'$-halo $C_{1-6}$ alkyl, $-(CR_{a1}'R_{b1}')_u'-O-(CR_{a2}'R_{b2}')_v'-C_{3-8}$ cycloalkyl, $-(CR_{a1}'R_{b1}')_u'-O-(CR_{a2}'R_{b2}')_v'$-3- to 6-membered heterocycloalkyl, $-(CR_{a1}'R_{b1}')_u'-O-(CR_{a2}'R_{b2}')_v$-phenyl, $-(CR_{a1}'R_{b1}')_u'-O-(CR_{a2}'R_{b2}')_v'$-5- or 6-membered monocyclic heteroaryl, $-(CR_{a1}'R_{b1}')_u-S-(CR_{a2}'R_{b2}')_v'$-phenyl, $-(CR_{a1}'R_{b1}')_u'-SO_2-(CR_{a2}'R_{b2}')_v'$-phenyl, $-(CR_{a1}'R_{b1}')_u'-O-C(O)NR_{a0}'R_{b0}'$, $-(CR_{a1}'R_{b1}')_u'-O-(CR_{a2}'R_{b2}')_v'-C_{1-6}$ alkoxy, $-(CR_{a1}'R_{b1}')_u'-O-(CR_{a2}'R_{b2}')_v'$-hydroxyl, $-(CR_{a1}'R_{b1}')_u'-SO_2C_{1-6}$ alkyl, $-(CR_{a1}'R_{b1}')_u'-SO_2NR_{a0}'R_{b0}'$, $-(CR_{a1}'R_{b1}')_u'-C(O)NR_{a0}'R_{b0}'$, —$(CR_{a1}'R_{b1}')_{u'}$—C(O)phenyl, —$(CR_{a1}'R_{b1}')_{u'}$—C(O) $C_{1-6}$ alkyl, —C(O)O$C_{1-6}$ alkyl, and —C(O)—$(CR_{a2}'R_{b2}')_{v'}$- hydroxyl, wherein the $C_{3-8}$ cycloalkyl, 3- to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u' and v' are each independently 0, 1, 2, 3 or 4; $R_{a0}'$ and $R_{b0}'$ are each independently hydrogen or $C_{1-3}$ alkyl; or $R_{a0}'$ and $R_{b0}'$ form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$ alkyl; $R_{a1}'$, $R_{b1}'$, $R_{a2}'$ and $R_{b2}'$ are the same or different, and are each independently hydrogen, hydroxyl, $C_{1-3}$ alkyl or halo $C_{1-3}$ alkyl.

2. The compound or the pharmaceutically acceptable salt, the stereoisomer, the solvate or the prodrug thereof according to claim 1, wherein with regard to A, the 8- to 10-membered bicyclic heteroaryl formed by fusing a 5- or 6-membered monocyclic heteroaryl ring with a 5- or 6-membered monocyclic heteroaryl ring has a structure represented by formula (A1), formula (A2) or formula (A3):

A1

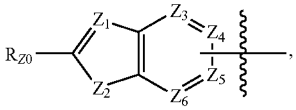

A2

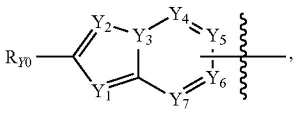

A3

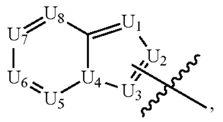

wherein $Z_1$ is N or $CR_{Z1}$; $Z_2$ is $NR_{Z2}$ or O; $Z_3$ is N or $CR_{Z3}$; $Z_4$ is N or $CR_{Z4}$; $Z_5$ is N or $CR_{Z5}$; $Z_6$ is N or $CR_{Z6}$; $Z_3$, $Z_4$, $Z_5$ and $Z_6$ are not N at the same time; and at least one of $Z_3$, $Z_4$, $Z_5$ and $Z_6$ is N; $Y_1$ is N or $CR_{Y1}$; $Y_2$ is N or $CR_{Y2}$; $Y_3$ is N or $CR_{Y3}$; $Y_4$ is N or $CR_{Y4}$; $Y_5$ is N or $CR_{Y5}$; $Y_6$ is N or $CR_{Y6}$; $Y_7$ is N or $CR_{Y7}$; $Y_3$, $Y_4$, $Y_5$, $Y_6$ and $Y_7$ are not N at the same time; and at least one of $Y_1$, $Y_2$, $Y_3$, $Y_4$, $Y_5$, $Y_6$ and $Y_7$ is N; $U_1$ is N or $CR_{U1}$; $U_2$ is N or $CR_{U2}$; $U_3$ is N or $CR_{U3}$; $U_4$ is N or $CR_{U4}$; $U_5$ is N or $CR_{U5}$; $U_6$ is N or $CR_{U6}$; $U_7$ is N or $CR_{U7}$; $U_8$ is N or $CR_{U8}$; $U_4$, $U_5$, $U_6$, $U_7$ and $U_8$ are not N at the same time; and at least one of $U_1$, $U_2$, $U_3$, $U_4$, $U_5$, $U_6$, $U_7$ and $U_8$ is N; $R_{Z0}$, $R_{Y0}$, $R_{Z1}$, $R_{Z2}$, $R_{Z3}$, $R_{Z4}$, $R_{Z5}$, $R_{Z6}$, $R_{Y1}$, $R_{Y2}$, $R_{Y3}$, $R_{Y4}$, $R_{Y5}$, $R_{Y6}$, $R_{Y7}$, $R_{U1}$, $R_{U2}$, $R_{U3}$, $R_{U4}$, $R_{U5}$, $R_{U6}$, $R_{U7}$ and $R_{U8}$ are each independently hydrogen or the substituent from group S.

3. The compound or the pharmaceutically acceptable salt, the stereoisomer, the solvate or the prodrug thereof according to claim 1, wherein the 9- or 10-membered bicyclic heteroaryl said in A formed by fusing a benzene ring with a 5- or 6-membered monocyclic heteroaryl ring has a structure represented by formula (A4):

A4

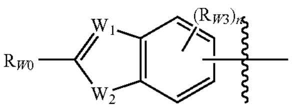

wherein $W_1$ is N or $CR_{W1}$; $W_2$ is $NR_{W2}$ or O; n is 1, 2 or 3; $R_{W0}$, $R_{W1}$, $R_{W2}$ and $R_{W3}$ are each independently hydrogen or the substituent from group S.

4. The compound or the pharmaceutically acceptable salt, the stereoisomer, the solvate or the prodrug thereof according to claim 1, wherein the 8- to 10-membered bicyclic heteroaryl said in A formed by fusing a 5- or 6-membered monocyclic heteroaryl ring with a 5- or 6-membered monocyclic heterocycloalkyl ring has a structure represented by formula (A5):

A5

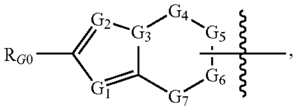

wherein $G_1$ is N or $CR_{G1}$; $G_2$ is N or $CR_{G2}$; $G_3$ is N or $CR_{G3}$; $G_4$ is $NR_{G4a}$, O or $CR_{G4b}R_{G4c}$; $G_5$ is $NR_{G5a}$, O or $CR_{G5b}R_{G5c}$; $G_6$ is $NR_{G6a}$, O or $CR_{G6b}R_{G6c}$; $G_7$ is $NR_{G7a}$, O or $CR_{G7b}R_{G7c}$; at least one of $G_3$, $G_4$, $G_5$, $G_6$ and $G_7$ is N; and the ring part of -$G_3$-$G_4$-$G_5$-$G_6$-$G_7$- does not comprise —O—O—, —O—N— or —N—N—; $R_{G0}$, $R_{G1}$, $R_{G2}$, $R_{G3}$, $R_{G4a}$, $R_{G4b}$, $R_{G4c}$, $R_{G5a}$, $R_{G5b}$, $R_{G5c}$, $R_{G6a}$, $R_{G6b}$, $R_{G6c}$, $R_{G7a}$, $R_{G7b}$ and $R_{G7c}$ are each independently hydrogen or the substituent from group S.

5. The compound or the pharmaceutically acceptable salt, the stereoisomer, the solvate or the prodrug thereof according to claim 1, wherein the compound has a structure represented by formula (I-1):

(I-1)

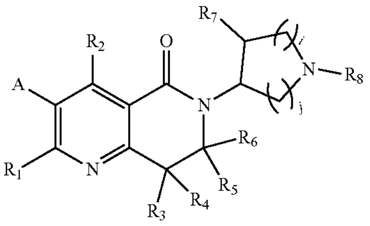

wherein, i and j are each independently 0, 1 or 2; and i and j are not 0 at the same time; $R_7$ is hydrogen, deuterium, halogen, nitro, oxo, —$C_{1-6}$ alkyl, -halo $C_{1-6}$ alkyl, -deuterated $C_{1-6}$ alkyl, —S—$C_{1-6}$ alkyl, —S-halo $C_{1-6}$ alkyl, —$(CR_{a1}R_{b1})_u$-cyano, —$(CR_{a1}R_{b1})_u$-hydroxyl, —$(CR_{a1}R_{b1})_u$—$C_{1-6}$ alkoxy, —$(CR_{a1}R_{b1})_u$-halo $C_{1-6}$ alkoxy, —$(CR_{a1}R_{b1})_u$-halo $C_{1-6}$ alkyl, —$(CR_{a1}R_{b1})_u$-deuterated $C_{1-6}$ alkoxy, —$(CR_{a1}R_{b1})_u$-deuterated $C_{1-6}$ alkyl, —$(CR_{a1}R_{b1})_u$-3- to 6-membered heterocycloalkyl, —$(CR_{a1}R_{b1})_u$—$C_{3-8}$ cycloalkyl, —$(CR_{a1}R_{b1})_u$-phenyl, —$(CR_{a1}R_{b1})_u$-5- or 6-membered monocyclic heteroaryl, —$(CR_{a1}R_{b1})_u$—O—$(CR_{a2}R_{b2})_v$-halo $C_{1-6}$ alkyl, —$(CR_{a1}R_{b1})_u$—O—$(CR_{a2}R_{b2})_v$—$C_{3-8}$ cycloalkyl, —$(CR_{a1}R_{b1})_u$—O—$(CR_{a2}R_{b2})_v$-3- to 6-membered heterocycloalkyl, —$(CR_{a1}R_{b1})_u$—O—$(CR_{a2}R_{b2})_v$- phenyl, —$(CR_{a1}R_{b1})_u$—O—$(CR_{a2}R_{b2})_v$-5- or 6-membered monocyclic heteroaryl, —$(CR_{a1}R_{b1})_u$ —S—$(CR_{a2}R_{b2})_v$-phenyl, —$(CR_{a1}R_{b1})_u$ —$SO_2$—$(CR_{a2}R_{b2})_v$-phenyl, —$(CR_{a1}R_{b1})_u$—O—C(O)$NR_{a0}R_{b0}$, —$(CR_{a1}R_{b1})_u$—O—$(CR_{a2}R_{b2})_v$—$C_{1-6}$ alkoxy, —$(CR_{a1}R_{b1})_u$—O—$(CR_{a2}R_{b2})_v$-hydroxyl, —$(CR_{a1}R_{b1})_u$—$SO_2C_{1-6}$ alkyl, —$(CR_{a1}R_{b1})_u$—$SO_2NR_{a0}R_{b0}$, —$(CR_{a1}R_{b1})_u$—C(O)$NR_{a0}R_{b0}$, —$(CR_{a1}R_{b1})_u$—C(O)phenyl, —$(CR_{a1}R_{b1})_u$—C(O)$C_{1-6}$ alkyl, —C(O)O$C_{1-6}$ alkyl, —C(O)—$(CR_{a2}R_{b2})_v$-hydroxyl, —$(CR_{a1}R_{b1})_u$—$NR_{a0}R_{b0}$, —$NR_{a0}$C(O)—$C_{1-6}$ alkyl, —$NR_{a0}$C(O)-deuterated $C_{1-6}$ alkyl, —$NR_{a0}$C(O)—$(CR_{a1}R_{b1})_u$-hydroxyl, —$NR_{a0}$C(O)—$(CR_{a1}R_{b1})_u$—O—$(CR_{a2}R_{b2})_v$—C(O)$C_{1-6}$ alkyl, —$NR_{a0}$C(O)—$(CR_{a1}R_{b1})_u$—O—$(CR_{a2}R_{b2})_v$-phenyl, —$NR_{a0}$C(O)—$C_{3-8}$ cycloalkyl, —$NR_{a0}$C(O)—$(CR_{a1}R_{b1})_u$—$NR_{a0}R_{b0}$, or —$NR_{a0}$C(O)-halo $C_{1-6}$ alkyl, wherein the $C_{3-8}$ cycloalkyl, 3-to 6-membered heterocycloalkyl, phenyl, and 5- or 6-membered monocyclic heteroaryl are optionally substituted with 1, 2 or 3 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3- to 8-membered nitrogen-containing heterocycloalkyl, wherein the 3- to 8-membered nitrogen-containing heterocycloalkyl is optionally substituted with 1, 2 or 3 halogens or $C_{1-3}$ alkyl; $R_{a1}$, $R_{b1}$, $R_{a2}$ and $R_{b2}$ are the same or different, and are each independently hydrogen, hydroxyl, $C_{1-3}$ alkyl or halo $C_{1-3}$ alkyl; $R_8$ is hydrogen, —$(CR_{a1}R_{b1})_u$—$SO_2$—$(CR_{a2}R_{b2})_v$-phenyl, —$(CR_{a1}R_{b1})_u$—$SO_2C_{1-6}$ alkyl, —$(CR_{a1}R_{b1})_u$—$SO_2NR_{a0}R_{b0}$, —$(CR_{a1}R_{b1})_u$—C(O)$NR_{a0}R_{b0}$, —$(CR_{a1}R_{b1})_u$—C(O)phenyl, —$(CR_{a1}R_{b1})_u$—C(O)$C_{1-6}$ alkyl, or —C(O)—$(CR_{a2}R_{b2})_v$-hydroxyl, wherein the phenyl and $C_{1-6}$ alkyl are optionally substituted with 1, 2, 3 or 4 substituents selected from hydroxyl, hydroxymethyl, hydroxyethyl, halogen, cyano, cyanomethyl, cyanoethyl, $C_{1-3}$ alkyl, halo $C_{1-3}$ alkyl, $C_{1-3}$ alkoxy, halo $C_{1-3}$ alkoxy, $C_{3-6}$ cycloalkyl and halo $C_{3-6}$ cycloalkyl; u and v are each independently 0, 1, 2, 3 or 4; $R_{a0}$ and $R_{b0}$ are each independently hydrogen or $C_{1-3}$ alkyl; or $R_{a0}$ and $R_{b0}$ form together with the nitrogen atom adjacent thereto a 3-to 8-membered nitrogen-containing heterocycloalkyl; $R_{a1}$, $R_{b1}$, $R_{a2}$ and $R_{b2}$ are the same or different, and are each independently hydrogen, hydroxyl, $C_{1-3}$ alkyl or halo $C_{1-3}$ alkyl; the other groups are as defined in claim 1.

6. The compound or the pharmaceutically acceptable salt, the stereoisomer, the solvate or the prodrug thereof according to claim 5, wherein the compound of formula (I-1) has a structure represented by formula (I-1-a), formula (I-1-b), formula (I-1-c) or formula (I-1-d):

I-1-a

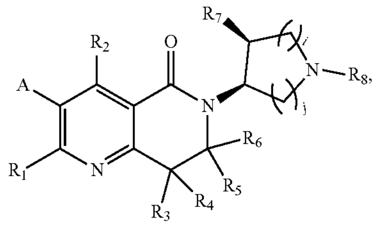

I-1-b

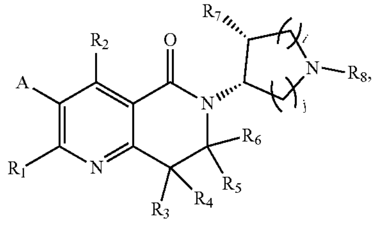

I-1-c

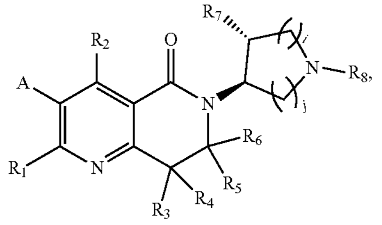

I-1-d

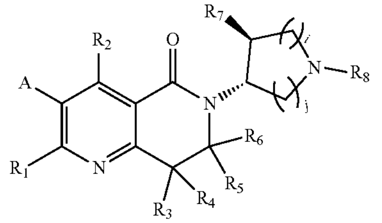

wherein, each group is as defined in claim 5.

7. The compound or the pharmaceutically acceptable salt, the stereoisomer, the solvate or the prodrug thereof according to claim 1, wherein A has a structure selected from:

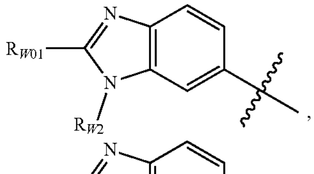

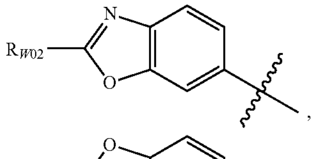

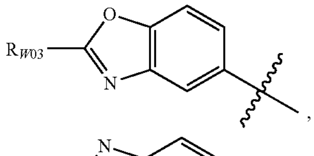

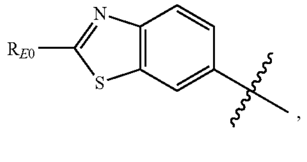

-continued

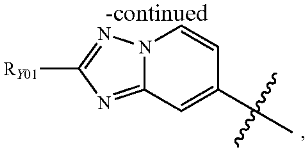
,

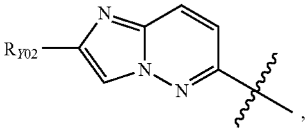
,

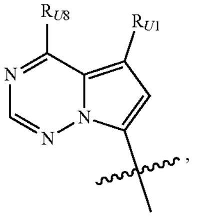
, and

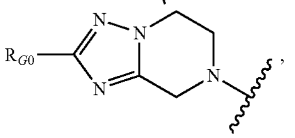
, wherein $R_{W01}$, $R_{W2}$, $R_{W02}$, $R_{W03}$, $R_{Y01}$, $R_{Y02}$, $R_{U8}$, $R_{U1}$ and $R_{G0}$ are each independently hydrogen or the substituent from group S; $R_{E0}$ is hydrogen or the substituent from group S'.

8. The compound or the pharmaceutically acceptable salt, the stereoisomer, the solvate or the prodrug thereof according to claim 1, wherein the $C_{6-14}$ aryl said in $R_0$ is phenyl, naphthyl, or is a 9- or 10-membered aromatic fused bicyclic ring formed by fusing phenyl with a non-aromatic ring; the non-aromatic ring is 3- to 6-membered saturated or partially unsaturated monocyclic heterocycloalkyl or 3- to 6-membered saturated or partially unsaturated monocyclic cycloalkyl, wherein the 3- to 6-membered saturated or partially unsaturated monocyclic heterocycloalkyl is selected from aziridine, ethylene oxide, azetidine, azetidine-2-one, oxetane, oxetane-2-one, oxazolidine, pyrrolidine-2-one, pyrrolidine-2,5-dione, 1,3-dioxolane, dihydrofuran-2(3H)-one, dihydrofuran-2,5-dione, piperidine-2-one, piperidine-2,6-dione, tetrahydro-2H-pyran-2-one, imidazolidine, tetrahydrofuran, tetrahydrothiophene, tetrahydropyrrole, 1,3-dioxolane-2-one, oxazolidine-2-one, imidazolidine-2-one, piperidine, piperazine, piperazine-2-one, morpholine, morpholine-3-one, morpholine-2-one, thiomorpholine-3-one 1,1-dioxide, thiomorpholine, thiomorpholine-1,1-dioxide, tetrahydropyran, 1,2-dihydroazetidine, 1,2-dihydrooxetadiene, 2,5-dihydro-1H-pyrrole, 2,5-dihydrofuran, 2,3-dihydrofuran, 2,3-dihydro-1H-pyrrole, 3,4-dihydro-2H-pyran, 1,2,3,4-tetrahydropyridine, 3,6-dihydro-2H-pyran, 1,2,3,6-tetrahydropyridine, 1,3-oxazinane, hexahydropyrimidine, 1,4-dioxane, tetrahydropyrimidine-2(1H)-one, 1,4-dioxane-2-one, and 5,6-dihydro-2H-pyran-2-one; the 3- to 6-membered saturated or partially unsaturated monocyclic cycloalkyl is selected from cyclopropyl, cyclobutyl, cyclopentyl, cyclopentenyl, cyclohexyl, cyclohexenyl, cyclohexadienyl, cyclobutanone, cyclobutane-1,2-dione, cyclopentanone, cyclopentane-1,3-dione, cyclohexanone, and cyclohexane-1,3-dione; the phenyl, naphthyl, or 9- or 10-membered aromatic fused bicyclic ring is unsubstituted or substituted with 1, 2, 3 or 4 substituents each independently selected from group S.

9. The compound or the pharmaceutically acceptable salt, the stereoisomer, the solvate or the prodrug thereof according to claim 1, wherein the 5- to 14-membered heteroaryl said in $R_0$ is 5- or 6-membered monocyclic heteroaryl, wherein the 5- or 6-membered monocyclic heteroaryl is selected from thiophene, N-alkyl pyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine; the 5- or 6-membered monocyclic heteroaryl is unsubstituted or substituted with 1, 2, 3 or 4 substituents each independently selected from group S; or the 5- to 14-membered heteroaryl said in $R_0$ is 9- or 10-membered bicyclic heteroaryl formed by fusing phenyl with 5- or 6-membered monocyclic heteroaryl, wherein the 5- or 6-membered monocyclic heteroaryl is selected from thiophene, N-alkyl pyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine; the 9- or 10-membered bicyclic heteroaryl is unsubstituted or substituted with 1, 2, 3 or 4 substituents each independently selected from group S; or the 5- to 14-membered heteroaryl said in $R_0$ is 8- to 10-membered bicyclic heteroaryl formed by fusing 5- or 6-membered monocyclic heteroaryl with 5- or 6-membered monocyclic heteroaryl, wherein the 5- or 6-membered monocyclic heteroaryl is selected from thiophene, N-alkyl pyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine; the 8- to 10-membered bicyclic heteroaryl is unsubstituted or substituted with 1, 2, 3 or 4 substituents each independently selected from group S; or the 5- to 14-membered heteroaryl said in $R_0$ is 8- to 10-membered bicyclic heteroaryl formed by fusing 5- or 6-membered monocyclic heteroaryl with a non-aromatic ring, wherein the non-aromatic ring is 3- to 6-membered saturated or partially unsaturated monocyclic heterocycloalkyl or 3- to 6-membered saturated or partially unsaturated monocyclic cycloalkyl; the 5- or 6-membered monocyclic heteroaryl is selected from thiophene, N-alkyl pyrrolidone, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine or pyrazine; the 3- to 6-membered saturated or partially unsaturated monocyclic heterocycloalkyl is selected from aziridine, ethylene oxide, azetidine, azetidine-2-one, oxetane, oxetane-2-one, oxazolidine, pyrrolidine-2-one, pyrrolidine-2,5-dione, 1,3-dioxolane, dihydrofuran-2(3H)-one, dihydrofuran-2,5-dione, piperidine-2-one, piperidine-2,6-dione, tetrahydro-2H-pyran-2-one, imidazolidine, tetrahydrofuran, tetrahydrothiophene, tetrahydropyrrole, 1,3-dioxolane-2-one, oxazolidine-2-one, imidazolidine-2-one, piperidine, piperazine, piperazine-2-one, morpholine, morpholine-3-one, morpholine-2-one, thiomorpholine-3-one 1,1-dioxide, thiomorpholine, thiomorpholine-1,1-dioxide, tetrahydropyran, 1,2-dihydroazetidine, 1,2-dihydrooxetadiene, 2,5-dihydro-1H-pyrrole, 2,5-dihydrofuran, 2,3-dihydrofuran, 2,3-dihydro-1H-pyrrole, 3,4-dihydro-2H-pyran, 1,2,3,4-tetrahydropyridine, 3,6-dihydro-2H-pyran, 1,2,3,6-tetrahydropyridine, 1,3-oxazinane, hexahydropyrimidine, 1,4-dioxane, tetrahydropyrimidine-2(1H)-one, 1,4-dioxane-2-one, and 5,6-dihydro-2H-pyran-2-one; the 3- to 6-membered saturated or partially unsaturated monocyclic cycloalkyl is selected from cyclopropyl, cyclobutyl, cyclopentyl, cyclopentenyl, cyclohexyl, cyclohexenyl, cyclohexadienyl, cyclobutanone, cyclobutane-1,2-dione, cyclopentanone, cyclopentane-1,3-dione, cyclohexanone, and cyclohexane-1,3-dione; the 8- to 10-membered bicyclic heteroaryl is unsubstituted or substituted with 1, 2, 3 or 4 substituents each independently selected from group S.

10. The compound or the pharmaceutically acceptable salt, the stereoisomer, the solvate or the prodrug thereof according to claim 1, wherein the 5- to 14-membered heterocycloalkyl said in $R_0$ is 5- to 6-membered heterocycloalkyl, wherein the 5- to 6-membered heterocycloalkyl is selected from oxazolidine, pyrrolidine-2-one, pyrrolidine-2,5-dione, 1,3-dioxolane, dihydrofuran-2(3H)-one, dihydrofuran-2,5-dione, piperidine-2-one, piperidine-2,6-dione, tetrahydro-2H-pyran-2-one, imidazolidine, tetrahydrofuran, tetrahydrothiophene, tetrahydropyrrole, 1,3-dioxolane-2-one, oxazolidine-2-one, imidazolidine-2-one, piperidine, piperazine, piperazine-2-one, morpholine, morpholine-3-one, morpholine-2-one, thiomorpholine-3-one 1,1-dioxide, thiomorpholine, thiomorpholine-1,1-dioxide, tetrahydropyran, 1,2-dihydroazetidine, 1,2-dihydrooxetadiene, 2,5-dihydro-1H-pyrrole, 2,5-dihydrofuran, 2,3-dihydrofuran, 2,3-dihydro-1H-pyrrole, 3,4-dihydro-2H-pyran, 1,2,3,4-tetrahydropyridine, 3,6-dihydro-2H-pyran, 1,2,3,6-tetrahydropyridine, 1,3-oxazinane, hexahydropyrimidine, 1,4-dioxane, tetrahydropyrimidine-2(1H)-one, 1,4-dioxane-2-one, and 5,6-dihydro-2H-pyran-2-one; the 5- to 6-membered heterocycloalkyl is unsubstituted or substituted with 1, 2, 3 or 4 substituents each independently selected from group S.

11. The compound or the pharmaceutically acceptable salt, the stereoisomer, the solvate or the prodrug thereof according to claim 1, wherein $R_0$ is substituted or unsubstituted phenyl, substituted or unsubstituted pyridyl, substituted or unsubstituted pyrazolyl or substituted or unsubstituted tetrahydropyrrolyl; wherein the "substituted" means that 1, 2, 3 or 4 hydrogen atoms in the group are substituted with substituent(s) each independently selected from group S.

12. The compound or the pharmaceutically acceptable salt, the stereoisomer, the solvate or the prodrug thereof according to claim 1, wherein the compound of formula (I) has a structure selected from the following group:

1

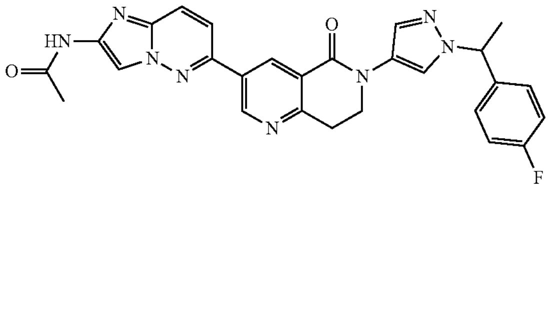

-continued

2

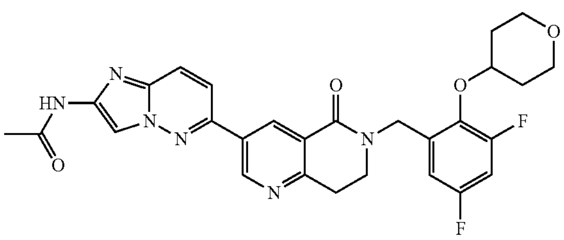

3

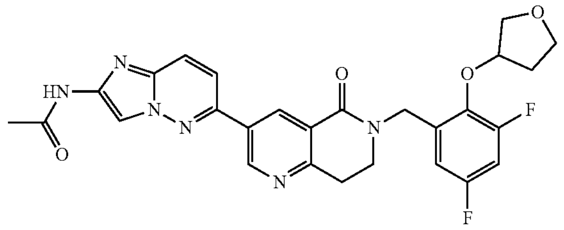

4

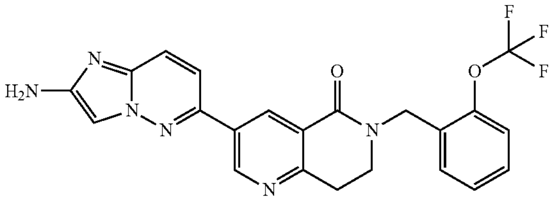

5

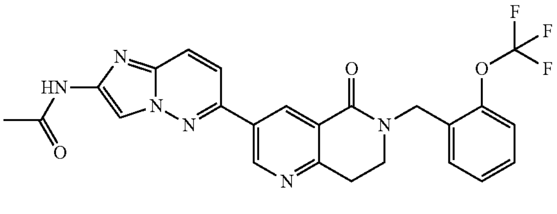

6

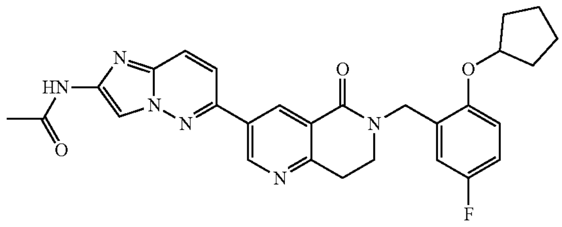

7

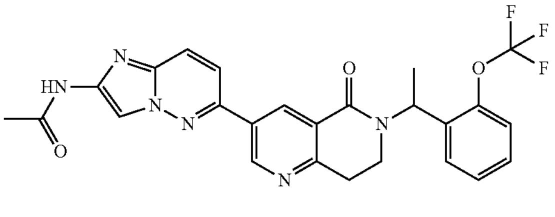

8

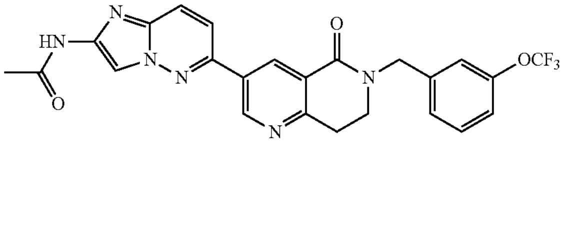

-continued
9
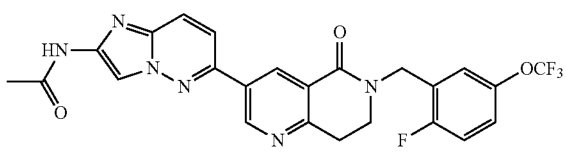
10
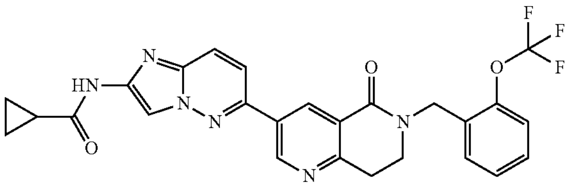
13
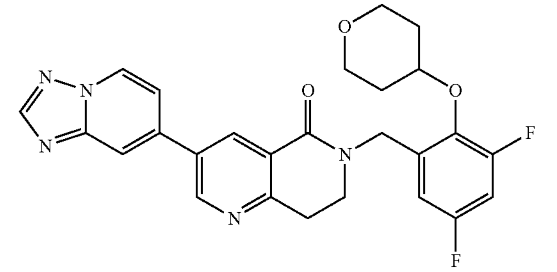
14
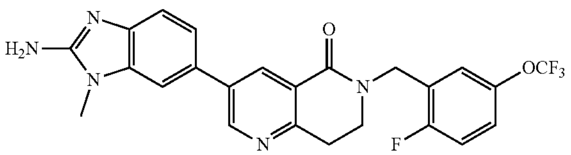
15
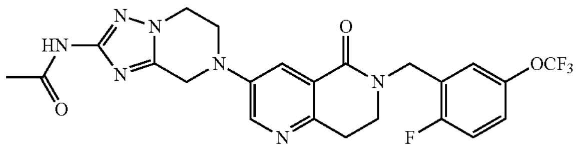
16
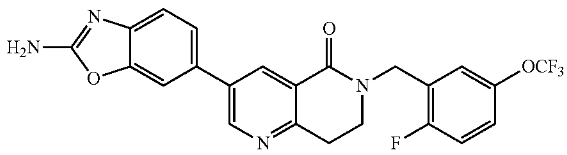
17
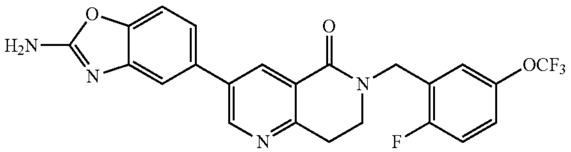
18
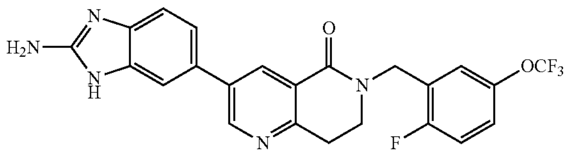
-continued
19
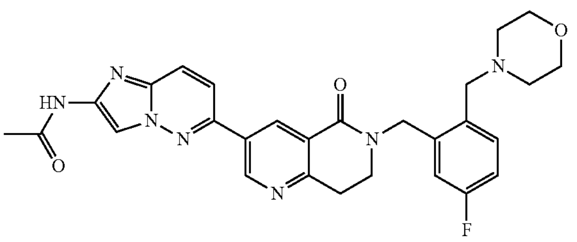
20
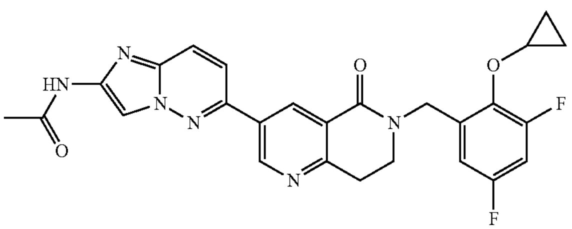
21
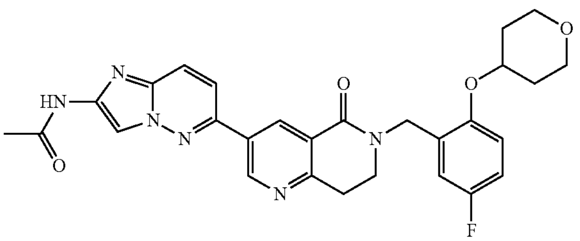
22
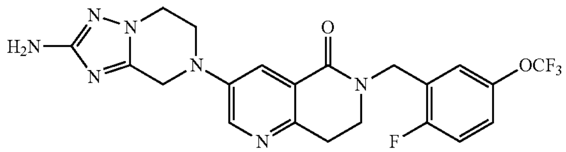
23
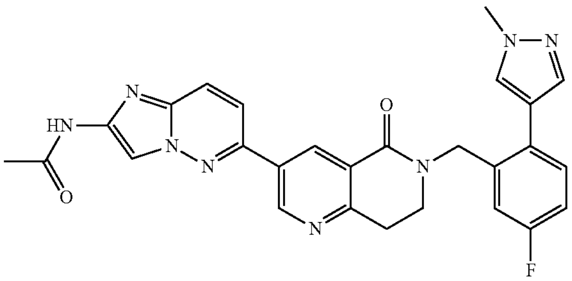
24
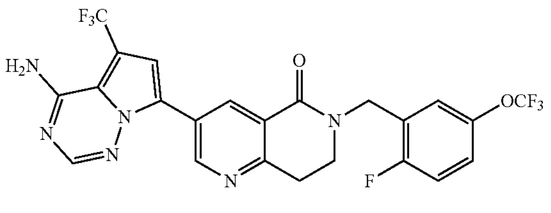

-continued
25
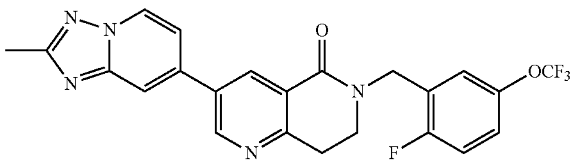
26
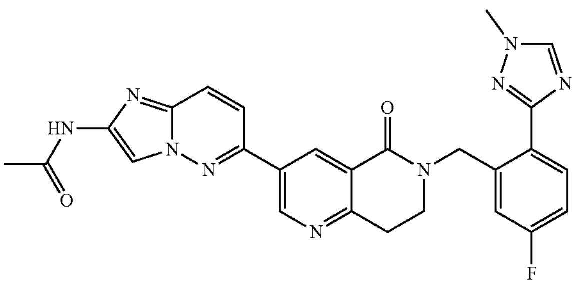
27
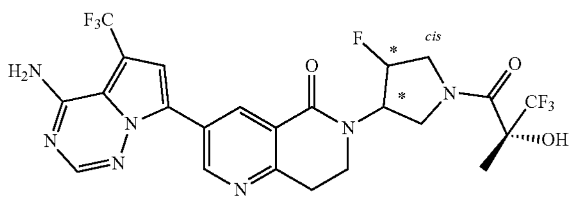
28
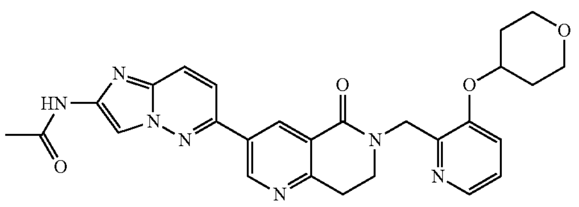
27-1
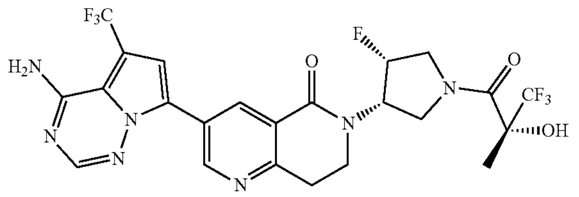
27-2
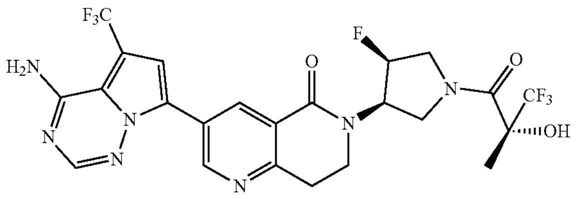
29
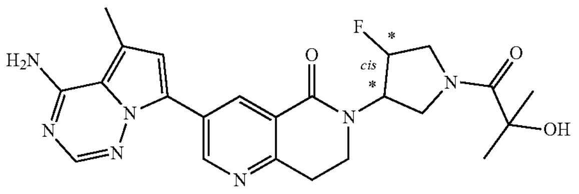
-continued
30
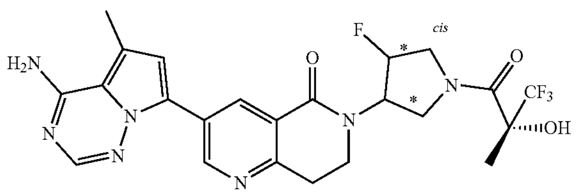
30-1
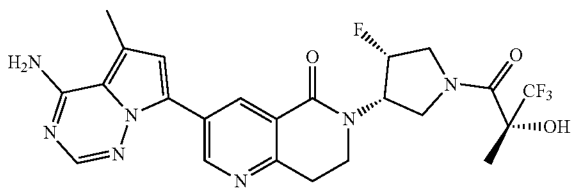
30-2
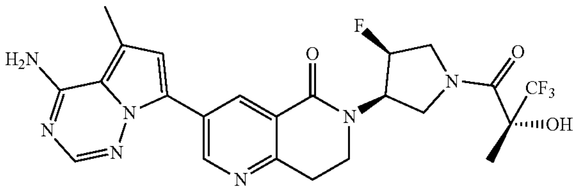
31
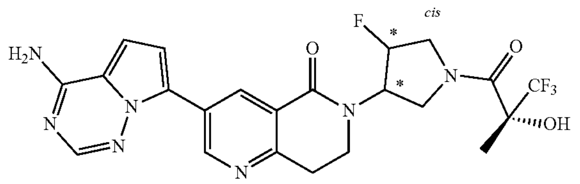
32
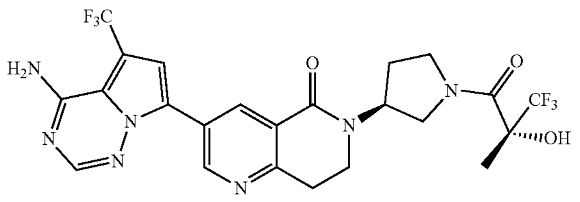
31-1
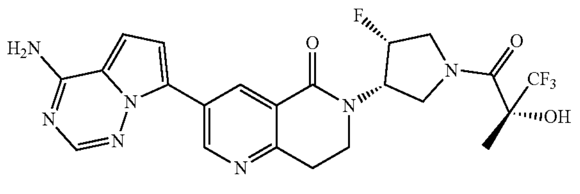
31-2
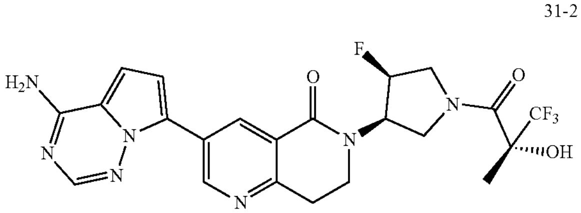

-continued
33
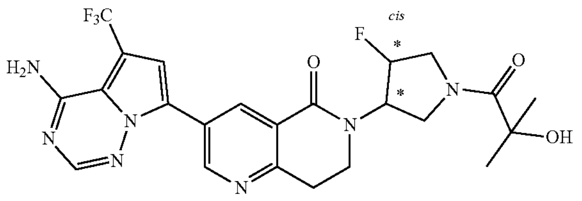
34
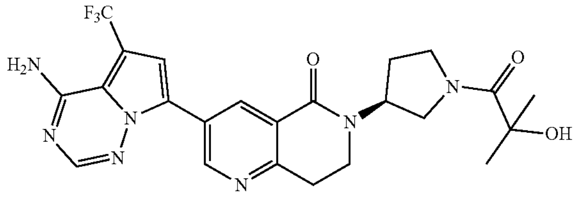
35
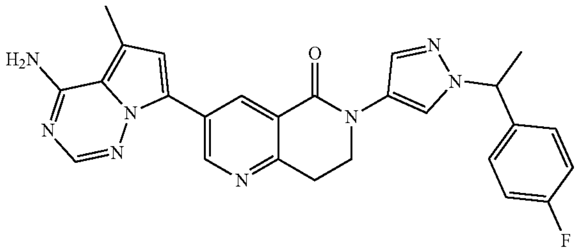
36
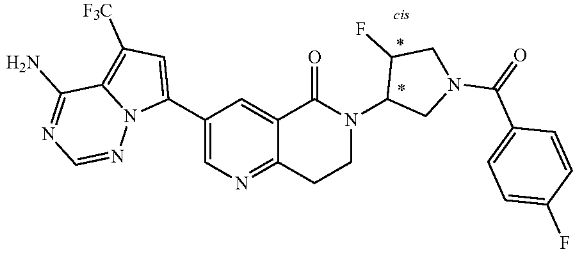
35-1
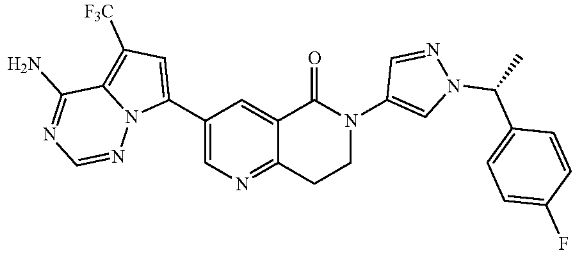
35-2
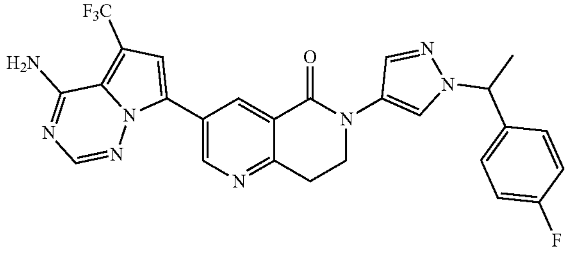
-continued
37
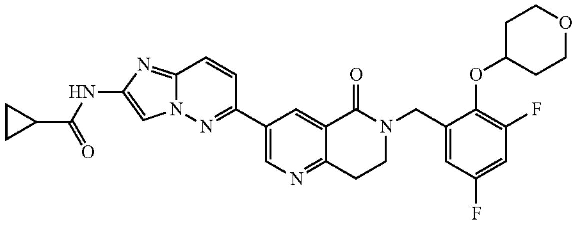
38
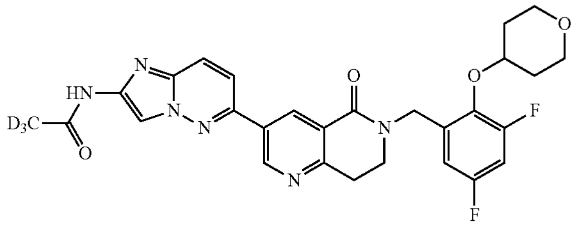
39
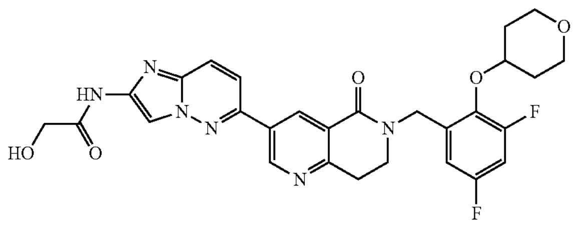
96
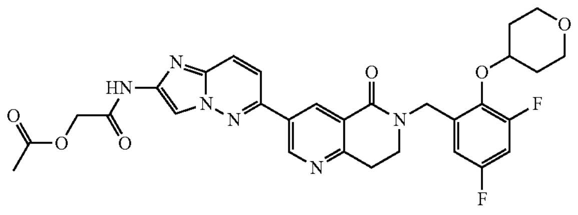
40
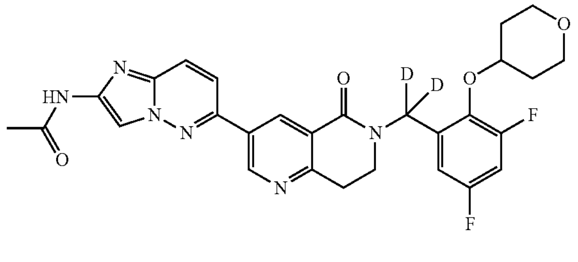
44
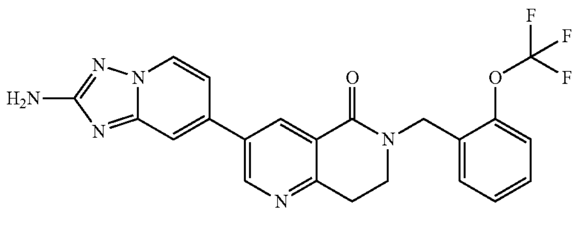

-continued
45
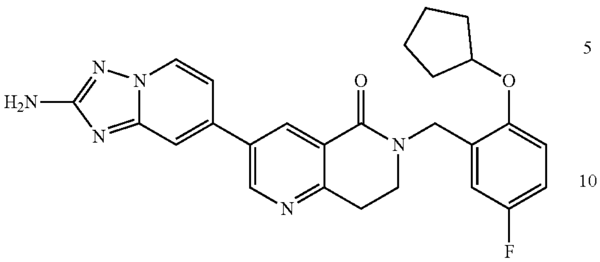
46
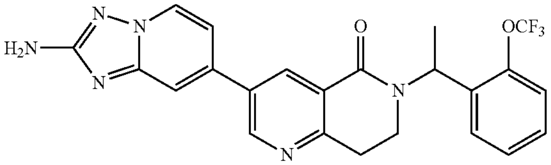
46-1
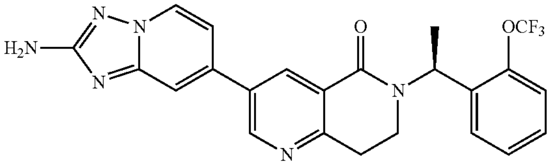
46-2
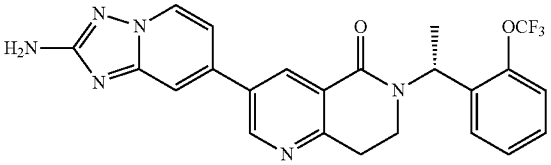
47
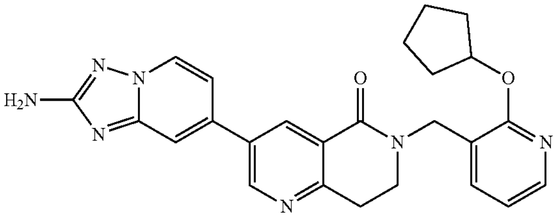
48
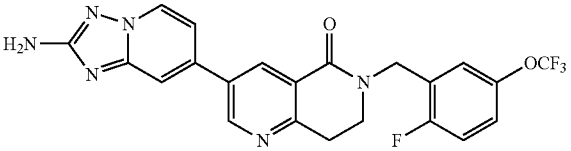
49
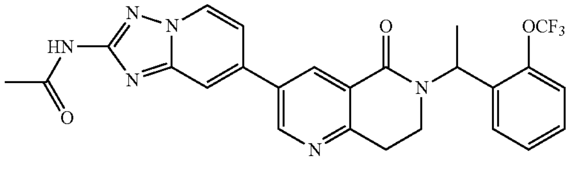
-continued
50
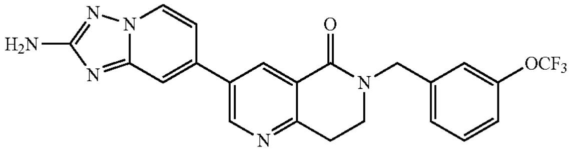
51
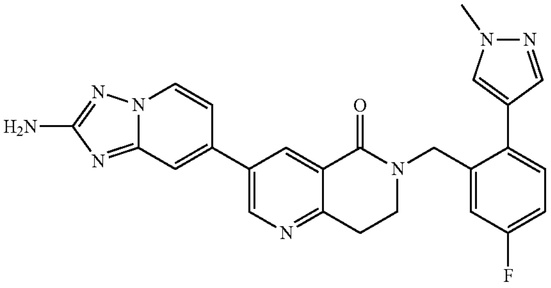
52
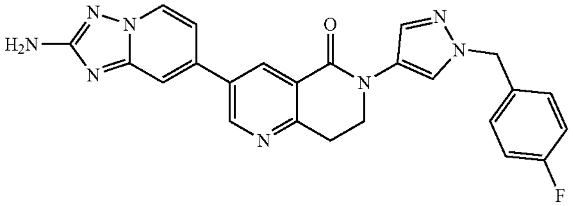
53
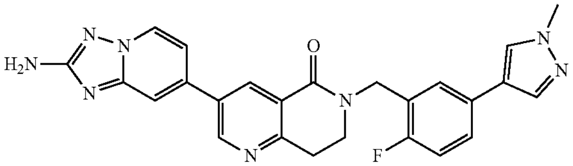
54
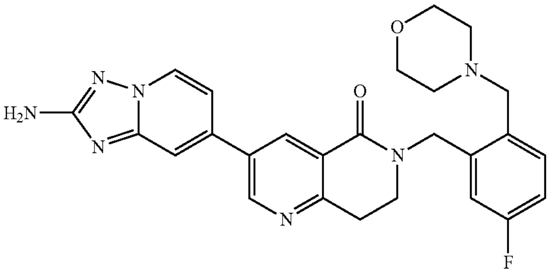
55
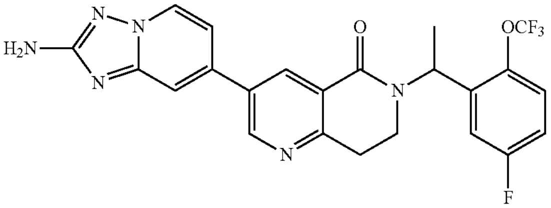
56
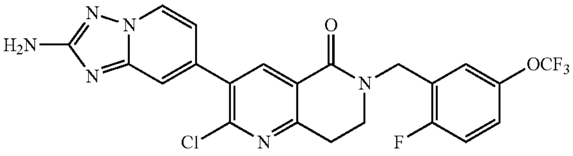

-continued
57
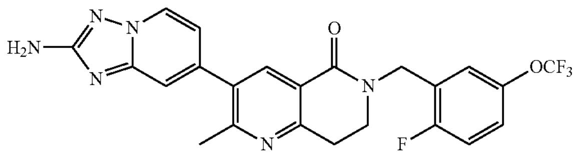
58
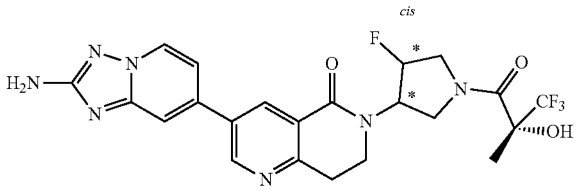
59
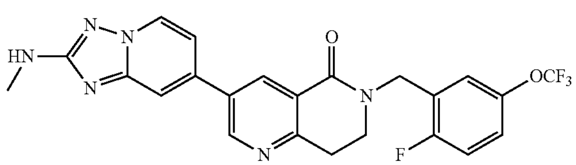
-continued
60
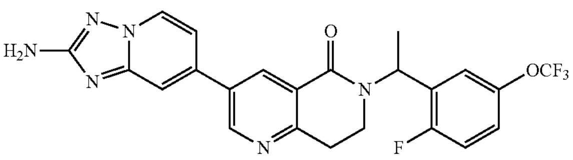
61
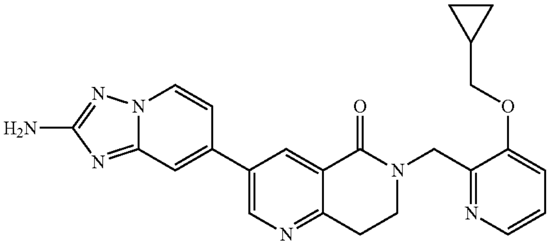
62
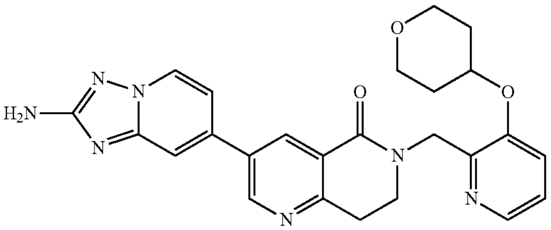
63
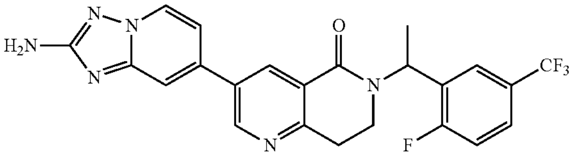
64
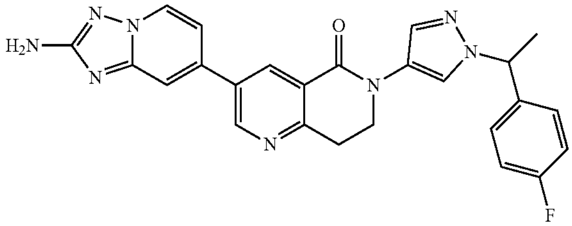
65
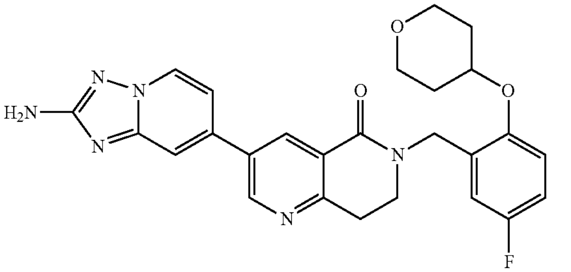
66
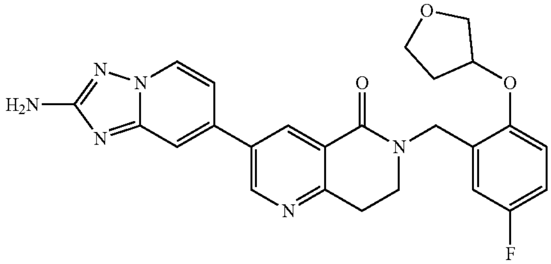
67
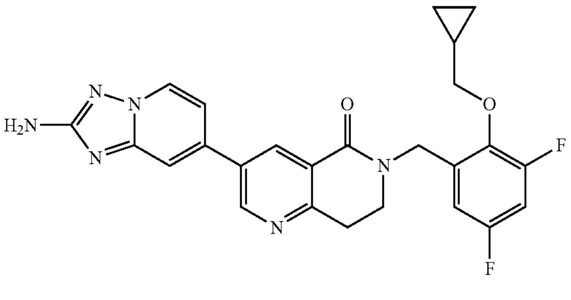
68
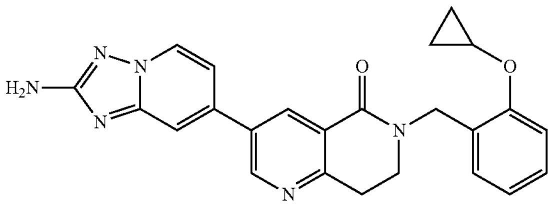

-continued
69
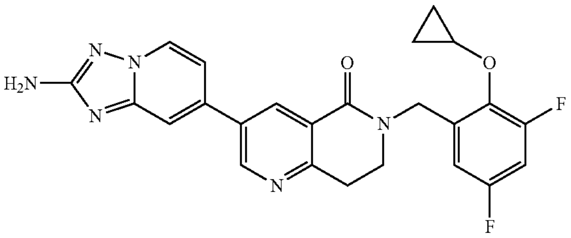
70
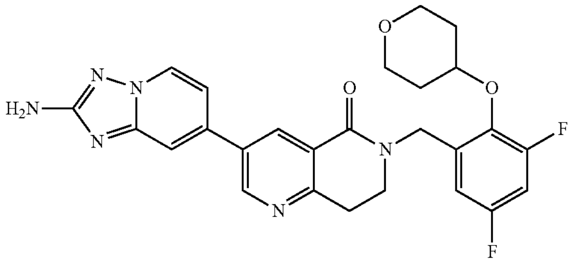
71
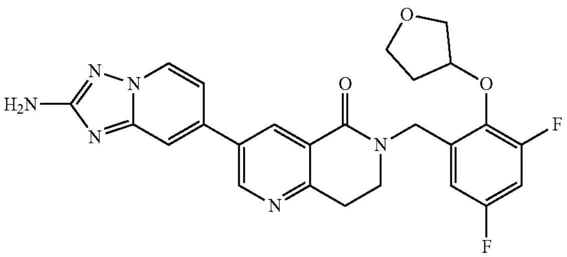
72
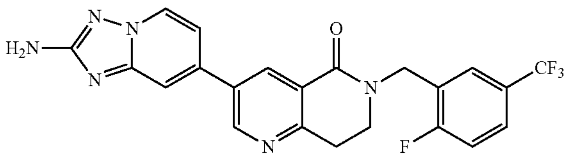
73
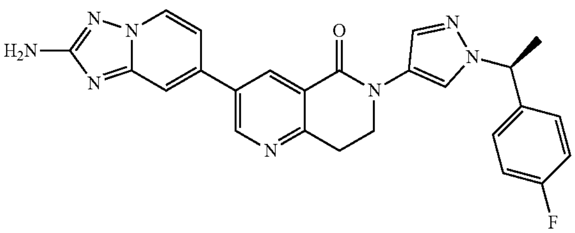
74
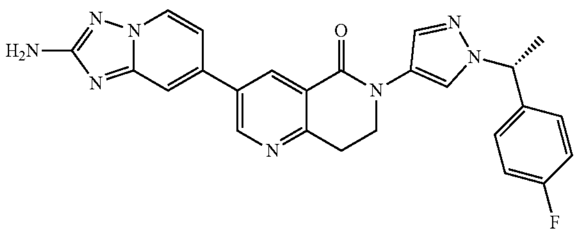
75
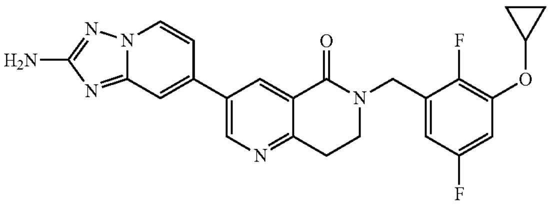
76
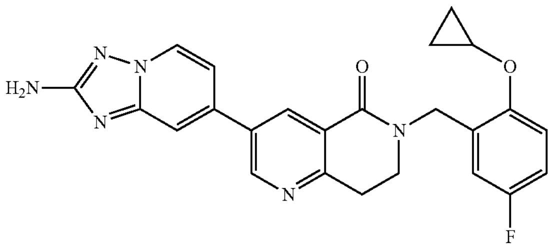
77
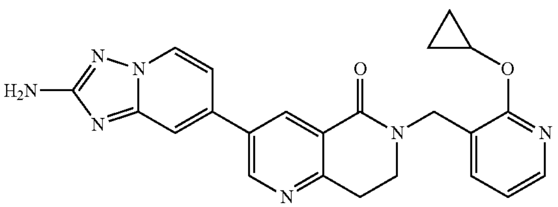
78
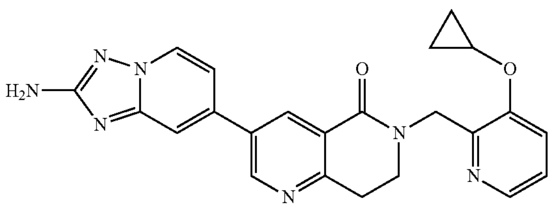
79
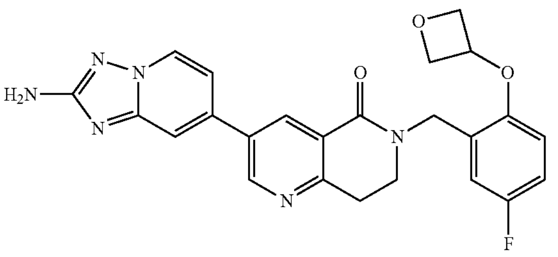
80
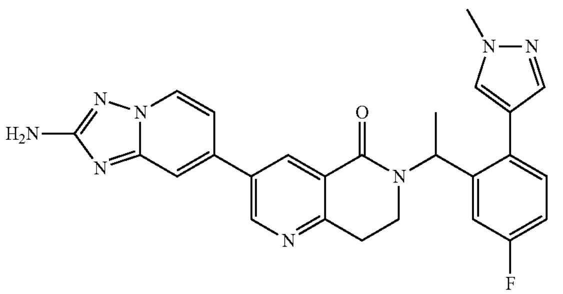

-continued
81
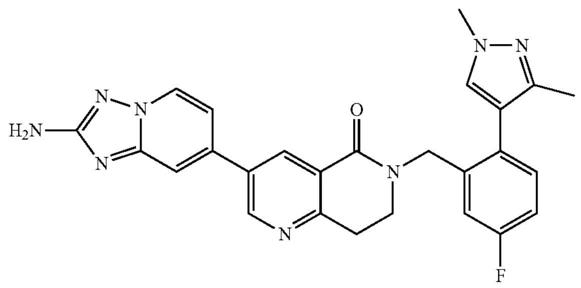
82
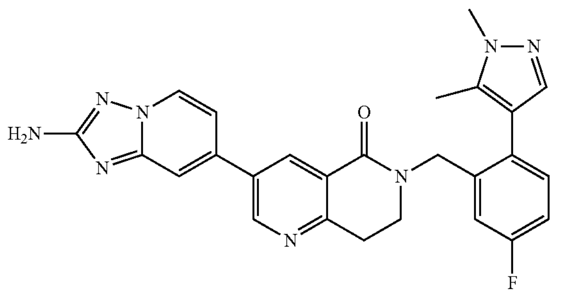
84
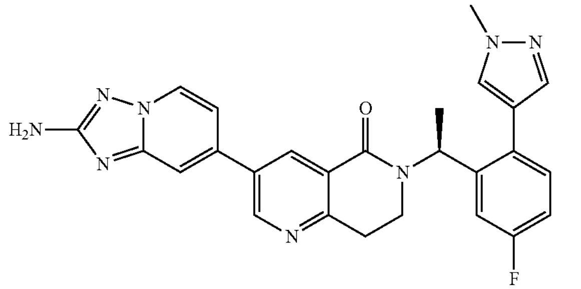
85
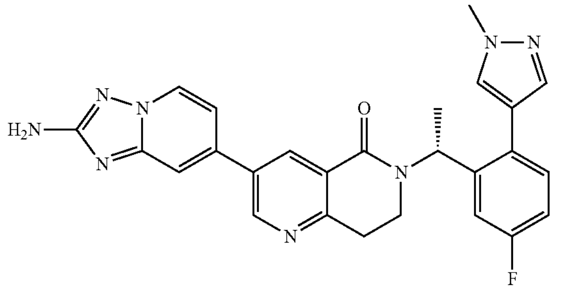
93
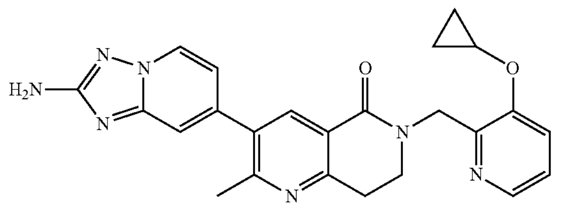
94
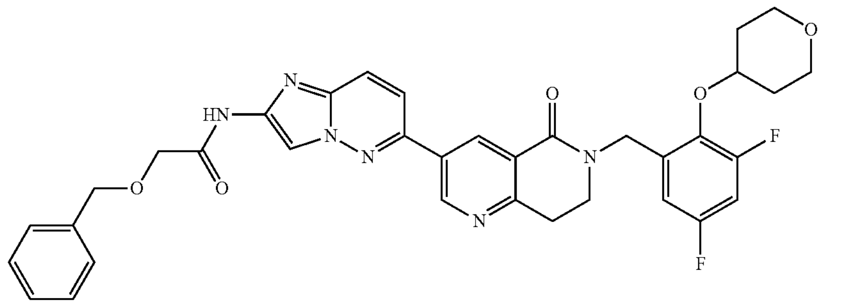
97
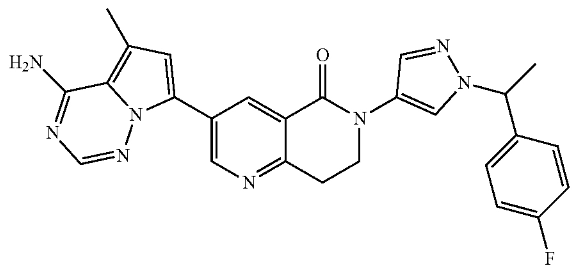
98
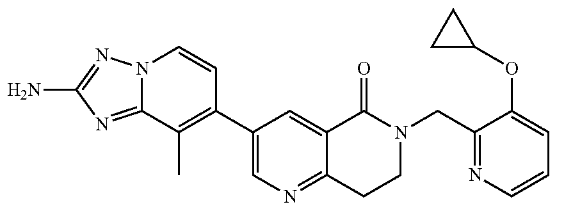

-continued

102

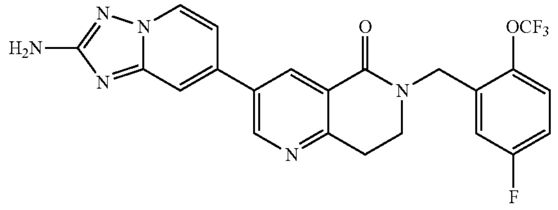

13. A pharmaceutical composition comprising the compound or the pharmaceutically acceptable salt, the stereoisomer, the solvate or the prodrug thereof according to claim 1 and a pharmaceutically acceptable carrier.

14. A method for treating a disease, comprising administering to a subject in need thereof the compound or the pharmaceutically acceptable salt, the stereoisomer, the solvate or the prodrug thereof according to claim 1, wherein the disease is selected from the group consisting of stroke, inflammatory bowel disease, ulcerative colitis, Crohn's disease, psoriasis, rheumatoid arthritis, NASH and heart failure.

15. A method for treating RIPK1-related diseases or conditions, comprising administering to a subject in need thereof the compound or the pharmaceutically acceptable salt, the stereoisomer, the solvate or the prodrug thereof according to claim 1:

the RIPK1-related diseases or conditions are selected from the group consisting of inflammatory disease, atherosclerosis and ischemia reperfusion injury.

16. A method for treating a disease, comprising administering to a subject in need thereof the pharmaceutical composition according to claim 13, wherein the disease is selected from the group consisting of stroke, inflammatory bowel disease, ulcerative colitis, Crohn's disease, psoriasis, rheumatoid arthritis, NASH and heart failure.

17. A method for treating RIPK1-related diseases or conditions, comprising administering to a subject in need thereof the pharmaceutical composition according to claim 13:

the RIPK1-related diseases or conditions are selected from the group consisting of inflammatory disease, atherosclerosis and ischemia reperfusion injury.

18. A compound or the pharmaceutically acceptable salt, wherein the compound is

Z48

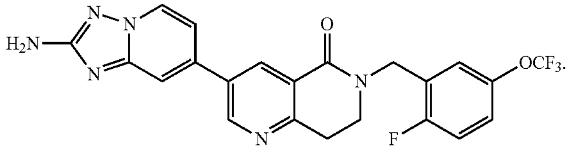

19. A compound or the pharmaceutically acceptable salt, wherein the compound is

Z69

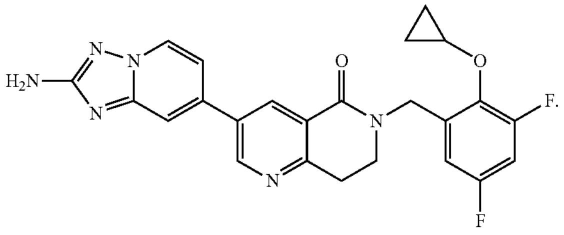

* * * * *